US006387641B1

(12) United States Patent
Bellon et al.

(10) Patent No.: US 6,387,641 B1
(45) Date of Patent: May 14, 2002

(54) CRYSTALLIZED P38 COMPLEXES

(75) Inventors: Steven Bellon, Wellesly; Guy Bemis, Arlington; Keith Wilson, Boston; Matthew Fitzgibbon, Millis, all of MA (US)

(73) Assignee: Vertex Pharmaceuticals Incorporated, Cambridge, MA (US)

( * ) Notice: Subject to any disclaimer, the term of this patent is extended or adjusted under 35 U.S.C. 154(b) by 0 days.

(21) Appl. No.: 09/457,040

(22) Filed: Dec. 8, 1999

Related U.S. Application Data

(60) Provisional application No. 60/112,354, filed on Dec. 16, 1998, and provisional application No. 60/163,373, filed on Nov. 3, 1999.

(51) Int. Cl.$^7$ .............................. C12Q 1/48; G06F 19/00

(52) U.S. Cl. ............................. 435/15; 702/19; 702/22

(58) Field of Search ........................ 435/15; 702/19, 702/22

(56) References Cited

PUBLICATIONS

Bellon, The Structure of Phosphorylated P38 is Monomeric Structure, vol. 7, No. 9, pp. 1057–1065.
Robinson, Mitogen–activated Protein Kinase Pathways, Cell Regulation, 1999, pp. 180–186.
Li, The Primary Structureof P38: A New Member of p38 Group, Biochem & Biophy, 228, (1996) pp 334–340.
Kultz, Phylogentic and Functional Classification of Mitogen—, J. Mol. Evol (1998), 46:571–588.
Russo, Structural Basis of cyclin–dependent Kinase Activation by Phosphorylation, Nat. Struct. Bio, vol. 3, (1996) 696–700.
Yamaguchi, Structural Basis for Activation of Human Lyphocyte Kinase, Nature vol. 384, (1996), 484–489.
Narayana, A Binary COmplex of the Catalytic Subunit of cAMP–Dependent Protein Kinase, Structure vol. 5 No. 7, (1997) 921 935.
Bossemeyer, Phosphotransferase and Substrate binding . . . EMBO J 12, 849–859, (1993).
Fox, A Single Amino Acid Substitution Makes ERK2 . . . , Prot. Sci (1998), 7:2249–2255.
Beyaert, The P38/RK Mitogen–activated protein kinase, EMBO Jour., vol. 15 No. 8, pp 1914–1923 (1996).
Wilson, The structural basis for the specificity of pyridinylinidazole inhibitors, Chem. & Bio (1997), vol. 4 No. 6, pp 423–431.
Tong, A highly specific inhibitor of human p38 MAP Kinase. Nat. Struc. Bio. vol. 4, No. 4, Apr. 1997, pp 311–316.
Young, Pyrindinyl Imidazole Inhibitors . . . , Jour. of Bio. CHem. vol. 272, No. 18, May 2, 1997, pp 12116–12121.
Johnson, Active and Inactive Protein Kinases . . . , Cell, vol. 85, pp 149–158, Apr. 1996.

(List continued on next page.)

*Primary Examiner*—Nashaat T. Nashed
(74) *Attorney, Agent, or Firm*—Ian Silverma; Andrew S. Marks

(57) ABSTRACT

This invention provides certain crystallized, protein kinase-ligand complexes, in particular P38-ligand complexes, and their structure coordinates. The structure coordinates are based on the structure of a phosphorylated P38γ complex which has now been solved and which reveals new structural information useful for understanding the activated states of other, related kinase proteins as described herein. The key structural features of the proteins, particularly the shape of the substrate binding site, are useful in methods for designing or identifying selective inhibitors of the protein kinases, particularly P38γ and in solving the structures of other proteins with similar features. The structure coordinates may be encoded in a data storage medium for use with a computer for graphical three-dimensional representation of the structure and for computer-aided molecular design of new inhibitors.

17 Claims, 146 Drawing Sheets

PUBLICATIONS

Eck, Structure of the regulatory domains of the Src–family, Nature, vol. 368, Apr. 1994, pp 764–769.

Raingeaud, Pro–inflammatory Cytokines and Environmental Stress . . . , The Jour. of Bio. Chem., vol. 270, No. 13 Mar. 1995, pp 7420–7426.

Hubbard, Crystal Structur of Tyrosine Kinase . . . , Nature vol. 372, Dec. 1994, pp 746–754.

Canagaraja, Activation Mechanism of the MAP Kinase ERK2, Cell, vol. 90, pp 859–869, Sep. 1997.

Hubbard, Crystal Structure of the activated insulin receptor, EMBO Jour. vol. 16, No. 18, pp 5572–5581, 1997.

Wilson, Crystal Structure of p38 Mitogen–activated Kinase, Jour. Bio. Chem., vol. 271, No. 44, pp 27696–27700, 1996.

Zhang, Atomic Structur of MAP Kinase ERK2 . . . , Nature vol. 367, pp 704–710, Feb. 1994.

Zheng, A Refined Crystal Structure of the Catalytic Subunit, Acta Cryst. , D49, pp 362–365, 1993.

Wang, The structure of mitogen–activated protein kinases., Proc. Natl. Acad. Sci., vol. 94, pp 2327–2332, Mar. 1997.

Xie, Crystal Strucutre of JNK3: a Kinase implicated in neuronal apoptosis, Structure, vo. 6, No. 8, pp963–991 1998.

| ATOM | ATOM TYPE | RESIDUE | | # | X | Y | Z | OCC | B |
|---|---|---|---|---|---|---|---|---|---|
| 1 | N | ARG | A | 8 | 50.744 | 68.953 | -19.867 | 1 | 82.26 |
| 2 | CA | ARG | A | 8 | 51.733 | 70.011 | -19.529 | 1 | 82.91 |
| 3 | C | ARG | A | 8 | 52.844 | 69.485 | -18.592 | 1 | 83.38 |
| 4 | O | ARG | A | 8 | 52.777 | 68.355 | -18.091 | 1 | 83.08 |
| 5 | CB | ARG | A | 8 | 51.013 | 71.214 | -18.918 | 1 | 80.87 |
| 6 | N | SER | A | 9 | 53.885 | 70.296 | -18.408 | 1 | 83.59 |
| 7 | CA | SER | A | 9 | 55.028 | 69.954 | -17.564 | 1 | 82.36 |
| 8 | C | SER | A | 9 | 55.82 | 71.228 | -17.264 | 1 | 80.92 |
| 9 | O | SER | A | 9 | 55.748 | 72.203 | -18.014 | 1 | 79.73 |
| 10 | CB | SER | A | 9 | 55.931 | 68.93 | -18.27 | 1 | 85.39 |
| 11 | OG | SER | A | 9 | 56.938 | 68.428 | -17.399 | 1 | 87.48 |
| 12 | N | GLY | A | 10 | 56.597 | 71.198 | -16.181 | 1 | 80.75 |
| 13 | CA | GLY | A | 10 | 57.381 | 72.357 | -15.774 | 1 | 77.56 |
| 14 | C | GLY | A | 10 | 56.625 | 73.137 | -14.711 | 1 | 75.22 |
| 15 | O | GLY | A | 10 | 55.874 | 72.55 | -13.928 | 1 | 74.7 |
| 16 | N | PHE | A | 11 | 56.834 | 74.45 | -14.659 | 1 | 72.75 |
| 17 | CA | PHE | A | 11 | 56.147 | 75.305 | -13.687 | 1 | 68.57 |
| 18 | C | PHE | A | 11 | 55.637 | 76.563 | -14.371 | 1 | 69.71 |
| 19 | O | PHE | A | 11 | 55.787 | 76.723 | -15.583 | 1 | 70.87 |
| 20 | CB | PHE | A | 11 | 57.072 | 75.702 | -12.532 | 1 | 63.69 |
| 21 | CG | PHE | A | 11 | 57.413 | 74.576 | -11.61 | 1 | 60.38 |
| 22 | CD1 | PHE | A | 11 | 58.404 | 73.649 | -11.952 | 1 | 62.55 |
| 23 | CD2 | PHE | A | 11 | 56.744 | 74.425 | -10.402 | 1 | 60.69 |
| 24 | CE1 | PHE | A | 11 | 58.724 | 72.575 | -11.097 | 1 | 62.34 |
| 25 | CE2 | PHE | A | 11 | 57.054 | 73.352 | -9.535 | 1 | 63.35 |
| 26 | CZ | PHE | A | 11 | 58.047 | 72.427 | -9.886 | 1 | 60.96 |
| 27 | N | TYR | A | 12 | 54.981 | 77.421 | -13.597 | 1 | 70.53 |
| 28 | CA | TYR | A | 12 | 54.466 | 78.687 | -14.098 | 1 | 73.77 |
| 29 | C | TYR | A | 12 | 54.029 | 79.569 | -12.935 | 1 | 75.91 |
| 30 | O | TYR | A | 12 | 53.839 | 79.088 | -11.817 | 1 | 76.32 |
| 31 | CB | TYR | A | 12 | 53.378 | 78.485 | -15.165 | 1 | 74.03 |
| 32 | CG | TYR | A | 12 | 51.952 | 78.365 | -14.693 | 1 | 77.25 |
| 33 | CD1 | TYR | A | 12 | 51.387 | 77.116 | -14.424 | 1 | 76.91 |
| 34 | CD2 | TYR | A | 12 | 51.13 | 79.494 | -14.611 | 1 | 78.07 |
| 35 | CE1 | TYR | A | 12 | 50.036 | 76.99 | -14.094 | 1 | 78 |
| 36 | CE2 | TYR | A | 12 | 49.778 | 79.38 | -14.279 | 1 | 79.84 |
| 37 | CZ | TYR | A | 12 | 49.237 | 78.123 | -14.027 | 1 | 79.01 |
| 38 | OH | TYR | A | 12 | 47.896 | 77.997 | -13.743 | 1 | 80.18 |
| 39 | N | ARG | A | 13 | 53.909 | 80.867 | -13.187 | 1 | 78.58 |
| 40 | CA | ARG | A | 13 | 53.571 | 81.807 | -12.124 | 1 | 81.99 |

Fig. 1-1

| ATOM | ATOM TYPE | RESIDUE | | # | X | Y | Z | OCC | B |
|---|---|---|---|---|---|---|---|---|---|
| 41 | C | ARG | A | 13 | 52.314 | 82.607 | -12.411 | 1 | 82.41 |
| 42 | O | ARG | A | 13 | 52.003 | 82.886 | -13.565 | 1 | 82.24 |
| 43 | CB | ARG | A | 13 | 54.769 | 82.74 | -11.896 | 1 | 85.09 |
| 44 | CG | ARG | A | 13 | 56.127 | 81.98 | -11.974 | 1 | 91.35 |
| 45 | CD | ARG | A | 13 | 57.415 | 82.803 | -11.776 | 1 | 95.98 |
| 46 | NE | ARG | A | 13 | 57.109 | 83.991 | -11.068 | 1 | 99.39 |
| 47 | CZ | ARG | A | 13 | 57.291 | 84.52 | -9.871 | 1 | 100 |
| 48 | NH1 | ARG | A | 13 | 57.95 | 84.023 | -8.831 | 1 | 100 |
| 49 | NH2 | ARG | A | 13 | 56.578 | 85.628 | -9.741 | 1 | 99.54 |
| 50 | N | GLN | A | 14 | 51.6 | 82.986 | -11.354 | 1 | 83.93 |
| 51 | CA | GLN | A | 14 | 50.377 | 83.763 | -11.509 | 1 | 85.5 |
| 52 | C | GLN | A | 14 | 50.056 | 84.671 | -10.332 | 1 | 86.86 |
| 53 | O | GLN | A | 14 | 50.422 | 84.392 | -9.191 | 1 | 85.56 |
| 54 | CB | GLN | A | 14 | 49.187 | 82.834 | -11.751 | 1 | 86.15 |
| 55 | CG | GLN | A | 14 | 47.917 | 83.565 | -12.165 | 1 | 86.97 |
| 56 | CD | GLN | A | 14 | 46.734 | 82.636 | -12.364 | 1 | 87.55 |
| 57 | OE1 | GLN | A | 14 | 45.605 | 82.969 | -11.987 | 1 | 86.77 |
| 58 | NE2 | GLN | A | 14 | 46.979 | 81.473 | -12.966 | 1 | 87.48 |
| 59 | N | GLU | A | 15 | 49.405 | 85.785 | -10.651 | 1 | 90.02 |
| 60 | CA | GLU | A | 15 | 48.971 | 86.764 | -9.667 | 1 | 94 |
| 61 | C | GLU | A | 15 | 47.613 | 86.293 | -9.182 | 1 | 96.77 |
| 62 | O | GLU | A | 15 | 46.654 | 86.27 | -9.958 | 1 | 98.74 |
| 63 | CB | GLU | A | 15 | 48.793 | 88.135 | -10.328 | 1 | 95.34 |
| 64 | CG | GLU | A | 15 | 48.068 | 88.087 | -11.686 | 1 | 99.57 |
| 65 | CD | GLU | A | 15 | 47.489 | 89.436 | -12.131 | 1 | 100 |
| 66 | OE1 | GLU | A | 15 | 48.282 | 90.349 | -12.468 | 1 | 100 |
| 67 | OE2 | GLU | A | 15 | 46.24 | 89.564 | -12.173 | 1 | 100 |
| 68 | N | VAL | A | 16 | 47.523 | 85.869 | -7.927 | 1 | 98.29 |
| 69 | CA | VAL | A | 16 | 46.234 | 85.43 | -7.414 | 1 | 99.04 |
| 70 | C | VAL | A | 16 | 45.526 | 86.621 | -6.758 | 1 | 100 |
| 71 | O | VAL | A | 16 | 44.777 | 87.347 | -7.429 | 1 | 100 |
| 72 | CB | VAL | A | 16 | 46.382 | 84.225 | -6.476 | 1 | 99.49 |
| 73 | CG1 | VAL | A | 16 | 45.022 | 83.812 | -5.929 | 1 | 100 |
| 74 | CG2 | VAL | A | 16 | 46.965 | 83.07 | -7.261 | 1 | 98.21 |
| 75 | N | THR | A | 17 | 45.718 | 86.811 | -5.457 | 1 | 98.92 |
| 76 | CA | THR | A | 17 | 45.114 | 87.969 | -4.809 | 1 | 99.7 |
| 77 | C | THR | A | 17 | 46.237 | 88.998 | -4.8 | 1 | 100 |
| 78 | O | THR | A | 17 | 46.526 | 89.626 | -5.83 | 1 | 100 |
| 79 | CB | THR | A | 17 | 44.62 | 87.671 | -3.38 | 1 | 99.48 |
| 80 | OG1 | THR | A | 17 | 45.267 | 86.493 | -2.879 | 1 | 100 |

Fig. 1-2

| ATOM | ATOM TYPE | RESIDUE | | # | X | Y | Z | OCC | B |
|---|---|---|---|---|---|---|---|---|---|
| 81 | CG2 | THR | A | 17 | 43.094 | 87.496 | -3.367 | 1 | 97.76 |
| 82 | N | LYS | A | 18 | 46.915 | 89.11 | -3.663 | 1 | 100 |
| 83 | CA | LYS | A | 18 | 48.037 | 90.027 | -3.534 | 1 | 99.44 |
| 84 | C | LYS | A | 18 | 49.334 | 89.23 | -3.691 | 1 | 98.74 |
| 85 | O | LYS | A | 18 | 50.377 | 89.783 | -4.052 | 1 | 99.4 |
| 86 | CB | LYS | A | 18 | 47.997 | 90.713 | -2.167 | 1 | 99.64 |
| 87 | N | THR | A | 19 | 49.233 | 87.915 | -3.478 | 1 | 96.3 |
| 88 | CA | THR | A | 19 | 50.377 | 87.008 | -3.544 | 1 | 92.86 |
| 89 | C | THR | A | 19 | 50.692 | 86.417 | -4.909 | 1 | 89.53 |
| 90 | O | THR | A | 19 | 49.833 | 86.358 | -5.787 | 1 | 90.35 |
| 91 | CB | THR | A | 19 | 50.198 | 85.821 | -2.584 | 1 | 93.8 |
| 92 | OG1 | THR | A | 19 | 49.092 | 86.07 | -1.707 | 1 | 96.25 |
| 93 | CG2 | THR | A | 19 | 51.469 | 85.599 | -1.762 | 1 | 94.19 |
| 94 | N | ALA | A | 20 | 51.931 | 85.947 | -5.052 | 1 | 84.1 |
| 95 | CA | ALA | A | 20 | 52.392 | 85.322 | -6.279 | 1 | 80.21 |
| 96 | C | ALA | A | 20 | 52.686 | 83.861 | -6.032 | 1 | 79.19 |
| 97 | O | ALA | A | 20 | 53.447 | 83.499 | -5.123 | 1 | 79.32 |
| 98 | CB | ALA | A | 20 | 53.616 | 85.993 | -6.789 | 1 | 80.49 |
| 99 | N | TRP | A | 21 | 52.093 | 83.029 | -6.877 | 1 | 77.5 |
| 100 | CA | TRP | A | 21 | 52.244 | 81.579 | -6.794 | 1 | 77.45 |
| 101 | C | TRP | A | 21 | 53.081 | 81.073 | -7.941 | 1 | 74.6 |
| 102 | O | TRP | A | 21 | 53.083 | 81.667 | -9.006 | 1 | 74.48 |
| 103 | CB | TRP | A | 21 | 50.883 | 80.906 | -6.905 | 1 | 81.76 |
| 104 | CG | TRP | A | 21 | 49.905 | 81.312 | -5.877 | 1 | 85.09 |
| 105 | CD1 | TRP | A | 21 | 49.461 | 82.578 | -5.612 | 1 | 86.86 |
| 106 | CD2 | TRP | A | 21 | 49.174 | 80.443 | -5.022 | 1 | 86.32 |
| 107 | NE1 | TRP | A | 21 | 48.481 | 82.545 | -4.652 | 1 | 87.59 |
| 108 | CE2 | TRP | A | 21 | 48.287 | 81.242 | -4.272 | 1 | 87.85 |
| 109 | CE3 | TRP | A | 21 | 49.173 | 79.058 | -4.823 | 1 | 87.24 |
| 110 | CZ2 | TRP | A | 21 | 47.409 | 80.703 | -3.339 | 1 | 88.69 |
| 111 | CZ3 | TRP | A | 21 | 48.297 | 78.522 | -3.894 | 1 | 89.26 |
| 112 | CH2 | TRP | A | 21 | 47.426 | 79.344 | -3.163 | 1 | 88.37 |
| 113 | N | GLU | A | 22 | 53.772 | 79.962 | -7.727 | 1 | 72.87 |
| 114 | CA | GLU | A | 22 | 54.589 | 79.366 | -8.779 | 1 | 73.61 |
| 115 | C | GLU | A | 22 | 54.254 | 77.885 | -8.781 | 1 | 70.43 |
| 116 | O | GLU | A | 22 | 55.052 | 77.054 | -8.375 | 1 | 72.21 |
| 117 | CB | GLU | A | 22 | 56.095 | 79.588 | -8.526 | 1 | 78.55 |
| 118 | CG | GLU | A | 22 | 57.01 | 79.326 | -9.751 | 1 | 84.66 |
| 119 | CD | GLU | A | 22 | 58.516 | 79.511 | -9.469 | 1 | 88.22 |
| 120 | OE1 | GLU | A | 22 | 58.873 | 80.143 | -8.446 | 1 | 89.24 |

Fig. 1-3

| ATOM | ATOM TYPE | RESIDUE | | # | X | Y | Z | OCC | B |
|---|---|---|---|---|---|---|---|---|---|
| 121 | OE2 | GLU | A | 22 | 59.344 | 79.015 | -10.275 | 1 | 88.75 |
| 122 | N | VAL | A | 23 | 53.051 | 77.565 | -9.225 | 1 | 66.88 |
| 123 | CA | VAL | A | 23 | 52.581 | 76.187 | -9.26 | 1 | 65.06 |
| 124 | C | VAL | A | 23 | 53.091 | 75.411 | -10.474 | 1 | 64.88 |
| 125 | O | VAL | A | 23 | 53.841 | 75.948 | -11.284 | 1 | 66.97 |
| 126 | CB | VAL | A | 23 | 51.063 | 76.168 | -9.269 | 1 | 63.14 |
| 127 | CG1 | VAL | A | 23 | 50.547 | 76.87 | -8.039 | 1 | 61.87 |
| 128 | CG2 | VAL | A | 23 | 50.548 | 76.846 | -10.516 | 1 | 58.02 |
| 129 | N | ARG | A | 24 | 52.716 | 74.139 | -10.581 | 1 | 61.64 |
| 130 | CA | ARG | A | 24 | 53.142 | 73.344 | -11.721 | 1 | 60.93 |
| 131 | C | ARG | A | 24 | 52.273 | 73.684 | -12.899 | 1 | 60.82 |
| 132 | O | ARG | A | 24 | 51.128 | 74.079 | -12.72 | 1 | 62.47 |
| 133 | CB | ARG | A | 24 | 53.045 | 71.859 | -11.436 | 1 | 59.28 |
| 134 | CG | ARG | A | 24 | 54.046 | 71.385 | -10.446 | 1 | 57.53 |
| 135 | CD | ARG | A | 24 | 53.987 | 69.896 | -10.339 | 1 | 57.5 |
| 136 | NE | ARG | A | 24 | 54.976 | 69.412 | -9.399 | 1 | 58.33 |
| 137 | CZ | ARG | A | 24 | 54.993 | 68.182 | -8.913 | 1 | 60.97 |
| 138 | NH1 | ARG | A | 24 | 54.076 | 67.305 | -9.296 | 1 | 64.3 |
| 139 | NH2 | ARG | A | 24 | 55.929 | 67.827 | -8.048 | 1 | 61.56 |
| 140 | N | ALA | A | 25 | 52.821 | 73.512 | -14.102 | 1 | 61.32 |
| 141 | CA | ALA | A | 25 | 52.12 | 73.819 | -15.353 | 1 | 59.78 |
| 142 | C | ALA | A | 25 | 50.829 | 73.041 | -15.486 | 1 | 56.96 |
| 143 | O | ALA | A | 25 | 49.84 | 73.542 | -16.029 | 1 | 57.32 |
| 144 | CB | ALA | A | 25 | 53.021 | 73.533 | -16.544 | 1 | 61.78 |
| 145 | N | VAL | A | 26 | 50.861 | 71.816 | -14.974 | 1 | 53.53 |
| 146 | CA | VAL | A | 26 | 49.732 | 70.909 | -14.995 | 1 | 49.24 |
| 147 | C | VAL | A | 26 | 48.516 | 71.425 | -14.201 | 1 | 49.96 |
| 148 | O | VAL | A | 26 | 47.389 | 71.353 | -14.687 | 1 | 46.32 |
| 149 | CB | VAL | A | 26 | 50.194 | 69.545 | -14.528 | 1 | 47.82 |
| 150 | CG1 | VAL | A | 26 | 49.905 | 69.307 | -13.062 | 1 | 47.12 |
| 151 | CG2 | VAL | A | 26 | 49.614 | 68.51 | -15.411 | 1 | 54.88 |
| 152 | N | TYR | A | 27 | 48.755 | 71.961 | -12.999 | 1 | 50.2 |
| 153 | CA | TYR | A | 27 | 47.696 | 72.532 | -12.165 | 1 | 50.72 |
| 154 | C | TYR | A | 27 | 47.25 | 73.803 | -12.861 | 1 | 51.88 |
| 155 | O | TYR | A | 27 | 48.005 | 74.765 | -12.965 | 1 | 53.42 |
| 156 | CB | TYR | A | 27 | 48.217 | 72.83 | -10.76 | 1 | 44.91 |
| 157 | CG | TYR | A | 27 | 48.564 | 71.567 | -10.048 | 1 | 40.92 |
| 158 | CD1 | TYR | A | 27 | 47.638 | 70.524 | -9.97 | 1 | 38.22 |
| 159 | CD2 | TYR | A | 27 | 49.825 | 71.371 | -9.518 | 1 | 40.3 |
| 160 | CE1 | TYR | A | 27 | 47.961 | 69.309 | -9.39 | 1 | 35.92 |

Fig. 1-4

| ATOM | ATOM TYPE | RESIDUE | | # | X | Y | Z | OCC | B |
|---|---|---|---|---|---|---|---|---|---|
| 161 | CE2 | TYR | A | 27 | 50.167 | 70.152 | -8.926 | 1 | 45.49 |
| 162 | CZ | TYR | A | 27 | 49.22 | 69.125 | -8.869 | 1 | 42.37 |
| 163 | OH | TYR | A | 27 | 49.538 | 67.927 | -8.288 | 1 | 41.12 |
| 164 | N | ARG | A | 28 | 46.017 | 73.797 | -13.338 | 1 | 53.27 |
| 165 | CA | ARG | A | 28 | 45.503 | 74.918 | -14.09 | 1 | 57.84 |
| 166 | C | ARG | A | 28 | 44.336 | 75.676 | -13.474 | 1 | 57.15 |
| 167 | O | ARG | A | 28 | 43.803 | 75.275 | -12.459 | 1 | 58.08 |
| 168 | CB | ARG | A | 28 | 45.18 | 74.42 | -15.501 | 1 | 63.22 |
| 169 | CG | ARG | A | 28 | 46.386 | 73.708 | -16.155 | 1 | 70.45 |
| 170 | CD | ARG | A | 28 | 46.207 | 73.457 | -17.644 | 1 | 78.5 |
| 171 | NE | ARG | A | 28 | 45.79 | 74.672 | -18.345 | 1 | 85.36 |
| 172 | CZ | ARG | A | 28 | 45.119 | 74.693 | -19.497 | 1 | 87.56 |
| 173 | NH1 | ARG | A | 28 | 44.788 | 73.559 | -20.106 | 1 | 86.24 |
| 174 | NH2 | ARG | A | 28 | 44.742 | 75.854 | -20.02 | 1 | 88.04 |
| 175 | N | ASP | A | 29 | 43.986 | 76.802 | -14.093 | 1 | 60.24 |
| 176 | CA | ASP | A | 29 | 42.898 | 77.688 | -13.666 | 1 | 60.05 |
| 177 | C | ASP | A | 29 | 42.793 | 77.908 | -12.155 | 1 | 60.52 |
| 178 | O | ASP | A | 29 | 41.836 | 77.484 | -11.526 | 1 | 63.24 |
| 179 | CB | ASP | A | 29 | 41.554 | 77.224 | -14.241 | 1 | 61.34 |
| 180 | CG | ASP | A | 29 | 40.421 | 78.231 | -13.985 | 1 | 66.29 |
| 181 | OD1 | ASP | A | 29 | 40.714 | 79.436 | -13.803 | 1 | 70.52 |
| 182 | OD2 | ASP | A | 29 | 39.237 | 77.821 | -13.955 | 1 | 64.84 |
| 183 | N | LEU | A | 30 | 43.771 | 78.596 | -11.579 | 1 | 60.46 |
| 184 | CA | LEU | A | 30 | 43.779 | 78.865 | -10.147 | 1 | 59.31 |
| 185 | C | LEU | A | 30 | 42.689 | 79.847 | -9.722 | 1 | 61.11 |
| 186 | O | LEU | A | 30 | 42.378 | 80.795 | -10.438 | 1 | 62.1 |
| 187 | CB | LEU | A | 30 | 45.15 | 79.393 | -9.712 | 1 | 55.77 |
| 188 | CG | LEU | A | 30 | 46.34 | 78.442 | -9.76 | 1 | 54.22 |
| 189 | CD1 | LEU | A | 30 | 47.586 | 79.188 | -9.334 | 1 | 57.44 |
| 190 | CD2 | LEU | A | 30 | 46.114 | 77.282 | -8.824 | 1 | 55.22 |
| 191 | N | GLN | A | 31 | 42.115 | 79.598 | -8.547 | 1 | 64.21 |
| 192 | CA | GLN | A | 31 | 41.069 | 80.434 | -7.962 | 1 | 63.96 |
| 193 | C | GLN | A | 31 | 41.232 | 80.405 | -6.449 | 1 | 65.04 |
| 194 | O | GLN | A | 31 | 41.301 | 79.341 | -5.86 | 1 | 62.91 |
| 195 | CB | GLN | A | 31 | 39.692 | 79.885 | -8.315 | 1 | 64.63 |
| 196 | CG | GLN | A | 31 | 39.317 | 79.972 | -9.782 | 1 | 66.81 |
| 197 | CD | GLN | A | 31 | 38.999 | 81.384 | -10.212 | 1 | 69.14 |
| 198 | OE1 | GLN | A | 31 | 39.546 | 81.886 | -11.198 | 1 | 67.83 |
| 199 | NE2 | GLN | A | 31 | 38.11 | 82.04 | -9.469 | 1 | 68.7 |
| 200 | N | PRO | A | 32 | 41.287 | 81.58 | -5.804 | 1 | 67.25 |

Fig. 1-5

| ATOM | ATOM TYPE | RESIDUE | | # | X | Y | Z | OCC | B |
|---|---|---|---|---|---|---|---|---|---|
| 201 | CA | PRO | A | 32 | 41.441 | 81.695 | -4.348 | 1 | 67.88 |
| 202 | C | PRO | A | 32 | 40.188 | 81.22 | -3.605 | 1 | 65.58 |
| 203 | O | PRO | A | 32 | 39.088 | 81.238 | -4.153 | 1 | 65 |
| 204 | CB | PRO | A | 32 | 41.631 | 83.196 | -4.154 | 1 | 68.41 |
| 205 | CG | PRO | A | 32 | 40.687 | 83.747 | -5.184 | 1 | 69.28 |
| 206 | CD | PRO | A | 32 | 41.052 | 82.907 | -6.4 | 1 | 68.01 |
| 207 | N | VAL | A | 33 | 40.373 | 80.795 | -2.361 | 1 | 63.5 |
| 208 | CA | VAL | A | 33 | 39.281 | 80.321 | -1.518 | 1 | 62.28 |
| 209 | C | VAL | A | 33 | 39.604 | 80.58 | -0.051 | 1 | 66.64 |
| 210 | O | VAL | A | 33 | 38.638 | 80.628 | 0.755 | 1 | 69.45 |
| 211 | CB | VAL | A | 33 | 39.008 | 78.8 | -1.689 | 1 | 59.14 |
| 212 | CG1 | VAL | A | 33 | 38.129 | 78.554 | -2.889 | 1 | 59.56 |
| 213 | CG2 | VAL | A | 33 | 40.317 | 78.021 | -1.809 | 1 | 55.83 |
| 214 | OXT | VAL | A | 33 | 40.815 | 80.719 | 0.274 | 1 | 67.62 |
| 215 | N | ALA | A | 40 | 47.147 | 81.043 | 2.447 | 1 | 59.48 |
| 216 | CA | ALA | A | 40 | 46.242 | 81.104 | 1.261 | 1 | 58.1 |
| 217 | C | ALA | A | 40 | 46.223 | 79.775 | 0.482 | 1 | 57.51 |
| 218 | O | ALA | A | 40 | 47.24 | 79.084 | 0.319 | 1 | 56.32 |
| 219 | CB | ALA | A | 40 | 46.606 | 82.272 | 0.352 | 1 | 56.64 |
| 220 | N | VAL | A | 41 | 45.024 | 79.427 | 0.03 | 1 | 54.69 |
| 221 | CA | VAL | A | 41 | 44.766 | 78.197 | -0.682 | 1 | 50.72 |
| 222 | C | VAL | A | 41 | 44.027 | 78.556 | -1.944 | 1 | 50.04 |
| 223 | O | VAL | A | 41 | 43.247 | 79.512 | -1.973 | 1 | 50.25 |
| 224 | CB | VAL | A | 41 | 43.863 | 77.271 | 0.178 | 1 | 51.04 |
| 225 | CG1 | VAL | A | 41 | 43.434 | 76.049 | -0.596 | 1 | 50.63 |
| 226 | CG2 | VAL | A | 41 | 44.587 | 76.859 | 1.448 | 1 | 48.39 |
| 227 | N | CYS | A | 42 | 44.289 | 77.785 | -2.989 | 1 | 49.24 |
| 228 | CA | CYS | A | 42 | 43.65 | 77.99 | -4.273 | 1 | 51.1 |
| 229 | C | CYS | A | 42 | 43.018 | 76.715 | -4.796 | 1 | 50.56 |
| 230 | O | CYS | A | 42 | 43.478 | 75.605 | -4.514 | 1 | 52.01 |
| 231 | CB | CYS | A | 42 | 44.664 | 78.482 | -5.306 | 1 | 53.52 |
| 232 | SG | CYS | A | 42 | 44.777 | 80.249 | -5.429 | 1 | 57.08 |
| 233 | N | SER | A | 43 | 41.966 | 76.888 | -5.579 | 1 | 48.19 |
| 234 | CA | SER | A | 43 | 41.291 | 75.764 | -6.181 | 1 | 49.79 |
| 235 | C | SER | A | 43 | 41.768 | 75.733 | -7.623 | 1 | 51.48 |
| 236 | O | SER | A | 43 | 41.6 | 76.697 | -8.358 | 1 | 55.24 |
| 237 | CB | SER | A | 43 | 39.762 | 75.917 | -6.095 | 1 | 46.11 |
| 238 | OG | SER | A | 43 | 39.244 | 76.94 | -6.923 | 1 | 43.24 |
| 239 | N | ALA | A | 44 | 42.439 | 74.658 | -8.004 | 1 | 51.27 |
| 240 | CA | ALA | A | 44 | 42.933 | 74.528 | -9.359 | 1 | 50.45 |

Fig. 1-6

| ATOM | ATOM TYPE | RESIDUE | | # | X | Y | Z | OCC | B |
|---|---|---|---|---|---|---|---|---|---|
| 241 | C | ALA | A | 44 | 42.276 | 73.32 | -10.02 | 1 | 53.54 |
| 242 | O | ALA | A | 44 | 41.342 | 72.744 | -9.472 | 1 | 56.92 |
| 243 | CB | ALA | A | 44 | 44.423 | 74.352 | -9.327 | 1 | 52.24 |
| 244 | N | VAL | A | 45 | 42.736 | 72.967 | -11.216 | 1 | 52.87 |
| 245 | CA | VAL | A | 45 | 42.234 | 71.804 | -11.928 | 1 | 49.85 |
| 246 | C | VAL | A | 45 | 43.444 | 71.032 | -12.379 | 1 | 50.26 |
| 247 | O | VAL | A | 45 | 44.381 | 71.626 | -12.887 | 1 | 53.24 |
| 248 | CB | VAL | A | 45 | 41.499 | 72.188 | -13.18 | 1 | 50.42 |
| 249 | CG1 | VAL | A | 45 | 41.056 | 70.918 | -13.929 | 1 | 48.88 |
| 250 | CG2 | VAL | A | 45 | 40.335 | 73.095 | -12.847 | 1 | 47.94 |
| 251 | N | ASP | A | 46 | 43.472 | 69.723 | -12.159 | 1 | 52.8 |
| 252 | CA | ASP | A | 46 | 44.627 | 68.967 | -12.624 | 1 | 52.12 |
| 253 | C | ASP | A | 46 | 44.399 | 68.883 | -14.125 | 1 | 54.38 |
| 254 | O | ASP | A | 46 | 43.435 | 68.27 | -14.577 | 1 | 55.61 |
| 255 | CB | ASP | A | 46 | 44.695 | 67.575 | -12.002 | 1 | 49.52 |
| 256 | CG | ASP | A | 46 | 46.008 | 66.869 | -12.304 | 1 | 51.61 |
| 257 | OD1 | ASP | A | 46 | 46.696 | 67.264 | -13.269 | 1 | 55.2 |
| 258 | OD2 | ASP | A | 46 | 46.368 | 65.917 | -11.584 | 1 | 48.33 |
| 259 | N | GLY | A | 47 | 45.246 | 69.571 | -14.884 | 1 | 54.36 |
| 260 | CA | GLY | A | 47 | 45.104 | 69.592 | -16.325 | 1 | 52.61 |
| 261 | C | GLY | A | 47 | 45.091 | 68.208 | -16.919 | 1 | 52.87 |
| 262 | O | GLY | A | 47 | 44.491 | 67.989 | -17.967 | 1 | 55.54 |
| 263 | N | ARG | A | 48 | 45.746 | 67.28 | -16.237 | 1 | 51.72 |
| 264 | CA | ARG | A | 48 | 45.826 | 65.902 | -16.684 | 1 | 54.21 |
| 265 | C | ARG | A | 48 | 44.537 | 65.08 | -16.561 | 1 | 55.33 |
| 266 | O | ARG | A | 48 | 44.334 | 64.136 | -17.331 | 1 | 59.88 |
| 267 | CB | ARG | A | 48 | 46.922 | 65.172 | -15.915 | 1 | 54.16 |
| 268 | CG | ARG | A | 48 | 48.313 | 65.67 | -16.187 | 1 | 53.52 |
| 269 | CD | ARG | A | 48 | 49.274 | 65.108 | -15.175 | 1 | 49.08 |
| 270 | NE | ARG | A | 48 | 49.024 | 65.689 | -13.867 | 1 | 50.85 |
| 271 | CZ | ARG | A | 48 | 49.732 | 65.422 | -12.778 | 1 | 51.07 |
| 272 | NH1 | ARG | A | 48 | 50.739 | 64.56 | -12.841 | 1 | 53.13 |
| 273 | NH2 | ARG | A | 48 | 49.444 | 66.035 | -11.637 | 1 | 50.48 |
| 274 | N | THR | A | 49 | 43.672 | 65.41 | -15.605 | 1 | 52.12 |
| 275 | CA | THR | A | 49 | 42.468 | 64.615 | -15.422 | 1 | 51.49 |
| 276 | C | THR | A | 49 | 41.136 | 65.324 | -15.484 | 1 | 52.42 |
| 277 | O | THR | A | 49 | 40.143 | 64.715 | -15.876 | 1 | 54.52 |
| 278 | CB | THR | A | 49 | 42.53 | 63.809 | -14.123 | 1 | 53.04 |
| 279 | OG1 | THR | A | 49 | 42.626 | 64.693 | -12.999 | 1 | 52.46 |
| 280 | CG2 | THR | A | 49 | 43.725 | 62.874 | -14.135 | 1 | 51.95 |

Fig. 1-7

| ATOM | ATOM TYPE | RESIDUE | | # | X | Y | Z | OCC | B |
|---|---|---|---|---|---|---|---|---|---|
| 281 | N | GLY | A | 50 | 41.1 | 66.585 | -15.07 | 1 | 52.62 |
| 282 | CA | GLY | A | 50 | 39.862 | 67.352 | -15.112 | 1 | 52.55 |
| 283 | C | GLY | A | 50 | 39.207 | 67.479 | -13.756 | 1 | 52.32 |
| 284 | O | GLY | A | 50 | 38.128 | 68.069 | -13.621 | 1 | 53.3 |
| 285 | N | ALA | A | 51 | 39.883 | 66.926 | -12.752 | 1 | 50.64 |
| 286 | CA | ALA | A | 51 | 39.431 | 66.92 | -11.365 | 1 | 50.52 |
| 287 | C | ALA | A | 51 | 39.877 | 68.166 | -10.59 | 1 | 52.14 |
| 288 | O | ALA | A | 51 | 41.081 | 68.467 | -10.566 | 1 | 53.63 |
| 289 | CB | ALA | A | 51 | 39.966 | 65.684 | -10.681 | 1 | 45.09 |
| 290 | N | LYS | A | 52 | 38.926 | 68.864 | -9.945 | 1 | 48.65 |
| 291 | CA | LYS | A | 52 | 39.249 | 70.056 | -9.163 | 1 | 45.14 |
| 292 | C | LYS | A | 52 | 40.142 | 69.618 | -8.017 | 1 | 46.17 |
| 293 | O | LYS | A | 52 | 39.985 | 68.532 | -7.439 | 1 | 45.35 |
| 294 | CB | LYS | A | 52 | 38.006 | 70.786 | -8.634 | 1 | 43.45 |
| 295 | CG | LYS | A | 52 | 37.131 | 71.423 | -9.709 | 1 | 50.2 |
| 296 | CD | LYS | A | 52 | 35.83 | 72.047 | -9.172 | 1 | 53.93 |
| 297 | CE | LYS | A | 52 | 36.067 | 73.417 | -8.544 | 1 | 58.33 |
| 298 | NZ | LYS | A | 52 | 34.789 | 74.037 | -8.052 | 1 | 60.69 |
| 299 | N | VAL | A | 53 | 41.088 | 70.486 | -7.698 | 1 | 45.92 |
| 300 | CA | VAL | A | 53 | 42.068 | 70.228 | -6.669 | 1 | 44.29 |
| 301 | C | VAL | A | 53 | 42.237 | 71.479 | -5.803 | 1 | 44.97 |
| 302 | O | VAL | A | 53 | 41.795 | 72.571 | -6.185 | 1 | 47.43 |
| 303 | CB | VAL | A | 53 | 43.384 | 69.828 | -7.372 | 1 | 44.62 |
| 304 | CG1 | VAL | A | 53 | 44.586 | 70.526 | -6.774 | 1 | 49.16 |
| 305 | CG2 | VAL | A | 53 | 43.54 | 68.34 | -7.335 | 1 | 42.42 |
| 306 | N | ALA | A | 54 | 42.78 | 71.3 | -4.603 | 1 | 42.17 |
| 307 | CA | ALA | A | 54 | 43.039 | 72.414 | -3.703 | 1 | 40.52 |
| 308 | C | ALA | A | 54 | 44.548 | 72.526 | -3.542 | 1 | 43.59 |
| 309 | O | ALA | A | 54 | 45.222 | 71.529 | -3.252 | 1 | 40.54 |
| 310 | CB | ALA | A | 54 | 42.392 | 72.182 | -2.369 | 1 | 38.36 |
| 311 | N | ILE | A | 55 | 45.076 | 73.727 | -3.786 | 1 | 46.03 |
| 312 | CA | ILE | A | 55 | 46.511 | 73.991 | -3.671 | 1 | 45.31 |
| 313 | C | ILE | A | 55 | 46.762 | 75.019 | -2.596 | 1 | 46.51 |
| 314 | O | ILE | A | 55 | 46.271 | 76.145 | -2.681 | 1 | 47.39 |
| 315 | CB | ILE | A | 55 | 47.101 | 74.522 | -4.981 | 1 | 45.99 |
| 316 | CG1 | ILE | A | 55 | 46.829 | 73.537 | -6.122 | 1 | 40.24 |
| 317 | CG2 | ILE | A | 55 | 48.607 | 74.712 | -4.835 | 1 | 46.63 |
| 318 | CD1 | ILE | A | 55 | 47.34 | 74.043 | -7.442 | 1 | 41.71 |
| 319 | N | LYS | A | 56 | 47.539 | 74.618 | -1.594 | 1 | 48.16 |
| 320 | CA | LYS | A | 56 | 47.882 | 75.462 | -0.454 | 1 | 49.54 |

Fig. 1-8

| ATOM | ATOM TYPE | RESIDUE | | # | X | Y | Z | OCC | B |
|---|---|---|---|---|---|---|---|---|---|
| 321 | C | LYS | A | 56 | 49.334 | 75.862 | -0.501 | 1 | 52.71 |
| 322 | O | LYS | A | 56 | 50.209 | 75.006 | -0.512 | 1 | 50.43 |
| 323 | CB | LYS | A | 56 | 47.645 | 74.703 | 0.858 | 1 | 50.38 |
| 324 | CG | LYS | A | 56 | 47.957 | 75.5 | 2.112 | 1 | 46.35 |
| 325 | CD | LYS | A | 56 | 47.618 | 74.715 | 3.332 | 1 | 46.29 |
| 326 | CE | LYS | A | 56 | 47.542 | 75.613 | 4.542 | 1 | 46.07 |
| 327 | NZ | LYS | A | 56 | 47.036 | 74.905 | 5.754 | 1 | 41.31 |
| 328 | N | LYS | A | 57 | 49.581 | 77.166 | -0.487 | 1 | 58.23 |
| 329 | CA | LYS | A | 57 | 50.939 | 77.706 | -0.508 | 1 | 61.77 |
| 330 | C | LYS | A | 57 | 51.336 | 78.06 | 0.92 | 1 | 62.18 |
| 331 | O | LYS | A | 57 | 50.678 | 78.863 | 1.562 | 1 | 62.18 |
| 332 | CB | LYS | A | 57 | 50.99 | 78.95 | -1.404 | 1 | 61.46 |
| 333 | CG | LYS | A | 57 | 52.283 | 79.76 | -1.353 | 1 | 63.67 |
| 334 | CD | LYS | A | 57 | 52.172 | 81.017 | -2.244 | 1 | 66.85 |
| 335 | CE | LYS | A | 57 | 53.323 | 82.015 | -2.034 | 1 | 67.4 |
| 336 | NZ | LYS | A | 57 | 54.669 | 81.4 | -2.232 | 1 | 64.73 |
| 337 | N | LEU | A | 58 | 52.355 | 77.386 | 1.444 | 1 | 66.78 |
| 338 | CA | LEU | A | 58 | 52.839 | 77.672 | 2.789 | 1 | 69.76 |
| 339 | C | LEU | A | 58 | 53.453 | 79.067 | 2.742 | 1 | 73.97 |
| 340 | O | LEU | A | 58 | 54.463 | 79.302 | 2.064 | 1 | 72.46 |
| 341 | CB | LEU | A | 58 | 53.897 | 76.659 | 3.232 | 1 | 66.96 |
| 342 | CG | LEU | A | 58 | 53.463 | 75.428 | 4.023 | 1 | 67.54 |
| 343 | CD1 | LEU | A | 58 | 52.732 | 75.852 | 5.276 | 1 | 67.95 |
| 344 | CD2 | LEU | A | 58 | 52.596 | 74.518 | 3.184 | 1 | 66.08 |
| 345 | N | TYR | A | 59 | 52.782 | 79.996 | 3.412 | 1 | 79.16 |
| 346 | CA | TYR | A | 59 | 53.196 | 81.389 | 3.495 | 1 | 84.09 |
| 347 | C | TYR | A | 59 | 54.514 | 81.684 | 4.236 | 1 | 83.49 |
| 348 | O | TYR | A | 59 | 54.537 | 81.738 | 5.476 | 1 | 83.18 |
| 349 | CB | TYR | A | 59 | 52.095 | 82.18 | 4.22 | 1 | 89.86 |
| 350 | CG | TYR | A | 59 | 52.387 | 83.653 | 4.452 | 1 | 96.71 |
| 351 | CD1 | TYR | A | 59 | 52.845 | 84.477 | 3.41 | 1 | 98.52 |
| 352 | CD2 | TYR | A | 59 | 52.201 | 84.228 | 5.723 | 1 | 97.81 |
| 353 | CE1 | TYR | A | 59 | 53.112 | 85.84 | 3.629 | 1 | 100 |
| 354 | CE2 | TYR | A | 59 | 52.463 | 85.585 | 5.953 | 1 | 100 |
| 355 | CZ | TYR | A | 59 | 52.92 | 86.384 | 4.903 | 1 | 100 |
| 356 | OH | TYR | A | 59 | 53.201 | 87.715 | 5.13 | 1 | 99.54 |
| 357 | N | ARG | A | 60 | 55.588 | 81.894 | 3.467 | 1 | 80.81 |
| 358 | CA | ARG | A | 60 | 56.942 | 82.136 | 3.989 | 1 | 79.04 |
| 359 | C | ARG | A | 60 | 57.262 | 81.241 | 5.189 | 1 | 77.23 |
| 360 | O | ARG | A | 60 | 57.52 | 81.726 | 6.282 | 1 | 77.48 |

Fig. 1-9

| ATOM | ATOM TYPE | RESIDUE | | # | X | Y | Z | OCC | B |
|---|---|---|---|---|---|---|---|---|---|
| 361 | CB | ARG | A | 60 | 57.146 | 83.614 | 4.354 | 1 | 78.7 |
| 362 | N | PRO | A | 61 | 57.263 | 79.915 | 4.984 | 1 | 75.75 |
| 363 | CA | PRO | A | 61 | 57.535 | 78.92 | 6.024 | 1 | 75.16 |
| 364 | C | PRO | A | 61 | 58.874 | 79.027 | 6.739 | 1 | 76.74 |
| 365 | O | PRO | A | 61 | 59.016 | 78.553 | 7.866 | 1 | 74.75 |
| 366 | CB | PRO | A | 61 | 57.406 | 77.602 | 5.267 | 1 | 75.2 |
| 367 | CG | PRO | A | 61 | 57.838 | 77.965 | 3.887 | 1 | 73.62 |
| 368 | CD | PRO | A | 61 | 57.131 | 79.264 | 3.67 | 1 | 74.21 |
| 369 | N | PHE | A | 62 | 59.854 | 79.652 | 6.095 | 1 | 79.59 |
| 370 | CA | PHE | A | 62 | 61.178 | 79.781 | 6.699 | 1 | 82.49 |
| 371 | C | PHE | A | 62 | 61.542 | 81.222 | 7.058 | 1 | 84.85 |
| 372 | O | PHE | A | 62 | 62.671 | 81.685 | 6.861 | 1 | 84.23 |
| 373 | CB | PHE | A | 62 | 62.217 | 79.112 | 5.8 | 1 | 80.91 |
| 374 | CG | PHE | A | 62 | 61.86 | 77.702 | 5.451 | 1 | 78.9 |
| 375 | CD1 | PHE | A | 62 | 61.675 | 76.756 | 6.454 | 1 | 79.17 |
| 376 | CD2 | PHE | A | 62 | 61.611 | 77.338 | 4.138 | 1 | 78.6 |
| 377 | CE1 | PHE | A | 62 | 61.239 | 75.469 | 6.152 | 1 | 79.7 |
| 378 | CE2 | PHE | A | 62 | 61.176 | 76.057 | 3.826 | 1 | 79.46 |
| 379 | CZ | PHE | A | 62 | 60.987 | 75.119 | 4.837 | 1 | 79.38 |
| 380 | N | GLN | A | 63 | 60.55 | 81.909 | 7.618 | 1 | 87.09 |
| 381 | CA | GLN | A | 63 | 60.67 | 83.288 | 8.059 | 1 | 88.09 |
| 382 | C | GLN | A | 63 | 61.031 | 83.287 | 9.551 | 1 | 89.23 |
| 383 | O | GLN | A | 63 | 61.468 | 84.303 | 10.09 | 1 | 89.69 |
| 384 | CB | GLN | A | 63 | 59.342 | 84.008 | 7.844 | 1 | 86.79 |
| 385 | CG | GLN | A | 63 | 59.392 | 85.501 | 8.076 | 1 | 90.37 |
| 386 | CD | GLN | A | 63 | 58.008 | 86.123 | 8.229 | 1 | 91.87 |
| 387 | OE1 | GLN | A | 63 | 57.047 | 85.458 | 8.628 | 1 | 90.69 |
| 388 | NE2 | GLN | A | 63 | 57.906 | 87.414 | 7.924 | 1 | 92.09 |
| 389 | N | SER | A | 64 | 60.851 | 82.142 | 10.209 | 1 | 88.73 |
| 390 | CA | SER | A | 64 | 61.162 | 82.007 | 11.634 | 1 | 89 |
| 391 | C | SER | A | 64 | 61.337 | 80.541 | 12.01 | 1 | 87.92 |
| 392 | O | SER | A | 64 | 61.401 | 79.679 | 11.145 | 1 | 88.84 |
| 393 | CB | SER | A | 64 | 60.047 | 82.617 | 12.495 | 1 | 89.8 |
| 394 | OG | SER | A | 64 | 58.882 | 81.807 | 12.478 | 1 | 90.99 |
| 395 | N | GLU | A | 65 | 61.434 | 80.265 | 13.304 | 1 | 86.8 |
| 396 | CA | GLU | A | 65 | 61.586 | 78.897 | 13.774 | 1 | 86.76 |
| 397 | C | GLU | A | 65 | 60.199 | 78.343 | 14.075 | 1 | 85.63 |
| 398 | O | GLU | A | 65 | 59.949 | 77.138 | 13.952 | 1 | 82.75 |
| 399 | CB | GLU | A | 65 | 62.447 | 78.859 | 15.039 | 1 | 88.85 |
| 400 | CG | GLU | A | 65 | 62.723 | 77.449 | 15.547 | 1 | 90.47 |

Fig. 1-10

| ATOM | ATOM TYPE | RESIDUE | | # | X | Y | Z | OCC | B |
|---|---|---|---|---|---|---|---|---|---|
| 401 | CD | GLU | A | 65 | 63.541 | 77.428 | 16.823 | 1 | 91.83 |
| 402 | OE1 | GLU | A | 65 | 64.692 | 77.918 | 16.811 | 1 | 91.06 |
| 403 | OE2 | GLU | A | 65 | 63.027 | 76.917 | 17.84 | 1 | 91.98 |
| 404 | N | LEU | A | 66 | 59.312 | 79.24 | 14.504 | 1 | 85.03 |
| 405 | CA | LEU | A | 66 | 57.937 | 78.884 | 14.827 | 1 | 82.7 |
| 406 | C | LEU | A | 66 | 57.237 | 78.532 | 13.525 | 1 | 80.07 |
| 407 | O | LEU | A | 66 | 56.487 | 77.566 | 13.464 | 1 | 81.57 |
| 408 | CB | LEU | A | 66 | 57.208 | 80.052 | 15.521 | 1 | 82.72 |
| 409 | CG | LEU | A | 66 | 55.744 | 79.853 | 15.958 | 1 | 81.69 |
| 410 | CD1 | LEU | A | 66 | 55.678 | 78.924 | 17.166 | 1 | 80.22 |
| 411 | CD2 | LEU | A | 66 | 55.079 | 81.191 | 16.286 | 1 | 80.13 |
| 412 | N | PHE | A | 67 | 57.498 | 79.303 | 12.479 | 1 | 77.41 |
| 413 | CA | PHE | A | 67 | 56.875 | 79.035 | 11.191 | 1 | 76.85 |
| 414 | C | PHE | A | 67 | 57.401 | 77.74 | 10.571 | 1 | 75.25 |
| 415 | O | PHE | A | 67 | 56.617 | 76.893 | 10.117 | 1 | 75.35 |
| 416 | CB | PHE | A | 67 | 57.065 | 80.217 | 10.235 | 1 | 77.22 |
| 417 | CG | PHE | A | 67 | 56.089 | 81.341 | 10.456 | 1 | 78.26 |
| 418 | CD1 | PHE | A | 67 | 55.474 | 81.52 | 11.691 | 1 | 79.82 |
| 419 | CD2 | PHE | A | 67 | 55.79 | 82.229 | 9.425 | 1 | 80.64 |
| 420 | CE1 | PHE | A | 67 | 54.577 | 82.568 | 11.899 | 1 | 80.89 |
| 421 | CE2 | PHE | A | 67 | 54.892 | 83.285 | 9.622 | 1 | 81.11 |
| 422 | CZ | PHE | A | 67 | 54.287 | 83.452 | 10.861 | 1 | 81.63 |
| 423 | N | ALA | A | 68 | 58.722 | 77.577 | 10.597 | 1 | 71.6 |
| 424 | CA | ALA | A | 68 | 59.365 | 76.39 | 10.05 | 1 | 68.46 |
| 425 | C | ALA | A | 68 | 58.858 | 75.138 | 10.743 | 1 | 66.83 |
| 426 | O | ALA | A | 68 | 58.439 | 74.183 | 10.085 | 1 | 67.36 |
| 427 | CB | ALA | A | 68 | 60.863 | 76.493 | 10.201 | 1 | 68.03 |
| 428 | N | LYS | A | 69 | 58.868 | 75.161 | 12.07 | 1 | 63.84 |
| 429 | CA | LYS | A | 69 | 58.412 | 74.026 | 12.855 | 1 | 66.01 |
| 430 | C | LYS | A | 69 | 57 | 73.596 | 12.453 | 1 | 65.55 |
| 431 | O | LYS | A | 69 | 56.727 | 72.415 | 12.264 | 1 | 66.35 |
| 432 | CB | LYS | A | 69 | 58.468 | 74.355 | 14.356 | 1 | 68.13 |
| 433 | CG | LYS | A | 69 | 58.167 | 73.161 | 15.276 | 1 | 69.3 |
| 434 | CD | LYS | A | 69 | 58.343 | 73.504 | 16.752 | 1 | 71.56 |
| 435 | CE | LYS | A | 69 | 57.347 | 74.573 | 17.222 | 1 | 73.6 |
| 436 | NZ | LYS | A | 69 | 57.501 | 74.89 | 18.682 | 1 | 72.45 |
| 437 | N | ARG | A | 70 | 56.112 | 74.564 | 12.292 | 1 | 65.13 |
| 438 | CA | ARG | A | 70 | 54.743 | 74.266 | 11.919 | 1 | 65.16 |
| 439 | C | ARG | A | 70 | 54.672 | 73.674 | 10.513 | 1 | 64.97 |
| 440 | O | ARG | A | 70 | 54.035 | 72.641 | 10.303 | 1 | 63.41 |

Fig. 1-11

| ATOM | ATOM TYPE | RESIDUE | | # | X | Y | Z | OCC | B |
|---|---|---|---|---|---|---|---|---|---|
| 441 | CB | ARG | A | 70 | 53.879 | 75.524 | 12.064 | 1 | 67.13 |
| 442 | CG | ARG | A | 70 | 53.753 | 75.954 | 13.527 | 1 | 67.32 |
| 443 | CD | ARG | A | 70 | 53.006 | 77.26 | 13.737 | 1 | 70.96 |
| 444 | NE | ARG | A | 70 | 52.859 | 77.501 | 15.174 | 1 | 78.02 |
| 445 | CZ | ARG | A | 70 | 52.083 | 78.433 | 15.73 | 1 | 79.23 |
| 446 | NH1 | ARG | A | 70 | 51.36 | 79.248 | 14.972 | 1 | 78.6 |
| 447 | NH2 | ARG | A | 70 | 52.034 | 78.548 | 17.057 | 1 | 78.22 |
| 448 | N | ALA | A | 71 | 55.39 | 74.289 | 9.576 | 1 | 62.89 |
| 449 | CA | ALA | A | 71 | 55.413 | 73.83 | 8.2 | 1 | 58.75 |
| 450 | C | ALA | A | 71 | 55.821 | 72.365 | 8.139 | 1 | 58.63 |
| 451 | O | ALA | A | 71 | 55.147 | 71.549 | 7.517 | 1 | 62.12 |
| 452 | CB | ALA | A | 71 | 56.355 | 74.67 | 7.397 | 1 | 54.6 |
| 453 | N | TYR | A | 72 | 56.917 | 72.029 | 8.803 | 1 | 59.16 |
| 454 | CA | TYR | A | 72 | 57.399 | 70.653 | 8.822 | 1 | 57.38 |
| 455 | C | TYR | A | 72 | 56.383 | 69.735 | 9.494 | 1 | 57.72 |
| 456 | O | TYR | A | 72 | 56.133 | 68.633 | 9.011 | 1 | 60.07 |
| 457 | CB | TYR | A | 72 | 58.763 | 70.571 | 9.518 | 1 | 55.15 |
| 458 | CG | TYR | A | 72 | 59.223 | 69.169 | 9.889 | 1 | 56.2 |
| 459 | CD1 | TYR | A | 72 | 58.836 | 68.581 | 11.094 | 1 | 56.75 |
| 460 | CD2 | TYR | A | 72 | 60.072 | 68.452 | 9.059 | 1 | 56.1 |
| 461 | CE1 | TYR | A | 72 | 59.284 | 67.32 | 11.455 | 1 | 59.23 |
| 462 | CE2 | TYR | A | 72 | 60.529 | 67.191 | 9.413 | 1 | 55.79 |
| 463 | CZ | TYR | A | 72 | 60.134 | 66.631 | 10.605 | 1 | 58.73 |
| 464 | OH | TYR | A | 72 | 60.591 | 65.38 | 10.953 | 1 | 62.36 |
| 465 | N | ARG | A | 73 | 55.798 | 70.177 | 10.605 | 1 | 57.84 |
| 466 | CA | ARG | A | 73 | 54.805 | 69.36 | 11.302 | 1 | 58.98 |
| 467 | C | ARG | A | 73 | 53.582 | 69.089 | 10.428 | 1 | 59.45 |
| 468 | O | ARG | A | 73 | 53.042 | 67.985 | 10.45 | 1 | 60.42 |
| 469 | CB | ARG | A | 73 | 54.343 | 70.02 | 12.595 | 1 | 59.06 |
| 470 | CG | ARG | A | 73 | 55.309 | 69.986 | 13.742 | 1 | 58.15 |
| 471 | CD | ARG | A | 73 | 54.492 | 70.074 | 14.992 | 1 | 59.34 |
| 472 | NE | ARG | A | 73 | 55.261 | 70.369 | 16.191 | 1 | 62.16 |
| 473 | CZ | ARG | A | 73 | 55.198 | 71.528 | 16.839 | 1 | 63.83 |
| 474 | NH1 | ARG | A | 73 | 54.451 | 72.523 | 16.359 | 1 | 61.55 |
| 475 | NH2 | ARG | A | 73 | 55.915 | 71.708 | 17.943 | 1 | 65.35 |
| 476 | N | GLU | A | 74 | 53.147 | 70.11 | 9.683 | 1 | 58.14 |
| 477 | CA | GLU | A | 74 | 51.994 | 70.007 | 8.781 | 1 | 55.64 |
| 478 | C | GLU | A | 74 | 52.268 | 69.037 | 7.636 | 1 | 54.71 |
| 479 | O | GLU | A | 74 | 51.427 | 68.195 | 7.309 | 1 | 54.12 |
| 480 | CB | GLU | A | 74 | 51.629 | 71.375 | 8.21 | 1 | 52.31 |

Fig. 1-12

| ATOM | ATOM TYPE | RESIDUE | | # | X | Y | Z | OCC | B |
|---|---|---|---|---|---|---|---|---|---|
| 481 | CG | GLU | A | 74 | 50.352 | 71.364 | 7.403 | 1 | 52.21 |
| 482 | CD | GLU | A | 74 | 49.819 | 72.753 | 7.096 | 1 | 56.83 |
| 483 | OE1 | GLU | A | 74 | 50.516 | 73.765 | 7.39 | 1 | 55 |
| 484 | OE2 | GLU | A | 74 | 48.689 | 72.823 | 6.556 | 1 | 54.47 |
| 485 | N | LEU | A | 75 | 53.429 | 69.179 | 7.005 | 1 | 52.6 |
| 486 | CA | LEU | A | 75 | 53.796 | 68.283 | 5.928 | 1 | 51.01 |
| 487 | C | LEU | A | 75 | 53.833 | 66.843 | 6.457 | 1 | 54.72 |
| 488 | O | LEU | A | 75 | 53.061 | 65.985 | 6.008 | 1 | 54.29 |
| 489 | CB | LEU | A | 75 | 55.157 | 68.663 | 5.384 | 1 | 46.85 |
| 490 | CG | LEU | A | 75 | 55.634 | 67.823 | 4.199 | 1 | 46.71 |
| 491 | CD1 | LEU | A | 75 | 54.583 | 67.788 | 3.113 | 1 | 44.45 |
| 492 | CD2 | LEU | A | 75 | 56.929 | 68.405 | 3.671 | 1 | 45.07 |
| 493 | N | ARG | A | 76 | 54.68 | 66.622 | 7.463 | 1 | 54.57 |
| 494 | CA | ARG | A | 76 | 54.868 | 65.321 | 8.09 | 1 | 58.08 |
| 495 | C | ARG | A | 76 | 53.606 | 64.583 | 8.527 | 1 | 59.56 |
| 496 | O | ARG | A | 76 | 53.472 | 63.384 | 8.279 | 1 | 62.82 |
| 497 | CB | ARG | A | 76 | 55.816 | 65.449 | 9.278 | 1 | 62.65 |
| 498 | CG | ARG | A | 76 | 57.29 | 65.37 | 8.912 | 1 | 69.78 |
| 499 | CD | ARG | A | 76 | 57.787 | 63.926 | 8.83 | 1 | 74.86 |
| 500 | NE | ARG | A | 76 | 57.941 | 63.301 | 10.145 | 1 | 76.79 |
| 501 | CZ | ARG | A | 76 | 58.335 | 62.046 | 10.334 | 1 | 77.88 |
| 502 | NH1 | ARG | A | 76 | 58.631 | 61.273 | 9.297 | 1 | 81.32 |
| 503 | NH2 | ARG | A | 76 | 58.443 | 61.561 | 11.562 | 1 | 79.04 |
| 504 | N | LEU | A | 77 | 52.712 | 65.271 | 9.229 | 1 | 57.83 |
| 505 | CA | LEU | A | 77 | 51.478 | 64.648 | 9.689 | 1 | 53.05 |
| 506 | C | LEU | A | 77 | 50.576 | 64.294 | 8.503 | 1 | 53.62 |
| 507 | O | LEU | A | 77 | 49.931 | 63.242 | 8.489 | 1 | 53.17 |
| 508 | CB | LEU | A | 77 | 50.726 | 65.579 | 10.635 | 1 | 48.14 |
| 509 | CG | LEU | A | 77 | 51.398 | 65.899 | 11.956 | 1 | 46.47 |
| 510 | CD1 | LEU | A | 77 | 50.762 | 67.127 | 12.558 | 1 | 45.51 |
| 511 | CD2 | LEU | A | 77 | 51.287 | 64.739 | 12.889 | 1 | 44.58 |
| 512 | N | LEU | A | 78 | 50.52 | 65.18 | 7.515 | 1 | 54 |
| 513 | CA | LEU | A | 78 | 49.677 | 64.958 | 6.342 | 1 | 54.05 |
| 514 | C | LEU | A | 78 | 50.209 | 63.795 | 5.538 | 1 | 54.59 |
| 515 | O | LEU | A | 78 | 49.441 | 62.996 | 5.029 | 1 | 57.31 |
| 516 | CB | LEU | A | 78 | 49.572 | 66.226 | 5.484 | 1 | 51.25 |
| 517 | CG | LEU | A | 78 | 48.559 | 67.272 | 5.972 | 1 | 51.72 |
| 518 | CD1 | LEU | A | 78 | 48.601 | 68.498 | 5.08 | 1 | 49.51 |
| 519 | CD2 | LEU | A | 78 | 47.159 | 66.673 | 5.99 | 1 | 50.28 |
| 520 | N | LYS | A | 79 | 51.529 | 63.686 | 5.453 | 1 | 55 |

Fig. 1-13

| ATOM | ATOM TYPE | RESIDUE | | # | X | Y | Z | OCC | B |
|---|---|---|---|---|---|---|---|---|---|
| 521 | CA | LYS | A | 79 | 52.144 | 62.59 | 4.731 | 1 | 54.39 |
| 522 | C | LYS | A | 79 | 51.903 | 61.267 | 5.457 | 1 | 57.12 |
| 523 | O | LYS | A | 79 | 51.818 | 60.221 | 4.822 | 1 | 59.25 |
| 524 | CB | LYS | A | 79 | 53.638 | 62.833 | 4.559 | 1 | 53.25 |
| 525 | CG | LYS | A | 79 | 53.982 | 63.834 | 3.47 | 1 | 57.31 |
| 526 | CD | LYS | A | 79 | 55.487 | 64.061 | 3.378 | 1 | 61.85 |
| 527 | CE | LYS | A | 79 | 56.26 | 62.734 | 3.196 | 1 | 64.8 |
| 528 | NZ | LYS | A | 79 | 57.754 | 62.904 | 3.194 | 1 | 61.46 |
| 529 | N | HIS | A | 80 | 51.745 | 61.317 | 6.777 | 1 | 57.54 |
| 530 | CA | HIS | A | 80 | 51.515 | 60.117 | 7.567 | 1 | 58.53 |
| 531 | C | HIS | A | 80 | 50.06 | 59.65 | 7.692 | 1 | 57 |
| 532 | O | HIS | A | 80 | 49.762 | 58.487 | 7.459 | 1 | 58.22 |
| 533 | CB | HIS | A | 80 | 52.13 | 60.287 | 8.963 | 1 | 63.78 |
| 534 | CG | HIS | A | 80 | 51.692 | 59.252 | 9.96 | 1 | 72.54 |
| 535 | ND1 | HIS | A | 80 | 52.39 | 58.086 | 10.188 | 1 | 75.69 |
| 536 | CD2 | HIS | A | 80 | 50.625 | 59.219 | 10.8 | 1 | 76.59 |
| 537 | CE1 | HIS | A | 80 | 51.773 | 57.379 | 11.121 | 1 | 78.51 |
| 538 | NE2 | HIS | A | 80 | 50.699 | 58.044 | 11.509 | 1 | 76.52 |
| 539 | N | MET | A | 81 | 49.164 | 60.544 | 8.088 | 1 | 55.91 |
| 540 | CA | MET | A | 81 | 47.765 | 60.188 | 8.307 | 1 | 52.11 |
| 541 | C | MET | A | 81 | 47.084 | 59.652 | 7.069 | 1 | 51.18 |
| 542 | O | MET | A | 81 | 47.472 | 60.005 | 5.959 | 1 | 52.82 |
| 543 | CB | MET | A | 81 | 46.98 | 61.394 | 8.839 | 1 | 54.12 |
| 544 | CG | MET | A | 81 | 47.498 | 62.012 | 10.144 | 1 | 52.22 |
| 545 | SD | MET | A | 81 | 46.569 | 63.514 | 10.586 | 1 | 47.79 |
| 546 | CE | MET | A | 81 | 46.89 | 64.523 | 9.116 | 1 | 44.95 |
| 547 | N | ARG | A | 82 | 46.101 | 58.767 | 7.266 | 1 | 47.75 |
| 548 | CA | ARG | A | 82 | 45.31 | 58.191 | 6.17 | 1 | 48.03 |
| 549 | C | ARG | A | 82 | 43.913 | 57.82 | 6.687 | 1 | 47.76 |
| 550 | O | ARG | A | 82 | 43.724 | 56.759 | 7.281 | 1 | 48.95 |
| 551 | CB | ARG | A | 82 | 46.003 | 56.968 | 5.561 | 1 | 46.76 |
| 552 | N | HIS | A | 83 | 42.943 | 58.708 | 6.463 | 1 | 45.54 |
| 553 | CA | HIS | A | 83 | 41.569 | 58.501 | 6.909 | 1 | 42.87 |
| 554 | C | HIS | A | 83 | 40.533 | 59.198 | 6.027 | 1 | 44.5 |
| 555 | O | HIS | A | 83 | 40.708 | 60.334 | 5.628 | 1 | 50.18 |
| 556 | CB | HIS | A | 83 | 41.407 | 58.992 | 8.347 | 1 | 44.03 |
| 557 | CG | HIS | A | 83 | 40.116 | 58.584 | 8.976 | 1 | 41.92 |
| 558 | ND1 | HIS | A | 83 | 38.927 | 59.234 | 8.723 | 1 | 45.82 |
| 559 | CD2 | HIS | A | 83 | 39.809 | 57.533 | 9.766 | 1 | 37.46 |
| 560 | CE1 | HIS | A | 83 | 37.94 | 58.592 | 9.321 | 1 | 40.61 |

Fig. 1-14

| ATOM | ATOM TYPE | RESIDUE | | # | X | Y | Z | OCC | B |
|---|---|---|---|---|---|---|---|---|---|
| 561 | NE2 | HIS | A | 83 | 38.448 | 57.556 | 9.96 | 1 | 40.41 |
| 562 | N | GLU | A | 84 | 39.405 | 58.538 | 5.817 | 1 | 47.02 |
| 563 | CA | GLU | A | 84 | 38.315 | 59.045 | 4.995 | 1 | 50.31 |
| 564 | C | GLU | A | 84 | 37.833 | 60.441 | 5.429 | 1 | 48.46 |
| 565 | O | GLU | A | 84 | 37.189 | 61.159 | 4.658 | 1 | 51.03 |
| 566 | CB | GLU | A | 84 | 37.147 | 58.026 | 5.038 | 1 | 55.9 |
| 567 | CG | GLU | A | 84 | 36.066 | 58.171 | 3.928 | 1 | 70.58 |
| 568 | CD | GLU | A | 84 | 36.529 | 57.735 | 2.501 | 1 | 79.83 |
| 569 | OE1 | GLU | A | 84 | 36.563 | 56.51 | 2.209 | 1 | 81.21 |
| 570 | OE2 | GLU | A | 84 | 36.821 | 58.623 | 1.654 | 1 | 81.75 |
| 571 | N | ASN | A | 85 | 38.164 | 60.829 | 6.651 | 1 | 46.02 |
| 572 | CA | ASN | A | 85 | 37.729 | 62.1 | 7.192 | 1 | 46.01 |
| 573 | C | ASN | A | 85 | 38.863 | 63.06 | 7.541 | 1 | 44.93 |
| 574 | O | ASN | A | 85 | 38.697 | 63.956 | 8.353 | 1 | 39.85 |
| 575 | CB | ASN | A | 85 | 36.87 | 61.846 | 8.424 | 1 | 46.88 |
| 576 | CG | ASN | A | 85 | 35.616 | 61.07 | 8.105 | 1 | 47.63 |
| 577 | OD1 | ASN | A | 85 | 35.427 | 59.943 | 8.573 | 1 | 46.51 |
| 578 | ND2 | ASN | A | 85 | 34.741 | 61.671 | 7.307 | 1 | 48.35 |
| 579 | N | VAL | A | 86 | 40.029 | 62.837 | 6.958 | 1 | 44.98 |
| 580 | CA | VAL | A | 86 | 41.17 | 63.697 | 7.201 | 1 | 44.9 |
| 581 | C | VAL | A | 86 | 41.751 | 63.969 | 5.836 | 1 | 46.35 |
| 582 | O | VAL | A | 86 | 42.034 | 63.029 | 5.075 | 1 | 48.49 |
| 583 | CB | VAL | A | 86 | 42.23 | 63.007 | 8.085 | 1 | 47.54 |
| 584 | CG1 | VAL | A | 86 | 43.422 | 63.942 | 8.327 | 1 | 41.99 |
| 585 | CG2 | VAL | A | 86 | 41.607 | 62.561 | 9.419 | 1 | 43.09 |
| 586 | N | ILE | A | 87 | 41.912 | 65.251 | 5.516 | 1 | 44.44 |
| 587 | CA | ILE | A | 87 | 42.439 | 65.651 | 4.217 | 1 | 39.92 |
| 588 | C | ILE | A | 87 | 43.739 | 64.943 | 3.869 | 1 | 36.81 |
| 589 | O | ILE | A | 87 | 44.565 | 64.666 | 4.735 | 1 | 36.32 |
| 590 | CB | ILE | A | 87 | 42.627 | 67.182 | 4.118 | 1 | 37.31 |
| 591 | CG1 | ILE | A | 87 | 42.612 | 67.591 | 2.654 | 1 | 36.65 |
| 592 | CG2 | ILE | A | 87 | 43.897 | 67.624 | 4.791 | 1 | 35.5 |
| 593 | CD1 | ILE | A | 87 | 41.289 | 67.258 | 1.966 | 1 | 36.11 |
| 594 | N | GLY | A | 88 | 43.925 | 64.676 | 2.588 | 1 | 35.21 |
| 595 | CA | GLY | A | 88 | 45.122 | 63.989 | 2.171 | 1 | 36.07 |
| 596 | C | GLY | A | 88 | 45.894 | 64.681 | 1.073 | 1 | 39.81 |
| 597 | O | GLY | A | 88 | 45.375 | 65.515 | 0.33 | 1 | 42.56 |
| 598 | N | LEU | A | 89 | 47.166 | 64.328 | 0.988 | 1 | 41.01 |
| 599 | CA | LEU | A | 89 | 48.043 | 64.879 | -0.012 | 1 | 40.55 |
| 600 | C | LEU | A | 89 | 47.959 | 64.106 | -1.315 | 1 | 41.14 |

Fig. 1-15

| ATOM | ATOM TYPE | RESIDUE | | # | X | Y | Z | OCC | B |
|---|---|---|---|---|---|---|---|---|---|
| 601 | O | LEU | A | 89 | 47.919 | 62.882 | -1.309 | 1 | 41.18 |
| 602 | CB | LEU | A | 89 | 49.478 | 64.853 | 0.51 | 1 | 38.81 |
| 603 | CG | LEU | A | 89 | 50.039 | 66.136 | 1.124 | 1 | 36.07 |
| 604 | CD1 | LEU | A | 89 | 48.974 | 67.226 | 1.216 | 1 | 35.5 |
| 605 | CD2 | LEU | A | 89 | 50.617 | 65.821 | 2.46 | 1 | 36.48 |
| 606 | N | LEU | A | 90 | 47.886 | 64.834 | -2.422 | 1 | 42.87 |
| 607 | CA | LEU | A | 90 | 47.86 | 64.242 | -3.749 | 1 | 44 |
| 608 | C | LEU | A | 90 | 49.222 | 64.527 | -4.364 | 1 | 49.61 |
| 609 | O | LEU | A | 90 | 49.729 | 63.765 | -5.192 | 1 | 51.69 |
| 610 | CB | LEU | A | 90 | 46.808 | 64.899 | -4.628 | 1 | 40.97 |
| 611 | CG | LEU | A | 90 | 45.336 | 64.575 | -4.414 | 1 | 43.8 |
| 612 | CD1 | LEU | A | 90 | 44.508 | 65.359 | -5.395 | 1 | 39.75 |
| 613 | CD2 | LEU | A | 90 | 45.081 | 63.095 | -4.597 | 1 | 44.12 |
| 614 | N | ASP | A | 91 | 49.82 | 65.633 | -3.935 | 1 | 53.92 |
| 615 | CA | ASP | A | 91 | 51.116 | 66.07 | -4.452 | 1 | 54.97 |
| 616 | C | ASP | A | 91 | 51.6 | 67.179 | -3.528 | 1 | 57.31 |
| 617 | O | ASP | A | 91 | 50.82 | 67.773 | -2.785 | 1 | 60.61 |
| 618 | CB | ASP | A | 91 | 50.912 | 66.604 | -5.891 | 1 | 53.32 |
| 619 | CG | ASP | A | 91 | 52.201 | 67.054 | -6.588 | 1 | 51.11 |
| 620 | OD1 | ASP | A | 91 | 53.292 | 66.508 | -6.328 | 1 | 52.23 |
| 621 | OD2 | ASP | A | 91 | 52.102 | 67.95 | -7.453 | 1 | 49.12 |
| 622 | N | VAL | A | 92 | 52.908 | 67.37 | -3.511 | 1 | 58.83 |
| 623 | CA | VAL | A | 92 | 53.553 | 68.42 | -2.741 | 1 | 61.14 |
| 624 | C | VAL | A | 92 | 54.767 | 68.768 | -3.588 | 1 | 61.33 |
| 625 | O | VAL | A | 92 | 55.463 | 67.878 | -4.097 | 1 | 60.24 |
| 626 | CB | VAL | A | 92 | 53.983 | 67.948 | -1.33 | 1 | 63.19 |
| 627 | CG1 | VAL | A | 92 | 54.781 | 66.698 | -1.423 | 1 | 64.54 |
| 628 | CG2 | VAL | A | 92 | 54.816 | 69.013 | -0.644 | 1 | 62.43 |
| 629 | N | PHE | A | 93 | 55.005 | 70.057 | -3.771 | 1 | 60.48 |
| 630 | CA | PHE | A | 93 | 56.116 | 70.469 | -4.593 | 1 | 60.78 |
| 631 | C | PHE | A | 93 | 56.71 | 71.795 | -4.206 | 1 | 62.75 |
| 632 | O | PHE | A | 93 | 56.156 | 72.522 | -3.399 | 1 | 65.72 |
| 633 | CB | PHE | A | 93 | 55.654 | 70.55 | -6.044 | 1 | 60.61 |
| 634 | CG | PHE | A | 93 | 54.602 | 71.611 | -6.299 | 1 | 57.76 |
| 635 | CD1 | PHE | A | 93 | 54.968 | 72.922 | -6.602 | 1 | 54.62 |
| 636 | CD2 | PHE | A | 93 | 53.252 | 71.291 | -6.275 | 1 | 53.86 |
| 637 | CE1 | PHE | A | 93 | 54.005 | 73.891 | -6.88 | 1 | 51.44 |
| 638 | CE2 | PHE | A | 93 | 52.279 | 72.262 | -6.553 | 1 | 50.12 |
| 639 | CZ | PHE | A | 93 | 52.661 | 73.56 | -6.855 | 1 | 49.84 |
| 640 | N | THR | A | 94 | 57.835 | 72.11 | -4.832 | 1 | 65.79 |

Fig. 1-16

| ATOM | ATOM TYPE | RESIDUE | | # | X | Y | Z | OCC | B |
|---|---|---|---|---|---|---|---|---|---|
| 641 | CA | THR | A | 94 | 58.532 | 73.372 | -4.636 | 1 | 66.86 |
| 642 | C | THR | A | 94 | 59.221 | 73.728 | -5.949 | 1 | 69.15 |
| 643 | O | THR | A | 94 | 59.919 | 72.898 | -6.541 | 1 | 68.3 |
| 644 | CB | THR | A | 94 | 59.567 | 73.314 | -3.498 | 1 | 68.11 |
| 645 | OG1 | THR | A | 94 | 60.271 | 74.561 | -3.442 | 1 | 66.88 |
| 646 | CG2 | THR | A | 94 | 60.561 | 72.172 | -3.703 | 1 | 69.02 |
| 647 | N | PRO | A | 95 | 58.969 | 74.944 | -6.46 | 1 | 70.44 |
| 648 | CA | PRO | A | 95 | 59.543 | 75.445 | -7.709 | 1 | 72.34 |
| 649 | C | PRO | A | 95 | 60.983 | 75.916 | -7.519 | 1 | 76.59 |
| 650 | O | PRO | A | 95 | 61.492 | 76.743 | -8.278 | 1 | 76.44 |
| 651 | CB | PRO | A | 95 | 58.613 | 76.595 | -8.052 | 1 | 70.61 |
| 652 | CG | PRO | A | 95 | 58.295 | 77.156 | -6.716 | 1 | 69.15 |
| 653 | CD | PRO | A | 95 | 58.022 | 75.923 | -5.895 | 1 | 70.42 |
| 654 | N | ASP | A | 96 | 61.607 | 75.411 | -6.46 | 1 | 81.15 |
| 655 | CA | ASP | A | 96 | 62.985 | 75.731 | -6.124 | 1 | 85.89 |
| 656 | C | ASP | A | 96 | 63.795 | 74.46 | -6.371 | 1 | 89.23 |
| 657 | O | ASP | A | 96 | 63.591 | 73.427 | -5.719 | 1 | 89.09 |
| 658 | CB | ASP | A | 96 | 63.088 | 76.171 | -4.657 | 1 | 87.26 |
| 659 | CG | ASP | A | 96 | 62.166 | 77.351 | -4.321 | 1 | 88.52 |
| 660 | OD1 | ASP | A | 96 | 61.895 | 78.193 | -5.211 | 1 | 88.78 |
| 661 | OD2 | ASP | A | 96 | 61.714 | 77.434 | -3.157 | 1 | 87.39 |
| 662 | N | GLU | A | 97 | 64.702 | 74.548 | -7.336 | 1 | 92.57 |
| 663 | CA | GLU | A | 97 | 65.538 | 73.426 | -7.742 | 1 | 94.8 |
| 664 | C | GLU | A | 97 | 66.617 | 72.953 | -6.762 | 1 | 95.78 |
| 665 | O | GLU | A | 97 | 67.025 | 71.791 | -6.813 | 1 | 96.37 |
| 666 | CB | GLU | A | 97 | 66.151 | 73.735 | -9.11 | 1 | 96.5 |
| 667 | CG | GLU | A | 97 | 65.097 | 73.913 | -10.206 | 1 | 99.27 |
| 668 | CD | GLU | A | 97 | 65.631 | 74.572 | -11.474 | 1 | 100 |
| 669 | OE1 | GLU | A | 97 | 66.764 | 74.241 | -11.898 | 1 | 100 |
| 670 | OE2 | GLU | A | 97 | 64.904 | 75.418 | -12.049 | 1 | 98.59 |
| 671 | N | THR | A | 98 | 67.065 | 73.833 | -5.866 | 1 | 96.37 |
| 672 | CA | THR | A | 98 | 68.109 | 73.474 | -4.897 | 1 | 97.94 |
| 673 | C | THR | A | 98 | 67.76 | 73.865 | -3.464 | 1 | 98.61 |
| 674 | O | THR | A | 98 | 67.021 | 74.825 | -3.24 | 1 | 100 |
| 675 | CB | THR | A | 98 | 69.457 | 74.157 | -5.242 | 1 | 99.32 |
| 676 | OG1 | THR | A | 98 | 69.295 | 75.584 | -5.22 | 1 | 100 |
| 677 | CG2 | THR | A | 98 | 69.954 | 73.722 | -6.628 | 1 | 100 |
| 678 | N | LEU | A | 99 | 68.33 | 73.147 | -2.497 | 1 | 98.76 |
| 679 | CA | LEU | A | 99 | 68.096 | 73.435 | -1.077 | 1 | 98.58 |
| 680 | C | LEU | A | 99 | 68.555 | 74.843 | -0.699 | 1 | 98.17 |

Fig. 1-17

| ATOM | ATOM TYPE | RESIDUE | | # | X | Y | Z | OCC | B |
|---|---|---|---|---|---|---|---|---|---|
| 681 | O | LEU | A | 99 | 67.985 | 75.475 | 0.196 | 1 | 97.49 |
| 682 | CB | LEU | A | 99 | 68.82 | 72.412 | -0.193 | 1 | 98.45 |
| 683 | CG | LEU | A | 99 | 68.935 | 72.699 | 1.314 | 1 | 98.85 |
| 684 | CD1 | LEU | A | 99 | 67.591 | 73.085 | 1.918 | 1 | 97.72 |
| 685 | CD2 | LEU | A | 99 | 69.513 | 71.48 | 2.027 | 1 | 99.45 |
| 686 | N | ASP | A | 100 | 69.589 | 75.32 | -1.388 | 1 | 98.74 |
| 687 | CA | ASP | A | 100 | 70.148 | 76.645 | -1.147 | 1 | 98.98 |
| 688 | C | ASP | A | 100 | 69.092 | 77.761 | -1.248 | 1 | 98.38 |
| 689 | O | ASP | A | 100 | 68.933 | 78.546 | -0.306 | 1 | 98.44 |
| 690 | CB | ASP | A | 100 | 71.322 | 76.902 | -2.099 | 1 | 98.45 |
| 691 | N | ASP | A | 101 | 68.357 | 77.824 | -2.361 | 1 | 96.77 |
| 692 | CA | ASP | A | 101 | 67.326 | 78.857 | -2.511 | 1 | 96.16 |
| 693 | C | ASP | A | 101 | 65.875 | 78.393 | -2.274 | 1 | 93.79 |
| 694 | O | ASP | A | 101 | 64.919 | 79.116 | -2.59 | 1 | 93.07 |
| 695 | CB | ASP | A | 101 | 67.472 | 79.644 | -3.834 | 1 | 97.52 |
| 696 | CG | ASP | A | 101 | 67.524 | 78.752 | -5.066 | 1 | 98.89 |
| 697 | OD1 | ASP | A | 101 | 68.63 | 78.305 | -5.442 | 1 | 98.35 |
| 698 | OD2 | ASP | A | 101 | 66.463 | 78.532 | -5.685 | 1 | 100 |
| 699 | N | PHE | A | 102 | 65.732 | 77.214 | -1.665 | 1 | 90.1 |
| 700 | CA | PHE | A | 102 | 64.436 | 76.619 | -1.327 | 1 | 85.47 |
| 701 | C | PHE | A | 102 | 63.737 | 77.494 | -0.301 | 1 | 83.16 |
| 702 | O | PHE | A | 102 | 63.994 | 77.37 | 0.891 | 1 | 84.51 |
| 703 | CB | PHE | A | 102 | 64.664 | 75.22 - | 0.744 | 1 | 85.53 |
| 704 | CG | PHE | A | 102 | 63.471 | 74.632 | -0.028 | 1 | 85.34 |
| 705 | CD1 | PHE | A | 102 | 62.226 | 74.559 | -0.644 | 1 | 86.01 |
| 706 | CD2 | PHE | A | 102 | 63.617 | 74.089 | 1.247 | 1 | 85.55 |
| 707 | CE1 | PHE | A | 102 | 61.149 | 73.951 | -0.003 | 1 | 85.1 |
| 708 | CE2 | PHE | A | 102 | 62.548 | 73.479 | 1.895 | 1 | 85.8 |
| 709 | CZ | PHE | A | 102 | 61.313 | 73.407 | 1.269 | 1 | 85.19 |
| 710 | N | THR | A | 103 | 62.858 | 78.38 | -0.756 | 1 | 79.68 |
| 711 | CA | THR | A | 103 | 62.163 | 79.263 | 0.167 | 1 | 77.22 |
| 712 | C | THR | A | 103 | 60.772 | 78.795 | 0.565 | 1 | 75.88 |
| 713 | O | THR | A | 103 | 60.351 | 79.009 | 1.702 | 1 | 75.73 |
| 714 | CB | THR | A | 103 | 62.075 | 80.7 | -0.368 | 1 | 77.75 |
| 715 | OG1 | THR | A | 103 | 61.275 | 80.724 | -1.555 | 1 | 79.96 |
| 716 | CG2 | THR | A | 103 | 63.464 | 81.237 | -0.677 | 1 | 78.64 |
| 717 | N | ASP | A | 104 | 60.061 | 78.144 | -0.352 | 1 | 74.5 |
| 718 | CA | ASP | A | 104 | 58.707 | 77.673 | -0.05 | 1 | 72.91 |
| 719 | C | ASP | A | 104 | 58.263 | 76.397 | -0.751 | 1 | 68.34 |
| 720 | O | ASP | A | 104 | 58.992 | 75.83 | -1.559 | 1 | 67.75 |

Fig. 1-18

| ATOM | ATOM TYPE | RESIDUE | | # | X | Y | Z | OCC | B |
|---|---|---|---|---|---|---|---|---|---|
| 721 | CB | ASP | A | 104 | 57.679 | 78.788 | -0.302 | 1 | 77.02 |
| 722 | CG | ASP | A | 104 | 57.929 | 79.544 | -1.6 | 1 | 80.09 |
| 723 | OD1 | ASP | A | 104 | 58.292 | 78.915 | -2.62 | 1 | 81.9 |
| 724 | OD2 | ASP | A | 104 | 57.766 | 80.781 | -1.593 | 1 | 82.01 |
| 725 | N | PHE | A | 105 | 57.064 | 75.94 | -0.402 | 1 | 64.51 |
| 726 | CA | PHE | A | 105 | 56.501 | 74.744 | -0.998 | 1 | 59.22 |
| 727 | C | PHE | A | 105 | 54.993 | 74.747 | -0.952 | 1 | 57.83 |
| 728 | O | PHE | A | 105 | 54.387 | 75.38 | -0.086 | 1 | 56.36 |
| 729 | CB | PHE | A | 105 | 57.048 | 73.483 | -0.339 | 1 | 60.04 |
| 730 | CG | PHE | A | 105 | 56.637 | 73.298 | 1.092 | 1 | 59.53 |
| 731 | CD1 | PHE | A | 105 | 57.204 | 74.071 | 2.101 | 1 | 58.67 |
| 732 | CD2 | PHE | A | 105 | 55.726 | 72.302 | 1.435 | 1 | 60.43 |
| 733 | CE1 | PHE | A | 105 | 56.876 | 73.853 | 3.43 | 1 | 58.7 |
| 734 | CE2 | PHE | A | 105 | 55.387 | 72.073 | 2.76 | 1 | 61.55 |
| 735 | CZ | PHE | A | 105 | 55.966 | 72.853 | 3.765 | 1 | 62.44 |
| 736 | N | TYR | A | 106 | 54.403 | 74.009 | -1.886 | 1 | 56.78 |
| 737 | CA | TYR | A | 106 | 52.958 | 73.908 | -2.025 | 1 | 55.81 |
| 738 | C | TYR | A | 106 | 52.402 | 72.516 | -1.712 | 1 | 55.14 |
| 739 | O | TYR | A | 106 | 53.028 | 71.5 | -2.01 | 1 | 57.87 |
| 740 | CB | TYR | A | 106 | 52.552 | 74.303 | -3.444 | 1 | 54.84 |
| 741 | CG | TYR | A | 106 | 52.95 | 75.707 | -3.856 | 1 | 56.08 |
| 742 | CD1 | TYR | A | 106 | 54.294 | 76.081 | -3.961 | 1 | 57.27 |
| 743 | CD2 | TYR | A | 106 | 51.981 | 76.648 | -4.184 | 1 | 56.2 |
| 744 | CE1 | TYR | A | 106 | 54.657 | 77.357 | -4.385 | 1 | 57.12 |
| 745 | CE2 | TYR | A | 106 | 52.326 | 77.921 | -4.609 | 1 | 59.97 |
| 746 | CZ | TYR | A | 106 | 53.663 | 78.273 | -4.708 | 1 | 61.4 |
| 747 | OH | TYR | A | 106 | 53.98 | 79.544 | -5.138 | 1 | 63.17 |
| 748 | N | LEU | A | 107 | 51.218 | 72.487 | -1.109 | 1 | 53.1 |
| 749 | CA | LEU | A | 107 | 50.549 | 71.244 | -0.753 | 1 | 48.73 |
| 750 | C | LEU | A | 107 | 49.338 | 71.108 | -1.653 | 1 | 47.83 |
| 751 | O | LEU | A | 107 | 48.596 | 72.075 | -1.872 | 1 | 48.03 |
| 752 | CB | LEU | A | 107 | 50.085 | 71.261 | 0.715 | 1 | 46.75 |
| 753 | CG | LEU | A | 107 | 51.063 | 71.22 | 1.888 | 1 | 40.76 |
| 754 | CD1 | LEU | A | 107 | 50.24 | 71.058 | 3.143 | 1 | 37.5 |
| 755 | CD2 | LEU | A | 107 | 52.044 | 70.064 | 1.76 | 1 | 37.48 |
| 756 | N | VAL | A | 108 | 49.138 | 69.905 | -2.178 | 1 | 46.88 |
| 757 | CA | VAL | A | 108 | 48.009 | 69.649 | -3.057 | 1 | 45.15 |
| 758 | C | VAL | A | 108 | 47.071 | 68.598 | -2.468 | 1 | 47.06 |
| 759 | O | VAL | A | 108 | 47.483 | 67.481 | -2.158 | 1 | 48.67 |
| 760 | CB | VAL | A | 108 | 48.464 | 69.195 | -4.447 | 1 | 42.12 |

Fig. 1-19

| ATOM | ATOM TYPE | RESIDUE | | # | X | Y | Z | OCC | B |
|---|---|---|---|---|---|---|---|---|---|
| 761 | CG1 | VAL | A | 108 | 47.31 | 69.231 | -5.402 | 1 | 43.19 |
| 762 | CG2 | VAL | A | 108 | 49.539 | 70.093 | -4.963 | 1 | 44.55 |
| 763 | N | MET | A | 109 | 45.818 | 68.998 | -2.268 | 1 | 47.49 |
| 764 | CA | MET | A | 109 | 44.795 | 68.114 | -1.735 | 1 | 45.79 |
| 765 | C | MET | A | 109 | 43.597 | 68.19 | -2.665 | 1 | 44.25 |
| 766 | O | MET | A | 109 | 43.472 | 69.123 | -3.459 | 1 | 46.15 |
| 767 | CB | MET | A | 109 | 44.351 | 68.553 | -0.339 | 1 | 48.67 |
| 768 | CG | MET | A | 109 | 45.454 | 68.705 | 0.676 | 1 | 49.92 |
| 769 | SD | MET | A | 109 | 45.744 | 70.455 | 0.986 | 1 | 58.39 |
| 770 | CE | MET | A | 109 | 44.059 | 70.98 | 1.494 | 1 | 44.53 |
| 771 | N | PRO | A | 110 | 42.726 | 67.174 | -2.614 | 1 | 41.04 |
| 772 | CA | PRO | A | 110 | 41.539 | 67.148 | -3.456 | 1 | 40.26 |
| 773 | C | PRO | A | 110 | 40.596 | 68.287 | -3.077 | 1 | 43.35 |
| 774 | O | PRO | A | 110 | 40.508 | 68.664 | -1.912 | 1 | 46.92 |
| 775 | CB | PRO | A | 110 | 40.932 | 65.794 | -3.117 | 1 | 37.25 |
| 776 | CG | PRO | A | 110 | 41.426 | 65.508 | -1.777 | 1 | 32.12 |
| 777 | CD | PRO | A | 110 | 42.829 | 65.932 | -1.831 | 1 | 36.38 |
| 778 | N | PHE | A | 111 | 39.925 | 68.88 | -4.05 | 1 | 44.9 |
| 779 | CA | PHE | A | 111 | 39.007 | 69.951 | -3.708 | 1 | 47.51 |
| 780 | C | PHE | A | 111 | 37.834 | 69.313 | -2.982 | 1 | 49.49 |
| 781 | O | PHE | A | 111 | 37.23 | 68.37 | -3.474 | 1 | 52.02 |
| 782 | CB | PHE | A | 111 | 38.526 | 70.664 | -4.956 | 1 | 45.19 |
| 783 | CG | PHE | A | 111 | 37.633 | 71.819 | -4.682 | 1 | 46.14 |
| 784 | CD1 | PHE | A | 111 | 38.153 | 73.028 | -4.214 | 1 | 45.08 |
| 785 | CD2 | PHE | A | 111 | 36.272 | 71.722 | -4.946 | 1 | 47.21 |
| 786 | CE1 | PHE | A | 111 | 37.326 | 74.138 | -4.016 | 1 | 46.51 |
| 787 | CE2 | PHE | A | 111 | 35.429 | 72.827 | -4.75 | 1 | 53.09 |
| 788 | CZ | PHE | A | 111 | 35.964 | 74.042 | -4.284 | 1 | 51.54 |
| 789 | N | MET | A | 112 | 37.524 | 69.824 | -1.801 | 1 | 50.56 |
| 790 | CA | MET | A | 112 | 36.439 | 69.288 | -1.015 | 1 | 48.58 |
| 791 | C | MET | A | 112 | 35.167 | 70.111 | -0.943 | 1 | 48.3 |
| 792 | O | MET | A | 112 | 34.406 | 69.952 | 0 | 1 | 53.66 |
| 793 | CB | MET | A | 112 | 36.924 | 68.992 | 0.393 | 1 | 50.44 |
| 794 | CG | MET | A | 112 | 37.582 | 67.658 | 0.536 | 1 | 55.21 |
| 795 | SD | MET | A | 112 | 36.429 | 66.367 | 0.188 | 1 | 63.36 |
| 796 | CE | MET | A | 112 | 35.082 | 66.752 | 1.329 | 1 | 62.09 |
| 797 | N | GLY | A | 113 | 34.913 | 70.971 | -1.917 | 1 | 46.06 |
| 798 | CA | GLY | A | 113 | 33.68 | 71.743 | -1.886 | 1 | 49.08 |
| 799 | C | GLY | A | 113 | 33.795 | 73.136 | -1.299 | 1 | 52.52 |
| 800 | O | GLY | A | 113 | 33.97 | 74.113 | -2.051 | 1 | 55.04 |

Fig. 1-20

| ATOM | ATOM TYPE | RESIDUE | | # | X | Y | Z | OCC | B |
|---|---|---|---|---|---|---|---|---|---|
| 801 | N | THR | A | 114 | 33.579 | 73.236 | 0.015 | 1 | 49.83 |
| 802 | CA | THR | A | 114 | 33.679 | 74.495 | 0.772 | 1 | 51.27 |
| 803 | C | THR | A | 114 | 33.915 | 74.078 | 2.207 | 1 | 49.63 |
| 804 | O | THR | A | 114 | 33.834 | 72.9 | 2.521 | 1 | 50.55 |
| 805 | CB | THR | A | 114 | 32.378 | 75.376 | 0.761 | 1 | 50.33 |
| 806 | OG1 | THR | A | 114 | 31.265 | 74.617 | 1.241 | 1 | 53.18 |
| 807 | CG2 | THR | A | 114 | 32.076 | 75.919 | -0.621 | 1 | 55.28 |
| 808 | N | ASP | A | 115 | 34.206 | 75.041 | 3.071 | 1 | 47.27 |
| 809 | CA | ASP | A | 115 | 34.428 | 74.745 | 4.473 | 1 | 46.43 |
| 810 | C | ASP | A | 115 | 33.136 | 74.976 | 5.237 | 1 | 46.29 |
| 811 | O | ASP | A | 115 | 32.325 | 75.801 | 4.834 | 1 | 47.91 |
| 812 | CB | ASP | A | 115 | 35.549 | 75.612 | 5.034 | 1 | 51.48 |
| 813 | CG | ASP | A | 115 | 35.25 | 77.094 | 4.937 | 1 | 50.44 |
| 814 | OD1 | ASP | A | 115 | 34.349 | 77.574 | 5.644 | 1 | 48.52 |
| 815 | OD2 | ASP | A | 115 | 35.929 | 77.778 | 4.155 | 1 | 52.81 |
| 816 | N | LEU | A | 116 | 32.964 | 74.271 | 6.353 | 1 | 46.55 |
| 817 | CA | LEU | A | 116 | 31.754 | 74.37 | 7.166 | 1 | 47.95 |
| 818 | C | LEU | A | 116 | 31.354 | 75.806 | 7.512 | 1 | 49.33 |
| 819 | O | LEU | A | 116 | 30.171 | 76.121 | 7.607 | 1 | 46.66 |
| 820 | CB | LEU | A | 116 | 31.908 | 73.554 | 8.45 | 1 | 46.71 |
| 821 | CG | LEU | A | 116 | 30.608 | 73.242 | 9.198 | 1 | 46.23 |
| 822 | CD1 | LEU | A | 116 | 29.69 | 72.401 | 8.323 | 1 | 44.27 |
| 823 | CD2 | LEU | A | 116 | 30.916 | 72.522 | 10.5 | 1 | 47.75 |
| 824 | N | GLY | A | 117 | 32.353 | 76.661 | 7.704 | 1 | 51.04 |
| 825 | CA | GLY | A | 117 | 32.109 | 78.05 | 8.033 | 1 | 51.06 |
| 826 | C | GLY | A | 117 | 31.264 | 78.745 | 6.993 | 1 | 51.94 |
| 827 | O | GLY | A | 117 | 30.255 | 79.353 | 7.323 | 1 | 52.26 |
| 828 | N | LYS | A | 118 | 31.682 | 78.648 | 5.734 | 1 | 55.84 |
| 829 | CA | LYS | A | 118 | 30.971 | 79.265 | 4.622 | 1 | 57.26 |
| 830 | C | LYS | A | 118 | 29.635 | 78.575 | 4.437 | 1 | 57.6 |
| 831 | O | LYS | A | 118 | 28.616 | 79.219 | 4.214 | 1 | 60.23 |
| 832 | CB | LYS | A | 118 | 31.776 | 79.157 | 3.321 | 1 | 57.89 |
| 833 | CG | LYS | A | 118 | 33.095 | 79.911 | 3.322 | 1 | 65.65 |
| 834 | CD | LYS | A | 118 | 33.743 | 79.925 | 1.929 | 1 | 72.34 |
| 835 | CE | LYS | A | 118 | 35.239 | 80.336 | 1.959 | 1 | 76.97 |
| 836 | NZ | LYS | A | 118 | 35.517 | 81.689 | 2.559 | 1 | 78.9 |
| 837 | N | LEU | A | 119 | 29.642 | 77.257 | 4.529 | 1 | 56.2 |
| 838 | CA | LEU | A | 119 | 28.416 | 76.499 | 4.366 | 1 | 56.49 |
| 839 | C | LEU | A | 119 | 27.33 | 76.967 | 5.329 | 1 | 55.55 |
| 840 | O | LEU | A | 119 | 26.181 | 77.051 | 4.953 | 1 | 58.41 |

Fig. 1-21

| ATOM | ATOM TYPE | RESIDUE | | # | X | Y | Z | OCC | B |
|---|---|---|---|---|---|---|---|---|---|
| 841 | CB | LEU | A | 119 | 28.705 | 75.009 | 4.558 | 1 | 56.15 |
| 842 | CG | LEU | A | 119 | 27.554 | 74.018 | 4.424 | 1 | 55.81 |
| 843 | CD1 | LEU | A | 119 | 26.804 | 74.27 | 3.137 | 1 | 58.27 |
| 844 | CD2 | LEU | A | 119 | 28.089 | 72.601 | 4.46 | 1 | 54.15 |
| 845 | N | MET | A | 120 | 27.713 | 77.333 | 6.547 | 1 | 57.14 |
| 846 | CA | MET | A | 120 | 26.763 | 77.776 | 7.569 | 1 | 59.71 |
| 847 | C | MET | A | 120 | 26.266 | 79.201 | 7.427 | 1 | 62.43 |
| 848 | O | MET | A | 120 | 25.229 | 79.563 | 7.982 | 1 | 62.45 |
| 849 | CB | MET | A | 120 | 27.372 | 77.63 | 8.962 | 1 | 59.46 |
| 850 | CG | MET | A | 120 | 27.575 | 76.207 | 9.433 | 1 | 54.09 |
| 851 | SD | MET | A | 120 | 27.971 | 76.282 | 11.148 | 1 | 53.4 |
| 852 | CE | MET | A | 120 | 29.672 | 75.842 | 11.164 | 1 | 50.57 |
| 853 | N | LYS | A | 121 | 27.064 | 80.016 | 6.753 | 1 | 66.75 |
| 854 | CA | LYS | A | 121 | 26.759 | 81.413 | 6.522 | 1 | 71.15 |
| 855 | C | LYS | A | 121 | 25.654 | 81.551 | 5.483 | 1 | 74.01 |
| 856 | O | LYS | A | 121 | 24.809 | 82.439 | 5.576 | 1 | 74.24 |
| 857 | CB | LYS | A | 121 | 28.029 | 82.116 | 6.049 | 1 | 71.3 |
| 858 | CG | LYS | A | 121 | 27.95 | 83.619 | 5.966 | 1 | 75.75 |
| 859 | CD | LYS | A | 121 | 29.326 | 84.168 | 5.646 | 1 | 79.68 |
| 860 | CE | LYS | A | 121 | 29.387 | 85.683 | 5.715 | 1 | 80.99 |
| 861 | NZ | LYS | A | 121 | 30.794 | 86.136 | 5.51 | 1 | 82.29 |
| 862 | N | HIS | A | 122 | 25.659 | 80.643 | 4.513 | 1 | 77.93 |
| 863 | CA | HIS | A | 122 | 24.681 | 80.634 | 3.43 | 1 | 82.53 |
| 864 | C | HIS | A | 122 | 23.38 | 79.928 | 3.793 | 1 | 83.37 |
| 865 | O | HIS | A | 122 | 22.296 | 80.405 | 3.453 | 1 | 84.28 |
| 866 | CB | HIS | A | 122 | 25.272 | 79.976 | 2.173 | 1 | 88.04 |
| 867 | CG | HIS | A | 122 | 26.441 | 80.713 | 1.58 | 1 | 96.17 |
| 868 | ND1 | HIS | A | 122 | 26.95 | 81.881 | 2.115 | 1 | 97.93 |
| 869 | CD2 | HIS | A | 122 | 27.21 | 80.435 | 0.497 | 1 | 98.4 |
| 870 | CE1 | HIS | A | 122 | 27.979 | 82.287 | 1.392 | 1 | 97.07 |
| 871 | NE2 | HIS | A | 122 | 28.158 | 81.428 | 0.405 | 1 | 99.19 |
| 872 | N | GLU | A | 123 | 23.482 | 78.81 | 4.51 | 1 | 83.41 |
| 873 | CA | GLU | A | 123 | 22.296 | 78.043 | 4.884 | 1 | 83.3 |
| 874 | C | GLU | A | 123 | 22.251 | 77.469 | 6.309 | 1 | 82.55 |
| 875 | O | GLU | A | 123 | 23.276 | 77.374 | 6.992 | 1 | 81.73 |
| 876 | CB | GLU | A | 123 | 22.093 | 76.919 | 3.872 | 1 | 83.31 |
| 877 | CG | GLU | A | 123 | 23.317 | 76.054 | 3.689 | 1 | 84.61 |
| 878 | CD | GLU | A | 123 | 23.157 | 75.037 | 2.576 | 1 | 87.3 |
| 879 | OE1 | GLU | A | 123 | 23.424 | 75.39 | 1.405 | 1 | 84.97 |
| 880 | OE2 | GLU | A | 123 | 22.779 | 73.881 | 2.879 | 1 | 88.03 |

Fig. 1-22

| ATOM | ATOM TYPE | RESIDUE | | # | X | Y | Z | OCC | B |
|---|---|---|---|---|---|---|---|---|---|
| 881 | N | LYS | A | 124 | 21.033 | 77.163 | 6.77 | 1 | 81.94 |
| 882 | CA | LYS | A | 124 | 20.823 | 76.569 | 8.089 | 1 | 80.88 |
| 883 | C | LYS | A | 124 | 20.889 | 75.086 | 7.817 | 1 | 76.97 |
| 884 | O | LYS | A | 124 | 20.334 | 74.613 | 6.821 | 1 | 76.35 |
| 885 | CB | LYS | A | 124 | 19.458 | 76.931 | 8.679 | 1 | 84.45 |
| 886 | CG | LYS | A | 124 | 19.39 | 76.759 | 10.205 | 1 | 87.45 |
| 887 | CD | LYS | A | 124 | 20.477 | 77.588 | 10.902 | 1 | 90.82 |
| 888 | CE | LYS | A | 124 | 20.239 | 77.712 | 12.404 | 1 | 92.72 |
| 889 | NZ | LYS | A | 124 | 19.21 | 78.733 | 12.762 | 1 | 92.32 |
| 890 | N | LEU | A | 125 | 21.528 | 74.352 | 8.717 | 1 | 72.26 |
| 891 | CA | LEU | A | 125 | 21.717 | 72.938 | 8.512 | 1 | 67.61 |
| 892 | C | LEU | A | 125 | 20.543 | 71.977 | 8.622 | 1 | 67.65 |
| 893 | O | LEU | A | 125 | 19.974 | 71.575 | 7.607 | 1 | 67.88 |
| 894 | CB | LEU | A | 125 | 22.925 | 72.478 | 9.302 | 1 | 64.04 |
| 895 | CG | LEU | A | 125 | 24.214 | 73.08 | 8.725 | 1 | 60.3 |
| 896 | CD1 | LEU | A | 125 | 25.386 | 72.691 | 9.583 | 1 | 57.58 |
| 897 | CD2 | LEU | A | 125 | 24.441 | 72.617 | 7.287 | 1 | 55.29 |
| 898 | N | GLY | A | 126 | 20.172 | 71.588 | 9.825 | 1 | 67.54 |
| 899 | CA | GLY | A | 126 | 19.072 | 70.652 | 9.933 | 1 | 69.82 |
| 900 | C | GLY | A | 126 | 19.518 | 69.367 | 10.595 | 1 | 71.75 |
| 901 | O | GLY | A | 126 | 20.573 | 68.822 | 10.27 | 1 | 70.63 |
| 902 | N | GLU | A | 127 | 18.667 | 68.862 | 11.484 | 1 | 73.97 |
| 903 | CA | GLU | A | 127 | 18.936 | 67.661 | 12.265 | 1 | 75.92 |
| 904 | C | GLU | A | 127 | 19.748 | 66.546 | 11.631 | 1 | 72.94 |
| 905 | O | GLU | A | 127 | 20.819 | 66.213 | 12.125 | 1 | 72.42 |
| 906 | CB | GLU | A | 127 | 17.639 | 67.112 | 12.865 | 1 | 80.91 |
| 907 | CG | GLU | A | 127 | 17.025 | 68.048 | 13.897 | 1 | 87.05 |
| 908 | CD | GLU | A | 127 | 16.044 | 67.355 | 14.827 | 1 | 89.95 |
| 909 | OE1 | GLU | A | 127 | 16.337 | 66.229 | 15.288 | 1 | 90.58 |
| 910 | OE2 | GLU | A | 127 | 14.986 | 67.955 | 15.116 | 1 | 92.8 |
| 911 | N | ASP | A | 128 | 19.257 | 65.975 | 10.542 | 1 | 72.81 |
| 912 | CA | ASP | A | 128 | 19.973 | 64.879 | 9.899 | 1 | 73.38 |
| 913 | C | ASP | A | 128 | 21.368 | 65.292 | 9.448 | 1 | 72.23 |
| 914 | O | ASP | A | 128 | 22.338 | 64.566 | 9.694 | 1 | 73.38 |
| 915 | CB | ASP | A | 128 | 19.164 | 64.303 | 8.723 | 1 | 76.74 |
| 916 | CG | ASP | A | 128 | 18.08 | 63.295 | 9.165 | 1 | 77.99 |
| 917 | OD1 | ASP | A | 128 | 17.682 | 63.292 | 10.357 | 1 | 75.87 |
| 918 | OD2 | ASP | A | 128 | 17.624 | 62.504 | 8.298 | 1 | 77.29 |
| 919 | N | ARG | A | 129 | 21.461 | 66.471 | 8.827 | 1 | 71.28 |
| 920 | CA | ARG | A | 129 | 22.728 | 67.029 | 8.325 | 1 | 68.06 |

Fig. 1-23

| ATOM | ATOM TYPE | RESIDUE | | # | X | Y | Z | OCC | B |
|---|---|---|---|---|---|---|---|---|---|
| 921 | C | ARG | A | 129 | 23.748 | 67.271 | 9.439 | 1 | 63.77 |
| 922 | O | ARG | A | 129 | 24.887 | 66.799 | 9.374 | 1 | 60.78 |
| 923 | CB | ARG | A | 129 | 22.475 | 68.353 | 7.584 | 1 | 72.15 |
| 924 | CG | ARG | A | 129 | 22.456 | 68.246 | 6.058 | 1 | 78.33 |
| 925 | CD | ARG | A | 129 | 22.037 | 69.537 | 5.322 | 1 | 87.4 |
| 926 | NE | ARG | A | 129 | 23.139 | 70.236 | 4.751 | 1 | 95.58 |
| 927 | CZ | ARG | A | 129 | 23.622 | 70.544 | 3.547 | 1 | 99.37 |
| 928 | NH1 | ARG | A | 129 | 23.141 | 70.253 | 2.339 | 1 | 100 |
| 929 | NH2 | ARG | A | 129 | 24.763 | 71.201 | 3.646 | 1 | 99.39 |
| 930 | N | ILE | A | 130 | 23.33 | 68.025 | 10.45 | 1 | 59.15 |
| 931 | CA | ILE | A | 130 | 24.18 | 68.344 | 11.583 | 1 | 55.33 |
| 932 | C | ILE | A | 130 | 24.747 | 67.091 | 12.218 | 1 | 56.26 |
| 933 | O | ILE | A | 130 | 25.909 | 67.081 | 12.606 | 1 | 58.43 |
| 934 | CB | ILE | A | 130 | 23.41 | 69.145 | 12.622 | 1 | 53.82 |
| 935 | CG1 | ILE | A | 130 | 22.945 | 70.462 | 12.001 | 1 | 55.35 |
| 936 | CG2 | ILE | A | 130 | 24.265 | 69.397 | 13.843 | 1 | 54.6 |
| 937 | CD1 | ILE | A | 130 | 21.997 | 71.288 | 12.858 | 1 | 55.35 |
| 938 | N | GLN | A | 131 | 23.938 | 66.032 | 12.293 | 1 | 57.96 |
| 939 | CA | GLN | A | 131 | 24.362 | 64.752 | 12.877 | 1 | 57.75 |
| 940 | C | GLN | A | 131 | 25.443 | 64.097 | 12.042 | 1 | 56.11 |
| 941 | O | GLN | A | 131 | 26.488 | 63.708 | 12.556 | 1 | 57.65 |
| 942 | CB | GLN | A | 131 | 23.193 | 63.769 | 12.988 | 1 | 58.05 |
| 943 | CG | GLN | A | 131 | 23.615 | 62.429 | 13.583 | 1 | 60.25 |
| 944 | CD | GLN | A | 131 | 22.59 | 61.316 | 13.389 | 1 | 63.87 |
| 945 | OE1 | GLN | A | 131 | 22.302 | 60.555 | 14.315 | 1 | 63.78 |
| 946 | NE2 | GLN | A | 131 | 22.062 | 61.195 | 12.172 | 1 | 68.48 |
| 947 | N | PHE | A | 132 | 25.165 | 63.96 | 10.751 | 1 | 55.06 |
| 948 | CA | PHE | A | 132 | 26.098 | 63.339 | 9.822 | 1 | 50.74 |
| 949 | C | PHE | A | 132 | 27.425 | 64.062 | 9.837 | 1 | 49.52 |
| 950 | O | PHE | A | 132 | 28.479 | 63.439 | 9.941 | 1 | 52.09 |
| 951 | CB | PHE | A | 132 | 25.522 | 63.36 | 8.412 | 1 | 51.78 |
| 952 | CG | PHE | A | 132 | 26.273 | 62.501 | 7.44 | 1 | 52.91 |
| 953 | CD1 | PHE | A | 132 | 26.813 | 61.281 | 7.846 | 1 | 55.98 |
| 954 | CD2 | PHE | A | 132 | 26.43 | 62.897 | 6.114 | 1 | 50.3 |
| 955 | CE1 | PHE | A | 132 | 27.502 | 60.463 | 6.947 | 1 | 55.67 |
| 956 | CE2 | PHE | A | 132 | 27.111 | 62.096 | 5.206 | 1 | 52.66 |
| 957 | CZ | PHE | A | 132 | 27.651 | 60.874 | 5.621 | 1 | 55.48 |
| 958 | N | LEU | A | 133 | 27.371 | 65.389 | 9.789 | 1 | 44.97 |
| 959 | CA | LEU | A | 133 | 28.59 | 66.181 | 9.785 | 1 | 39.06 |
| 960 | C | LEU | A | 133 | 29.426 | 65.962 | 11.02 | 1 | 38.59 |

Fig. 1-24

| ATOM | ATOM TYPE | RESIDUE | | # | X | Y | Z | OCC | B |
|---|---|---|---|---|---|---|---|---|---|
| 961 | O | LEU | A | 133 | 30.605 | 65.639 | 10.902 | 1 | 34 |
| 962 | CB | LEU | A | 133 | 28.282 | 67.668 | 9.587 | 1 | 36.47 |
| 963 | CG | LEU | A | 133 | 27.721 | 68.033 | 8.21 | 1 | 33.49 |
| 964 | CD1 | LEU | A | 133 | 27.493 | 69.52 | 8.108 | 1 | 37.55 |
| 965 | CD2 | LEU | A | 133 | 28.669 | 67.569 | 7.13 | 1 | 29.96 |
| 966 | N | VAL | A | 134 | 28.799 | 66.072 | 12.2 | 1 | 40.9 |
| 967 | CA | VAL | A | 134 | 29.497 | 65.891 | 13.482 | 1 | 39.65 |
| 968 | C | VAL | A | 134 | 30.038 | 64.473 | 13.681 | 1 | 44.86 |
| 969 | O | VAL | A | 134 | 31.095 | 64.291 | 14.284 | 1 | 47.17 |
| 970 | CB | VAL | A | 134 | 28.619 | 66.268 | 14.668 | 1 | 34.96 |
| 971 | CG1 | VAL | A | 134 | 29.425 | 66.21 | 15.96 | 1 | 28.7 |
| 972 | CG2 | VAL | A | 134 | 28.046 | 67.654 | 14.464 | 1 | 35.8 |
| 973 | N | TYR | A | 135 | 29.309 | 63.48 | 13.177 | 1 | 44.23 |
| 974 | CA | TYR | A | 135 | 29.735 | 62.102 | 13.264 | 1 | 47.58 |
| 975 | C | TYR | A | 135 | 31.095 | 62.005 | 12.583 | 1 | 49.53 |
| 976 | O | TYR | A | 135 | 32.04 | 61.432 | 13.13 | 1 | 50.28 |
| 977 | CB | TYR | A | 135 | 28.729 | 61.2 | 12.535 | 1 | 52.5 |
| 978 | CG | TYR | A | 135 | 29.086 | 59.735 | 12.572 | 1 | 53.91 |
| 979 | CD1 | TYR | A | 135 | 29.414 | 59.107 | 13.774 | 1 | 56.68 |
| 980 | CD2 | TYR | A | 135 | 29.116 | 58.979 | 11.408 | 1 | 58.07 |
| 981 | CE1 | TYR | A | 135 | 29.766 | 57.755 | 13.815 | 1 | 57.41 |
| 982 | CE2 | TYR | A | 135 | 29.47 | 57.62 | 11.436 | 1 | 60.91 |
| 983 | CZ | TYR | A | 135 | 29.793 | 57.02 | 12.645 | 1 | 58.95 |
| 984 | OH | TYR | A | 135 | 30.15 | 55.692 | 12.677 | 1 | 64.25 |
| 985 | N | GLN | A | 136 | 31.185 | 62.609 | 11.398 | 1 | 47.85 |
| 986 | CA | GLN | A | 136 | 32.4 | 62.618 | 10.608 | 1 | 45.5 |
| 987 | C | GLN | A | 136 | 33.541 | 63.388 | 11.264 | 1 | 46.31 |
| 988 | O | GLN | A | 136 | 34.702 | 62.979 | 11.164 | 1 | 50.07 |
| 989 | CB | GLN | A | 136 | 32.109 | 63.17 | 9.221 | 1 | 49.4 |
| 990 | CG | GLN | A | 136 | 30.982 | 62.473 | 8.514 | 1 | 47.41 |
| 991 | CD | GLN | A | 136 | 30.897 | 62.878 | 7.07 | 1 | 50.36 |
| 992 | OE1 | GLN | A | 136 | 31.781 | 62.556 | 6.285 | 1 | 55.22 |
| 993 | NE2 | GLN | A | 136 | 29.829 | 63.584 | 6.702 | 1 | 48.7 |
| 994 | N | MET | A | 137 | 33.236 | 64.504 | 11.919 | 1 | 43.82 |
| 995 | CA | MET | A | 137 | 34.29 | 65.255 | 12.608 | 1 | 44.92 |
| 996 | C | MET | A | 137 | 34.949 | 64.309 | 13.596 | 1 | 45.12 |
| 997 | O | MET | A | 137 | 36.173 | 64.21 | 13.673 | 1 | 46.05 |
| 998 | CB | MET | A | 137 | 33.704 | 66.41 | 13.419 | 1 | 38.65 |
| 999 | CG | MET | A | 137 | 33.589 | 67.694 | 12.681 | 1 | 43.6 |
| 1000 | SD | MET | A | 137 | 32.38 | 68.73 | 13.498 | 1 | 50.1 |

Fig. 1-25

| ATOM | ATOM TYPE | RESIDUE | | # | X | Y | Z | OCC | B |
|---|---|---|---|---|---|---|---|---|---|
| 1001 | CE | MET | A | 137 | 31.132 | 68.848 | 12.246 | 1 | 41.53 |
| 1002 | N | LEU | A | 138 | 34.094 | 63.597 | 14.326 | 1 | 44.55 |
| 1003 | CA | LEU | A | 138 | 34.51 | 62.674 | 15.356 | 1 | 43.19 |
| 1004 | C | LEU | A | 138 | 35.265 | 61.402 | 14.919 | 1 | 44.47 |
| 1005 | O | LEU | A | 138 | 36.187 | 60.962 | 15.603 | 1 | 39.7 |
| 1006 | CB | LEU | A | 138 | 33.322 | 62.377 | 16.243 | 1 | 41.24 |
| 1007 | CG | LEU | A | 138 | 32.93 | 63.617 | 17.05 | 1 | 38.94 |
| 1008 | CD1 | LEU | A | 138 | 31.635 | 63.383 | 17.805 | 1 | 38.16 |
| 1009 | CD2 | LEU | A | 138 | 34.04 | 63.949 | 18.014 | 1 | 36.58 |
| 1010 | N | LYS | A | 139 | 34.902 | 60.815 | 13.787 | 1 | 44.25 |
| 1011 | CA | LYS | A | 139 | 35.642 | 59.645 | 13.332 | 1 | 46.56 |
| 1012 | C | LYS | A | 139 | 37.025 | 60.141 | 12.938 | 1 | 44.45 |
| 1013 | O | LYS | A | 139 | 38.039 | 59.494 | 13.226 | 1 | 46.5 |
| 1014 | CB | LYS | A | 139 | 34.962 | 58.954 | 12.139 | 1 | 47.78 |
| 1015 | CG | LYS | A | 139 | 33.628 | 58.301 | 12.473 | 1 | 52.83 |
| 1016 | CD | LYS | A | 139 | 33.344 | 57.067 | 11.63 | 1 | 56.92 |
| 1017 | CE | LYS | A | 139 | 33.274 | 57.39 | 10.137 | 1 | 67.21 |
| 1018 | NZ | LYS | A | 139 | 33.193 | 56.167 | 9.254 | 1 | 69.28 |
| 1019 | N | GLY | A | 140 | 37.054 | 61.305 | 12.295 | 1 | 41.44 |
| 1020 | CA | GLY | A | 140 | 38.313 | 61.885 | 11.885 | 1 | 37.3 |
| 1021 | C | GLY | A | 140 | 39.137 | 62.143 | 13.119 | 1 | 38.11 |
| 1022 | O | GLY | A | 140 | 40.314 | 61.776 | 13.177 | 1 | 39.32 |
| 1023 | N | LEU | A | 141 | 38.488 | 62.682 | 14.149 | 1 | 38.56 |
| 1024 | CA | LEU | A | 141 | 39.176 | 62.964 | 15.401 | 1 | 42.52 |
| 1025 | C | LEU | A | 141 | 39.698 | 61.715 | 16.083 | 1 | 46.46 |
| 1026 | O | LEU | A | 141 | 40.857 | 61.678 | 16.482 | 1 | 50.8 |
| 1027 | CB | LEU | A | 141 | 38.284 | 63.71 | 16.369 | 1 | 38.9 |
| 1028 | CG | LEU | A | 141 | 38.71 | 65.138 | 16.657 | 1 | 37.62 |
| 1029 | CD1 | LEU | A | 141 | 38.106 | 65.52 | 17.99 | 1 | 34.75 |
| 1030 | CD2 | LEU | A | 141 | 40.219 | 65.27 | 16.691 | 1 | 32.26 |
| 1031 | N | ARG | A | 142 | 38.849 | 60.69 | 16.191 | 1 | 48.56 |
| 1032 | CA | ARG | A | 142 | 39.233 | 59.44 | 16.817 | 1 | 50.78 |
| 1033 | C | ARG | A | 142 | 40.478 | 58.898 | 16.154 | 1 | 52.86 |
| 1034 | O | ARG | A | 142 | 41.332 | 58.336 | 16.824 | 1 | 56.57 |
| 1035 | CB | ARG | A | 142 | 38.119 | 58.395 | 16.734 | 1 | 55.32 |
| 1036 | CG | ARG | A | 142 | 38.279 | 57.285 | 17.763 | 1 | 57.07 |
| 1037 | CD | ARG | A | 142 | 37.897 | 55.939 | 17.207 | 1 | 63.65 |
| 1038 | NE | ARG | A | 142 | 36.586 | 55.94 | 16.561 | 1 | 66.88 |
| 1039 | CZ | ARG | A | 142 | 36.189 | 55.007 | 15.697 | 1 | 72.69 |
| 1040 | NH1 | ARG | A | 142 | 37.001 | 54 | 15.383 | 1 | 76.63 |

Fig. 1-26

| ATOM | ATOM TYPE | RESIDUE | | # | X | Y | Z | OCC | B |
|---|---|---|---|---|---|---|---|---|---|
| 1041 | NH2 | ARG | A | 142 | 34.996 | 55.086 | 15.121 | 1 | 71.99 |
| 1042 | N | TYR | A | 143 | 40.572 | 59.054 | 14.839 | 1 | 52.65 |
| 1043 | CA | TYR | A | 143 | 41.742 | 58.598 | 14.121 | 1 | 52.95 |
| 1044 | C | TYR | A | 143 | 42.951 | 59.447 | 14.516 | 1 | 54.05 |
| 1045 | O | TYR | A | 143 | 43.945 | 58.928 | 14.997 | 1 | 55.5 |
| 1046 | CB | TYR | A | 143 | 41.528 | 58.698 | 12.616 | 1 | 56.17 |
| 1047 | CG | TYR | A | 143 | 42.776 | 58.374 | 11.819 | 1 | 54.26 |
| 1048 | CD1 | TYR | A | 143 | 43.197 | 57.057 | 11.66 | 1 | 52.3 |
| 1049 | CD2 | TYR | A | 143 | 43.571 | 59.39 | 11.288 | 1 | 52.16 |
| 1050 | CE1 | TYR | A | 143 | 44.381 | 56.757 | 11.002 | 1 | 52.59 |
| 1051 | CE2 | TYR | A | 143 | 44.758 | 59.101 | 10.631 | 1 | 53.06 |
| 1052 | CZ | TYR | A | 143 | 45.161 | 57.781 | 10.493 | 1 | 52.48 |
| 1053 | OH | TYR | A | 143 | 46.351 | 57.485 | 9.862 | 1 | 52.78 |
| 1054 | N | ILE | A | 144 | 42.859 | 60.755 | 14.32 | 1 | 52.84 |
| 1055 | CA | ILE | A | 144 | 43.962 | 61.655 | 14.641 | 1 | 50.01 |
| 1056 | C | ILE | A | 144 | 44.504 | 61.418 | 16.043 | 1 | 53.24 |
| 1057 | O | ILE | A | 144 | 45.724 | 61.403 | 16.254 | 1 | 56.72 |
| 1058 | CB | ILE | A | 144 | 43.513 | 63.118 | 14.495 | 1 | 44.87 |
| 1059 | CG1 | ILE | A | 144 | 43.101 | 63.375 | 13.06 | 1 | 37.49 |
| 1060 | CG2 | ILE | A | 144 | 44.63 | 64.074 | 14.858 | 1 | 44.29 |
| 1061 | CD1 | ILE | A | 144 | 42.184 | 64.534 | 12.93 | 1 | 38.97 |
| 1062 | N | HIS | A | 145 | 43.596 | 61.187 | 16.989 | 1 | 53.4 |
| 1063 | CA | HIS | A | 145 | 43.96 | 60.948 | 18.388 | 1 | 52.46 |
| 1064 | C | HIS | A | 145 | 44.546 | 59.571 | 18.668 | 1 | 52.21 |
| 1065 | O | HIS | A | 145 | 45.54 | 59.449 | 19.375 | 1 | 52.67 |
| 1066 | CB | HIS | A | 145 | 42.76 | 61.191 | 19.294 | 1 | 50.19 |
| 1067 | CG | HIS | A | 145 | 42.404 | 62.635 | 19.439 | 1 | 50.08 |
| 1068 | ND1 | HIS | A | 145 | 41.191 | 63.058 | 19.937 | 1 | 48.29 |
| 1069 | CD2 | HIS | A | 145 | 43.116 | 63.757 | 19.178 | 1 | 48.9 |
| 1070 | CE1 | HIS | A | 145 | 41.173 | 64.378 | 19.979 | 1 | 47.85 |
| 1071 | NE2 | HIS | A | 145 | 42.328 | 64.827 | 19.524 | 1 | 46.55 |
| 1072 | N | ALA | A | 146 | 43.907 | 58.53 | 18.143 | 1 | 55.63 |
| 1073 | CA | ALA | A | 146 | 44.383 | 57.161 | 18.329 | 1 | 55.06 |
| 1074 | C | ALA | A | 146 | 45.801 | 57.099 | 17.777 | 1 | 54.86 |
| 1075 | O | ALA | A | 146 | 46.623 | 56.304 | 18.234 | 1 | 57.57 |
| 1076 | CB | ALA | A | 146 | 43.478 | 56.174 | 17.603 | 1 | 51.16 |
| 1077 | N | ALA | A | 147 | 46.077 | 57.968 | 16.808 | 1 | 51.91 |
| 1078 | CA | ALA | A | 147 | 47.385 | 58.047 | 16.189 | 1 | 50.99 |
| 1079 | C | ALA | A | 147 | 48.319 | 58.889 | 17.046 | 1 | 52.19 |
| 1080 | O | ALA | A | 147 | 49.448 | 59.167 | 16.646 | 1 | 55.85 |

Fig. 1-27

| ATOM | ATOM TYPE | RESIDUE | | # | X | Y | Z | OCC | B |
|---|---|---|---|---|---|---|---|---|---|
| 1081 | CB | ALA | A | 147 | 47.269 | 58.628 | 14.801 | 1 | 45.44 |
| 1082 | N | GLY | A | 148 | 47.839 | 59.299 | 18.218 | 1 | 53.06 |
| 1083 | CA | GLY | A | 148 | 48.635 | 60.11 | 19.134 | 1 | 53.77 |
| 1084 | C | GLY | A | 148 | 48.864 | 61.564 | 18.744 | 1 | 53.6 |
| 1085 | O | GLY | A | 148 | 49.719 | 62.24 | 19.334 | 1 | 52.84 |
| 1086 | N | ILE | A | 149 | 48.109 | 62.038 | 17.748 | 1 | 53.9 |
| 1087 | CA | ILE | A | 149 | 48.204 | 63.419 | 17.247 | 1 | 51.44 |
| 1088 | C | ILE | A | 149 | 47.161 | 64.32 | 17.913 | 1 | 49.55 |
| 1089 | O | ILE | A | 149 | 46.113 | 63.845 | 18.372 | 1 | 46.83 |
| 1090 | CB | ILE | A | 149 | 47.966 | 63.456 | 15.702 | 1 | 50.09 |
| 1091 | CG1 | ILE | A | 149 | 49.077 | 62.7 | 14.977 | 1 | 51.56 |
| 1092 | CG2 | ILE | A | 149 | 47.895 | 64.887 | 15.185 | 1 | 50.53 |
| 1093 | CD1 | ILE | A | 149 | 48.795 | 62.448 | 13.509 | 1 | 50.48 |
| 1094 | N | ILE | A | 150 | 47.48 | 65.61 | 18.005 | 1 | 48.52 |
| 1095 | CA | ILE | A | 150 | 46.561 | 66.602 | 18.565 | 1 | 46.97 |
| 1096 | C | ILE | A | 150 | 46.448 | 67.684 | 17.489 | 1 | 48.58 |
| 1097 | O | ILE | A | 150 | 47.469 | 68.126 | 16.927 | 1 | 50.54 |
| 1098 | CB | ILE | A | 150 | 47.058 | 67.16 | 19.906 | 1 | 45.4 |
| 1099 | CG1 | ILE | A | 150 | 46.063 | 68.172 | 20.441 | 1 | 42 |
| 1100 | CG2 | ILE | A | 150 | 48.435 | 67.777 | 19.764 | 1 | 46.23 |
| 1101 | CD1 | ILE | A | 150 | 46.248 | 68.454 | 21.885 | 1 | 38.12 |
| 1102 | N | HIS | A | 151 | 45.208 | 68.07 | 17.173 | 1 | 45.3 |
| 1103 | CA | HIS | A | 151 | 44.963 | 69.027 | 16.109 | 1 | 41.66 |
| 1104 | C | HIS | A | 151 | 45.164 | 70.498 | 16.468 | 1 | 41.51 |
| 1105 | O | HIS | A | 151 | 45.734 | 71.256 | 15.686 | 1 | 38.81 |
| 1106 | CB | HIS | A | 151 | 43.569 | 68.8 | 15.51 | 1 | 41.5 |
| 1107 | CG | HIS | A | 151 | 43.283 | 69.667 | 14.322 | 1 | 38.77 |
| 1108 | ND1 | HIS | A | 151 | 43.002 | 71.018 | 14.434 | 1 | 34.51 |
| 1109 | CD2 | HIS | A | 151 | 43.332 | 69.4 | 12.996 | 1 | 37.51 |
| 1110 | CE1 | HIS | A | 151 | 42.906 | 71.541 | 13.226 | 1 | 36.48 |
| 1111 | NE2 | HIS | A | 151 | 43.1 | 70.583 | 12.335 | 1 | 34.1 |
| 1112 | N | ARG | A | 152 | 44.589 | 70.907 | 17.593 | 1 | 42.49 |
| 1113 | CA | ARG | A | 152 | 44.696 | 72.282 | 18.094 | 1 | 44.3 |
| 1114 | C | ARG | A | 152 | 44.091 | 73.432 | 17.286 | 1 | 42.7 |
| 1115 | O | ARG | A | 152 | 44.51 | 74.574 | 17.45 | 1 | 45.98 |
| 1116 | CB | ARG | A | 152 | 46.152 | 72.616 | 18.434 | 1 | 42.63 |
| 1117 | CG | ARG | A | 152 | 46.692 | 71.773 | 19.563 | 1 | 44.71 |
| 1118 | CD | ARG | A | 152 | 48.061 | 71.339 | 19.209 | 1 | 46 |
| 1119 | NE | ARG | A | 152 | 49.055 | 71.932 | 20.082 | 1 | 48 |
| 1120 | CZ | ARG | A | 152 | 50.197 | 72.456 | 19.653 | 1 | 44.87 |

Fig. 1-28

| ATOM | ATOM TYPE | RESIDUE | | # | X | Y | Z | OCC | B |
|---|---|---|---|---|---|---|---|---|---|
| 1121 | NH1 | ARG | A | 152 | 50.47 | 72.482 | 18.368 | 1 | 39.28 |
| 1122 | NH2 | ARG | A | 152 | 51.115 | 72.84 | 20.522 | 1 | 47.52 |
| 1123 | N | ASP | A | 153 | 43.145 | 73.152 | 16.401 | 1 | 37.86 |
| 1124 | CA | ASP | A | 153 | 42.537 | 74.229 | 15.657 | 1 | 33.03 |
| 1125 | C | ASP | A | 153 | 41.237 | 73.882 | 14.934 | 1 | 34.11 |
| 1126 | O | ASP | A | 153 | 40.935 | 74.422 | 13.858 | 1 | 30.96 |
| 1127 | CB | ASP | A | 153 | 43.536 | 74.834 | 14.681 | 1 | 35.33 |
| 1128 | CG | ASP | A | 153 | 43.171 | 76.265 | 14.312 | 1 | 38.12 |
| 1129 | OD1 | ASP | A | 153 | 42.713 | 76.977 | 15.228 | 1 | 37.65 |
| 1130 | OD2 | ASP | A | 153 | 43.304 | 76.666 | 13.136 | 1 | 33.42 |
| 1131 | N | LEU | A | 154 | 40.456 | 72.989 | 15.519 | 1 | 31.67 |
| 1132 | CA | LEU | A | 154 | 39.215 | 72.62 | 14.884 | 1 | 34.72 |
| 1133 | C | LEU | A | 154 | 38.261 | 73.801 | 14.986 | 1 | 33.66 |
| 1134 | O | LEU | A | 154 | 37.984 | 74.316 | 16.07 | 1 | 36.09 |
| 1135 | CB | LEU | A | 154 | 38.629 | 71.363 | 15.537 | 1 | 32.99 |
| 1136 | CG | LEU | A | 154 | 39.621 | 70.225 | 15.391 | 1 | 37.07 |
| 1137 | CD1 | LEU | A | 154 | 39.04 | 68.954 | 15.949 | 1 | 38.07 |
| 1138 | CD2 | LEU | A | 154 | 39.952 | 70.048 | 13.923 | 1 | 37.8 |
| 1139 | N | LYS | A | 155 | 37.817 | 74.275 | 13.84 | 1 | 33.76 |
| 1140 | CA | LYS | A | 155 | 36.886 | 75.388 | 13.785 | 1 | 33.65 |
| 1141 | C | LYS | A | 155 | 36.179 | 75.165 | 12.483 | 1 | 33.44 |
| 1142 | O | LYS | A | 155 | 36.662 | 74.419 | 11.638 | 1 | 38.45 |
| 1143 | CB | LYS | A | 155 | 37.633 | 76.721 | 13.812 | 1 | 34.17 |
| 1144 | CG | LYS | A | 155 | 38.57 | 76.962 | 12.662 | 1 | 36.29 |
| 1145 | CD | LYS | A | 155 | 39.46 | 78.147 | 12.994 | 1 | 40.9 |
| 1146 | CE | LYS | A | 155 | 40.19 | 78.649 | 11.761 | 1 | 44.08 |
| 1147 | NZ | LYS | A | 155 | 40.597 | 80.069 | 11.942 | 1 | 48.37 |
| 1148 | N | PRO | A | 156 | 35.031 | 75.798 | 12.285 | 1 | 34.12 |
| 1149 | CA | PRO | A | 156 | 34.295 | 75.603 | 11.035 | 1 | 36.23 |
| 1150 | C | PRO | A | 156 | 35.141 | 75.803 | 9.781 | 1 | 38.17 |
| 1151 | O | PRO | A | 156 | 35.019 | 75.056 | 8.801 | 1 | 44.37 |
| 1152 | CB | PRO | A | 156 | 33.173 | 76.632 | 11.146 | 1 | 38.31 |
| 1153 | CG | PRO | A | 156 | 32.977 | 76.791 | 12.656 | 1 | 32.77 |
| 1154 | CD | PRO | A | 156 | 34.387 | 76.82 | 13.132 | 1 | 36.22 |
| 1155 | N | GLY | A | 157 | 36.032 | 76.782 | 9.825 | 1 | 36.42 |
| 1156 | CA | GLY | A | 157 | 36.869 | 77.05 | 8.672 | 1 | 36.45 |
| 1157 | C | GLY | A | 157 | 37.888 | 75.984 | 8.31 | 1 | 37.09 |
| 1158 | O | GLY | A | 157 | 38.461 | 76.025 | 7.222 | 1 | 39.63 |
| 1159 | N | ASN | A | 158 | 38.189 | 75.092 | 9.243 | 1 | 35.94 |
| 1160 | CA | ASN | A | 158 | 39.134 | 74.022 | 8.98 | 1 | 38 |

Fig. 1-29

| ATOM | ATOM TYPE | RESIDUE | # | X | Y | Z | OCC | B |
|---|---|---|---|---|---|---|---|---|
| 1161 | C | ASN A | 158 | 38.407 | 72.69 | 8.827 | 1 | 40.26 |
| 1162 | O | ASN A | 158 | 38.937 | 71.653 | 9.224 | 1 | 40.86 |
| 1163 | CB | ASN A | 158 | 40.154 | 73.878 | 10.098 | 1 | 40.07 |
| 1164 | CG | ASN A | 158 | 41.023 | 75.098 | 10.258 | 1 | 43.16 |
| 1165 | OD1 | ASN A | 158 | 41.442 | 75.723 | 9.272 | 1 | 37.2 |
| 1166 | ND2 | ASN A | 158 | 41.318 | 75.441 | 11.515 | 1 | 34.89 |
| 1167 | N | LEU A | 159 | 37.18 | 72.725 | 8.317 | 1 | 37.04 |
| 1168 | CA | LEU A | 159 | 36.431 | 71.504 | 8.087 | 1 | 38.44 |
| 1169 | C | LEU A | 159 | 35.781 | 71.608 | 6.719 | 1 | 39.1 |
| 1170 | O | LEU A | 159 | 34.894 | 72.428 | 6.52 | 1 | 41.71 |
| 1171 | CB | LEU A | 159 | 35.36 | 71.292 | 9.152 | 1 | 37.87 |
| 1172 | CG | LEU A | 159 | 35.789 | 71.147 | 10.614 | 1 | 38.17 |
| 1173 | CD1 | LEU A | 159 | 34.536 | 71.153 | 11.472 | 1 | 31.96 |
| 1174 | CD2 | LEU A | 159 | 36.626 | 69.872 | 10.825 | 1 | 33.65 |
| 1175 | N | ALA A | 160 | 36.217 | 70.766 | 5.784 | 1 | 38.19 |
| 1176 | CA | ALA A | 160 | 35.68 | 70.784 | 4.428 | 1 | 41.44 |
| 1177 | C | ALA A | 160 | 34.483 | 69.84 | 4.243 | 1 | 43.35 |
| 1178 | O | ALA A | 160 | 34.45 | 68.741 | 4.794 | 1 | 44.14 |
| 1179 | CB | ALA A | 160 | 36.768 | 70.479 | 3.426 | 1 | 39.51 |
| 1180 | N | VAL A | 161 | 33.514 | 70.279 | 3.445 | 1 | 42.13 |
| 1181 | CA | VAL A | 161 | 32.301 | 69.534 | 3.22 | 1 | 43.71 |
| 1182 | C | VAL A | 161 | 31.932 | 69.638 | 1.759 | 1 | 46.04 |
| 1183 | O | VAL A | 161 | 31.724 | 70.74 | 1.273 | 1 | 50.8 |
| 1184 | CB | VAL A | 161 | 31.125 | 70.168 | 4.04 | 1 | 45.02 |
| 1185 | CG1 | VAL A | 161 | 29.842 | 69.37 | 3.846 | 1 | 45.25 |
| 1186 | CG2 | VAL A | 161 | 31.473 | 70.275 | 5.51 | 1 | 40.03 |
| 1187 | N | ASN A | 162 | 31.809 | 68.512 | 1.061 | 1 | 47.62 |
| 1188 | CA | ASN A | 162 | 31.429 | 68.556 | -0.349 | 1 | 49.32 |
| 1189 | C | ASN A | 162 | 29.905 | 68.461 | -0.598 | 1 | 51.11 |
| 1190 | O | ASN A | 162 | 29.111 | 68.428 | 0.343 | 1 | 48.96 |
| 1191 | CB | ASN A | 162 | 32.185 | 67.492 | -1.14 | 1 | 50.43 |
| 1192 | CG | ASN A | 162 | 31.84 | 66.079 | -0.711 | 1 | 52.01 |
| 1193 | OD1 | ASN A | 162 | 30.747 | 65.82 | -0.199 | 1 | 51.44 |
| 1194 | ND2 | ASN A | 162 | 32.779 | 65.15 | -0.92 | 1 | 48.74 |
| 1195 | N | GLU A | 163 | 29.512 | 68.433 | -1.87 | 1 | 55.5 |
| 1196 | CA | GLU A | 163 | 28.1 | 68.35 | -2.278 | 1 | 61.45 |
| 1197 | C | GLU A | 163 | 27.335 | 67.162 | -1.671 | 1 | 60.68 |
| 1198 | O | GLU A | 163 | 26.124 | 67.239 | -1.46 | 1 | 58.41 |
| 1199 | CB | GLU A | 163 | 27.988 | 68.234 | -3.803 | 1 | 68.07 |
| 1200 | CG | GLU A | 163 | 28.672 | 69.316 | -4.629 | 1 | 73.73 |

Fig. 1-30

| ATOM | ATOM TYPE | RESIDUE | | # | X | Y | Z | OCC | B |
|---|---|---|---|---|---|---|---|---|---|
| 1201 | CD | GLU | A | 163 | 28.449 | 69.101 | -6.127 | 1 | 77.17 |
| 1202 | OE1 | GLU | A | 163 | 28.698 | 67.969 | -6.62 | 1 | 79.46 |
| 1203 | OE2 | GLU | A | 163 | 28.014 | 70.059 | -6.802 | 1 | 76.47 |
| 1204 | N | ASP | A | 164 | 28.037 | 66.05 | -1.47 | 1 | 60.54 |
| 1205 | CA | ASP | A | 164 | 27.45 | 64.848 | -0.894 | 1 | 61.87 |
| 1206 | C | ASP | A | 164 | 27.58 | 64.809 | 0.628 | 1 | 60.86 |
| 1207 | O | ASP | A | 164 | 27.508 | 63.751 | 1.243 | 1 | 61.26 |
| 1208 | CB | ASP | A | 164 | 28.088 | 63.607 | -1.52 | 1 | 65.4 |
| 1209 | CG | ASP | A | 164 | 27.698 | 63.419 | -2.985 | 1 | 70.38 |
| 1210 | OD1 | ASP | A | 164 | 26.792 | 64.138 | -3.475 | 1 | 75.26 |
| 1211 | OD2 | ASP | A | 164 | 28.289 | 62.537 | -3.65 | 1 | 72.93 |
| 1212 | N | CYS | A | 165 | 27.725 | 65.987 | 1.224 | 1 | 61.1 |
| 1213 | CA | CYS | A | 165 | 27.869 | 66.163 | 2.667 | 1 | 59.91 |
| 1214 | C | CYS | A | 165 | 28.969 | 65.351 | 3.355 | 1 | 56.36 |
| 1215 | O | CYS | A | 165 | 28.874 | 65.03 | 4.541 | 1 | 55.67 |
| 1216 | CB | CYS | A | 165 | 26.522 | 66.006 | 3.378 | 1 | 62.25 |
| 1217 | SG | CYS | A | 165 | 25.575 | 67.549 | 3.459 | 1 | 69.45 |
| 1218 | N | GLU | A | 166 | 30.027 | 65.049 | 2.611 | 1 | 53.49 |
| 1219 | CA | GLU | A | 166 | 31.156 | 64.314 | 3.156 | 1 | 51.71 |
| 1220 | C | GLU | A | 166 | 32.117 | 65.345 | 3.744 | 1 | 50.11 |
| 1221 | O | GLU | A | 166 | 32.265 | 66.456 | 3.22 | 1 | 49.13 |
| 1222 | CB | GLU | A | 166 | 31.81 | 63.479 | 2.065 | 1 | 56.51 |
| 1223 | CG | GLU | A | 166 | 30.799 | 62.576 | 1.368 | 1 | 61.45 |
| 1224 | CD | GLU | A | 166 | 31.419 | 61.668 | 0.323 | 1 | 65.93 |
| 1225 | OE1 | GLU | A | 166 | 32.019 | 62.19 | -0.637 | 1 | 64.13 |
| 1226 | OE2 | GLU | A | 166 | 31.286 | 60.429 | 0.453 | 1 | 68.55 |
| 1227 | N | LEU | A | 167 | 32.735 | 64.998 | 4.864 | 1 | 45.15 |
| 1228 | CA | LEU | A | 167 | 33.616 | 65.93 | 5.53 | 1 | 40.51 |
| 1229 | C | LEU | A | 167 | 35.027 | 65.419 | 5.676 | 1 | 41 |
| 1230 | O | LEU | A | 167 | 35.252 | 64.219 | 5.774 | 1 | 40.97 |
| 1231 | CB | LEU | A | 167 | 33.032 | 66.3 | 6.905 | 1 | 39.98 |
| 1232 | CG | LEU | A | 167 | 33.838 | 67.137 | 7.921 | 1 | 38.58 |
| 1233 | CD1 | LEU | A | 167 | 32.926 | 67.97 | 8.808 | 1 | 27.71 |
| 1234 | CD2 | LEU | A | 167 | 34.751 | 66.237 | 8.771 | 1 | 34.34 |
| 1235 | N | LYS | A | 168 | 35.973 | 66.355 | 5.642 | 1 | 40.86 |
| 1236 | CA | LYS | A | 168 | 37.392 | 66.079 | 5.814 | 1 | 42.41 |
| 1237 | C | LYS | A | 168 | 38.004 | 67.211 | 6.659 | 1 | 43.49 |
| 1238 | O | LYS | A | 168 | 37.774 | 68.406 | 6.403 | 1 | 46.01 |
| 1239 | CB | LYS | A | 168 | 38.098 | 65.929 | 4.46 | 1 | 42.92 |
| 1240 | CG | LYS | A | 168 | 37.872 | 64.56 | 3.787 | 1 | 44.62 |

Fig. 1-31

| ATOM | ATOM TYPE | RESIDUE | | # | X | Y | Z | OCC | B |
|---|---|---|---|---|---|---|---|---|---|
| 1241 | CD | LYS | A | 168 | 38.198 | 64.587 | 2.296 | 1 | 52.06 |
| 1242 | CE | LYS | A | 168 | 38.285 | 63.188 | 1.673 | 1 | 57.6 |
| 1243 | NZ | LYS | A | 168 | 39.581 | 62.471 | 1.984 | 1 | 61.25 |
| 1244 | N | ILE | A | 169 | 38.672 | 66.826 | 7.741 | 1 | 39.75 |
| 1245 | CA | ILE | A | 169 | 39.303 | 67.784 | 8.636 | 1 | 41.55 |
| 1246 | C | ILE | A | 169 | 40.495 | 68.401 | 7.937 | 1 | 42.13 |
| 1247 | O | ILE | A | 169 | 41.334 | 67.691 | 7.391 | 1 | 43.01 |
| 1248 | CB | ILE | A | 169 | 39.748 | 67.105 | 9.942 | 1 | 42.17 |
| 1249 | CG1 | ILE | A | 169 | 38.511 | 66.618 | 10.701 | 1 | 34.99 |
| 1250 | CG2 | ILE | A | 169 | 40.62 | 68.051 | 10.78 | 1 | 40.6 |
| 1251 | CD1 | ILE | A | 169 | 38.838 | 65.903 | 11.945 | 1 | 36.55 |
| 1252 | N | LEU | A | 170 | 40.547 | 69.729 | 7.938 | 1 | 42.65 |
| 1253 | CA | LEU | A | 170 | 41.627 | 70.449 | 7.274 | 1 | 40.48 |
| 1254 | C | LEU | A | 170 | 42.579 | 71.106 | 8.242 | 1 | 41.06 |
| 1255 | O | LEU | A | 170 | 42.46 | 70.963 | 9.453 | 1 | 44.82 |
| 1256 | CB | LEU | A | 170 | 41.044 | 71.549 | 6.392 | 1 | 36.56 |
| 1257 | CG | LEU | A | 170 | 40.081 | 71.17 | 5.282 | 1 | 33.24 |
| 1258 | CD1 | LEU | A | 170 | 39.44 | 72.425 | 4.712 | 1 | 27.21 |
| 1259 | CD2 | LEU | A | 170 | 40.827 | 70.367 | 4.212 | 1 | 35.84 |
| 1260 | N | ASP | A | 171 | 43.548 | 71.808 | 7.666 | 1 | 43.17 |
| 1261 | CA | ASP | A | 171 | 44.527 | 72.593 | 8.393 | 1 | 40.3 |
| 1262 | C | ASP | A | 171 | 45.268 | 71.961 | 9.536 | 1 | 42.45 |
| 1263 | O | ASP | A | 171 | 44.912 | 72.174 | 10.691 | 1 | 43.81 |
| 1264 | CB | ASP | A | 171 | 43.844 | 73.848 | 8.921 | 1 | 42.72 |
| 1265 | CG | ASP | A | 171 | 44.799 | 75.005 | 9.097 | 1 | 44.84 |
| 1266 | OD1 | ASP | A | 171 | 46.025 | 74.775 | 9.215 | 1 | 47.06 |
| 1267 | OD2 | ASP | A | 171 | 44.312 | 76.146 | 9.106 | 1 | 39.79 |
| 1268 | N | PHE | A | 172 | 46.327 | 71.218 | 9.246 | 1 | 46.22 |
| 1269 | CA | PHE | A | 172 | 47.108 | 70.653 | 10.337 | 1 | 43.13 |
| 1270 | C | PHE | A | 172 | 48.268 | 71.569 | 10.653 | 1 | 44.84 |
| 1271 | O | PHE | A | 172 | 49.223 | 71.164 | 11.295 | 1 | 50.63 |
| 1272 | CB | PHE | A | 172 | 47.57 | 69.249 | 10.004 | 1 | 40.11 |
| 1273 | CG | PHE | A | 172 | 46.511 | 68.227 | 10.222 | 1 | 42.51 |
| 1274 | CD1 | PHE | A | 172 | 45.443 | 68.113 | 9.334 | 1 | 37.18 |
| 1275 | CD2 | PHE | A | 172 | 46.538 | 67.42 | 11.351 | 1 | 43.32 |
| 1276 | CE1 | PHE | A | 172 | 44.424 | 67.219 | 9.574 | 1 | 39.35 |
| 1277 | CE2 | PHE | A | 172 | 45.509 | 66.507 | 11.602 | 1 | 42.4 |
| 1278 | CZ | PHE | A | 172 | 44.449 | 66.412 | 10.708 | 1 | 40.02 |
| 1279 | N | GLY | A | 173 | 48.127 | 72.835 | 10.269 | 1 | 45.22 |
| 1280 | CA | GLY | A | 173 | 49.171 | 73.821 | 10.489 | 1 | 46.84 |

Fig. 1-32

| ATOM | ATOM TYPE | RESIDUE | | # | X | Y | Z | OCC | B |
|---|---|---|---|---|---|---|---|---|---|
| 1281 | C | GLY | A | 173 | 49.545 | 74.088 | 11.934 | 1 | 47.38 |
| 1282 | O | GLY | A | 173 | 50.623 | 74.616 | 12.205 | 1 | 49.51 |
| 1283 | N | LEU | A | 174 | 48.646 | 73.763 | 12.856 | 1 | 45.52 |
| 1284 | CA | LEU | A | 174 | 48.916 | 73.957 | 14.271 | 1 | 44.63 |
| 1285 | C | LEU | A | 174 | 48.941 | 72.605 | 14.969 | 1 | 44.93 |
| 1286 | O | LEU | A | 174 | 49.053 | 72.541 | 16.182 | 1 | 47.2 |
| 1287 | CB | LEU | A | 174 | 47.856 | 74.841 | 14.908 | 1 | 44.61 |
| 1288 | CG | LEU | A | 174 | 48.229 | 75.406 | 16.275 | 1 | 49.88 |
| 1289 | CD1 | LEU | A | 174 | 49.408 | 76.35 | 16.138 | 1 | 50.28 |
| 1290 | CD2 | LEU | A | 174 | 47.046 | 76.133 | 16.893 | 1 | 54.32 |
| 1291 | N | ALA | A | 175 | 48.845 | 71.517 | 14.208 | 1 | 45.79 |
| 1292 | CA | ALA | A | 175 | 48.854 | 70.176 | 14.807 | 1 | 44.94 |
| 1293 | C | ALA | A | 175 | 50.243 | 69.692 | 15.171 | 1 | 44.54 |
| 1294 | O | ALA | A | 175 | 51.235 | 70.27 | 14.75 | 1 | 41.86 |
| 1295 | CB | ALA | A | 175 | 48.187 | 69.187 | 13.888 | 1 | 46.67 |
| 1296 | N | ARG | A | 176 | 50.296 | 68.641 | 15.985 | 1 | 49.19 |
| 1297 | CA | ARG | A | 176 | 51.561 | 68.042 | 16.44 | 1 | 51.9 |
| 1298 | C | ARG | A | 176 | 51.247 | 66.701 | 17.116 | 1 | 55.98 |
| 1299 | O | ARG | A | 176 | 50.073 | 66.283 | 17.216 | 1 | 51.59 |
| 1300 | CB | ARG | A | 176 | 52.271 | 68.948 | 17.464 | 1 | 51.52 |
| 1301 | CG | ARG | A | 176 | 51.857 | 68.668 | 18.925 | 1 | 55.87 |
| 1302 | CD | ARG | A | 176 | 52.19 | 69.783 | 19.899 | 1 | 61.12 |
| 1303 | NE | ARG | A | 176 | 53.611 | 69.945 | 20.212 | 1 | 62.43 |
| 1304 | CZ | ARG | A | 176 | 54.355 | 69.049 | 20.846 | 1 | 61.3 |
| 1305 | NH1 | ARG | A | 176 | 53.838 | 67.888 | 21.224 | 1 | 64.17 |
| 1306 | NH2 | ARG | A | 176 | 55.584 | 69.365 | 21.216 | 1 | 58.26 |
| 1307 | N | GLN | A | 177 | 52.308 | 66.044 | 17.587 | 1 | 60.36 |
| 1308 | CA | GLN | A | 177 | 52.184 | 64.772 | 18.293 | 1 | 63.98 |
| 1309 | C | GLN | A | 177 | 51.927 | 65.126 | 19.758 | 1 | 63.42 |
| 1310 | O | GLN | A | 177 | 52.665 | 65.916 | 20.353 | 1 | 60.44 |
| 1311 | CB | GLN | A | 177 | 53.48 | 63.968 | 18.168 | 1 | 67.7 |
| 1312 | CG | GLN | A | 177 | 53.409 | 62.558 | 18.744 | 1 | 74.25 |
| 1313 | CD | GLN | A | 177 | 54.789 | 61.941 | 18.914 | 1 | 79.21 |
| 1314 | OE1 | GLN | A | 177 | 55.633 | 62.471 | 19.64 | 1 | 82.48 |
| 1315 | NE2 | GLN | A | 177 | 55.028 | 60.825 | 18.239 | 1 | 79.83 |
| 1316 | N | ALA | A | 178 | 50.862 | 64.57 | 20.323 | 1 | 64.02 |
| 1317 | CA | ALA | A | 178 | 50.519 | 64.844 | 21.716 | 1 | 65.23 |
| 1318 | C | ALA | A | 178 | 51.662 | 64.478 | 22.66 | 1 | 66.35 |
| 1319 | O | ALA | A | 178 | 52.307 | 63.438 | 22.512 | 1 | 69.08 |
| 1320 | CB | ALA | A | 178 | 49.238 | 64.103 | 22.111 | 1 | 60.29 |

Fig. 1-33

| ATOM | ATOM TYPE | RESIDUE | | # | X | Y | Z | OCC | B |
|---|---|---|---|---|---|---|---|---|---|
| 1321 | N | ASP | A | 179 | 51.94 | 65.372 | 23.596 | 1 | 67.31 |
| 1322 | CA | ASP | A | 179 | 52.993 | 65.158 | 24.576 | 1 | 68.71 |
| 1323 | C | ASP | A | 179 | 52.537 | 65.78 | 25.894 | 1 | 68.87 |
| 1324 | O | ASP | A | 179 | 51.394 | 66.21 | 26.01 | 1 | 70.97 |
| 1325 | CB | ASP | A | 179 | 54.304 | 65.777 | 24.083 | 1 | 71.26 |
| 1326 | CG | ASP | A | 179 | 55.52 | 65.295 | 24.869 | 1 | 73.83 |
| 1327 | OD1 | ASP | A | 179 | 55.531 | 64.124 | 25.314 | 1 | 74.47 |
| 1328 | OD2 | ASP | A | 179 | 56.471 | 66.089 | 25.034 | 1 | 73.49 |
| 1329 | N | SER | A | 180 | 53.411 | 65.817 | 26.891 | 1 | 69.23 |
| 1330 | CA | SER | A | 180 | 53.046 | 66.368 | 28.19 | 1 | 68.77 |
| 1331 | C | SER | A | 180 | 53.043 | 67.885 | 28.307 | 1 | 67.64 |
| 1332 | O | SER | A | 180 | 52.133 | 68.46 | 28.891 | 1 | 66.44 |
| 1333 | CB | SER | A | 180 | 53.922 | 65.76 | 29.281 | 1 | 70.3 |
| 1334 | OG | SER | A | 180 | 53.473 | 64.456 | 29.611 | 1 | 71.23 |
| 1335 | N | GLU | A | 181 | 54.052 | 68.534 | 27.748 | 1 | 68.69 |
| 1336 | CA | GLU | A | 181 | 54.143 | 69.984 | 27.823 | 1 | 71.37 |
| 1337 | C | GLU | A | 181 | 54.198 | 70.612 | 26.431 | 1 | 71.61 |
| 1338 | O | GLU | A | 181 | 55.273 | 70.689 | 25.82 | 1 | 74.1 |
| 1339 | CB | GLU | A | 181 | 55.388 | 70.373 | 28.61 | 1 | 75.55 |
| 1340 | CG | GLU | A | 181 | 55.149 | 71.368 | 29.736 | 1 | 83.03 |
| 1341 | CD | GLU | A | 181 | 56.454 | 71.85 | 30.376 | 1 | 87.43 |
| 1342 | OE1 | GLU | A | 181 | 57.151 | 71.028 | 31.014 | 1 | 90.21 |
| 1343 | OE2 | GLU | A | 181 | 56.787 | 73.05 | 30.235 | 1 | 87.65 |
| 1344 | N | MET | A | 182 | 53.042 | 71.05 | 25.929 | 1 | 68.51 |
| 1345 | CA | MET | A | 182 | 52.94 | 71.662 | 24.599 | 1 | 64.13 |
| 1346 | C | MET | A | 182 | 52.932 | 73.194 | 24.612 | 1 | 61.59 |
| 1347 | O | MET | A | 182 | 52.872 | 73.807 | 25.675 | 1 | 64.31 |
| 1348 | CB | MET | A | 182 | 51.709 | 71.109 | 23.875 | 1 | 59.85 |
| 1349 | CG | MET | A | 182 | 51.801 | 69.609 | 23.696 | 1 | 56.94 |
| 1350 | SD | MET | A | 182 | 50.316 | 68.824 | 23.14 | 1 | 53.18 |
| 1351 | CE | MET | A | 182 | 49.474 | 68.578 | 24.651 | 1 | 54.19 |
| 1352 | N | TPO | A | 183 | 53.021 | 73.803 | 23.431 | 1 | 59.32 |
| 1353 | CA | TPO | A | 183 | 53.028 | 75.263 | 23.3 | 1 | 58 |
| 1354 | CB | TPO | A | 183 | 53.464 | 75.683 | 21.864 | 1 | 57.99 |
| 1355 | CG2 | TPO | A | 183 | 52.956 | 77.088 | 21.485 | 1 | 58.26 |
| 1356 | OG1 | TPO | A | 183 | 52.97 | 74.713 | 20.996 | 1 | 56.3 |
| 1357 | P | TPO | A | 183 | 53.924 | 73.74 | 20.272 | 1 | 55.49 |
| 1358 | O1P | TPO | A | 183 | 53.848 | 72.446 | 20.99 | 1 | 45.8 |
| 1359 | O2P | TPO | A | 183 | 55.271 | 74.333 | 20.324 | 1 | 54.53 |
| 1360 | O3P | TPO | A | 183 | 53.385 | 73.561 | 18.894 | 1 | 49.97 |

Fig. 1-34

| ATOM | ATOM TYPE | RESIDUE | | # | X | Y | Z | OCC | B |
|---|---|---|---|---|---|---|---|---|---|
| 1361 | C | TPO | A | 183 | 51.691 | 75.873 | 23.781 | 1 | 57 |
| 1362 | O | TPO | A | 183 | 50.611 | 75.331 | 23.535 | 1 | 56.36 |
| 1363 | N | GLY | A | 184 | 51.804 | 76.966 | 24.533 | 1 | 55.74 |
| 1364 | CA | GLY | A | 184 | 50.66 | 77.612 | 25.145 | 1 | 51.9 |
| 1365 | C | GLY | A | 184 | 49.537 | 78.229 | 24.343 | 1 | 53.51 |
| 1366 | O | GLY | A | 184 | 48.381 | 77.829 | 24.499 | 1 | 54.51 |
| 1367 | N | PTR | A | 185 | 49.836 | 79.254 | 23.553 | 1 | 49.84 |
| 1368 | CA | PTR | A | 185 | 48.793 | 79.908 | 22.779 | 1 | 49.06 |
| 1369 | C | PTR | A | 185 | 48.389 | 79.089 | 21.547 | 1 | 48.67 |
| 1370 | O | PTR | A | 185 | 48.974 | 79.231 | 20.469 | 1 | 48.26 |
| 1371 | CB | PTR | A | 185 | 49.251 | 81.311 | 22.385 | 1 | 51.6 |
| 1372 | CG | PTR | A | 185 | 48.096 | 82.259 | 22.464 | 1 | 50.44 |
| 1373 | CD1 | PTR | A | 185 | 47.895 | 83.132 | 21.354 | 1 | 53.05 |
| 1374 | CD2 | PTR | A | 185 | 47.219 | 82.274 | 23.574 | 1 | 49.54 |
| 1375 | CE1 | PTR | A | 185 | 46.807 | 84.037 | 21.331 | 1 | 50.75 |
| 1376 | CE2 | PTR | A | 185 | 46.129 | 83.18 | 23.553 | 1 | 49.06 |
| 1377 | CZ | PTR | A | 185 | 45.936 | 84.047 | 22.439 | 1 | 52.04 |
| 1378 | OH | PTR | A | 185 | 44.93 | 84.97 | 22.508 | 1 | 54.28 |
| 1379 | P | PTR | A | 185 | 43.857 | 85.166 | 21.396 | 1 | 57.49 |
| 1380 | O1P | PTR | A | 185 | 44.167 | 84.404 | 20.185 | 1 | 59.75 |
| 1381 | O2P | PTR | A | 185 | 43.939 | 86.616 | 21.029 | 1 | 55.95 |
| 1382 | O3P | PTR | A | 185 | 42.56 | 84.882 | 21.969 | 1 | 52.04 |
| 1383 | N | VAL | A | 186 | 47.394 | 78.224 | 21.719 | 1 | 43.44 |
| 1384 | CA | VAL | A | 186 | 46.934 | 77.368 | 20.63 | 1 | 43.98 |
| 1385 | C | VAL | A | 186 | 45.399 | 77.374 | 20.506 | 1 | 43.27 |
| 1386 | O | VAL | A | 186 | 44.709 | 77.71 | 21.459 | 1 | 43.93 |
| 1387 | CB | VAL | A | 186 | 47.453 | 75.918 | 20.82 | 1 | 45.53 |
| 1388 | CG1 | VAL | A | 186 | 48.985 | 75.906 | 20.878 | 1 | 41.3 |
| 1389 | CG2 | VAL | A | 186 | 46.861 | 75.297 | 22.085 | 1 | 41.14 |
| 1390 | N | VAL | A | 187 | 44.876 | 76.987 | 19.339 | 1 | 42.53 |
| 1391 | CA | VAL | A | 187 | 43.424 | 76.965 | 19.044 | 1 | 39.94 |
| 1392 | C | VAL | A | 187 | 42.882 | 78.366 | 18.846 | 1 | 40.34 |
| 1393 | O | VAL | A | 187 | 43.285 | 79.282 | 19.544 | 1 | 42.95 |
| 1394 | CB | VAL | A | 187 | 42.552 | 76.336 | 20.154 | 1 | 35.61 |
| 1395 | CG1 | VAL | A | 187 | 41.151 | 76.138 | 19.63 | 1 | 28.79 |
| 1396 | CG2 | VAL | A | 187 | 43.126 | 75.015 | 20.638 | 1 | 40.37 |
| 1397 | N | THR | A | 188 | 41.973 | 78.537 | 17.894 | 1 | 41.92 |
| 1398 | CA | THR | A | 188 | 41.383 | 79.843 | 17.653 | 1 | 40.96 |
| 1399 | C | THR | A | 188 | 40.489 | 80.137 | 18.835 | 1 | 42.63 |
| 1400 | O | THR | A | 188 | 39.72 | 79.274 | 19.256 | 1 | 42.64 |

Fig. 1-35

| ATOM | ATOM TYPE | RESIDUE | | # | X | Y | Z | OCC | B |
|---|---|---|---|---|---|---|---|---|---|
| 1401 | CB | THR | A | 188 | 40.589 | 79.88 | 16.351 | 1 | 43.57 |
| 1402 | OG1 | THR | A | 188 | 41.488 | 79.684 | 15.247 | 1 | 44.23 |
| 1403 | CG2 | THR | A | 188 | 39.871 | 81.233 | 16.185 | 1 | 39.7 |
| 1404 | N | ARG | A | 189 | 40.589 | 81.364 | 19.356 | 1 | 47.22 |
| 1405 | CA | ARG | A | 189 | 39.832 | 81.805 | 20.541 | 1 | 46.27 |
| 1406 | C | ARG | A | 189 | 38.411 | 81.281 | 20.796 | 1 | 43.48 |
| 1407 | O | ARG | A | 189 | 38.168 | 80.638 | 21.809 | 1 | 43.66 |
| 1408 | CB | ARG | A | 189 | 39.832 | 83.337 | 20.661 | 1 | 44.74 |
| 1409 | CG | ARG | A | 189 | 39.276 | 83.826 | 22.001 | 1 | 44.51 |
| 1410 | CD | ARG | A | 189 | 39.046 | 85.319 | 22.042 | 1 | 50.52 |
| 1411 | NE | ARG | A | 189 | 40.285 | 86.078 | 21.856 | 1 | 52.32 |
| 1412 | CZ | ARG | A | 189 | 40.414 | 87.123 | 21.041 | 1 | 48.94 |
| 1413 | NH1 | ARG | A | 189 | 39.377 | 87.551 | 20.338 | 1 | 46.67 |
| 1414 | NH2 | ARG | A | 189 | 41.593 | 87.711 | 20.897 | 1 | 49 |
| 1415 | N | TRP | A | 190 | 37.472 | 81.54 | 19.899 | 1 | 42.94 |
| 1416 | CA | TRP | A | 190 | 36.1 | 81.095 | 20.16 | 1 | 47.7 |
| 1417 | C | TRP | A | 190 | 35.934 | 79.58 | 20.28 | 1 | 46.92 |
| 1418 | O | TRP | A | 190 | 34.914 | 79.111 | 20.771 | 1 | 45.1 |
| 1419 | CB | TRP | A | 190 | 35.109 | 81.689 | 19.133 | 1 | 51.97 |
| 1420 | CG | TRP | A | 190 | 35.14 | 83.211 | 19.07 | 1 | 60.34 |
| 1421 | CD1 | TRP | A | 190 | 35.588 | 84.059 | 20.042 | 1 | 61.7 |
| 1422 | CD2 | TRP | A | 190 | 34.766 | 84.045 | 17.962 | 1 | 65.03 |
| 1423 | NE1 | TRP | A | 190 | 35.526 | 85.36 | 19.613 | 1 | 64.05 |
| 1424 | CE2 | TRP | A | 190 | 35.024 | 85.384 | 18.341 | 1 | 67.03 |
| 1425 | CE3 | TRP | A | 190 | 34.243 | 83.791 | 16.684 | 1 | 69.62 |
| 1426 | CZ2 | TRP | A | 190 | 34.777 | 86.469 | 17.49 | 1 | 68.94 |
| 1427 | CZ3 | TRP | A | 190 | 33.998 | 84.875 | 15.832 | 1 | 71.43 |
| 1428 | CH2 | TRP | A | 190 | 34.267 | 86.199 | 16.244 | 1 | 71.73 |
| 1429 | N | TYR | A | 191 | 36.958 | 78.818 | 19.9 | 1 | 45.76 |
| 1430 | CA | TYR | A | 191 | 36.87 | 77.358 | 19.95 | 1 | 44.82 |
| 1431 | C | TYR | A | 191 | 37.866 | 76.795 | 20.928 | 1 | 45.92 |
| 1432 | O | TYR | A | 191 | 37.965 | 75.582 | 21.129 | 1 | 47.32 |
| 1433 | CB | TYR | A | 191 | 37.074 | 76.77 | 18.551 | 1 | 45.18 |
| 1434 | CG | TYR | A | 191 | 36.101 | 77.347 | 17.549 | 1 | 44.44 |
| 1435 | CD1 | TYR | A | 191 | 34.805 | 76.844 | 17.441 | 1 | 45.23 |
| 1436 | CD2 | TYR | A | 191 | 36.431 | 78.484 | 16.807 | 1 | 46.36 |
| 1437 | CE1 | TYR | A | 191 | 33.857 | 77.471 | 16.632 | 1 | 46.26 |
| 1438 | CE2 | TYR | A | 191 | 35.491 | 79.113 | 15.999 | 1 | 44.56 |
| 1439 | CZ | TYR | A | 191 | 34.213 | 78.606 | 15.925 | 1 | 44.09 |
| 1440 | OH | TYR | A | 191 | 33.284 | 79.254 | 15.17 | 1 | 50.17 |

Fig. 1-36

| ATOM | ATOM TYPE | RESIDUE | | # | X | Y | Z | OCC | B |
|---|---|---|---|---|---|---|---|---|---|
| 1441 | N | ARG | A | 192 | 38.553 | 77.709 | 21.597 | 1 | 47.41 |
| 1442 | CA | ARG | A | 192 | 39.555 | 77.373 | 22.588 | 1 | 45.02 |
| 1443 | C | ARG | A | 192 | 38.92 | 76.95 | 23.916 | 1 | 47.93 |
| 1444 | O | ARG | A | 192 | 38.024 | 77.608 | 24.442 | 1 | 51.1 |
| 1445 | CB | ARG | A | 192 | 40.475 | 78.57 | 22.786 | 1 | 41.99 |
| 1446 | CG | ARG | A | 192 | 41.584 | 78.332 | 23.742 | 1 | 40.62 |
| 1447 | CD | ARG | A | 192 | 42.805 | 79.03 | 23.235 | 1 | 43.71 |
| 1448 | NE | ARG | A | 192 | 42.746 | 80.46 | 23.469 | 1 | 48.59 |
| 1449 | CZ | ARG | A | 192 | 43.082 | 81.378 | 22.579 | 1 | 49.04 |
| 1450 | NH1 | ARG | A | 192 | 43.491 | 81.023 | 21.374 | 1 | 45.98 |
| 1451 | NH2 | ARG | A | 192 | 43.089 | 82.654 | 22.93 | 1 | 56.7 |
| 1452 | N | ALA | A | 193 | 39.371 | 75.818 | 24.436 | 1 | 48.22 |
| 1453 | CA | ALA | A | 193 | 38.869 | 75.295 | 25.688 | 1 | 44.88 |
| 1454 | C | ALA | A | 193 | 39.508 | 76.082 | 26.807 | 1 | 44.69 |
| 1455 | O | ALA | A | 193 | 40.666 | 76.484 | 26.71 | 1 | 48.77 |
| 1456 | CB | ALA | A | 193 | 39.229 | 73.835 | 25.817 | 1 | 42.35 |
| 1457 | N | PRO | A | 194 | 38.792 | 76.243 | 27.924 | 1 | 43.42 |
| 1458 | CA | PRO | A | 194 | 39.31 | 76.989 | 29.071 | 1 | 42.8 |
| 1459 | C | PRO | A | 194 | 40.691 | 76.564 | 29.592 | 1 | 44.92 |
| 1460 | O | PRO | A | 194 | 41.541 | 77.421 | 29.911 | 1 | 45.24 |
| 1461 | CB | PRO | A | 194 | 38.217 | 76.794 | 30.12 | 1 | 39.72 |
| 1462 | CG | PRO | A | 194 | 37.561 | 75.517 | 29.702 | 1 | 42.17 |
| 1463 | CD | PRO | A | 194 | 37.483 | 75.65 | 28.237 | 1 | 38.63 |
| 1464 | N | GLU | A | 195 | 40.943 | 75.259 | 29.64 | 1 | 43.82 |
| 1465 | CA | GLU | A | 195 | 42.215 | 74.81 | 30.171 | 1 | 40.22 |
| 1466 | C | GLU | A | 195 | 43.414 | 75.237 | 29.371 | 1 | 38.03 |
| 1467 | O | GLU | A | 195 | 44.526 | 75.174 | 29.874 | 1 | 34.35 |
| 1468 | CB | GLU | A | 195 | 42.231 | 73.305 | 30.443 | 1 | 42.63 |
| 1469 | CG | GLU | A | 195 | 42.296 | 72.44 | 29.238 | 1 | 44.64 |
| 1470 | CD | GLU | A | 195 | 40.954 | 72.224 | 28.571 | 1 | 49.9 |
| 1471 | OE1 | GLU | A | 195 | 39.9 | 72.67 | 29.096 | 1 | 50.67 |
| 1472 | OE2 | GLU | A | 195 | 40.968 | 71.587 | 27.498 | 1 | 50.63 |
| 1473 | N | VAL | A | 196 | 43.21 | 75.708 | 28.142 | 1 | 40.58 |
| 1474 | CA | VAL | A | 196 | 44.36 | 76.166 | 27.357 | 1 | 44.46 |
| 1475 | C | VAL | A | 196 | 44.997 | 77.345 | 28.104 | 1 | 48.11 |
| 1476 | O | VAL | A | 196 | 46.2 | 77.606 | 27.997 | 1 | 50.59 |
| 1477 | CB | VAL | A | 196 | 43.965 | 76.621 | 25.944 | 1 | 42.44 |
| 1478 | CG1 | VAL | A | 196 | 45.201 | 77.098 | 25.184 | 1 | 40.12 |
| 1479 | CG2 | VAL | A | 196 | 43.298 | 75.48 | 25.198 | 1 | 41.61 |
| 1480 | N | ILE | A | 197 | 44.176 | 78.018 | 28.908 | 1 | 48.55 |

Fig. 1-37

| ATOM | ATOM TYPE | RESIDUE | | # | X | Y | Z | OCC | B |
|---|---|---|---|---|---|---|---|---|---|
| 1481 | CA | ILE | A | 197 | 44.633 | 79.15 | 29.68 | 1 | 46.36 |
| 1482 | C | ILE | A | 197 | 44.757 | 78.862 | 31.169 | 1 | 45 |
| 1483 | O | ILE | A | 197 | 45.778 | 79.186 | 31.778 | 1 | 44.15 |
| 1484 | CB | ILE | A | 197 | 43.753 | 80.354 | 29.402 | 1 | 47.63 |
| 1485 | CG1 | ILE | A | 197 | 43.949 | 80.746 | 27.941 | 1 | 44.16 |
| 1486 | CG2 | ILE | A | 197 | 44.118 | 81.523 | 30.327 | 1 | 49.36 |
| 1487 | CD1 | ILE | A | 197 | 43.114 | 81.88 | 27.533 | 1 | 52.88 |
| 1488 | N | LEU | A | 198 | 43.742 | 78.241 | 31.757 | 1 | 43.62 |
| 1489 | CA | LEU | A | 198 | 43.807 | 77.903 | 33.176 | 1 | 46.21 |
| 1490 | C | LEU | A | 198 | 44.936 | 76.915 | 33.436 | 1 | 49.78 |
| 1491 | O | LEU | A | 198 | 45.58 | 76.949 | 34.482 | 1 | 53.09 |
| 1492 | CB | LEU | A | 198 | 42.491 | 77.304 | 33.665 | 1 | 43.96 |
| 1493 | CG | LEU | A | 198 | 41.284 | 78.234 | 33.487 | 1 | 48.66 |
| 1494 | CD1 | LEU | A | 198 | 40.06 | 77.679 | 34.234 | 1 | 37.35 |
| 1495 | CD2 | LEU | A | 198 | 41.664 | 79.652 | 33.977 | 1 | 43.46 |
| 1496 | N | ASN | A | 199 | 45.178 | 76.044 | 32.462 | 1 | 52.51 |
| 1497 | CA | ASN | A | 199 | 46.217 | 75.042 | 32.566 | 1 | 52.27 |
| 1498 | C | ASN | A | 199 | 47.276 | 75.249 | 31.508 | 1 | 52.19 |
| 1499 | O | ASN | A | 199 | 47.615 | 74.329 | 30.782 | 1 | 55.24 |
| 1500 | CB | ASN | A | 199 | 45.614 | 73.642 | 32.428 | 1 | 54.1 |
| 1501 | CG | ASN | A | 199 | 46.574 | 72.559 | 32.856 | 1 | 55 |
| 1502 | OD1 | ASN | A | 199 | 47.741 | 72.839 | 33.178 | 1 | 47.2 |
| 1503 | ND2 | ASN | A | 199 | 46.092 | 71.315 | 32.879 | 1 | 55.42 |
| 1504 | N | TRP | A | 200 | 47.823 | 76.454 | 31.459 | 1 | 53.79 |
| 1505 | CA | TRP | A | 200 | 48.861 | 76.824 | 30.496 | 1 | 55.23 |
| 1506 | C | TRP | A | 200 | 49.845 | 75.687 | 30.219 | 1 | 56.22 |
| 1507 | O | TRP | A | 200 | 50.379 | 75.081 | 31.153 | 1 | 57.24 |
| 1508 | CB | TRP | A | 200 | 49.623 | 78.037 | 31.019 | 1 | 51.9 |
| 1509 | CG | TRP | A | 200 | 50.569 | 78.629 | 30.051 | 1 | 52.56 |
| 1510 | CD1 | TRP | A | 200 | 51.938 | 78.625 | 30.125 | 1 | 53.16 |
| 1511 | CD2 | TRP | A | 200 | 50.228 | 79.384 | 28.885 | 1 | 51.63 |
| 1512 | NE1 | TRP | A | 200 | 52.472 | 79.347 | 29.07 | 1 | 52.41 |
| 1513 | CE2 | TRP | A | 200 | 51.444 | 79.822 | 28.298 | 1 | 51.06 |
| 1514 | CE3 | TRP | A | 200 | 49.018 | 79.74 | 28.28 | 1 | 48.62 |
| 1515 | CZ2 | TRP | A | 200 | 51.474 | 80.597 | 27.138 | 1 | 50.38 |
| 1516 | CZ3 | TRP | A | 200 | 49.051 | 80.512 | 27.127 | 1 | 48.8 |
| 1517 | CH2 | TRP | A | 200 | 50.274 | 80.934 | 26.567 | 1 | 47.32 |
| 1518 | N | MET | A | 201 | 49.994 | 75.362 | 28.932 | 1 | 56.44 |
| 1519 | CA | MET | A | 201 | 50.899 | 74.322 | 28.421 | 1 | 53.74 |
| 1520 | C | MET | A | 201 | 50.652 | 72.856 | 28.789 | 1 | 53.26 |

Fig. 1-38

| ATOM | ATOM TYPE | RESIDUE | | # | X | Y | Z | OCC | B |
|---|---|---|---|---|---|---|---|---|---|
| 1521 | O | MET | A | 201 | 51.457 | 71.998 | 28.416 | 1 | 53.36 |
| 1522 | CB | MET | A | 201 | 52.353 | 74.674 | 28.741 | 1 | 51.39 |
| 1523 | CG | MET | A | 201 | 52.822 | 75.945 | 28.1 | 1 | 52.93 |
| 1524 | SD | MET | A | 201 | 54.585 | 76.266 | 28.35 | 1 | 57.67 |
| 1525 | CE | MET | A | 201 | 54.759 | 77.836 | 27.394 | 1 | 54.12 |
| 1526 | N | ARG | A | 202 | 49.549 | 72.545 | 29.468 | 1 | 48.76 |
| 1527 | CA | ARG | A | 202 | 49.305 | 71.159 | 29.848 | 1 | 49.12 |
| 1528 | C | ARG | A | 202 | 47.927 | 70.604 | 29.522 | 1 | 50.94 |
| 1529 | O | ARG | A | 202 | 47.401 | 69.76 | 30.252 | 1 | 52.21 |
| 1530 | CB | ARG | A | 202 | 49.613 | 70.952 | 31.33 | 1 | 51.67 |
| 1531 | CG | ARG | A | 202 | 51.028 | 71.375 | 31.726 | 1 | 53.45 |
| 1532 | CD | ARG | A | 202 | 51.303 | 71.081 | 33.186 | 1 | 54.45 |
| 1533 | NE | ARG | A | 202 | 52.706 | 71.309 | 33.524 | 1 | 59.92 |
| 1534 | CZ | ARG | A | 202 | 53.184 | 72.441 | 34.034 | 1 | 60.71 |
| 1535 | NH1 | ARG | A | 202 | 52.361 | 73.459 | 34.275 | 1 | 63.06 |
| 1536 | NH2 | ARG | A | 202 | 54.485 | 72.559 | 34.288 | 1 | 55.04 |
| 1537 | N | TYR | A | 203 | 47.34 | 71.091 | 28.433 | 1 | 51.16 |
| 1538 | CA | TYR | A | 203 | 46.035 | 70.622 | 27.967 | 1 | 50.51 |
| 1539 | C | TYR | A | 203 | 46.277 | 69.312 | 27.212 | 1 | 51.12 |
| 1540 | O | TYR | A | 203 | 47.418 | 68.937 | 26.951 | 1 | 49.65 |
| 1541 | CB | TYR | A | 203 | 45.43 | 71.641 | 27.01 | 1 | 44.92 |
| 1542 | CG | TYR | A | 203 | 46.398 | 72.03 | 25.929 | 1 | 41.85 |
| 1543 | CD1 | TYR | A | 203 | 47.29 | 73.073 | 26.126 | 1 | 44.76 |
| 1544 | CD2 | TYR | A | 203 | 46.445 | 71.348 | 24.717 | 1 | 42.63 |
| 1545 | CE1 | TYR | A | 203 | 48.216 | 73.435 | 25.144 | 1 | 46.08 |
| 1546 | CE2 | TYR | A | 203 | 47.365 | 71.704 | 23.732 | 1 | 43.91 |
| 1547 | CZ | TYR | A | 203 | 48.245 | 72.755 | 23.962 | 1 | 43.02 |
| 1548 | OH | TYR | A | 203 | 49.143 | 73.143 | 23.013 | 1 | 48.44 |
| 1549 | N | THR | A | 204 | 45.206 | 68.631 | 26.837 | 1 | 51.91 |
| 1550 | CA | THR | A | 204 | 45.353 | 67.381 | 26.112 | 1 | 53.02 |
| 1551 | C | THR | A | 204 | 44.521 | 67.339 | 24.848 | 1 | 53.44 |
| 1552 | O | THR | A | 204 | 43.982 | 68.348 | 24.403 | 1 | 54.4 |
| 1553 | CB | THR | A | 204 | 44.992 | 66.157 | 26.978 | 1 | 52.28 |
| 1554 | OG1 | THR | A | 204 | 43.626 | 66.228 | 27.379 | 1 | 50.51 |
| 1555 | CG2 | THR | A | 204 | 45.861 | 66.085 | 28.194 | 1 | 53.26 |
| 1556 | N | GLN | A | 205 | 44.423 | 66.147 | 24.272 | 1 | 51.77 |
| 1557 | CA | GLN | A | 205 | 43.671 | 65.952 | 23.059 | 1 | 47.48 |
| 1558 | C | GLN | A | 205 | 42.221 | 66.284 | 23.296 | 1 | 47.68 |
| 1559 | O | GLN | A | 205 | 41.445 | 66.363 | 22.356 | 1 | 51.93 |
| 1560 | CB | GLN | A | 205 | 43.783 | 64.514 | 22.612 | 1 | 48.68 |

Fig. 1-39

| ATOM | ATOM TYPE | RESIDUE | | # | X | Y | Z | OCC | B |
|---|---|---|---|---|---|---|---|---|---|
| 1561 | CG | GLN | A | 205 | 45.191 | 63.988 | 22.561 | 1 | 55.89 |
| 1562 | CD | GLN | A | 205 | 45.222 | 62.55 | 22.116 | 1 | 53.57 |
| 1563 | OE1 | GLN | A | 205 | 44.566 | 61.692 | 22.704 | 1 | 58.78 |
| 1564 | NE2 | GLN | A | 205 | 45.947 | 62.285 | 21.054 | 1 | 50.87 |
| 1565 | N | THR | A | 206 | 41.823 | 66.431 | 24.552 | 1 | 48.65 |
| 1566 | CA | THR | A | 206 | 40.428 | 66.768 | 24.813 | 1 | 46.66 |
| 1567 | C | THR | A | 206 | 40.084 | 68.191 | 24.363 | 1 | 43.42 |
| 1568 | O | THR | A | 206 | 38.904 | 68.518 | 24.225 | 1 | 44.4 |
| 1569 | CB | THR | A | 206 | 40.041 | 66.601 | 26.288 | 1 | 47.5 |
| 1570 | OG1 | THR | A | 206 | 41.097 | 67.087 | 27.128 | 1 | 46.28 |
| 1571 | CG2 | THR | A | 206 | 39.718 | 65.163 | 26.588 | 1 | 46.28 |
| 1572 | N | VAL | A | 207 | 41.099 | 69.026 | 24.133 | 1 | 35.84 |
| 1573 | CA | VAL | A | 207 | 40.833 | 70.378 | 23.695 | 1 | 35.15 |
| 1574 | C | VAL | A | 207 | 40.127 | 70.341 | 22.361 | 1 | 38.57 |
| 1575 | O | VAL | A | 207 | 39.278 | 71.196 | 22.089 | 1 | 40.83 |
| 1576 | CB | VAL | A | 207 | 42.085 | 71.257 | 23.578 | 1 | 32.83 |
| 1577 | CG1 | VAL | A | 207 | 42.909 | 71.118 | 24.788 | 1 | 36.23 |
| 1578 | CG2 | VAL | A | 207 | 42.86 | 70.97 | 22.327 | 1 | 25.7 |
| 1579 | N | ASP | A | 208 | 40.44 | 69.325 | 21.553 | 1 | 39.59 |
| 1580 | CA | ASP | A | 208 | 39.82 | 69.159 | 20.237 | 1 | 38.84 |
| 1581 | C | ASP | A | 208 | 38.353 | 68.767 | 20.424 | 1 | 38.51 |
| 1582 | O | ASP | A | 208 | 37.529 | 68.978 | 19.546 | 1 | 42.24 |
| 1583 | CB | ASP | A | 208 | 40.553 | 68.078 | 19.413 | 1 | 41.46 |
| 1584 | CG | ASP | A | 208 | 41.987 | 68.475 | 19.019 | 1 | 47.15 |
| 1585 | OD1 | ASP | A | 208 | 42.281 | 69.691 | 18.87 | 1 | 52.58 |
| 1586 | OD2 | ASP | A | 208 | 42.825 | 67.568 | 18.821 | 1 | 46.19 |
| 1587 | N | ILE | A | 209 | 38.027 | 68.159 | 21.558 | 1 | 39.36 |
| 1588 | CA | ILE | A | 209 | 36.639 | 67.793 | 21.816 | 1 | 43.32 |
| 1589 | C | ILE | A | 209 | 35.886 | 69.057 | 22.188 | 1 | 43.82 |
| 1590 | O | ILE | A | 209 | 34.718 | 69.21 | 21.846 | 1 | 46.67 |
| 1591 | CB | ILE | A | 209 | 36.502 | 66.733 | 22.934 | 1 | 44.35 |
| 1592 | CG1 | ILE | A | 209 | 37.085 | 65.408 | 22.455 | 1 | 44.48 |
| 1593 | CG2 | ILE | A | 209 | 35.041 | 66.512 | 23.292 | 1 | 44.55 |
| 1594 | CD1 | ILE | A | 209 | 36.376 | 64.872 | 21.245 | 1 | 48.72 |
| 1595 | N | TRP | A | 210 | 36.567 | 69.974 | 22.867 | 1 | 44.58 |
| 1596 | CA | TRP | A | 210 | 35.952 | 71.235 | 23.238 | 1 | 44.7 |
| 1597 | C | TRP | A | 210 | 35.56 | 71.921 | 21.938 | 1 | 46.84 |
| 1598 | O | TRP | A | 210 | 34.385 | 72.195 | 21.707 | 1 | 48.19 |
| 1599 | CB | TRP | A | 210 | 36.92 | 72.114 | 24.034 | 1 | 46.84 |
| 1600 | CG | TRP | A | 210 | 36.274 | 73.413 | 24.467 | 1 | 47.76 |

Fig. 1-40

| ATOM | ATOM TYPE | RESIDUE | | # | X | Y | Z | OCC | B |
|---|---|---|---|---|---|---|---|---|---|
| 1601 | CD1 | TRP | A | 210 | 36.216 | 74.577 | 23.75 | 1 | 50.28 |
| 1602 | CD2 | TRP | A | 210 | 35.514 | 73.641 | 25.658 | 1 | 45.56 |
| 1603 | NE1 | TRP | A | 210 | 35.451 | 75.504 | 24.413 | 1 | 50.26 |
| 1604 | CE2 | TRP | A | 210 | 35.007 | 74.956 | 25.587 | 1 | 48.25 |
| 1605 | CE3 | TRP | A | 210 | 35.204 | 72.859 | 26.776 | 1 | 45.53 |
| 1606 | CZ2 | TRP | A | 210 | 34.209 | 75.507 | 26.59 | 1 | 46.57 |
| 1607 | CZ3 | TRP | A | 210 | 34.41 | 73.405 | 27.775 | 1 | 45.12 |
| 1608 | CH2 | TRP | A | 210 | 33.921 | 74.718 | 27.672 | 1 | 48.42 |
| 1609 | N | SER | A | 211 | 36.544 | 72.137 | 21.065 | 1 | 46.81 |
| 1610 | CA | SER | A | 211 | 36.308 | 72.765 | 19.769 | 1 | 43.53 |
| 1611 | C | SER | A | 211 | 35.138 | 72.107 | 19.041 | 1 | 44 |
| 1612 | O | SER | A | 211 | 34.242 | 72.796 | 18.551 | 1 | 46.51 |
| 1613 | CB | SER | A | 211 | 37.571 | 72.707 | 18.92 | 1 | 43.53 |
| 1614 | OG | SER | A | 211 | 38.633 | 73.428 | 19.535 | 1 | 40.65 |
| 1615 | N | VAL | A | 212 | 35.105 | 70.778 | 19.002 | 1 | 39.83 |
| 1616 | CA | VAL | A | 212 | 33.981 | 70.097 | 18.344 | 1 | 34.15 |
| 1617 | C | VAL | A | 212 | 32.631 | 70.45 | 18.997 | 1 | 31.62 |
| 1618 | O | VAL | A | 212 | 31.613 | 70.506 | 18.338 | 1 | 29.16 |
| 1619 | CB | VAL | A | 212 | 34.19 | 68.574 | 18.336 | 1 | 28.26 |
| 1620 | CG1 | VAL | A | 212 | 32.964 | 67.879 | 17.829 | 1 | 26.78 |
| 1621 | CG2 | VAL | A | 212 | 35.343 | 68.245 | 17.417 | 1 | 31.42 |
| 1622 | N | GLY | A | 213 | 32.629 | 70.683 | 20.301 | 1 | 33.4 |
| 1623 | CA | GLY | A | 213 | 31.392 | 71.036 | 20.973 | 1 | 35.22 |
| 1624 | C | GLY | A | 213 | 30.918 | 72.426 | 20.56 | 1 | 37.95 |
| 1625 | O | GLY | A | 213 | 29.744 | 72.615 | 20.289 | 1 | 35.24 |
| 1626 | N | CYS | A | 214 | 31.834 | 73.392 | 20.538 | 1 | 37.44 |
| 1627 | CA | CYS | A | 214 | 31.508 | 74.749 | 20.147 | 1 | 41.88 |
| 1628 | C | CYS | A | 214 | 31.043 | 74.72 | 18.702 | 1 | 40.71 |
| 1629 | O | CYS | A | 214 | 30.112 | 75.433 | 18.307 | 1 | 39.35 |
| 1630 | CB | CYS | A | 214 | 32.745 | 75.643 | 20.252 | 1 | 41.96 |
| 1631 | SG | CYS | A | 214 | 33.384 | 75.795 | 21.892 | 1 | 39.81 |
| 1632 | N | ILE | A | 215 | 31.7 | 73.886 | 17.913 | 1 | 37.31 |
| 1633 | CA | ILE | A | 215 | 31.339 | 73.782 | 16.507 | 1 | 38.73 |
| 1634 | C | ILE | A | 215 | 29.956 | 73.153 | 16.373 | 1 | 38.02 |
| 1635 | O | ILE | A | 215 | 29.1 | 73.682 | 15.688 | 1 | 42.97 |
| 1636 | CB | ILE | A | 215 | 32.409 | 72.992 | 15.684 | 1 | 32.03 |
| 1637 | CG1 | ILE | A | 215 | 33.782 | 73.656 | 15.818 | 1 | 33.57 |
| 1638 | CG2 | ILE | A | 215 | 32.071 | 73.014 | 14.236 | 1 | 31.47 |
| 1639 | CD1 | ILE | A | 215 | 34.962 | 72.869 | 15.198 | 1 | 24.34 |
| 1640 | N | MET | A | 216 | 29.722 | 72.035 | 17.044 | 1 | 42.7 |

Fig. 1-41

| ATOM | ATOM TYPE | RESIDUE | | # | X | Y | Z | OCC | B |
|---|---|---|---|---|---|---|---|---|---|
| 1641 | CA | MET | A | 216 | 28.414 | 71.385 | 16.965 | 1 | 45.15 |
| 1642 | C | MET | A | 216 | 27.326 | 72.326 | 17.486 | 1 | 44.3 |
| 1643 | O | MET | A | 216 | 26.244 | 72.404 | 16.935 | 1 | 45 |
| 1644 | CB | MET | A | 216 | 28.397 | 70.087 | 17.769 | 1 | 42.87 |
| 1645 | CG | MET | A | 216 | 27.181 | 69.246 | 17.493 | 1 | 46.65 |
| 1646 | SD | MET | A | 216 | 26.807 | 68.048 | 18.765 | 1 | 48.35 |
| 1647 | CE | MET | A | 216 | 25.21 | 67.551 | 18.193 | 1 | 52.21 |
| 1648 | N | ALA | A | 217 | 27.641 | 73.06 | 18.539 | 1 | 46.2 |
| 1649 | CA | ALA | A | 217 | 26.706 | 73.989 | 19.14 | 1 | 44.76 |
| 1650 | C | ALA | A | 217 | 26.377 | 75.105 | 18.157 | 1 | 48.08 |
| 1651 | O | ALA | A | 217 | 25.232 | 75.528 | 18.056 | 1 | 49.39 |
| 1652 | CB | ALA | A | 217 | 27.311 | 74.562 | 20.395 | 1 | 46.54 |
| 1653 | N | GLU | A | 218 | 27.387 | 75.553 | 17.41 | 1 | 49.97 |
| 1654 | CA | GLU | A | 218 | 27.221 | 76.619 | 16.433 | 1 | 47.93 |
| 1655 | C | GLU | A | 218 | 26.371 | 76.173 | 15.268 | 1 | 49.11 |
| 1656 | O | GLU | A | 218 | 25.577 | 76.952 | 14.743 | 1 | 52 |
| 1657 | CB | GLU | A | 218 | 28.574 | 77.097 | 15.924 | 1 | 46.1 |
| 1658 | CG | GLU | A | 218 | 28.487 | 78.409 | 15.194 | 1 | 47.97 |
| 1659 | CD | GLU | A | 218 | 29.831 | 78.956 | 14.768 | 1 | 47.47 |
| 1660 | OE1 | GLU | A | 218 | 30.825 | 78.726 | 15.481 | 1 | 44.18 |
| 1661 | OE2 | GLU | A | 218 | 29.882 | 79.637 | 13.721 | 1 | 48.14 |
| 1662 | N | MET | A | 219 | 26.554 | 74.935 | 14.833 | 1 | 48.28 |
| 1663 | CA | MET | A | 219 | 25.76 | 74.427 | 13.727 | 1 | 50.18 |
| 1664 | C | MET | A | 219 | 24.273 | 74.473 | 14.092 | 1 | 55.31 |
| 1665 | O | MET | A | 219 | 23.442 | 74.875 | 13.278 | 1 | 60.29 |
| 1666 | CB | MET | A | 219 | 26.156 | 72.996 | 13.397 | 1 | 46.12 |
| 1667 | CG | MET | A | 219 | 27.522 | 72.854 | 12.822 | 1 | 40.5 |
| 1668 | SD | MET | A | 219 | 28.039 | 71.143 | 12.889 | 1 | 39.2 |
| 1669 | CE | MET | A | 219 | 27.603 | 70.545 | 11.311 | 1 | 39.33 |
| 1670 | N | ILE | A | 220 | 23.95 | 74.109 | 15.333 | 1 | 57.04 |
| 1671 | CA | ILE | A | 220 | 22.564 | 74.082 | 15.806 | 1 | 57.34 |
| 1672 | C | ILE | A | 220 | 21.914 | 75.458 | 16.006 | 1 | 58.12 |
| 1673 | O | ILE | A | 220 | 20.817 | 75.71 | 15.512 | 1 | 56.89 |
| 1674 | CB | ILE | A | 220 | 22.454 | 73.302 | 17.128 | 1 | 55.22 |
| 1675 | CG1 | ILE | A | 220 | 23.106 | 71.93 | 16.982 | 1 | 52.68 |
| 1676 | CG2 | ILE | A | 220 | 21 | 73.13 | 17.501 | 1 | 57.26 |
| 1677 | CD1 | ILE | A | 220 | 23.204 | 71.173 | 18.267 | 1 | 52.7 |
| 1678 | N | THR | A | 221 | 22.575 | 76.317 | 16.778 | 1 | 58.79 |
| 1679 | CA | THR | A | 221 | 22.064 | 77.651 | 17.067 | 1 | 57.98 |
| 1680 | C | THR | A | 221 | 22.22 | 78.605 | 15.904 | 1 | 58.94 |

Fig. 1-42

| ATOM | ATOM TYPE | RESIDUE | | # | X | Y | Z | OCC | B |
|---|---|---|---|---|---|---|---|---|---|
| 1681 | O | THR | A | 221 | 21.296 | 79.333 | 15.573 | 1 | 64.25 |
| 1682 | CB | THR | A | 221 | 22.782 | 78.293 | 18.256 | 1 | 57.73 |
| 1683 | OG1 | THR | A | 221 | 24.127 | 78.607 | 17.885 | 1 | 56.32 |
| 1684 | CG2 | THR | A | 221 | 22.777 | 77.357 | 19.464 | 1 | 58.26 |
| 1685 | N | GLY | A | 222 | 23.407 | 78.618 | 15.31 | 1 | 59.14 |
| 1686 | CA | GLY | A | 222 | 23.687 | 79.505 | 14.198 | 1 | 56.36 |
| 1687 | C | GLY | A | 222 | 24.582 | 80.643 | 14.652 | 1 | 55.05 |
| 1688 | O | GLY | A | 222 | 25.162 | 81.36 | 13.845 | 1 | 55.58 |
| 1689 | N | LYS | A | 223 | 24.713 | 80.785 | 15.962 | 1 | 54.94 |
| 1690 | CA | LYS | A | 223 | 25.526 | 81.831 | 16.556 | 1 | 56.18 |
| 1691 | C | LYS | A | 223 | 26.764 | 81.202 | 17.174 | 1 | 57.53 |
| 1692 | O | LYS | A | 223 | 26.759 | 80.029 | 17.531 | 1 | 59.83 |
| 1693 | CB | LYS | A | 223 | 24.709 | 82.569 | 17.648 | 1 | 54.06 |
| 1694 | N | THR | A | 224 | 27.833 | 81.979 | 17.277 | 1 | 58.39 |
| 1695 | CA | THR | A | 224 | 29.065 | 81.505 | 17.894 | 1 | 57.22 |
| 1696 | C | THR | A | 224 | 28.724 | 81.331 | 19.373 | 1 | 59.77 |
| 1697 | O | THR | A | 224 | 28.139 | 82.233 | 19.984 | 1 | 62.77 |
| 1698 | CB | THR | A | 224 | 30.161 | 82.544 | 17.736 | 1 | 55.38 |
| 1699 | OG1 | THR | A | 224 | 30.399 | 82.741 | 16.341 | 1 | 55.02 |
| 1700 | CG2 | THR | A | 224 | 31.436 | 82.108 | 18.435 | 1 | 51.61 |
| 1701 | N | LEU | A | 225 | 29.09 | 80.181 | 19.943 | 1 | 59.25 |
| 1702 | CA | LEU | A | 225 | 28.768 | 79.863 | 21.332 | 1 | 55.72 |
| 1703 | C | LEU | A | 225 | 29.428 | 80.748 | 22.359 | 1 | 52.47 |
| 1704 | O | LEU | A | 225 | 28.741 | 81.315 | 23.198 | 1 | 53.73 |
| 1705 | CB | LEU | A | 225 | 29.03 | 78.38 | 21.638 | 1 | 54.46 |
| 1706 | CG | LEU | A | 225 | 28.621 | 77.909 | 23.038 | 1 | 55.79 |
| 1707 | CD1 | LEU | A | 225 | 27.169 | 78.259 | 23.299 | 1 | 55.88 |
| 1708 | CD2 | LEU | A | 225 | 28.844 | 76.42 | 23.185 | 1 | 52.89 |
| 1709 | N | PHE | A | 226 | 30.747 | 80.861 | 22.31 | 1 | 49.89 |
| 1710 | CA | PHE | A | 226 | 31.455 | 81.695 | 23.273 | 1 | 52.29 |
| 1711 | C | PHE | A | 226 | 32.285 | 82.726 | 22.52 | 1 | 55.03 |
| 1712 | O | PHE | A | 226 | 33.462 | 82.5 | 22.252 | 1 | 58.57 |
| 1713 | CB | PHE | A | 226 | 32.365 | 80.847 | 24.2 | 1 | 49.67 |
| 1714 | CG | PHE | A | 226 | 31.652 | 79.684 | 24.9 | 1 | 50.17 |
| 1715 | CD1 | PHE | A | 226 | 30.515 | 79.896 | 25.674 | 1 | 46.15 |
| 1716 | CD2 | PHE | A | 226 | 32.115 | 78.376 | 24.755 | 1 | 45.89 |
| 1717 | CE1 | PHE | A | 226 | 29.857 | 78.834 | 26.279 | 1 | 47.66 |
| 1718 | CE2 | PHE | A | 226 | 31.457 | 77.306 | 25.361 | 1 | 46.03 |
| 1719 | CZ | PHE | A | 226 | 30.328 | 77.531 | 26.122 | 1 | 46.99 |
| 1720 | N | LYS | A | 227 | 31.672 | 83.852 | 22.163 | 1 | 56.37 |

Fig. 1-43

| ATOM | ATOM TYPE | RESIDUE | | # | X | Y | Z | OCC | B |
|---|---|---|---|---|---|---|---|---|---|
| 1721 | CA | LYS | A | 227 | 32.391 | 84.894 | 21.429 | 1 | 58.68 |
| 1722 | C | LYS | A | 227 | 33.043 | 85.866 | 22.4 | 1 | 60.44 |
| 1723 | O | LYS | A | 227 | 32.417 | 86.835 | 22.818 | 1 | 66.55 |
| 1724 | CB | LYS | A | 227 | 31.442 | 85.638 | 20.472 | 1 | 57.97 |
| 1725 | N | GLY | A | 228 | 34.284 | 85.602 | 22.785 | 1 | 56.04 |
| 1726 | CA | GLY | A | 228 | 34.948 | 86.499 | 23.711 | 1 | 57.52 |
| 1727 | C | GLY | A | 228 | 35.807 | 87.542 | 23.033 | 1 | 58.39 |
| 1728 | O | GLY | A | 228 | 36.307 | 87.299 | 21.943 | 1 | 60.34 |
| 1729 | N | SER | A | 229 | 36.031 | 88.677 | 23.693 | 1 | 60.8 |
| 1730 | CA | SER | A | 229 | 36.841 | 89.753 | 23.109 | 1 | 62.63 |
| 1731 | C | SER | A | 229 | 38.347 | 89.487 | 23.137 | 1 | 61.84 |
| 1732 | O | SER | A | 229 | 39.062 | 89.861 | 22.205 | 1 | 60.42 |
| 1733 | CB | SER | A | 229 | 36.518 | 91.112 | 23.754 | 1 | 65.47 |
| 1734 | OG | SER | A | 229 | 36.901 | 91.182 | 25.121 | 1 | 68.06 |
| 1735 | N | ASP | A | 230 | 38.829 | 88.889 | 24.223 | 1 | 61.24 |
| 1736 | CA | ASP | A | 230 | 40.245 | 88.546 | 24.348 | 1 | 62.31 |
| 1737 | C | ASP | A | 230 | 40.345 | 87.171 | 25.004 | 1 | 61.21 |
| 1738 | O | ASP | A | 230 | 39.328 | 86.63 | 25.459 | 1 | 58.76 |
| 1739 | CB | ASP | A | 230 | 41.051 | 89.616 | 25.118 | 1 | 65.38 |
| 1740 | CG | ASP | A | 230 | 40.501 | 89.898 | 26.522 | 1 | 72.67 |
| 1741 | OD1 | ASP | A | 230 | 39.61 | 90.774 | 26.644 | 1 | 74.17 |
| 1742 | OD2 | ASP | A | 230 | 40.969 | 89.266 | 27.507 | 1 | 74.27 |
| 1743 | N | HIS | A | 231 | 41.556 | 86.614 | 25.07 | 1 | 59.36 |
| 1744 | CA | HIS | A | 231 | 41.722 | 85.284 | 25.642 | 1 | 57.51 |
| 1745 | C | HIS | A | 231 | 41.203 | 85.131 | 27.056 | 1 | 58.59 |
| 1746 | O | HIS | A | 231 | 40.656 | 84.084 | 27.408 | 1 | 57.97 |
| 1747 | CB | HIS | A | 231 | 43.158 | 84.802 | 25.535 | 1 | 56.81 |
| 1748 | CG | HIS | A | 231 | 44.141 | 85.592 | 26.341 | 1 | 58.17 |
| 1749 | ND1 | HIS | A | 231 | 44.74 | 86.738 | 25.862 | 1 | 58.28 |
| 1750 | CD2 | HIS | A | 231 | 44.715 | 85.34 | 27.539 | 1 | 56.46 |
| 1751 | CE1 | HIS | A | 231 | 45.649 | 87.148 | 26.725 | 1 | 60.01 |
| 1752 | NE2 | HIS | A | 231 | 45.655 | 86.318 | 27.754 | 1 | 58.55 |
| 1753 | N | LEU | A | 232 | 41.352 | 86.178 | 27.863 | 1 | 59.32 |
| 1754 | CA | LEU | A | 232 | 40.868 | 86.131 | 29.233 | 1 | 56.31 |
| 1755 | C | LEU | A | 232 | 39.36 | 86.303 | 29.226 | 1 | 54.89 |
| 1756 | O | LEU | A | 232 | 38.647 | 85.625 | 29.959 | 1 | 53.63 |
| 1757 | CB | LEU | A | 232 | 41.507 | 87.239 | 30.063 | 1 | 57.78 |
| 1758 | CG | LEU | A | 232 | 43.006 | 87.152 | 30.33 | 1 | 58.25 |
| 1759 | CD1 | LEU | A | 232 | 43.424 | 88.343 | 31.192 | 1 | 57.87 |
| 1760 | CD2 | LEU | A | 232 | 43.33 | 85.839 | 31.029 | 1 | 57.82 |

Fig. 1-44

| ATOM | ATOM TYPE | RESIDUE | | # | X | Y | Z | OCC | B |
|---|---|---|---|---|---|---|---|---|---|
| 1761 | N | ASP | A | 233 | 38.873 | 87.203 | 28.381 | 1 | 52.94 |
| 1762 | CA | ASP | A | 233 | 37.438 | 87.447 | 28.317 | 1 | 52.88 |
| 1763 | C | ASP | A | 233 | 36.691 | 86.212 | 27.817 | 1 | 51.75 |
| 1764 | O | ASP | A | 233 | 35.496 | 86.041 | 28.086 | 1 | 50.37 |
| 1765 | CB | ASP | A | 233 | 37.137 | 88.65 | 27.428 | 1 | 50.13 |
| 1766 | CG | ASP | A | 233 | 35.659 | 89.001 | 27.41 | 1 | 53.12 |
| 1767 | OD1 | ASP | A | 233 | 35.084 | 89.224 | 28.499 | 1 | 50.34 |
| 1768 | OD2 | ASP | A | 233 | 35.064 | 89.05 | 26.308 | 1 | 54.43 |
| 1769 | N | GLN | A | 234 | 37.406 | 85.364 | 27.08 | 1 | 50.61 |
| 1770 | CA | GLN | A | 234 | 36.846 | 84.131 | 26.541 | 1 | 49.41 |
| 1771 | C | GLN | A | 234 | 36.494 | 83.222 | 27.717 | 1 | 49.27 |
| 1772 | O | GLN | A | 234 | 35.467 | 82.524 | 27.707 | 1 | 50.65 |
| 1773 | CB | GLN | A | 234 | 37.863 | 83.453 | 25.624 | 1 | 49.04 |
| 1774 | CG | GLN | A | 234 | 37.375 | 82.151 | 25.006 | 1 | 47.78 |
| 1775 | CD | GLN | A | 234 | 36.36 | 82.361 | 23.905 | 1 | 47.73 |
| 1776 | OE1 | GLN | A | 234 | 36.505 | 83.262 | 23.083 | 1 | 47.97 |
| 1777 | NE2 | GLN | A | 234 | 35.334 | 81.515 | 23.869 | 1 | 45.6 |
| 1778 | N | LEU | A | 235 | 37.33 | 83.261 | 28.749 | 1 | 45.01 |
| 1779 | CA | LEU | A | 235 | 37.07 | 82.47 | 29.927 | 1 | 46.44 |
| 1780 | C | LEU | A | 235 | 35.735 | 82.904 | 30.48 | 1 | 51.21 |
| 1781 | O | LEU | A | 235 | 34.843 | 82.074 | 30.645 | 1 | 53.59 |
| 1782 | CB | LEU | A | 235 | 38.168 | 82.654 | 30.964 | 1 | 44.69 |
| 1783 | CG | LEU | A | 235 | 39.524 | 82.06 | 30.559 | 1 | 47.12 |
| 1784 | CD1 | LEU | A | 235 | 40.508 | 82.181 | 31.694 | 1 | 44.48 |
| 1785 | CD2 | LEU | A | 235 | 39.365 | 80.586 | 30.187 | 1 | 44.56 |
| 1786 | N | LYS | A | 236 | 35.55 | 84.219 | 30.641 | 1 | 55.97 |
| 1787 | CA | LYS | A | 236 | 34.286 | 84.755 | 31.169 | 1 | 55.78 |
| 1788 | C | LYS | A | 236 | 33.093 | 84.311 | 30.339 | 1 | 53.9 |
| 1789 | O | LYS | A | 236 | 32.08 | 83.872 | 30.892 | 1 | 54.18 |
| 1790 | CB | LYS | A | 236 | 34.305 | 86.293 | 31.304 | 1 | 58.61 |
| 1791 | CG | LYS | A | 236 | 32.938 | 86.905 | 31.713 | 1 | 62.72 |
| 1792 | CD | LYS | A | 236 | 33.029 | 88.206 | 32.529 | 1 | 68.09 |
| 1793 | CE | LYS | A | 236 | 33.62 | 89.388 | 31.748 | 1 | 70.68 |
| 1794 | NZ | LYS | A | 236 | 33.684 | 90.65 | 32.563 | 1 | 68.15 |
| 1795 | N | GLU | A | 237 | 33.209 | 84.405 | 29.019 | 1 | 50.88 |
| 1796 | CA | GLU | A | 237 | 32.1 | 83.99 | 28.186 | 1 | 54.56 |
| 1797 | C | GLU | A | 237 | 31.757 | 82.531 | 28.433 | 1 | 56.25 |
| 1798 | O | GLU | A | 237 | 30.587 | 82.191 | 28.598 | 1 | 57.45 |
| 1799 | CB | GLU | A | 237 | 32.373 | 84.243 | 26.7 | 1 | 56.02 |
| 1800 | CG | GLU | A | 237 | 32.014 | 85.656 | 26.21 | 1 | 56.39 |

Fig. 1-45

| ATOM | ATOM TYPE | RESIDUE | | # | X | Y | Z | OCC | B |
|---|---|---|---|---|---|---|---|---|---|
| 1801 | CD | GLU | A | 237 | 30.623 | 86.1 | 26.643 | 1 | 55.6 |
| 1802 | OE1 | GLU | A | 237 | 29.628 | 85.45 | 26.253 | 1 | 56.67 |
| 1803 | OE2 | GLU | A | 237 | 30.531 | 87.102 | 27.387 | 1 | 56.02 |
| 1804 | N | ILE | A | 238 | 32.781 | 81.681 | 28.531 | 1 | 57.26 |
| 1805 | CA | ILE | A | 238 | 32.562 | 80.256 | 28.762 | 1 | 53.01 |
| 1806 | C | ILE | A | 238 | 31.946 | 80.045 | 30.121 | 1 | 52.69 |
| 1807 | O | ILE | A | 238 | 30.942 | 79.351 | 30.265 | 1 | 54.46 |
| 1808 | CB | ILE | A | 238 | 33.877 | 79.482 | 28.711 | 1 | 51.46 |
| 1809 | CG1 | ILE | A | 238 | 34.454 | 79.532 | 27.292 | 1 | 45.54 |
| 1810 | CG2 | ILE | A | 238 | 33.664 | 78.052 | 29.221 | 1 | 45 |
| 1811 | CD1 | ILE | A | 238 | 35.9 | 79.119 | 27.202 | 1 | 40.99 |
| 1812 | N | MET | A | 239 | 32.551 | 80.68 | 31.111 | 1 | 51.8 |
| 1813 | CA | MET | A | 239 | 32.101 | 80.565 | 32.484 | 1 | 53.98 |
| 1814 | C | MET | A | 239 | 30.633 | 80.944 | 32.639 | 1 | 54.25 |
| 1815 | O | MET | A | 239 | 29.916 | 80.323 | 33.41 | 1 | 53.75 |
| 1816 | CB | MET | A | 239 | 32.951 | 81.457 | 33.39 | 1 | 58.39 |
| 1817 | CG | MET | A | 239 | 34.465 | 81.251 | 33.285 | 1 | 59.22 |
| 1818 | SD | MET | A | 239 | 35.103 | 79.889 | 34.221 | 1 | 53.8 |
| 1819 | CE | MET | A | 239 | 36.7 | 79.701 | 33.468 | 1 | 56.98 |
| 1820 | N | LYS | A | 240 | 30.178 | 81.953 | 31.902 | 1 | 53.74 |
| 1821 | CA | LYS | A | 240 | 28.789 | 82.378 | 32.015 | 1 | 53.83 |
| 1822 | C | LYS | A | 240 | 27.85 | 81.21 | 31.7 | 1 | 56.3 |
| 1823 | O | LYS | A | 240 | 26.7 | 81.176 | 32.15 | 1 | 58.97 |
| 1824 | CB | LYS | A | 240 | 28.512 | 83.594 | 31.106 | 1 | 47.67 |
| 1825 | N | VAL | A | 241 | 28.383 | 80.206 | 31.006 | 1 | 59.49 |
| 1826 | CA | VAL | A | 241 | 27.612 | 79.025 | 30.622 | 1 | 59.78 |
| 1827 | C | VAL | A | 241 | 27.917 | 77.786 | 31.451 | 1 | 59.47 |
| 1828 | O | VAL | A | 241 | 27.003 | 77.11 | 31.917 | 1 | 57.29 |
| 1829 | CB | VAL | A | 241 | 27.853 | 78.679 | 29.162 | 1 | 60.56 |
| 1830 | CG1 | VAL | A | 241 | 27.066 | 77.44 | 28.772 | 1 | 62.14 |
| 1831 | CG2 | VAL | A | 241 | 27.469 | 79.851 | 28.302 | 1 | 63.26 |
| 1832 | N | THR | A | 242 | 29.204 | 77.498 | 31.633 | 1 | 60.72 |
| 1833 | CA | THR | A | 242 | 29.634 | 76.313 | 32.385 | 1 | 61.22 |
| 1834 | C | THR | A | 242 | 29.802 | 76.57 | 33.867 | 1 | 61.59 |
| 1835 | O | THR | A | 242 | 30.175 | 75.683 | 34.618 | 1 | 63.32 |
| 1836 | CB | THR | A | 242 | 31.002 | 75.798 | 31.892 | 1 | 60.58 |
| 1837 | OG1 | THR | A | 242 | 32.034 | 76.682 | 32.35 | 1 | 55.53 |
| 1838 | CG2 | THR | A | 242 | 31.041 | 75.718 | 30.365 | 1 | 60.52 |
| 1839 | N | GLY | A | 243 | 29.542 | 77.789 | 34.294 | 1 | 62.62 |
| 1840 | CA | GLY | A | 243 | 29.74 | 78.092 | 35.691 | 1 | 62.61 |

Fig. 1-46

| ATOM | ATOM TYPE | RESIDUE | | # | X | Y | Z | OCC | B |
|---|---|---|---|---|---|---|---|---|---|
| 1841 | C | GLY | A | 243 | 31.229 | 78.278 | 35.899 | 1 | 63.54 |
| 1842 | O | GLY | A | 243 | 32.044 | 77.976 | 35.011 | 1 | 64.34 |
| 1843 | N | THR | A | 244 | 31.587 | 78.805 | 37.061 | 1 | 63.44 |
| 1844 | CA | THR | A | 244 | 32.982 | 79.029 | 37.398 | 1 | 64.76 |
| 1845 | C | THR | A | 244 | 33.44 | 77.917 | 38.333 | 1 | 65.99 |
| 1846 | O | THR | A | 244 | 32.622 | 77.309 | 39.033 | 1 | 66.76 |
| 1847 | CB | THR | A | 244 | 33.149 | 80.373 | 38.11 | 1 | 62.43 |
| 1848 | OG1 | THR | A | 244 | 32.192 | 80.46 | 39.177 | 1 | 63.24 |
| 1849 | CG2 | THR | A | 244 | 32.941 | 81.52 | 37.138 | 1 | 61.77 |
| 1850 | N | PRO | A | 245 | 34.752 | 77.628 | 38.354 | 1 | 66.25 |
| 1851 | CA | PRO | A | 245 | 35.312 | 76.582 | 39.218 | 1 | 68.52 |
| 1852 | C | PRO | A | 245 | 35.248 | 77.051 | 40.677 | 1 | 70.05 |
| 1853 | O | PRO | A | 245 | 34.965 | 78.224 | 40.948 | 1 | 71.64 |
| 1854 | CB | PRO | A | 245 | 36.782 | 76.521 | 38.775 | 1 | 65.48 |
| 1855 | CG | PRO | A | 245 | 36.797 | 77.145 | 37.444 | 1 | 65.27 |
| 1856 | CD | PRO | A | 245 | 35.815 | 78.257 | 37.563 | 1 | 65.64 |
| 1857 | N | PRO | A | 246 | 35.473 | 76.136 | 41.633 | 1 | 70.03 |
| 1858 | CA | PRO | A | 246 | 35.441 | 76.521 | 43.046 | 1 | 69.69 |
| 1859 | C | PRO | A | 246 | 36.547 | 77.541 | 43.347 | 1 | 69.33 |
| 1860 | O | PRO | A | 246 | 37.622 | 77.508 | 42.741 | 1 | 64.19 |
| 1861 | CB | PRO | A | 246 | 35.669 | 75.191 | 43.769 | 1 | 71.23 |
| 1862 | CG | PRO | A | 246 | 36.38 | 74.335 | 42.744 | 1 | 71.1 |
| 1863 | CD | PRO | A | 246 | 35.623 | 74.679 | 41.496 | 1 | 71.65 |
| 1864 | N | ALA | A | 247 | 36.258 | 78.451 | 44.275 | 1 | 70.91 |
| 1865 | CA | ALA | A | 247 | 37.192 | 79.503 | 44.646 | 1 | 71.76 |
| 1866 | C | ALA | A | 247 | 38.542 | 79 | 45.155 | 1 | 72.39 |
| 1867 | O | ALA | A | 247 | 39.572 | 79.646 | 44.922 | 1 | 71.39 |
| 1868 | CB | ALA | A | 247 | 36.55 | 80.434 | 45.659 | 1 | 74.06 |
| 1869 | N | GLU | A | 248 | 38.54 | 77.85 | 45.833 | 1 | 72.68 |
| 1870 | CA | GLU | A | 248 | 39.783 | 77.273 | 46.363 | 1 | 72.35 |
| 1871 | C | GLU | A | 248 | 40.704 | 76.777 | 45.25 | 1 | 69.53 |
| 1872 | O | GLU | A | 248 | 41.926 | 76.767 | 45.401 | 1 | 68.72 |
| 1873 | CB | GLU | A | 248 | 39.482 | 76.149 | 47.366 | 1 | 75.32 |
| 1874 | CG | GLU | A | 248 | 38.774 | 74.912 | 46.792 | 1 | 78.97 |
| 1875 | CD | GLU | A | 248 | 39.72 | 73.968 | 46.064 | 1 | 77.64 |
| 1876 | OE1 | GLU | A | 248 | 40.911 | 73.895 | 46.45 | 1 | 78.83 |
| 1877 | OE2 | GLU | A | 248 | 39.267 | 73.309 | 45.101 | 1 | 76.1 |
| 1878 | N | PHE | A | 249 | 40.103 | 76.372 | 44.133 | 1 | 66.74 |
| 1879 | CA | PHE | A | 249 | 40.853 | 75.898 | 42.976 | 1 | 64.3 |
| 1880 | C | PHE | A | 249 | 41.598 | 77.042 | 42.316 | 1 | 61.39 |

Fig. 1-47

| ATOM | ATOM TYPE | RESIDUE | | # | X | Y | Z | OCC | B |
|---|---|---|---|---|---|---|---|---|---|
| 1881 | O | PHE | A | 249 | 42.794 | 76.949 | 42.054 | 1 | 60.61 |
| 1882 | CB | PHE | A | 249 | 39.916 | 75.243 | 41.941 | 1 | 65.74 |
| 1883 | CG | PHE | A | 249 | 40.554 | 75.039 | 40.585 | 1 | 65.12 |
| 1884 | CD1 | PHE | A | 249 | 41.65 | 74.199 | 40.436 | 1 | 64.44 |
| 1885 | CD2 | PHE | A | 249 | 40.09 | 75.731 | 39.474 | 1 | 65.16 |
| 1886 | CE1 | PHE | A | 249 | 42.274 | 74.056 | 39.204 | 1 | 65.96 |
| 1887 | CE2 | PHE | A | 249 | 40.709 | 75.594 | 38.235 | 1 | 65.98 |
| 1888 | CZ | PHE | A | 249 | 41.803 | 74.758 | 38.098 | 1 | 65.67 |
| 1889 | N | VAL | A | 250 | 40.87 | 78.116 | 42.035 | 1 | 58.42 |
| 1890 | CA | VAL | A | 250 | 41.451 | 79.271 | 41.381 | 1 | 58.47 |
| 1891 | C | VAL | A | 250 | 42.524 | 79.945 | 42.234 | 1 | 59.92 |
| 1892 | O | VAL | A | 250 | 43.397 | 80.641 | 41.724 | 1 | 59.56 |
| 1893 | CB | VAL | A | 250 | 40.328 | 80.239 | 40.857 | 1 | 58.77 |
| 1894 | CG1 | VAL | A | 250 | 39.005 | 79.926 | 41.527 | 1 | 55.42 |
| 1895 | CG2 | VAL | A | 250 | 40.716 | 81.713 | 41.014 | 1 | 57.44 |
| 1896 | N | GLN | A | 251 | 42.498 | 79.655 | 43.528 | 1 | 63.44 |
| 1897 | CA | GLN | A | 251 | 43.46 | 80.201 | 44.477 | 1 | 66.17 |
| 1898 | C | GLN | A | 251 | 44.842 | 79.658 | 44.173 | 1 | 65.76 |
| 1899 | O | GLN | A | 251 | 45.834 | 80.39 | 44.193 | 1 | 64.04 |
| 1900 | CB | GLN | A | 251 | 43.089 | 79.744 | 45.89 | 1 | 72.98 |
| 1901 | CG | GLN | A | 251 | 42.041 | 80.587 | 46.593 | 1 | 82.34 |
| 1902 | CD | GLN | A | 251 | 42.66 | 81.677 | 47.455 | 1 | 87.06 |
| 1903 | OE1 | GLN | A | 251 | 43.662 | 82.315 | 47.075 | 1 | 89.37 |
| 1904 | NE2 | GLN | A | 251 | 42.074 | 81.889 | 48.634 | 1 | 87.39 |
| 1905 | N | ARG | A | 252 | 44.87 | 78.352 | 43.91 | 1 | 65.24 |
| 1906 | CA | ARG | A | 252 | 46.084 | 77.583 | 43.641 | 1 | 61.76 |
| 1907 | C | ARG | A | 252 | 46.553 | 77.567 | 42.191 | 1 | 61.07 |
| 1908 | O | ARG | A | 252 | 47.524 | 76.877 | 41.868 | 1 | 60.87 |
| 1909 | CB | ARG | A | 252 | 45.878 | 76.139 | 44.113 | 1 | 60.12 |
| 1910 | CG | ARG | A | 252 | 45.375 | 76.036 | 45.527 | 1 | 56.26 |
| 1911 | CD | ARG | A | 252 | 45.228 | 74.603 | 45.943 | 1 | 57.65 |
| 1912 | NE | ARG | A | 252 | 44.008 | 73.977 | 45.447 | 1 | 58.68 |
| 1913 | CZ | ARG | A | 252 | 43.978 | 72.812 | 44.807 | 1 | 64.29 |
| 1914 | NH1 | ARG | A | 252 | 45.115 | 72.148 | 44.566 | 1 | 64.56 |
| 1915 | NH2 | ARG | A | 252 | 42.807 | 72.262 | 44.484 | 1 | 63.9 |
| 1916 | N | LEU | A | 253 | 45.856 | 78.283 | 41.313 | 1 | 58.85 |
| 1917 | CA | LEU | A | 253 | 46.252 | 78.328 | 39.907 | 1 | 58.13 |
| 1918 | C | LEU | A | 253 | 47.706 | 78.736 | 39.756 | 1 | 57.02 |
| 1919 | O | LEU | A | 253 | 48.157 | 79.699 | 40.357 | 1 | 54.31 |
| 1920 | CB | LEU | A | 253 | 45.365 | 79.286 | 39.113 | 1 | 55.76 |

Fig. 1-48

| ATOM | ATOM TYPE | RESIDUE | | # | X | Y | Z | OCC | B |
|---|---|---|---|---|---|---|---|---|---|
| 1921 | CG | LEU | A | 253 | 44.028 | 78.643 | 38.775 | 1 | 56 |
| 1922 | CD1 | LEU | A | 253 | 43.136 | 79.649 | 38.066 | 1 | 55.5 |
| 1923 | CD2 | LEU | A | 253 | 44.272 | 77.395 | 37.943 | 1 | 50.77 |
| 1924 | N | GLN | A | 254 | 48.424 | 77.955 | 38.963 | 1 | 58.4 |
| 1925 | CA | GLN | A | 254 | 49.83 | 78.175 | 38.69 | 1 | 60.84 |
| 1926 | C | GLN | A | 254 | 50.021 | 79.454 | 37.877 | 1 | 63.09 |
| 1927 | O | GLN | A | 254 | 50.902 | 80.264 | 38.168 | 1 | 62.24 |
| 1928 | CB | GLN | A | 254 | 50.369 | 76.983 | 37.901 | 1 | 64.22 |
| 1929 | CG | GLN | A | 254 | 51.66 | 76.409 | 38.424 | 1 | 68.16 |
| 1930 | CD | GLN | A | 254 | 52.749 | 77.44 | 38.513 | 1 | 72.41 |
| 1931 | OE1 | GLN | A | 254 | 53.249 | 77.737 | 39.603 | 1 | 76.25 |
| 1932 | NE2 | GLN | A | 254 | 53.118 | 78.014 | 37.368 | 1 | 72.87 |
| 1933 | N | SER | A | 255 | 49.205 | 79.614 | 36.838 | 1 | 65.92 |
| 1934 | CA | SER | A | 255 | 49.284 | 80.793 | 35.987 | 1 | 69.87 |
| 1935 | C | SER | A | 255 | 48.805 | 82.037 | 36.742 | 1 | 71.99 |
| 1936 | O | SER | A | 255 | 47.654 | 82.094 | 37.2 | 1 | 71.07 |
| 1937 | CB | SER | A | 255 | 48.452 | 80.6 | 34.715 | 1 | 68.37 |
| 1938 | OG | SER | A | 255 | 48.798 | 81.571 | 33.732 | 1 | 69.97 |
| 1939 | N | ASP | A | 256 | 49.705 | 83.011 | 36.899 | 1 | 73 |
| 1940 | CA | ASP | A | 256 | 49.374 | 84.255 | 37.59 | 1 | 73.33 |
| 1941 | C | ASP | A | 256 | 48.264 | 84.982 | 36.838 | 1 | 72.86 |
| 1942 | O | ASP | A | 256 | 47.215 | 85.294 | 37.409 | 1 | 71.63 |
| 1943 | CB | ASP | A | 256 | 50.613 | 85.157 | 37.714 | 1 | 74.14 |
| 1944 | CG | ASP | A | 256 | 51.581 | 84.69 | 38.803 | 1 | 75.83 |
| 1945 | OD1 | ASP | A | 256 | 51.381 | 83.585 | 39.366 | 1 | 72.12 |
| 1946 | OD2 | ASP | A | 256 | 52.539 | 85.444 | 39.1 | 1 | 75.25 |
| 1947 | N | GLU | A | 257 | 48.48 | 85.18 | 35.539 | 1 | 71.33 |
| 1948 | CA | GLU | A | 257 | 47.515 | 85.857 | 34.693 | 1 | 70.82 |
| 1949 | C | GLU | A | 257 | 46.122 | 85.235 | 34.825 | 1 | 69 |
| 1950 | O | GLU | A | 257 | 45.142 | 85.943 | 35.057 | 1 | 70.87 |
| 1951 | CB | GLU | A | 257 | 47.975 | 85.815 | 33.237 | 1 | 73.48 |
| 1952 | CG | GLU | A | 257 | 47.138 | 86.692 | 32.312 | 1 | 79.68 |
| 1953 | CD | GLU | A | 257 | 47.393 | 86.421 | 30.838 | 1 | 83.87 |
| 1954 | OE1 | GLU | A | 257 | 46.896 | 85.392 | 30.329 | 1 | 87.45 |
| 1955 | OE2 | GLU | A | 257 | 48.075 | 87.241 | 30.185 | 1 | 84.43 |
| 1956 | N | ALA | A | 258 | 46.047 | 83.912 | 34.746 | 1 | 64.38 |
| 1957 | CA | ALA | A | 258 | 44.773 | 83.22 | 34.848 | 1 | 61.36 |
| 1958 | C | ALA | A | 258 | 44.162 | 83.323 | 36.239 | 1 | 62.25 |
| 1959 | O | ALA | A | 258 | 42.939 | 83.437 | 36.38 | 1 | 62.23 |
| 1960 | CB | ALA | A | 258 | 44.947 | 81.778 | 34.472 | 1 | 61.51 |

Fig. 1-49

| ATOM | ATOM TYPE | RESIDUE | | # | X | Y | Z | OCC | B |
|---|---|---|---|---|---|---|---|---|---|
| 1961 | N | LYS | A | 259 | 45.016 | 83.273 | 37.261 | 1 | 62.86 |
| 1962 | CA | LYS | A | 259 | 44.575 | 83.336 | 38.658 | 1 | 62.1 |
| 1963 | C | LYS | A | 259 | 43.967 | 84.69 | 38.983 | 1 | 61.36 |
| 1964 | O | LYS | A | 259 | 42.892 | 84.768 | 39.568 | 1 | 61.36 |
| 1965 | CB | LYS | A | 259 | 45.742 | 83.053 | 39.607 | 1 | 61.01 |
| 1966 | CG | LYS | A | 259 | 45.335 | 82.949 | 41.071 | 1 | 59.43 |
| 1967 | CD | LYS | A | 259 | 46.552 | 82.934 | 41.973 | 1 | 61.81 |
| 1968 | CE | LYS | A | 259 | 47.336 | 84.23 | 41.841 | 1 | 62.87 |
| 1969 | NZ | LYS | A | 259 | 48.63 | 84.199 | 42.57 | 1 | 65.85 |
| 1970 | N | ASN | A | 260 | 44.676 | 85.752 | 38.621 | 1 | 61.56 |
| 1971 | CA | ASN | A | 260 | 44.187 | 87.098 | 38.854 | 1 | 63.85 |
| 1972 | C | ASN | A | 260 | 42.846 | 87.277 | 38.131 | 1 | 62.65 |
| 1973 | O | ASN | A | 260 | 41.862 | 87.685 | 38.745 | 1 | 63.44 |
| 1974 | CB | ASN | A | 260 | 45.21 | 88.15 | 38.367 | 1 | 66.73 |
| 1975 | CG | ASN | A | 260 | 46.539 | 88.11 | 39.157 | 1 | 70.36 |
| 1976 | OD1 | ASN | A | 260 | 47.609 | 88.416 | 38.61 | 1 | 69.25 |
| 1977 | ND2 | ASN | A | 260 | 46.467 | 87.738 | 40.443 | 1 | 68.95 |
| 1978 | N | TYR | A | 261 | 42.785 | 86.905 | 36.854 | 1 | 60.38 |
| 1979 | CA | TYR | A | 261 | 41.549 | 87.056 | 36.098 | 1 | 59.21 |
| 1980 | C | TYR | A | 261 | 40.364 | 86.345 | 36.74 | 1 | 60.2 |
| 1981 | O | TYR | A | 261 | 39.337 | 86.96 | 37.003 | 1 | 62.83 |
| 1982 | CB | TYR | A | 261 | 41.712 | 86.583 | 34.652 | 1 | 55.63 |
| 1983 | CG | TYR | A | 261 | 40.477 | 86.86 | 33.839 | 1 | 54.34 |
| 1984 | CD1 | TYR | A | 261 | 40.187 | 88.154 | 33.412 | 1 | 53.78 |
| 1985 | CD2 | TYR | A | 261 | 39.541 | 85.855 | 33.585 | 1 | 51.88 |
| 1986 | CE1 | TYR | A | 261 | 38.998 | 88.449 | 32.764 | 1 | 53.32 |
| 1987 | CE2 | TYR | A | 261 | 38.341 | 86.137 | 32.939 | 1 | 52.07 |
| 1988 | CZ | TYR | A | 261 | 38.074 | 87.439 | 32.535 | 1 | 55.96 |
| 1989 | OH | TYR | A | 261 | 36.87 | 87.744 | 31.941 | 1 | 56.83 |
| 1990 | N | MET | A | 262 | 40.509 | 85.055 | 36.999 | 1 | 61.91 |
| 1991 | CA | MET | A | 262 | 39.44 | 84.268 | 37.614 | 1 | 67 |
| 1992 | C | MET | A | 262 | 39.025 | 84.771 | 39.016 | 1 | 70.53 |
| 1993 | O | MET | A | 262 | 37.904 | 84.508 | 39.493 | 1 | 69.52 |
| 1994 | CB | MET | A | 262 | 39.87 | 82.797 | 37.691 | 1 | 65.79 |
| 1995 | CG | MET | A | 262 | 39.973 | 82.113 | 36.351 | 1 | 61.11 |
| 1996 | SD | MET | A | 262 | 38.363 | 81.953 | 35.587 | 1 | 69.48 |
| 1997 | CE | MET | A | 262 | 37.512 | 80.925 | 36.813 | 1 | 60.57 |
| 1998 | N | LYS | A | 263 | 39.952 | 85.472 | 39.671 | 1 | 73.96 |
| 1999 | CA | LYS | A | 263 | 39.754 | 86.027 | 41.014 | 1 | 75.91 |
| 2000 | C | LYS | A | 263 | 38.761 | 87.179 | 40.918 | 1 | 78.18 |

Fig. 1-50

| ATOM | ATOM TYPE | RESIDUE | | # | X | Y | Z | OCC | B |
|---|---|---|---|---|---|---|---|---|---|
| 2001 | O | LYS | A | 263 | 37.725 | 87.174 | 41.582 | 1 | 78.79 |
| 2002 | CB | LYS | A | 263 | 41.087 | 86.561 | 41.544 | 1 | 76.69 |
| 2003 | CG | LYS | A | 263 | 41.411 | 86.279 | 43.008 | 1 | 79.65 |
| 2004 | CD | LYS | A | 263 | 41.962 | 84.873 | 43.22 | 1 | 80.55 |
| 2005 | CE | LYS | A | 263 | 42.666 | 84.728 | 44.584 | 1 | 82.92 |
| 2006 | NZ | LYS | A | 263 | 44.035 | 85.351 | 44.641 | 1 | 83.41 |
| 2007 | N | GLY | A | 264 | 39.079 | 88.148 | 40.063 | 1 | 79.73 |
| 2008 | CA | GLY | A | 264 | 38.219 | 89.306 | 39.872 | 1 | 82.86 |
| 2009 | C | GLY | A | 264 | 36.864 | 88.972 | 39.274 | 1 | 83.39 |
| 2010 | O | GLY | A | 264 | 35.882 | 89.699 | 39.45 | 1 | 83.61 |
| 2011 | N | LEU | A | 265 | 36.808 | 87.854 | 38.57 | 1 | 84.09 |
| 2012 | CA | LEU | A | 265 | 35.577 | 87.408 | 37.946 | 1 | 85.51 |
| 2013 | C | LEU | A | 265 | 34.524 | 87.075 | 39.006 | 1 | 85.92 |
| 2014 | O | LEU | A | 265 | 34.862 | 86.627 | 40.104 | 1 | 86.1 |
| 2015 | CB | LEU | A | 265 | 35.865 | 86.153 | 37.127 | 1 | 86.17 |
| 2016 | CG | LEU | A | 265 | 34.918 | 85.819 | 35.986 | 1 | 84.25 |
| 2017 | CD1 | LEU | A | 265 | 35.147 | 86.837 | 34.89 | 1 | 85.31 |
| 2018 | CD2 | LEU | A | 265 | 35.195 | 84.415 | 35.476 | 1 | 85.83 |
| 2019 | N | PRO | A | 266 | 33.237 | 87.34 | 38.706 | 1 | 86.24 |
| 2020 | CA | PRO | A | 266 | 32.13 | 87.055 | 39.627 | 1 | 85.3 |
| 2021 | C | PRO | A | 266 | 32.04 | 85.55 | 39.858 | 1 | 84.88 |
| 2022 | O | PRO | A | 266 | 32.84 | 84.786 | 39.324 | 1 | 87.31 |
| 2023 | CB | PRO | A | 266 | 30.913 | 87.534 | 38.846 | 1 | 85.43 |
| 2024 | CG | PRO | A | 266 | 31.455 | 88.678 | 38.043 | 1 | 87.16 |
| 2025 | CD | PRO | A | 266 | 32.765 | 88.126 | 37.549 | 1 | 87.36 |
| 2026 | N | GLU | A | 267 | 31.067 | 85.117 | 40.644 | 1 | 83.69 |
| 2027 | CA | GLU | A | 267 | 30.911 | 83.693 | 40.901 | 1 | 82.37 |
| 2028 | C | GLU | A | 267 | 29.679 | 83.245 | 40.13 | 1 | 79.96 |
| 2029 | O | GLU | A | 267 | 28.548 | 83.476 | 40.557 | 1 | 80.72 |
| 2030 | CB | GLU | A | 267 | 30.773 | 83.437 | 42.408 | 1 | 85.51 |
| 2031 | CG | GLU | A | 267 | 30.846 | 81.966 | 42.816 | 1 | 89.58 |
| 2032 | CD | GLU | A | 267 | 31.638 | 81.744 | 44.108 | 1 | 92.32 |
| 2033 | OE1 | GLU | A | 267 | 32.873 | 81.566 | 44.028 | 1 | 90.72 |
| 2034 | OE2 | GLU | A | 267 | 31.028 | 81.738 | 45.202 | 1 | 95.1 |
| 2035 | N | LEU | A | 268 | 29.912 | 82.646 | 38.965 | 1 | 77.43 |
| 2036 | CA | LEU | A | 268 | 28.836 | 82.182 | 38.086 | 1 | 74.63 |
| 2037 | C | LEU | A | 268 | 28.381 | 80.744 | 38.319 | 1 | 73.3 |
| 2038 | O | LEU | A | 268 | 29.169 | 79.886 | 38.709 | 1 | 74.73 |
| 2039 | CB | LEU | A | 268 | 29.257 | 82.37 | 36.633 | 1 | 73.36 |
| 2040 | CG | LEU | A | 268 | 29.478 | 83.844 | 36.289 | 1 | 75.38 |

Fig. 1-51

| ATOM | ATOM TYPE | RESIDUE | | # | X | Y | Z | OCC | B |
|---|---|---|---|---|---|---|---|---|---|
| 2041 | CD1 | LEU | A | 268 | 30.569 | 84.017 | 35.246 | 1 | 75.55 |
| 2042 | CD2 | LEU | A | 268 | 28.162 | 84.464 | 35.838 | 1 | 76.3 |
| 2043 | N | GLU | A | 269 | 27.096 | 80.494 | 38.086 | 1 | 72.05 |
| 2044 | CA | GLU | A | 269 | 26.518 | 79.163 | 38.258 | 1 | 68.74 |
| 2045 | C | GLU | A | 269 | 26.299 | 78.507 | 36.899 | 1 | 68.69 |
| 2046 | O | GLU | A | 269 | 26.07 | 79.195 | 35.894 | 1 | 68.02 |
| 2047 | CB | GLU | A | 269 | 25.197 | 79.253 | 39.022 | 1 | 69.8 |
| 2048 | N | LYS | A | 270 | 26.365 | 77.177 | 36.877 | 1 | 67.81 |
| 2049 | CA | LYS | A | 270 | 26.187 | 76.399 | 35.651 | 1 | 66.51 |
| 2050 | C | LYS | A | 270 | 24.744 | 76.474 | 35.145 | 1 | 64.72 |
| 2051 | O | LYS | A | 270 | 23.809 | 76.242 | 35.901 | 1 | 63.39 |
| 2052 | CB | LYS | A | 270 | 26.579 | 74.939 | 35.906 | 1 | 65.95 |
| 2053 | CG | LYS | A | 270 | 27.495 | 74.318 | 34.859 | 1 | 65.03 |
| 2054 | CD | LYS | A | 270 | 26.752 | 73.866 | 33.611 | 1 | 67.47 |
| 2055 | CE | LYS | A | 270 | 25.843 | 72.662 | 33.871 | 1 | 65.62 |
| 2056 | NZ | LYS | A | 270 | 25.301 | 72.077 | 32.593 | 1 | 63.93 |
| 2057 | N | LYS | A | 271 | 24.578 | 76.816 | 33.869 | 1 | 64.97 |
| 2058 | CA | LYS | A | 271 | 23.26 | 76.915 | 33.253 | 1 | 66.39 |
| 2059 | C | LYS | A | 271 | 22.95 | 75.599 | 32.56 | 1 | 67.32 |
| 2060 | O | LYS | A | 271 | 23.857 | 74.886 | 32.149 | 1 | 66.32 |
| 2061 | CB | LYS | A | 271 | 23.218 | 78.07 | 32.236 | 1 | 64.29 |
| 2062 | N | ASP | A | 272 | 21.669 | 75.258 | 32.479 | 1 | 68.76 |
| 2063 | CA | ASP | A | 272 | 21.243 | 74.034 | 31.817 | 1 | 69.07 |
| 2064 | C | ASP | A | 272 | 21.464 | 74.304 | 30.34 | 1 | 69.46 |
| 2065 | O | ASP | A | 272 | 21.092 | 75.377 | 29.85 | 1 | 70.94 |
| 2066 | CB | ASP | A | 272 | 19.754 | 73.789 | 32.075 | 1 | 71.48 |
| 2067 | CG | ASP | A | 272 | 19.306 | 72.392 | 31.667 | 1 | 73.84 |
| 2068 | OD1 | ASP | A | 272 | 19.171 | 72.114 | 30.454 | 1 | 71.55 |
| 2069 | OD2 | ASP | A | 272 | 19.089 | 71.564 | 32.575 | 1 | 77.98 |
| 2070 | N | PHE | A | 273 | 22.067 | 73.352 | 29.628 | 1 | 67.27 |
| 2071 | CA | PHE | A | 273 | 22.322 | 73.555 | 28.206 | 1 | 65.52 |
| 2072 | C | PHE | A | 273 | 21.072 | 73.694 | 27.354 | 1 | 64.48 |
| 2073 | O | PHE | A | 273 | 21.047 | 74.484 | 26.418 | 1 | 61.6 |
| 2074 | CB | PHE | A | 273 | 23.25 | 72.476 | 27.651 | 1 | 64.25 |
| 2075 | CG | PHE | A | 273 | 24.709 | 72.749 | 27.9 | 1 | 62.46 |
| 2076 | CD1 | PHE | A | 273 | 25.107 | 73.61 | 28.917 | 1 | 60.94 |
| 2077 | CD2 | PHE | A | 273 | 25.685 | 72.128 | 27.137 | 1 | 61.49 |
| 2078 | CE1 | PHE | A | 273 | 26.451 | 73.841 | 29.174 | 1 | 61.06 |
| 2079 | CE2 | PHE | A | 273 | 27.036 | 72.354 | 27.388 | 1 | 61.15 |
| 2080 | CZ | PHE | A | 273 | 27.418 | 73.209 | 28.408 | 1 | 61.2 |

Fig. 1-52

| ATOM | ATOM TYPE | RESIDUE | | # | X | Y | Z | OCC | B |
|---|---|---|---|---|---|---|---|---|---|
| 2081 | N | ALA | A | 274 | 20.022 | 72.964 | 27.715 | 1 | 68.22 |
| 2082 | CA | ALA | A | 274 | 18.75 | 73.008 | 26.985 | 1 | 70.31 |
| 2083 | C | ALA | A | 274 | 18.172 | 74.422 | 26.963 | 1 | 71.26 |
| 2084 | O | ALA | A | 274 | 17.389 | 74.76 | 26.076 | 1 | 70.9 |
| 2085 | CB | ALA | A | 274 | 17.743 | 72.036 | 27.613 | 1 | 70.17 |
| 2086 | N | SER | A | 275 | 18.58 | 75.233 | 27.942 | 1 | 72.7 |
| 2087 | CA | SER | A | 275 | 18.137 | 76.62 | 28.082 | 1 | 75.09 |
| 2088 | C | SER | A | 275 | 18.812 | 77.541 | 27.068 | 1 | 76.67 |
| 2089 | O | SER | A | 275 | 18.351 | 78.658 | 26.835 | 1 | 77.53 |
| 2090 | CB | SER | A | 275 | 18.414 | 77.119 | 29.507 | 1 | 71.52 |
| 2091 | N | ILE | A | 276 | 19.91 | 77.065 | 26.482 | 1 | 78.33 |
| 2092 | CA | ILE | A | 276 | 20.68 | 77.826 | 25.501 | 1 | 79.35 |
| 2093 | C | ILE | A | 276 | 20.347 | 77.388 | 24.082 | 1 | 81.21 |
| 2094 | O | ILE | A | 276 | 20.114 | 78.219 | 23.201 | 1 | 82.83 |
| 2095 | CB | ILE | A | 276 | 22.197 | 77.612 | 25.695 | 1 | 78.11 |
| 2096 | CG1 | ILE | A | 276 | 22.574 | 77.792 | 27.161 | 1 | 76.81 |
| 2097 | CG2 | ILE | A | 276 | 22.989 | 78.578 | 24.816 | 1 | 77.7 |
| 2098 | CD1 | ILE | A | 276 | 24.002 | 77.443 | 27.441 | 1 | 78.58 |
| 2099 | N | LEU | A | 277 | 20.374 | 76.078 | 23.861 | 1 | 82.38 |
| 2100 | CA | LEU | A | 277 | 20.097 | 75.498 | 22.551 | 1 | 84.58 |
| 2101 | C | LEU | A | 277 | 18.588 | 75.43 | 22.323 | 1 | 88.19 |
| 2102 | O | LEU | A | 277 | 17.954 | 74.398 | 22.58 | 1 | 88.83 |
| 2103 | CB | LEU | A | 277 | 20.715 | 74.104 | 22.471 | 1 | 82.44 |
| 2104 | CG | LEU | A | 277 | 22.094 | 73.954 | 23.123 | 1 | 78.99 |
| 2105 | CD1 | LEU | A | 277 | 22.548 | 72.525 | 23.032 | 1 | 77.89 |
| 2106 | CD2 | LEU | A | 277 | 23.094 | 74.877 | 22.479 | 1 | 78.9 |
| 2107 | N | THR | A | 278 | 18.037 | 76.533 | 21.809 | 1 | 91.86 |
| 2108 | CA | THR | A | 278 | 16.602 | 76.687 | 21.542 | 1 | 95.6 |
| 2109 | C | THR | A | 278 | 15.878 | 75.502 | 20.89 | 1 | 96.73 |
| 2110 | O | THR | A | 278 | 15.055 | 74.85 | 21.54 | 1 | 96.5 |
| 2111 | CB | THR | A | 278 | 16.305 | 77.987 | 20.731 | 1 | 96.74 |
| 2112 | OG1 | THR | A | 278 | 17.175 | 78.065 | 19.592 | 1 | 97.74 |
| 2113 | CG2 | THR | A | 278 | 16.488 | 79.226 | 21.604 | 1 | 96.8 |
| 2114 | N | ASN | A | 279 | 16.173 | 75.233 | 19.618 | 1 | 97.17 |
| 2115 | CA | ASN | A | 279 | 15.521 | 74.139 | 18.895 | 1 | 97.22 |
| 2116 | C | ASN | A | 279 | 16.34 | 72.842 | 18.716 | 1 | 95.08 |
| 2117 | O | ASN | A | 279 | 16.081 | 72.042 | 17.806 | 1 | 94.98 |
| 2118 | CB | ASN | A | 279 | 14.947 | 74.643 | 17.547 | 1 | 98.87 |
| 2119 | CG | ASN | A | 279 | 16.007 | 75.289 | 16.622 | 1 | 98.85 |
| 2120 | OD1 | ASN | A | 279 | 15.748 | 75.51 | 15.433 | 1 | 97.86 |

Fig. 1-53

| ATOM | ATOM TYPE | RESIDUE | | # | X | Y | Z | OCC | B |
|---|---|---|---|---|---|---|---|---|---|
| 2121 | ND2 | ASN | A | 279 | 17.181 | 75.6 | 17.167 | 1 | 98.78 |
| 2122 | N | ALA | A | 280 | 17.294 | 72.621 | 19.617 | 1 | 91.73 |
| 2123 | CA | ALA | A | 280 | 18.14 | 71.431 | 19.582 | 1 | 88.32 |
| 2124 | C | ALA | A | 280 | 17.423 | 70.196 | 20.111 | 1 | 85.96 |
| 2125 | O | ALA | A | 280 | 16.43 | 70.315 | 20.816 | 1 | 87.39 |
| 2126 | CB | ALA | A | 280 | 19.401 | 71.676 | 20.378 | 1 | 86.22 |
| 2127 | N | SER | A | 281 | 17.929 | 69.011 | 19.783 | 1 | 83.44 |
| 2128 | CA | SER | A | 281 | 17.314 | 67.768 | 20.251 | 1 | 81.03 |
| 2129 | C | SER | A | 281 | 17.841 | 67.429 | 21.658 | 1 | 80.89 |
| 2130 | O | SER | A | 281 | 18.879 | 67.962 | 22.088 | 1 | 80.28 |
| 2131 | CB | SER | A | 281 | 17.611 | 66.616 | 19.28 | 1 | 80.4 |
| 2132 | OG | SER | A | 281 | 18.755 | 65.858 | 19.658 | 1 | 78.93 |
| 2133 | N | PRO | A | 282 | 17.123 | 66.558 | 22.402 | 1 | 79.46 |
| 2134 | CA | PRO | A | 282 | 17.503 | 66.136 | 23.757 | 1 | 76 |
| 2135 | C | PRO | A | 282 | 18.875 | 65.447 | 23.813 | 1 | 72.47 |
| 2136 | O | PRO | A | 282 | 19.733 | 65.847 | 24.601 | 1 | 72.15 |
| 2137 | CB | PRO | A | 282 | 16.368 | 65.18 | 24.14 | 1 | 77.79 |
| 2138 | CG | PRO | A | 282 | 15.89 | 64.639 | 22.826 | 1 | 78.34 |
| 2139 | CD | PRO | A | 282 | 15.867 | 65.899 | 22 | 1 | 80.18 |
| 2140 | N | LEU | A | 283 | 19.074 | 64.441 | 22.962 | 1 | 69.58 |
| 2141 | CA | LEU | A | 283 | 20.334 | 63.697 | 22.892 | 1 | 66.84 |
| 2142 | C | LEU | A | 283 | 21.498 | 64.606 | 22.501 | 1 | 65.21 |
| 2143 | O | LEU | A | 283 | 22.634 | 64.415 | 22.951 | 1 | 62.73 |
| 2144 | CB | LEU | A | 283 | 20.214 | 62.581 | 21.857 | 1 | 67.61 |
| 2145 | CG | LEU | A | 283 | 19.279 | 61.417 | 22.157 | 1 | 67.77 |
| 2146 | CD1 | LEU | A | 283 | 19.057 | 60.566 | 20.908 | 1 | 67.54 |
| 2147 | CD2 | LEU | A | 283 | 19.88 | 60.589 | 23.283 | 1 | 66.72 |
| 2148 | N | ALA | A | 284 | 21.203 | 65.569 | 21.629 | 1 | 63.12 |
| 2149 | CA | ALA | A | 284 | 22.191 | 66.522 | 21.133 | 1 | 60.14 |
| 2150 | C | ALA | A | 284 | 22.663 | 67.359 | 22.286 | 1 | 59.39 |
| 2151 | O | ALA | A | 284 | 23.859 | 67.632 | 22.431 | 1 | 60.98 |
| 2152 | CB | ALA | A | 284 | 21.578 | 67.419 | 20.064 | 1 | 61.39 |
| 2153 | N | VAL | A | 285 | 21.709 | 67.762 | 23.118 | 1 | 57.13 |
| 2154 | CA | VAL | A | 285 | 22.024 | 68.581 | 24.278 | 1 | 52.53 |
| 2155 | C | VAL | A | 285 | 22.856 | 67.757 | 25.239 | 1 | 52.85 |
| 2156 | O | VAL | A | 285 | 23.844 | 68.241 | 25.796 | 1 | 54.74 |
| 2157 | CB | VAL | A | 285 | 20.761 | 69.083 | 24.952 | 1 | 46.76 |
| 2158 | CG1 | VAL | A | 285 | 21.095 | 69.769 | 26.245 | 1 | 46.62 |
| 2159 | CG2 | VAL | A | 285 | 20.047 | 70.021 | 24.03 | 1 | 43.24 |
| 2160 | N | ASN | A | 286 | 22.504 | 66.487 | 25.384 | 1 | 53.65 |

Fig. 1-54

| ATOM | ATOM TYPE | RESIDUE | | # | X | Y | Z | OCC | B |
|---|---|---|---|---|---|---|---|---|---|
| 2161 | CA | ASN | A | 286 | 23.262 | 65.634 | 26.285 | 1 | 54.13 |
| 2162 | C | ASN | A | 286 | 24.699 | 65.505 | 25.803 | 1 | 52.66 |
| 2163 | O | ASN | A | 286 | 25.612 | 65.766 | 26.571 | 1 | 53.03 |
| 2164 | CB | ASN | A | 286 | 22.612 | 64.26 | 26.458 | 1 | 55.87 |
| 2165 | CG | ASN | A | 286 | 23.331 | 63.41 | 27.474 | 1 | 56.36 |
| 2166 | OD1 | ASN | A | 286 | 23.119 | 63.548 | 28.674 | 1 | 59.83 |
| 2167 | ND2 | ASN | A | 286 | 24.224 | 62.557 | 27.002 | 1 | 57.96 |
| 2168 | N | LEU | A | 287 | 24.9 | 65.17 | 24.529 | 1 | 51.12 |
| 2169 | CA | LEU | A | 287 | 26.254 | 65.045 | 23.99 | 1 | 52.14 |
| 2170 | C | LEU | A | 287 | 27.072 | 66.322 | 24.2 | 1 | 51.93 |
| 2171 | O | LEU | A | 287 | 28.222 | 66.274 | 24.641 | 1 | 51.31 |
| 2172 | CB | LEU | A | 287 | 26.211 | 64.727 | 22.504 | 1 | 49.83 |
| 2173 | CG | LEU | A | 287 | 27.583 | 64.605 | 21.842 | 1 | 50.21 |
| 2174 | CD1 | LEU | A | 287 | 28.442 | 63.532 | 22.51 | 1 | 47.77 |
| 2175 | CD2 | LEU | A | 287 | 27.382 | 64.329 | 20.366 | 1 | 51 |
| 2176 | N | LEU | A | 288 | 26.464 | 67.459 | 23.882 | 1 | 52.28 |
| 2177 | CA | LEU | A | 288 | 27.119 | 68.749 | 24.037 | 1 | 51.31 |
| 2178 | C | LEU | A | 288 | 27.546 | 68.951 | 25.478 | 1 | 52.12 |
| 2179 | O | LEU | A | 288 | 28.676 | 69.352 | 25.754 | 1 | 50.35 |
| 2180 | CB | LEU | A | 288 | 26.186 | 69.871 | 23.568 | 1 | 48.57 |
| 2181 | CG | LEU | A | 288 | 26.175 | 70.031 | 22.05 | 1 | 43.02 |
| 2182 | CD1 | LEU | A | 288 | 25.19 | 71.084 | 21.626 | 1 | 45.13 |
| 2183 | CD2 | LEU | A | 288 | 27.569 | 70.4 | 21.596 | 1 | 45.57 |
| 2184 | N | GLU | A | 289 | 26.64 | 68.613 | 26.391 | 1 | 56.07 |
| 2185 | CA | GLU | A | 289 | 26.884 | 68.72 | 27.826 | 1 | 57.96 |
| 2186 | C | GLU | A | 289 | 28.117 | 67.876 | 28.195 | 1 | 57.14 |
| 2187 | O | GLU | A | 289 | 28.948 | 68.295 | 28.995 | 1 | 59.49 |
| 2188 | CB | GLU | A | 289 | 25.644 | 68.239 | 28.592 | 1 | 61.42 |
| 2189 | CG | GLU | A | 289 | 25.4 | 68.936 | 29.934 | 1 | 70.06 |
| 2190 | CD | GLU | A | 289 | 24.156 | 69.828 | 29.929 | 1 | 75.57 |
| 2191 | OE1 | GLU | A | 289 | 23.07 | 69.36 | 29.504 | 1 | 79.13 |
| 2192 | OE2 | GLU | A | 289 | 24.257 | 70.996 | 30.367 | 1 | 77.67 |
| 2193 | N | LYS | A | 290 | 28.254 | 66.711 | 27.565 | 1 | 57.77 |
| 2194 | CA | LYS | A | 290 | 29.382 | 65.814 | 27.813 | 1 | 56.73 |
| 2195 | C | LYS | A | 290 | 30.664 | 66.299 | 27.153 | 1 | 54.56 |
| 2196 | O | LYS | A | 290 | 31.747 | 65.972 | 27.628 | 1 | 55.32 |
| 2197 | CB | LYS | A | 290 | 29.072 | 64.396 | 27.331 | 1 | 59 |
| 2198 | CG | LYS | A | 290 | 28.246 | 63.563 | 28.289 | 1 | 65.3 |
| 2199 | CD | LYS | A | 290 | 27.831 | 62.249 | 27.636 | 1 | 70.07 |
| 2200 | CE | LYS | A | 290 | 27.253 | 61.264 | 28.642 | 1 | 72.6 |

Fig. 1-55

| ATOM | ATOM TYPE | RESIDUE | | # | X | Y | Z | OCC | B |
|---|---|---|---|---|---|---|---|---|---|
| 2201 | NZ | LYS | A | 290 | 26.061 | 61.794 | 29.375 | 1 | 75.97 |
| 2202 | N | MET | A | 291 | 30.548 | 67.033 | 26.046 | 1 | 50.46 |
| 2203 | CA | MET | A | 291 | 31.729 | 67.551 | 25.361 | 1 | 49.47 |
| 2204 | C | MET | A | 291 | 32.207 | 68.879 | 25.947 | 1 | 48.92 |
| 2205 | O | MET | A | 291 | 33.397 | 69.155 | 25.977 | 1 | 47.63 |
| 2206 | CB | MET | A | 291 | 31.475 | 67.733 | 23.86 | 1 | 50.79 |
| 2207 | CG | MET | A | 291 | 31.118 | 66.472 | 23.107 | 1 | 51.91 |
| 2208 | SD | MET | A | 291 | 31.272 | 66.605 | 21.305 | 1 | 53.03 |
| 2209 | CE | MET | A | 291 | 29.663 | 67.185 | 20.858 | 1 | 50.33 |
| 2210 | N | LEU | A | 292 | 31.282 | 69.701 | 26.429 | 1 | 52.57 |
| 2211 | CA | LEU | A | 292 | 31.651 | 71.003 | 26.977 | 1 | 51.71 |
| 2212 | C | LEU | A | 292 | 31.808 | 71.099 | 28.483 | 1 | 52.95 |
| 2213 | O | LEU | A | 292 | 31.595 | 72.157 | 29.065 | 1 | 55.5 |
| 2214 | CB | LEU | A | 292 | 30.701 | 72.073 | 26.465 | 1 | 47.99 |
| 2215 | CG | LEU | A | 292 | 30.881 | 72.248 | 24.969 | 1 | 42.58 |
| 2216 | CD1 | LEU | A | 292 | 29.864 | 73.233 | 24.449 | 1 | 43.81 |
| 2217 | CD2 | LEU | A | 292 | 32.283 | 72.736 | 24.724 | 1 | 44 |
| 2218 | N | VAL | A | 293 | 32.185 | 69.992 | 29.115 | 1 | 54.34 |
| 2219 | CA | VAL | A | 293 | 32.424 | 69.982 | 30.551 | 1 | 54.23 |
| 2220 | C | VAL | A | 293 | 33.725 | 70.746 | 30.8 | 1 | 56.33 |
| 2221 | O | VAL | A | 293 | 34.662 | 70.668 | 30.009 | 1 | 59.41 |
| 2222 | CB | VAL | A | 293 | 32.518 | 68.562 | 31.078 | 1 | 53.83 |
| 2223 | CG1 | VAL | A | 293 | 33.25 | 68.539 | 32.409 | 1 | 59.94 |
| 2224 | CG2 | VAL | A | 293 | 31.12 | 68 | 31.248 | 1 | 55.41 |
| 2225 | N | LEU | A | 294 | 33.761 | 71.502 | 31.888 | 1 | 56.82 |
| 2226 | CA | LEU | A | 294 | 34.903 | 72.332 | 32.236 | 1 | 57.42 |
| 2227 | C | LEU | A | 294 | 36.154 | 71.535 | 32.626 | 1 | 59.44 |
| 2228 | O | LEU | A | 294 | 37.299 | 71.966 | 32.404 | 1 | 55.27 |
| 2229 | CB | LEU | A | 294 | 34.479 | 73.263 | 33.368 | 1 | 56.3 |
| 2230 | CG | LEU | A | 294 | 35.393 | 74.456 | 33.587 | 1 | 61.01 |
| 2231 | CD1 | LEU | A | 294 | 35.302 | 75.375 | 32.387 | 1 | 60.96 |
| 2232 | CD2 | LEU | A | 294 | 34.999 | 75.181 | 34.848 | 1 | 63.07 |
| 2233 | N | ASP | A | 295 | 35.892 | 70.37 | 33.215 | 1 | 63.78 |
| 2234 | CA | ASP | A | 295 | 36.891 | 69.426 | 33.697 | 1 | 65.51 |
| 2235 | C | ASP | A | 295 | 37.369 | 68.562 | 32.533 | 1 | 66.04 |
| 2236 | O | ASP | A | 295 | 36.697 | 67.605 | 32.145 | 1 | 66.19 |
| 2237 | CB | ASP | A | 295 | 36.239 | 68.552 | 34.785 | 1 | 70.58 |
| 2238 | CG | ASP | A | 295 | 37.219 | 67.586 | 35.466 | 1 | 75.84 |
| 2239 | OD1 | ASP | A | 295 | 38.46 | 67.725 | 35.307 | 1 | 76.64 |
| 2240 | OD2 | ASP | A | 295 | 36.723 | 66.687 | 36.19 | 1 | 75.05 |

Fig. 1-56

| ATOM | ATOM TYPE | RESIDUE | | # | X | Y | Z | OCC | B |
|---|---|---|---|---|---|---|---|---|---|
| 2241 | N | ALA | A | 296 | 38.539 | 68.895 | 31.998 | 1 | 64.2 |
| 2242 | CA | ALA | A | 296 | 39.122 | 68.169 | 30.881 | 1 | 64.21 |
| 2243 | C | ALA | A | 296 | 39.072 | 66.653 | 31.017 | 1 | 66.32 |
| 2244 | O | ALA | A | 296 | 38.827 | 65.952 | 30.035 | 1 | 68.03 |
| 2245 | CB | ALA | A | 296 | 40.551 | 68.617 | 30.666 | 1 | 66.83 |
| 2246 | N | GLU | A | 297 | 39.282 | 66.146 | 32.229 | 1 | 67.54 |
| 2247 | CA | GLU | A | 297 | 39.28 | 64.701 | 32.465 | 1 | 69.08 |
| 2248 | C | GLU | A | 297 | 37.939 | 63.982 | 32.271 | 1 | 69.12 |
| 2249 | O | GLU | A | 297 | 37.899 | 62.89 | 31.7 | 1 | 68.24 |
| 2250 | CB | GLU | A | 297 | 39.837 | 64.39 | 33.857 | 1 | 73.29 |
| 2251 | CG | GLU | A | 297 | 41.315 | 64.755 | 34.046 | 1 | 77.9 |
| 2252 | CD | GLU | A | 297 | 42.278 | 63.895 | 33.215 | 1 | 76.74 |
| 2253 | OE1 | GLU | A | 297 | 42.214 | 62.645 | 33.321 | 1 | 76.29 |
| 2254 | OE2 | GLU | A | 297 | 43.116 | 64.476 | 32.484 | 1 | 68.77 |
| 2255 | N | GLN | A | 298 | 36.856 | 64.569 | 32.782 | 1 | 70.3 |
| 2256 | CA | GLN | A | 298 | 35.509 | 63.988 | 32.664 | 1 | 70.51 |
| 2257 | C | GLN | A | 298 | 34.925 | 64.235 | 31.279 | 1 | 67.98 |
| 2258 | O | GLN | A | 298 | 33.889 | 63.681 | 30.916 | 1 | 67.58 |
| 2259 | CB | GLN | A | 298 | 34.557 | 64.59 | 33.712 | 1 | 77.11 |
| 2260 | CG | GLN | A | 298 | 34.963 | 64.386 | 35.18 | 1 | 84.98 |
| 2261 | CD | GLN | A | 298 | 35.069 | 62.916 | 35.57 | 1 | 89.04 |
| 2262 | OE1 | GLN | A | 298 | 36.034 | 62.5 | 36.231 | 1 | 88.81 |
| 2263 | NE2 | GLN | A | 298 | 34.078 | 62.119 | 35.158 | 1 | 89.92 |
| 2264 | N | ARG | A | 299 | 35.601 | 65.087 | 30.515 | 1 | 65.78 |
| 2265 | CA | ARG | A | 299 | 35.175 | 65.441 | 29.173 | 1 | 61.73 |
| 2266 | C | ARG | A | 299 | 35.263 | 64.218 | 28.264 | 1 | 61 |
| 2267 | O | ARG | A | 299 | 36.294 | 63.532 | 28.206 | 1 | 62.34 |
| 2268 | CB | ARG | A | 299 | 36.032 | 66.602 | 28.65 | 1 | 58.4 |
| 2269 | CG | ARG | A | 299 | 35.414 | 67.371 | 27.505 | 1 | 54.82 |
| 2270 | CD | ARG | A | 299 | 35.606 | 68.862 | 27.702 | 1 | 51.47 |
| 2271 | NE | ARG | A | 299 | 36.961 | 69.289 | 27.398 | 1 | 49.45 |
| 2272 | CZ | ARG | A | 299 | 37.593 | 70.286 | 28.008 | 1 | 45.18 |
| 2273 | NH1 | ARG | A | 299 | 37.021 | 70.984 | 28.968 | 1 | 41.01 |
| 2274 | NH2 | ARG | A | 299 | 38.811 | 70.586 | 27.647 | 1 | 41.47 |
| 2275 | N | VAL | A | 300 | 34.163 | 63.936 | 27.58 | 1 | 57.9 |
| 2276 | CA | VAL | A | 300 | 34.072 | 62.799 | 26.674 | 1 | 58.42 |
| 2277 | C | VAL | A | 300 | 35.218 | 62.777 | 25.649 | 1 | 58.99 |
| 2278 | O | VAL | A | 300 | 35.803 | 63.812 | 25.336 | 1 | 59.7 |
| 2279 | CB | VAL | A | 300 | 32.705 | 62.816 | 25.939 | 1 | 57.66 |
| 2280 | CG1 | VAL | A | 300 | 32.824 | 63.453 | 24.56 | 1 | 55.44 |

Fig. 1-57

| ATOM | ATOM TYPE | RESIDUE | | # | X | Y | Z | OCC | B |
|---|---|---|---|---|---|---|---|---|---|
| 2281 | CG2 | VAL | A | 300 | 32.115 | 61.428 | 25.872 | 1 | 55.5 |
| 2282 | N | THR | A | 301 | 35.589 | 61.584 | 25.193 | 1 | 59.9 |
| 2283 | CA | THR | A | 301 | 36.648 | 61.461 | 24.193 | 1 | 58.31 |
| 2284 | C | THR | A | 301 | 35.954 | 61.227 | 22.858 | 1 | 60.17 |
| 2285 | O | THR | A | 301 | 34.751 | 60.924 | 22.817 | 1 | 58.15 |
| 2286 | CB | THR | A | 301 | 37.584 | 60.256 | 24.448 | 1 | 57.9 |
| 2287 | OG1 | THR | A | 301 | 36.829 | 59.036 | 24.363 | 1 | 56.38 |
| 2288 | CG2 | THR | A | 301 | 38.266 | 60.361 | 25.802 | 1 | 50.97 |
| 2289 | N | ALA | A | 302 | 36.714 | 61.355 | 21.773 | 1 | 59.12 |
| 2290 | CA | ALA | A | 302 | 36.175 | 61.149 | 20.44 | 1 | 55.83 |
| 2291 | C | ALA | A | 302 | 35.57 | 59.758 | 20.348 | 1 | 56.24 |
| 2292 | O | ALA | A | 302 | 34.484 | 59.596 | 19.803 | 1 | 58.36 |
| 2293 | CB | ALA | A | 302 | 37.251 | 61.325 | 19.409 | 1 | 55.91 |
| 2294 | N | GLY | A | 303 | 36.26 | 58.762 | 20.906 | 1 | 57.09 |
| 2295 | CA | GLY | A | 303 | 35.752 | 57.402 | 20.888 | 1 | 56.42 |
| 2296 | C | GLY | A | 303 | 34.413 | 57.338 | 21.6 | 1 | 60.07 |
| 2297 | O | GLY | A | 303 | 33.407 | 56.881 | 21.03 | 1 | 60.46 |
| 2298 | N | GLU | A | 304 | 34.397 | 57.837 | 22.84 | 1 | 61.02 |
| 2299 | CA | GLU | A | 304 | 33.193 | 57.86 | 23.667 | 1 | 60.96 |
| 2300 | C | GLU | A | 304 | 32.113 | 58.67 | 22.965 | 1 | 60.89 |
| 2301 | O | GLU | A | 304 | 30.95 | 58.245 | 22.903 | 1 | 61.63 |
| 2302 | CB | GLU | A | 304 | 33.487 | 58.484 | 25.041 | 1 | 65.27 |
| 2303 | CG | GLU | A | 304 | 34.485 | 57.735 | 25.924 | 1 | 69.45 |
| 2304 | CD | GLU | A | 304 | 34.757 | 58.462 | 27.247 | 1 | 75.82 |
| 2305 | OE1 | GLU | A | 304 | 33.801 | 59.023 | 27.833 | 1 | 78.78 |
| 2306 | OE2 | GLU | A | 304 | 35.924 | 58.471 | 27.71 | 1 | 77.52 |
| 2307 | N | ALA | A | 305 | 32.513 | 59.826 | 22.425 | 1 | 58.26 |
| 2308 | CA | ALA | A | 305 | 31.609 | 60.724 | 21.709 | 1 | 54.78 |
| 2309 | C | ALA | A | 305 | 30.825 | 59.965 | 20.64 | 1 | 53.25 |
| 2310 | O | ALA | A | 305 | 29.61 | 60.047 | 20.594 | 1 | 51.95 |
| 2311 | CB | ALA | A | 305 | 32.395 | 61.863 | 21.083 | 1 | 51.09 |
| 2312 | N | LEU | A | 306 | 31.533 | 59.2 | 19.814 | 1 | 53.54 |
| 2313 | CA | LEU | A | 306 | 30.931 | 58.41 | 18.746 | 1 | 52.85 |
| 2314 | C | LEU | A | 306 | 29.978 | 57.358 | 19.285 | 1 | 57.51 |
| 2315 | O | LEU | A | 306 | 28.951 | 57.058 | 18.671 | 1 | 55.46 |
| 2316 | CB | LEU | A | 306 | 32.022 | 57.711 | 17.953 | 1 | 50.42 |
| 2317 | CG | LEU | A | 306 | 32.92 | 58.585 | 17.089 | 1 | 49.59 |
| 2318 | CD1 | LEU | A | 306 | 34.102 | 57.793 | 16.604 | 1 | 43.28 |
| 2319 | CD2 | LEU | A | 306 | 32.114 | 59.131 | 15.916 | 1 | 49.83 |
| 2320 | N | ALA | A | 307 | 30.339 | 56.788 | 20.433 | 1 | 62.58 |

Fig. 1-58

| ATOM | ATOM TYPE | RESIDUE | | # | X | Y | Z | OCC | B |
|---|---|---|---|---|---|---|---|---|---|
| 2321 | CA | ALA | A | 307 | 29.533 | 55.755 | 21.091 | 1 | 63.64 |
| 2322 | C | ALA | A | 307 | 28.195 | 56.262 | 21.655 | 1 | 63.94 |
| 2323 | O | ALA | A | 307 | 27.332 | 55.457 | 22.02 | 1 | 66.89 |
| 2324 | CB | ALA | A | 307 | 30.35 | 55.09 | 22.202 | 1 | 61.54 |
| 2325 | N | HIS | A | 308 | 28.018 | 57.586 | 21.699 | 1 | 59.49 |
| 2326 | CA | HIS | A | 308 | 26.806 | 58.207 | 22.238 | 1 | 55.38 |
| 2327 | C | HIS | A | 308 | 25.512 | 57.913 | 21.459 | 1 | 56.49 |
| 2328 | O | HIS | A | 308 | 25.512 | 57.769 | 20.244 | 1 | 55.81 |
| 2329 | CB | HIS | A | 308 | 27.03 | 59.708 | 22.355 | 1 | 48.83 |
| 2330 | CG | HIS | A | 308 | 26.025 | 60.414 | 23.208 | 1 | 45.66 |
| 2331 | ND1 | HIS | A | 308 | 24.826 | 60.892 | 22.713 | 1 | 43.32 |
| 2332 | CD2 | HIS | A | 308 | 26.062 | 60.768 | 24.514 | 1 | 42.3 |
| 2333 | CE1 | HIS | A | 308 | 24.174 | 61.513 | 23.676 | 1 | 39.82 |
| 2334 | NE2 | HIS | A | 308 | 24.899 | 61.455 | 24.778 | 1 | 40.32 |
| 2335 | N | PRO | A | 309 | 24.379 | 57.823 | 22.169 | 1 | 60.56 |
| 2336 | CA | PRO | A | 309 | 23.085 | 57.544 | 21.542 | 1 | 61.17 |
| 2337 | C | PRO | A | 309 | 22.665 | 58.535 | 20.471 | 1 | 61.9 |
| 2338 | O | PRO | A | 309 | 21.673 | 58.306 | 19.78 | 1 | 64.35 |
| 2339 | CB | PRO | A | 309 | 22.127 | 57.592 | 22.728 | 1 | 61.18 |
| 2340 | CG | PRO | A | 309 | 22.961 | 57.081 | 23.847 | 1 | 63.08 |
| 2341 | CD | PRO | A | 309 | 24.244 | 57.833 | 23.639 | 1 | 61.55 |
| 2342 | N | TYR | A | 310 | 23.376 | 59.654 | 20.367 | 1 | 60.89 |
| 2343 | CA | TYR | A | 310 | 23.052 | 60.676 | 19.369 | 1 | 60.03 |
| 2344 | C | TYR | A | 310 | 23.376 | 60.143 | 17.976 | 1 | 59.78 |
| 2345 | O | TYR | A | 310 | 22.63 | 60.362 | 17.016 | 1 | 55.61 |
| 2346 | CB | TYR | A | 310 | 23.865 | 61.959 | 19.634 | 1 | 60.71 |
| 2347 | CG | TYR | A | 310 | 23.661 | 63.068 | 18.614 | 1 | 57.56 |
| 2348 | CD1 | TYR | A | 310 | 22.395 | 63.613 | 18.399 | 1 | 58.7 |
| 2349 | CD2 | TYR | A | 310 | 24.733 | 63.575 | 17.872 | 1 | 54.92 |
| 2350 | CE1 | TYR | A | 310 | 22.193 | 64.642 | 17.471 | 1 | 57.82 |
| 2351 | CE2 | TYR | A | 310 | 24.543 | 64.601 | 16.935 | 1 | 55.04 |
| 2352 | CZ | TYR | A | 310 | 23.268 | 65.133 | 16.745 | 1 | 55.99 |
| 2353 | OH | TYR | A | 310 | 23.049 | 66.16 | 15.856 | 1 | 51.18 |
| 2354 | N | PHE | A | 311 | 24.48 | 59.407 | 17.901 | 1 | 62.46 |
| 2355 | CA | PHE | A | 311 | 24.976 | 58.831 | 16.662 | 1 | 66.25 |
| 2356 | C | PHE | A | 311 | 24.476 | 57.404 | 16.464 | 1 | 72.07 |
| 2357 | O | PHE | A | 311 | 25.114 | 56.616 | 15.757 | 1 | 75.44 |
| 2358 | CB | PHE | A | 311 | 26.508 | 58.854 | 16.681 | 1 | 62.42 |
| 2359 | CG | PHE | A | 311 | 27.094 | 60.23 | 16.884 | 1 | 60.59 |
| 2360 | CD1 | PHE | A | 311 | 26.792 | 61.272 | 16.007 | 1 | 61.21 |

Fig. 1-59

| ATOM | ATOM TYPE | RESIDUE | | # | X | Y | Z | OCC | B |
|---|---|---|---|---|---|---|---|---|---|
| 2361 | CD2 | PHE | A | 311 | 27.95 | 60.492 | 17.95 | 1 | 59.64 |
| 2362 | CE1 | PHE | A | 311 | 27.338 | 62.552 | 16.194 | 1 | 58.52 |
| 2363 | CE2 | PHE | A | 311 | 28.5 | 61.77 | 18.143 | 1 | 58.27 |
| 2364 | CZ | PHE | A | 311 | 28.193 | 62.795 | 17.266 | 1 | 55.34 |
| 2365 | N | GLU | A | 312 | 23.319 | 57.097 | 17.056 | 1 | 75.2 |
| 2366 | CA | GLU | A | 312 | 22.697 | 55.767 | 17.002 | 1 | 77.76 |
| 2367 | C | GLU | A | 312 | 22.472 | 55.231 | 15.583 | 1 | 77.48 |
| 2368 | O | GLU | A | 312 | 22.915 | 54.123 | 15.245 | 1 | 75.56 |
| 2369 | CB | GLU | A | 312 | 21.367 | 55.793 | 17.772 | 1 | 83.58 |
| 2370 | CG | GLU | A | 312 | 20.645 | 54.446 | 17.91 | 1 | 89.04 |
| 2371 | CD | GLU | A | 312 | 19.245 | 54.583 | 18.507 | 1 | 91.58 |
| 2372 | OE1 | GLU | A | 312 | 18.421 | 55.321 | 17.924 | 1 | 94.32 |
| 2373 | OE2 | GLU | A | 312 | 18.962 | 53.952 | 19.549 | 1 | 91.87 |
| 2374 | N | SER | A | 313 | 21.807 | 56.036 | 14.754 | 1 | 76.34 |
| 2375 | CA | SER | A | 313 | 21.498 | 55.662 | 13.372 | 1 | 74.37 |
| 2376 | C | SER | A | 313 | 22.704 | 55.621 | 12.43 | 1 | 73.93 |
| 2377 | O | SER | A | 313 | 22.549 | 55.396 | 11.228 | 1 | 71.9 |
| 2378 | CB | SER | A | 313 | 20.431 | 56.601 | 12.798 | 1 | 72.62 |
| 2379 | OG | SER | A | 313 | 20.929 | 57.916 | 12.647 | 1 | 70.9 |
| 2380 | N | LEU | A | 314 | 23.901 | 55.802 | 12.976 | 1 | 73.98 |
| 2381 | CA | LEU | A | 314 | 25.102 | 55.794 | 12.157 | 1 | 75.64 |
| 2382 | C | LEU | A | 314 | 26.186 | 54.828 | 12.657 | 1 | 78.57 |
| 2383 | O | LEU | A | 314 | 27.044 | 54.404 | 11.874 | 1 | 78.19 |
| 2384 | CB | LEU | A | 314 | 25.672 | 57.218 | 12.071 | 1 | 74.66 |
| 2385 | CG | LEU | A | 314 | 24.779 | 58.387 | 11.625 | 1 | 71.8 |
| 2386 | CD1 | LEU | A | 314 | 25.527 | 59.698 | 11.801 | 1 | 69.63 |
| 2387 | CD2 | LEU | A | 314 | 24.348 | 58.222 | 10.177 | 1 | 70.16 |
| 2388 | N | HIS | A | 315 | 26.12 | 54.465 | 13.945 | 1 | 81.27 |
| 2389 | CA | HIS | A | 315 | 27.088 | 53.569 | 14.61 | 1 | 83.32 |
| 2390 | C | HIS | A | 315 | 27.419 | 52.221 | 13.922 | 1 | 84.7 |
| 2391 | O | HIS | A | 315 | 26.613 | 51.753 | 13.084 | 1 | 85.92 |
| 2392 | CB | HIS | A | 315 | 26.651 | 53.328 | 16.069 | 1 | 81.93 |
| 2393 | OXT | HIS | A | 315 | 28.491 | 51.636 | 14.23 | 1 | 82.02 |
| 2394 | N | GLN | A | 322 | 42.293 | 49.682 | 13.733 | 1 | 86.57 |
| 2395 | CA | GLN | A | 322 | 43.44 | 50.091 | 14.6 | 1 | 88.79 |
| 2396 | C | GLN | A | 322 | 44.391 | 51.01 | 13.816 | 1 | 89.57 |
| 2397 | O | GLN | A | 322 | 44.502 | 50.893 | 12.582 | 1 | 88.38 |
| 2398 | CB | GLN | A | 322 | 44.176 | 48.854 | 15.122 | 1 | 89.1 |
| 2399 | N | VAL | A | 323 | 45.078 | 51.914 | 14.527 | 1 | 88.86 |
| 2400 | CA | VAL | A | 323 | 45.981 | 52.874 | 13.872 | 1 | 88.07 |

Fig. 1-60

| ATOM | ATOM TYPE | RESIDUE | | # | X | Y | Z | OCC | B |
|---|---|---|---|---|---|---|---|---|---|
| 2401 | C | VAL | A | 323 | 47.447 | 52.934 | 14.322 | 1 | 87.21 |
| 2402 | O | VAL | A | 323 | 47.788 | 52.739 | 15.501 | 1 | 85.22 |
| 2403 | CB | VAL | A | 323 | 45.417 | 54.326 | 13.922 | 1 | 87.12 |
| 2404 | CG1 | VAL | A | 323 | 43.921 | 54.343 | 13.623 | 1 | 86.52 |
| 2405 | CG2 | VAL | A | 323 | 45.701 | 54.951 | 15.255 | 1 | 86.12 |
| 2406 | N | GLN | A | 324 | 48.289 | 53.298 | 13.36 | 1 | 85.99 |
| 2407 | CA | GLN | A | 324 | 49.727 | 53.418 | 13.559 | 1 | 85.96 |
| 2408 | C | GLN | A | 324 | 50.086 | 54.782 | 14.13 | 1 | 84.87 |
| 2409 | O | GLN | A | 324 | 49.899 | 55.816 | 13.477 | 1 | 86.2 |
| 2410 | CB | GLN | A | 324 | 50.463 | 53.192 | 12.227 | 1 | 87.87 |
| 2411 | N | LYS | A | 325 | 50.621 | 54.777 | 15.344 | 1 | 81.3 |
| 2412 | CA | LYS | A | 325 | 51.015 | 56.009 | 15.998 | 1 | 79.16 |
| 2413 | C | LYS | A | 325 | 52.109 | 56.733 | 15.228 | 1 | 77.26 |
| 2414 | O | LYS | A | 325 | 53.028 | 56.112 | 14.713 | 1 | 77.74 |
| 2415 | CB | LYS | A | 325 | 51.475 | 55.729 | 17.426 | 1 | 80.69 |
| 2416 | CG | LYS | A | 325 | 50.351 | 55.287 | 18.366 | 1 | 84.68 |
| 2417 | CD | LYS | A | 325 | 50.725 | 55.552 | 19.819 | 1 | 88.94 |
| 2418 | CE | LYS | A | 325 | 51.212 | 56.998 | 19.995 | 1 | 91.51 |
| 2419 | NZ | LYS | A | 325 | 51.477 | 57.37 | 21.416 | 1 | 91.97 |
| 2420 | N | TYR | A | 326 | 51.968 | 58.047 | 15.108 | 1 | 76.32 |
| 2421 | CA | TYR | A | 326 | 52.948 | 58.874 | 14.418 | 1 | 76.35 |
| 2422 | C | TYR | A | 326 | 54.211 | 58.921 | 15.29 | 1 | 80.86 |
| 2423 | O | TYR | A | 326 | 54.115 | 58.889 | 16.519 | 1 | 82 |
| 2424 | CB | TYR | A | 326 | 52.352 | 60.272 | 14.195 | 1 | 68.98 |
| 2425 | CG | TYR | A | 326 | 53.311 | 61.304 | 13.668 | 1 | 63.42 |
| 2426 | CD1 | TYR | A | 326 | 53.667 | 61.346 | 12.329 | 1 | 65.98 |
| 2427 | CD2 | TYR | A | 326 | 53.874 | 62.24 | 14.52 | 1 | 64.75 |
| 2428 | CE1 | TYR | A | 326 | 54.573 | 62.307 | 11.851 | 1 | 67.91 |
| 2429 | CE2 | TYR | A | 326 | 54.778 | 63.198 | 14.064 | 1 | 66.04 |
| 2430 | CZ | TYR | A | 326 | 55.126 | 63.23 | 12.733 | 1 | 67.09 |
| 2431 | OH | TYR | A | 326 | 56.029 | 64.183 | 12.307 | 1 | 66.12 |
| 2432 | N | ASP | A | 327 | 55.386 | 58.966 | 14.66 | 1 | 85.46 |
| 2433 | CA | ASP | A | 327 | 56.665 | 58.996 | 15.385 | 1 | 88.92 |
| 2434 | C | ASP | A | 327 | 57.555 | 60.122 | 14.835 | 1 | 89.81 |
| 2435 | O | ASP | A | 327 | 57.327 | 60.579 | 13.717 | 1 | 89.6 |
| 2436 | CB | ASP | A | 327 | 57.356 | 57.64 | 15.207 | 1 | 92.6 |
| 2437 | CG | ASP | A | 327 | 58.449 | 57.395 | 16.228 | 1 | 96.72 |
| 2438 | OD1 | ASP | A | 327 | 58.152 | 57.452 | 17.449 | 1 | 97.04 |
| 2439 | OD2 | ASP | A | 327 | 59.597 | 57.128 | 15.802 | 1 | 96.71 |
| 2440 | N | ASP | A | 328 | 58.567 | 60.561 | 15.589 | 1 | 91.43 |

Fig. 1-61

| ATOM | ATOM TYPE | RESIDUE | # | X | Y | Z | OCC | B |
|---|---|---|---|---|---|---|---|---|
| 2441 | CA | ASP A | 328 | 59.437 | 61.641 | 15.098 | 1 | 95.64 |
| 2442 | C | ASP A | 328 | 60.7 | 62.002 | 15.914 | 1 | 96.78 |
| 2443 | O | ASP A | 328 | 60.964 | 61.456 | 16.994 | 1 | 94.25 |
| 2444 | CB | ASP A | 328 | 58.594 | 62.915 | 14.876 | 1 | 98.53 |
| 2445 | CG | ASP A | 328 | 59.321 | 63.985 | 14.058 | 1 | 99.84 |
| 2446 | OD1 | ASP A | 328 | 59.618 | 63.737 | 12.868 | 1 | 99.15 |
| 2447 | OD2 | ASP A | 328 | 59.596 | 65.074 | 14.614 | 1 | 100 |
| 2448 | N | SER A | 329 | 61.483 | 62.912 | 15.329 | 1 | 97.59 |
| 2449 | CA | SER A | 329 | 62.716 | 63.461 | 15.888 | 1 | 98.55 |
| 2450 | C | SER A | 329 | 62.967 | 64.84 | 15.233 | 1 | 98.82 |
| 2451 | O | SER A | 329 | 63.589 | 64.92 | 14.149 | 1 | 97.91 |
| 2452 | CB | SER A | 329 | 63.911 | 62.5 | 15.681 | 1 | 98.4 |
| 2453 | OG | SER A | 329 | 64.182 | 62.229 | 14.313 | 1 | 95.53 |
| 2454 | OXT | SER A | 329 | 62.472 | 65.842 | 15.793 | 1 | 99.25 |
| 2455 | N | ARG A | 335 | 66.574 | 73.051 | 17.072 | 1 | 96.21 |
| 2456 | CA | ARG A | 335 | 67.107 | 73.039 | 15.674 | 1 | 97.17 |
| 2457 | C | ARG A | 335 | 67.192 | 74.454 | 15.088 | 1 | 97.18 |
| 2458 | O | ARG A | 335 | 66.399 | 75.327 | 15.442 | 1 | 96.48 |
| 2459 | CB | ARG A | 335 | 66.235 | 72.14 | 14.791 | 1 | 95.49 |
| 2460 | N | THR A | 336 | 68.168 | 74.677 | 14.209 | 1 | 98.59 |
| 2461 | CA | THR A | 336 | 68.366 | 75.984 | 13.564 | 1 | 99.84 |
| 2462 | C | THR A | 336 | 67.368 | 76.221 | 12.418 | 1 | 99.87 |
| 2463 | O | THR A | 336 | 66.68 | 75.293 | 11.987 | 1 | 99.03 |
| 2464 | CB | THR A | 336 | 69.833 | 76.154 | 13.014 | 1 | 100 |
| 2465 | OG1 | THR A | 336 | 70.094 | 75.2 | 11.975 | 1 | 98.96 |
| 2466 | CG2 | THR A | 336 | 70.854 | 75.962 | 14.128 | 1 | 100 |
| 2467 | N | LEU A | 337 | 67.282 | 77.466 | 11.94 | 1 | 100 |
| 2468 | CA | LEU A | 337 | 66.375 | 77.812 | 10.841 | 1 | 99.62 |
| 2469 | C | LEU A | 337 | 66.735 | 76.959 | 9.63 | 1 | 100 |
| 2470 | O | LEU A | 337 | 65.857 | 76.453 | 8.926 | 1 | 100 |
| 2471 | CB | LEU A | 337 | 66.479 | 79.303 | 10.497 | 1 | 97.19 |
| 2472 | N | ASP A | 338 | 68.036 | 76.768 | 9.427 | 1 | 100 |
| 2473 | CA | ASP A | 338 | 68.538 | 75.964 | 8.321 | 1 | 99.97 |
| 2474 | C | ASP A | 338 | 68.368 | 74.459 | 8.529 | 1 | 100 |
| 2475 | O | ASP A | 338 | 68.46 | 73.689 | 7.569 | 1 | 100 |
| 2476 | CB | ASP A | 338 | 69.997 | 76.304 | 8.033 | 1 | 99.46 |
| 2477 | CG | ASP A | 338 | 70.143 | 77.587 | 7.243 | 1 | 100 |
| 2478 | OD1 | ASP A | 338 | 69.313 | 78.511 | 7.425 | 1 | 99.14 |
| 2479 | OD2 | ASP A | 338 | 71.088 | 77.659 | 6.427 | 1 | 100 |
| 2480 | N | GLU A | 339 | 68.156 | 74.04 | 9.779 | 1 | 100 |

Fig. 1-62

| ATOM | ATOM TYPE | RESIDUE | | # | X | Y | Z | OCC | B |
|---|---|---|---|---|---|---|---|---|---|
| 2481 | CA | GLU | A | 339 | 67.939 | 72.623 | 10.086 | 1 | 99.87 |
| 2482 | C | GLU | A | 339 | 66.495 | 72.269 | 9.739 | 1 | 99.1 |
| 2483 | O | GLU | A | 339 | 66.23 | 71.212 | 9.162 | 1 | 100 |
| 2484 | CB | GLU | A | 339 | 68.235 | 72.311 | 11.559 | 1 | 99.85 |
| 2485 | CG | GLU | A | 339 | 69.713 | 72.036 | 11.844 | 1 | 100 |
| 2486 | CD | GLU | A | 339 | 70.015 | 71.802 | 13.32 | 1 | 100 |
| 2487 | OE1 | GLU | A | 339 | 69.468 | 70.835 | 13.901 | 1 | 100 |
| 2488 | OE2 | GLU | A | 339 | 70.814 | 72.579 | 13.894 | 1 | 99.8 |
| 2489 | N | TRP | A | 340 | 65.571 | 73.17 | 10.074 | 1 | 97.23 |
| 2490 | CA | TRP | A | 340 | 64.155 | 72.979 | 9.765 | 1 | 94.09 |
| 2491 | C | TRP | A | 340 | 63.972 | 72.993 | 8.252 | 1 | 93.74 |
| 2492 | O | TRP | A | 340 | 63.292 | 72.131 | 7.696 | 1 | 92.91 |
| 2493 | CB | TRP | A | 340 | 63.308 | 74.092 | 10.383 | 1 | 90.8 |
| 2494 | CG | TRP | A | 340 | 63.087 | 73.947 | 11.846 | 1 | 87.46 |
| 2495 | CD1 | TRP | A | 340 | 63.553 | 74.769 | 12.83 | 1 | 86.61 |
| 2496 | CD2 | TRP | A | 340 | 62.339 | 72.917 | 12.503 | 1 | 84.86 |
| 2497 | NE1 | TRP | A | 340 | 63.143 | 74.313 | 14.058 | 1 | 85.54 |
| 2498 | CE2 | TRP | A | 340 | 62.396 | 73.177 | 13.885 | 1 | 84.66 |
| 2499 | CE3 | TRP | A | 340 | 61.628 | 71.798 | 12.056 | 1 | 83.2 |
| 2500 | CZ2 | TRP | A | 340 | 61.766 | 72.359 | 14.829 | 1 | 84.88 |
| 2501 | CZ3 | TRP | A | 340 | 61.002 | 70.984 | 12.996 | 1 | 83.43 |
| 2502 | CH2 | TRP | A | 340 | 61.076 | 71.27 | 14.365 | 1 | 83.1 |
| 2503 | N | LYS | A | 341 | 64.609 | 73.97 | 7.605 | 1 | 92.33 |
| 2504 | CA | LYS | A | 341 | 64.564 | 74.15 | 6.156 | 1 | 90.6 |
| 2505 | C | LYS | A | 341 | 65.068 | 72.888 | 5.442 | 1 | 89.72 |
| 2506 | O | LYS | A | 341 | 64.451 | 72.415 | 4.482 | 1 | 88.1 |
| 2507 | CB | LYS | A | 341 | 65.415 | 75.37 | 5.793 | 1 | 90.99 |
| 2508 | CG | LYS | A | 341 | 65.331 | 75.864 | 4.365 | 1 | 91.86 |
| 2509 | CD | LYS | A | 341 | 66.055 | 77.205 | 4.263 | 1 | 93.95 |
| 2510 | CE | LYS | A | 341 | 66.187 | 77.697 | 2.831 | 1 | 95.81 |
| 2511 | NZ | LYS | A | 341 | 66.808 | 79.05 | 2.76 | 1 | 96.07 |
| 2512 | N | ARG | A | 342 | 66.159 | 72.321 | 5.957 | 1 | 89.21 |
| 2513 | CA | ARG | A | 342 | 66.758 | 71.108 | 5.395 | 1 | 88.95 |
| 2514 | C | ARG | A | 342 | 65.911 | 69.868 | 5.677 | 1 | 87.46 |
| 2515 | O | ARG | A | 342 | 65.649 | 69.071 | 4.772 | 1 | 87.88 |
| 2516 | CB | ARG | A | 342 | 68.181 | 70.91 | 5.932 | 1 | 89.22 |
| 2517 | N | VAL | A | 343 | 65.503 | 69.701 | 6.935 | 1 | 84.84 |
| 2518 | CA | VAL | A | 343 | 64.675 | 68.566 | 7.332 | 1 | 82.31 |
| 2519 | C | VAL | A | 343 | 63.38 | 68.568 | 6.512 | 1 | 82.44 |
| 2520 | O | VAL | A | 343 | 62.898 | 67.511 | 6.095 | 1 | 83.25 |

Fig. 1-63

| ATOM | ATOM TYPE | RESIDUE | | # | X | Y | Z | OCC | B |
|---|---|---|---|---|---|---|---|---|---|
| 2521 | CB | VAL | A | 343 | 64.364 | 68.634 | 8.824 | 1 | 78.29 |
| 2522 | N | THR | A | 344 | 62.854 | 69.766 | 6.251 | 1 | 80.67 |
| 2523 | CA | THR | A | 344 | 61.627 | 69.949 | 5.478 | 1 | 77.41 |
| 2524 | C | THR | A | 344 | 61.846 | 69.587 | 4.018 | 1 | 77.01 |
| 2525 | O | THR | A | 344 | 61.12 | 68.759 | 3.467 | 1 | 75.78 |
| 2526 | CB | THR | A | 344 | 61.124 | 71.416 | 5.569 | 1 | 77.39 |
| 2527 | OG1 | THR | A | 344 | 60.759 | 71.713 | 6.923 | 1 | 77.62 |
| 2528 | CG2 | THR | A | 344 | 59.921 | 71.641 | 4.677 | 1 | 75.64 |
| 2529 | N | TYR | A | 345 | 62.852 | 70.211 | 3.403 | 1 | 77.47 |
| 2530 | CA | TYR | A | 345 | 63.193 | 69.974 | 1.996 | 1 | 76.55 |
| 2531 | C | TYR | A | 345 | 63.248 | 68.477 | 1.699 | 1 | 74.62 |
| 2532 | O | TYR | A | 345 | 62.768 | 68.028 | 0.664 | 1 | 74.1 |
| 2533 | CB | TYR | A | 345 | 64.538 | 70.626 | 1.665 | 1 | 76.48 |
| 2534 | CG | TYR | A | 345 | 64.883 | 70.636 | 0.195 | 1 | 79.82 |
| 2535 | CD1 | TYR | A | 345 | 64.058 | 71.276 | -0.727 | 1 | 81.53 |
| 2536 | CD2 | TYR | A | 345 | 66.039 | 70.007 | -0.278 | 1 | 81.39 |
| 2537 | CE1 | TYR | A | 345 | 64.369 | 71.29 | -2.094 | 1 | 83.78 |
| 2538 | CE2 | TYR | A | 345 | 66.363 | 70.014 | -1.642 | 1 | 82.74 |
| 2539 | CZ | TYR | A | 345 | 65.521 | 70.658 | -2.545 | 1 | 84.59 |
| 2540 | OH | TYR | A | 345 | 65.81 | 70.654 | -3.897 | 1 | 86.28 |
| 2541 | N | LYS | A | 346 | 63.81 | 67.715 | 2.636 | 1 | 75.04 |
| 2542 | CA | LYS | A | 346 | 63.928 | 66.265 | 2.513 | 1 | 74.66 |
| 2543 | C | LYS | A | 346 | 62.549 | 65.592 | 2.472 | 1 | 74.18 |
| 2544 | O | LYS | A | 346 | 62.288 | 64.749 | 1.614 | 1 | 75.1 |
| 2545 | CB | LYS | A | 346 | 64.767 | 65.71 | 3.66 | 1 | 72.9 |
| 2546 | N | GLU | A | 347 | 61.659 | 65.99 | 3.378 | 1 | 74.17 |
| 2547 | CA | GLU | A | 347 | 60.308 | 65.433 | 3.424 | 1 | 72.66 |
| 2548 | C | GLU | A | 347 | 59.482 | 65.854 | 2.209 | 1 | 72.93 |
| 2549 | O | GLU | A | 347 | 58.482 | 65.223 | 1.896 | 1 | 74.79 |
| 2550 | CB | GLU | A | 347 | 59.591 | 65.826 | 4.72 | 1 | 70.51 |
| 2551 | CG | GLU | A | 347 | 60.099 | 65.119 | 5.985 | 1 | 72.71 |
| 2552 | CD | GLU | A | 347 | 59.707 | 63.633 | 6.07 | 1 | 76.33 |
| 2553 | OE1 | GLU | A | 347 | 58.563 | 63.277 | 5.706 | 1 | 75.42 |
| 2554 | OE2 | GLU | A | 347 | 60.536 | 62.818 | 6.535 | 1 | 75.05 |
| 2555 | N | VAL | A | 348 | 59.898 | 66.916 | 1.525 | 1 | 72.95 |
| 2556 | CA | VAL | A | 348 | 59.183 | 67.384 | 0.338 | 1 | 73.7 |
| 2557 | C | VAL | A | 348 | 59.567 | 66.529 | -0.875 | 1 | 74.8 |
| 2558 | O | VAL | A | 348 | 58.71 | 66.081 | -1.642 | 1 | 74.45 |
| 2559 | CB | VAL | A | 348 | 59.493 | 68.883 | 0.02 | 1 | 71.95 |
| 2560 | CG1 | VAL | A | 348 | 58.76 | 69.319 | -1.23 | 1 | 68.63 |

Fig. 1-64

| ATOM | ATOM TYPE | RESIDUE | | # | X | Y | Z | OCC | B |
|---|---|---|---|---|---|---|---|---|---|
| 2561 | CG2 | VAL | A | 348 | 59.088 | 69.769 | 1.183 | 1 | 70.64 |
| 2562 | N | LEU | A | 349 | 60.864 | 66.286 | -1.025 | 1 | 75.31 |
| 2563 | CA | LEU | A | 349 | 61.366 | 65.506 | -2.142 | 1 | 73.24 |
| 2564 | C | LEU | A | 349 | 61.069 | 64.018 | -2.026 | 1 | 71.64 |
| 2565 | O | LEU | A | 349 | 61.005 | 63.323 | -3.037 | 1 | 72.52 |
| 2566 | CB | LEU | A | 349 | 62.866 | 65.734 | -2.305 | 1 | 74.06 |
| 2567 | CG | LEU | A | 349 | 63.296 | 67.181 | -2.558 | 1 | 74.01 |
| 2568 | CD1 | LEU | A | 349 | 64.79 | 67.214 | -2.831 | 1 | 74.92 |
| 2569 | CD2 | LEU | A | 349 | 62.532 | 67.775 | -3.733 | 1 | 73.53 |
| 2570 | N | SER | A | 350 | 60.882 | 63.535 | -0.801 | 1 | 69.25 |
| 2571 | CA | SER | A | 350 | 60.594 | 62.116 | -0.573 | 1 | 69.89 |
| 2572 | C | SER | A | 350 | 59.115 | 61.741 | -0.741 | 1 | 70.37 |
| 2573 | O | SER | A | 350 | 58.715 | 60.607 | -0.471 | 1 | 68.27 |
| 2574 | CB | SER | A | 350 | 61.096 | 61.671 | 0.815 | 1 | 70.53 |
| 2575 | OG | SER | A | 350 | 60.405 | 62.298 | 1.889 | 1 | 68.02 |
| 2576 | N | PHE | A | 351 | 58.314 | 62.679 | -1.232 | 1 | 69.89 |
| 2577 | CA | PHE | A | 351 | 56.898 | 62.419 | -1.396 | 1 | 69.52 |
| 2578 | C | PHE | A | 351 | 56.532 | 61.61 | -2.624 | 1 | 70.22 |
| 2579 | O | PHE | A | 351 | 56.872 | 61.976 | -3.748 | 1 | 69.53 |
| 2580 | CB | PHE | A | 351 | 56.113 | 63.721 | -1.417 | 1 | 67.98 |
| 2581 | CG | PHE | A | 351 | 54.63 | 63.52 | -1.457 | 1 | 65.98 |
| 2582 | CD1 | PHE | A | 351 | 53.958 | 63.017 | -0.349 | 1 | 68.72 |
| 2583 | CD2 | PHE | A | 351 | 53.907 | 63.808 | -2.598 | 1 | 63.74 |
| 2584 | CE1 | PHE | A | 351 | 52.592 | 62.805 | -0.384 | 1 | 65.61 |
| 2585 | CE2 | PHE | A | 351 | 52.544 | 63.6 | -2.64 | 1 | 64.05 |
| 2586 | CZ | PHE | A | 351 | 51.887 | 63.097 | -1.533 | 1 | 64.85 |
| 2587 | N | LYS | A | 352 | 55.793 | 60.531 | -2.395 | 1 | 70.08 |
| 2588 | CA | LYS | A | 352 | 55.334 | 59.674 | -3.476 | 1 | 71.74 |
| 2589 | C | LYS | A | 352 | 53.814 | 59.789 | -3.503 | 1 | 72.63 |
| 2590 | O | LYS | A | 352 | 53.152 | 59.52 - | 2.501 | 1 | 73.05 |
| 2591 | CB | LYS | A | 352 | 55.761 | 58.234 | -3.227 | 1 | 71.17 |
| 2592 | N | PRO | A | 353 | 53.244 | 60.221 | -4.641 | 1 | 73.37 |
| 2593 | CA | PRO | A | 353 | 51.804 | 60.405 | -4.87 | 1 | 76.13 |
| 2594 | C | PRO | A | 353 | 50.886 | 59.222 | -4.526 | 1 | 78.04 |
| 2595 | O | PRO | A | 353 | 51.403 | 58.154 | -4.134 | 1 | 79.75 |
| 2596 | CB | PRO | A | 353 | 51.747 | 60.745 | -6.355 | 1 | 76.14 |
| 2597 | CG | PRO | A | 353 | 53.007 | 61.522 | -6.56 | 1 | 75.41 |
| 2598 | CD | PRO | A | 353 | 54.014 | 60.675 | -5.813 | 1 | 74.92 |
| 2599 | OXT | PRO | A | 353 | 49.646 | 59.384 | -4.641 | 1 | 78.78 |
| 2600 | | PRO | A | 353 | | | | | |

Fig. 1-65

| ATOM | ATOM TYPE | RESIDUE | | # | X | Y | Z | OCC | B |
|---|---|---|---|---|---|---|---|---|---|
| 2601 | N | ARG | B | 1008 | 15.392 | 29.317 | 71.275 | 1 | 83.05 |
| 2602 | CA | ARG | B | 1008 | 14.307 | 28.341 | 70.997 | 1 | 83.28 |
| 2603 | C | ARG | B | 1008 | 14.782 | 27.225 | 70.048 | 1 | 84.92 |
| 2604 | O | ARG | B | 1008 | 15.892 | 27.289 | 69.491 | 1 | 85.42 |
| 2605 | CB | ARG | B | 1008 | 13.09 | 29.068 | 70.431 | 1 | 79.92 |
| 2606 | N | SER | B | 1009 | 13.957 | 26.183 | 69.917 | 1 | 84.43 |
| 2607 | CA | SER | B | 1009 | 14.251 | 25.03 | 69.064 | 1 | 82.74 |
| 2608 | C | SER | B | 1009 | 12.961 | 24.248 | 68.825 | 1 | 81.88 |
| 2609 | O | SER | B | 1009 | 12.018 | 24.341 | 69.621 | 1 | 82.17 |
| 2610 | CB | SER | B | 1009 | 15.29 | 24.126 | 69.728 | 1 | 85.86 |
| 2611 | OG | SER | B | 1009 | 15.746 | 23.124 | 68.834 | 1 | 89.93 |
| 2612 | N | GLY | B | 1010 | 12.938 | 23.461 | 67.746 | 1 | 79.73 |
| 2613 | CA | GLY | B | 1010 | 11.755 | 22.687 | 67.393 | 1 | 75.86 |
| 2614 | C | GLY | B | 1010 | 10.933 | 23.446 | 66.363 | 1 | 74.57 |
| 2615 | O | GLY | B | 1010 | 11.497 | 24.194 | 65.55 | 1 | 74.45 |
| 2616 | N | PHE | B | 1011 | 9.612 | 23.255 | 66.377 | 1 | 71.17 |
| 2617 | CA | PHE | B | 1011 | 8.712 | 23.944 | 65.445 | 1 | 67.53 |
| 2618 | C | PHE | B | 1011 | 7.493 | 24.464 | 66.178 | 1 | 68.57 |
| 2619 | O | PHE | B | 1011 | 7.383 | 24.316 | 67.392 | 1 | 70.69 |
| 2620 | CB | PHE | B | 1011 | 8.254 | 23.023 | 64.31 | 1 | 61.94 |
| 2621 | CG | PHE | B | 1011 | 9.338 | 22.666 | 63.343 | 1 | 59.04 |
| 2622 | CD1 | PHE | B | 1011 | 10.255 | 21.653 | 63.641 | 1 | 60.36 |
| 2623 | CD2 | PHE | B | 1011 | 9.45 | 23.335 | 62.132 | 1 | 59.42 |
| 2624 | CE1 | PHE | B | 1011 | 11.278 | 21.306 | 62.743 | 1 | 60.46 |
| 2625 | CE2 | PHE | B | 1011 | 10.47 | 23.003 | 61.213 | 1 | 62.65 |
| 2626 | CZ | PHE | B | 1011 | 11.389 | 21.981 | 61.522 | 1 | 61.24 |
| 2627 | N | TYR | B | 1012 | 6.608 | 25.12 | 65.44 | 1 | 69.65 |
| 2628 | CA | TYR | B | 1012 | 5.375 | 25.653 | 65.998 | 1 | 73.68 |
| 2629 | C | TYR | B | 1012 | 4.446 | 26.096 | 64.871 | 1 | 76.63 |
| 2630 | O | TYR | B | 1012 | 4.886 | 26.28 | 63.735 | 1 | 77.42 |
| 2631 | CB | TYR | B | 1012 | 5.638 | 26.759 | 67.037 | 1 | 74.22 |
| 2632 | CG | TYR | B | 1012 | 5.747 | 28.185 | 66.54 | 1 | 76.73 |
| 2633 | CD1 | TYR | B | 1012 | 6.984 | 28.732 | 66.202 | 1 | 76.4 |
| 2634 | CD2 | TYR | B | 1012 | 4.629 | 29.017 | 66.511 | 1 | 77.35 |
| 2635 | CE1 | TYR | B | 1012 | 7.112 | 30.075 | 65.86 | 1 | 78.03 |
| 2636 | CE2 | TYR | B | 1012 | 4.742 | 30.358 | 66.167 | 1 | 80.11 |
| 2637 | CZ | TYR | B | 1012 | 5.988 | 30.887 | 65.848 | 1 | 79.91 |
| 2638 | OH | TYR | B | 1012 | 6.108 | 32.231 | 65.556 | 1 | 79.31 |
| 2639 | N | ARG | B | 1013 | 3.16 | 26.244 | 65.18 | 1 | 79.26 |
| 2640 | CA | ARG | B | 1013 | 2.177 | 26.589 | 64.159 | 1 | 81.64 |

Fig. 1-66

| ATOM | ATOM TYPE | RESIDUE | | # | X | Y | Z | OCC | B |
|---|---|---|---|---|---|---|---|---|---|
| 2641 | C | ARG | B | 1013 | 1.4 | 27.85 | 64.478 | 1 | 82.41 |
| 2642 | O | ARG | B | 1013 | 1.181 | 28.173 | 65.643 | 1 | 82.46 |
| 2643 | CB | ARG | B | 1013 | 1.217 | 25.422 | 63.978 | 1 | 83.6 |
| 2644 | CG | ARG | B | 1013 | 1.889 | 24.058 | 64.054 | 1 | 89.93 |
| 2645 | CD | ARG | B | 1013 | 0.806 | 23.013 | 64.153 | 1 | 95.11 |
| 2646 | NE | ARG | B | 1013 | 0.367 | 22.626 | 62.863 | 1 | 97.65 |
| 2647 | CZ | ARG | B | 1013 | -0.628 | 22.871 | 62.023 | 1 | 98.87 |
| 2648 | NH1 | ARG | B | 1013 | -1.694 | 23.657 | 62.174 | 1 | 100 |
| 2649 | NH2 | ARG | B | 1013 | -0.45 | 22.207 | 60.898 | 1 | 97.49 |
| 2650 | N | GLN | B | 1014 | 0.971 | 28.553 | 63.433 | 1 | 84.44 |
| 2651 | CA | GLN | B | 1014 | 0.217 | 29.791 | 63.611 | 1 | 86.4 |
| 2652 | C | GLN | B | 1014 | -0.744 | 30.103 | 62.47 | 1 | 87.23 |
| 2653 | O | GLN | B | 1014 | -0.535 | 29.714 | 61.321 | 1 | 85.7 |
| 2654 | CB | GLN | B | 1014 | 1.175 | 30.982 | 63.798 | 1 | 85.77 |
| 2655 | CG | GLN | B | 1014 | 0.482 | 32.265 | 64.231 | 1 | 85.42 |
| 2656 | CD | GLN | B | 1014 | 1.43 | 33.439 | 64.38 | 1 | 87.14 |
| 2657 | OE1 | GLN | B | 1014 | 1.093 | 34.568 | 64.013 | 1 | 84.55 |
| 2658 | NE2 | GLN | B | 1014 | 2.616 | 33.188 | 64.936 | 1 | 88.89 |
| 2659 | N | GLU | B | 1015 | -1.826 | 30.779 | 62.831 | 1 | 90.63 |
| 2660 | CA | GLU | B | 1015 | -2.848 | 31.213 | 61.89 | 1 | 94.09 |
| 2661 | C | GLU | B | 1015 | -2.388 | 32.564 | 61.377 | 1 | 96.22 |
| 2662 | O | GLU | B | 1015 | -2.318 | 33.531 | 62.142 | 1 | 97.87 |
| 2663 | CB | GLU | B | 1015 | -4.184 | 31.399 | 62.619 | 1 | 95.54 |
| 2664 | CG | GLU | B | 1015 | -4.057 | 32.143 | 63.968 | 1 | 99.7 |
| 2665 | CD | GLU | B | 1015 | -5.372 | 32.746 | 64.473 | 1 | 100 |
| 2666 | OE1 | GLU | B | 1015 | -6.287 | 31.966 | 64.845 | 1 | 100 |
| 2667 | OE2 | GLU | B | 1015 | -5.474 | 34.001 | 64.518 | 1 | 100 |
| 2668 | N | VAL | B | 1016 | -2.019 | 32.636 | 60.107 | 1 | 97.88 |
| 2669 | CA | VAL | B | 1016 | -1.588 | 33.919 | 59.565 | 1 | 99.97 |
| 2670 | C | VAL | B | 1016 | -2.798 | 34.646 | 58.96 | 1 | 100 |
| 2671 | O | VAL | B | 1016 | -3.478 | 35.414 | 59.659 | 1 | 100 |
| 2672 | CB | VAL | B | 1016 | -0.418 | 33.757 | 58.571 | 1 | 100 |
| 2673 | CG1 | VAL | B | 1016 | -0.013 | 35.12 | 58.006 | 1 | 100 |
| 2674 | CG2 | VAL | B | 1016 | 0.767 | 33.161 | 59.3 | 1 | 98.23 |
| 2675 | N | THR | B | 1017 | -3.047 | 34.451 | 57.669 | 1 | 99.17 |
| 2676 | CA | THR | B | 1017 | -4.221 | 35.064 | 57.068 | 1 | 99.53 |
| 2677 | C | THR | B | 1017 | -5.262 | 33.954 | 57.11 | 1 | 100 |
| 2678 | O | THR | B | 1017 | -5.856 | 33.693 | 58.166 | 1 | 100 |
| 2679 | CB | THR | B | 1017 | -3.979 | 35.538 | 55.624 | 1 | 99.86 |
| 2680 | OG1 | THR | B | 1017 | -2.826 | 34.876 | 55.081 | 1 | 100 |

Fig. 1-67

| ATOM | ATOM TYPE | RESIDUE | | # | X | Y | Z | OCC | B |
|---|---|---|---|---|---|---|---|---|---|
| 2681 | CG2 | THR | B | 1017 | -3.802 | 37.059 | 55.586 | 1 | 97.41 |
| 2682 | N | LYS | B | 1018 | -5.42 | 33.249 | 55.992 | 1 | 100 |
| 2683 | CA | LYS | B | 1018 | -6.361 | 32.141 | 55.915 | 1 | 99.37 |
| 2684 | C | LYS | B | 1018 | -5.574 | 30.839 | 56.041 | 1 | 98.26 |
| 2685 | O | LYS | B | 1018 | -6.108 | 29.802 | 56.441 | 1 | 99.14 |
| 2686 | CB | LYS | B | 1018 | -7.118 | 32.184 | 54.581 | 1 | 100 |
| 2687 | N | THR | B | 1019 | -4.277 | 30.932 | 55.766 | 1 | 96.74 |
| 2688 | CA | THR | B | 1019 | -3.387 | 29.771 | 55.8 | 1 | 94.46 |
| 2689 | C | THR | B | 1019 | -2.738 | 29.458 | 57.137 | 1 | 91.56 |
| 2690 | O | THR | B | 1019 | -2.628 | 30.323 | 58.016 | 1 | 92.58 |
| 2691 | CB | THR | B | 1019 | -2.238 | 29.922 | 54.784 | 1 | 95.45 |
| 2692 | OG1 | THR | B | 1019 | -2.502 | 31.034 | 53.911 | 1 | 99.16 |
| 2693 | CG2 | THR | B | 1019 | -2.074 | 28.641 | 53.969 | 1 | 94.6 |
| 2694 | N | ALA | B | 1020 | -2.271 | 28.213 | 57.252 | 1 | 87.6 |
| 2695 | CA | ALA | B | 1020 | -1.59 | 27.743 | 58.453 | 1 | 84.33 |
| 2696 | C | ALA | B | 1020 | -0.139 | 27.431 | 58.153 | 1 | 81.1 |
| 2697 | O | ALA | B | 1020 | 0.171 | 26.651 | 57.24 | 1 | 78.36 |
| 2698 | CB | ALA | B | 1020 | -2.267 | 26.522 | 59.007 | 1 | 83.52 |
| 2699 | N | TRP | B | 1021 | 0.735 | 28.034 | 58.954 | 1 | 79.36 |
| 2700 | CA | TRP | B | 1021 | 2.174 | 27.871 | 58.813 | 1 | 77.91 |
| 2701 | C | TRP | B | 1021 | 2.716 | 27.026 | 59.942 | 1 | 74.81 |
| 2702 | O | TRP | B | 1021 | 2.159 | 27.02 | 61.029 | 1 | 73.4 |
| 2703 | CB | TRP | B | 1021 | 2.857 | 29.231 | 58.888 | 1 | 81.21 |
| 2704 | CG | TRP | B | 1021 | 2.419 | 30.198 | 57.877 | 1 | 83.81 |
| 2705 | CD1 | TRP | B | 1021 | 1.155 | 30.652 | 57.673 | 1 | 85.5 |
| 2706 | CD2 | TRP | B | 1021 | 3.259 | 30.917 | 56.977 | 1 | 86.46 |
| 2707 | NE1 | TRP | B | 1021 | 1.154 | 31.63 | 56.709 | 1 | 87.55 |
| 2708 | CE2 | TRP | B | 1021 | 2.436 | 31.809 | 56.263 | 1 | 88.07 |
| 2709 | CE3 | TRP | B | 1021 | 4.634 | 30.9 | 56.712 | 1 | 87.08 |
| 2710 | CZ2 | TRP | B | 1021 | 2.94 | 32.679 | 55.298 | 1 | 88.43 |
| 2711 | CZ3 | TRP | B | 1021 | 5.136 | 31.765 | 55.754 | 1 | 88.61 |
| 2712 | CH2 | TRP | B | 1021 | 4.288 | 32.643 | 55.058 | 1 | 89.09 |
| 2713 | N | GLU | B | 1022 | 3.812 | 26.325 | 59.682 | 1 | 72.48 |
| 2714 | CA | GLU | B | 1022 | 4.451 | 25.509 | 60.704 | 1 | 73.8 |
| 2715 | C | GLU | B | 1022 | 5.936 | 25.824 | 60.635 | 1 | 71.25 |
| 2716 | O | GLU | B | 1022 | 6.738 | 25.001 | 60.196 | 1 | 71.35 |
| 2717 | CB | GLU | B | 1022 | 4.206 | 24.007 | 60.474 | 1 | 79.31 |
| 2718 | CG | GLU | B | 1022 | 4.517 | 23.095 | 61.701 | 1 | 84.5 |
| 2719 | CD | GLU | B | 1022 | 4.301 | 21.588 | 61.443 | 1 | 85.91 |
| 2720 | OE1 | GLU | B | 1022 | 3.614 | 21.221 | 60.456 | 1 | 85.61 |

Fig. 1-68

| ATOM | ATOM TYPE | RESIDUE | | # | X | Y | Z | OCC | B |
|---|---|---|---|---|---|---|---|---|---|
| 2721 | OE2 | GLU | B | 1022 | 4.828 | 20.772 | 62.235 | 1 | 85.16 |
| 2722 | N | VAL | B | 1023 | 6.29 | 27.034 | 61.052 | 1 | 67.98 |
| 2723 | CA | VAL | B | 1023 | 7.676 | 27.489 | 61.027 | 1 | 65.19 |
| 2724 | C | VAL | B | 1023 | 8.494 | 26.977 | 62.217 | 1 | 65.74 |
| 2725 | O | VAL | B | 1023 | 7.983 | 26.244 | 63.065 | 1 | 66.88 |
| 2726 | CB | VAL | B | 1023 | 7.712 | 29 | 61.026 | 1 | 62.43 |
| 2727 | CG1 | VAL | B | 1023 | 6.959 | 29.513 | 59.825 | 1 | 61.52 |
| 2728 | CG2 | VAL | B | 1023 | 7.098 | 29.527 | 62.307 | 1 | 58.2 |
| 2729 | N | ARG | B | 1024 | 9.777 | 27.323 | 62.261 | 1 | 64.48 |
| 2730 | CA | ARG | B | 1024 | 10.619 | 26.898 | 63.375 | 1 | 61.55 |
| 2731 | C | ARG | B | 1024 | 10.345 | 27.797 | 64.562 | 1 | 61.75 |
| 2732 | O | ARG | B | 1024 | 9.95 | 28.958 | 64.392 | 1 | 61.74 |
| 2733 | CB | ARG | B | 1024 | 12.091 | 26.978 | 63.02 | 1 | 60.44 |
| 2734 | CG | ARG | B | 1024 | 12.504 | 25.966 | 62.016 | 1 | 57.18 |
| 2735 | CD | ARG | B | 1024 | 13.98 | 26.016 | 61.83 | 1 | 58.85 |
| 2736 | NE | ARG | B | 1024 | 14.41 | 25.011 | 60.87 | 1 | 60.61 |
| 2737 | CZ | ARG | B | 1024 | 15.62 | 24.972 | 60.329 | 1 | 61.41 |
| 2738 | NH1 | ARG | B | 1024 | 16.526 | 25.883 | 60.674 | 1 | 66.93 |
| 2739 | NH2 | ARG | B | 1024 | 15.924 | 24.028 | 59.449 | 1 | 56.73 |
| 2740 | N | ALA | B | 1025 | 10.567 | 27.252 | 65.759 | 1 | 60.76 |
| 2741 | CA | ALA | B | 1025 | 10.329 | 27.965 | 67.012 | 1 | 57.56 |
| 2742 | C | ALA | B | 1025 | 11.127 | 29.244 | 67.089 | 1 | 54.88 |
| 2743 | O | ALA | B | 1025 | 10.67 | 30.252 | 67.628 | 1 | 56.15 |
| 2744 | CB | ALA | B | 1025 | 10.661 | 27.071 | 68.192 | 1 | 59.62 |
| 2745 | N | VAL | B | 1026 | 12.311 | 29.197 | 66.499 | 1 | 52.15 |
| 2746 | CA | VAL | B | 1026 | 13.228 | 30.317 | 66.48 | 1 | 50.17 |
| 2747 | C | VAL | B | 1026 | 12.692 | 31.528 | 65.713 | 1 | 49.17 |
| 2748 | O | VAL | B | 1026 | 12.807 | 32.658 | 66.179 | 1 | 46.54 |
| 2749 | CB | VAL | B | 1026 | 14.575 | 29.85 | 65.964 | 1 | 49.05 |
| 2750 | CG1 | VAL | B | 1026 | 14.742 | 30.139 | 64.484 | 1 | 48.71 |
| 2751 | CG2 | VAL | B | 1026 | 15.649 | 30.434 | 66.796 | 1 | 53.91 |
| 2752 | N | TYR | B | 1027 | 12.079 | 31.279 | 64.555 | 1 | 49.98 |
| 2753 | CA | TYR | B | 1027 | 11.488 | 32.344 | 63.734 | 1 | 51.49 |
| 2754 | C | TYR | B | 1027 | 10.266 | 32.797 | 64.48 | 1 | 52.19 |
| 2755 | O | TYR | B | 1027 | 9.315 | 32.035 | 64.62 | 1 | 53.66 |
| 2756 | CB | TYR | B | 1027 | 11.121 | 31.845 | 62.326 | 1 | 43.78 |
| 2757 | CG | TYR | B | 1027 | 12.35 | 31.484 | 61.54 | 1 | 40.04 |
| 2758 | CD1 | TYR | B | 1027 | 13.39 | 32.403 | 61.398 | 1 | 33.52 |
| 2759 | CD2 | TYR | B | 1027 | 12.523 | 30.195 | 61.026 | 1 | 40.23 |
| 2760 | CE1 | TYR | B | 1027 | 14.576 | 32.047 | 60.782 | 1 | 37.28 |

Fig. 1-69

| ATOM | ATOM TYPE | RESIDUE | | # | X | Y | Z | OCC | B |
|---|---|---|---|---|---|---|---|---|---|
| 2761 | CE2 | TYR | B | 1027 | 13.71 | 29.823 | 60.392 | 1 | 41.78 |
| 2762 | CZ | TYR | B | 1027 | 14.738 | 30.754 | 60.276 | 1 | 42.27 |
| 2763 | OH | TYR | B | 1027 | 15.928 | 30.4 | 59.666 | 1 | 40.36 |
| 2764 | N | ARG | B | 1028 | 10.301 | 34.036 | 64.954 | 1 | 53.3 |
| 2765 | CA | ARG | B | 1028 | 9.219 | 34.571 | 65.746 | 1 | 56.32 |
| 2766 | C | ARG | B | 1028 | 8.473 | 35.767 | 65.169 | 1 | 58.02 |
| 2767 | O | ARG | B | 1028 | 8.881 | 36.338 | 64.164 | 1 | 58.88 |
| 2768 | CB | ARG | B | 1028 | 9.779 | 34.902 | 67.128 | 1 | 63.3 |
| 2769 | CG | ARG | B | 1028 | 10.518 | 33.704 | 67.758 | 1 | 69.98 |
| 2770 | CD | ARG | B | 1028 | 10.844 | 33.91 | 69.234 | 1 | 78.35 |
| 2771 | NE | ARG | B | 1028 | 9.665 | 34.345 | 69.984 | 1 | 84.1 |
| 2772 | CZ | ARG | B | 1028 | 9.703 | 35.023 | 71.13 | 1 | 86.57 |
| 2773 | NH1 | ARG | B | 1028 | 10.865 | 35.347 | 71.685 | 1 | 86.22 |
| 2774 | NH2 | ARG | B | 1028 | 8.574 | 35.411 | 71.704 | 1 | 84.89 |
| 2775 | N | ASP | B | 1029 | 7.366 | 36.12 | 65.821 | 1 | 61.08 |
| 2776 | CA | ASP | B | 1029 | 6.467 | 37.216 | 65.434 | 1 | 60.46 |
| 2777 | C | ASP | B | 1029 | 6.184 | 37.324 | 63.937 | 1 | 61.99 |
| 2778 | O | ASP | B | 1029 | 6.596 | 38.29 | 63.29 | 1 | 64.59 |
| 2779 | CB | ASP | B | 1029 | 6.963 | 38.56 | 65.975 | 1 | 61.19 |
| 2780 | CG | ASP | B | 1029 | 5.962 | 39.7 | 65.736 | 1 | 64.61 |
| 2781 | OD1 | ASP | B | 1029 | 4.752 | 39.427 | 65.602 | 1 | 66.52 |
| 2782 | OD2 | ASP | B | 1029 | 6.38 | 40.877 | 65.68 | 1 | 63.58 |
| 2783 | N | LEU | B | 1030 | 5.452 | 36.346 | 63.4 | 1 | 62.42 |
| 2784 | CA | LEU | B | 1030 | 5.102 | 36.317 | 61.979 | 1 | 59.79 |
| 2785 | C | LEU | B | 1030 | 4.113 | 37.408 | 61.58 | 1 | 61.03 |
| 2786 | O | LEU | B | 1030 | 3.206 | 37.74 | 62.326 | 1 | 62.72 |
| 2787 | CB | LEU | B | 1030 | 4.546 | 34.951 | 61.588 | 1 | 53.81 |
| 2788 | CG | LEU | B | 1030 | 5.494 | 33.753 | 61.569 | 1 | 54.22 |
| 2789 | CD1 | LEU | B | 1030 | 4.73 | 32.506 | 61.178 | 1 | 55.1 |
| 2790 | CD2 | LEU | B | 1030 | 6.597 | 33.966 | 60.577 | 1 | 55.29 |
| 2791 | N | GLN | B | 1031 | 4.315 | 37.967 | 60.393 | 1 | 64.68 |
| 2792 | CA | GLN | B | 1031 | 3.466 | 39.025 | 59.844 | 1 | 66.39 |
| 2793 | C | GLN | B | 1031 | 3.441 | 38.849 | 58.326 | 1 | 68.35 |
| 2794 | O | GLN | B | 1031 | 4.491 | 38.772 | 57.682 | 1 | 67.74 |
| 2795 | CB | GLN | B | 1031 | 4.044 | 40.405 | 60.16 | 1 | 67.52 |
| 2796 | CG | GLN | B | 1031 | 4.037 | 40.788 | 61.622 | 1 | 69.37 |
| 2797 | CD | GLN | B | 1031 | 2.655 | 41.127 | 62.108 | 1 | 70.2 |
| 2798 | OE1 | GLN | B | 1031 | 2.198 | 40.598 | 63.122 | 1 | 69.64 |
| 2799 | NE2 | GLN | B | 1031 | 1.975 | 42.022 | 61.388 | 1 | 69.2 |
| 2800 | N | PRO | B | 1032 | 2.239 | 38.816 | 57.733 | 1 | 68.45 |

Fig. 1-70

| ATOM | ATOM TYPE | RESIDUE | | # | X | Y | Z | OCC | B |
|---|---|---|---|---|---|---|---|---|---|
| 2801 | CA | PRO | B | 1032 | 2.06 | 38.652 | 56.289 | 1 | 68.35 |
| 2802 | C | PRO | B | 1032 | 2.523 | 39.887 | 55.52 | 1 | 66.87 |
| 2803 | O | PRO | B | 1032 | 2.544 | 40.992 | 56.066 | 1 | 67.31 |
| 2804 | CB | PRO | B | 1032 | 0.549 | 38.485 | 56.171 | 1 | 69.44 |
| 2805 | CG | PRO | B | 1032 | 0.061 | 39.446 | 57.216 | 1 | 67.89 |
| 2806 | CD | PRO | B | 1032 | 0.947 | 39.083 | 58.387 | 1 | 69.43 |
| 2807 | N | VAL | B | 1033 | 2.887 | 39.688 | 54.257 | 1 | 64.21 |
| 2808 | CA | VAL | B | 1033 | 3.333 | 40.775 | 53.39 | 1 | 63.04 |
| 2809 | C | VAL | B | 1033 | 3.004 | 40.457 | 51.934 | 1 | 67.16 |
| 2810 | O | VAL | B | 1033 | 2.912 | 41.424 | 51.129 | 1 | 68.52 |
| 2811 | CB | VAL | B | 1033 | 4.853 | 41.025 | 53.497 | 1 | 60.21 |
| 2812 | CG1 | VAL | B | 1033 | 5.16 | 41.909 | 54.675 | 1 | 61.04 |
| 2813 | CG2 | VAL | B | 1033 | 5.615 | 39.705 | 53.595 | 1 | 57.1 |
| 2814 | OXT | VAL | B | 1033 | 2.842 | 39.243 | 51.623 | 1 | 69.07 |
| 2815 | N | ALA | B | 1040 | 2.347 | 32.902 | 49.519 | 1 | 58.98 |
| 2816 | CA | ALA | B | 1040 | 2.347 | 33.811 | 50.696 | 1 | 58.02 |
| 2817 | C | ALA | B | 1040 | 3.704 | 33.817 | 51.416 | 1 | 56.39 |
| 2818 | O | ALA | B | 1040 | 4.386 | 32.793 | 51.559 | 1 | 56.11 |
| 2819 | CB | ALA | B | 1040 | 1.208 | 33.469 | 51.658 | 1 | 56.78 |
| 2820 | N | VAL | B | 1041 | 4.089 | 35.015 | 51.826 | 1 | 53.11 |
| 2821 | CA | VAL | B | 1041 | 5.348 | 35.262 | 52.488 | 1 | 51.25 |
| 2822 | C | VAL | B | 1041 | 5.056 | 36.015 | 53.769 | 1 | 51.9 |
| 2823 | O | VAL | B | 1041 | 4.111 | 36.83 | 53.833 | 1 | 51.33 |
| 2824 | CB | VAL | B | 1041 | 6.248 | 36.146 | 51.588 | 1 | 49.54 |
| 2825 | CG1 | VAL | B | 1041 | 7.51 | 36.559 | 52.307 | 1 | 49.63 |
| 2826 | CG2 | VAL | B | 1041 | 6.587 | 35.412 | 50.315 | 1 | 47.38 |
| 2827 | N | CYS | B | 1042 | 5.873 | 35.742 | 54.782 | 1 | 49.82 |
| 2828 | CA | CYS | B | 1042 | 5.736 | 36.399 | 56.066 | 1 | 51.12 |
| 2829 | C | CYS | B | 1042 | 7.04 | 37.024 | 56.515 | 1 | 50.9 |
| 2830 | O | CYS | B | 1042 | 8.134 | 36.541 | 56.187 | 1 | 51.95 |
| 2831 | CB | CYS | B | 1042 | 5.278 | 35.402 | 57.135 | 1 | 54.35 |
| 2832 | SG | CYS | B | 1042 | 3.513 | 35.225 | 57.304 | 1 | 55.44 |
| 2833 | N | SER | B | 1043 | 6.913 | 38.093 | 57.285 | 1 | 49.19 |
| 2834 | CA | SER | B | 1043 | 8.067 | 38.754 | 57.837 | 1 | 49.38 |
| 2835 | C | SER | B | 1043 | 8.149 | 38.277 | 59.287 | 1 | 52.16 |
| 2836 | O | SER | B | 1043 | 7.215 | 38.462 | 60.059 | 1 | 54.98 |
| 2837 | CB | SER | B | 1043 | 7.907 | 40.281 | 57.76 | 1 | 47.15 |
| 2838 | OG | SER | B | 1043 | 6.884 | 40.777 | 58.609 | 1 | 38.5 |
| 2839 | N | ALA | B | 1044 | 9.232 | 37.597 | 59.632 | 1 | 52.48 |
| 2840 | CA | ALA | B | 1044 | 9.426 | 37.112 | 60.988 | 1 | 51.72 |

Fig. 1-71

| ATOM | ATOM TYPE | RESIDUE | | # | X | Y | Z | OCC | B |
|---|---|---|---|---|---|---|---|---|---|
| 2841 | C | ALA | B | 1044 | 10.672 | 37.762 | 61.587 | 1 | 52.53 |
| 2842 | O | ALA | B | 1044 | 11.23 | 38.689 | 61.008 | 1 | 55.34 |
| 2843 | CB | ALA | B | 1044 | 9.585 | 35.623 | 60.963 | 1 | 52.76 |
| 2844 | N | VAL | B | 1045 | 11.077 | 37.299 | 62.766 | 1 | 50.78 |
| 2845 | CA | VAL | B | 1045 | 12.276 | 37.798 | 63.426 | 1 | 50.51 |
| 2846 | C | VAL | B | 1045 | 13.061 | 36.58 | 63.847 | 1 | 52.51 |
| 2847 | O | VAL | B | 1045 | 12.48 | 35.646 | 64.383 | 1 | 55.24 |
| 2848 | CB | VAL | B | 1045 | 11.956 | 38.552 | 64.702 | 1 | 49.88 |
| 2849 | CG1 | VAL | B | 1045 | 13.252 | 38.976 | 65.38 | 1 | 46.66 |
| 2850 | CG2 | VAL | B | 1045 | 11.045 | 39.741 | 64.404 | 1 | 48.94 |
| 2851 | N | ASP | B | 1046 | 14.358 | 36.534 | 63.56 | 1 | 52.69 |
| 2852 | CA | ASP | B | 1046 | 15.116 | 35.376 | 64.003 | 1 | 52.1 |
| 2853 | C | ASP | B | 1046 | 15.274 | 35.628 | 65.494 | 1 | 55.1 |
| 2854 | O | ASP | B | 1046 | 15.903 | 36.604 | 65.911 | 1 | 54.02 |
| 2855 | CB | ASP | B | 1046 | 16.473 | 35.29 | 63.327 | 1 | 50.62 |
| 2856 | CG | ASP | B | 1046 | 17.168 | 33.976 | 63.6 | 1 | 53.2 |
| 2857 | OD1 | ASP | B | 1046 | 16.811 | 33.305 | 64.59 | 1 | 55.53 |
| 2858 | OD2 | ASP | B | 1046 | 18.075 | 33.602 | 62.825 | 1 | 55.04 |
| 2859 | N | GLY | B | 1047 | 14.62 | 34.79 | 66.291 | 1 | 55.42 |
| 2860 | CA | GLY | B | 1047 | 14.667 | 34.953 | 67.733 | 1 | 53.43 |
| 2861 | C | GLY | B | 1047 | 16.078 | 34.95 | 68.258 | 1 | 54.89 |
| 2862 | O | GLY | B | 1047 | 16.361 | 35.559 | 69.286 | 1 | 59.29 |
| 2863 | N | ARG | B | 1048 | 16.96 | 34.266 | 67.543 | 1 | 52.22 |
| 2864 | CA | ARG | B | 1048 | 18.352 | 34.175 | 67.926 | 1 | 54.57 |
| 2865 | C | ARG | B | 1048 | 19.189 | 35.457 | 67.767 | 1 | 55.48 |
| 2866 | O | ARG | B | 1048 | 20.173 | 35.646 | 68.488 | 1 | 57.76 |
| 2867 | CB | ARG | B | 1048 | 19.017 | 33.07 | 67.117 | 1 | 55.1 |
| 2868 | CG | ARG | B | 1048 | 18.525 | 31.692 | 67.436 | 1 | 52.83 |
| 2869 | CD | ARG | B | 1048 | 19.044 | 30.726 | 66.411 | 1 | 50.53 |
| 2870 | NE | ARG | B | 1048 | 18.397 | 30.965 | 65.126 | 1 | 52.56 |
| 2871 | CZ | ARG | B | 1048 | 18.608 | 30.244 | 64.03 | 1 | 51.67 |
| 2872 | NH1 | ARG | B | 1048 | 19.461 | 29.227 | 64.049 | 1 | 53.11 |
| 2873 | NH2 | ARG | B | 1048 | 17.954 | 30.532 | 62.919 | 1 | 52.77 |
| 2874 | N | THR | B | 1049 | 18.829 | 36.321 | 66.818 | 1 | 55.31 |
| 2875 | CA | THR | B | 1049 | 19.617 | 37.526 | 66.583 | 1 | 52.48 |
| 2876 | C | THR | B | 1049 | 18.921 | 38.858 | 66.674 | 1 | 53.13 |
| 2877 | O | THR | B | 1049 | 19.552 | 39.845 | 67.057 | 1 | 58.57 |
| 2878 | CB | THR | B | 1049 | 20.362 | 37.459 | 65.253 | 1 | 53.85 |
| 2879 | OG1 | THR | B | 1049 | 19.424 | 37.397 | 64.171 | 1 | 54.93 |
| 2880 | CG2 | THR | B | 1049 | 21.297 | 36.24 | 65.228 | 1 | 52.75 |

Fig. 1-72

| ATOM | ATOM TYPE | RESIDUE | | # | X | Y | Z | OCC | B |
|---|---|---|---|---|---|---|---|---|---|
| 2881 | N | GLY | B | 1050 | 17.643 | 38.906 | 66.311 | 1 | 54 |
| 2882 | CA | GLY | B | 1050 | 16.889 | 40.154 | 66.385 | 1 | 52.59 |
| 2883 | C | GLY | B | 1050 | 16.698 | 40.799 | 65.023 | 1 | 53.82 |
| 2884 | O | GLY | B | 1050 | 16.094 | 41.88 | 64.901 | 1 | 51.92 |
| 2885 | N | ALA | B | 1051 | 17.2 | 40.103 | 64.004 | 1 | 50.7 |
| 2886 | CA | ALA | B | 1051 | 17.148 | 40.552 | 62.623 | 1 | 52.2 |
| 2887 | C | ALA | B | 1051 | 15.856 | 40.123 | 61.918 | 1 | 53.58 |
| 2888 | O | ALA | B | 1051 | 15.524 | 38.931 | 61.937 | 1 | 53.97 |
| 2889 | CB | ALA | B | 1051 | 18.354 | 39.981 | 61.876 | 1 | 49.63 |
| 2890 | N | LYS | B | 1052 | 15.143 | 41.077 | 61.297 | 1 | 50.05 |
| 2891 | CA | LYS | B | 1052 | 13.917 | 40.765 | 60.553 | 1 | 45.76 |
| 2892 | C | LYS | B | 1052 | 14.285 | 39.87 | 59.39 | 1 | 45.14 |
| 2893 | O | LYS | B | 1052 | 15.336 | 40.031 | 58.757 | 1 | 44.51 |
| 2894 | CB | LYS | B | 1052 | 13.199 | 42.012 | 60.035 | 1 | 44.02 |
| 2895 | CG | LYS | B | 1052 | 12.616 | 42.884 | 61.127 | 1 | 51.41 |
| 2896 | CD | LYS | B | 1052 | 11.984 | 44.183 | 60.604 | 1 | 56.7 |
| 2897 | CE | LYS | B | 1052 | 10.575 | 43.968 | 60.069 | 1 | 60.61 |
| 2898 | NZ | LYS | B | 1052 | 9.957 | 45.254 | 59.614 | 1 | 61.15 |
| 2899 | N | VAL | B | 1053 | 13.406 | 38.913 | 59.13 | 1 | 45.74 |
| 2900 | CA | VAL | B | 1053 | 13.607 | 37.921 | 58.095 | 1 | 43.54 |
| 2901 | C | VAL | B | 1053 | 12.327 | 37.752 | 57.285 | 1 | 42.33 |
| 2902 | O | VAL | B | 1053 | 11.263 | 38.192 | 57.707 | 1 | 43.53 |
| 2903 | CB | VAL | B | 1053 | 14.026 | 36.607 | 58.784 | 1 | 42.05 |
| 2904 | CG1 | VAL | B | 1053 | 13.293 | 35.404 | 58.222 | 1 | 44.58 |
| 2905 | CG2 | VAL | B | 1053 | 15.516 | 36.439 | 58.677 | 1 | 43.33 |
| 2906 | N | ALA | B | 1054 | 12.453 | 37.217 | 56.078 | 1 | 40.46 |
| 2907 | CA | ALA | B | 1054 | 11.287 | 36.955 | 55.24 | 1 | 41.2 |
| 2908 | C | ALA | B | 1054 | 11.143 | 35.444 | 55.09 | 1 | 43.49 |
| 2909 | O | ALA | B | 1054 | 12.115 | 34.738 | 54.746 | 1 | 38.93 |
| 2910 | CB | ALA | B | 1054 | 11.447 | 37.591 | 53.892 | 1 | 39.99 |
| 2911 | N | ILE | B | 1055 | 9.945 | 34.945 | 55.396 | 1 | 45.58 |
| 2912 | CA | ILE | B | 1055 | 9.659 | 33.509 | 55.299 | 1 | 45.26 |
| 2913 | C | ILE | B | 1055 | 8.573 | 33.256 | 54.27 | 1 | 44.36 |
| 2914 | O | ILE | B | 1055 | 7.459 | 33.754 | 54.396 | 1 | 42.33 |
| 2915 | CB | ILE | B | 1055 | 9.195 | 32.914 | 56.649 | 1 | 47.38 |
| 2916 | CG1 | ILE | B | 1055 | 10.234 | 33.175 | 57.737 | 1 | 39.2 |
| 2917 | CG2 | ILE | B | 1055 | 9.017 | 31.386 | 56.522 | 1 | 47.65 |
| 2918 | CD1 | ILE | B | 1055 | 9.787 | 32.681 | 59.055 | 1 | 41.28 |
| 2919 | N | LYS | B | 1056 | 8.922 | 32.471 | 53.259 | 1 | 45.93 |
| 2920 | CA | LYS | B | 1056 | 8.02 | 32.127 | 52.172 | 1 | 48.46 |

Fig. 1-73

| ATOM | ATOM TYPE | RESIDUE | | # | X | Y | Z | OCC | B |
|---|---|---|---|---|---|---|---|---|---|
| 2921 | C | LYS | B | 1056 | 7.622 | 30.673 | 52.244 | 1 | 53.81 |
| 2922 | O | LYS | B | 1056 | 8.477 | 29.784 | 52.21 | 1 | 51.61 |
| 2923 | CB | LYS | B | 1056 | 8.721 | 32.349 | 50.829 | 1 | 52.2 |
| 2924 | CG | LYS | B | 1056 | 7.869 | 2.05 | 49.604 | 1 | 49.14 |
| 2925 | CD | LYS | B | 1056 | 8.612 | 32.385 | 48.334 | 1 | 47.25 |
| 2926 | CE | LYS | B | 1056 | 7.648 | 32.471 | 47.177 | 1 | 45.82 |
| 2927 | NZ | LYS | B | 1056 | 8.316 | 32.917 | 45.925 | 1 | 41.67 |
| 2928 | N | LYS | B | 1057 | 6.317 | 30.438 | 52.302 | 1 | 58.57 |
| 2929 | CA | LYS | B | 1057 | 5.77 | 29.086 | 52.349 | 1 | 62.42 |
| 2930 | C | LYS | B | 1057 | 5.339 | 28.686 | 50.935 | 1 | 64.09 |
| 2931 | O | LYS | B | 1057 | 4.495 | 29.354 | 50.32 | 1 | 62.73 |
| 2932 | CB | LYS | B | 1057 | 4.568 | 29.052 | 53.306 | 1 | 63.07 |
| 2933 | CG | LYS | B | 1057 | 3.743 | 27.763 | 53.313 | 1 | 63.63 |
| 2934 | CD | LYS | B | 1057 | 2.538 | 27.893 | 54.269 | 1 | 65.76 |
| 2935 | CE | LYS | B | 1057 | 1.512 | 26.763 | 54.102 | 1 | 65.42 |
| 2936 | NZ | LYS | B | 1057 | 2.111 | 25.406 | 54.277 | 1 | 65.13 |
| 2937 | N | LEU | B | 1058 | 5.981 | 27.655 | 50.393 | 1 | 67.19 |
| 2938 | CA | LEU | B | 1058 | 5.628 | 27.157 | 49.069 | 1 | 70.29 |
| 2939 | C | LEU | B | 1058 | 4.233 | 26.562 | 49.182 | 1 | 74.52 |
| 2940 | O | LEU | B | 1058 | 4.022 | 25.558 | 49.878 | 1 | 72.44 |
| 2941 | CB | LEU | B | 1058 | 6.607 | 26.077 | 48.588 | 1 | 68.22 |
| 2942 | CG | LEU | B | 1058 | 7.813 | 26.489 | 47.735 | 1 | 67.54 |
| 2943 | CD1 | LEU | B | 1058 | 7.346 | 27.223 | 46.488 | 1 | 68.66 |
| 2944 | CD2 | LEU | B | 1058 | 8.758 | 27.362 | 48.536 | 1 | 66.95 |
| 2945 | N | TYR | B | 1059 | 3.282 | 27.24 | 48.546 | 1 | 79.9 |
| 2946 | CA | TYR | B | 1059 | 1.879 | 26.844 | 48.534 | 1 | 84.03 |
| 2947 | C | TYR | B | 1059 | 1.556 | 25.525 | 47.821 | 1 | 83.03 |
| 2948 | O | TYR | B | 1059 | 1.497 | 25.483 | 46.584 | 1 | 83.61 |
| 2949 | CB | TYR | B | 1059 | 1.069 | 27.947 | 47.833 | 1 | 89.51 |
| 2950 | CG | TYR | B | 1059 | -0.415 | 27.667 | 47.676 | 1 | 95.91 |
| 2951 | CD1 | TYR | B | 1059 | -1.194 | 27.226 | 48.758 | 1 | 97.58 |
| 2952 | CD2 | TYR | B | 1059 | -1.045 | 27.85 | 46.437 | 1 | 97.29 |
| 2953 | CE1 | TYR | B | 1059 | -2.562 | 26.976 | 48.605 | 1 | 100 |
| 2954 | CE2 | TYR | B | 1059 | -2.411 | 27.603 | 46.274 | 1 | 100 |
| 2955 | CZ | TYR | B | 1059 | -3.162 | 27.165 | 47.358 | 1 | 100 |
| 2956 | OH | TYR | B | 1059 | -4.504 | 26.902 | 47.189 | 1 | 100 |
| 2957 | N | ARG | B | 1060 | 1.363 | 24.463 | 48.608 | 1 | 81.09 |
| 2958 | CA | ARG | B | 1060 | 1.069 | 23.112 | 48.101 | 1 | 79.82 |
| 2959 | C | ARG | B | 1060 | 1.907 | 22.76 | 46.865 | 1 | 76.79 |
| 2960 | O | ARG | B | 1060 | 1.367 | 22.474 | 45.8 | 1 | 75.28 |

Fig. 1-74

| ATOM | ATOM TYPE | RESIDUE | | # | X | Y | Z | OCC | B |
|---|---|---|---|---|---|---|---|---|---|
| 2961 | CB | ARG | B | 1060 | -0.426 | 22.934 | 47.805 | 1 | 80.83 |
| 2962 | N | PRO | B | 1061 | 3.241 | 22.75 | 47.01 | 1 | 75.64 |
| 2963 | CA | PRO | B | 1061 | 4.187 | 22.449 | 45.932 | 1 | 75.15 |
| 2964 | C | PRO | B | 1061 | 4.029 | 21.104 | 45.246 | 1 | 76.53 |
| 2965 | O | PRO | B | 1061 | 4.451 | 20.938 | 44.1 | 1 | 75.82 |
| 2966 | CB | PRO | B | 1061 | 5.54 | 22.567 | 46.627 | 1 | 73.66 |
| 2967 | CG | PRO | B | 1061 | 5.236 | 22.159 | 48.021 | 1 | 73.69 |
| 2968 | CD | PRO | B | 1061 | 3.951 | 22.885 | 48.294 | 1 | 73.79 |
| 2969 | N | PHE | B | 1062 | 3.423 | 20.144 | 45.932 | 1 | 78.61 |
| 2970 | CA | PHE | B | 1062 | 3.249 | 18.823 | 45.337 | 1 | 83.23 |
| 2971 | C | PHE | B | 1062 | 1.789 | 18.471 | 45.038 | 1 | 84.85 |
| 2972 | O | PHE | B | 1062 | 1.325 | 17.346 | 45.253 | 1 | 83.78 |
| 2973 | CB | PHE | B | 1062 | 3.957 | 17.773 | 46.197 | 1 | 81.92 |
| 2974 | CG | PHE | B | 1062 | 5.388 | 18.114 | 46.472 | 1 | 78.99 |
| 2975 | CD1 | PHE | B | 1062 | 6.289 | 18.268 | 45.426 | 1 | 78.21 |
| 2976 | CD2 | PHE | B | 1062 | 5.813 | 18.38 | 47.764 | 1 | 79.56 |
| 2977 | CE1 | PHE | B | 1062 | 7.589 | 18.691 | 45.666 | 1 | 79.26 |
| 2978 | CE2 | PHE | B | 1062 | 7.113 | 18.803 | 48.015 | 1 | 79.59 |
| 2979 | CZ | PHE | B | 1062 | 8.002 | 18.962 | 46.965 | 1 | 79.58 |
| 2980 | N | GLN | B | 1063 | 1.091 | 19.468 | 44.503 | 1 | 86.52 |
| 2981 | CA | GLN | B | 1063 | -0.303 | 19.356 | 44.126 | 1 | 87.56 |
| 2982 | C | GLN | B | 1063 | -0.371 | 18.984 | 42.636 | 1 | 89.04 |
| 2983 | O | GLN | B | 1063 | -1.414 | 18.556 | 42.145 | 1 | 91.08 |
| 2984 | CB | GLN | B | 1063 | -0.997 | 20.697 | 44.371 | 1 | 87.04 |
| 2985 | CG | GLN | B | 1063 | -2.5 | 20.66 | 44.201 | 1 | 91.31 |
| 2986 | CD | GLN | B | 1063 | -3.11 | 22.043 | 44.065 | 1 | 92.41 |
| 2987 | OE1 | GLN | B | 1063 | -2.447 | 22.991 | 43.63 | 1 | 90.05 |
| 2988 | NE2 | GLN | B | 1063 | -4.39 | 22.164 | 44.426 | 1 | 93.3 |
| 2989 | N | SER | B | 1064 | 0.741 | 19.148 | 41.921 | 1 | 87.83 |
| 2990 | CA | SER | B | 1064 | 0.801 | 18.821 | 40.496 | 1 | 88.42 |
| 2991 | C | SER | B | 1064 | 2.241 | 18.622 | 40.054 | 1 | 88.42 |
| 2992 | O | SER | B | 1064 | 3.142 | 18.548 | 40.88 | 1 | 90.12 |
| 2993 | CB | SER | B | 1064 | 0.174 | 19.936 | 39.658 | 1 | 88.4 |
| 2994 | OG | SER | B | 1064 | 1.002 | 21.083 | 39.633 | 1 | 89.39 |
| 2995 | N | GLU | B | 1065 | 2.453 | 18.518 | 38.747 | 1 | 87.68 |
| 2996 | CA | GLU | B | 1065 | 3.798 | 18.351 | 38.216 | 1 | 87.25 |
| 2997 | C | GLU | B | 1065 | 4.353 | 19.729 | 37.875 | 1 | 85.74 |
| 2998 | O | GLU | B | 1065 | 5.564 | 19.964 | 37.937 | 1 | 84.48 |
| 2999 | CB | GLU | B | 1065 | 3.775 | 17.475 | 36.963 | 1 | 90.5 |
| 3000 | CG | GLU | B | 1065 | 5.164 | 17.181 | 36.392 | 1 | 91.77 |

Fig. 1-75

| ATOM | ATOM TYPE | RESIDUE | | # | X | Y | Z | OCC | B |
|---|---|---|---|---|---|---|---|---|---|
| 3001 | CD | GLU | B | 1065 | 5.121 | 16.354 | 35.12 | 1 | 92.8 |
| 3002 | OE1 | GLU | B | 1065 | 4.616 | 15.204 | 35.171 | 1 | 92.42 |
| 3003 | OE2 | GLU | B | 1065 | 5.598 | 16.86 | 34.075 | 1 | 91.25 |
| 3004 | N | LEU | B | 1066 | 3.45 | 20.622 | 37.477 | 1 | 84.13 |
| 3005 | CA | LEU | B | 1066 | 3.814 | 21.987 | 37.131 | 1 | 82.1 |
| 3006 | C | LEU | B | 1066 | 4.241 | 22.689 | 38.412 | 1 | 81.17 |
| 3007 | O | LEU | B | 1066 | 5.235 | 23.415 | 38.421 | 1 | 82.66 |
| 3008 | CB | LEU | B | 1066 | 2.626 | 22.731 | 36.498 | 1 | 82.35 |
| 3009 | CG | LEU | B | 1066 | 2.818 | 24.195 | 36.051 | 1 | 81.61 |
| 3010 | CD1 | LEU | B | 1066 | 3.698 | 24.249 | 34.803 | 1 | 80.78 |
| 3011 | CD2 | LEU | B | 1066 | 1.469 | 24.868 | 35.779 | 1 | 79.54 |
| 3012 | N | PHE | B | 1067 | 3.51 | 22.451 | 39.499 | 1 | 77.92 |
| 3013 | CA | PHE | B | 1067 | 3.844 | 23.08 | 40.773 | 1 | 76.72 |
| 3014 | C | PHE | B | 1067 | 5.154 | 22.548 | 41.339 | 1 | 74.37 |
| 3015 | O | PHE | B | 1067 | 6.024 | 23.323 | 41.754 | 1 | 74.07 |
| 3016 | CB | PHE | B | 1067 | 2.705 | 22.913 | 41.783 | 1 | 77.35 |
| 3017 | CG | PHE | B | 1067 | 1.578 | 23.901 | 41.604 | 1 | 79.09 |
| 3018 | CD1 | PHE | B | 1067 | 1.35 | 24.512 | 40.373 | 1 | 80.39 |
| 3019 | CD2 | PHE | B | 1067 | 0.741 | 24.218 | 42.672 | 1 | 81.18 |
| 3020 | CE1 | PHE | B | 1067 | 0.302 | 25.419 | 40.206 | 1 | 81.06 |
| 3021 | CE2 | PHE | B | 1067 | -0.314 | 25.127 | 42.519 | 1 | 82.12 |
| 3022 | CZ | PHE | B | 1067 | -0.532 | 25.728 | 41.282 | 1 | 81.41 |
| 3023 | N | ALA | B | 1068 | 5.305 | 21.227 | 41.306 | 1 | 71.57 |
| 3024 | CA | ALA | B | 1068 | 6.506 | 20.57 | 41.803 | 1 | 68.96 |
| 3025 | C | ALA | B | 1068 | 7.731 | 21.057 | 41.054 | 1 | 67.07 |
| 3026 | O | ALA | B | 1068 | 8.705 | 21.48 | 41.663 | 1 | 68.86 |
| 3027 | CB | ALA | B | 1068 | 6.377 | 19.076 | 41.668 | 1 | 68.15 |
| 3028 | N | LYS | B | 1069 | 7.658 | 21.03 | 39.73 | 1 | 66.12 |
| 3029 | CA | LYS | B | 1069 | 8.761 | 21.473 | 38.888 | 1 | 65.77 |
| 3030 | C | LYS | B | 1069 | 9.215 | 22.887 | 39.261 | 1 | 64.66 |
| 3031 | O | LYS | B | 1069 | 10.411 | 23.152 | 39.394 | 1 | 63.82 |
| 3032 | CB | LYS | B | 1069 | 8.359 | 21.416 | 37.406 | 1 | 67.34 |
| 3033 | CG | LYS | B | 1069 | 9.509 | 21.705 | 36.432 | 1 | 68.81 |
| 3034 | CD | LYS | B | 1069 | 9.098 | 21.528 | 34.972 | 1 | 71.88 |
| 3035 | CE | LYS | B | 1069 | 8.014 | 22.526 | 34.544 | 1 | 73.43 |
| 3036 | NZ | LYS | B | 1069 | 7.635 | 22.362 | 33.102 | 1 | 72.84 |
| 3037 | N | ARG | B | 1070 | 8.258 | 23.783 | 39.464 | 1 | 64.21 |
| 3038 | CA | ARG | B | 1070 | 8.581 | 25.156 | 39.81 | 1 | 64.05 |
| 3039 | C | ARG | B | 1070 | 9.233 | 25.236 | 41.181 | 1 | 63.96 |
| 3040 | O | ARG | B | 1070 | 10.281 | 25.857 | 41.341 | 1 | 63.7 |

Fig. 1-76

| ATOM | ATOM TYPE | RESIDUE | | # | X | Y | Z | OCC | B |
|---|---|---|---|---|---|---|---|---|---|
| 3041 | CB | ARG | B | 1070 | 7.329 | 26.028 | 39.714 | 1 | 65.64 |
| 3042 | CG | ARG | B | 1070 | 6.844 | 26.144 | 38.278 | 1 | 66.55 |
| 3043 | CD | ARG | B | 1070 | 5.532 | 26.898 | 38.111 | 1 | 72.46 |
| 3044 | NE | ARG | B | 1070 | 5.225 | 27.036 | 36.683 | 1 | 76.33 |
| 3045 | CZ | ARG | B | 1070 | 4.28 | 27.824 | 36.172 | 1 | 78.89 |
| 3046 | NH1 | ARG | B | 1070 | 3.511 | 28.564 | 36.969 | 1 | 77.33 |
| 3047 | NH2 | ARG | B | 1070 | 4.104 | 27.867 | 34.851 | 1 | 78.07 |
| 3048 | N | ALA | B | 1071 | 8.657 | 24.532 | 42.149 | 1 | 63.83 |
| 3049 | CA | ALA | B | 1071 | 9.189 | 24.516 | 43.508 | 1 | 59.39 |
| 3050 | C | ALA | B | 1071 | 10.658 | 24.095 | 43.502 | 1 | 58.85 |
| 3051 | O | ALA | B | 1071 | 11.503 | 24.776 | 44.068 | 1 | 59.6 |
| 3052 | CB | ALA | B | 1071 | 8.38 | 23.579 | 44.354 | 1 | 55.82 |
| 3053 | N | TYR | B | 1072 | 10.957 | 22.981 | 42.842 | 1 | 58.2 |
| 3054 | CA | TYR | B | 1072 | 12.321 | 22.484 | 42.756 | 1 | 57.56 |
| 3055 | C | TYR | B | 1072 | 13.212 | 23.48 | 42.029 | 1 | 57.39 |
| 3056 | O | TYR | B | 1072 | 14.332 | 23.724 | 42.45 | 1 | 60.24 |
| 3057 | CB | TYR | B | 1072 | 12.353 | 21.115 | 42.065 | 1 | 57.31 |
| 3058 | CG | TYR | B | 1072 | 13.731 | 20.64 | 41.637 | 1 | 56.65 |
| 3059 | CD1 | TYR | B | 1072 | 14.277 | 21.035 | 40.418 | 1 | 57.61 |
| 3060 | CD2 | TYR | B | 1072 | 14.467 | 19.76 | 42.431 | 1 | 56.47 |
| 3061 | CE1 | TYR | B | 1072 | 15.516 | 20.56 | 39.997 | 1 | 60.3 |
| 3062 | CE2 | TYR | B | 1072 | 15.703 | 19.278 | 42.021 | 1 | 55.38 |
| 3063 | CZ | TYR | B | 1072 | 16.221 | 19.681 | 40.805 | 1 | 59.49 |
| 3064 | OH | TYR | B | 1072 | 17.438 | 19.198 | 40.377 | 1 | 62.12 |
| 3065 | N | ARG | B | 1073 | 12.726 | 24.052 | 40.935 | 1 | 58 |
| 3066 | CA | ARG | B | 1073 | 13.517 | 25.037 | 40.201 | 1 | 58.76 |
| 3067 | C | ARG | B | 1073 | 13.847 | 26.265 | 41.057 | 1 | 59.42 |
| 3068 | O | ARG | B | 1073 | 14.961 | 26.792 | 40.979 | 1 | 62.91 |
| 3069 | CB | ARG | B | 1073 | 12.792 | 25.508 | 38.943 | 1 | 59.19 |
| 3070 | CG | ARG | B | 1073 | 12.761 | 24.532 | 37.796 | 1 | 60.52 |
| 3071 | CD | ARG | B | 1073 | 12.644 | 25.34 | 36.533 | 1 | 61.56 |
| 3072 | NE | ARG | B | 1073 | 12.287 | 24.561 | 35.354 | 1 | 62.56 |
| 3073 | CZ | ARG | B | 1073 | 11.099 | 24.621 | 34.768 | 1 | 61.61 |
| 3074 | NH1 | ARG | B | 1073 | 10.129 | 25.37 | 35.292 | 1 | 60.18 |
| 3075 | NH2 | ARG | B | 1073 | 10.871 | 23.898 | 33.686 | 1 | 62.46 |
| 3076 | N | GLU | B | 1074 | 12.869 | 26.724 | 41.845 | 1 | 56.17 |
| 3077 | CA | GLU | B | 1074 | 13.026 | 27.886 | 42.719 | 1 | 53.17 |
| 3078 | C | GLU | B | 1074 | 14.043 | 27.609 | 43.828 | 1 | 53.57 |
| 3079 | O | GLU | B | 1074 | 14.913 | 28.436 | 44.111 | 1 | 53.35 |
| 3080 | CB | GLU | B | 1074 | 11.681 | 28.282 | 43.328 | 1 | 49.09 |

Fig. 1-77

| ATOM | ATOM TYPE | RESIDUE | | # | X | Y | Z | OCC | B |
|---|---|---|---|---|---|---|---|---|---|
| 3081 | CG | GLU | B | 1074 | 11.742 | 29.562 | 44.131 | 1 | 49.98 |
| 3082 | CD | GLU | B | 1074 | 10.37 | 30.109 | 44.511 | 1 | 54.96 |
| 3083 | OE1 | GLU | B | 1074 | 9.342 | 29.41 | 44.261 | 1 | 53.01 |
| 3084 | OE2 | GLU | B | 1074 | 10.331 | 31.243 | 45.06 | 1 | 46.02 |
| 3085 | N | LEU | B | 1075 | 13.917 | 26.456 | 44.475 | 1 | 52.53 |
| 3086 | CA | LEU | B | 1075 | 14.855 | 26.089 | 45.515 | 1 | 51.1 |
| 3087 | C | LEU | B | 1075 | 16.262 | 26.035 | 44.912 | 1 | 53.67 |
| 3088 | O | LEU | B | 1075 | 17.131 | 26.81 | 45.302 | 1 | 53.33 |
| 3089 | CB | LEU | B | 1075 | 14.492 | 24.73 | 46.087 | 1 | 48.59 |
| 3090 | CG | LEU | B | 1075 | 15.38 | 24.258 | 47.233 | 1 | 45.59 |
| 3091 | CD1 | LEU | B | 1075 | 15.456 | 25.324 | 48.312 | 1 | 40.35 |
| 3092 | CD2 | LEU | B | 1075 | 14.829 | 22.968 | 47.779 | 1 | 45.47 |
| 3093 | N | ARG | B | 1076 | 16.437 | 25.17 | 43.913 | 1 | 54.76 |
| 3094 | CA | ARG | B | 1076 | 17.708 | 24.96 | 43.222 | 1 | 58 |
| 3095 | C | ARG | B | 1076 | 18.428 | 26.212 | 42.73 | 1 | 60.08 |
| 3096 | O | ARG | B | 1076 | 19.646 | 26.339 | 42.908 | 1 | 62.77 |
| 3097 | CB | ARG | B | 1076 | 17.518 | 23.999 | 42.047 | 1 | 63.86 |
| 3098 | CG | ARG | B | 1076 | 17.595 | 22.527 | 42.417 | 1 | 68.45 |
| 3099 | CD | ARG | B | 1076 | 19.031 | 22.022 | 42.442 | 1 | 72.55 |
| 3100 | NE | ARG | B | 1076 | 19.593 | 21.845 | 41.105 | 1 | 75.26 |
| 3101 | CZ | ARG | B | 1076 | 20.833 | 21.427 | 40.858 | 1 | 76.36 |
| 3102 | NH1 | ARG | B | 1076 | 21.655 | 21.129 | 41.85 | 1 | 80.23 |
| 3103 | NH2 | ARG | B | 1076 | 21.255 | 21.304 | 39.614 | 1 | 78.63 |
| 3104 | N | LEU | B | 1077 | 17.705 | 27.108 | 42.063 | 1 | 57.06 |
| 3105 | CA | LEU | B | 1077 | 18.317 | 28.337 | 41.567 | 1 | 53.84 |
| 3106 | C | LEU | B | 1077 | 18.745 | 29.242 | 42.718 | 1 | 52.29 |
| 3107 | O | LEU | B | 1077 | 19.81 | 29.856 | 42.67 | 1 | 51.17 |
| 3108 | CB | LEU | B | 1077 | 17.348 | 29.092 | 40.662 | 1 | 49.81 |
| 3109 | CG | LEU | B | 1077 | 16.963 | 28.408 | 39.366 | 1 | 45.19 |
| 3110 | CD1 | LEU | B | 1077 | 15.734 | 29.034 | 38.832 | 1 | 43.84 |
| 3111 | CD2 | LEU | B | 1077 | 18.086 | 28.497 | 38.375 | 1 | 45.19 |
| 3112 | N | LEU | B | 1078 | 17.901 | 29.33 | 43.743 | 1 | 53.72 |
| 3113 | CA | LEU | B | 1078 | 18.19 | 30.165 | 44.911 | 1 | 53.65 |
| 3114 | C | LEU | B | 1078 | 19.388 | 29.623 | 45.674 | 1 | 53.49 |
| 3115 | O | LEU | B | 1078 | 20.222 | 30.386 | 46.152 | 1 | 54.41 |
| 3116 | CB | LEU | B | 1078 | 16.965 | 30.275 | 45.819 | 1 | 49.27 |
| 3117 | CG | LEU | B | 1078 | 15.914 | 31.298 | 45.381 | 1 | 50.2 |
| 3118 | CD1 | LEU | B | 1078 | 14.734 | 31.297 | 46.33 | 1 | 47.11 |
| 3119 | CD2 | LEU | B | 1078 | 16.539 | 32.685 | 45.327 | 1 | 51.38 |
| 3120 | N | LYS | B | 1079 | 19.484 | 28.304 | 45.762 | 1 | 52.88 |

Fig. 1-78

| ATOM | ATOM TYPE | RESIDUE | | # | X | Y | Z | OCC | B |
|---|---|---|---|---|---|---|---|---|---|
| 3121 | CA | LYS | B | 1079 | 20.611 | 27.68 | 46.431 | 1 | 55.99 |
| 3122 | C | LYS | B | 1079 | 21.906 | 27.898 | 45.641 | 1 | 57.03 |
| 3123 | O | LYS | B | 1079 | 22.976 | 27.976 | 46.222 | 1 | 59.51 |
| 3124 | CB | LYS | B | 1079 | 20.366 | 26.186 | 46.631 | 1 | 53.8 |
| 3125 | CG | LYS | B | 1079 | 19.41 | 25.867 | 47.763 | 1 | 55.99 |
| 3126 | CD | LYS | B | 1079 | 19.179 | 24.358 | 47.883 | 1 | 61.83 |
| 3127 | CE | LYS | B | 1079 | 20.496 | 23.568 | 47.994 | 1 | 64.12 |
| 3128 | NZ | LYS | B | 1079 | 20.278 | 22.094 | 48.021 | 1 | 59.65 |
| 3129 | N | HIS | B | 1080 | 21.8 | 28.042 | 44.327 | 1 | 57.95 |
| 3130 | CA | HIS | B | 1080 | 22.974 | 28.248 | 43.487 | 1 | 59.32 |
| 3131 | C | HIS | B | 1080 | 23.44 | 29.704 | 43.322 | 1 | 57.63 |
| 3132 | O | HIS | B | 1080 | 24.62 | 30.006 | 43.494 | 1 | 56.73 |
| 3133 | CB | HIS | B | 1080 | 22.743 | 27.614 | 42.107 | 1 | 66 |
| 3134 | CG | HIS | B | 1080 | 23.724 | 28.049 | 41.056 | 1 | 73.25 |
| 3135 | ND1 | HIS | B | 1080 | 24.875 | 27.344 | 40.777 | 1 | 76.19 |
| 3136 | CD2 | HIS | B | 1080 | 23.717 | 29.108 | 40.206 | 1 | 75.77 |
| 3137 | CE1 | HIS | B | 1080 | 25.535 | 27.947 | 39.803 | 1 | 78.22 |
| 3138 | NE2 | HIS | B | 1080 | 24.855 | 29.02 | 39.437 | 1 | 77.24 |
| 3139 | N | MET | B | 1081 | 22.527 | 30.599 | 42.961 | 1 | 56.25 |
| 3140 | CA | MET | B | 1081 | 22.889 | 31.998 | 42.719 | 1 | 54.99 |
| 3141 | C | MET | B | 1081 | 23.491 | 32.695 | 43.932 | 1 | 52.29 |
| 3142 | O | MET | B | 1081 | 23.175 | 32.346 | 45.053 | 1 | 54.04 |
| 3143 | CB | MET | B | 1081 | 21.665 | 32.797 | 42.229 | 1 | 57.51 |
| 3144 | CG | MET | B | 1081 | 20.986 | 32.286 | 40.948 | 1 | 54.18 |
| 3145 | SD | MET | B | 1081 | 19.476 | 33.24 | 40.589 | 1 | 51.93 |
| 3146 | CE | MET | B | 1081 | 18.557 | 32.93 | 42.11 | 1 | 45.64 |
| 3147 | N | ARG | B | 1082 | 24.383 | 33.652 | 43.69 | 1 | 50.01 |
| 3148 | CA | ARG | B | 1082 | 25.007 | 34.445 | 44.756 | 1 | 50.78 |
| 3149 | C | ARG | B | 1082 | 25.377 | 35.835 | 44.211 | 1 | 49.52 |
| 3150 | O | ARG | B | 1082 | 26.421 | 35.995 | 43.554 | 1 | 50.33 |
| 3151 | CB | ARG | B | 1082 | 26.251 | 33.733 | 45.318 | 1 | 50.93 |
| 3152 | N | HIS | B | 1083 | 24.51 | 36.82 | 44.473 | 1 | 46.01 |
| 3153 | CA | HIS | B | 1083 | 24.709 | 38.19 | 43.998 | 1 | 44.84 |
| 3154 | C | HIS | B | 1083 | 24.067 | 39.236 | 44.89 | 1 | 46.37 |
| 3155 | O | HIS | B | 1083 | 22.943 | 39.071 | 45.349 | 1 | 49.77 |
| 3156 | CB | HIS | B | 1083 | 24.162 | 38.346 | 42.579 | 1 | 46.72 |
| 3157 | CG | HIS | B | 1083 | 24.558 | 39.632 | 41.935 | 1 | 46.28 |
| 3158 | ND1 | HIS | B | 1083 | 23.946 | 40.833 | 42.228 | 1 | 43.36 |
| 3159 | CD2 | HIS | B | 1083 | 25.563 | 39.92 | 41.072 | 1 | 43.95 |
| 3160 | CE1 | HIS | B | 1083 | 24.558 | 41.805 | 41.578 | 1 | 42.91 |

Fig. 1-79

| ATOM | ATOM TYPE | RESIDUE | | # | X | Y | Z | OCC | B |
|---|---|---|---|---|---|---|---|---|---|
| 3161 | NE2 | HIS | B | 1083 | 25.543 | 41.28 | 40.872 | 1 | 45.89 |
| 3162 | N | GLU | B | 1084 | 24.751 | 40.363 | 45.047 | 1 | 49.97 |
| 3163 | CA | GLU | B | 1084 | 24.298 | 41.473 | 45.894 | 1 | 50.68 |
| 3164 | C | GLU | B | 1084 | 22.89 | 41.971 | 45.522 | 1 | 50.28 |
| 3165 | O | GLU | B | 1084 | 22.216 | 42.638 | 46.317 | 1 | 51.66 |
| 3166 | CB | GLU | B | 1084 | 25.327 | 42.627 | 45.797 | 1 | 55.77 |
| 3167 | CG | GLU | B | 1084 | 25.246 | 43.712 | 46.896 | 1 | 71.29 |
| 3168 | CD | GLU | B | 1084 | 25.737 | 43.254 | 48.305 | 1 | 80.4 |
| 3169 | OE1 | GLU | B | 1084 | 26.976 | 43.217 | 48.538 | 1 | 81.58 |
| 3170 | OE2 | GLU | B | 1084 | 24.884 | 42.969 | 49.191 | 1 | 82.45 |
| 3171 | N | ASN | B | 1085 | 22.436 | 41.624 | 44.32 | 1 | 48.85 |
| 3172 | CA | ASN | B | 1085 | 21.137 | 42.069 | 43.832 | 1 | 46.27 |
| 3173 | C | ASN | B | 1085 | 20.153 | 40.942 | 43.543 | 1 | 44.89 |
| 3174 | O | ASN | B | 1085 | 19.226 | 41.106 | 42.783 | 1 | 44.96 |
| 3175 | CB | ASN | B | 1085 | 21.336 | 42.918 | 42.586 | 1 | 45.28 |
| 3176 | CG | ASN | B | 1085 | 22.155 | 44.166 | 42.858 | 1 | 47.36 |
| 3177 | OD1 | ASN | B | 1085 | 23.26 | 44.341 | 42.328 | 1 | 44.25 |
| 3178 | ND2 | ASN | B | 1085 | 21.617 | 45.041 | 43.692 | 1 | 49.42 |
| 3179 | N | VAL | B | 1086 | 20.391 | 39.777 | 44.115 | 1 | 45.32 |
| 3180 | CA | VAL | B | 1086 | 19.506 | 38.647 | 43.923 | 1 | 43.24 |
| 3181 | C | VAL | B | 1086 | 19.281 | 38.086 | 45.318 | 1 | 46.01 |
| 3182 | O | VAL | B | 1086 | 20.244 | 37.819 | 46.058 | 1 | 49.62 |
| 3183 | CB | VAL | B | 1086 | 20.142 | 37.578 | 43.03 | 1 | 43.45 |
| 3184 | CG1 | VAL | B | 1086 | 19.178 | 36.392 | 42.831 | 1 | 38.77 |
| 3185 | CG2 | VAL | B | 1086 | 20.535 | 38.19 | 41.693 | 1 | 43.89 |
| 3186 | N | ILE | B | 1087 | 18.016 | 37.944 | 45.696 | 1 | 43.02 |
| 3187 | CA | ILE | B | 1087 | 17.679 | 37.43 | 47.011 | 1 | 40.27 |
| 3188 | C | ILE | B | 1087 | 18.387 | 36.117 | 47.334 | 1 | 40.11 |
| 3189 | O | ILE | B | 1087 | 18.63 | 35.272 | 46.455 | 1 | 37.82 |
| 3190 | CB | ILE | B | 1087 | 16.174 | 37.256 | 47.178 | 1 | 40.31 |
| 3191 | CG1 | ILE | B | 1087 | 15.841 | 37.285 | 48.66 | 1 | 38.04 |
| 3192 | CG2 | ILE | B | 1087 | 15.695 | 35.979 | 46.499 | 1 | 36.21 |
| 3193 | CD1 | ILE | B | 1087 | 16.224 | 38.594 | 49.322 | 1 | 37.07 |
| 3194 | N | GLY | B | 1088 | 18.699 | 35.936 | 48.609 | 1 | 39 |
| 3195 | CA | GLY | B | 1088 | 19.407 | 34.736 | 49.001 | 1 | 39.21 |
| 3196 | C | GLY | B | 1088 | 18.76 | 33.982 | 50.121 | 1 | 40.6 |
| 3197 | O | GLY | B | 1088 | 17.953 | 34.518 | 50.887 | 1 | 41.48 |
| 3198 | N | LEU | B | 1089 | 19.119 | 32.712 | 50.204 | 1 | 41.27 |
| 3199 | CA | LEU | B | 1089 | 18.591 | 31.85 | 51.239 | 1 | 42.74 |
| 3200 | C | LEU | B | 1089 | 19.419 | 31.941 | 52.509 | 1 | 42.21 |

Fig. 1-80

| ATOM | ATOM TYPE | RESIDUE | | # | X | Y | Z | OCC | B |
|---|---|---|---|---|---|---|---|---|---|
| 3201 | O | LEU | B | 1089 | 20.651 | 31.985 | 52.452 | 1 | 40.32 |
| 3202 | CB | LEU | B | 1089 | 18.573 | 30.4 | 50.737 | 1 | 41.24 |
| 3203 | CG | LEU | B | 1089 | 17.256 | 29.862 | 50.183 | 1 | 37.8 |
| 3204 | CD1 | LEU | B | 1089 | 16.179 | 30.941 | 50.135 | 1 | 31.91 |
| 3205 | CD2 | LEU | B | 1089 | 17.508 | 29.277 | 48.82 | 1 | 36.34 |
| 3206 | N | LEU | B | 1090 | 18.73 | 32.045 | 53.64 | 1 | 41.39 |
| 3207 | CA | LEU | B | 1090 | 19.383 | 32.057 | 54.941 | 1 | 45.74 |
| 3208 | C | LEU | B | 1090 | 19.122 | 30.688 | 55.582 | 1 | 51.8 |
| 3209 | O | LEU | B | 1090 | 19.933 | 30.175 | 56.362 | 1 | 54.91 |
| 3210 | CB | LEU | B | 1090 | 18.782 | 33.114 | 55.85 | 1 | 41.25 |
| 3211 | CG | LEU | B | 1090 | 19.111 | 34.582 | 55.603 | 1 | 43.4 |
| 3212 | CD1 | LEU | B | 1090 | 18.361 | 35.428 | 56.599 | 1 | 40.33 |
| 3213 | CD2 | LEU | B | 1090 | 20.607 | 34.836 | 55.742 | 1 | 44.24 |
| 3214 | N | ASP | B | 1091 | 17.988 | 30.097 | 55.216 | 1 | 54.86 |
| 3215 | CA | ASP | B | 1091 | 17.56 | 28.818 | 55.755 | 1 | 56.17 |
| 3216 | C | ASP | B | 1091 | 16.404 | 28.346 | 54.886 | 1 | 58.98 |
| 3217 | O | ASP | B | 1091 | 15.781 | 29.139 | 54.174 | 1 | 58.18 |
| 3218 | CB | ASP | B | 1091 | 17.084 | 29.038 | 57.212 | 1 | 55.2 |
| 3219 | CG | ASP | B | 1091 | 16.659 | 27.744 | 57.944 | 1 | 50.83 |
| 3220 | OD1 | ASP | B | 1091 | 17.182 | 26.645 | 57.654 | 1 | 48.39 |
| 3221 | OD2 | ASP | B | 1091 | 15.817 | 27.859 | 58.867 | 1 | 48.11 |
| 3222 | N | VAL | B | 1092 | 16.198 | 27.035 | 54.889 | 1 | 60.54 |
| 3223 | CA | VAL | B | 1092 | 15.117 | 26.391 | 54.171 | 1 | 61.64 |
| 3224 | C | VAL | B | 1092 | 14.803 | 25.186 | 55.043 | 1 | 61.8 |
| 3225 | O | VAL | B | 1092 | 15.709 | 24.484 | 55.506 | 1 | 60.49 |
| 3226 | CB | VAL | B | 1092 | 15.523 | 25.948 | 52.746 | 1 | 63.63 |
| 3227 | CG1 | VAL | B | 1092 | 16.766 | 25.13 | 52.789 | 1 | 64.29 |
| 3228 | CG2 | VAL | B | 1092 | 14.412 | 25.119 | 52.11 | 1 | 64.21 |
| 3229 | N | PHE | B | 1093 | 13.522 | 24.959 | 55.291 | 1 | 62.04 |
| 3230 | CA | PHE | B | 1093 | 13.134 | 23.852 | 56.141 | 1 | 62.29 |
| 3231 | C | PHE | B | 1093 | 11.785 | 23.268 | 55.813 | 1 | 63.71 |
| 3232 | O | PHE | B | 1093 | 11.03 | 23.817 | 55.021 | 1 | 66.24 |
| 3233 | CB | PHE | B | 1093 | 13.116 | 24.324 | 57.593 | 1 | 59.66 |
| 3234 | CG | PHE | B | 1093 | 12.083 | 25.382 | 57.882 | 1 | 55.63 |
| 3235 | CD1 | PHE | B | 1093 | 10.784 | 25.026 | 58.25 | 1 | 53.36 |
| 3236 | CD2 | PHE | B | 1093 | 12.416 | 26.734 | 57.824 | 1 | 54.21 |
| 3237 | CE1 | PHE | B | 1093 | 9.827 | 26.011 | 58.562 | 1 | 52.77 |
| 3238 | CE2 | PHE | B | 1093 | 11.467 | 27.726 | 58.135 | 1 | 50.11 |
| 3239 | CZ | PHE | B | 1093 | 10.174 | 27.363 | 58.505 | 1 | 49.43 |
| 3240 | N | THR | B | 1094 | 11.485 | 22.161 | 56.477 | 1 | 66.12 |

Fig. 1-81

| ATOM | ATOM TYPE | RESIDUE | | # | X | Y | Z | OCC | B |
|---|---|---|---|---|---|---|---|---|---|
| 3241 | CA | THR | B | 1094 | 10.21 | 21.475 | 56.339 | 1 | 67.21 |
| 3242 | C | THR | B | 1094 | 9.905 | 20.799 | 57.671 | 1 | 69 |
| 3243 | O | THR | B | 1094 | 10.739 | 20.079 | 58.229 | 1 | 67.3 |
| 3244 | CB | THR | B | 1094 | 10.206 | 20.421 | 55.204 | 1 | 67.83 |
| 3245 | OG1 | THR | B | 1094 | 8.954 | 19.723 | 55.214 | 1 | 64.79 |
| 3246 | CG2 | THR | B | 1094 | 11.35 | 19.422 | 55.36 | 1 | 66.66 |
| 3247 | N | PRO | B | 1095 | 8.723 | 21.08 | 58.229 | 1 | 69.99 |
| 3248 | CA | PRO | B | 1095 | 8.275 | 20.519 | 59.497 | 1 | 72.97 |
| 3249 | C | PRO | B | 1095 | 7.784 | 19.079 | 59.333 | 1 | 77.44 |
| 3250 | O | PRO | B | 1095 | 6.995 | 18.58 | 60.139 | 1 | 79.83 |
| 3251 | CB | PRO | B | 1095 | 7.151 | 21.463 | 59.882 | 1 | 70.67 |
| 3252 | CG | PRO | B | 1095 | 6.537 | 21.771 | 58.577 | 1 | 70.21 |
| 3253 | CD | PRO | B | 1095 | 7.732 | 22.032 | 57.703 | 1 | 70.12 |
| 3254 | N | ASP | B | 1096 | 8.23 | 18.442 | 58.257 | 1 | 80.58 |
| 3255 | CA | ASP | B | 1096 | 7.876 | 17.064 | 57.952 | 1 | 84.96 |
| 3256 | C | ASP | B | 1096 | 9.146 | 16.236 | 58.15 | 1 | 88.49 |
| 3257 | O | ASP | B | 1096 | 10.153 | 16.423 | 57.453 | 1 | 88.53 |
| 3258 | CB | ASP | B | 1096 | 7.359 | 16.953 | 56.513 | 1 | 86.44 |
| 3259 | CG | ASP | B | 1096 | 6.175 | 17.893 | 56.228 | 1 | 88.55 |
| 3260 | OD1 | ASP | B | 1096 | 5.37 | 18.178 | 57.146 | 1 | 88.77 |
| 3261 | OD2 | ASP | B | 1096 | 6.048 | 18.35 | 55.07 | 1 | 88.75 |
| 3262 | N | GLU | B | 1097 | 9.089 | 15.332 | 59.124 | 1 | 92.02 |
| 3263 | CA | GLU | B | 1097 | 10.221 | 14.488 | 59.489 | 1 | 93.95 |
| 3264 | C | GLU | B | 1097 | 10.638 | 13.402 | 58.502 | 1 | 94.65 |
| 3265 | O | GLU | B | 1097 | 11.8 | 12.988 | 58.5 | 1 | 94.52 |
| 3266 | CB | GLU | B | 1097 | 9.973 | 13.892 | 60.874 | 1 | 95.63 |
| 3267 | CG | GLU | B | 1097 | 9.85 | 14.959 | 61.969 | 1 | 98.55 |
| 3268 | CD | GLU | B | 1097 | 9.248 | 14.44 | 63.272 | 1 | 99.67 |
| 3269 | OE1 | GLU | B | 1097 | 9.588 | 13.307 | 63.69 | 1 | 100 |
| 3270 | OE2 | GLU | B | 1097 | 8.437 | 15.177 | 63.88 | 1 | 97.51 |
| 3271 | N | THR | B | 1098 | 9.708 | 12.957 | 57.656 | 1 | 95.51 |
| 3272 | CA | THR | B | 1098 | 10 | 11.904 | 56.675 | 1 | 97.78 |
| 3273 | C | THR | B | 1098 | 9.549 | 12.247 | 55.253 | 1 | 97.73 |
| 3274 | O | THR | B | 1098 | 8.594 | 12.995 | 55.066 | 1 | 98.25 |
| 3275 | CB | THR | B | 1098 | 9.321 | 10.565 | 57.065 | 1 | 99.16 |
| 3276 | OG1 | THR | B | 1098 | 7.899 | 10.742 | 57.109 | 1 | 99.02 |
| 3277 | CG2 | THR | B | 1098 | 9.817 | 10.069 | 58.425 | 1 | 99.67 |
| 3278 | N | LEU | B | 1099 | 10.214 | 11.659 | 54.257 | 1 | 98.25 |
| 3279 | CA | LEU | B | 1099 | 9.871 | 11.887 | 52.85 | 1 | 98.51 |
| 3280 | C | LEU | B | 1099 | 8.448 | 11.445 | 52.546 | 1 | 98.29 |

Fig. 1-82

| ATOM | ATOM TYPE | RESIDUE | | # | X | Y | Z | OCC | B |
|---|---|---|---|---|---|---|---|---|---|
| 3281 | O | LEU | B | 1099 | 7.782 | 12.022 | 51.689 | 1 | 98.53 |
| 3282 | CB | LEU | B | 1099 | 10.845 | 11.144 | 51.927 | 1 | 98.49 |
| 3283 | CG | LEU | B | 1099 | 10.488 | 11.023 | 50.436 | 1 | 98.62 |
| 3284 | CD1 | LEU | B | 1099 | 10.1 | 12.371 | 49.846 | 1 | 97.83 |
| 3285 | CD2 | LEU | B | 1099 | 11.664 | 10.422 | 49.67 | 1 | 99.42 |
| 3286 | N | ASP | B | 1100 | 7.994 | 10.418 | 53.259 | 1 | 99.35 |
| 3287 | CA | ASP | B | 1100 | 6.656 | 9.874 | 53.084 | 1 | 99.24 |
| 3288 | C | ASP | B | 1100 | 5.561 | 10.946 | 53.226 | 1 | 98.81 |
| 3289 | O | ASP | B | 1100 | 4.741 | 11.109 | 52.315 | 1 | 99.71 |
| 3290 | CB | ASP | B | 1100 | 6.426 | 8.71 | 54.058 | 1 | 98.7 |
| 3291 | N | ASP | B | 1101 | 5.555 | 11.692 | 54.334 | 1 | 97.21 |
| 3292 | CA | ASP | B | 1101 | 4.537 | 12.732 | 54.522 | 1 | 95.45 |
| 3293 | C | ASP | B | 1101 | 4.998 | 14.166 | 54.253 | 1 | 92.22 |
| 3294 | O | ASP | B | 1101 | 4.298 | 15.12 | 54.579 | 1 | 92.05 |
| 3295 | CB | ASP | B | 1101 | 3.813 | 12.604 | 55.882 | 1 | 98.04 |
| 3296 | CG | ASP | B | 1101 | 4.762 | 12.55 | 57.072 | 1 | 99.4 |
| 3297 | OD1 | ASP | B | 1101 | 5.215 | 11.44 | 57.434 | 1 | 97.84 |
| 3298 | OD2 | ASP | B | 1101 | 5.014 | 13.616 | 57.677 | 1 | 100 |
| 3299 | N | PHE | B | 1102 | 6.15 | 14.293 | 53.596 | 1 | 89.67 |
| 3300 | CA | PHE | B | 1102 | 6.745 | 15.583 | 53.22 | 1 | 85.73 |
| 3301 | C | PHE | B | 1102 | 5.831 | 16.283 | 52.232 | 1 | 83.04 |
| 3302 | O | PHE | B | 1102 | 5.894 | 16.009 | 51.039 | 1 | 84.56 |
| 3303 | CB | PHE | B | 1102 | 8.114 | 15.331 | 52.566 | 1 | 86.09 |
| 3304 | CG | PHE | B | 1102 | 8.684 | 16.513 | 51.821 | 1 | 84.91 |
| 3305 | CD1 | PHE | B | 1102 | 8.796 | 17.761 | 52.424 | 1 | 85.67 |
| 3306 | CD2 | PHE | B | 1102 | 9.162 | 16.353 | 50.526 | 1 | 84.73 |
| 3307 | CE1 | PHE | B | 1102 | 9.385 | 18.829 | 51.748 | 1 | 85.4 |
| 3308 | CE2 | PHE | B | 1102 | 9.752 | 17.413 | 49.843 | 1 | 85.63 |
| 3309 | CZ | PHE | B | 1102 | 9.865 | 18.653 | 50.455 | 1 | 85.2 |
| 3310 | N | THR | B | 1103 | 4.975 | 17.174 | 52.72 | 1 | 78.84 |
| 3311 | CA | THR | B | 1103 | 4.061 | 17.874 | 51.831 | 1 | 77.63 |
| 3312 | C | THR | B | 1103 | 4.524 | 19.267 | 51.405 | 1 | 76.47 |
| 3313 | O | THR | B | 1103 | 4.256 | 19.693 | 50.278 | 1 | 76.17 |
| 3314 | CB | THR | B | 1103 | 2.658 | 17.979 | 52.426 | 1 | 78.02 |
| 3315 | OG1 | THR | B | 1103 | 2.697 | 18.793 | 53.603 | 1 | 81.65 |
| 3316 | CG2 | THR | B | 1103 | 2.127 | 16.597 | 52.776 | 1 | 79.08 |
| 3317 | N | ASP | B | 1104 | 5.228 | 19.972 | 52.285 | 1 | 75.04 |
| 3318 | CA | ASP | B | 1104 | 5.695 | 21.317 | 51.952 | 1 | 73.27 |
| 3319 | C | ASP | B | 1104 | 7.006 | 21.753 | 52.587 | 1 | 68.42 |
| 3320 | O | ASP | B | 1104 | 7.606 | 21.019 | 53.364 | 1 | 67.69 |

Fig. 1-83

| ATOM | ATOM TYPE | RESIDUE | | # | X | Y | Z | OCC | B |
|---|---|---|---|---|---|---|---|---|---|
| 3321 | CB | ASP | B | 1104 | 4.607 | 22.361 | 52.246 | 1 | 76.28 |
| 3322 | CG | ASP | B | 1104 | 3.916 | 22.14 | 53.571 | 1 | 78.1 |
| 3323 | OD1 | ASP | B | 1104 | 4.583 | 21.778 | 54.563 | 1 | 81.19 |
| 3324 | OD2 | ASP | B | 1104 | 2.689 | 22.334 | 53.612 | 1 | 80.9 |
| 3325 | N | PHE | B | 1105 | 7.456 | 22.947 | 52.212 | 1 | 63.56 |
| 3326 | CA | PHE | B | 1105 | 8.685 | 23.499 | 52.742 | 1 | 60.34 |
| 3327 | C | PHE | B | 1105 | 8.701 | 25.006 | 52.698 | 1 | 58.3 |
| 3328 | O | PHE | B | 1105 | 8.029 | 25.619 | 51.873 | 1 | 58.86 |
| 3329 | CB | PHE | B | 1105 | 9.908 | 22.931 | 52.024 | 1 | 59.78 |
| 3330 | CG | PHE | B | 1105 | 10.025 | 23.334 | 50.592 | 1 | 58.24 |
| 3331 | CD1 | PHE | B | 1105 | 9.211 | 22.762 | 49.629 | 1 | 57.99 |
| 3332 | CD2 | PHE | B | 1105 | 11.003 | 24.242 | 50.195 | 1 | 60.55 |
| 3333 | CE1 | PHE | B | 1105 | 9.371 | 23.082 | 48.282 | 1 | 60.21 |
| 3334 | CE2 | PHE | B | 1105 | 11.176 | 24.572 | 48.86 | 1 | 60.36 |
| 3335 | CZ | PHE | B | 1105 | 10.36 | 23.988 | 47.897 | 1 | 62.76 |
| 3336 | N | TYR | B | 1106 | 9.49 | 25.592 | 53.594 | 1 | 56.86 |
| 3337 | CA | TYR | B | 1106 | 9.617 | 27.041 | 53.713 | 1 | 54.84 |
| 3338 | C | TYR | B | 1106 | 10.991 | 27.583 | 53.327 | 1 | 54.24 |
| 3339 | O | TYR | B | 1106 | 12.019 | 26.948 | 53.568 | 1 | 56.01 |
| 3340 | CB | TYR | B | 1106 | 9.293 | 27.468 | 55.135 | 1 | 52.86 |
| 3341 | CG | TYR | B | 1106 | 7.904 | 27.082 | 55.615 | 1 | 55.79 |
| 3342 | CD1 | TYR | B | 1106 | 7.517 | 25.738 | 55.739 | 1 | 56.11 |
| 3343 | CD2 | TYR | B | 1106 | 6.989 | 28.061 | 55.977 | 1 | 54.96 |
| 3344 | CE1 | TYR | B | 1106 | 6.255 | 25.392 | 56.216 | 1 | 55.56 |
| 3345 | CE2 | TYR | B | 1106 | 5.73 | 27.729 | 56.451 | 1 | 59.19 |
| 3346 | CZ | TYR | B | 1106 | 5.363 | 26.398 | 56.571 | 1 | 60.07 |
| 3347 | OH | TYR | B | 1106 | 4.1 | 26.101 | 57.053 | 1 | 63.38 |
| 3348 | N | LEU | B | 1107 | 10.992 | 28.757 | 52.698 | 1 | 52.76 |
| 3349 | CA | LEU | B | 1107 | 12.227 | 29.418 | 52.273 | 1 | 47.82 |
| 3350 | C | LEU | B | 1107 | 12.437 | 30.64 | 53.15 | 1 | 44.87 |
| 3351 | O | LEU | B | 1107 | 11.497 | 31.41 | 53.398 | 1 | 45.31 |
| 3352 | CB | LEU | B | 1107 | 12.139 | 29.867 | 50.814 | 1 | 42.99 |
| 3353 | CG | LEU | B | 1107 | 12.135 | 28.875 | 49.658 | 1 | 40.78 |
| 3354 | CD1 | LEU | B | 1107 | 12.253 | 29.679 | 48.375 | 1 | 37.09 |
| 3355 | CD2 | LEU | B | 1107 | 13.288 | 27.887 | 49.757 | 1 | 37.49 |
| 3356 | N | VAL | B | 1108 | 13.666 | 30.819 | 53.619 | 1 | 43.23 |
| 3357 | CA | VAL | B | 1108 | 13.977 | 31.951 | 54.488 | 1 | 44.7 |
| 3358 | C | VAL | B | 1108 | 15 | 32.877 | 53.856 | 1 | 45 |
| 3359 | O | VAL | B | 1108 | 16.108 | 32.455 | 53.493 | 1 | 48.26 |
| 3360 | CB | VAL | B | 1108 | 14.491 | 31.492 | 55.88 | 1 | 42.36 |

Fig. 1-84

| ATOM | ATOM TYPE | RESIDUE | | # | X | Y | Z | OCC | B |
|---|---|---|---|---|---|---|---|---|---|
| 3361 | CG1 | VAL | B | 1108 | 14.5 | 32.645 | 56.832 | 1 | 41.98 |
| 3362 | CG2 | VAL | B | 1108 | 13.591 | 30.414 | 56.455 | 1 | 44.81 |
| 3363 | N | MET | B | 1109 | 14.593 | 34.128 | 53.667 | 1 | 44.32 |
| 3364 | CA | MET | B | 1109 | 15.462 | 35.143 | 53.088 | 1 | 44.35 |
| 3365 | C | MET | B | 1109 | 15.452 | 36.339 | 54.011 | 1 | 43.05 |
| 3366 | O | MET | B | 1109 | 14.554 | 36.492 | 54.837 | 1 | 46.87 |
| 3367 | CB | MET | B | 1109 | 14.958 | 35.596 | 51.717 | 1 | 45.3 |
| 3368 | CG | MET | B | 1109 | 14.765 | 34.5 | 50.703 | 1 | 50.96 |
| 3369 | SD | MET | B | 1109 | 13.017 | 34.213 | 50.488 | 1 | 64.31 |
| 3370 | CE | MET | B | 1109 | 12.485 | 35.892 | 49.997 | 1 | 45.61 |
| 3371 | N | PRO | B | 1110 | 16.466 | 37.202 | 53.906 | 1 | 40.77 |
| 3372 | CA | PRO | B | 1110 | 16.552 | 38.395 | 54.741 | 1 | 37.5 |
| 3373 | C | PRO | B | 1110 | 15.422 | 39.349 | 54.405 | 1 | 39.62 |
| 3374 | O | PRO | B | 1110 | 15.012 | 39.445 | 53.26 | 1 | 42.95 |
| 3375 | CB | PRO | B | 1110 | 17.886 | 38.976 | 54.331 | 1 | 36.57 |
| 3376 | CG | PRO | B | 1110 | 18.092 | 38.474 | 52.981 | 1 | 32.86 |
| 3377 | CD | PRO | B | 1110 | 17.658 | 37.08 | 53.061 | 1 | 37.59 |
| 3378 | N | PHE | B | 1111 | 14.862 | 40.019 | 55.394 | 1 | 43.29 |
| 3379 | CA | PHE | B | 1111 | 13.776 | 40.943 | 55.088 | 1 | 46.86 |
| 3380 | C | PHE | B | 1111 | 14.384 | 42.117 | 54.337 | 1 | 49.91 |
| 3381 | O | PHE | B | 1111 | 15.36 | 42.713 | 54.791 | 1 | 52.95 |
| 3382 | CB | PHE | B | 1111 | 13.104 | 41.412 | 56.352 | 1 | 44.83 |
| 3383 | CG | PHE | B | 1111 | 11.964 | 42.337 | 56.118 | 1 | 46.7 |
| 3384 | CD1 | PHE | B | 1111 | 10.736 | 41.841 | 55.727 | 1 | 47.93 |
| 3385 | CD2 | PHE | B | 1111 | 12.091 | 43.702 | 56.371 | 1 | 50.78 |
| 3386 | CE1 | PHE | B | 1111 | 9.627 | 42.685 | 55.594 | 1 | 46.11 |
| 3387 | CE2 | PHE | B | 1111 | 10.989 | 44.555 | 56.242 | 1 | 53.95 |
| 3388 | CZ | PHE | B | 1111 | 9.754 | 44.036 | 55.853 | 1 | 51.1 |
| 3389 | N | MET | B | 1112 | 13.825 | 42.423 | 53.177 | 1 | 49.74 |
| 3390 | CA | MET | B | 1112 | 14.344 | 43.496 | 52.362 | 1 | 49.77 |
| 3391 | C | MET | B | 1112 | 13.54 | 44.777 | 52.312 | 1 | 49.4 |
| 3392 | O | MET | B | 1112 | 13.663 | 45.514 | 51.353 | 1 | 54.65 |
| 3393 | CB | MET | B | 1112 | 14.572 | 42.996 | 50.948 | 1 | 51.73 |
| 3394 | CG | MET | B | 1112 | 15.907 | 42.356 | 50.734 | 1 | 57.71 |
| 3395 | SD | MET | B | 1112 | 17.232 | 43.558 | 50.992 | 1 | 59.73 |
| 3396 | CE | MET | B | 1112 | 16.8 | 44.823 | 49.883 | 1 | 59.1 |
| 3397 | N | GLY | B | 1113 | 12.732 | 45.057 | 53.324 | 1 | 47.34 |
| 3398 | CA | GLY | B | 1113 | 11.977 | 46.293 | 53.316 | 1 | 47.17 |
| 3399 | C | GLY | B | 1113 | 10.563 | 46.198 | 52.79 | 1 | 50.34 |
| 3400 | O | GLY | B | 1113 | 9.623 | 46.08 | 53.583 | 1 | 56.84 |

Fig. 1-85

| ATOM | ATOM TYPE | RESIDUE | | # | X | Y | Z | OCC | B |
|---|---|---|---|---|---|---|---|---|---|
| 3401 | N | THR | B | 1114 | 10.399 | 46.403 | 51.483 | 1 | 47.67 |
| 3402 | CA | THR | B | 1114 | 9.106 | 46.319 | 50.788 | 1 | 48.71 |
| 3403 | C | THR | B | 1114 | 9.448 | 46.065 | 49.338 | 1 | 48.49 |
| 3404 | O | THR | B | 1114 | 10.618 | 46.121 | 48.968 | 1 | 52.16 |
| 3405 | CB | THR | B | 1114 | 8.248 | 47.621 | 50.83 | 1 | 50.25 |
| 3406 | OG1 | THR | B | 1114 | 8.99 | 48.715 | 50.285 | 1 | 52.88 |
| 3407 | CG2 | THR | B | 1114 | 7.793 | 47.951 | 52.235 | 1 | 53.9 |
| 3408 | N | ASP | B | 1115 | 8.445 | 45.775 | 48.519 | 1 | 46.96 |
| 3409 | CA | ASP | B | 1115 | 8.681 | 45.519 | 47.108 | 1 | 46.31 |
| 3410 | C | ASP | B | 1115 | 8.426 | 46.811 | 46.352 | 1 | 45.48 |
| 3411 | O | ASP | B | 1115 | 7.636 | 47.63 | 46.796 | 1 | 44.32 |
| 3412 | CB | ASP | B | 1115 | 7.774 | 44.395 | 46.603 | 1 | 48.02 |
| 3413 | CG | ASP | B | 1115 | 6.303 | 44.719 | 46.757 | 1 | 51 |
| 3414 | OD1 | ASP | B | 1115 | 5.8 | 45.623 | 46.051 | 1 | 49.24 |
| 3415 | OD2 | ASP | B | 1115 | 5.649 | 44.078 | 47.602 | 1 | 54.92 |
| 3416 | N | LEU | B | 1116 | 9.063 | 46.961 | 45.193 | 1 | 44.79 |
| 3417 | CA | LEU | B | 1116 | 8.947 | 48.17 | 44.386 | 1 | 47.63 |
| 3418 | C | LEU | B | 1116 | 7.509 | 48.584 | 44.107 | 1 | 50.96 |
| 3419 | O | LEU | B | 1116 | 7.202 | 49.78 | 44.044 | 1 | 48.13 |
| 3420 | CB | LEU | B | 1116 | 9.705 | 48.007 | 43.066 | 1 | 48.87 |
| 3421 | CG | LEU | B | 1116 | 10.009 | 49.289 | 42.28 | 1 | 47.8 |
| 3422 | CD1 | LEU | B | 1116 | 10.892 | 50.213 | 43.113 | 1 | 46.89 |
| 3423 | CD2 | LEU | B | 1116 | 10.671 | 48.956 | 40.952 | 1 | 43.9 |
| 3424 | N | GLY | B | 1117 | 6.638 | 47.588 | 43.943 | 1 | 51.88 |
| 3425 | CA | GLY | B | 1117 | 5.238 | 47.857 | 43.676 | 1 | 51.75 |
| 3426 | C | GLY | B | 1117 | 4.587 | 48.722 | 44.734 | 1 | 52.41 |
| 3427 | O | GLY | B | 1117 | 3.961 | 49.724 | 44.403 | 1 | 51.13 |
| 3428 | N | LYS | B | 1118 | 4.732 | 48.321 | 45.997 | 1 | 55.29 |
| 3429 | CA | LYS | B | 1118 | 4.166 | 49.051 | 47.128 | 1 | 55.85 |
| 3430 | C | LYS | B | 1118 | 4.881 | 50.372 | 47.276 | 1 | 56.27 |
| 3431 | O | LYS | B | 1118 | 4.265 | 51.391 | 47.521 | 1 | 56.48 |
| 3432 | CB | LYS | B | 1118 | 4.318 | 48.256 | 48.434 | 1 | 59.36 |
| 3433 | CG | LYS | B | 1118 | 3.565 | 46.924 | 48.476 | 1 | 65.6 |
| 3434 | CD | LYS | B | 1118 | 3.613 | 46.283 | 49.873 | 1 | 72.16 |
| 3435 | CE | LYS | B | 1118 | 3.192 | 44.789 | 49.872 | 1 | 77.1 |
| 3436 | NZ | LYS | B | 1118 | 1.815 | 44.51 | 49.352 | 1 | 78.56 |
| 3437 | N | LEU | B | 1119 | 6.195 | 50.351 | 47.114 | 1 | 57.8 |
| 3438 | CA | LEU | B | 1119 | 6.986 | 51.562 | 47.242 | 1 | 58.21 |
| 3439 | C | LEU | B | 1119 | 6.492 | 52.65 | 46.297 | 1 | 58.79 |
| 3440 | O | LEU | B | 1119 | 6.452 | 53.811 | 46.667 | 1 | 61.19 |

Fig. 1-86

| ATOM | ATOM TYPE | RESIDUE | | # | X | Y | Z | OCC | B |
|---|---|---|---|---|---|---|---|---|---|
| 3441 | CB | LEU | B | 1119 | 8.465 | 51.252 | 46.982 | 1 | 57.62 |
| 3442 | CG | LEU | B | 1119 | 9.475 | 52.395 | 47.071 | 1 | 57.94 |
| 3443 | CD1 | LEU | B | 1119 | 9.294 | 53.145 | 48.369 | 1 | 61.13 |
| 3444 | CD2 | LEU | B | 1119 | 10.889 | 51.844 | 46.977 | 1 | 57.55 |
| 3445 | N | MET | B | 1120 | 6.07 | 52.258 | 45.1 | 1 | 59.1 |
| 3446 | CA | MET | B | 1120 | 5.588 | 53.199 | 44.086 | 1 | 62.27 |
| 3447 | C | MET | B | 1120 | 4.165 | 53.716 | 44.29 | 1 | 65.88 |
| 3448 | O | MET | B | 1120 | 3.782 | 54.753 | 43.749 | 1 | 64.99 |
| 3449 | CB | MET | B | 1120 | 5.661 | 52.564 | 42.697 | 1 | 59.98 |
| 3450 | CG | MET | B | 1120 | 7.043 | 52.365 | 42.158 | 1 | 54.51 |
| 3451 | SD | MET | B | 1120 | 6.871 | 51.966 | 40.439 | 1 | 55.01 |
| 3452 | CE | MET | B | 1120 | 7.327 | 50.238 | 40.4 | 1 | 48.49 |
| 3453 | N | LYS | B | 1121 | 3.364 | 52.929 | 44.995 | 1 | 70.84 |
| 3454 | CA | LYS | B | 1121 | 1.981 | 53.263 | 45.286 | 1 | 72.19 |
| 3455 | C | LYS | B | 1121 | 1.924 | 54.382 | 46.327 | 1 | 75.33 |
| 3456 | O | LYS | B | 1121 | 1.054 | 55.244 | 46.266 | 1 | 75.8 |
| 3457 | CB | LYS | B | 1121 | 1.291 | 52.01 | 45.815 | 1 | 70.77 |
| 3458 | CG | LYS | B | 1121 | -0.195 | 52.104 | 45.963 | 1 | 74.66 |
| 3459 | CD | LYS | B | 1121 | -0.739 | 50.731 | 46.312 | 1 | 80.54 |
| 3460 | CE | LYS | B | 1121 | -2.258 | 50.681 | 46.314 | 1 | 81.02 |
| 3461 | NZ | LYS | B | 1121 | -2.715 | 49.283 | 46.558 | 1 | 82.34 |
| 3462 | N | HIS | B | 1122 | 2.877 | 54.371 | 47.259 | 1 | 79.37 |
| 3463 | CA | HIS | B | 1122 | 2.941 | 55.355 | 48.339 | 1 | 84.05 |
| 3464 | C | HIS | B | 1122 | 3.634 | 56.648 | 47.932 | 1 | 83.81 |
| 3465 | O | HIS | B | 1122 | 3.183 | 57.738 | 48.287 | 1 | 83.68 |
| 3466 | CB | HIS | B | 1122 | 3.655 | 54.762 | 49.577 | 1 | 89.84 |
| 3467 | CG | HIS | B | 1122 | 2.937 | 53.6 | 50.214 | 1 | 97.14 |
| 3468 | ND1 | HIS | B | 1122 | 1.748 | 53.09 | 49.73 | 1 | 98.38 |
| 3469 | CD2 | HIS | B | 1122 | 3.253 | 52.846 | 51.297 | 1 | 98.8 |
| 3470 | CE1 | HIS | B | 1122 | 1.363 | 52.074 | 50.484 | 1 | 99.03 |
| 3471 | NE2 | HIS | B | 1122 | 2.26 | 51.904 | 51.443 | 1 | 100 |
| 3472 | N | GLU | B | 1123 | 4.705 | 56.53 | 47.153 | 1 | 83.96 |
| 3473 | CA | GLU | B | 1123 | 5.467 | 57.705 | 46.743 | 1 | 83.63 |
| 3474 | C | GLU | B | 1123 | 5.969 | 57.726 | 45.295 | 1 | 82.16 |
| 3475 | O | GLU | B | 1123 | 6.013 | 56.695 | 44.619 | 1 | 80.04 |
| 3476 | CB | GLU | B | 1123 | 6.647 | 57.901 | 47.71 | 1 | 84.93 |
| 3477 | CG | GLU | B | 1123 | 7.53 | 56.669 | 47.86 | 1 | 85.12 |
| 3478 | CD | GLU | B | 1123 | 8.589 | 56.83 | 48.925 | 1 | 86.79 |
| 3479 | OE1 | GLU | B | 1123 | 8.277 | 56.587 | 50.115 | 1 | 86.76 |
| 3480 | OE2 | GLU | B | 1123 | 9.732 | 57.189 | 48.566 | 1 | 86.46 |

Fig. 1-87

| ATOM | ATOM TYPE | RESIDUE | | # | X | Y | Z | OCC | B |
|---|---|---|---|---|---|---|---|---|---|
| 3481 | N | LYS | B | 1124 | 6.28 | 58.933 | 44.814 | 1 | 82.56 |
| 3482 | CA | LYS | B | 1124 | 6.821 | 59.132 | 43.465 | 1 | 81.06 |
| 3483 | C | LYS | B | 1124 | 8.317 | 59.052 | 43.668 | 1 | 77.78 |
| 3484 | O | LYS | B | 1124 | 8.841 | 59.618 | 44.636 | 1 | 78.5 |
| 3485 | CB | LYS | B | 1124 | 6.458 | 60.504 | 42.892 | 1 | 84.26 |
| 3486 | CG | LYS | B | 1124 | 6.548 | 60.575 | 41.366 | 1 | 86.98 |
| 3487 | CD | LYS | B | 1124 | 5.693 | 59.475 | 40.717 | 1 | 91.96 |
| 3488 | CE | LYS | B | 1124 | 5.502 | 59.697 | 39.216 | 1 | 94.56 |
| 3489 | NZ | LYS | B | 1124 | 4.471 | 60.739 | 38.898 | 1 | 96.11 |
| 3490 | N | LEU | B | 1125 | 9.003 | 58.395 | 42.741 | 1 | 71.62 |
| 3491 | CA | LEU | B | 1125 | 10.426 | 58.19 | 42.889 | 1 | 67.92 |
| 3492 | C | LEU | B | 1125 | 11.399 | 59.349 | 42.723 | 1 | 68.88 |
| 3493 | O | LEU | B | 1125 | 11.86 | 59.913 | 43.716 | 1 | 71.34 |
| 3494 | CB | LEU | B | 1125 | 10.845 | 56.958 | 42.1 | 1 | 64.73 |
| 3495 | CG | LEU | B | 1125 | 10.259 | 55.671 | 42.703 | 1 | 59.06 |
| 3496 | CD1 | LEU | B | 1125 | 10.574 | 54.504 | 41.839 | 1 | 54.98 |
| 3497 | CD2 | LEU | B | 1125 | 10.797 | 55.439 | 44.109 | 1 | 54.83 |
| 3498 | N | GLY | B | 1126 | 11.736 | 59.716 | 41.501 | 1 | 67.61 |
| 3499 | CA | GLY | B | 1126 | 12.683 | 60.804 | 41.356 | 1 | 70.66 |
| 3500 | C | GLY | B | 1126 | 13.93 | 60.337 | 40.63 | 1 | 73.02 |
| 3501 | O | GLY | B | 1126 | 14.472 | 59.271 | 40.922 | 1 | 72.39 |
| 3502 | N | GLU | B | 1127 | 14.401 | 61.173 | 39.711 | 1 | 74.64 |
| 3503 | CA | GLU | B | 1127 | 15.554 | 60.88 | 38.874 | 1 | 76.17 |
| 3504 | C | GLU | B | 1127 | 16.695 | 60.069 | 39.461 | 1 | 74.33 |
| 3505 | O | GLU | B | 1127 | 17.004 | 58.999 | 38.945 | 1 | 72.9 |
| 3506 | CB | GLU | B | 1127 | 16.087 | 62.162 | 38.234 | 1 | 81.52 |
| 3507 | CG | GLU | B | 1127 | 15.108 | 62.779 | 37.241 | 1 | 86.13 |
| 3508 | CD | GLU | B | 1127 | 15.767 | 63.745 | 36.27 | 1 | 89.36 |
| 3509 | OE1 | GLU | B | 1127 | 16.875 | 63.441 | 35.766 | 1 | 89.13 |
| 3510 | OE2 | GLU | B | 1127 | 15.158 | 64.804 | 35.998 | 1 | 92.24 |
| 3511 | N | ASP | B | 1128 | 17.328 | 60.567 | 40.519 | 1 | 73.57 |
| 3512 | CA | ASP | B | 1128 | 18.445 | 59.84 | 41.116 | 1 | 73.67 |
| 3513 | C | ASP | B | 1128 | 18.035 | 58.45 | 41.601 | 1 | 72.87 |
| 3514 | O | ASP | B | 1128 | 18.734 | 57.467 | 41.336 | 1 | 73.04 |
| 3515 | CB | ASP | B | 1128 | 19.077 | 60.646 | 42.258 | 1 | 75.81 |
| 3516 | CG | ASP | B | 1128 | 20.069 | 61.706 | 41.765 | 1 | 77.88 |
| 3517 | OD1 | ASP | B | 1128 | 20.028 | 62.093 | 40.572 | 1 | 76.08 |
| 3518 | OD2 | ASP | B | 1128 | 20.902 | 62.154 | 42.586 | 1 | 78.33 |
| 3519 | N | ARG | B | 1129 | 16.881 | 58.373 | 42.269 | 1 | 71.72 |
| 3520 | CA | ARG | B | 1129 | 16.342 | 57.116 | 42.809 | 1 | 69.85 |

Fig. 1-88

| ATOM | ATOM TYPE | RESIDUE | | # | X | Y | Z | OCC | B |
|---|---|---|---|---|---|---|---|---|---|
| 3521 | C | ARG | B | 1129 | 16.04 | 56.084 | 41.718 | 1 | 65.08 |
| 3522 | O | ARG | B | 1129 | 16.503 | 54.943 | 41.771 | 1 | 60.98 |
| 3523 | CB | ARG | B | 1129 | 15.058 | 57.391 | 43.596 | 1 | 74.44 |
| 3524 | CG | ARG | B | 1129 | 15.165 | 57.417 | 45.108 | 1 | 79.34 |
| 3525 | CD | ARG | B | 1129 | 13.729 | 57.482 | 45.602 | 1 | 86.88 |
| 3526 | NE | ARG | B | 1129 | 13.599 | 57.222 | 46.985 | 1 | 95.02 |
| 3527 | CZ | ARG | B | 1129 | 13.062 | 56.309 | 47.786 | 1 | 98.4 |
| 3528 | NH1 | ARG | B | 1129 | 12.4 | 55.196 | 47.479 | 1 | 98.08 |
| 3529 | NH2 | ARG | B | 1129 | 13.275 | 56.613 | 49.054 | 1 | 100 |
| 3530 | N | ILE | B | 1130 | 15.239 | 56.501 | 40.744 | 1 | 61.08 |
| 3531 | CA | ILE | B | 1130 | 14.856 | 55.648 | 39.632 | 1 | 56.02 |
| 3532 | C | ILE | B | 1130 | 16.072 | 55.059 | 38.945 | 1 | 55.95 |
| 3533 | O | ILE | B | 1130 | 16.047 | 53.896 | 38.555 | 1 | 57.22 |
| 3534 | CB | ILE | B | 1130 | 14.014 | 56.434 | 38.618 | 1 | 53.66 |
| 3535 | CG1 | ILE | B | 1130 | 12.74 | 56.926 | 39.3 | 1 | 54.96 |
| 3536 | CG2 | ILE | B | 1130 | 13.699 | 55.578 | 37.408 | 1 | 53.66 |
| 3537 | CD1 | ILE | B | 1130 | 11.897 | 57.876 | 38.479 | 1 | 55.23 |
| 3538 | N | GLN | B | 1131 | 17.137 | 55.856 | 38.821 | 1 | 57.03 |
| 3539 | CA | GLN | B | 1131 | 18.384 | 55.423 | 38.182 | 1 | 57.03 |
| 3540 | C | GLN | B | 1131 | 19.067 | 54.345 | 38.994 | 1 | 56.82 |
| 3541 | O | GLN | B | 1131 | 19.425 | 53.283 | 38.48 | 1 | 57.84 |
| 3542 | CB | GLN | B | 1131 | 19.371 | 56.58 | 38.027 | 1 | 59.35 |
| 3543 | CG | GLN | B | 1131 | 20.68 | 56.139 | 37.365 | 1 | 63.44 |
| 3544 | CD | GLN | B | 1131 | 21.801 | 57.156 | 37.493 | 1 | 64.89 |
| 3545 | OE1 | GLN | B | 1131 | 22.522 | 57.429 | 36.53 | 1 | 64.54 |
| 3546 | NE2 | GLN | B | 1131 | 21.976 | 57.694 | 38.694 | 1 | 68.97 |
| 3547 | N | PHE | B | 1132 | 19.268 | 54.64 | 40.269 | 1 | 55.63 |
| 3548 | CA | PHE | B | 1132 | 19.913 | 53.7 | 41.168 | 1 | 52.85 |
| 3549 | C | PHE | B | 1132 | 19.169 | 52.372 | 41.178 | 1 | 49.79 |
| 3550 | O | PHE | B | 1132 | 19.774 | 51.307 | 41.038 | 1 | 51.14 |
| 3551 | CB | PHE | B | 1132 | 19.95 | 54.278 | 42.587 | 1 | 53.09 |
| 3552 | CG | PHE | B | 1132 | 20.853 | 53.528 | 43.521 | 1 | 53.2 |
| 3553 | CD1 | PHE | B | 1132 | 22.053 | 52.968 | 43.06 | 1 | 54.16 |
| 3554 | CD2 | PHE | B | 1132 | 20.514 | 53.384 | 44.854 | 1 | 50.23 |
| 3555 | CE1 | PHE | B | 1132 | 22.9 | 52.273 | 43.918 | 1 | 53.87 |
| 3556 | CE2 | PHE | B | 1132 | 21.354 | 52.691 | 45.723 | 1 | 55.54 |
| 3557 | CZ | PHE | B | 1132 | 22.553 | 52.132 | 45.251 | 1 | 54.71 |
| 3558 | N | LEU | B | 1133 | 17.851 | 52.445 | 41.305 | 1 | 44.05 |
| 3559 | CA | LEU | B | 1133 | 17.052 | 51.238 | 41.358 | 1 | 41.13 |
| 3560 | C | LEU | B | 1133 | 17.215 | 50.404 | 40.118 | 1 | 42.01 |

Fig. 1-89

| ATOM | ATOM TYPE | RESIDUE | | # | X | Y | Z | OCC | B |
|---|---|---|---|---|---|---|---|---|---|
| 3561 | O | LEU | B | 1133 | 17.571 | 49.24 | 40.218 | 1 | 42.85 |
| 3562 | CB | LEU | B | 1133 | 15.578 | 51.553 | 41.62 | 1 | 35.84 |
| 3563 | CG | LEU | B | 1133 | 15.285 | 52.134 | 43.011 | 1 | 32.28 |
| 3564 | CD1 | LEU | B | 1133 | 13.802 | 52.374 | 43.2 | 1 | 35.05 |
| 3565 | CD2 | LEU | B | 1133 | 15.803 | 51.202 | 44.074 | 1 | 32.13 |
| 3566 | N | VAL | B | 1134 | 17.079 | 51.032 | 38.95 | 1 | 43.76 |
| 3567 | CA | VAL | B | 1134 | 17.178 | 50.314 | 37.671 | 1 | 41.86 |
| 3568 | C | VAL | B | 1134 | 18.558 | 49.742 | 37.409 | 1 | 45.23 |
| 3569 | O | VAL | B | 1134 | 18.697 | 48.68 | 36.792 | 1 | 49.26 |
| 3570 | CB | VAL | B | 1134 | 16.751 | 51.193 | 36.484 | 1 | 36.34 |
| 3571 | CG1 | VAL | B | 1134 | 16.726 | 50.378 | 35.205 | 1 | 31.6 |
| 3572 | CG2 | VAL | B | 1134 | 15.381 | 51.776 | 36.738 | 1 | 37.61 |
| 3573 | N | TYR | B | 1135 | 19.576 | 50.453 | 37.877 | 1 | 47.4 |
| 3574 | CA | TYR | B | 1135 | 20.954 | 50.017 | 37.718 | 1 | 48.59 |
| 3575 | C | TYR | B | 1135 | 21.077 | 48.657 | 38.404 | 1 | 49.03 |
| 3576 | O | TYR | B | 1135 | 21.611 | 47.705 | 37.834 | 1 | 47.74 |
| 3577 | CB | TYR | B | 1135 | 21.895 | 51.026 | 38.388 | 1 | 52.16 |
| 3578 | CG | TYR | B | 1135 | 23.359 | 50.648 | 38.29 | 1 | 57.47 |
| 3579 | CD1 | TYR | B | 1135 | 23.928 | 50.297 | 37.058 | 1 | 58.3 |
| 3580 | CD2 | TYR | B | 1135 | 24.171 | 50.619 | 39.424 | 1 | 58.11 |
| 3581 | CE1 | TYR | B | 1135 | 25.266 | 49.93 | 36.959 | 1 | 58.53 |
| 3582 | CE2 | TYR | B | 1135 | 25.513 | 50.246 | 39.334 | 1 | 60.23 |
| 3583 | CZ | TYR | B | 1135 | 26.053 | 49.905 | 38.097 | 1 | 61.07 |
| 3584 | OH | TYR | B | 1135 | 27.382 | 49.535 | 37.994 | 1 | 66.1 |
| 3585 | N | GLN | B | 1136 | 20.525 | 48.583 | 39.615 | 1 | 48.47 |
| 3586 | CA | GLN | B | 1136 | 20.533 | 47.374 | 40.419 | 1 | 47.8 |
| 3587 | C | GLN | B | 1136 | 19.713 | 46.227 | 39.804 | 1 | 48.71 |
| 3588 | O | GLN | B | 1136 | 20.118 | 45.062 | 39.878 | 1 | 49.82 |
| 3589 | CB | GLN | B | 1136 | 20.044 | 47.691 | 41.816 | 1 | 50.54 |
| 3590 | CG | GLN | B | 1136 | 20.795 | 48.813 | 42.479 | 1 | 48.71 |
| 3591 | CD | GLN | B | 1136 | 20.47 | 48.908 | 43.943 | 1 | 51.78 |
| 3592 | OE1 | GLN | B | 1136 | 20.809 | 48.009 | 44.724 | 1 | 53.24 |
| 3593 | NE2 | GLN | B | 1136 | 19.804 | 49.99 | 44.334 | 1 | 48.84 |
| 3594 | N | MET | B | 1137 | 18.562 | 46.536 | 39.215 | 1 | 44.32 |
| 3595 | CA | MET | B | 1137 | 17.775 | 45.493 | 38.564 | 1 | 46.03 |
| 3596 | C | MET | B | 1137 | 18.674 | 44.815 | 37.53 | 1 | 49.34 |
| 3597 | O | MET | B | 1137 | 18.766 | 43.58 | 37.457 | 1 | 50.26 |
| 3598 | CB | MET | B | 1137 | 16.598 | 46.098 | 37.805 | 1 | 40.63 |
| 3599 | CG | MET | B | 1137 | 15.353 | 46.242 | 38.588 | 1 | 42.48 |
| 3600 | SD | MET | B | 1137 | 14.318 | 47.431 | 37.791 | 1 | 47.34 |

Fig. 1-90

| ATOM | ATOM TYPE | RESIDUE | | # | X | Y | Z | OCC | B |
|---|---|---|---|---|---|---|---|---|---|
| 3601 | CE | MET | B | 1137 | 14.255 | 48.7 | 39.048 | 1 | 42.91 |
| 3602 | N | LEU | B | 1138 | 19.366 | 45.661 | 36.766 | 1 | 48.43 |
| 3603 | CA | LEU | B | 1138 | 20.234 | 45.229 | 35.695 | 1 | 45.62 |
| 3604 | C | LEU | B | 1138 | 21.501 | 44.467 | 36.066 | 1 | 45.99 |
| 3605 | O | LEU | B | 1138 | 21.898 | 43.554 | 35.339 | 1 | 44.39 |
| 3606 | CB | LEU | B | 1138 | 20.506 | 46.415 | 34.78 | 1 | 43.96 |
| 3607 | CG | LEU | B | 1138 | 19.232 | 46.802 | 34.017 | 1 | 41.59 |
| 3608 | CD1 | LEU | B | 1138 | 19.445 | 48.074 | 33.245 | 1 | 42.5 |
| 3609 | CD2 | LEU | B | 1138 | 18.843 | 45.669 | 33.069 | 1 | 38.1 |
| 3610 | N | LYS | B | 1139 | 22.14 | 44.816 | 37.179 | 1 | 46.62 |
| 3611 | CA | LYS | B | 1139 | 23.337 | 44.071 | 37.576 | 1 | 46.94 |
| 3612 | C | LYS | B | 1139 | 22.842 | 42.694 | 38.006 | 1 | 45.46 |
| 3613 | O | LYS | B | 1139 | 23.434 | 41.667 | 37.688 | 1 | 47.02 |
| 3614 | CB | LYS | B | 1139 | 24.088 | 44.755 | 38.728 | 1 | 48.43 |
| 3615 | CG | LYS | B | 1139 | 24.737 | 46.083 | 38.351 | 1 | 54.08 |
| 3616 | CD | LYS | B | 1139 | 26.007 | 46.372 | 39.143 | 1 | 58.36 |
| 3617 | CE | LYS | B | 1139 | 25.758 | 46.451 | 40.654 | 1 | 66.2 |
| 3618 | NZ | LYS | B | 1139 | 27.03 | 46.525 | 41.469 | 1 | 67.31 |
| 3619 | N | GLY | B | 1140 | 21.703 | 42.688 | 38.682 | 1 | 42.91 |
| 3620 | CA | GLY | B | 1140 | 21.136 | 41.445 | 39.131 | 1 | 38.97 |
| 3621 | C | GLY | B | 1140 | 20.835 | 40.616 | 37.923 | 1 | 41.74 |
| 3622 | O | GLY | B | 1140 | 21.195 | 39.435 | 37.861 | 1 | 42.79 |
| 3623 | N | LEU | B | 1141 | 20.247 | 41.265 | 36.92 | 1 | 43.16 |
| 3624 | CA | LEU | B | 1141 | 19.887 | 40.577 | 35.692 | 1 | 44.48 |
| 3625 | C | LEU | B | 1141 | 21.094 | 40.037 | 34.951 | 1 | 47.53 |
| 3626 | O | LEU | B | 1141 | 21.101 | 38.867 | 34.557 | 1 | 49.29 |
| 3627 | CB | LEU | B | 1141 | 19.096 | 41.483 | 34.781 | 1 | 40.49 |
| 3628 | CG | LEU | B | 1141 | 17.649 | 41.057 | 34.565 | 1 | 40.66 |
| 3629 | CD1 | LEU | B | 1141 | 17.207 | 41.641 | 33.228 | 1 | 42.75 |
| 3630 | CD2 | LEU | B | 1141 | 17.518 | 39.547 | 34.53 | 1 | 35.6 |
| 3631 | N | ARG | B | 1142 | 22.12 | 40.877 | 34.799 | 1 | 49.33 |
| 3632 | CA | ARG | B | 1142 | 23.34 | 40.474 | 34.107 | 1 | 52.44 |
| 3633 | C | ARG | B | 1142 | 23.904 | 39.219 | 34.753 | 1 | 54.8 |
| 3634 | O | ARG | B | 1142 | 24.424 | 38.343 | 34.051 | 1 | 55.56 |
| 3635 | CB | ARG | B | 1142 | 24.398 | 41.574 | 34.125 | 1 | 53.1 |
| 3636 | CG | ARG | B | 1142 | 25.461 | 41.382 | 33.054 | 1 | 55.22 |
| 3637 | CD | ARG | B | 1142 | 26.847 | 41.755 | 33.538 | 1 | 61.94 |
| 3638 | NE | ARG | B | 1142 | 26.895 | 43.071 | 34.173 | 1 | 68.45 |
| 3639 | CZ | ARG | B | 1142 | 27.861 | 43.467 | 34.998 | 1 | 71.59 |
| 3640 | NH1 | ARG | B | 1142 | 28.863 | 42.648 | 35.282 | 1 | 76.4 |

Fig. 1-91

| ATOM | ATOM TYPE | RESIDUE | | # | X | Y | Z | OCC | B |
|---|---|---|---|---|---|---|---|---|---|
| 3641 | NH2 | ARG | B | 1142 | 27.806 | 44.661 | 35.577 | 1 | 73.39 |
| 3642 | N | TYR | B | 1143 | 23.795 | 39.139 | 36.083 | 1 | 54.15 |
| 3643 | CA | TYR | B | 1143 | 24.267 | 37.976 | 36.802 | 1 | 54.04 |
| 3644 | C | TYR | B | 1143 | 23.401 | 36.768 | 36.452 | 1 | 55 |
| 3645 | O | TYR | B | 1143 | 23.902 | 35.763 | 35.948 | 1 | 56.08 |
| 3646 | CB | TYR | B | 1143 | 24.24 | 38.206 | 38.312 | 1 | 55.69 |
| 3647 | CG | TYR | B | 1143 | 24.59 | 36.957 | 39.109 | 1 | 54.84 |
| 3648 | CD1 | TYR | B | 1143 | 25.91 | 36.512 | 39.197 | 1 | 54.34 |
| 3649 | CD2 | TYR | B | 1143 | 23.595 | 36.177 | 39.697 | 1 | 52.78 |
| 3650 | CE1 | TYR | B | 1143 | 26.231 | 35.319 | 39.839 | 1 | 51.48 |
| 3651 | CE2 | TYR | B | 1143 | 23.9 | 34.986 | 40.334 | 1 | 53.29 |
| 3652 | CZ | TYR | B | 1143 | 25.224 | 34.56 | 40.402 | 1 | 53.23 |
| 3653 | OH | TYR | B | 1143 | 25.54 | 33.374 | 41.029 | 1 | 52.52 |
| 3654 | N | ILE | B | 1144 | 22.1 | 36.875 | 36.704 | 1 | 53.33 |
| 3655 | CA | ILE | B | 1144 | 21.177 | 35.778 | 36.426 | 1 | 50.27 |
| 3656 | C | ILE | B | 1144 | 21.347 | 35.226 | 35.011 | 1 | 53.25 |
| 3657 | O | ILE | B | 1144 | 21.354 | 34.014 | 34.806 | 1 | 56.43 |
| 3658 | CB | ILE | B | 1144 | 19.732 | 36.242 | 36.637 | 1 | 46.32 |
| 3659 | CG1 | ILE | B | 1144 | 19.554 | 36.678 | 38.083 | 1 | 40.16 |
| 3660 | CG2 | ILE | B | 1144 | 18.745 | 35.118 | 36.34 | 1 | 44.48 |
| 3661 | CD1 | ILE | B | 1144 | 18.392 | 37.594 | 38.271 | 1 | 41.57 |
| 3662 | N | HIS | B | 1145 | 21.538 | 36.123 | 34.049 | 1 | 53.89 |
| 3663 | CA | HIS | B | 1145 | 21.71 | 35.745 | 32.651 | 1 | 53.63 |
| 3664 | C | HIS | B | 1145 | 23.061 | 35.143 | 32.313 | 1 | 55.06 |
| 3665 | O | HIS | B | 1145 | 23.132 | 34.137 | 31.603 | 1 | 55.93 |
| 3666 | CB | HIS | B | 1145 | 21.446 | 36.945 | 31.755 | 1 | 53.17 |
| 3667 | CG | HIS | B | 1145 | 20.003 | 37.313 | 31.673 | 1 | 51.03 |
| 3668 | ND1 | HIS | B | 1145 | 19.575 | 38.535 | 31.207 | 1 | 49.45 |
| 3669 | CD2 | HIS | B | 1145 | 18.89 | 36.609 | 31.979 | 1 | 49.05 |
| 3670 | CE1 | HIS | B | 1145 | 18.255 | 38.567 | 31.227 | 1 | 51.87 |
| 3671 | NE2 | HIS | B | 1145 | 17.815 | 37.409 | 31.69 | 1 | 51.75 |
| 3672 | N | ALA | B | 1146 | 24.133 | 35.785 | 32.773 | 1 | 56.94 |
| 3673 | CA | ALA | B | 1146 | 25.491 | 35.271 | 32.539 | 1 | 57.72 |
| 3674 | C | ALA | B | 1146 | 25.566 | 33.856 | 33.098 | 1 | 55.26 |
| 3675 | O | ALA | B | 1146 | 26.329 | 33.015 | 32.617 | 1 | 57.5 |
| 3676 | CB | ALA | B | 1146 | 26.537 | 36.16 | 33.226 | 1 | 56.09 |
| 3677 | N | ALA | B | 1147 | 24.743 | 33.606 | 34.11 | 1 | 52.41 |
| 3678 | CA | ALA | B | 1147 | 24.676 | 32.31 | 34.742 | 1 | 52.4 |
| 3679 | C | ALA | B | 1147 | 23.785 | 31.378 | 33.932 | 1 | 53.33 |
| 3680 | O | ALA | B | 1147 | 23.518 | 30.25 | 34.356 | 1 | 56.66 |

Fig. 1-92

| ATOM | ATOM TYPE | RESIDUE | | # | X | Y | Z | OCC | B |
|---|---|---|---|---|---|---|---|---|---|
| 3681 | CB | ALA | B | 1147 | 24.156 | 32.451 | 36.156 | 1 | 47 |
| 3682 | N | GLY | B | 1148 | 23.331 | 31.853 | 32.771 | 1 | 53.31 |
| 3683 | CA | GLY | B | 1148 | 22.464 | 31.058 | 31.904 | 1 | 53.81 |
| 3684 | C | GLY | B | 1148 | 21.023 | 30.837 | 32.372 | 1 | 51.69 |
| 3685 | O | GLY | B | 1148 | 20.321 | 29.973 | 31.842 | 1 | 50.84 |
| 3686 | N | ILE | B | 1149 | 20.602 | 31.6 | 33.38 | 1 | 50.99 |
| 3687 | CA | ILE | B | 1149 | 19.249 | 31.531 | 33.941 | 1 | 49.74 |
| 3688 | C | ILE | B | 1149 | 18.325 | 32.594 | 33.301 | 1 | 48.79 |
| 3689 | O | ILE | B | 1149 | 18.779 | 33.633 | 32.802 | 1 | 44.6 |
| 3690 | CB | ILE | B | 1149 | 19.281 | 31.772 | 35.488 | 1 | 48.77 |
| 3691 | CG1 | ILE | B | 1149 | 20.061 | 30.663 | 36.184 | 1 | 50.52 |
| 3692 | CG2 | ILE | B | 1149 | 17.888 | 31.843 | 36.069 | 1 | 47.26 |
| 3693 | CD1 | ILE | B | 1149 | 20.388 | 30.955 | 37.632 | 1 | 50.13 |
| 3694 | N | ILE | B | 1150 | 17.031 | 32.291 | 33.28 | 1 | 47.03 |
| 3695 | CA | ILE | B | 1150 | 16.029 | 33.208 | 32.764 | 1 | 45.69 |
| 3696 | C | ILE | B | 1150 | 15.001 | 33.335 | 33.896 | 1 | 47.53 |
| 3697 | O | ILE | B | 1150 | 14.569 | 32.326 | 34.478 | 1 | 47.87 |
| 3698 | CB | ILE | B | 1150 | 15.402 | 32.702 | 31.45 | 1 | 45.45 |
| 3699 | CG1 | ILE | B | 1150 | 14.366 | 33.696 | 30.957 | 1 | 42.45 |
| 3700 | CG2 | ILE | B | 1150 | 14.792 | 31.315 | 31.624 | 1 | 46.3 |
| 3701 | CD1 | ILE | B | 1150 | 14.018 | 33.491 | 29.527 | 1 | 43.98 |
| 3702 | N | HIS | B | 1151 | 14.635 | 34.575 | 34.223 | 1 | 44.2 |
| 3703 | CA | HIS | B | 1151 | 13.73 | 34.841 | 35.321 | 1 | 37.69 |
| 3704 | C | HIS | B | 1151 | 12.252 | 34.662 | 35.031 | 1 | 41.01 |
| 3705 | O | HIS | B | 1151 | 11.512 | 34.109 | 35.861 | 1 | 40.05 |
| 3706 | CB | HIS | B | 1151 | 13.994 | 36.241 | 35.882 | 1 | 37.84 |
| 3707 | CG | HIS | B | 1151 | 13.195 | 36.547 | 37.104 | 1 | 30.23 |
| 3708 | ND1 | HIS | B | 1151 | 11.845 | 36.824 | 37.052 | 1 | 30.05 |
| 3709 | CD2 | HIS | B | 1151 | 13.523 | 36.513 | 38.416 | 1 | 31.02 |
| 3710 | CE1 | HIS | B | 1151 | 11.376 | 36.933 | 38.285 | 1 | 32.07 |
| 3711 | NE2 | HIS | B | 1151 | 12.375 | 36.749 | 39.132 | 1 | 26.47 |
| 3712 | N | ARG | B | 1152 | 11.807 | 35.217 | 33.906 | 1 | 41.8 |
| 3713 | CA | ARG | B | 1152 | 10.407 | 35.129 | 33.465 | 1 | 42.27 |
| 3714 | C | ARG | B | 1152 | 9.3 | 35.758 | 34.32 | 1 | 41.18 |
| 3715 | O | ARG | B | 1152 | 8.134 | 35.367 | 34.192 | 1 | 43.19 |
| 3716 | CB | ARG | B | 1152 | 10.043 | 33.68 | 33.16 | 1 | 39.46 |
| 3717 | CG | ARG | B | 1152 | 10.84 | 33.125 | 32.027 | 1 | 41.9 |
| 3718 | CD | ARG | B | 1152 | 11.24 | 31.746 | 32.375 | 1 | 42.14 |
| 3719 | NE | ARG | B | 1152 | 10.593 | 30.76 | 31.527 | 1 | 47.05 |
| 3720 | CZ | ARG | B | 1152 | 10.056 | 29.636 | 31.976 | 1 | 43.86 |

Fig. 1-93

| ATOM | ATOM TYPE | RESIDUE | | # | X | Y | Z | OCC | B |
|---|---|---|---|---|---|---|---|---|---|
| 3721 | NH1 | ARG | B | 1152 | 10.068 | 29.377 | 33.265 | 1 | 41.3 |
| 3722 | NH2 | ARG | B | 1152 | 9.627 | 28.716 | 31.125 | 1 | 46.12 |
| 3723 | N | ASP | B | 1153 | 9.64 | 36.691 | 35.203 | 1 | 34.87 |
| 3724 | CA | ASP | B | 1153 | 8.597 | 37.328 | 35.988 | 1 | 33.15 |
| 3725 | C | ASP | B | 1153 | 8.991 | 38.637 | 36.669 | 1 | 34.98 |
| 3726 | O | ASP | B | 1153 | 8.511 | 38.949 | 37.755 | 1 | 32.43 |
| 3727 | CB | ASP | B | 1153 | 8.034 | 36.368 | 37.019 | 1 | 31.59 |
| 3728 | CG | ASP | B | 1153 | 6.608 | 36.738 | 37.428 | 1 | 38.53 |
| 3729 | OD1 | ASP | B | 1153 | 5.83 | 37.15 | 36.54 | 1 | 40.91 |
| 3730 | OD2 | ASP | B | 1153 | 6.25 | 36.64 | 38.623 | 1 | 36.3 |
| 3731 | N | LEU | B | 1154 | 9.864 | 39.411 | 36.039 | 1 | 31.7 |
| 3732 | CA | LEU | B | 1154 | 10.268 | 40.657 | 36.643 | 1 | 33.64 |
| 3733 | C | LEU | B | 1154 | 9.09 | 41.626 | 36.595 | 1 | 31.96 |
| 3734 | O | LEU | B | 1154 | 8.514 | 41.89 | 35.554 | 1 | 32.06 |
| 3735 | CB | LEU | B | 1154 | 11.492 | 41.228 | 35.924 | 1 | 33.58 |
| 3736 | CG | LEU | B | 1154 | 12.621 | 40.214 | 36.031 | 1 | 36.54 |
| 3737 | CD1 | LEU | B | 1154 | 13.852 | 40.778 | 35.404 | 1 | 39.3 |
| 3738 | CD2 | LEU | B | 1154 | 12.876 | 39.873 | 37.506 | 1 | 33.9 |
| 3739 | N | LYS | B | 1155 | 8.673 | 42.074 | 37.757 | 1 | 31.22 |
| 3740 | CA | LYS | B | 1155 | 7.578 | 43.005 | 37.854 | 1 | 33.96 |
| 3741 | C | LYS | B | 1155 | 7.878 | 43.708 | 39.137 | 1 | 35.23 |
| 3742 | O | LYS | B | 1155 | 8.661 | 43.209 | 39.931 | 1 | 36.46 |
| 3743 | CB | LYS | B | 1155 | 6.236 | 42.285 | 37.907 | 1 | 35.04 |
| 3744 | CG | LYS | B | 1155 | 6.012 | 41.375 | 39.086 | 1 | 36.77 |
| 3745 | CD | LYS | B | 1155 | 4.832 | 40.474 | 38.802 | 1 | 40.8 |
| 3746 | CE | LYS | B | 1155 | 4.382 | 39.777 | 40.057 | 1 | 43.85 |
| 3747 | NZ | LYS | B | 1155 | 2.96 | 39.391 | 39.94 | 1 | 46.98 |
| 3748 | N | PRO | B | 1156 | 7.276 | 44.88 | 39.361 | 1 | 36.93 |
| 3749 | CA | PRO | B | 1156 | 7.527 | 45.632 | 40.592 | 1 | 37.08 |
| 3750 | C | PRO | B | 1156 | 7.374 | 44.792 | 41.865 | 1 | 39.23 |
| 3751 | O | PRO | B | 1156 | 8.157 | 44.92 | 42.805 | 1 | 43.87 |
| 3752 | CB | PRO | B | 1156 | 6.47 | 46.734 | 40.523 | 1 | 41.2 |
| 3753 | CG | PRO | B | 1156 | 6.275 | 46.932 | 39.024 | 1 | 37.21 |
| 3754 | CD | PRO | B | 1156 | 6.21 | 45.512 | 38.555 | 1 | 36.35 |
| 3755 | N | GLY | B | 1157 | 6.376 | 43.914 | 41.878 | 1 | 38.41 |
| 3756 | CA | GLY | B | 1157 | 6.141 | 43.076 | 43.037 | 1 | 37.48 |
| 3757 | C | GLY | B | 1157 | 7.209 | 42.039 | 43.348 | 1 | 36.76 |
| 3758 | O | GLY | B | 1157 | 7.212 | 41.466 | 44.433 | 1 | 39.68 |
| 3759 | N | ASN | B | 1158 | 8.069 | 41.744 | 42.391 | 1 | 33.82 |
| 3760 | CA | ASN | B | 1158 | 9.139 | 40.788 | 42.613 | 1 | 37.83 |

Fig. 1-94

| ATOM | ATOM TYPE | RESIDUE | | # | X | Y | Z | OCC | B |
|---|---|---|---|---|---|---|---|---|---|
| 3761 | C | ASN | B | 1158 | 10.473 | 41.493 | 42.694 | 1 | 38.7 |
| 3762 | O | ASN | B | 1158 | 11.476 | 40.95 | 42.248 | 1 | 38.46 |
| 3763 | CB | ASN | B | 1158 | 9.222 | 39.743 | 41.505 | 1 | 38.35 |
| 3764 | CG | ASN | B | 1158 | 7.994 | 38.896 | 41.417 | 1 | 40.45 |
| 3765 | OD1 | ASN | B | 1158 | 7.414 | 38.505 | 42.436 | 1 | 35.16 |
| 3766 | ND2 | ASN | B | 1158 | 7.573 | 38.606 | 40.19 | 1 | 38.65 |
| 3767 | N | LEU | B | 1159 | 10.473 | 42.725 | 43.196 | 1 | 38.47 |
| 3768 | CA | LEU | B | 1159 | 11.714 | 43.473 | 43.359 | 1 | 39.51 |
| 3769 | C | LEU | B | 1159 | 11.681 | 44.133 | 44.723 | 1 | 40.21 |
| 3770 | O | LEU | B | 1159 | 10.867 | 45.03 | 44.946 | 1 | 43.09 |
| 3771 | CB | LEU | B | 1159 | 11.869 | 44.542 | 42.28 | 1 | 37.49 |
| 3772 | CG | LEU | B | 1159 | 11.956 | 44.088 | 40.824 | 1 | 38.03 |
| 3773 | CD1 | LEU | B | 1159 | 11.944 | 45.331 | 39.963 | 1 | 29.48 |
| 3774 | CD2 | LEU | B | 1159 | 13.208 | 43.208 | 40.554 | 1 | 36.35 |
| 3775 | N | ALA | B | 1160 | 12.559 | 43.692 | 45.628 | 1 | 38.14 |
| 3776 | CA | ALA | B | 1160 | 12.608 | 44.242 | 46.983 | 1 | 41.34 |
| 3777 | C | ALA | B | 1160 | 13.56 | 45.428 | 47.111 | 1 | 41.67 |
| 3778 | O | ALA | B | 1160 | 14.634 | 45.45 | 46.521 | 1 | 45.76 |
| 3779 | CB | ALA | B | 1160 | 12.954 | 43.161 | 47.974 | 1 | 39.03 |
| 3780 | N | VAL | B | 1161 | 13.167 | 46.397 | 47.916 | 1 | 41.49 |
| 3781 | CA | VAL | B | 1161 | 13.954 | 47.606 | 48.1 | 1 | 45.96 |
| 3782 | C | VAL | B | 1161 | 13.927 | 47.998 | 49.568 | 1 | 46.67 |
| 3783 | O | VAL | B | 1161 | 12.847 | 48.223 | 50.116 | 1 | 47.58 |
| 3784 | CB | VAL | B | 1161 | 13.309 | 48.779 | 47.309 | 1 | 46.19 |
| 3785 | CG1 | VAL | B | 1161 | 14.121 | 50.031 | 47.469 | 1 | 49.32 |
| 3786 | CG2 | VAL | B | 1161 | 13.165 | 48.427 | 45.85 | 1 | 44.43 |
| 3787 | N | ASN | B | 1162 | 15.092 | 48.109 | 50.205 | 1 | 47.85 |
| 3788 | CA | ASN | B | 1162 | 15.123 | 48.506 | 51.615 | 1 | 50.5 |
| 3789 | C | ASN | B | 1162 | 15.252 | 50.021 | 51.847 | 1 | 53.04 |
| 3790 | O | ASN | B | 1162 | 15.29 | 50.8 | 50.893 | 1 | 51.83 |
| 3791 | CB | ASN | B | 1162 | 16.217 | 47.751 | 52.369 | 1 | 50.67 |
| 3792 | CG | ASN | B | 1162 | 17.599 | 48.075 | 51.87 | 1 | 54 |
| 3793 | OD1 | ASN | B | 1162 | 17.852 | 49.168 | 51.346 | 1 | 49.99 |
| 3794 | ND2 | ASN | B | 1162 | 18.519 | 47.113 | 52.023 | 1 | 54.01 |
| 3795 | N | GLU | B | 1163 | 15.332 | 50.423 | 53.116 | 1 | 56.87 |
| 3796 | CA | GLU | B | 1163 | 15.444 | 51.834 | 53.512 | 1 | 61.04 |
| 3797 | C | GLU | B | 1163 | 16.598 | 52.572 | 52.847 | 1 | 61.38 |
| 3798 | O | GLU | B | 1163 | 16.512 | 53.781 | 52.623 | 1 | 62.21 |
| 3799 | CB | GLU | B | 1163 | 15.631 | 51.968 | 55.024 | 1 | 66.73 |
| 3800 | CG | GLU | B | 1163 | 14.589 | 51.295 | 55.909 | 1 | 74.14 |

Fig. 1-95

| ATOM | ATOM TYPE | RESIDUE | | # | X | Y | Z | OCC | B |
|---|---|---|---|---|---|---|---|---|---|
| 3801 | CD | GLU | B | 1163 | 14.869 | 51.531 | 57.391 | 1 | 78.04 |
| 3802 | OE1 | GLU | B | 1163 | 16.024 | 51.294 | 57.844 | 1 | 80.69 |
| 3803 | OE2 | GLU | B | 1163 | 13.935 | 51.973 | 58.097 | 1 | 79.71 |
| 3804 | N | ASP | B | 1164 | 17.695 | 51.859 | 52.604 | 1 | 60.92 |
| 3805 | CA | ASP | B | 1164 | 18.875 | 52.439 | 51.97 | 1 | 62.75 |
| 3806 | C | ASP | B | 1164 | 18.841 | 52.303 | 50.44 | 1 | 62.79 |
| 3807 | O | ASP | B | 1164 | 19.881 | 52.346 | 49.77 | 1 | 64.03 |
| 3808 | CB | ASP | B | 1164 | 20.148 | 51.799 | 52.541 | 1 | 64.9 |
| 3809 | CG | ASP | B | 1164 | 20.409 | 52.198 | 53.99 | 1 | 70.14 |
| 3810 | OD1 | ASP | B | 1164 | 19.718 | 53.106 | 54.513 | 1 | 72.87 |
| 3811 | OD2 | ASP | B | 1164 | 21.319 | 51.608 | 54.612 | 1 | 73.36 |
| 3812 | N | CYS | B | 1165 | 17.634 | 52.157 | 49.903 | 1 | 61.53 |
| 3813 | CA | CYS | B | 1165 | 17.4 | 52.004 | 48.47 | 1 | 60.6 |
| 3814 | C | CYS | B | 1165 | 18.173 | 50.895 | 47.763 | 1 | 55.92 |
| 3815 | O | CYS | B | 1165 | 18.451 | 50.986 | 46.57 | 1 | 55.05 |
| 3816 | CB | CYS | B | 1165 | 17.549 | 53.344 | 47.739 | 1 | 64.16 |
| 3817 | SG | CYS | B | 1165 | 15.997 | 54.299 | 47.695 | 1 | 75.2 |
| 3818 | N | GLU | B | 1166 | 18.491 | 49.835 | 48.497 | 1 | 52.23 |
| 3819 | CA | GLU | B | 1166 | 19.191 | 48.696 | 47.918 | 1 | 51.52 |
| 3820 | C | GLU | B | 1166 | 18.129 | 47.746 | 47.377 | 1 | 49.56 |
| 3821 | O | GLU | B | 1166 | 17.038 | 47.62 | 47.951 | 1 | 52.89 |
| 3822 | CB | GLU | B | 1166 | 20.076 | 48.033 | 48.971 | 1 | 56.91 |
| 3823 | CG | GLU | B | 1166 | 21.022 | 49.044 | 49.621 | 1 | 61.48 |
| 3824 | CD | GLU | B | 1166 | 21.976 | 48.429 | 50.62 | 1 | 65.34 |
| 3825 | OE1 | GLU | B | 1166 | 21.493 | 47.855 | 51.615 | 1 | 68.02 |
| 3826 | OE2 | GLU | B | 1166 | 23.208 | 48.545 | 50.425 | 1 | 63.05 |
| 3827 | N | LEU | B | 1167 | 18.41 | 47.123 | 46.242 | 1 | 43.77 |
| 3828 | CA | LEU | B | 1167 | 17.435 | 46.245 | 45.642 | 1 | 38.48 |
| 3829 | C | LEU | B | 1167 | 17.915 | 44.82 | 45.491 | 1 | 40.25 |
| 3830 | O | LEU | B | 1167 | 19.106 | 44.574 | 45.306 | 1 | 40.47 |
| 3831 | CB | LEU | B | 1167 | 17.019 | 46.808 | 44.276 | 1 | 39.35 |
| 3832 | CG | LEU | B | 1167 | 16.113 | 46.007 | 43.309 | 1 | 38.05 |
| 3833 | CD1 | LEU | B | 1167 | 15.269 | 46.928 | 42.471 | 1 | 32.6 |
| 3834 | CD2 | LEU | B | 1167 | 16.921 | 45.079 | 42.409 | 1 | 38.83 |
| 3835 | N | LYS | B | 1168 | 16.968 | 43.89 | 45.575 | 1 | 39.06 |
| 3836 | CA | LYS | B | 1168 | 17.233 | 42.461 | 45.383 | 1 | 42.57 |
| 3837 | C | LYS | B | 1168 | 16.053 | 41.856 | 44.592 | 1 | 40.77 |
| 3838 | O | LYS | B | 1168 | 14.887 | 42.08 | 44.899 | 1 | 41.04 |
| 3839 | CB | LYS | B | 1168 | 17.451 | 41.733 | 46.724 | 1 | 45.45 |
| 3840 | CG | LYS | B | 1168 | 18.852 | 41.937 | 47.345 | 1 | 47.6 |

Fig. 1-96

| ATOM | ATOM TYPE | RESIDUE | | # | X | Y | Z | OCC | B |
|---|---|---|---|---|---|---|---|---|---|
| 3841 | CD | LYS | B | 1168 | 18.883 | 41.639 | 48.845 | 1 | 51.98 |
| 3842 | CE | LYS | B | 1168 | 20.306 | 41.553 | 49.405 | 1 | 57.36 |
| 3843 | NZ | LYS | B | 1168 | 20.995 | 40.257 | 49.063 | 1 | 60.39 |
| 3844 | N | ILE | B | 1169 | 16.37 | 41.193 | 43.494 | 1 | 38.08 |
| 3845 | CA | ILE | B | 1169 | 15.364 | 40.565 | 42.659 | 1 | 39.04 |
| 3846 | C | ILE | B | 1169 | 14.774 | 39.378 | 43.4 | 1 | 41.65 |
| 3847 | O | ILE | B | 1169 | 15.509 | 38.53 | 43.925 | 1 | 42.84 |
| 3848 | CB | ILE | B | 1169 | 15.983 | 40.093 | 41.344 | 1 | 39.72 |
| 3849 | CG1 | ILE | B | 1169 | 16.444 | 41.311 | 40.547 | 1 | 34.39 |
| 3850 | CG2 | ILE | B | 1169 | 15.01 | 39.204 | 40.567 | 1 | 39.03 |
| 3851 | CD1 | ILE | B | 1169 | 17.087 | 40.976 | 39.258 | 1 | 34.86 |
| 3852 | N | LEU | B | 1170 | 13.448 | 39.349 | 43.482 | 1 | 38.67 |
| 3853 | CA | LEU | B | 1170 | 12.75 | 38.278 | 44.165 | 1 | 39.63 |
| 3854 | C | LEU | B | 1170 | 12.047 | 37.313 | 43.234 | 1 | 39.3 |
| 3855 | O | LEU | B | 1170 | 12.133 | 37.402 | 42.02 | 1 | 41.56 |
| 3856 | CB | LEU | B | 1170 | 11.688 | 38.868 | 45.087 | 1 | 36.72 |
| 3857 | CG | LEU | B | 1170 | 12.138 | 39.823 | 46.176 | 1 | 36.16 |
| 3858 | CD1 | LEU | B | 1170 | 10.912 | 40.462 | 46.8 | 1 | 30.53 |
| 3859 | CD2 | LEU | B | 1170 | 12.998 | 39.088 | 47.217 | 1 | 36.94 |
| 3860 | N | ASP | B | 1171 | 11.368 | 36.357 | 43.851 | 1 | 44.43 |
| 3861 | CA | ASP | B | 1171 | 10.535 | 35.378 | 43.162 | 1 | 41.68 |
| 3862 | C | ASP | B | 1171 | 11.11 | 34.617 | 42.001 | 1 | 41.67 |
| 3863 | O | ASP | B | 1171 | 10.858 | 34.961 | 40.852 | 1 | 43.91 |
| 3864 | CB | ASP | B | 1171 | 9.255 | 36.071 | 42.69 | 1 | 42.47 |
| 3865 | CG | ASP | B | 1171 | 8.075 | 35.127 | 42.578 | 1 | 45.71 |
| 3866 | OD1 | ASP | B | 1171 | 8.295 | 33.891 | 42.466 | 1 | 45.02 |
| 3867 | OD2 | ASP | B | 1171 | 6.923 | 35.631 | 42.62 | 1 | 36.4 |
| 3868 | N | PHE | B | 1172 | 11.857 | 33.56 | 42.274 | 1 | 43.92 |
| 3869 | CA | PHE | B | 1172 | 12.361 | 32.758 | 41.174 | 1 | 42.77 |
| 3870 | C | PHE | B | 1172 | 11.424 | 31.6 | 40.909 | 1 | 43.77 |
| 3871 | O | PHE | B | 1172 | 11.796 | 30.635 | 40.264 | 1 | 50.44 |
| 3872 | CB | PHE | B | 1172 | 13.77 | 32.292 | 41.445 | 1 | 39.54 |
| 3873 | CG | PHE | B | 1172 | 14.785 | 33.339 | 41.165 | 1 | 41.01 |
| 3874 | CD1 | PHE | B | 1172 | 14.953 | 34.404 | 42.037 | 1 | 39.05 |
| 3875 | CD2 | PHE | B | 1172 | 15.538 | 33.301 | 39.994 | 1 | 42.1 |
| 3876 | CE1 | PHE | B | 1172 | 15.86 | 35.426 | 41.745 | 1 | 40.54 |
| 3877 | CE2 | PHE | B | 1172 | 16.448 | 34.315 | 39.692 | 1 | 39.85 |
| 3878 | CZ | PHE | B | 1172 | 16.606 | 35.377 | 40.571 | 1 | 40.67 |
| 3879 | N | GLY | B | 1173 | 10.174 | 31.756 | 41.341 | 1 | 44.58 |
| 3880 | CA | GLY | B | 1173 | 9.154 | 30.73 | 41.17 | 1 | 47.24 |

Fig. 1-97

| ATOM | ATOM TYPE | RESIDUE | | # | X | Y | Z | OCC | B |
|---|---|---|---|---|---|---|---|---|---|
| 3881 | C | GLY | B | 1173 | 8.817 | 30.344 | 39.744 | 1 | 48.98 |
| 3882 | O | GLY | B | 1173 | 8.271 | 29.268 | 39.509 | 1 | 50.09 |
| 3883 | N | LEU | B | 1174 | 9.113 | 31.23 | 38.796 | 1 | 47.5 |
| 3884 | CA | LEU | B | 1174 | 8.86 | 30.958 | 37.396 | 1 | 44.45 |
| 3885 | C | LEU | B | 1174 | 10.175 | 30.92 | 36.64 | 1 | 44.98 |
| 3886 | O | LEU | B | 1174 | 10.18 | 30.786 | 35.425 | 1 | 49.18 |
| 3887 | CB | LEU | B | 1174 | 7.959 | 32.025 | 36.795 | 1 | 46.57 |
| 3888 | CG | LEU | B | 1174 | 7.335 | 31.658 | 35.449 | 1 | 49.49 |
| 3889 | CD1 | LEU | B | 1174 | 6.384 | 30.477 | 35.635 | 1 | 52.43 |
| 3890 | CD2 | LEU | B | 1174 | 6.585 | 32.852 | 34.878 | 1 | 54.72 |
| 3891 | N | ALA | B | 1175 | 11.295 | 31.019 | 37.348 | 1 | 43.44 |
| 3892 | CA | ALA | B | 1175 | 12.597 | 30.992 | 36.694 | 1 | 42.54 |
| 3893 | C | ALA | B | 1175 | 13.053 | 29.576 | 36.298 | 1 | 43.79 |
| 3894 | O | ALA | B | 1175 | 12.481 | 28.576 | 36.74 | 1 | 38.37 |
| 3895 | CB | ALA | B | 1175 | 13.614 | 31.648 | 37.571 | 1 | 40.52 |
| 3896 | N | ARG | B | 1176 | 14.066 | 29.511 | 35.432 | 1 | 47.34 |
| 3897 | CA | ARG | B | 1176 | 14.631 | 28.248 | 34.956 | 1 | 50.47 |
| 3898 | C | ARG | B | 1176 | 15.938 | 28.524 | 34.223 | 1 | 53.83 |
| 3899 | O | ARG | B | 1176 | 16.373 | 29.68 | 34.108 | 1 | 52.97 |
| 3900 | CB | ARG | B | 1176 | 13.667 | 27.551 | 33.992 | 1 | 54.56 |
| 3901 | CG | ARG | B | 1176 | 13.876 | 27.945 | 32.523 | 1 | 57.15 |
| 3902 | CD | ARG | B | 1176 | 12.712 | 27.603 | 31.618 | 1 | 59.93 |
| 3903 | NE | ARG | B | 1176 | 12.533 | 26.177 | 31.324 | 1 | 63.13 |
| 3904 | CZ | ARG | B | 1176 | 13.4 | 25.413 | 30.662 | 1 | 61.48 |
| 3905 | NH1 | ARG | B | 1176 | 14.547 | 25.912 | 30.236 | 1 | 63.98 |
| 3906 | NH2 | ARG | B | 1176 | 13.06 | 24.185 | 30.3 | 1 | 58.38 |
| 3907 | N | GLN | B | 1177 | 16.567 | 27.451 | 33.745 | 1 | 57.87 |
| 3908 | CA | GLN | B | 1177 | 17.808 | 27.555 | 32.985 | 1 | 62.7 |
| 3909 | C | GLN | B | 1177 | 17.404 | 27.809 | 31.532 | 1 | 63.38 |
| 3910 | O | GLN | B | 1177 | 16.599 | 27.068 | 30.969 | 1 | 62.96 |
| 3911 | CB | GLN | B | 1177 | 18.593 | 26.249 | 33.08 | 1 | 67.17 |
| 3912 | CG | GLN | B | 1177 | 19.975 | 26.305 | 32.45 | 1 | 74.7 |
| 3913 | CD | GLN | B | 1177 | 20.57 | 24.92 | 32.26 | 1 | 80.17 |
| 3914 | OE1 | GLN | B | 1177 | 19.995 | 24.077 | 31.559 | 1 | 83.06 |
| 3915 | NE2 | GLN | B | 1177 | 21.716 | 24.67 | 32.889 | 1 | 80.44 |
| 3916 | N | ALA | B | 1178 | 17.94 | 28.866 | 30.934 | 1 | 63.49 |
| 3917 | CA | ALA | B | 1178 | 17.599 | 29.202 | 29.562 | 1 | 64.11 |
| 3918 | C | ALA | B | 1178 | 17.903 | 28.05 | 28.622 | 1 | 65.94 |
| 3919 | O | ALA | B | 1178 | 18.943 | 27.397 | 28.742 | 1 | 69.41 |
| 3920 | CB | ALA | B | 1178 | 18.339 | 30.459 | 29.127 | 1 | 59.96 |

Fig. 1-98

| ATOM | ATOM TYPE | RESIDUE | | # | X | Y | Z | OCC | B |
|---|---|---|---|---|---|---|---|---|---|
| 3921 | N | ASP | B | 1179 | 16.964 | 27.773 | 27.724 | 1 | 68.01 |
| 3922 | CA | ASP | B | 1179 | 17.115 | 26.712 | 26.736 | 1 | 69.02 |
| 3923 | C | ASP | B | 1179 | 16.449 | 27.178 | 25.445 | 1 | 69.54 |
| 3924 | O | ASP | B | 1179 | 16.035 | 28.333 | 25.341 | 1 | 69.63 |
| 3925 | CB | ASP | B | 1179 | 16.483 | 25.418 | 27.246 | 1 | 69.96 |
| 3926 | CG | ASP | B | 1179 | 16.933 | 24.192 | 26.46 | 1 | 74.7 |
| 3927 | OD1 | ASP | B | 1179 | 18.092 | 24.163 | 25.974 | 1 | 75.27 |
| 3928 | OD2 | ASP | B | 1179 | 16.118 | 23.252 | 26.33 | 1 | 75.59 |
| 3929 | N | SER | B | 1180 | 16.357 | 26.298 | 24.456 | 1 | 70.8 |
| 3930 | CA | SER | B | 1180 | 15.753 | 26.656 | 23.175 | 1 | 69.23 |
| 3931 | C | SER | B | 1180 | 14.234 | 26.679 | 23.136 | 1 | 68.81 |
| 3932 | O | SER | B | 1180 | 13.647 | 27.604 | 22.579 | 1 | 69.52 |
| 3933 | CB | SER | B | 1180 | 16.294 | 25.759 | 22.064 | 1 | 69.96 |
| 3934 | OG | SER | B | 1180 | 17.59 | 26.187 | 21.685 | 1 | 71.51 |
| 3935 | N | GLU | B | 1181 | 13.599 | 25.675 | 23.73 | 1 | 69.72 |
| 3936 | CA | GLU | B | 1181 | 12.144 | 25.597 | 23.726 | 1 | 71.3 |
| 3937 | C | GLU | B | 1181 | 11.594 | 25.559 | 25.15 | 1 | 70.66 |
| 3938 | O | GLU | B | 1181 | 11.546 | 24.498 | 25.777 | 1 | 73.66 |
| 3939 | CB | GLU | B | 1181 | 11.698 | 24.353 | 22.958 | 1 | 74.63 |
| 3940 | CG | GLU | B | 1181 | 10.653 | 24.601 | 21.881 | 1 | 80.88 |
| 3941 | CD | GLU | B | 1181 | 10.135 | 23.304 | 21.266 | 1 | 87.34 |
| 3942 | OE1 | GLU | B | 1181 | 10.923 | 22.595 | 20.598 | 1 | 90.4 |
| 3943 | OE2 | GLU | B | 1181 | 8.938 | 22.987 | 21.46 | 1 | 88.92 |
| 3944 | N | MET | B | 1182 | 11.172 | 26.719 | 25.65 | 1 | 67.19 |
| 3945 | CA | MET | B | 1182 | 10.629 | 26.837 | 27.005 | 1 | 64.01 |
| 3946 | C | MET | B | 1182 | 9.095 | 26.854 | 27.064 | 1 | 60.76 |
| 3947 | O | MET | B | 1182 | 8.434 | 26.902 | 26.039 | 1 | 63.29 |
| 3948 | CB | MET | B | 1182 | 11.226 | 28.075 | 27.689 | 1 | 60.43 |
| 3949 | CG | MET | B | 1182 | 12.73 | 27.982 | 27.816 | 1 | 57.06 |
| 3950 | SD | MET | B | 1182 | 13.528 | 29.48 | 28.35 | 1 | 56.31 |
| 3951 | CE | MET | B | 1182 | 13.742 | 30.289 | 26.803 | 1 | 57.39 |
| 3952 | N | TPO | B | 1183 | 8.541 | 26.8 | 28.27 | 1 | 57.45 |
| 3953 | CA | TPO | B | 1183 | 7.098 | 26.799 | 28.461 | 1 | 57.48 |
| 3954 | CB | TPO | B | 1183 | 6.738 | 26.374 | 29.934 | 1 | 57.7 |
| 3955 | CG2 | TPO | B | 1183 | 5.351 | 26.891 | 30.377 | 1 | 58.92 |
| 3956 | OG1 | TPO | B | 1183 | 7.748 | 26.891 | 30.753 | 1 | 54.66 |
| 3957 | P | TPO | B | 1183 | 8.733 | 25.956 | 31.446 | 1 | 55.58 |
| 3958 | O1P | TPO | B | 1183 | 10.016 | 25.979 | 30.672 | 1 | 44.08 |
| 3959 | O2P | TPO | B | 1183 | 8.095 | 24.586 | 31.429 | 1 | 54.5 |
| 3960 | O3P | TPO | B | 1183 | 8.998 | 26.512 | 32.775 | 1 | 47.5 |

Fig. 1-99

| ATOM | ATOM TYPE | RESIDUE | | # | X | Y | Z | OCC | B |
|---|---|---|---|---|---|---|---|---|---|
| 3961 | C | TPO | B | 1183 | 6.492 | 28.142 | 27.99 | 1 | 57.58 |
| 3962 | O | TPO | B | 1183 | 7.073 | 29.217 | 28.188 | 1 | 56.01 |
| 3963 | N | GLY | B | 1184 | 5.358 | 28.037 | 27.295 | 1 | 55.43 |
| 3964 | CA | GLY | B | 1184 | 4.683 | 29.179 | 26.707 | 1 | 52.19 |
| 3965 | C | GLY | B | 1184 | 4.124 | 30.308 | 27.537 | 1 | 54.15 |
| 3966 | O | GLY | B | 1184 | 4.546 | 31.465 | 27.368 | 1 | 55.41 |
| 3967 | N | PTR | B | 1185 | 3.135 | 30.016 | 28.38 | 1 | 52.22 |
| 3968 | CA | PTR | B | 1185 | 2.522 | 31.071 | 29.187 | 1 | 51.44 |
| 3969 | C | PTR | B | 1185 | 3.404 | 31.475 | 30.376 | 1 | 50.95 |
| 3970 | O | PTR | B | 1185 | 3.3 | 30.894 | 31.46 | 1 | 51.63 |
| 3971 | CB | PTR | B | 1185 | 1.129 | 30.637 | 29.648 | 1 | 50.17 |
| 3972 | CG | PTR | B | 1185 | 0.187 | 31.812 | 29.599 | 1 | 49.77 |
| 3973 | CD1 | PTR | B | 1185 | -0.641 | 32.039 | 30.723 | 1 | 51.36 |
| 3974 | CD2 | PTR | B | 1185 | 0.138 | 32.682 | 28.503 | 1 | 50.95 |
| 3975 | CE1 | PTR | B | 1185 | -1.527 | 33.122 | 30.776 | 1 | 48.41 |
| 3976 | CE2 | PTR | B | 1185 | -0.754 | 33.778 | 28.565 | 1 | 50.34 |
| 3977 | CZ | PTR | B | 1185 | -1.578 | 33.986 | 29.696 | 1 | 49.75 |
| 3978 | OH | PTR | B | 1185 | -2.507 | 34.994 | 29.665 | 1 | 52.59 |
| 3979 | P | PTR | B | 1185 | -2.638 | 36.081 | 30.757 | 1 | 55.23 |
| 3980 | O1P | PTR | B | 1185 | -1.812 | 35.798 | 31.921 | 1 | 60.66 |
| 3981 | O2P | PTR | B | 1185 | -4.028 | 36.033 | 31.2 | 1 | 55.96 |
| 3982 | O3P | PTR | B | 1185 | -2.363 | 37.376 | 30.187 | 1 | 55.33 |
| 3983 | N | VAL | B | 1186 | 4.27 | 32.468 | 30.162 | 1 | 47.01 |
| 3984 | CA | VAL | B | 1186 | 5.18 | 32.936 | 31.2 | 1 | 43.17 |
| 3985 | C | VAL | B | 1186 | 5.185 | 34.455 | 31.307 | 1 | 41.43 |
| 3986 | O | VAL | B | 1186 | 4.803 | 35.126 | 30.375 | 1 | 44.65 |
| 3987 | CB | VAL | B | 1186 | 6.612 | 32.412 | 30.933 | 1 | 45.49 |
| 3988 | CG1 | VAL | B | 1186 | 6.614 | 30.873 | 30.884 | 1 | 46.53 |
| 3989 | CG2 | VAL | B | 1186 | 7.156 | 32.969 | 29.63 | 1 | 42.01 |
| 3990 | N | VAL | B | 1187 | 5.645 | 34.99 | 32.437 | 1 | 43.35 |
| 3991 | CA | VAL | B | 1187 | 5.694 | 36.448 | 32.719 | 1 | 41.61 |
| 3992 | C | VAL | B | 1187 | 4.305 | 37.012 | 32.991 | 1 | 41.24 |
| 3993 | O | VAL | B | 1187 | 3.343 | 36.61 | 32.357 | 1 | 44.73 |
| 3994 | CB | VAL | B | 1187 | 6.28 | 37.298 | 31.573 | 1 | 36.39 |
| 3995 | CG1 | VAL | B | 1187 | 6.545 | 38.697 | 32.074 | 1 | 37.09 |
| 3996 | CG2 | VAL | B | 1187 | 7.552 | 36.705 | 31.04 | 1 | 41.27 |
| 3997 | N | THR | B | 1188 | 4.193 | 37.932 | 33.942 | 1 | 44.12 |
| 3998 | CA | THR | B | 1188 | 2.9 | 38.547 | 34.239 | 1 | 42.9 |
| 3999 | C | THR | B | 1188 | 2.558 | 39.438 | 33.068 | 1 | 42.74 |
| 4000 | O | THR | B | 1188 | 3.414 | 40.187 | 32.586 | 1 | 42.98 |

Fig. 1-100

| ATOM | ATOM TYPE | RESIDUE | | # | X | Y | Z | OCC | B |
|---|---|---|---|---|---|---|---|---|---|
| 4001 | CB | THR | B | 1188 | 2.941 | 39.365 | 35.521 | 1 | 44.42 |
| 4002 | OG1 | THR | B | 1188 | 3.198 | 38.49 | 36.639 | 1 | 44.96 |
| 4003 | CG2 | THR | B | 1188 | 1.611 | 40.092 | 35.724 | 1 | 41.85 |
| 4004 | N | ARG | B | 1189 | 1.317 | 39.33 | 32.596 | 1 | 46.74 |
| 4005 | CA | ARG | B | 1189 | 0.83 | 40.083 | 31.423 | 1 | 48.63 |
| 4006 | C | ARG | B | 1189 | 1.354 | 41.508 | 31.138 | 1 | 45.25 |
| 4007 | O | ARG | B | 1189 | 1.954 | 41.739 | 30.1 | 1 | 46.29 |
| 4008 | CB | ARG | B | 1189 | -0.708 | 40.08 | 31.367 | 1 | 48.77 |
| 4009 | CG | ARG | B | 1189 | -1.259 | 40.65 | 30.054 | 1 | 50.27 |
| 4010 | CD | ARG | B | 1189 | -2.764 | 40.895 | 30.08 | 1 | 48.77 |
| 4011 | NE | ARG | B | 1189 | -3.498 | 39.663 | 30.322 | 1 | 47.77 |
| 4012 | CZ | ARG | B | 1189 | -4.501 | 39.549 | 31.181 | 1 | 48.48 |
| 4013 | NH1 | ARG | B | 1189 | -4.904 | 40.603 | 31.887 | 1 | 50.17 |
| 4014 | NH2 | ARG | B | 1189 | -5.089 | 38.377 | 31.35 | 1 | 45.66 |
| 4015 | N | TRP | B | 1190 | 1.145 | 42.453 | 32.039 | 1 | 41.32 |
| 4016 | CA | TRP | B | 1190 | 1.596 | 43.809 | 31.762 | 1 | 48.65 |
| 4017 | C | TRP | B | 1190 | 3.102 | 43.966 | 31.58 | 1 | 46.42 |
| 4018 | O | TRP | B | 1190 | 3.558 | 44.979 | 31.072 | 1 | 46.22 |
| 4019 | CB | TRP | B | 1190 | 1.053 | 44.813 | 32.808 | 1 | 53.47 |
| 4020 | CG | TRP | B | 1190 | -0.461 | 44.8 | 32.938 | 1 | 60.03 |
| 4021 | CD1 | TRP | B | 1190 | -1.354 | 44.345 | 32.01 | 1 | 63.94 |
| 4022 | CD2 | TRP | B | 1190 | -1.244 | 45.197 | 34.076 | 1 | 64.5 |
| 4023 | NE1 | TRP | B | 1190 | -2.636 | 44.422 | 32.499 | 1 | 66.54 |
| 4024 | CE2 | TRP | B | 1190 | -2.596 | 44.943 | 33.764 | 1 | 67.44 |
| 4025 | CE3 | TRP | B | 1190 | -0.931 | 45.734 | 35.331 | 1 | 69.36 |
| 4026 | CZ2 | TRP | B | 1190 | -3.637 | 45.207 | 34.663 | 1 | 68.28 |
| 4027 | CZ3 | TRP | B | 1190 | -1.968 | 45.995 | 36.226 | 1 | 68.93 |
| 4028 | CH2 | TRP | B | 1190 | -3.303 | 45.73 | 35.883 | 1 | 70 |
| 4029 | N | TYR | B | 1191 | 3.865 | 42.94 | 31.922 | 1 | 44.91 |
| 4030 | CA | TYR | B | 1191 | 5.311 | 43.014 | 31.792 | 1 | 44.62 |
| 4031 | C | TYR | B | 1191 | 5.815 | 42.002 | 30.787 | 1 | 46.4 |
| 4032 | O | TYR | B | 1191 | 7.015 | 41.881 | 30.531 | 1 | 49.89 |
| 4033 | CB | TYR | B | 1191 | 5.96 | 42.814 | 33.162 | 1 | 45.67 |
| 4034 | CG | TYR | B | 1191 | 5.439 | 43.799 | 34.167 | 1 | 43.36 |
| 4035 | CD1 | TYR | B | 1191 | 5.962 | 45.089 | 34.24 | 1 | 44.9 |
| 4036 | CD2 | TYR | B | 1191 | 4.341 | 43.487 | 34.961 | 1 | 46.89 |
| 4037 | CE1 | TYR | B | 1191 | 5.386 | 46.048 | 35.063 | 1 | 46.19 |
| 4038 | CE2 | TYR | B | 1191 | 3.762 | 44.436 | 35.793 | 1 | 46.56 |
| 4039 | CZ | TYR | B | 1191 | 4.286 | 45.712 | 35.83 | 1 | 46.76 |
| 4040 | OH | TYR | B | 1191 | 3.685 | 46.663 | 36.611 | 1 | 52.39 |

Fig. 1-101

| ATOM | ATOM TYPE | RESIDUE | | # | X | Y | Z | OCC | B |
|---|---|---|---|---|---|---|---|---|---|
| 4041 | N | ARG | B | 1192 | 4.865 | 41.316 | 30.175 | 1 | 47.02 |
| 4042 | CA | ARG | B | 1192 | 5.15 | 40.305 | 29.183 | 1 | 44.82 |
| 4043 | C | ARG | B | 1192 | 5.523 | 40.921 | 27.83 | 1 | 46 |
| 4044 | O | ARG | B | 1192 | 4.841 | 41.812 | 27.326 | 1 | 48.59 |
| 4045 | CB | ARG | B | 1192 | 3.937 | 39.389 | 29.057 | 1 | 39.1 |
| 4046 | CG | ARG | B | 1192 | 4.123 | 38.28 | 28.102 | 1 | 39.95 |
| 4047 | CD | ARG | B | 1192 | 3.436 | 37.072 | 28.632 | 1 | 43.68 |
| 4048 | NE | ARG | B | 1192 | 2 | 37.133 | 28.453 | 1 | 47.31 |
| 4049 | CZ | ARG | B | 1192 | 1.121 | 36.801 | 29.384 | 1 | 48.78 |
| 4050 | NH1 | ARG | B | 1192 | 1.539 | 36.401 | 30.566 | 1 | 44.85 |
| 4051 | NH2 | ARG | B | 1192 | -0.174 | 36.817 | 29.104 | 1 | 53.73 |
| 4052 | N | ALA | B | 1193 | 6.631 | 40.454 | 27.264 | 1 | 45.8 |
| 4053 | CA | ALA | B | 1193 | 7.098 | 40.932 | 25.983 | 1 | 42.03 |
| 4054 | C | ALA | B | 1193 | 6.251 | 40.291 | 24.897 | 1 | 44.54 |
| 4055 | O | ALA | B | 1193 | 5.815 | 39.139 | 25.025 | 1 | 46.29 |
| 4056 | CB | ALA | B | 1193 | 8.527 | 40.567 | 25.803 | 1 | 40.43 |
| 4057 | N | PRO | B | 1194 | 6.044 | 41.009 | 23.786 | 1 | 42.28 |
| 4058 | CA | PRO | B | 1194 | 5.243 | 40.493 | 22.679 | 1 | 42.12 |
| 4059 | C | PRO | B | 1194 | 5.642 | 39.107 | 22.143 | 1 | 44.43 |
| 4060 | O | PRO | B | 1194 | 4.773 | 38.267 | 21.841 | 1 | 44.4 |
| 4061 | CB | PRO | B | 1194 | 5.405 | 41.575 | 21.618 | 1 | 40.5 |
| 4062 | CG | PRO | B | 1194 | 6.706 | 42.209 | 21.963 | 1 | 41.2 |
| 4063 | CD | PRO | B | 1194 | 6.632 | 42.31 | 23.44 | 1 | 38.61 |
| 4064 | N | GLU | B | 1195 | 6.942 | 38.845 | 22.051 | 1 | 41.59 |
| 4065 | CA | GLU | B | 1195 | 7.349 | 37.564 | 21.512 | 1 | 41.49 |
| 4066 | C | GLU | B | 1195 | 6.949 | 36.356 | 22.333 | 1 | 41.11 |
| 4067 | O | GLU | B | 1195 | 6.965 | 35.247 | 21.817 | 1 | 41.88 |
| 4068 | CB | GLU | B | 1195 | 8.827 | 37.521 | 21.164 | 1 | 42.13 |
| 4069 | CG | GLU | B | 1195 | 9.752 | 37.453 | 22.326 | 1 | 46.22 |
| 4070 | CD | GLU | B | 1195 | 10.016 | 38.791 | 22.979 | 1 | 47.44 |
| 4071 | OE1 | GLU | B | 1195 | 9.548 | 39.851 | 22.489 | 1 | 46.07 |
| 4072 | OE2 | GLU | B | 1195 | 10.715 | 38.756 | 24.004 | 1 | 44.98 |
| 4073 | N | VAL | B | 1196 | 6.546 | 36.554 | 23.588 | 1 | 43.14 |
| 4074 | CA | VAL | B | 1196 | 6.104 | 35.42 | 24.405 | 1 | 42.76 |
| 4075 | C | VAL | B | 1196 | 4.893 | 34.8 | 23.714 | 1 | 48.78 |
| 4076 | O | VAL | B | 1196 | 4.632 | 33.599 | 23.836 | 1 | 49.71 |
| 4077 | CB | VAL | B | 1196 | 5.696 | 35.85 | 25.82 | 1 | 41.44 |
| 4078 | CG1 | VAL | B | 1196 | 5.223 | 34.652 | 26.627 | 1 | 37.67 |
| 4079 | CG2 | VAL | B | 1196 | 6.876 | 36.52 | 26.508 | 1 | 43.73 |
| 4080 | N | ILE | B | 1197 | 4.19 | 35.623 | 22.933 | 1 | 51.47 |

Fig. 1-102

| ATOM | ATOM TYPE | RESIDUE | | # | X | Y | Z | OCC | B |
|---|---|---|---|---|---|---|---|---|---|
| 4081 | CA | ILE | B | 1197 | 3.007 | 35.176 | 22.214 | 1 | 48.3 |
| 4082 | C | ILE | B | 1197 | 3.227 | 35.039 | 20.719 | 1 | 45.29 |
| 4083 | O | ILE | B | 1197 | 2.86 | 34.021 | 20.145 | 1 | 42.3 |
| 4084 | CB | ILE | B | 1197 | 1.809 | 36.087 | 22.54 | 1 | 50.42 |
| 4085 | CG1 | ILE | B | 1197 | 1.466 | 35.909 | 24.015 | 1 | 47.59 |
| 4086 | CG2 | ILE | B | 1197 | 0.593 | 35.742 | 21.672 | 1 | 49.15 |
| 4087 | CD1 | ILE | B | 1197 | 0.372 | 36.762 | 24.447 | 1 | 51.83 |
| 4088 | N | LEU | B | 1198 | 3.849 | 36.039 | 20.1 | 1 | 44.39 |
| 4089 | CA | LEU | B | 1198 | 4.104 | 35.978 | 18.665 | 1 | 47.5 |
| 4090 | C | LEU | B | 1198 | 5.068 | 34.848 | 18.371 | 1 | 51.67 |
| 4091 | O | LEU | B | 1198 | 4.983 | 34.199 | 17.321 | 1 | 55.4 |
| 4092 | CB | LEU | B | 1198 | 4.677 | 37.298 | 18.137 | 1 | 45.4 |
| 4093 | CG | LEU | B | 1198 | 3.763 | 38.513 | 18.347 | 1 | 47.12 |
| 4094 | CD1 | LEU | B | 1198 | 4.272 | 39.714 | 17.583 | 1 | 38.91 |
| 4095 | CD2 | LEU | B | 1198 | 2.348 | 38.162 | 17.924 | 1 | 44.07 |
| 4096 | N | ASN | B | 1199 | 5.978 | 34.608 | 19.312 | 1 | 52.22 |
| 4097 | CA | ASN | B | 1199 | 6.964 | 33.552 | 19.166 | 1 | 52.73 |
| 4098 | C | ASN | B | 1199 | 6.79 | 32.502 | 20.251 | 1 | 53.9 |
| 4099 | O | ASN | B | 1199 | 7.739 | 32.176 | 20.959 | 1 | 55.29 |
| 4100 | CB | ASN | B | 1199 | 8.37 | 34.136 | 19.238 | 1 | 54.27 |
| 4101 | CG | ASN | B | 1199 | 9.428 | 33.161 | 18.776 | 1 | 53.46 |
| 4102 | OD1 | ASN | B | 1199 | 9.13 | 32.006 | 18.464 | 1 | 47.79 |
| 4103 | ND2 | ASN | B | 1199 | 10.672 | 33.626 | 18.717 | 1 | 50.82 |
| 4104 | N | TRP | B | 1200 | 5.578 | 31.966 | 20.359 | 1 | 54.16 |
| 4105 | CA | TRP | B | 1200 | 5.236 | 30.941 | 21.337 | 1 | 54.29 |
| 4106 | C | TRP | B | 1200 | 6.371 | 29.938 | 21.568 | 1 | 55.78 |
| 4107 | O | TRP | B | 1200 | 6.907 | 29.371 | 20.614 | 1 | 56.65 |
| 4108 | CB | TRP | B | 1200 | 3.992 | 30.194 | 20.859 | 1 | 53.09 |
| 4109 | CG | TRP | B | 1200 | 3.419 | 29.254 | 21.855 | 1 | 53.23 |
| 4110 | CD1 | TRP | B | 1200 | 3.405 | 27.884 | 21.788 | 1 | 55.49 |
| 4111 | CD2 | TRP | B | 1200 | 2.728 | 29.605 | 23.054 | 1 | 52.08 |
| 4112 | NE1 | TRP | B | 1200 | 2.733 | 27.362 | 22.877 | 1 | 54.45 |
| 4113 | CE2 | TRP | B | 1200 | 2.308 | 28.397 | 23.668 | 1 | 51.15 |
| 4114 | CE3 | TRP | B | 1200 | 2.414 | 30.825 | 23.673 | 1 | 51.63 |
| 4115 | CZ2 | TRP | B | 1200 | 1.593 | 28.377 | 24.865 | 1 | 50.67 |
| 4116 | CZ3 | TRP | B | 1200 | 1.706 | 30.809 | 24.856 | 1 | 48.87 |
| 4117 | CH2 | TRP | B | 1200 | 1.3 | 29.588 | 25.444 | 1 | 51.53 |
| 4118 | N | MET | B | 1201 | 6.77 | 29.804 | 22.835 | 1 | 55.53 |
| 4119 | CA | MET | B | 1201 | 7.822 | 28.887 | 23.304 | 1 | 52.33 |
| 4120 | C | MET | B | 1201 | 9.266 | 29.122 | 22.873 | 1 | 52.99 |

Fig. 1-103

| ATOM | ATOM TYPE | RESIDUE | | # | X | Y | Z | OCC | B |
|---|---|---|---|---|---|---|---|---|---|
| 4121 | O | MET | B | 1201 | 10.136 | 28.319 | 23.216 | 1 | 53.52 |
| 4122 | CB | MET | B | 1201 | 7.448 | 27.433 | 23.007 | 1 | 48.18 |
| 4123 | CG | MET | B | 1201 | 6.198 | 26.983 | 23.704 | 1 | 52.88 |
| 4124 | SD | MET | B | 1201 | 5.807 | 25.24 | 23.47 | 1 | 59.31 |
| 4125 | CE | MET | B | 1201 | 4.293 | 25.095 | 24.49 | 1 | 52.9 |
| 4126 | N | ARG | B | 1202 | 9.553 | 30.213 | 22.166 | 1 | 49.95 |
| 4127 | CA | ARG | B | 1202 | 10.927 | 30.433 | 21.719 | 1 | 48.96 |
| 4128 | C | ARG | B | 1202 | 11.506 | 31.808 | 22.016 | 1 | 49.58 |
| 4129 | O | ARG | B | 1202 | 12.319 | 32.329 | 21.254 | 1 | 50.5 |
| 4130 | CB | ARG | B | 1202 | 11.063 | 30.111 | 20.231 | 1 | 51.19 |
| 4131 | CG | ARG | B | 1202 | 10.613 | 28.697 | 19.868 | 1 | 55.45 |
| 4132 | CD | ARG | B | 1202 | 10.812 | 28.416 | 18.388 | 1 | 56.08 |
| 4133 | NE | ARG | B | 1202 | 10.561 | 27.016 | 18.069 | 1 | 58.32 |
| 4134 | CZ | ARG | B | 1202 | 9.41 | 26.548 | 17.604 | 1 | 60.02 |
| 4135 | NH1 | ARG | B | 1202 | 8.396 | 27.376 | 17.399 | 1 | 59.12 |
| 4136 | NH2 | ARG | B | 1202 | 9.275 | 25.249 | 17.347 | 1 | 59.14 |
| 4137 | N | TYR | B | 1203 | 11.075 | 32.401 | 23.119 | 1 | 48.73 |
| 4138 | CA | TYR | B | 1203 | 11.584 | 33.698 | 23.544 | 1 | 51.01 |
| 4139 | C | TYR | B | 1203 | 12.92 | 33.455 | 24.252 | 1 | 52.73 |
| 4140 | O | TYR | B | 1203 | 13.288 | 32.312 | 24.525 | 1 | 52.4 |
| 4141 | CB | TYR | B | 1203 | 10.619 | 34.336 | 24.534 | 1 | 50.36 |
| 4142 | CG | TYR | B | 1203 | 10.247 | 33.392 | 25.653 | 1 | 49.96 |
| 4143 | CD1 | TYR | B | 1203 | 9.194 | 32.5 | 25.505 | 1 | 47.63 |
| 4144 | CD2 | TYR | B | 1203 | 10.985 | 33.35 | 26.849 | 1 | 52.8 |
| 4145 | CE1 | TYR | B | 1203 | 8.882 | 31.578 | 26.51 | 1 | 50.33 |
| 4146 | CE2 | TYR | B | 1203 | 10.669 | 32.424 | 27.868 | 1 | 47.24 |
| 4147 | CZ | TYR | B | 1203 | 9.618 | 31.553 | 27.674 | 1 | 47.25 |
| 4148 | OH | TYR | B | 1203 | 9.27 | 30.656 | 28.638 | 1 | 55.01 |
| 4149 | N | THR | B | 1204 | 13.631 | 34.525 | 24.585 | 1 | 53.03 |
| 4150 | CA | THR | B | 1204 | 14.908 | 34.37 | 25.253 | 1 | 53.27 |
| 4151 | C | THR | B | 1204 | 15.014 | 35.208 | 26.507 | 1 | 52.16 |
| 4152 | O | THR | B | 1204 | 14.031 | 35.755 | 26.997 | 1 | 53.18 |
| 4153 | CB | THR | B | 1204 | 16.104 | 34.71 | 24.33 | 1 | 54.94 |
| 4154 | OG1 | THR | B | 1204 | 16.035 | 36.083 | 23.922 | 1 | 54.05 |
| 4155 | CG2 | THR | B | 1204 | 16.12 | 33.805 | 23.119 | 1 | 55.19 |
| 4156 | N | GLN | B | 1205 | 16.227 | 35.291 | 27.028 | 1 | 50.17 |
| 4157 | CA | GLN | B | 1205 | 16.487 | 36.052 | 28.22 | 1 | 48.17 |
| 4158 | C | GLN | B | 1205 | 16.165 | 37.505 | 27.982 | 1 | 46.85 |
| 4159 | O | GLN | B | 1205 | 16.147 | 38.288 | 28.918 | 1 | 48.64 |
| 4160 | CB | GLN | B | 1205 | 17.948 | 35.928 | 28.607 | 1 | 50.3 |

Fig. 1-104

| ATOM | ATOM TYPE | RESIDUE | | # | X | Y | Z | OCC | B |
|---|---|---|---|---|---|---|---|---|---|
| 4161 | CG | GLN | B | 1205 | 18.464 | 34.511 | 28.626 | 1 | 56.04 |
| 4162 | CD | GLN | B | 1205 | 19.92 | 34.468 | 29.005 | 1 | 57.7 |
| 4163 | OE1 | GLN | B | 1205 | 20.753 | 35.119 | 28.367 | 1 | 63.39 |
| 4164 | NE2 | GLN | B | 1205 | 20.235 | 33.745 | 30.075 | 1 | 55.88 |
| 4165 | N | THR | B | 1206 | 15.959 | 37.894 | 26.732 | 1 | 46.01 |
| 4166 | CA | THR | B | 1206 | 15.631 | 39.287 | 26.472 | 1 | 46.63 |
| 4167 | C | THR | B | 1206 | 14.243 | 39.658 | 26.978 | 1 | 44.63 |
| 4168 | O | THR | B | 1206 | 13.938 | 40.852 | 27.125 | 1 | 44.04 |
| 4169 | CB | THR | B | 1206 | 15.734 | 39.655 | 24.998 | 1 | 47.86 |
| 4170 | OG1 | THR | B | 1206 | 15.217 | 38.583 | 24.208 | 1 | 49.04 |
| 4171 | CG2 | THR | B | 1206 | 17.172 | 39.971 | 24.62 | 1 | 47.78 |
| 4172 | N | VAL | B | 1207 | 13.412 | 38.653 | 27.259 | 1 | 38.86 |
| 4173 | CA | VAL | B | 1207 | 12.074 | 38.944 | 27.756 | 1 | 37.69 |
| 4174 | C | VAL | B | 1207 | 12.178 | 39.641 | 29.088 | 1 | 36.51 |
| 4175 | O | VAL | B | 1207 | 11.324 | 40.445 | 29.415 | 1 | 39.99 |
| 4176 | CB | VAL | B | 1207 | 11.181 | 37.701 | 27.914 | 1 | 36.07 |
| 4177 | CG1 | VAL | B | 1207 | 11.301 | 36.835 | 26.716 | 1 | 38.1 |
| 4178 | CG2 | VAL | B | 1207 | 11.517 | 36.941 | 29.17 | 1 | 33.88 |
| 4179 | N | ASP | B | 1208 | 13.234 | 39.34 | 29.841 | 1 | 36.82 |
| 4180 | CA | ASP | B | 1208 | 13.453 | 39.964 | 31.144 | 1 | 38.33 |
| 4181 | C | ASP | B | 1208 | 13.838 | 41.421 | 30.931 | 1 | 38.75 |
| 4182 | O | ASP | B | 1208 | 13.662 | 42.243 | 31.818 | 1 | 42.78 |
| 4183 | CB | ASP | B | 1208 | 14.567 | 39.243 | 31.933 | 1 | 40.62 |
| 4184 | CG | ASP | B | 1208 | 14.18 | 37.822 | 32.362 | 1 | 47.14 |
| 4185 | OD1 | ASP | B | 1208 | 12.971 | 37.558 | 32.556 | 1 | 51.31 |
| 4186 | OD2 | ASP | B | 1208 | 15.091 | 36.975 | 32.54 | 1 | 47.58 |
| 4187 | N | ILE | B | 1209 | 14.415 | 41.736 | 29.772 | 1 | 40.72 |
| 4188 | CA | ILE | B | 1209 | 14.795 | 43.118 | 29.488 | 1 | 44.12 |
| 4189 | C | ILE | B | 1209 | 13.523 | 43.88 | 29.167 | 1 | 43.61 |
| 4190 | O | ILE | B | 1209 | 13.395 | 45.046 | 29.52 | 1 | 44.66 |
| 4191 | CB | ILE | B | 1209 | 15.803 | 43.233 | 28.321 | 1 | 46.12 |
| 4192 | CG1 | ILE | B | 1209 | 17.142 | 42.634 | 28.744 | 1 | 46.44 |
| 4193 | CG2 | ILE | B | 1209 | 16.025 | 44.709 | 27.951 | 1 | 46.63 |
| 4194 | CD1 | ILE | B | 1209 | 17.735 | 43.33 | 29.925 | 1 | 47.31 |
| 4195 | N | TRP | B | 1210 | 12.569 | 43.201 | 28.53 | 1 | 42.85 |
| 4196 | CA | TRP | B | 1210 | 11.303 | 43.82 | 28.216 | 1 | 43.23 |
| 4197 | C | TRP | B | 1210 | 10.684 | 44.24 | 29.538 | 1 | 47.23 |
| 4198 | O | TRP | B | 1210 | 10.439 | 45.436 | 29.765 | 1 | 50.13 |
| 4199 | CB | TRP | B | 1210 | 10.375 | 42.86 | 27.472 | 1 | 44.24 |
| 4200 | CG | TRP | B | 1210 | 9.059 | 43.522 | 27.091 | 1 | 46.15 |

Fig. 1-105

| ATOM | ATOM TYPE | RESIDUE | | # | X | Y | Z | OCC | B |
|---|---|---|---|---|---|---|---|---|---|
| 4201 | CD1 | TRP | B | 1210 | 7.934 | 43.604 | 27.859 | 1 | 47.45 |
| 4202 | CD2 | TRP | B | 1210 | 8.784 | 44.275 | 25.904 | 1 | 43.99 |
| 4203 | NE1 | TRP | B | 1210 | 6.986 | 44.37 | 27.235 | 1 | 47.93 |
| 4204 | CE2 | TRP | B | 1210 | 7.482 | 44.794 | 26.032 | 1 | 48.37 |
| 4205 | CE3 | TRP | B | 1210 | 9.514 | 44.566 | 24.749 | 1 | 45.13 |
| 4206 | CZ2 | TRP | B | 1210 | 6.892 | 45.597 | 25.043 | 1 | 48.76 |
| 4207 | CZ3 | TRP | B | 1210 | 8.929 | 45.356 | 23.769 | 1 | 45.48 |
| 4208 | CH2 | TRP | B | 1210 | 7.632 | 45.863 | 23.922 | 1 | 45.3 |
| 4209 | N | SER | B | 1211 | 10.491 | 43.265 | 30.428 | 1 | 45.87 |
| 4210 | CA | SER | B | 1211 | 9.929 | 43.521 | 31.752 | 1 | 43.19 |
| 4211 | C | SER | B | 1211 | 10.64 | 44.688 | 32.436 | 1 | 42.84 |
| 4212 | O | SER | B | 1211 | 9.997 | 45.594 | 32.962 | 1 | 47.32 |
| 4213 | CB | SER | B | 1211 | 10.013 | 42.268 | 32.62 | 1 | 41.32 |
| 4214 | OG | SER | B | 1211 | 9.246 | 41.22 | 32.055 | 1 | 44.51 |
| 4215 | N | VAL | B | 1212 | 11.963 | 44.703 | 32.406 | 1 | 38.65 |
| 4216 | CA | VAL | B | 1212 | 12.675 | 45.821 | 33.03 | 1 | 36.73 |
| 4217 | C | VAL | B | 1212 | 12.3 | 47.176 | 32.381 | 1 | 35.46 |
| 4218 | O | VAL | B | 1212 | 12.285 | 48.215 | 33.041 | 1 | 31.21 |
| 4219 | CB | VAL | B | 1212 | 14.212 | 45.6 | 32.994 | 1 | 33.77 |
| 4220 | CG1 | VAL | B | 1212 | 14.938 | 46.829 | 33.476 | 1 | 26.48 |
| 4221 | CG2 | VAL | B | 1212 | 14.577 | 44.417 | 33.893 | 1 | 33.6 |
| 4222 | N | GLY | B | 1213 | 11.983 | 47.15 | 31.09 | 1 | 33.45 |
| 4223 | CA | GLY | B | 1213 | 11.618 | 48.379 | 30.408 | 1 | 37.91 |
| 4224 | C | GLY | B | 1213 | 10.272 | 48.894 | 30.88 | 1 | 40.63 |
| 4225 | O | GLY | B | 1213 | 10.111 | 50.078 | 31.154 | 1 | 42.93 |
| 4226 | N | CYS | B | 1214 | 9.296 | 47.996 | 30.95 | 1 | 40.03 |
| 4227 | CA | CYS | B | 1214 | 7.974 | 48.342 | 31.414 | 1 | 38.79 |
| 4228 | C | CYS | B | 1214 | 8.087 | 48.81 | 32.856 | 1 | 40.72 |
| 4229 | O | CYS | B | 1214 | 7.409 | 49.744 | 33.278 | 1 | 44.91 |
| 4230 | CB | CYS | B | 1214 | 7.077 | 47.111 | 31.376 | 1 | 41.67 |
| 4231 | SG | CYS | B | 1214 | 6.855 | 46.384 | 29.756 | 1 | 44.47 |
| 4232 | N | ILE | B | 1215 | 8.948 | 48.155 | 33.618 | 1 | 39.23 |
| 4233 | CA | ILE | B | 1215 | 9.11 | 48.518 | 35.019 | 1 | 39.92 |
| 4234 | C | ILE | B | 1215 | 9.77 | 49.895 | 35.114 | 1 | 39.91 |
| 4235 | O | ILE | B | 1215 | 9.287 | 50.756 | 35.826 | 1 | 44.16 |
| 4236 | CB | ILE | B | 1215 | 9.92 | 47.443 | 35.818 | 1 | 31.4 |
| 4237 | CG1 | ILE | B | 1215 | 9.236 | 46.068 | 35.736 | 1 | 34.39 |
| 4238 | CG2 | ILE | B | 1215 | 9.971 | 47.809 | 37.246 | 1 | 31.38 |
| 4239 | CD1 | ILE | B | 1215 | 10.017 | 44.906 | 36.35 | 1 | 20.27 |
| 4240 | N | MET | B | 1216 | 10.844 | 50.115 | 34.375 | 1 | 40.74 |

Fig. 1-106

| ATOM | ATOM TYPE | RESIDUE | | # | X | Y | Z | OCC | B |
|---|---|---|---|---|---|---|---|---|---|
| 4241 | CA | MET | B | 1216 | 11.52 | 51.411 | 34.428 | 1 | 45.73 |
| 4242 | C | MET | B | 1216 | 10.573 | 52.508 | 33.94 | 1 | 47.65 |
| 4243 | O | MET | B | 1216 | 10.555 | 53.611 | 34.478 | 1 | 47.43 |
| 4244 | CB | MET | B | 1216 | 12.776 | 51.415 | 33.556 | 1 | 44.71 |
| 4245 | CG | MET | B | 1216 | 13.646 | 52.632 | 33.797 | 1 | 48.1 |
| 4246 | SD | MET | B | 1216 | 14.799 | 53.015 | 32.451 | 1 | 49.17 |
| 4247 | CE | MET | B | 1216 | 15.345 | 54.577 | 33.017 | 1 | 51.17 |
| 4248 | N | ALA | B | 1217 | 9.768 | 52.174 | 32.934 | 1 | 48.37 |
| 4249 | CA | ALA | B | 1217 | 8.818 | 53.102 | 32.358 | 1 | 48.15 |
| 4250 | C | ALA | B | 1217 | 7.761 | 53.474 | 33.387 | 1 | 51.73 |
| 4251 | O | ALA | B | 1217 | 7.374 | 54.639 | 33.507 | 1 | 54.48 |
| 4252 | CB | ALA | B | 1217 | 8.173 | 52.479 | 31.149 | 1 | 44.59 |
| 4253 | N | GLU | B | 1218 | 7.332 | 52.478 | 34.158 | 1 | 52.41 |
| 4254 | CA | GLU | B | 1218 | 6.318 | 52.675 | 35.182 | 1 | 50.52 |
| 4255 | C | GLU | B | 1218 | 6.837 | 53.53 | 36.327 | 1 | 50.04 |
| 4256 | O | GLU | B | 1218 | 6.101 | 54.324 | 36.889 | 1 | 51.73 |
| 4257 | CB | GLU | B | 1218 | 5.835 | 51.329 | 35.717 | 1 | 49.08 |
| 4258 | CG | GLU | B | 1218 | 4.569 | 51.44 | 36.529 | 1 | 47.77 |
| 4259 | CD | GLU | B | 1218 | 4.022 | 50.097 | 36.961 | 1 | 48.84 |
| 4260 | OE1 | GLU | B | 1218 | 4.236 | 49.088 | 36.262 | 1 | 42.73 |
| 4261 | OE2 | GLU | B | 1218 | 3.354 | 50.055 | 38.01 | 1 | 52.26 |
| 4262 | N | MET | B | 1219 | 8.095 | 53.343 | 36.699 | 1 | 49.38 |
| 4263 | CA | MET | B | 1219 | 8.661 | 54.13 | 37.774 | 1 | 50.62 |
| 4264 | C | MET | B | 1219 | 8.607 | 55.613 | 37.403 | 1 | 54.4 |
| 4265 | O | MET | B | 1219 | 8.24 | 56.455 | 38.228 | 1 | 56.92 |
| 4266 | CB | MET | B | 1219 | 10.11 | 53.72 | 38.032 | 1 | 45.89 |
| 4267 | CG | MET | B | 1219 | 10.271 | 52.373 | 38.645 | 1 | 42.73 |
| 4268 | SD | MET | B | 1219 | 11.979 | 51.838 | 38.549 | 1 | 43.34 |
| 4269 | CE | MET | B | 1219 | 12.61 | 52.259 | 40.04 | 1 | 38.93 |
| 4270 | N | ILE | B | 1220 | 8.925 | 55.916 | 36.147 | 1 | 55.54 |
| 4271 | CA | ILE | B | 1220 | 8.945 | 57.291 | 35.662 | 1 | 58.01 |
| 4272 | C | ILE | B | 1220 | 7.569 | 57.967 | 35.515 | 1 | 60 |
| 4273 | O | ILE | B | 1220 | 7.362 | 59.084 | 36.01 | 1 | 61.51 |
| 4274 | CB | ILE | B | 1220 | 9.661 | 57.378 | 34.308 | 1 | 57.72 |
| 4275 | CG1 | ILE | B | 1220 | 11.024 | 56.706 | 34.388 | 1 | 52.49 |
| 4276 | CG2 | ILE | B | 1220 | 9.842 | 58.844 | 33.915 | 1 | 59.88 |
| 4277 | CD1 | ILE | B | 1220 | 11.711 | 56.607 | 33.053 | 1 | 50.93 |
| 4278 | N | THR | B | 1221 | 6.657 | 57.308 | 34.798 | 1 | 58.95 |
| 4279 | CA | THR | B | 1221 | 5.322 | 57.835 | 34.564 | 1 | 56.6 |
| 4280 | C | THR | B | 1221 | 4.424 | 57.702 | 35.765 | 1 | 58.55 |

Fig. 1-107

| ATOM | ATOM TYPE | RESIDUE | | # | X | Y | Z | OCC | B |
|---|---|---|---|---|---|---|---|---|---|
| 4281 | O | THR | B | 1221 | 3.714 | 58.638 | 36.113 | 1 | 64.3 |
| 4282 | CB | THR | B | 1221 | 4.614 | 57.113 | 33.425 | 1 | 57.49 |
| 4283 | OG1 | THR | B | 1221 | 4.306 | 55.778 | 33.838 | 1 | 56.17 |
| 4284 | CG2 | THR | B | 1221 | 5.478 | 57.101 | 32.156 | 1 | 58.21 |
| 4285 | N | GLY | B | 1222 | 4.423 | 56.522 | 36.371 | 1 | 58.22 |
| 4286 | CA | GLY | B | 1222 | 3.575 | 56.277 | 37.527 | 1 | 56.24 |
| 4287 | C | GLY | B | 1222 | 2.405 | 55.392 | 37.142 | 1 | 55.43 |
| 4288 | O | GLY | B | 1222 | 1.722 | 54.827 | 38 | 1 | 54.04 |
| 4289 | N | LYS | B | 1223 | 2.21 | 55.25 | 35.836 | 1 | 55.15 |
| 4290 | CA | LYS | B | 1223 | 1.14 | 54.435 | 35.287 | 1 | 57.33 |
| 4291 | C | LYS | B | 1223 | 1.728 | 53.179 | 34.653 | 1 | 57.5 |
| 4292 | O | LYS | B | 1223 | 2.881 | 53.171 | 34.245 | 1 | 58.38 |
| 4293 | CB | LYS | B | 1223 | 0.364 | 55.241 | 34.224 | 1 | 55.24 |
| 4294 | N | THR | B | 1224 | 0.936 | 52.114 | 34.597 | 1 | 57.62 |
| 4295 | CA | THR | B | 1224 | 1.36 | 50.872 | 33.969 | 1 | 56.46 |
| 4296 | C | THR | B | 1224 | 1.478 | 51.199 | 32.486 | 1 | 58.78 |
| 4297 | O | THR | B | 1224 | 0.557 | 51.793 | 31.908 | 1 | 61.77 |
| 4298 | CB | THR | B | 1224 | 0.305 | 49.786 | 34.185 | 1 | 55.89 |
| 4299 | OG1 | THR | B | 1224 | 0.174 | 49.546 | 35.593 | 1 | 57.63 |
| 4300 | CG2 | THR | B | 1224 | 0.681 | 48.497 | 33.469 | 1 | 54.77 |
| 4301 | N | LEU | B | 1225 | 2.606 | 50.834 | 31.877 | 1 | 57.8 |
| 4302 | CA | LEU | B | 1225 | 2.853 | 51.133 | 30.467 | 1 | 55.6 |
| 4303 | C | LEU | B | 1225 | 1.908 | 50.463 | 29.478 | 1 | 53.47 |
| 4304 | O | LEU | B | 1225 | 1.3 | 51.131 | 28.663 | 1 | 54.96 |
| 4305 | CB | LEU | B | 1225 | 4.311 | 50.849 | 30.097 | 1 | 54.83 |
| 4306 | CG | LEU | B | 1225 | 4.717 | 51.246 | 28.676 | 1 | 56.4 |
| 4307 | CD1 | LEU | B | 1225 | 4.379 | 52.7 | 28.434 | 1 | 56.41 |
| 4308 | CD2 | LEU | B | 1225 | 6.196 | 51.004 | 28.464 | 1 | 55.43 |
| 4309 | N | PHE | B | 1226 | 1.79 | 49.148 | 29.538 | 1 | 52.6 |
| 4310 | CA | PHE | B | 1226 | 0.901 | 48.444 | 28.619 | 1 | 54.7 |
| 4311 | C | PHE | B | 1226 | -0.112 | 47.622 | 29.436 | 1 | 57.14 |
| 4312 | O | PHE | B | 1226 | 0.115 | 46.441 | 29.711 | 1 | 58.96 |
| 4313 | CB | PHE | B | 1226 | 1.7 | 47.523 | 27.663 | 1 | 50.21 |
| 4314 | CG | PHE | B | 1226 | 2.827 | 48.218 | 26.914 | 1 | 48.07 |
| 4315 | CD1 | PHE | B | 1226 | 2.588 | 49.345 | 26.136 | 1 | 47.09 |
| 4316 | CD2 | PHE | B | 1226 | 4.136 | 47.748 | 27.009 | 1 | 46.21 |
| 4317 | CE1 | PHE | B | 1226 | 3.633 | 49.99 | 25.474 | 1 | 45.24 |
| 4318 | CE2 | PHE | B | 1226 | 5.182 | 48.389 | 26.35 | 1 | 44.35 |
| 4319 | CZ | PHE | B | 1226 | 4.927 | 49.511 | 25.585 | 1 | 44.76 |
| 4320 | N | LYS | B | 1227 | -1.213 | 48.253 | 29.841 | 1 | 57.52 |

Fig. 1-108

| ATOM | ATOM TYPE | RESIDUE | | # | X | Y | Z | OCC | B |
|---|---|---|---|---|---|---|---|---|---|
| 4321 | CA | LYS | B | 1227 | -2.229 | 47.564 | 30.627 | 1 | 59.66 |
| 4322 | C | LYS | B | 1227 | -3.262 | 46.911 | 29.711 | 1 | 61.37 |
| 4323 | O | LYS | B | 1227 | -4.25 | 47.535 | 29.346 | 1 | 66.75 |
| 4324 | CB | LYS | B | 1227 | -2.907 | 48.544 | 31.599 | 1 | 59.39 |
| 4325 | N | GLY | B | 1228 | -3.026 | 45.666 | 29.312 | 1 | 58.81 |
| 4326 | CA | GLY | B | 1228 | -3.969 | 45.006 | 28.429 | 1 | 58.75 |
| 4327 | C | GLY | B | 1228 | -4.983 | 44.165 | 29.168 | 1 | 59.74 |
| 4328 | O | GLY | B | 1228 | -4.687 | 43.673 | 30.254 | 1 | 60.68 |
| 4329 | N | SER | B | 1229 | -6.148 | 43.944 | 28.559 | 1 | 60.74 |
| 4330 | CA | SER | B | 1229 | -7.206 | 43.153 | 29.196 | 1 | 62.57 |
| 4331 | C | SER | B | 1229 | -6.961 | 41.647 | 29.164 | 1 | 61.96 |
| 4332 | O | SER | B | 1229 | -7.304 | 40.947 | 30.122 | 1 | 60.7 |
| 4333 | CB | SER | B | 1229 | -8.585 | 43.495 | 28.622 | 1 | 63.3 |
| 4334 | OG | SER | B | 1229 | -8.71 | 43.085 | 27.275 | 1 | 66.67 |
| 4335 | N | ASP | B | 1230 | -6.411 | 41.148 | 28.058 | 1 | 61.15 |
| 4336 | CA | ASP | B | 1230 | -6.088 | 39.724 | 27.93 | 1 | 62.19 |
| 4337 | C | ASP | B | 1230 | -4.755 | 39.597 | 27.216 | 1 | 60.17 |
| 4338 | O | ASP | B | 1230 | -4.221 | 40.601 | 26.738 | 1 | 60.7 |
| 4339 | CB | ASP | B | 1230 | -7.196 | 38.919 | 27.22 | 1 | 66.13 |
| 4340 | CG | ASP | B | 1230 | -7.542 | 39.459 | 25.835 | 1 | 71.54 |
| 4341 | OD1 | ASP | B | 1230 | -8.415 | 40.346 | 25.744 | 1 | 73.7 |
| 4342 | OD2 | ASP | B | 1230 | -6.968 | 38.977 | 24.834 | 1 | 74.52 |
| 4343 | N | HIS | B | 1231 | -4.219 | 38.38 | 27.128 | 1 | 59.02 |
| 4344 | CA | HIS | B | 1231 | -2.913 | 38.189 | 26.494 | 1 | 58.04 |
| 4345 | C | HIS | B | 1231 | -2.807 | 38.689 | 25.069 | 1 | 57.96 |
| 4346 | O | HIS | B | 1231 | -1.771 | 39.219 | 24.671 | 1 | 58.46 |
| 4347 | CB | HIS | B | 1231 | -2.429 | 36.747 | 26.602 | 1 | 55.94 |
| 4348 | CG | HIS | B | 1231 | -3.263 | 35.763 | 25.851 | 1 | 56.86 |
| 4349 | ND1 | HIS | B | 1231 | -4.4 | 35.196 | 26.383 | 1 | 56.73 |
| 4350 | CD2 | HIS | B | 1231 | -3.073 | 35.17 | 24.652 | 1 | 57.29 |
| 4351 | CE1 | HIS | B | 1231 | -4.87 | 34.29 | 25.543 | 1 | 58.59 |
| 4352 | NE2 | HIS | B | 1231 | -4.083 | 34.255 | 24.484 | 1 | 59.01 |
| 4353 | N | LEU | B | 1232 | -3.885 | 38.543 | 24.308 | 1 | 58.32 |
| 4354 | CA | LEU | B | 1232 | -3.911 | 39.027 | 22.941 | 1 | 54.34 |
| 4355 | C | LEU | B | 1232 | -4.072 | 40.539 | 22.947 | 1 | 54.1 |
| 4356 | O | LEU | B | 1232 | -3.415 | 41.241 | 22.183 | 1 | 56.3 |
| 4357 | CB | LEU | B | 1232 | -5.064 | 38.405 | 22.182 | 1 | 55.14 |
| 4358 | CG | LEU | B | 1232 | -4.998 | 36.905 | 21.922 | 1 | 57.44 |
| 4359 | CD1 | LEU | B | 1232 | -6.223 | 36.494 | 21.117 | 1 | 57.88 |
| 4360 | CD2 | LEU | B | 1232 | -3.715 | 36.556 | 21.162 | 1 | 56.89 |

Fig. 1-109

| ATOM | ATOM TYPE | RESIDUE | | # | X | Y | Z | OCC | B |
|---|---|---|---|---|---|---|---|---|---|
| 4361 | N | ASP | B | 1233 | -4.927 | 41.047 | 23.826 | 1 | 51.61 |
| 4362 | CA | ASP | B | 1233 | -5.149 | 42.486 | 23.896 | 1 | 52.19 |
| 4363 | C | ASP | B | 1233 | -3.875 | 43.223 | 24.331 | 1 | 52.92 |
| 4364 | O | ASP | B | 1233 | -3.689 | 44.419 | 24.033 | 1 | 50.75 |
| 4365 | CB | ASP | B | 1233 | -6.303 | 42.803 | 24.849 | 1 | 50.34 |
| 4366 | CG | ASP | B | 1233 | -6.653 | 44.28 | 24.864 | 1 | 52.85 |
| 4367 | OD1 | ASP | B | 1233 | -6.945 | 44.836 | 23.79 | 1 | 52.13 |
| 4368 | OD2 | ASP | B | 1233 | -6.629 | 44.892 | 25.949 | 1 | 56.19 |
| 4369 | N | GLN | B | 1234 | -3.007 | 42.498 | 25.04 | 1 | 50.31 |
| 4370 | CA | GLN | B | 1234 | -1.744 | 43.053 | 25.517 | 1 | 50.45 |
| 4371 | C | GLN | B | 1234 | -0.887 | 43.389 | 24.293 | 1 | 50.93 |
| 4372 | O | GLN | B | 1234 | -0.176 | 44.407 | 24.261 | 1 | 51.59 |
| 4373 | CB | GLN | B | 1234 | -1.041 | 42.04 | 26.421 | 1 | 45.74 |
| 4374 | CG | GLN | B | 1234 | 0.279 | 42.508 | 26.982 | 1 | 46.08 |
| 4375 | CD | GLN | B | 1234 | 0.134 | 43.546 | 28.077 | 1 | 46.94 |
| 4376 | OE1 | GLN | B | 1234 | -0.707 | 43.407 | 28.943 | 1 | 46.68 |
| 4377 | NE2 | GLN | B | 1234 | 0.989 | 44.578 | 28.062 | 1 | 46.35 |
| 4378 | N | LEU | B | 1235 | -0.977 | 42.539 | 23.274 | 1 | 48.65 |
| 4379 | CA | LEU | B | 1235 | -0.237 | 42.782 | 22.055 | 1 | 48.98 |
| 4380 | C | LEU | B | 1235 | -0.691 | 44.123 | 21.516 | 1 | 52.23 |
| 4381 | O | LEU | B | 1235 | 0.142 | 45.004 | 21.303 | 1 | 53.03 |
| 4382 | CB | LEU | B | 1235 | -0.488 | 41.68 | 21.036 | 1 | 45.58 |
| 4383 | CG | LEU | B | 1235 | 0.095 | 40.327 | 21.433 | 1 | 44.53 |
| 4384 | CD1 | LEU | B | 1235 | -0.092 | 39.335 | 20.314 | 1 | 43.17 |
| 4385 | CD2 | LEU | B | 1235 | 1.581 | 40.49 | 21.733 | 1 | 46.57 |
| 4386 | N | LYS | B | 1236 | -2.012 | 44.319 | 21.416 | 1 | 54.96 |
| 4387 | CA | LYS | B | 1236 | -2.557 | 45.585 | 20.909 | 1 | 54.89 |
| 4388 | C | LYS | B | 1236 | -2.069 | 46.787 | 21.708 | 1 | 54.06 |
| 4389 | O | LYS | B | 1236 | -1.66 | 47.797 | 21.131 | 1 | 54.93 |
| 4390 | CB | LYS | B | 1236 | -4.095 | 45.581 | 20.841 | 1 | 57.59 |
| 4391 | CG | LYS | B | 1236 | -4.71 | 46.952 | 20.449 | 1 | 62.19 |
| 4392 | CD | LYS | B | 1236 | -6.05 | 46.867 | 19.682 | 1 | 67.51 |
| 4393 | CE | LYS | B | 1236 | -7.204 | 46.304 | 20.517 | 1 | 71.25 |
| 4394 | NZ | LYS | B | 1236 | -8.498 | 46.253 | 19.768 | 1 | 69.27 |
| 4395 | N | GLU | B | 1237 | -2.096 | 46.688 | 23.03 | 1 | 52.2 |
| 4396 | CA | GLU | B | 1237 | -1.63 | 47.803 | 23.831 | 1 | 53.59 |
| 4397 | C | GLU | B | 1237 | -0.178 | 48.115 | 23.526 | 1 | 55.73 |
| 4398 | O | GLU | B | 1237 | 0.175 | 49.275 | 23.364 | 1 | 59.93 |
| 4399 | CB | GLU | B | 1237 | -1.819 | 47.55 | 25.324 | 1 | 54.74 |
| 4400 | CG | GLU | B | 1237 | -3.207 | 47.909 | 25.861 | 1 | 54.47 |

Fig. 1-110

| ATOM | ATOM TYPE | RESIDUE | | # | X | Y | Z | OCC | B |
|---|---|---|---|---|---|---|---|---|---|
| 4401 | CD | GLU | B | 1237 | -3.65 | 49.307 | 25.47 | 1 | 53.34 |
| 4402 | OE1 | GLU | B | 1237 | -2.963 | 50.291 | 25.822 | 1 | 53.72 |
| 4403 | OE2 | GLU | B | 1237 | -4.687 | 49.412 | 24.791 | 1 | 51.62 |
| 4404 | N | ILE | B | 1238 | 0.652 | 47.08 | 23.389 | 1 | 56.11 |
| 4405 | CA | ILE | B | 1238 | 2.068 | 47.279 | 23.091 | 1 | 52.93 |
| 4406 | C | ILE | B | 1238 | 2.224 | 47.88 | 21.71 | 1 | 54.32 |
| 4407 | O | ILE | B | 1238 | 2.93 | 48.883 | 21.522 | 1 | 57.33 |
| 4408 | CB | ILE | B | 1238 | 2.833 | 45.961 | 23.119 | 1 | 50.68 |
| 4409 | CG1 | ILE | B | 1238 | 2.839 | 45.397 | 24.538 | 1 | 46.12 |
| 4410 | CG2 | ILE | B | 1238 | 4.23 | 46.155 | 22.553 | 1 | 45.3 |
| 4411 | CD1 | ILE | B | 1238 | 3.235 | 43.941 | 24.621 | 1 | 42.78 |
| 4412 | N | MET | B | 1239 | 1.535 | 47.273 | 20.754 | 1 | 51.63 |
| 4413 | CA | MET | B | 1239 | 1.587 | 47.714 | 19.374 | 1 | 53.66 |
| 4414 | C | MET | B | 1239 | 1.216 | 49.18 | 19.217 | 1 | 53.7 |
| 4415 | O | MET | B | 1239 | 1.804 | 49.873 | 18.397 | 1 | 53.08 |
| 4416 | CB | MET | B | 1239 | 0.655 | 46.866 | 18.515 | 1 | 57.16 |
| 4417 | CG | MET | B | 1239 | 0.845 | 45.359 | 18.634 | 1 | 58.29 |
| 4418 | SD | MET | B | 1239 | 2.149 | 44.69 | 17.65 | 1 | 56.59 |
| 4419 | CE | MET | B | 1239 | 2.394 | 43.102 | 18.409 | 1 | 57.01 |
| 4420 | N | LYS | B | 1240 | 0.255 | 49.659 | 20.008 | 1 | 53.9 |
| 4421 | CA | LYS | B | 1240 | -0.16 | 51.05 | 19.913 | 1 | 53.89 |
| 4422 | C | LYS | B | 1240 | 1.035 | 51.977 | 20.172 | 1 | 56.36 |
| 4423 | O | LYS | B | 1240 | 1.06 | 53.122 | 19.715 | 1 | 57.18 |
| 4424 | CB | LYS | B | 1240 | -1.322 | 51.339 | 20.876 | 1 | 47.38 |
| 4425 | N | VAL | B | 1241 | 2.065 | 51.435 | 20.82 | 1 | 58.45 |
| 4426 | CA | VAL | B | 1241 | 3.263 | 52.195 | 21.135 | 1 | 59.79 |
| 4427 | C | VAL | B | 1241 | 4.454 | 51.881 | 20.248 | 1 | 60.04 |
| 4428 | O | VAL | B | 1241 | 5.123 | 52.791 | 19.746 | 1 | 59.07 |
| 4429 | CB | VAL | B | 1241 | 3.671 | 51.966 | 22.578 | 1 | 60.53 |
| 4430 | CG1 | VAL | B | 1241 | 4.93 | 52.746 | 22.909 | 1 | 62.42 |
| 4431 | CG2 | VAL | B | 1241 | 2.547 | 52.379 | 23.483 | 1 | 63.8 |
| 4432 | N | THR | B | 1242 | 4.728 | 50.592 | 20.074 | 1 | 60.8 |
| 4433 | CA | THR | B | 1242 | 5.869 | 50.145 | 19.267 | 1 | 61.17 |
| 4434 | C | THR | B | 1242 | 5.535 | 49.966 | 17.795 | 1 | 61.01 |
| 4435 | O | THR | B | 1242 | 6.382 | 49.57 | 17.003 | 1 | 62.55 |
| 4436 | CB | THR | B | 1242 | 6.393 | 48.775 | 19.75 | 1 | 60.5 |
| 4437 | OG1 | THR | B | 1242 | 5.483 | 47.75 | 19.343 | 1 | 54.06 |
| 4438 | CG2 | THR | B | 1242 | 6.534 | 48.75 | 21.26 | 1 | 60.41 |
| 4439 | N | GLY | B | 1243 | 4.3 | 50.242 | 17.425 | 1 | 60.4 |
| 4440 | CA | GLY | B | 1243 | 3.921 | 50.032 | 16.05 | 1 | 60.89 |

Fig. 1-111

| ATOM | ATOM TYPE | RESIDUE | | # | X | Y | Z | OCC | B |
|---|---|---|---|---|---|---|---|---|---|
| 4441 | C | GLY | B | 1243 | 3.718 | 48.541 | 15.864 | 1 | 61.31 |
| 4442 | O | GLY | B | 1243 | 4.048 | 47.741 | 16.746 | 1 | 60.67 |
| 4443 | N | THR | B | 1244 | 3.149 | 48.172 | 14.725 | 1 | 60.7 |
| 4444 | CA | THR | B | 1244 | 2.893 | 46.78 | 14.406 | 1 | 62.38 |
| 4445 | C | THR | B | 1244 | 3.947 | 46.309 | 13.419 | 1 | 64.56 |
| 4446 | O | THR | B | 1244 | 4.515 | 47.119 | 12.683 | 1 | 66.73 |
| 4447 | CB | THR | B | 1244 | 1.519 | 46.622 | 13.762 | 1 | 61.2 |
| 4448 | OG1 | THR | B | 1244 | 1.395 | 47.563 | 12.691 | 1 | 62.03 |
| 4449 | CG2 | THR | B | 1244 | 0.421 | 46.862 | 14.778 | 1 | 60.25 |
| 4450 | N | PRO | B | 1245 | 4.229 | 44.997 | 13.392 | 1 | 64.25 |
| 4451 | CA | PRO | B | 1245 | 5.222 | 44.421 | 12.486 | 1 | 66.03 |
| 4452 | C | PRO | B | 1245 | 4.69 | 44.482 | 11.056 | 1 | 67.01 |
| 4453 | O | PRO | B | 1245 | 3.521 | 44.798 | 10.839 | 1 | 67.35 |
| 4454 | CB | PRO | B | 1245 | 5.302 | 42.957 | 12.944 | 1 | 64.72 |
| 4455 | CG | PRO | B | 1245 | 4.745 | 42.951 | 14.292 | 1 | 64.39 |
| 4456 | CD | PRO | B | 1245 | 3.633 | 43.943 | 14.221 | 1 | 65.95 |
| 4457 | N | PRO | B | 1246 | 5.556 | 44.235 | 10.059 | 1 | 67.67 |
| 4458 | CA | PRO | B | 1246 | 5.106 | 44.261 | 8.668 | 1 | 67.56 |
| 4459 | C | PRO | B | 1246 | 4.065 | 43.167 | 8.418 | 1 | 68.23 |
| 4460 | O | PRO | B | 1246 | 4.116 | 42.086 | 9.01 | 1 | 65.68 |
| 4461 | CB | PRO | B | 1246 | 6.397 | 44.008 | 7.89 | 1 | 69.36 |
| 4462 | CG | PRO | B | 1246 | 7.288 | 43.3 | 8.877 | 1 | 69.55 |
| 4463 | CD | PRO | B | 1246 | 7.015 | 44.068 | 10.129 | 1 | 68.44 |
| 4464 | N | ALA | B | 1247 | 3.111 | 43.461 | 7.544 | 1 | 70.38 |
| 4465 | CA | ALA | B | 1247 | 2.037 | 42.526 | 7.227 | 1 | 71.09 |
| 4466 | C | ALA | B | 1247 | 2.508 | 41.169 | 6.707 | 1 | 71.05 |
| 4467 | O | ALA | B | 1247 | 1.873 | 40.15 | 6.976 | 1 | 70.69 |
| 4468 | CB | ALA | B | 1247 | 1.066 | 43.164 | 6.25 | 1 | 72.54 |
| 4469 | N | GLU | B | 1248 | 3.619 | 41.155 | 5.974 | 1 | 72.45 |
| 4470 | CA | GLU | B | 1248 | 4.161 | 39.908 | 5.425 | 1 | 72.67 |
| 4471 | C | GLU | B | 1248 | 4.692 | 38.986 | 6.522 | 1 | 70.87 |
| 4472 | O | GLU | B | 1248 | 4.681 | 37.764 | 6.373 | 1 | 69.68 |
| 4473 | CB | GLU | B | 1248 | 5.247 | 40.197 | 4.373 | 1 | 74.65 |
| 4474 | CG | GLU | B | 1248 | 6.514 | 40.891 | 4.886 | 1 | 76.7 |
| 4475 | CD | GLU | B | 1248 | 7.487 | 39.939 | 5.576 | 1 | 77.13 |
| 4476 | OE1 | GLU | B | 1248 | 7.53 | 38.739 | 5.208 | 1 | 78.5 |
| 4477 | OE2 | GLU | B | 1248 | 8.203 | 40.399 | 6.494 | 1 | 74.44 |
| 4478 | N | PHE | B | 1249 | 5.153 | 39.589 | 7.619 | 1 | 69.03 |
| 4479 | CA | PHE | B | 1249 | 5.681 | 38.845 | 8.76 | 1 | 65.7 |
| 4480 | C | PHE | B | 1249 | 4.565 | 38.116 | 9.479 | 1 | 62.87 |

Fig. 1-112

| ATOM | ATOM TYPE | RESIDUE | | # | X | Y | Z | OCC | B |
|---|---|---|---|---|---|---|---|---|---|
| 4481 | O | PHE | B | 1249 | 4.667 | 36.918 | 9.757 | 1 | 62.94 |
| 4482 | CB | PHE | B | 1249 | 6.387 | 39.781 | 9.755 | 1 | 64.18 |
| 4483 | CG | PHE | B | 1249 | 6.648 | 39.151 | 11.101 | 1 | 62.94 |
| 4484 | CD1 | PHE | B | 1249 | 7.501 | 38.062 | 11.224 | 1 | 62.78 |
| 4485 | CD2 | PHE | B | 1249 | 6.008 | 39.625 | 12.238 | 1 | 62.7 |
| 4486 | CE1 | PHE | B | 1249 | 7.707 | 37.454 | 12.458 | 1 | 63.19 |
| 4487 | CE2 | PHE | B | 1249 | 6.207 | 39.022 | 13.476 | 1 | 63.66 |
| 4488 | CZ | PHE | B | 1249 | 7.058 | 37.933 | 13.586 | 1 | 62.65 |
| 4489 | N | VAL | B | 1250 | 3.508 | 38.857 | 9.791 | 1 | 59.53 |
| 4490 | CA | VAL | B | 1250 | 2.377 | 38.294 | 10.501 | 1 | 58.75 |
| 4491 | C | VAL | B | 1250 | 1.651 | 37.229 | 9.687 | 1 | 58.44 |
| 4492 | O | VAL | B | 1250 | 0.964 | 36.378 | 10.242 | 1 | 58.71 |
| 4493 | CB | VAL | B | 1250 | 1.446 | 39.427 | 11.07 | 1 | 58.48 |
| 4494 | CG1 | VAL | B | 1250 | 1.746 | 40.757 | 10.389 | 1 | 55.48 |
| 4495 | CG2 | VAL | B | 1250 | -0.031 | 39.053 | 10.968 | 1 | 54.45 |
| 4496 | N | GLN | B | 1251 | 1.894 | 37.231 | 8.382 | 1 | 60.21 |
| 4497 | CA | GLN | B | 1251 | 1.297 | 36.273 | 7.466 | 1 | 63.14 |
| 4498 | C | GLN | B | 1251 | 1.841 | 34.889 | 7.751 | 1 | 61.1 |
| 4499 | O | GLN | B | 1251 | 1.109 | 33.898 | 7.765 | 1 | 59.02 |
| 4500 | CB | GLN | B | 1251 | 1.68 | 36.639 | 6.034 | 1 | 70.12 |
| 4501 | CG | GLN | B | 1251 | 0.812 | 37.685 | 5.368 | 1 | 79.74 |
| 4502 | CD | GLN | B | 1251 | -0.318 | 37.068 | 4.555 | 1 | 85.42 |
| 4503 | OE1 | GLN | B | 1251 | -0.951 | 36.085 | 4.972 | 1 | 88.27 |
| 4504 | NE2 | GLN | B | 1251 | -0.571 | 37.639 | 3.382 | 1 | 86.1 |
| 4505 | N | ARG | B | 1252 | 3.152 | 34.859 | 7.965 | 1 | 59.95 |
| 4506 | CA | ARG | B | 1252 | 3.921 | 33.648 | 8.21 | 1 | 57.86 |
| 4507 | C | ARG | B | 1252 | 3.999 | 33.181 | 9.656 | 1 | 57.82 |
| 4508 | O | ARG | B | 1252 | 4.692 | 32.207 | 9.941 | 1 | 57.09 |
| 4509 | CB | ARG | B | 1252 | 5.338 | 33.851 | 7.682 | 1 | 56.27 |
| 4510 | CG | ARG | B | 1252 | 5.388 | 34.332 | 6.263 | 1 | 52.49 |
| 4511 | CD | ARG | B | 1252 | 6.794 | 34.432 | 5.769 | 1 | 54.01 |
| 4512 | NE | ARG | B | 1252 | 7.457 | 35.651 | 6.211 | 1 | 58.28 |
| 4513 | CZ | ARG | B | 1252 | 8.648 | 35.676 | 6.8 | 1 | 61.18 |
| 4514 | NH1 | ARG | B | 1252 | 9.301 | 34.539 | 7.03 | 1 | 63.42 |
| 4515 | NH2 | ARG | B | 1252 | 9.217 | 36.836 | 7.097 | 1 | 59.41 |
| 4516 | N | LEU | B | 1253 | 3.336 | 33.886 | 10.571 | 1 | 55.24 |
| 4517 | CA | LEU | B | 1253 | 3.348 | 33.497 | 11.971 | 1 | 54.39 |
| 4518 | C | LEU | B | 1253 | 2.926 | 32.055 | 12.163 | 1 | 55.48 |
| 4519 | O | LEU | B | 1253 | 1.91 | 31.612 | 11.625 | 1 | 53.53 |
| 4520 | CB | LEU | B | 1253 | 2.449 | 34.402 | 12.796 | 1 | 53.23 |

Fig. 1-113

| ATOM | ATOM TYPE | RESIDUE | | # | X | Y | Z | OCC | B |
|---|---|---|---|---|---|---|---|---|---|
| 4521 | CG | LEU | B | 1253 | 3.108 | 35.739 | 13.091 | 1 | 53.33 |
| 4522 | CD1 | LEU | B | 1253 | 2.156 | 36.657 | 13.837 | 1 | 51.4 |
| 4523 | CD2 | LEU | B | 1253 | 4.367 | 35.493 | 13.874 | 1 | 49.5 |
| 4524 | N | GLN | B | 1254 | 3.74 | 31.33 | 12.923 | 1 | 57.13 |
| 4525 | CA | GLN | B | 1254 | 3.516 | 29.927 | 13.221 | 1 | 60.09 |
| 4526 | C | GLN | B | 1254 | 2.269 | 29.742 | 14.074 | 1 | 62.32 |
| 4527 | O | GLN | B | 1254 | 1.442 | 28.869 | 13.804 | 1 | 62.17 |
| 4528 | CB | GLN | B | 1254 | 4.726 | 29.378 | 13.968 | 1 | 61.41 |
| 4529 | CG | GLN | B | 1254 | 5.259 | 28.079 | 13.42 | 1 | 68.18 |
| 4530 | CD | GLN | B | 1254 | 4.211 | 26.998 | 13.381 | 1 | 70.52 |
| 4531 | OE1 | GLN | B | 1254 | 3.855 | 26.492 | 12.312 | 1 | 74.41 |
| 4532 | NE2 | GLN | B | 1254 | 3.69 | 26.65 | 14.546 | 1 | 71.4 |
| 4533 | N | SER | B | 1255 | 2.152 | 30.563 | 15.115 | 1 | 65.61 |
| 4534 | CA | SER | B | 1255 | 1.011 | 30.507 | 16.022 | 1 | 68.55 |
| 4535 | C | SER | B | 1255 | -0.249 | 30.996 | 15.327 | 1 | 69.94 |
| 4536 | O | SER | B | 1255 | -0.306 | 32.14 | 14.876 | 1 | 70.72 |
| 4537 | CB | SER | B | 1255 | 1.268 | 31.356 | 17.275 | 1 | 69.1 |
| 4538 | OG | SER | B | 1255 | 0.355 | 31.03 | 18.313 | 1 | 68.78 |
| 4539 | N | ASP | B | 1256 | -1.238 | 30.109 | 15.204 | 1 | 70.64 |
| 4540 | CA | ASP | B | 1256 | -2.51 | 30.454 | 14.575 | 1 | 70.68 |
| 4541 | C | ASP | B | 1256 | -3.187 | 31.581 | 15.353 | 1 | 70.67 |
| 4542 | O | ASP | B | 1256 | -3.499 | 32.634 | 14.792 | 1 | 69.86 |
| 4543 | CB | ASP | B | 1256 | -3.43 | 29.231 | 14.505 | 1 | 71.75 |
| 4544 | CG | ASP | B | 1256 | -3.024 | 28.242 | 13.41 | 1 | 74.47 |
| 4545 | OD1 | ASP | B | 1256 | -1.945 | 28.417 | 12.805 | 1 | 74.25 |
| 4546 | OD2 | ASP | B | 1256 | -3.793 | 27.288 | 13.146 | 1 | 73.44 |
| 4547 | N | GLU | B | 1257 | -3.333 | 31.379 | 16.66 | 1 | 70.16 |
| 4548 | CA | GLU | B | 1257 | -3.959 | 32.355 | 17.535 | 1 | 69.38 |
| 4549 | C | GLU | B | 1257 | -3.324 | 33.741 | 17.363 | 1 | 67.98 |
| 4550 | O | GLU | B | 1257 | -4.021 | 34.736 | 17.168 | 1 | 66.91 |
| 4551 | CB | GLU | B | 1257 | -3.854 | 31.9 | 18.989 | 1 | 71.08 |
| 4552 | CG | GLU | B | 1257 | -4.666 | 32.752 | 19.943 | 1 | 79.31 |
| 4553 | CD | GLU | B | 1257 | -4.33 | 32.504 | 21.401 | 1 | 83.72 |
| 4554 | OE1 | GLU | B | 1257 | -3.268 | 32.985 | 21.862 | 1 | 86.7 |
| 4555 | OE2 | GLU | B | 1257 | -5.133 | 31.841 | 22.088 | 1 | 86.01 |
| 4556 | N | ALA | B | 1258 | -1.999 | 33.792 | 17.368 | 1 | 63.29 |
| 4557 | CA | ALA | B | 1258 | -1.3 | 35.055 | 17.223 | 1 | 60.57 |
| 4558 | C | ALA | B | 1258 | -1.461 | 35.663 | 15.844 | 1 | 61.7 |
| 4559 | O | ALA | B | 1258 | -1.562 | 36.886 | 15.704 | 1 | 61.55 |
| 4560 | CB | ALA | B | 1258 | 0.153 | 34.869 | 17.525 | 1 | 60.8 |

Fig. 1-114

| ATOM | ATOM TYPE | RESIDUE | | # | X | Y | Z | OCC | B |
|---|---|---|---|---|---|---|---|---|---|
| 4561 | N | LYS | B | 1259 | -1.478 | 34.799 | 14.828 | 1 | 62.12 |
| 4562 | CA | LYS | B | 1259 | -1.599 | 35.225 | 13.433 | 1 | 60.44 |
| 4563 | C | LYS | B | 1259 | -2.955 | 35.851 | 13.166 | 1 | 61.2 |
| 4564 | O | LYS | B | 1259 | -3.045 | 36.935 | 12.593 | 1 | 59.62 |
| 4565 | CB | LYS | B | 1259 | -1.378 | 34.045 | 12.487 | 1 | 58.41 |
| 4566 | CG | LYS | B | 1259 | -1.323 | 34.438 | 11.015 | 1 | 57.86 |
| 4567 | CD | LYS | B | 1259 | -1.352 | 33.213 | 10.127 | 1 | 58.74 |
| 4568 | CE | LYS | B | 1259 | -2.645 | 32.447 | 10.319 | 1 | 61.03 |
| 4569 | NZ | LYS | B | 1259 | -2.675 | 31.156 | 9.596 | 1 | 63.9 |
| 4570 | N | ASN | B | 1260 | -4.008 | 35.156 | 13.58 | 1 | 61.15 |
| 4571 | CA | ASN | B | 1260 | -5.355 | 35.66 | 13.406 | 1 | 62.06 |
| 4572 | C | ASN | B | 1260 | -5.492 | 37.005 | 14.129 | 1 | 61.36 |
| 4573 | O | ASN | B | 1260 | -5.934 | 37.982 | 13.541 | 1 | 62.21 |
| 4574 | CB | ASN | B | 1260 | -6.386 | 34.652 | 13.94 | 1 | 65.52 |
| 4575 | CG | ASN | B | 1260 | -6.39 | 33.318 | 13.161 | 1 | 67.85 |
| 4576 | OD1 | ASN | B | 1260 | -6.67 | 32.257 | 13.728 | 1 | 69.36 |
| 4577 | ND2 | ASN | B | 1260 | -6.094 | 33.377 | 11.867 | 1 | 66.47 |
| 4578 | N | TYR | B | 1261 | -5.049 | 37.075 | 15.38 | 1 | 61.18 |
| 4579 | CA | TYR | B | 1261 | -5.154 | 38.315 | 16.14 | 1 | 59.38 |
| 4580 | C | TYR | B | 1261 | -4.462 | 39.487 | 15.459 | 1 | 60.07 |
| 4581 | O | TYR | B | 1261 | -5.082 | 40.513 | 15.223 | 1 | 62.69 |
| 4582 | CB | TYR | B | 1261 | -4.618 | 38.156 | 17.568 | 1 | 54.17 |
| 4583 | CG | TYR | B | 1261 | -4.846 | 39.396 | 18.386 | 1 | 50.61 |
| 4584 | CD1 | TYR | B | 1261 | -6.115 | 39.698 | 18.875 | 1 | 51.79 |
| 4585 | CD2 | TYR | B | 1261 | -3.826 | 40.323 | 18.583 | 1 | 51.69 |
| 4586 | CE1 | TYR | B | 1261 | -6.371 | 40.892 | 19.529 | 1 | 52.22 |
| 4587 | CE2 | TYR | B | 1261 | -4.062 | 41.536 | 19.235 | 1 | 53.13 |
| 4588 | CZ | TYR | B | 1261 | -5.343 | 41.815 | 19.704 | 1 | 56.41 |
| 4589 | OH | TYR | B | 1261 | -5.619 | 43.019 | 20.318 | 1 | 55.85 |
| 4590 | N | MET | B | 1262 | -3.185 | 39.33 | 15.136 | 1 | 63.11 |
| 4591 | CA | MET | B | 1262 | -2.417 | 40.392 | 14.486 | 1 | 65.26 |
| 4592 | C | MET | B | 1262 | -2.973 | 40.799 | 13.108 | 1 | 68.67 |
| 4593 | O | MET | B | 1262 | -2.717 | 41.916 | 12.619 | 1 | 67.05 |
| 4594 | CB | MET | B | 1262 | -0.962 | 39.949 | 14.352 | 1 | 64.37 |
| 4595 | CG | MET | B | 1262 | -0.211 | 39.85 | 15.655 | 1 | 59.25 |
| 4596 | SD | MET | B | 1262 | 0.018 | 41.481 | 16.394 | 1 | 67.15 |
| 4597 | CE | MET | B | 1262 | 0.971 | 42.304 | 15.118 | 1 | 58.72 |
| 4598 | N | LYS | B | 1263 | -3.713 | 39.875 | 12.491 | 1 | 72.15 |
| 4599 | CA | LYS | B | 1263 | -4.33 | 40.067 | 11.174 | 1 | 75.66 |
| 4600 | C | LYS | B | 1263 | -5.469 | 41.074 | 11.312 | 1 | 76.85 |

Fig. 1-115

| ATOM | ATOM TYPE | RESIDUE | | # | X | Y | Z | OCC | B |
|---|---|---|---|---|---|---|---|---|---|
| 4601 | O | LYS | B | 1263 | -5.491 | 42.096 | 10.632 | 1 | 77.11 |
| 4602 | CB | LYS | B | 1263 | -4.903 | 38.732 | 10.675 | 1 | 76.85 |
| 4603 | CG | LYS | B | 1263 | -4.698 | 38.397 | 9.199 | 1 | 79.3 |
| 4604 | CD | LYS | B | 1263 | -3.306 | 37.827 | 8.928 | 1 | 79.93 |
| 4605 | CE | LYS | B | 1263 | -3.221 | 37.108 | 7.576 | 1 | 81.06 |
| 4606 | NZ | LYS | B | 1263 | -3.864 | 35.758 | 7.571 | 1 | 81.5 |
| 4607 | N | GLY | B | 1264 | -6.397 | 40.777 | 12.219 | 1 | 78.8 |
| 4608 | CA | GLY | B | 1264 | -7.539 | 41.646 | 12.452 | 1 | 81.83 |
| 4609 | C | GLY | B | 1264 | -7.163 | 43.001 | 13.018 | 1 | 81.51 |
| 4610 | O | GLY | B | 1264 | -7.882 | 43.98 | 12.869 | 1 | 81.91 |
| 4611 | N | LEU | B | 1265 | -6.016 | 43.054 | 13.668 | 1 | 83.44 |
| 4612 | CA | LEU | B | 1265 | -5.525 | 44.284 | 14.264 | 1 | 84.73 |
| 4613 | C | LEU | B | 1265 | -5.23 | 45.323 | 13.186 | 1 | 85.19 |
| 4614 | O | LEU | B | 1265 | -4.826 | 44.976 | 12.072 | 1 | 86.18 |
| 4615 | CB | LEU | B | 1265 | -4.234 | 43.984 | 15.024 | 1 | 85.1 |
| 4616 | CG | LEU | B | 1265 | -3.838 | 44.932 | 16.144 | 1 | 83.99 |
| 4617 | CD1 | LEU | B | 1265 | -4.807 | 44.721 | 17.284 | 1 | 84.37 |
| 4618 | CD2 | LEU | B | 1265 | -2.419 | 44.648 | 16.594 | 1 | 84.44 |
| 4619 | N | PRO | B | 1266 | -5.47 | 46.612 | 13.486 | 1 | 86.14 |
| 4620 | CA | PRO | B | 1266 | -5.215 | 47.709 | 12.539 | 1 | 85.42 |
| 4621 | C | PRO | B | 1266 | -3.721 | 47.775 | 12.234 | 1 | 84.5 |
| 4622 | O | PRO | B | 1266 | -2.945 | 46.96 | 12.723 | 1 | 86.42 |
| 4623 | CB | PRO | B | 1266 | -5.644 | 48.945 | 13.329 | 1 | 85.91 |
| 4624 | CG | PRO | B | 1266 | -6.754 | 48.42 | 14.199 | 1 | 88.17 |
| 4625 | CD | PRO | B | 1266 | -6.193 | 47.102 | 14.677 | 1 | 87.57 |
| 4626 | N | GLU | B | 1267 | -3.312 | 48.741 | 11.428 | 1 | 83.25 |
| 4627 | CA | GLU | B | 1267 | -1.903 | 48.882 | 11.104 | 1 | 81.19 |
| 4628 | C | GLU | B | 1267 | -1.411 | 50.118 | 11.848 | 1 | 79.24 |
| 4629 | O | GLU | B | 1267 | -1.658 | 51.249 | 11.434 | 1 | 79.45 |
| 4630 | CB | GLU | B | 1267 | -1.718 | 49.009 | 9.586 | 1 | 84.26 |
| 4631 | CG | GLU | B | 1267 | -0.27 | 48.931 | 9.107 | 1 | 89.83 |
| 4632 | CD | GLU | B | 1267 | -0.113 | 48.13 | 7.813 | 1 | 94.51 |
| 4633 | OE1 | GLU | B | 1267 | 0.07 | 46.895 | 7.904 | 1 | 94.61 |
| 4634 | OE2 | GLU | B | 1267 | -0.164 | 48.73 | 6.71 | 1 | 95.62 |
| 4635 | N | LEU | B | 1268 | -0.752 | 49.887 | 12.981 | 1 | 76.7 |
| 4636 | CA | LEU | B | 1268 | -0.236 | 50.959 | 13.833 | 1 | 73.83 |
| 4637 | C | LEU | B | 1268 | 1.193 | 51.403 | 13.535 | 1 | 71.42 |
| 4638 | O | LEU | B | 1268 | 2.028 | 50.609 | 13.109 | 1 | 71.74 |
| 4639 | CB | LEU | B | 1268 | -0.368 | 50.543 | 15.297 | 1 | 72.92 |
| 4640 | CG | LEU | B | 1268 | -1.83 | 50.345 | 15.713 | 1 | 75.22 |

Fig. 1-116

| ATOM | ATOM TYPE | RESIDUE | | # | X | Y | Z | OCC | B |
|---|---|---|---|---|---|---|---|---|---|
| 4641 | CD1 | LEU | B | 1268 | -1.97 | 49.261 | 16.769 | 1 | 75.1 |
| 4642 | CD2 | LEU | B | 1268 | -2.413 | 51.674 | 16.181 | 1 | 76.24 |
| 4643 | N | GLU | B | 1269 | 1.456 | 52.687 | 13.745 | 1 | 69.3 |
| 4644 | CA | GLU | B | 1269 | 2.778 | 53.253 | 13.51 | 1 | 68.33 |
| 4645 | C | GLU | B | 1269 | 3.51 | 53.472 | 14.84 | 1 | 68.25 |
| 4646 | O | GLU | B | 1269 | 2.887 | 53.727 | 15.871 | 1 | 66.89 |
| 4647 | CB | GLU | B | 1269 | 2.664 | 54.573 | 12.73 | 1 | 67.48 |
| 4648 | N | LYS | B | 1270 | 4.836 | 53.387 | 14.803 | 1 | 66.93 |
| 4649 | CA | LYS | B | 1270 | 5.668 | 53.561 | 15.988 | 1 | 65.75 |
| 4650 | C | LYS | B | 1270 | 5.632 | 55.004 | 16.477 | 1 | 66.16 |
| 4651 | O | LYS | B | 1270 | 5.849 | 55.935 | 15.7 | 1 | 64.99 |
| 4652 | CB | LYS | B | 1270 | 7.11 | 53.152 | 15.666 | 1 | 66.19 |
| 4653 | CG | LYS | B | 1270 | 7.773 | 52.241 | 16.695 | 1 | 66.44 |
| 4654 | CD | LYS | B | 1270 | 8.293 | 52.985 | 17.917 | 1 | 67.33 |
| 4655 | CE | LYS | B | 1270 | 9.494 | 53.881 | 17.588 | 1 | 65.09 |
| 4656 | NZ | LYS | B | 1270 | 10.128 | 54.429 | 18.833 | 1 | 60.85 |
| 4657 | N | LYS | B | 1271 | 5.361 | 55.18 | 17.769 | 1 | 67.55 |
| 4658 | CA | LYS | B | 1271 | 5.303 | 56.508 | 18.383 | 1 | 67.77 |
| 4659 | C | LYS | B | 1271 | 6.647 | 56.811 | 19.017 | 1 | 67.69 |
| 4660 | O | LYS | B | 1271 | 7.36 | 55.897 | 19.424 | 1 | 67.47 |
| 4661 | CB | LYS | B | 1271 | 4.183 | 56.571 | 19.45 | 1 | 65.91 |
| 4662 | N | ASP | B | 1272 | 7.005 | 58.091 | 19.063 | 1 | 69.61 |
| 4663 | CA | ASP | B | 1272 | 8.263 | 58.513 | 19.664 | 1 | 69.98 |
| 4664 | C | ASP | B | 1272 | 8.058 | 58.314 | 21.153 | 1 | 69.48 |
| 4665 | O | ASP | B | 1272 | 7.026 | 58.714 | 21.682 | 1 | 70.79 |
| 4666 | CB | ASP | B | 1272 | 8.512 | 59.991 | 19.375 | 1 | 72.7 |
| 4667 | CG | ASP | B | 1272 | 9.923 | 60.425 | 19.713 | 1 | 74.97 |
| 4668 | OD1 | ASP | B | 1272 | 10.25 | 60.564 | 20.918 | 1 | 75 |
| 4669 | OD2 | ASP | B | 1272 | 10.706 | 60.632 | 18.759 | 1 | 78.18 |
| 4670 | N | PHE | B | 1273 | 9.024 | 57.697 | 21.829 | 1 | 68.18 |
| 4671 | CA | PHE | B | 1273 | 8.889 | 57.453 | 23.261 | 1 | 65.46 |
| 4672 | C | PHE | B | 1273 | 8.816 | 58.714 | 24.099 | 1 | 65.24 |
| 4673 | O | PHE | B | 1273 | 8.08 | 58.754 | 25.081 | 1 | 61.9 |
| 4674 | CB | PHE | B | 1273 | 9.983 | 56.513 | 23.774 | 1 | 64.16 |
| 4675 | CG | PHE | B | 1273 | 9.687 | 55.049 | 23.54 | 1 | 63.69 |
| 4676 | CD1 | PHE | B | 1273 | 8.772 | 54.649 | 22.567 | 1 | 61.12 |
| 4677 | CD2 | PHE | B | 1273 | 10.338 | 54.069 | 24.279 | 1 | 63.74 |
| 4678 | CE1 | PHE | B | 1273 | 8.515 | 53.306 | 22.334 | 1 | 60.04 |
| 4679 | CE2 | PHE | B | 1273 | 10.082 | 52.715 | 24.048 | 1 | 63.22 |
| 4680 | CZ | PHE | B | 1273 | 9.171 | 52.335 | 23.074 | 1 | 61.04 |

Fig. 1-117

| ATOM | ATOM TYPE | RESIDUE | | # | X | Y | Z | OCC | B |
|---|---|---|---|---|---|---|---|---|---|
| 4681 | N | ALA | B | 1274 | 9.539 | 59.753 | 23.686 | 1 | 66.63 |
| 4682 | CA | ALA | B | 1274 | 9.542 | 61.025 | 24.408 | 1 | 69.62 |
| 4683 | C | ALA | B | 1274 | 8.14 | 61.632 | 24.491 | 1 | 70.5 |
| 4684 | O | ALA | B | 1274 | 7.856 | 62.443 | 25.377 | 1 | 69.92 |
| 4685 | CB | ALA | B | 1274 | 10.497 | 62.003 | 23.743 | 1 | 69.88 |
| 4686 | N | SER | B | 1275 | 7.275 | 61.217 | 23.563 | 1 | 72.43 |
| 4687 | CA | SER | B | 1275 | 5.884 | 61.673 | 23.487 | 1 | 73.84 |
| 4688 | C | SER | B | 1275 | 4.998 | 61.015 | 24.546 | 1 | 74.53 |
| 4689 | O | SER | B | 1275 | 3.901 | 61.491 | 24.82 | 1 | 75.39 |
| 4690 | CB | SER | B | 1275 | 5.319 | 61.388 | 22.096 | 1 | 71.41 |
| 4691 | N | ILE | B | 1276 | 5.48 | 59.914 | 25.118 | 1 | 77.16 |
| 4692 | CA | ILE | B | 1276 | 4.763 | 59.158 | 26.144 | 1 | 77.51 |
| 4693 | C | ILE | B | 1276 | 5.278 | 59.493 | 27.539 | 1 | 79 |
| 4694 | O | ILE | B | 1276 | 4.498 | 59.738 | 28.455 | 1 | 79.83 |
| 4695 | CB | ILE | B | 1276 | 4.956 | 57.642 | 25.949 | 1 | 77.77 |
| 4696 | CG1 | ILE | B | 1276 | 4.703 | 57.255 | 24.496 | 1 | 76.62 |
| 4697 | CG2 | ILE | B | 1276 | 4.026 | 56.864 | 26.868 | 1 | 77.73 |
| 4698 | CD1 | ILE | B | 1276 | 5.015 | 55.809 | 24.212 | 1 | 79.55 |
| 4699 | N | LEU | B | 1277 | 6.597 | 59.452 | 27.7 | 1 | 80.74 |
| 4700 | CA | LEU | B | 1277 | 7.247 | 59.737 | 28.979 | 1 | 84.06 |
| 4701 | C | LEU | B | 1277 | 7.34 | 61.249 | 29.199 | 1 | 86.87 |
| 4702 | O | LEU | B | 1277 | 8.358 | 61.875 | 28.894 | 1 | 85.95 |
| 4703 | CB | LEU | B | 1277 | 8.64 | 59.106 | 28.995 | 1 | 82.05 |
| 4704 | CG | LEU | B | 1277 | 8.746 | 57.727 | 28.339 | 1 | 78.97 |
| 4705 | CD1 | LEU | B | 1277 | 10.171 | 57.254 | 28.36 | 1 | 76.91 |
| 4706 | CD2 | LEU | B | 1277 | 7.835 | 56.744 | 29.036 | 1 | 79.91 |
| 4707 | N | THR | B | 1278 | 6.27 | 61.808 | 29.76 | 1 | 90.84 |
| 4708 | CA | THR | B | 1278 | 6.145 | 63.243 | 30.015 | 1 | 95.63 |
| 4709 | C | THR | B | 1278 | 7.367 | 63.958 | 30.606 | 1 | 97.4 |
| 4710 | O | THR | B | 1278 | 7.998 | 64.773 | 29.925 | 1 | 97.16 |
| 4711 | CB | THR | B | 1278 | 4.887 | 63.562 | 30.881 | 1 | 96.55 |
| 4712 | OG1 | THR | B | 1278 | 4.847 | 62.699 | 32.027 | 1 | 97.43 |
| 4713 | CG2 | THR | B | 1278 | 3.609 | 63.392 | 30.064 | 1 | 96.74 |
| 4714 | N | ASN | B | 1279 | 7.688 | 63.672 | 31.865 | 1 | 97.5 |
| 4715 | CA | ASN | B | 1279 | 8.816 | 64.331 | 32.521 | 1 | 97.54 |
| 4716 | C | ASN | B | 1279 | 10.112 | 63.507 | 32.643 | 1 | 95.91 |
| 4717 | O | ASN | B | 1279 | 10.955 | 63.765 | 33.515 | 1 | 96.48 |
| 4718 | CB | ASN | B | 1279 | 8.383 | 64.916 | 33.886 | 1 | 100 |
| 4719 | CG | ASN | B | 1279 | 7.771 | 63.865 | 34.852 | 1 | 100 |
| 4720 | OD1 | ASN | B | 1279 | 7.607 | 64.136 | 36.051 | 1 | 99.54 |

Fig. 1-118

| ATOM | ATOM TYPE | RESIDUE | | # | X | Y | Z | OCC | B |
|---|---|---|---|---|---|---|---|---|---|
| 4721 | ND2 | ASN | B | 1279 | 7.423 | 62.685 | 34.33 | 1 | 100 |
| 4722 | N | ALA | B | 1280 | 10.284 | 62.544 | 31.74 | 1 | 92.84 |
| 4723 | CA | ALA | B | 1280 | 11.466 | 61.685 | 31.734 | 1 | 88.93 |
| 4724 | C | ALA | B | 1280 | 12.689 | 62.38 | 31.14 | 1 | 86.6 |
| 4725 | O | ALA | B | 1280 | 12.556 | 63.374 | 30.435 | 1 | 87.14 |
| 4726 | CB | ALA | B | 1280 | 11.173 | 60.409 | 30.972 | 1 | 88.35 |
| 4727 | N | SER | B | 1281 | 13.88 | 61.855 | 31.418 | 1 | 84.02 |
| 4728 | CA | SER | B | 1281 | 15.106 | 62.446 | 30.888 | 1 | 81.36 |
| 4729 | C | SER | B | 1281 | 15.379 | 61.907 | 29.475 | 1 | 80.26 |
| 4730 | O | SER | B | 1281 | 14.831 | 60.874 | 29.082 | 1 | 80.23 |
| 4731 | CB | SER | B | 1281 | 16.291 | 62.135 | 31.808 | 1 | 80.61 |
| 4732 | OG | SER | B | 1281 | 17.021 | 60.996 | 31.368 | 1 | 78.03 |
| 4733 | N | PRO | B | 1282 | 16.224 | 62.607 | 28.692 | 1 | 77.9 |
| 4734 | CA | PRO | B | 1282 | 16.578 | 62.212 | 27.325 | 1 | 75.18 |
| 4735 | C | PRO | B | 1282 | 17.242 | 60.834 | 27.247 | 1 | 73.25 |
| 4736 | O | PRO | B | 1282 | 16.805 | 59.972 | 26.472 | 1 | 72.63 |
| 4737 | CB | PRO | B | 1282 | 17.538 | 63.323 | 26.891 | 1 | 75.48 |
| 4738 | CG | PRO | B | 1282 | 18.127 | 63.809 | 28.174 | 1 | 75.62 |
| 4739 | CD | PRO | B | 1282 | 16.914 | 63.858 | 29.052 | 1 | 78.3 |
| 4740 | N | LEU | B | 1283 | 18.283 | 60.635 | 28.053 | 1 | 71.62 |
| 4741 | CA | LEU | B | 1283 | 19.02 | 59.364 | 28.104 | 1 | 68.65 |
| 4742 | C | LEU | B | 1283 | 18.113 | 58.211 | 28.547 | 1 | 67.58 |
| 4743 | O | LEU | B | 1283 | 18.264 | 57.07 | 28.084 | 1 | 66.85 |
| 4744 | CB | LEU | B | 1283 | 20.183 | 59.476 | 29.083 | 1 | 67.7 |
| 4745 | CG | LEU | B | 1283 | 21.339 | 60.392 | 28.714 | 1 | 67.35 |
| 4746 | CD1 | LEU | B | 1283 | 22.242 | 60.618 | 29.916 | 1 | 66.53 |
| 4747 | CD2 | LEU | B | 1283 | 22.1 | 59.773 | 27.563 | 1 | 65.79 |
| 4748 | N | ALA | B | 1284 | 17.199 | 58.519 | 29.471 | 1 | 64.43 |
| 4749 | CA | ALA | B | 1284 | 16.249 | 57.545 | 30.006 | 1 | 59.58 |
| 4750 | C | ALA | B | 1284 | 15.356 | 57.075 | 28.895 | 1 | 57.72 |
| 4751 | O | ALA | B | 1284 | 15.077 | 55.893 | 28.767 | 1 | 59.25 |
| 4752 | CB | ALA | B | 1284 | 15.408 | 58.18 | 31.106 | 1 | 61.25 |
| 4753 | N | VAL | B | 1285 | 14.904 | 58.025 | 28.087 | 1 | 56.46 |
| 4754 | CA | VAL | B | 1285 | 14.044 | 57.711 | 26.965 | 1 | 52.37 |
| 4755 | C | VAL | B | 1285 | 14.823 | 56.858 | 25.98 | 1 | 52.62 |
| 4756 | O | VAL | B | 1285 | 14.306 | 55.869 | 25.459 | 1 | 52.67 |
| 4757 | CB | VAL | B | 1285 | 13.535 | 58.993 | 26.294 | 1 | 46.38 |
| 4758 | CG1 | VAL | B | 1285 | 12.781 | 58.673 | 25.043 | 1 | 46.24 |
| 4759 | CG2 | VAL | B | 1285 | 12.64 | 59.722 | 27.236 | 1 | 45.78 |
| 4760 | N | ASN | B | 1286 | 16.089 | 57.204 | 25.769 | 1 | 53.19 |

Fig. 1-119

| ATOM | ATOM TYPE | RESIDUE | | # | X | Y | Z | OCC | B |
|---|---|---|---|---|---|---|---|---|---|
| 4761 | CA | ASN | B | 1286 | 16.882 | 56.434 | 24.828 | 1 | 55.25 |
| 4762 | C | ASN | B | 1286 | 17.013 | 54.992 | 25.302 | 1 | 53.6 |
| 4763 | O | ASN | B | 1286 | 16.718 | 54.077 | 24.546 | 1 | 53.58 |
| 4764 | CB | ASN | B | 1286 | 18.254 | 57.065 | 24.577 | 1 | 56.34 |
| 4765 | CG | ASN | B | 1286 | 19.043 | 56.31 | 23.519 | 1 | 58.72 |
| 4766 | OD1 | ASN | B | 1286 | 18.835 | 56.494 | 22.317 | 1 | 61.07 |
| 4767 | ND2 | ASN | B | 1286 | 19.914 | 55.416 | 23.962 | 1 | 58.48 |
| 4768 | N | LEU | B | 1287 | 17.401 | 54.796 | 26.56 | 1 | 52.93 |
| 4769 | CA | LEU | B | 1287 | 17.541 | 53.449 | 27.108 | 1 | 52.01 |
| 4770 | C | LEU | B | 1287 | 16.252 | 52.656 | 26.966 | 1 | 52.32 |
| 4771 | O | LEU | B | 1287 | 16.261 | 51.509 | 26.529 | 1 | 55.79 |
| 4772 | CB | LEU | B | 1287 | 17.928 | 53.497 | 28.582 | 1 | 49.29 |
| 4773 | CG | LEU | B | 1287 | 18.069 | 52.126 | 29.257 | 1 | 49.59 |
| 4774 | CD1 | LEU | B | 1287 | 19.102 | 51.235 | 28.562 | 1 | 48.36 |
| 4775 | CD2 | LEU | B | 1287 | 18.422 | 52.332 | 30.71 | 1 | 49.9 |
| 4776 | N | LEU | B | 1288 | 15.139 | 53.275 | 27.333 | 1 | 52.77 |
| 4777 | CA | LEU | B | 1288 | 13.839 | 52.625 | 27.238 | 1 | 52.03 |
| 4778 | C | LEU | B | 1288 | 13.568 | 52.187 | 25.807 | 1 | 53.2 |
| 4779 | O | LEU | B | 1288 | 13.146 | 51.055 | 25.557 | 1 | 50.69 |
| 4780 | CB | LEU | B | 1288 | 12.749 | 53.575 | 27.739 | 1 | 50.77 |
| 4781 | CG | LEU | B | 1288 | 12.651 | 53.597 | 29.265 | 1 | 47.67 |
| 4782 | CD1 | LEU | B | 1288 | 11.625 | 54.601 | 29.738 | 1 | 49.99 |
| 4783 | CD2 | LEU | B | 1288 | 12.267 | 52.206 | 29.737 | 1 | 49.57 |
| 4784 | N | GLU | B | 1289 | 13.873 | 53.085 | 24.873 | 1 | 56.08 |
| 4785 | CA | GLU | B | 1289 | 13.699 | 52.834 | 23.448 | 1 | 57.88 |
| 4786 | C | GLU | B | 1289 | 14.511 | 51.59 | 23.057 | 1 | 55.48 |
| 4787 | O | GLU | B | 1289 | 14.044 | 50.752 | 22.284 | 1 | 57.31 |
| 4788 | CB | GLU | B | 1289 | 14.158 | 54.062 | 22.651 | 1 | 60.3 |
| 4789 | CG | GLU | B | 1289 | 13.409 | 54.308 | 21.35 | 1 | 69.07 |
| 4790 | CD | GLU | B | 1289 | 12.532 | 55.562 | 21.39 | 1 | 75.71 |
| 4791 | OE1 | GLU | B | 1289 | 13.025 | 56.647 | 21.781 | 1 | 77.13 |
| 4792 | OE2 | GLU | B | 1289 | 11.345 | 55.467 | 21.005 | 1 | 78.96 |
| 4793 | N | LYS | B | 1290 | 15.701 | 51.455 | 23.63 | 1 | 53.91 |
| 4794 | CA | LYS | B | 1290 | 16.572 | 50.313 | 23.354 | 1 | 56.54 |
| 4795 | C | LYS | B | 1290 | 16.103 | 49.029 | 24.043 | 1 | 55 |
| 4796 | O | LYS | B | 1290 | 16.398 | 47.931 | 23.567 | 1 | 56.1 |
| 4797 | CB | LYS | B | 1290 | 18.012 | 50.615 | 23.774 | 1 | 59.63 |
| 4798 | CG | LYS | B | 1290 | 18.82 | 51.418 | 22.768 | 1 | 65.47 |
| 4799 | CD | LYS | B | 1290 | 20.177 | 51.801 | 23.344 | 1 | 68.89 |
| 4800 | CE | LYS | B | 1290 | 21.126 | 52.353 | 22.284 | 1 | 70.03 |

Fig. 1-120

| ATOM | ATOM TYPE | RESIDUE | | # | X | Y | Z | OCC | B |
|---|---|---|---|---|---|---|---|---|---|
| 4801 | NZ | LYS | B | 1290 | 20.585 | 53.559 | 21.593 | 1 | 76.91 |
| 4802 | N | MET | B | 1291 | 15.417 | 49.165 | 25.18 | 1 | 51.73 |
| 4803 | CA | MET | B | 1291 | 14.913 | 47.995 | 25.907 | 1 | 52.36 |
| 4804 | C | MET | B | 1291 | 13.555 | 47.521 | 25.385 | 1 | 51.34 |
| 4805 | O | MET | B | 1291 | 13.272 | 46.327 | 25.372 | 1 | 47.34 |
| 4806 | CB | MET | B | 1291 | 14.802 | 48.255 | 27.416 | 1 | 50.01 |
| 4807 | CG | MET | B | 1291 | 16.095 | 48.612 | 28.097 | 1 | 50.51 |
| 4808 | SD | MET | B | 1291 | 15.987 | 48.458 | 29.879 | 1 | 54.34 |
| 4809 | CE | MET | B | 1291 | 15.499 | 50.088 | 30.376 | 1 | 48.91 |
| 4810 | N | LEU | B | 1292 | 12.729 | 48.454 | 24.928 | 1 | 52.59 |
| 4811 | CA | LEU | B | 1292 | 11.406 | 48.096 | 24.437 | 1 | 51.71 |
| 4812 | C | LEU | B | 1292 | 11.237 | 47.921 | 22.936 | 1 | 51.8 |
| 4813 | O | LEU | B | 1292 | 10.163 | 48.152 | 22.388 | 1 | 53.68 |
| 4814 | CB | LEU | B | 1292 | 10.381 | 49.073 | 24.996 | 1 | 49.81 |
| 4815 | CG | LEU | B | 1292 | 10.265 | 48.902 | 26.507 | 1 | 43.92 |
| 4816 | CD1 | LEU | B | 1292 | 9.328 | 49.934 | 27.07 | 1 | 46.13 |
| 4817 | CD2 | LEU | B | 1292 | 9.758 | 47.485 | 26.802 | 1 | 44.69 |
| 4818 | N | VAL | B | 1293 | 12.3 | 47.506 | 22.268 | 1 | 55.13 |
| 4819 | CA | VAL | B | 1293 | 12.246 | 47.27 | 20.833 | 1 | 55.88 |
| 4820 | C | VAL | B | 1293 | 11.467 | 45.981 | 20.636 | 1 | 57 |
| 4821 | O | VAL | B | 1293 | 11.569 | 45.059 | 21.438 | 1 | 58.7 |
| 4822 | CB | VAL | B | 1293 | 13.646 | 47.169 | 20.231 | 1 | 55.38 |
| 4823 | CG1 | VAL | B | 1293 | 13.602 | 46.431 | 18.91 | 1 | 58.99 |
| 4824 | CG2 | VAL | B | 1293 | 14.212 | 48.584 | 20.023 | 1 | 57.62 |
| 4825 | N | LEU | B | 1294 | 10.659 | 45.948 | 19.586 | 1 | 58.16 |
| 4826 | CA | LEU | B | 1294 | 9.8 | 44.816 | 19.281 | 1 | 57.29 |
| 4827 | C | LEU | B | 1294 | 10.57 | 43.563 | 18.867 | 1 | 58.55 |
| 4828 | O | LEU | B | 1294 | 10.149 | 42.429 | 19.124 | 1 | 56.4 |
| 4829 | CB | LEU | B | 1294 | 8.829 | 45.249 | 18.183 | 1 | 56.93 |
| 4830 | CG | LEU | B | 1294 | 7.611 | 44.35 | 18.02 | 1 | 61.81 |
| 4831 | CD1 | LEU | B | 1294 | 6.749 | 44.437 | 19.261 | 1 | 61.22 |
| 4832 | CD2 | LEU | B | 1294 | 6.837 | 44.756 | 16.796 | 1 | 62.66 |
| 4833 | N | ASP | B | 1295 | 11.704 | 43.808 | 18.22 | 1 | 63.7 |
| 4834 | CA | ASP | B | 1295 | 12.619 | 42.797 | 17.697 | 1 | 66.56 |
| 4835 | C | ASP | B | 1295 | 13.536 | 42.308 | 18.815 | 1 | 66.13 |
| 4836 | O | ASP | B | 1295 | 14.537 | 42.951 | 19.136 | 1 | 66.23 |
| 4837 | CB | ASP | B | 1295 | 13.448 | 43.434 | 16.561 | 1 | 70.74 |
| 4838 | CG | ASP | B | 1295 | 14.362 | 42.437 | 15.839 | 1 | 76.92 |
| 4839 | OD1 | ASP | B | 1295 | 14.219 | 41.198 | 16.033 | 1 | 77.65 |
| 4840 | OD2 | ASP | B | 1295 | 15.225 | 42.916 | 15.056 | 1 | 75.82 |

Fig. 1-121

| ATOM | ATOM TYPE | RESIDUE | | # | X | Y | Z | OCC | B |
|---|---|---|---|---|---|---|---|---|---|
| 4841 | N | ALA | B | 1296 | 13.194 | 41.16 | 19.388 | 1 | 64.53 |
| 4842 | CA | ALA | B | 1296 | 13.966 | 40.569 | 20.471 | 1 | 65.27 |
| 4843 | C | ALA | B | 1296 | 15.479 | 40.597 | 20.257 | 1 | 67.51 |
| 4844 | O | ALA | B | 1296 | 16.221 | 40.839 | 21.202 | 1 | 71.04 |
| 4845 | CB | ALA | B | 1296 | 13.506 | 39.145 | 20.708 | 1 | 66.62 |
| 4846 | N | GLU | B | 1297 | 15.934 | 40.371 | 19.025 | 1 | 68.4 |
| 4847 | CA | GLU | B | 1297 | 17.368 | 40.359 | 18.721 | 1 | 69.59 |
| 4848 | C | GLU | B | 1297 | 18.103 | 41.69 | 18.87 | 1 | 68.8 |
| 4849 | O | GLU | B | 1297 | 19.209 | 41.72 | 19.398 | 1 | 67.73 |
| 4850 | CB | GLU | B | 1297 | 17.614 | 39.789 | 17.322 | 1 | 73.1 |
| 4851 | CG | GLU | B | 1297 | 17.217 | 38.324 | 17.16 | 1 | 76.58 |
| 4852 | CD | GLU | B | 1297 | 18.095 | 37.366 | 17.959 | 1 | 76.43 |
| 4853 | OE1 | GLU | B | 1297 | 19.337 | 37.418 | 17.794 | 1 | 75.95 |
| 4854 | OE2 | GLU | B | 1297 | 17.538 | 36.546 | 18.727 | 1 | 71.42 |
| 4855 | N | GLN | B | 1298 | 17.505 | 42.775 | 18.379 | 1 | 70.63 |
| 4856 | CA | GLN | B | 1298 | 18.113 | 44.116 | 18.461 | 1 | 72.42 |
| 4857 | C | GLN | B | 1298 | 17.933 | 44.715 | 19.854 | 1 | 70.29 |
| 4858 | O | GLN | B | 1298 | 18.52 | 45.757 | 20.182 | 1 | 70.45 |
| 4859 | CB | GLN | B | 1298 | 17.48 | 45.075 | 17.433 | 1 | 79.12 |
| 4860 | CG | GLN | B | 1298 | 17.606 | 44.655 | 15.964 | 1 | 85.31 |
| 4861 | CD | GLN | B | 1298 | 19.047 | 44.532 | 15.513 | 1 | 89.05 |
| 4862 | OE1 | GLN | B | 1298 | 19.427 | 43.561 | 14.839 | 1 | 87.96 |
| 4863 | NE2 | GLN | B | 1298 | 19.867 | 45.514 | 15.895 | 1 | 90.97 |
| 4864 | N | ARG | B | 1299 | 17.105 | 44.053 | 20.66 | 1 | 66.4 |
| 4865 | CA | ARG | B | 1299 | 16.818 | 44.499 | 22.014 | 1 | 62.11 |
| 4866 | C | ARG | B | 1299 | 18.079 | 44.4 | 22.862 | 1 | 61.11 |
| 4867 | O | ARG | B | 1299 | 18.751 | 43.361 | 22.891 | 1 | 61.27 |
| 4868 | CB | ARG | B | 1299 | 15.68 | 43.659 | 22.608 | 1 | 59.93 |
| 4869 | CG | ARG | B | 1299 | 14.971 | 44.296 | 23.803 | 1 | 55.45 |
| 4870 | CD | ARG | B | 1299 | 13.464 | 44.128 | 23.676 | 1 | 52.46 |
| 4871 | NE | ARG | B | 1299 | 13.026 | 42.783 | 23.992 | 1 | 49.75 |
| 4872 | CZ | ARG | B | 1299 | 11.996 | 42.161 | 23.421 | 1 | 45.3 |
| 4873 | NH1 | ARG | B | 1299 | 11.271 | 42.735 | 22.485 | 1 | 37.8 |
| 4874 | NH2 | ARG | B | 1299 | 11.696 | 40.946 | 23.803 | 1 | 43.43 |
| 4875 | N | VAL | B | 1300 | 18.398 | 45.499 | 23.536 | 1 | 60.09 |
| 4876 | CA | VAL | B | 1300 | 19.58 | 45.586 | 24.386 | 1 | 58.37 |
| 4877 | C | VAL | B | 1300 | 19.643 | 44.438 | 25.406 | 1 | 58.5 |
| 4878 | O | VAL | B | 1300 | 18.621 | 43.846 | 25.757 | 1 | 59.18 |
| 4879 | CB | VAL | B | 1300 | 19.605 | 46.968 | 25.107 | 1 | 56.62 |
| 4880 | CG1 | VAL | B | 1300 | 19.034 | 46.87 | 26.499 | 1 | 54.15 |

Fig. 1-122

| ATOM | ATOM TYPE | RESIDUE | | # | X | Y | Z | OCC | B |
|---|---|---|---|---|---|---|---|---|---|
| 4881 | CG2 | VAL | B | 1300 | 20.993 | 47.551 | 25.108 | 1 | 53.94 |
| 4882 | N | THR | B | 1301 | 20.85 | 44.067 | 25.815 | 1 | 59.53 |
| 4883 | CA | THR | B | 1301 | 21.01 | 43.014 | 26.818 | 1 | 58.64 |
| 4884 | C | THR | B | 1301 | 21.31 | 43.714 | 28.126 | 1 | 58.82 |
| 4885 | O | THR | B | 1301 | 21.614 | 44.91 | 28.139 | 1 | 57.1 |
| 4886 | CB | THR | B | 1301 | 22.189 | 42.052 | 26.521 | 1 | 57.11 |
| 4887 | OG1 | THR | B | 1301 | 23.422 | 42.782 | 26.547 | 1 | 55.86 |
| 4888 | CG2 | THR | B | 1301 | 22.005 | 41.354 | 25.178 | 1 | 49.79 |
| 4889 | N | ALA | B | 1302 | 21.24 | 42.96 | 29.219 | 1 | 58.97 |
| 4890 | CA | ALA | B | 1302 | 21.511 | 43.505 | 30.539 | 1 | 57.86 |
| 4891 | C | ALA | B | 1302 | 22.907 | 44.107 | 30.567 | 1 | 56.43 |
| 4892 | O | ALA | B | 1302 | 23.107 | 45.202 | 31.101 | 1 | 55.91 |
| 4893 | CB | ALA | B | 1302 | 21.373 | 42.424 | 31.581 | 1 | 58.03 |
| 4894 | N | GLY | B | 1303 | 23.859 | 43.391 | 29.966 | 1 | 57.56 |
| 4895 | CA | GLY | B | 1303 | 25.227 | 43.876 | 29.903 | 1 | 59.47 |
| 4896 | C | GLY | B | 1303 | 25.273 | 45.219 | 29.187 | 1 | 60.75 |
| 4897 | O | GLY | B | 1303 | 25.758 | 46.226 | 29.735 | 1 | 60.75 |
| 4898 | N | GLU | B | 1304 | 24.715 | 45.234 | 27.975 | 1 | 59.98 |
| 4899 | CA | GLU | B | 1304 | 24.659 | 46.435 | 27.148 | 1 | 60.78 |
| 4900 | C | GLU | B | 1304 | 23.889 | 47.531 | 27.873 | 1 | 58.84 |
| 4901 | O | GLU | B | 1304 | 24.313 | 48.686 | 27.896 | 1 | 60.91 |
| 4902 | CB | GLU | B | 1304 | 23.983 | 46.143 | 25.807 | 1 | 63.53 |
| 4903 | CG | GLU | B | 1304 | 24.674 | 45.123 | 24.904 | 1 | 67.68 |
| 4904 | CD | GLU | B | 1304 | 23.878 | 44.845 | 23.621 | 1 | 74.21 |
| 4905 | OE1 | GLU | B | 1304 | 23.297 | 45.802 | 23.05 | 1 | 78.48 |
| 4906 | OE2 | GLU | B | 1304 | 23.831 | 43.674 | 23.177 | 1 | 74.31 |
| 4907 | N | ALA | B | 1305 | 22.773 | 47.147 | 28.486 | 1 | 56.09 |
| 4908 | CA | ALA | B | 1305 | 21.921 | 48.063 | 29.231 | 1 | 53.83 |
| 4909 | C | ALA | B | 1305 | 22.731 | 48.843 | 30.253 | 1 | 54.47 |
| 4910 | O | ALA | B | 1305 | 22.653 | 50.072 | 30.317 | 1 | 55.75 |
| 4911 | CB | ALA | B | 1305 | 20.822 | 47.292 | 29.924 | 1 | 51.36 |
| 4912 | N | LEU | B | 1306 | 23.529 | 48.123 | 31.033 | 1 | 54.84 |
| 4913 | CA | LEU | B | 1306 | 24.37 | 48.724 | 32.065 | 1 | 55.91 |
| 4914 | C | LEU | B | 1306 | 25.407 | 49.67 | 31.476 | 1 | 59.33 |
| 4915 | O | LEU | B | 1306 | 25.729 | 50.704 | 32.068 | 1 | 61.01 |
| 4916 | CB | LEU | B | 1306 | 25.084 | 47.621 | 32.833 | 1 | 53 |
| 4917 | CG | LEU | B | 1306 | 24.24 | 46.747 | 33.754 | 1 | 47.56 |
| 4918 | CD1 | LEU | B | 1306 | 25.057 | 45.571 | 34.216 | 1 | 43.12 |
| 4919 | CD2 | LEU | B | 1306 | 23.776 | 47.565 | 34.943 | 1 | 48.23 |
| 4920 | N | ALA | B | 1307 | 25.927 | 49.297 | 30.307 | 1 | 63.38 |

Fig. 1-123

| ATOM | ATOM TYPE | RESIDUE | | # | X | Y | Z | OCC | B |
|---|---|---|---|---|---|---|---|---|---|
| 4921 | CA | ALA | B | 1307 | 26.931 | 50.088 | 29.584 | 1 | 64.24 |
| 4922 | C | ALA | B | 1307 | 26.412 | 51.429 | 29.027 | 1 | 63.84 |
| 4923 | O | ALA | B | 1307 | 27.211 | 52.28 | 28.623 | 1 | 66.62 |
| 4924 | CB | ALA | B | 1307 | 27.526 | 49.257 | 28.454 | 1 | 59.56 |
| 4925 | N | HIS | B | 1308 | 25.092 | 51.624 | 29.048 | 1 | 59.56 |
| 4926 | CA | HIS | B | 1308 | 24.463 | 52.835 | 28.529 | 1 | 56.83 |
| 4927 | C | HIS | B | 1308 | 24.811 | 54.127 | 29.284 | 1 | 58.09 |
| 4928 | O | HIS | B | 1308 | 25.02 | 54.121 | 30.493 | 1 | 61.2 |
| 4929 | CB | HIS | B | 1308 | 22.956 | 52.629 | 28.496 | 1 | 51.82 |
| 4930 | CG | HIS | B | 1308 | 22.22 | 53.628 | 27.662 | 1 | 46.18 |
| 4931 | ND1 | HIS | B | 1308 | 21.771 | 54.831 | 28.166 | 1 | 47.87 |
| 4932 | CD2 | HIS | B | 1308 | 21.809 | 53.58 | 26.373 | 1 | 37.9 |
| 4933 | CE1 | HIS | B | 1308 | 21.107 | 55.478 | 27.225 | 1 | 43.09 |
| 4934 | NE2 | HIS | B | 1308 | 21.114 | 54.74 | 26.129 | 1 | 40.01 |
| 4935 | N | PRO | B | 1309 | 24.883 | 55.256 | 28.569 | 1 | 59.7 |
| 4936 | CA | PRO | B | 1309 | 25.204 | 56.551 | 29.174 | 1 | 62.3 |
| 4937 | C | PRO | B | 1309 | 24.259 | 56.996 | 30.293 | 1 | 63.3 |
| 4938 | O | PRO | B | 1309 | 24.533 | 57.997 | 30.974 | 1 | 64.91 |
| 4939 | CB | PRO | B | 1309 | 25.121 | 57.506 | 27.983 | 1 | 63.19 |
| 4940 | CG | PRO | B | 1309 | 25.583 | 56.652 | 26.85 | 1 | 62.09 |
| 4941 | CD | PRO | B | 1309 | 24.82 | 55.377 | 27.102 | 1 | 61.18 |
| 4942 | N | TYR | B | 1310 | 23.134 | 56.294 | 30.45 | 1 | 61.17 |
| 4943 | CA | TYR | B | 1310 | 22.159 | 56.628 | 31.493 | 1 | 61.55 |
| 4944 | C | TYR | B | 1310 | 22.755 | 56.314 | 32.864 | 1 | 61.07 |
| 4945 | O | TYR | B | 1310 | 22.593 | 57.071 | 33.826 | 1 | 57.44 |
| 4946 | CB | TYR | B | 1310 | 20.858 | 55.826 | 31.288 | 1 | 59.61 |
| 4947 | CG | TYR | B | 1310 | 19.801 | 56.056 | 32.356 | 1 | 59.47 |
| 4948 | CD1 | TYR | B | 1310 | 19.282 | 57.337 | 32.593 | 1 | 58.59 |
| 4949 | CD2 | TYR | B | 1310 | 19.316 | 54.994 | 33.134 | 1 | 58.93 |
| 4950 | CE1 | TYR | B | 1310 | 18.308 | 57.558 | 33.568 | 1 | 56.43 |
| 4951 | CE2 | TYR | B | 1310 | 18.335 | 55.205 | 34.121 | 1 | 58.02 |
| 4952 | CZ | TYR | B | 1310 | 17.836 | 56.496 | 34.325 | 1 | 57.9 |
| 4953 | OH | TYR | B | 1310 | 16.855 | 56.74 | 35.261 | 1 | 55.83 |
| 4954 | N | PHE | B | 1311 | 23.487 | 55.207 | 32.907 | 1 | 63.08 |
| 4955 | CA | PHE | B | 1311 | 24.122 | 54.708 | 34.118 | 1 | 68.47 |
| 4956 | C | PHE | B | 1311 | 25.569 | 55.196 | 34.253 | 1 | 72.32 |
| 4957 | O | PHE | B | 1311 | 26.386 | 54.571 | 34.935 | 1 | 73.06 |
| 4958 | CB | PHE | B | 1311 | 24.077 | 53.169 | 34.112 | 1 | 64.71 |
| 4959 | CG | PHE | B | 1311 | 22.681 | 52.593 | 33.984 | 1 | 59.83 |
| 4960 | CD1 | PHE | B | 1311 | 21.689 | 52.918 | 34.9 | 1 | 58.99 |

Fig. 1-124

| ATOM | ATOM TYPE | RESIDUE | | # | X | Y | Z | OCC | B |
|---|---|---|---|---|---|---|---|---|---|
| 4961 | CD2 | PHE | B | 1311 | 22.364 | 51.739 | 32.941 | 1 | 58.65 |
| 4962 | CE1 | PHE | B | 1311 | 20.408 | 52.4 | 34.77 | 1 | 59.47 |
| 4963 | CE2 | PHE | B | 1311 | 21.079 | 51.218 | 32.809 | 1 | 57.68 |
| 4964 | CZ | PHE | B | 1311 | 20.104 | 51.547 | 33.719 | 1 | 54.46 |
| 4965 | N | GLU | B | 1312 | 25.856 | 56.339 | 33.634 | 1 | 76.5 |
| 4966 | CA | GLU | B | 1312 | 27.19 | 56.949 | 33.632 | 1 | 78.82 |
| 4967 | C | GLU | B | 1312 | 27.778 | 57.181 | 35.025 | 1 | 75.94 |
| 4968 | O | GLU | B | 1312 | 28.882 | 56.731 | 35.313 | 1 | 75.3 |
| 4969 | CB | GLU | B | 1312 | 27.141 | 58.278 | 32.855 | 1 | 85.41 |
| 4970 | CG | GLU | B | 1312 | 28.489 | 58.984 | 32.646 | 1 | 89.87 |
| 4971 | CD | GLU | B | 1312 | 28.337 | 60.388 | 32.051 | 1 | 93.07 |
| 4972 | OE1 | GLU | B | 1312 | 27.635 | 61.234 | 32.66 | 1 | 95.02 |
| 4973 | OE2 | GLU | B | 1312 | 28.931 | 60.649 | 30.978 | 1 | 94.03 |
| 4974 | N | SER | B | 1313 | 27.024 | 57.865 | 35.879 | 1 | 73.48 |
| 4975 | CA | SER | B | 1313 | 27.465 | 58.175 | 37.231 | 1 | 73.98 |
| 4976 | C | SER | B | 1313 | 27.536 | 56.974 | 38.174 | 1 | 73.7 |
| 4977 | O | SER | B | 1313 | 27.809 | 57.13 | 39.366 | 1 | 73.28 |
| 4978 | CB | SER | B | 1313 | 26.566 | 59.255 | 37.847 | 1 | 73.88 |
| 4979 | OG | SER | B | 1313 | 25.26 | 58.767 | 38.084 | 1 | 72.13 |
| 4980 | N | LEU | B | 1314 | 27.319 | 55.778 | 37.645 | 1 | 73.19 |
| 4981 | CA | LEU | B | 1314 | 27.349 | 54.587 | 38.48 | 1 | 75.67 |
| 4982 | C | LEU | B | 1314 | 28.277 | 53.491 | 37.948 | 1 | 78.49 |
| 4983 | O | LEU | B | 1314 | 28.727 | 52.636 | 38.714 | 1 | 78.97 |
| 4984 | CB | LEU | B | 1314 | 25.927 | 54.029 | 38.649 | 1 | 74.26 |
| 4985 | CG | LEU | B | 1314 | 24.789 | 54.937 | 39.148 | 1 | 71.09 |
| 4986 | CD1 | LEU | B | 1314 | 23.467 | 54.208 | 39.035 | 1 | 69.07 |
| 4987 | CD2 | LEU | B | 1314 | 25.023 | 55.378 | 40.575 | 1 | 69.89 |
| 4988 | N | HIS | B | 1315 | 28.584 | 53.548 | 36.649 | 1 | 81.55 |
| 4989 | CA | HIS | B | 1315 | 29.439 | 52.566 | 35.954 | 1 | 83.48 |
| 4990 | C | HIS | B | 1315 | 30.811 | 52.231 | 36.586 | 1 | 84.56 |
| 4991 | O | HIS | B | 1315 | 31.324 | 53.047 | 37.389 | 1 | 84.58 |
| 4992 | CB | HIS | B | 1315 | 29.614 | 52.982 | 34.475 | 1 | 81.89 |
| 4993 | OXT | HIS | B | 1315 | 31.364 | 51.146 | 36.262 | 1 | 83.36 |
| 4994 | N | GLN | B | 1322 | 33.191 | 37.322 | 36.761 | 1 | 90.82 |
| 4995 | CA | GLN | B | 1322 | 32.735 | 36.168 | 35.923 | 1 | 92.08 |
| 4996 | C | GLN | B | 1322 | 31.847 | 35.232 | 36.756 | 1 | 92.21 |
| 4997 | O | GLN | B | 1322 | 32.034 | 35.123 | 37.983 | 1 | 91.78 |
| 4998 | CB | GLN | B | 1322 | 33.94 | 35.411 | 35.358 | 1 | 93.05 |
| 4999 | N | VAL | B | 1323 | 30.899 | 34.552 | 36.095 | 1 | 88.96 |
| 5000 | CA | VAL | B | 1323 | 29.961 | 33.665 | 36.799 | 1 | 86.14 |

Fig. 1-125

| ATOM | ATOM TYPE | RESIDUE | | # | X | Y | Z | OCC | B |
|---|---|---|---|---|---|---|---|---|---|
| 5001 | C | VAL | B | 1323 | 29.865 | 32.199 | 36.37 | 1 | 84.66 |
| 5002 | O | VAL | B | 1323 | 30.009 | 31.846 | 35.192 | 1 | 81.99 |
| 5003 | CB | VAL | B | 1323 | 28.518 | 34.243 | 36.817 | 1 | 83.7 |
| 5004 | CG1 | VAL | B | 1323 | 28.536 | 35.737 | 37.113 | 1 | 81.83 |
| 5005 | CG2 | VAL | B | 1323 | 27.823 | 33.958 | 35.518 | 1 | 81.75 |
| 5006 | N | GLN | B | 1324 | 29.532 | 31.37 | 37.356 | 1 | 83.53 |
| 5007 | CA | GLN | B | 1324 | 29.385 | 29.931 | 37.181 | 1 | 83.72 |
| 5008 | C | GLN | B | 1324 | 27.998 | 29.582 | 36.675 | 1 | 81.62 |
| 5009 | O | GLN | B | 1324 | 27.004 | 29.778 | 37.378 | 1 | 78.62 |
| 5010 | CB | GLN | B | 1324 | 29.655 | 29.202 | 38.512 | 1 | 84.79 |
| 5011 | N | LYS | B | 1325 | 27.944 | 29.042 | 35.462 | 1 | 80.82 |
| 5012 | CA | LYS | B | 1325 | 26.677 | 28.653 | 34.861 | 1 | 80.84 |
| 5013 | C | LYS | B | 1325 | 25.979 | 27.572 | 35.674 | 1 | 80.58 |
| 5014 | O | LYS | B | 1325 | 26.62 | 26.65 | 36.176 | 1 | 83.59 |
| 5015 | CB | LYS | B | 1325 | 26.882 | 28.177 | 33.419 | 1 | 79.07 |
| 5016 | CG | LYS | B | 1325 | 27.298 | 29.284 | 32.451 | 1 | 79.16 |
| 5017 | CD | LYS | B | 1325 | 26.965 | 28.902 | 31.021 | 1 | 78.85 |
| 5018 | CE | LYS | B | 1325 | 25.514 | 28.446 | 30.922 | 1 | 78.35 |
| 5019 | NZ | LYS | B | 1325 | 25.086 | 28.186 | 29.521 | 1 | 82.1 |
| 5020 | N | TYR | B | 1326 | 24.674 | 27.729 | 35.858 | 1 | 79.6 |
| 5021 | CA | TYR | B | 1326 | 23.875 | 26.758 | 36.595 | 1 | 80.04 |
| 5022 | C | TYR | B | 1326 | 23.767 | 25.487 | 35.733 | 1 | 83.83 |
| 5023 | O | TYR | B | 1326 | 23.733 | 25.566 | 34.51 | 1 | 84.12 |
| 5024 | CB | TYR | B | 1326 | 22.503 | 27.365 | 36.888 | 1 | 74.1 |
| 5025 | CG | TYR | B | 1326 | 21.487 | 26.414 | 37.458 | 1 | 69.26 |
| 5026 | CD1 | TYR | B | 1326 | 21.497 | 26.071 | 38.803 | 1 | 69.12 |
| 5027 | CD2 | TYR | B | 1326 | 20.505 | 25.859 | 36.648 | 1 | 69.77 |
| 5028 | CE1 | TYR | B | 1326 | 20.547 | 25.193 | 39.328 | 1 | 69.52 |
| 5029 | CE2 | TYR | B | 1326 | 19.555 | 24.983 | 37.158 | 1 | 70.51 |
| 5030 | CZ | TYR | B | 1326 | 19.579 | 24.653 | 38.495 | 1 | 69.18 |
| 5031 | OH | TYR | B | 1326 | 18.632 | 23.778 | 38.979 | 1 | 71.04 |
| 5032 | N | ASP | B | 1327 | 23.743 | 24.32 | 36.37 | 1 | 88.48 |
| 5033 | CA | ASP | B | 1327 | 23.666 | 23.045 | 35.652 | 1 | 93.54 |
| 5034 | C | ASP | B | 1327 | 22.555 | 22.174 | 36.255 | 1 | 95.72 |
| 5035 | O | ASP | B | 1327 | 22.144 | 22.427 | 37.384 | 1 | 99.03 |
| 5036 | CB | ASP | B | 1327 | 25.02 | 22.339 | 35.782 | 1 | 96.66 |
| 5037 | CG | ASP | B | 1327 | 25.209 | 21.237 | 34.763 | 1 | 100 |
| 5038 | OD1 | ASP | B | 1327 | 25.101 | 21.532 | 33.541 | 1 | 99.85 |
| 5039 | OD2 | ASP | B | 1327 | 25.476 | 20.085 | 35.194 | 1 | 100 |
| 5040 | N | ASP | B | 1328 | 22.078 | 21.151 | 35.538 | 1 | 97.29 |

Fig. 1-126

| ATOM | ATOM TYPE | RESIDUE | | # | X | Y | Z | OCC | B |
|---|---|---|---|---|---|---|---|---|---|
| 5041 | CA | ASP | B | 1328 | 21.011 | 20.297 | 36.091 | 1 | 99.52 |
| 5042 | C | ASP | B | 1328 | 20.601 | 19.033 | 35.302 | 1 | 100 |
| 5043 | O | ASP | B | 1328 | 21.098 | 18.754 | 34.202 | 1 | 100 |
| 5044 | CB | ASP | B | 1328 | 19.756 | 21.159 | 36.369 | 1 | 100 |
| 5045 | CG | ASP | B | 1328 | 18.714 | 20.449 | 37.238 | 1 | 100 |
| 5046 | OD1 | ASP | B | 1328 | 19.012 | 20.156 | 38.417 | 1 | 98.29 |
| 5047 | OD2 | ASP | B | 1328 | 17.596 | 20.184 | 36.732 | 1 | 100 |
| 5048 | N | SER | B | 1329 | 19.709 | 18.263 | 35.934 | 1 | 100 |
| 5049 | CA | SER | B | 1329 | 19.116 | 17.033 | 35.405 | 1 | 99.65 |
| 5050 | C | SER | B | 1329 | 17.759 | 16.801 | 36.127 | 1 | 99.45 |
| 5051 | O | SER | B | 1329 | 17.721 | 16.19 | 37.218 | 1 | 98.29 |
| 5052 | CB | SER | B | 1329 | 20.074 | 15.831 | 35.571 | 1 | 97.33 |
| 5053 | OG | SER | B | 1329 | 20.4 | 15.573 | 36.927 | 1 | 93.65 |
| 5054 | OXT | SER | B | 1329 | 16.732 | 17.304 | 35.617 | 1 | 98.81 |
| 5055 | N | ARG | B | 1335 | 9.439 | 13.254 | 34.69 | 1 | 95.6 |
| 5056 | CA | ARG | B | 1335 | 9.514 | 12.74 | 36.088 | 1 | 96.62 |
| 5057 | C | ARG | B | 1335 | 8.129 | 12.68 | 36.737 | 1 | 97.23 |
| 5058 | O | ARG | B | 1335 | 7.254 | 13.488 | 36.417 | 1 | 96.98 |
| 5059 | CB | ARG | B | 1335 | 10.457 | 13.618 | 36.918 | 1 | 96.54 |
| 5060 | N | THR | B | 1336 | 7.936 | 11.716 | 37.641 | 1 | 98.37 |
| 5061 | CA | THR | B | 1336 | 6.656 | 11.537 | 38.35 | 1 | 99.77 |
| 5062 | C | THR | B | 1336 | 6.471 | 12.546 | 39.496 | 1 | 99.59 |
| 5063 | O | THR | B | 1336 | 7.422 | 13.227 | 39.882 | 1 | 100 |
| 5064 | CB | THR | B | 1336 | 6.501 | 10.079 | 38.92 | 1 | 100 |
| 5065 | OG1 | THR | B | 1336 | 7.503 | 9.824 | 39.912 | 1 | 98.6 |
| 5066 | CG2 | THR | B | 1336 | 6.634 | 9.038 | 37.808 | 1 | 100 |
| 5067 | N | LEU | B | 1337 | 5.249 | 12.652 | 40.024 | 1 | 98.78 |
| 5068 | CA | LEU | B | 1337 | 4.969 | 13.572 | 41.129 | 1 | 99.13 |
| 5069 | C | LEU | B | 1337 | 5.873 | 13.21 | 42.305 | 1 | 100 |
| 5070 | O | LEU | B | 1337 | 6.419 | 14.088 | 42.98 | 1 | 100 |
| 5071 | CB | LEU | B | 1337 | 3.496 | 13.495 | 41.544 | 1 | 97.48 |
| 5072 | N | ASP | B | 1338 | 6.063 | 11.908 | 42.508 | 1 | 100 |
| 5073 | CA | ASP | B | 1338 | 6.913 | 11.406 | 43.581 | 1 | 100 |
| 5074 | C | ASP | B | 1338 | 8.407 | 11.557 | 43.303 | 1 | 100 |
| 5075 | O | ASP | B | 1338 | 9.218 | 11.46 | 44.228 | 1 | 100 |
| 5076 | CB | ASP | B | 1338 | 6.574 | 9.951 | 43.899 | 1 | 100 |
| 5077 | CG | ASP | B | 1338 | 5.329 | 9.821 | 44.747 | 1 | 100 |
| 5078 | OD1 | ASP | B | 1338 | 4.407 | 10.659 | 44.592 | 1 | 100 |
| 5079 | OD2 | ASP | B | 1338 | 5.284 | 8.886 | 45.578 | 1 | 100 |
| 5080 | N | GLU | B | 1339 | 8.772 | 11.755 | 42.035 | 1 | 99.94 |

Fig. 1-127

| ATOM | ATOM TYPE | RESIDUE | | # | X | Y | Z | OCC | B |
|---|---|---|---|---|---|---|---|---|---|
| 5081 | CA | GLU | B | 1339 | 10.175 | 11.954 | 41.666 | 1 | 99.4 |
| 5082 | C | GLU | B | 1339 | 10.56 | 13.395 | 41.989 | 1 | 98.48 |
| 5083 | O | GLU | B | 1339 | 11.644 | 13.653 | 42.516 | 1 | 99.33 |
| 5084 | CB | GLU | B | 1339 | 10.416 | 11.645 | 40.182 | 1 | 99.75 |
| 5085 | CG | GLU | B | 1339 | 10.657 | 10.158 | 39.893 | 1 | 100 |
| 5086 | CD | GLU | B | 1339 | 10.823 | 9.844 | 38.409 | 1 | 100 |
| 5087 | OE1 | GLU | B | 1339 | 11.768 | 10.374 | 37.783 | 1 | 99.61 |
| 5088 | OE2 | GLU | B | 1339 | 10.014 | 9.054 | 37.873 | 1 | 100 |
| 5089 | N | TRP | B | 1340 | 9.651 | 14.324 | 41.697 | 1 | 96.8 |
| 5090 | CA | TRP | B | 1340 | 9.871 | 15.739 | 41.978 | 1 | 94.77 |
| 5091 | C | TRP | B | 1340 | 9.93 | 15.935 | 43.487 | 1 | 94.28 |
| 5092 | O | TRP | B | 1340 | 10.818 | 16.611 | 44.003 | 1 | 94.83 |
| 5093 | CB | TRP | B | 1340 | 8.738 | 16.594 | 41.398 | 1 | 91.56 |
| 5094 | CG | TRP | B | 1340 | 8.822 | 16.805 | 39.923 | 1 | 87.42 |
| 5095 | CD1 | TRP | B | 1340 | 7.96 | 16.335 | 38.983 | 1 | 86.35 |
| 5096 | CD2 | TRP | B | 1340 | 9.828 | 17.541 | 39.214 | 1 | 85.91 |
| 5097 | NE1 | TRP | B | 1340 | 8.364 | 16.728 | 37.73 | 1 | 85.95 |
| 5098 | CE2 | TRP | B | 1340 | 9.509 | 17.47 | 37.844 | 1 | 84.93 |
| 5099 | CE3 | TRP | B | 1340 | 10.972 | 18.251 | 39.607 | 1 | 85.21 |
| 5100 | CZ2 | TRP | B | 1340 | 10.291 | 18.083 | 36.856 | 1 | 83.82 |
| 5101 | CZ3 | TRP | B | 1340 | 11.751 | 18.86 | 38.622 | 1 | 84.21 |
| 5102 | CH2 | TRP | B | 1340 | 11.404 | 18.77 | 37.263 | 1 | 82.56 |
| 5103 | N | LYS | B | 1341 | 8.979 | 15.316 | 44.179 | 1 | 93.1 |
| 5104 | CA | LYS | B | 1341 | 8.87 | 15.378 | 45.633 | 1 | 91.46 |
| 5105 | C | LYS | B | 1341 | 10.155 | 14.868 | 46.29 | 1 | 90.23 |
| 5106 | O | LYS | B | 1341 | 10.673 | 15.49 | 47.22 | 1 | 89.13 |
| 5107 | CB | LYS | B | 1341 | 7.666 | 14.536 | 46.063 | 1 | 91.94 |
| 5108 | CG | LYS | B | 1341 | 7.238 | 14.636 | 47.513 | 1 | 92.72 |
| 5109 | CD | LYS | B | 1341 | 5.889 | 13.929 | 47.68 | 1 | 95.18 |
| 5110 | CE | LYS | B | 1341 | 5.456 | 13.808 | 49.135 | 1 | 96.47 |
| 5111 | NZ | LYS | B | 1341 | 4.096 | 13.201 | 49.263 | 1 | 95.26 |
| 5112 | N | ARG | B | 1342 | 10.687 | 13.767 | 45.76 | 1 | 90.08 |
| 5113 | CA | ARG | B | 1342 | 11.915 | 13.156 | 46.272 | 1 | 89.34 |
| 5114 | C | ARG | B | 1342 | 13.148 | 13.988 | 45.925 | 1 | 87.69 |
| 5115 | O | ARG | B | 1342 | 13.983 | 14.255 | 46.795 | 1 | 88.78 |
| 5116 | CB | ARG | B | 1342 | 12.072 | 11.721 | 45.738 | 1 | 89.2 |
| 5117 | N | VAL | B | 1343 | 13.266 | 14.38 | 44.656 | 1 | 84.09 |
| 5118 | CA | VAL | B | 1343 | 14.393 | 15.189 | 44.203 | 1 | 82.03 |
| 5119 | C | VAL | B | 1343 | 14.44 | 16.494 | 45.012 | 1 | 82.27 |
| 5120 | O | VAL | B | 1343 | 15.516 | 16.973 | 45.378 | 1 | 82.21 |

Fig. 1-128

| ATOM | ATOM TYPE | RESIDUE | | # | X | Y | Z | OCC | B |
|---|---|---|---|---|---|---|---|---|---|
| 5121 | CB | VAL | B | 1343 | 14.264 | 15.485 | 42.71 | 1 | 79.36 |
| 5122 | N | THR | B | 1344 | 13.259 | 17.03 4 | 5.325 | 1 | 80.68 |
| 5123 | CA | THR | B | 1344 | 13.123 | 18.265 | 46.093 | 1 | 78.06 |
| 5124 | C | THR | B | 1344 | 13.556 | 18.059 | 47.538 | 1 | 77.6 |
| 5125 | O | THR | B | 1344 | 14.425 | 18.784 | 48.038 | 1 | 76.34 |
| 5126 | CB | THR | B | 1344 | 11.663 | 18.788 | 46.06 | 1 | 75.74 |
| 5127 | OG1 | THR | B | 1344 | 11.321 | 19.15 | 44.72 | 1 | 74.27 |
| 5128 | CG2 | THR | B | 1344 | 11.495 | 20 | 46.954 | 1 | 74.75 |
| 5129 | N | TYR | B | 1345 | 12.952 | 17.064 | 48.191 | 1 | 77 |
| 5130 | CA | TYR | B | 1345 | 13.249 | 16.731 | 49.587 | 1 | 76.12 |
| 5131 | C | TYR | B | 1345 | 14.75 | 16.655 | 49.815 | 1 | 74.18 |
| 5132 | O | TYR | B | 1345 | 15.251 | 17.135 | 50.826 | 1 | 74.4 |
| 5133 | CB | TYR | B | 1345 | 12.598 | 15.396 | 49.96 | 1 | 78.36 |
| 5134 | CG | TYR | B | 1345 | 12.65 | 15.062 | 51.434 | 1 | 80.34 |
| 5135 | CD1 | TYR | B | 1345 | 12.062 | 15.902 | 52.379 | 1 | 81.68 |
| 5136 | CD2 | TYR | B | 1345 | 13.29 | 13.905 | 51.888 | 1 | 80.51 |
| 5137 | CE1 | TYR | B | 1345 | 12.111 | 15.602 | 53.744 | 1 | 83.58 |
| 5138 | CE2 | TYR | B | 1345 | 13.345 | 13.596 | 53.25 | 1 | 80.89 |
| 5139 | CZ | TYR | B | 1345 | 12.756 | 14.449 | 54.171 | 1 | 83.44 |
| 5140 | OH | TYR | B | 1345 | 12.828 | 14.173 | 55.523 | 1 | 86.8 |
| 5141 | N | LYS | B | 1346 | 15.459 | 16.079 | 48.848 | 1 | 73.97 |
| 5142 | CA | LYS | B | 1346 | 16.911 | 15.946 | 48.91 | 1 | 74.77 |
| 5143 | C | LYS | B | 1346 | 17.6 | 17.321 | 48.909 | 1 | 75.13 |
| 5144 | O | LYS | B | 1346 | 18.493 | 17.577 | 49.721 | 1 | 75.76 |
| 5145 | CB | LYS | B | 1346 | 17.415 | 15.078 | 47.744 | 1 | 72.36 |
| 5146 | N | GLU | B | 1347 | 17.159 | 18.213 | 48.021 | 1 | 75.84 |
| 5147 | CA | GLU | B | 1347 | 17.735 | 19.554 | 47.933 | 1 | 74.51 |
| 5148 | C | GLU | B | 1347 | 17.389 | 20.398 | 49.158 | 1 | 73.98 |
| 5149 | O | GLU | B | 1347 | 18.054 | 21.397 | 49.434 | 1 | 74.18 |
| 5150 | CB | GLU | B | 1347 | 17.285 | 20.262 | 46.647 | 1 | 72.61 |
| 5151 | CG | GLU | B | 1347 | 17.941 | 19.744 | 45.353 | 1 | 73.15 |
| 5152 | CD | GLU | B | 1347 | 19.427 | 20.115 | 45.208 | 1 | 76.28 |
| 5153 | OE1 | GLU | B | 1347 | 19.819 | 21.264 | 45.541 | 1 | 74.83 |
| 5154 | OE2 | GLU | B | 1347 | 20.205 | 19.257 | 44.728 | 1 | 76.09 |
| 5155 | N | VAL | B | 1348 | 16.355 | 19.993 | 49.892 | 1 | 73.02 |
| 5156 | CA | VAL | B | 1348 | 15.95 | 20.723 | 51.091 | 1 | 73.71 |
| 5157 | C | VAL | B | 1348 | 16.856 | 20.339 | 52.261 | 1 | 75.29 |
| 5158 | O | VAL | B | 1348 | 17.356 | 21.203 | 52.991 | 1 | 75.92 |
| 5159 | CB | VAL | B | 1348 | 14.472 | 20.438 | 51.483 | 1 | 72.39 |
| 5160 | CG1 | VAL | B | 1348 | 14.107 | 21.195 | 52.742 | 1 | 70.67 |

Fig. 1-129

| ATOM | ATOM TYPE | RESIDUE | | # | X | Y | Z | OCC | B |
|---|---|---|---|---|---|---|---|---|---|
| 5161 | CG2 | VAL | B | 1348 | 13.529 | 20.85 | 50.368 | 1 | 72.79 |
| 5162 | N | LEU | B | 1349 | 17.089 | 19.039 | 52.413 | 1 | 75.21 |
| 5163 | CA | LEU | B | 1349 | 17.923 | 18.534 | 53.499 | 1 | 73.36 |
| 5164 | C | LEU | B | 1349 | 19.406 | 18.823 | 53.318 | 1 | 71.93 |
| 5165 | O | LEU | B | 1349 | 20.148 | 18.903 | 54.301 | 1 | 72.07 |
| 5166 | CB | LEU | B | 1349 | 17.7 | 17.032 | 53.682 | 1 | 73.5 |
| 5167 | CG | LEU | B | 1349 | 16.258 | 16.621 | 54.005 | 1 | 76.3 |
| 5168 | CD1 | LEU | B | 1349 | 16.22 | 15.128 | 54.292 | 1 | 75.07 |
| 5169 | CD2 | LEU | B | 1349 | 15.709 | 17.419 | 55.203 | 1 | 74.88 |
| 5170 | N | SER | B | 1350 | 19.835 | 18.987 | 52.069 | 1 | 69.7 |
| 5171 | CA | SER | B | 1350 | 21.241 | 19.257 | 51.775 | 1 | 69.38 |
| 5172 | C | SER | B | 1350 | 21.628 | 20.733 | 51.914 | 1 | 69.94 |
| 5173 | O | SER | B | 1350 | 22.752 | 21.125 | 51.583 | 1 | 68.66 |
| 5174 | CB | SER | B | 1350 | 21.617 | 18.731 | 50.374 | 1 | 69.35 |
| 5175 | OG | SER | B | 1350 | 20.938 | 19.402 | 49.322 | 1 | 68.19 |
| 5176 | N | PHE | B | 1351 | 20.718 | 21.543 | 52.444 | 1 | 68.17 |
| 5177 | CA | PHE | B | 1351 | 21.006 | 22.955 | 52.584 | 1 | 69.97 |
| 5178 | C | PHE | B | 1351 | 21.881 | 23.323 | 53.769 | 1 | 71.08 |
| 5179 | O | PHE | B | 1351 | 21.565 | 22.995 | 54.909 | 1 | 72.12 |
| 5180 | CB | PHE | B | 1351 | 19.719 | 23.758 | 52.664 | 1 | 69.27 |
| 5181 | CG | PHE | B | 1351 | 19.941 | 25.246 | 52.675 | 1 | 67.44 |
| 5182 | CD1 | PHE | B | 1351 | 20.399 | 25.902 | 51.535 | 1 | 68.6 |
| 5183 | CD2 | PHE | B | 1351 | 19.72 | 25.984 | 53.826 | 1 | 65.72 |
| 5184 | CE1 | PHE | B | 1351 | 20.634 | 27.269 | 51.552 | 1 | 67.31 |
| 5185 | CE2 | PHE | B | 1351 | 19.951 | 27.347 | 53.85 | 1 | 64.46 |
| 5186 | CZ | PHE | B | 1351 | 20.409 | 27.989 | 52.713 | 1 | 65 |
| 5187 | N | LYS | B | 1352 | 22.956 | 24.05 | 53.489 | 1 | 70.89 |
| 5188 | CA | LYS | B | 1352 | 23.865 | 24.51 | 54.528 | 1 | 71.5 |
| 5189 | C | LYS | B | 1352 | 23.766 | 26.034 | 54.543 | 1 | 71.96 |
| 5190 | O | LYS | B | 1352 | 23.996 | 26.683 | 53.53 | 1 | 72.27 |
| 5191 | CB | LYS | B | 1352 | 25.288 | 24.066 | 54.219 | 1 | 71.53 |
| 5192 | N | PRO | B | 1353 | 23.386 | 26.617 | 55.686 | 1 | 73.32 |
| 5193 | CA | PRO | B | 1353 | 23.228 | 28.063 | 55.909 | 1 | 76.72 |
| 5194 | C | PRO | B | 1353 | 24.407 | 28.968 | 55.496 | 1 | 78.51 |
| 5195 | O | PRO | B | 1353 | 25.456 | 28.441 | 55.057 | 1 | 79.15 |
| 5196 | CB | PRO | B | 1353 | 22.962 | 28.14 | 57.413 | 1 | 76.75 |
| 5197 | CG | PRO | B | 1353 | 22.188 | 26.884 | 57.666 | 1 | 76.61 |
| 5198 | CD | PRO | B | 1353 | 22.983 | 25.859 | 56.883 | 1 | 75.53 |
| 5199 | OXT | PRO | B | 1353 | 24.258 | 30.21 | 55.615 | 1 | 78.87 |
| 5200 | | PRO | B | 1353 | | | | | |

Fig. 1-130

| ATOM | ATOM TYPE | RESIDUE | # | X | Y | Z | OCC | B |
|---|---|---|---|---|---|---|---|---|
| 5201 | MG | MG | 401 | 41.849 | 77.432 | 8.106 | 1 | 39.31 |
| 5202 | MG | MG | 402 | 47.016 | 76.86 | 9.607 | 1 | 42.84 |
| 5203 | MG | MG | 1401 | 5.69 | 38.173 | 43.651 | 1 | 41.28 |
| 5204 | MG | MG | 1402 | 6.189 | 32.966 | 42.139 | 1 | 48.92 |
| 5205 | PG | ANP | 400 | 44.037 | 79.054 | 8.861 | 1 | 66.71 |
| 5206 | O1G | ANP | 400 | 43.871 | 80.603 | 8.797 | 1 | 65.28 |
| 5207 | O2G | ANP | 400 | 42.804 | 78.446 | 9.688 | 1 | 64.26 |
| 5208 | O3G | ANP | 400 | 45.415 | 78.794 | 9.622 | 1 | 61.75 |
| 5209 | PB | ANP | 400 | 45.207 | 78.285 | 6.471 | 1 | 53.03 |
| 5210 | O1B | ANP | 400 | 45.357 | 79.52 | 5.523 | 1 | 54.98 |
| 5211 | O2B | ANP | 400 | 46.444 | 77.845 | 7.274 | 1 | 44.5 |
| 5212 | N3B | ANP | 400 | 44.026 | 78.547 | 7.417 | 1 | 55.71 |
| 5213 | PA | ANP | 400 | 43.636 | 76.122 | 5.359 | 1 | 45.13 |
| 5214 | O1A | ANP | 400 | 44.218 | 74.72 | 4.957 | 1 | 43.29 |
| 5215 | O2A | ANP | 400 | 42.982 | 76.037 | 6.707 | 1 | 39.7 |
| 5216 | O3A | ANP | 400 | 44.879 | 77.226 | 5.333 | 1 | 46.4 |
| 5217 | O5* | ANP | 400 | 42.52 | 76.556 | 4.302 | 1 | 44.29 |
| 5218 | C5* | ANP | 400 | 41.83 | 77.858 | 4.367 | 1 | 40.83 |
| 5219 | C4* | ANP | 400 | 40.642 | 77.72 | 3.427 | 1 | 40.7 |
| 5220 | O4* | ANP | 400 | 41.036 | 76.944 | 2.298 | 1 | 42.85 |
| 5221 | C3* | ANP | 400 | 39.56 | 76.822 | 4.049 | 1 | 44.36 |
| 5222 | O3* | ANP | 400 | 38.609 | 77.63 | 4.745 | 1 | 50.96 |
| 5223 | C2* | ANP | 400 | 38.862 | 76.098 | 2.89 | 1 | 40.35 |
| 5224 | O2* | ANP | 400 | 37.997 | 76.921 | 2.171 | 1 | 43.36 |
| 5225 | C1* | ANP | 400 | 40.071 | 75.951 | 1.995 | 1 | 37.7 |
| 5226 | N9 | ANP | 400 | 40.475 | 74.651 | 1.773 | 1 | 38.51 |
| 5227 | C8 | ANP | 400 | 41.646 | 74.092 | 2.267 | 1 | 41.44 |
| 5228 | N7 | ANP | 400 | 41.838 | 72.823 | 1.829 | 1 | 36.45 |
| 5229 | C5 | ANP | 400 | 40.747 | 72.594 | 1.026 | 1 | 38.52 |
| 5230 | C6 | ANP | 400 | 40.343 | 71.534 | 0.249 | 1 | 38.14 |
| 5231 | N6 | ANP | 400 | 41.13 | 70.37 | 0.215 | 1 | 36.43 |
| 5232 | N1 | ANP | 400 | 39.205 | 71.689 | -0.435 | 1 | 34.26 |
| 5233 | C2 | ANP | 400 | 38.426 | 72.775 | -0.424 | 1 | 33.3 |
| 5234 | N3 | ANP | 400 | 38.699 | 73.876 | 0.283 | 1 | 34.84 |
| 5235 | C4 | ANP | 400 | 39.852 | 73.774 | 0.992 | 1 | 38.04 |
| 5236 | PG | ANP | 1400 | 4.1 | 35.932 | 42.968 | 1 | 63.65 |
| 5237 | O1G | ANP | 1400 | 2.553 | 36.103 | 43.102 | 1 | 65.57 |
| 5238 | O2G | ANP | 1400 | 4.654 | 37.138 | 42.145 | 1 | 64.12 |
| 5239 | O3G | ANP | 1400 | 4.313 | 34.574 | 42.221 | 1 | 61.2 |
| 5240 | PB | ANP | 1400 | 4.902 | 34.747 | 45.367 | 1 | 56.74 |

Fig. 1-131

| ATOM | ATOM TYPE | RESIDUE | # | X | Y | Z | OCC | B |
|---|---|---|---|---|---|---|---|---|
| 5241 | O1B | ANP | 1400 | 3.744 | 34.632 | 46.371 | 1 | 55.92 |
| 5242 | O2B | ANP | 1400 | 5.312 | 33.508 | 44.575 | 1 | 48.81 |
| 5243 | N3B | ANP | 1400 | 4.635 | 35.94 | 44.396 | 1 | 57.4 |
| 5244 | PA | ANP | 1400 | 7.146 | 36.343 | 46.365 | 1 | 46.37 |
| 5245 | O1A | ANP | 1400 | 8.575 | 35.772 | 46.69 | 1 | 41.77 |
| 5246 | O2A | ANP | 1400 | 7.182 | 36.981 | 45.004 | 1 | 44.73 |
| 5247 | O3A | ANP | 1400 | 6.043 | 35.092 | 46.457 | 1 | 48.88 |
| 5248 | O5* | ANP | 1400 | 6.76 | 37.46 | 47.388 | 1 | 45.77 |
| 5249 | C5* | ANP | 1400 | 5.479 | 38.164 | 47.395 | 1 | 40.76 |
| 5250 | C4* | ANP | 1400 | 5.665 | 39.356 | 48.337 | 1 | 40.9 |
| 5251 | O4* | ANP | 1400 | 6.474 | 38.947 | 49.45 | 1 | 41.82 |
| 5252 | C3* | ANP | 1400 | 6.555 | 40.431 | 47.668 | 1 | 41.24 |
| 5253 | O3* | ANP | 1400 | 5.736 | 41.351 | 47.02 | 1 | 46.65 |
| 5254 | C2* | ANP | 1400 | 7.326 | 41.125 | 48.784 | 1 | 40.23 |
| 5255 | O2* | ANP | 1400 | 6.547 | 42.006 | 49.545 | 1 | 40.94 |
| 5256 | C1* | ANP | 1400 | 7.516 | 39.913 | 49.694 | 1 | 40.13 |
| 5257 | N9 | ANP | 1400 | 8.832 | 39.467 | 49.865 | 1 | 37.04 |
| 5258 | C8 | ANP | 1400 | 9.337 | 38.312 | 49.355 | 1 | 37.62 |
| 5259 | N7 | ANP | 1400 | 10.61 | 38.124 | 49.741 | 1 | 37.12 |
| 5260 | C5 | ANP | 1400 | 10.899 | 39.2 | 50.517 | 1 | 37.85 |
| 5261 | C6 | ANP | 1400 | 12 | 39.606 | 51.214 | 1 | 38.14 |
| 5262 | N6 | ANP | 1400 | 13.153 | 38.775 | 51.202 | 1 | 37.1 |
| 5263 | N1 | ANP | 1400 | 11.9 | 40.764 | 51.885 | 1 | 33.25 |
| 5264 | C2 | ANP | 1400 | 10.832 | 41.541 | 51.928 | 1 | 37.47 |
| 5265 | N3 | ANP | 1400 | 9.684 | 41.246 | 51.287 | 1 | 37.53 |
| 5266 | C4 | ANP | 1400 | 9.738 | 40.091 | 50.598 | 1 | 38.23 |
| 5267 | O | HOH | 2001 | 10.772 | 33.949 | 38.425 | 1 | 20.93 |
| 5268 | O | HOH | 2002 | 11.149 | 35.798 | 47.426 | 1 | 53.18 |
| 5269 | O | HOH | 2003 | 4.345 | 32.079 | 15.738 | 1 | 42.11 |
| 5270 | O | HOH | 2004 | 0.607 | 32.578 | 20.617 | 1 | 57.85 |
| 5271 | O | HOH | 2005 | 8.734 | 39.595 | 29.215 | 1 | 50.93 |
| 5272 | O | HOH | 2006 | 46.414 | 71.498 | 5.513 | 1 | 42.98 |
| 5273 | O | HOH | 2007 | 30.063 | 54.37 | 17.201 | 1 | 28.45 |
| 5274 | O | HOH | 2008 | 39.779 | 73.86 | 22.407 | 1 | 30.88 |
| 5275 | O | HOH | 2009 | 10.057 | 27.917 | 37.313 | 1 | 56.75 |
| 5276 | O | HOH | 2010 | 48.313 | 76.556 | 26.783 | 1 | 56.09 |
| 5277 | O | HOH | 2012 | 12.176 | 33.756 | 46.036 | 1 | 33.09 |
| 5278 | O | HOH | 2013 | 52.858 | 64.574 | -9.851 | 1 | 35.64 |
| 5279 | O | HOH | 2014 | 5.85 | 31.615 | 25.114 | 1 | 44.11 |
| 5280 | O | HOH | 2015 | 35.374 | 78.198 | 23.486 | 1 | 65.59 |

Fig. 1-132

| ATOM | ATOM TYPE | RESIDUE | # | X | Y | Z | OCC | B |
|---|---|---|---|---|---|---|---|---|
| 5281 | O | HOH | 2016 | 6.755 | 30.619 | 44.678 | 1 | 38.97 |
| 5282 | O | HOH | 2017 | 47.846 | 63.253 | -11.777 | 1 | 36.83 |
| 5283 | O | HOH | 2018 | 31.706 | 81.437 | 14.674 | 1 | 48.14 |
| 5284 | O | HOH | 2020 | 51.835 | 72.941 | 13.996 | 1 | 36.01 |
| 5285 | O | HOH | 2021 | 9.15 | 31.445 | 69.292 | 1 | 39.65 |
| 5286 | O | HOH | 2022 | 47.091 | 66.467 | -8.015 | 1 | 43.66 |
| 5287 | O | HOH | 2023 | 29.609 | 71.817 | -0.007 | 1 | 38.11 |
| 5288 | O | HOH | 2024 | 18.734 | 27.61 | 60.73 | 1 | 44.58 |
| 5289 | O | HOH | 2025 | 6.819 | 36.938 | 69.156 | 1 | 50.09 |
| 5290 | O | HOH | 2026 | 2.441 | 47.624 | 10.242 | 1 | 57.1 |
| 5291 | O | HOH | 2027 | 3.003 | 42.903 | 46.921 | 1 | 53.16 |
| 5292 | O | HOH | 2028 | 54.131 | 76.111 | 18.046 | 1 | 47.63 |
| 5293 | O | HOH | 2029 | 23.493 | 21.71 | 48.962 | 1 | 60.57 |
| 5294 | O | HOH | 2030 | 60.032 | 80.82 | 3.634 | 1 | 84.88 |
| 5295 | O | HOH | 2031 | 27.727 | 81.623 | 12.559 | 1 | 38.04 |
| 5296 | O | HOH | 2032 | 1.909 | 52.215 | 39.067 | 1 | 44.72 |
| 5297 | O | HOH | 2033 | -2.186 | 21.394 | 40.979 | 1 | 89.31 |
| 5298 | O | HOH | 2034 | 20.499 | 33.652 | 45.278 | 1 | 41.5 |
| 5299 | O | HOH | 2035 | 34.06 | 80.711 | 41.447 | 1 | 100 |
| 5300 | O | HOH | 2036 | 2.839 | 48.517 | 40.091 | 1 | 41.86 |
| 5301 | O | HOH | 2037 | 3.517 | 31.703 | 45.521 | 1 | 64.44 |
| 5302 | O | HOH | 2038 | 9.385 | 64.924 | 27.742 | 1 | 81.27 |
| 5303 | O | HOH | 2039 | 40.448 | 79.937 | 8.562 | 1 | 59.32 |
| 5304 | O | HOH | 2040 | 24.866 | 85.129 | 6.506 | 1 | 52.79 |
| 5305 | O | HOH | 2041 | 42.662 | 69.456 | 27.547 | 1 | 33.54 |
| 5306 | O | HOH | 2042 | 45.974 | 72.478 | 13.009 | 1 | 45.87 |
| 5307 | O | HOH | 2043 | 10.504 | 38.973 | 33.547 | 1 | 40.02 |
| 5308 | O | HOH | 2044 | 9.579 | 41.828 | 67.318 | 1 | 59.9 |
| 5309 | O | HOH | 2045 | 17.341 | 33.54 | 19.641 | 1 | 45.32 |
| 5310 | O | HOH | 2046 | 3.405 | 47.845 | 31.275 | 1 | 36.21 |
| 5311 | O | HOH | 2047 | 17.011 | 33.897 | 71.868 | 1 | 33.52 |
| 5312 | O | HOH | 2048 | 6.482 | 40.003 | 35.841 | 1 | 57.08 |
| 5313 | O | HOH | 2049 | 1.137 | 33.078 | 34.05 | 1 | 33.82 |
| 5314 | O | HOH | 2050 | 26.744 | 31.01 | 39.861 | 1 | 55.08 |
| 5315 | O | HOH | 2051 | 0.17 | 38.998 | 26.667 | 1 | 38.22 |
| 5316 | O | HOH | 2052 | 32.319 | 78.969 | 20.662 | 1 | 35.9 |
| 5317 | O | HOH | 2053 | 8.371 | 43.433 | 51.842 | 1 | 48.92 |
| 5318 | O | HOH | 2054 | 3.561 | 26.075 | 27.401 | 1 | 48.98 |
| 5319 | O | HOH | 2055 | 47.329 | 81.696 | 30.891 | 1 | 46.24 |
| 5320 | O | HOH | 2056 | 10.866 | 35.347 | 9.28 | 1 | 84.73 |

Fig. 1-133

| ATOM | ATOM TYPE | RESIDUE | # | X | Y | Z | OCC | B |
|---|---|---|---|---|---|---|---|---|
| 5321 | O | HOH | 2057 | 16.156 | 77.623 | 24.389 | 1 | 68.54 |
| 5322 | O | HOH | 2058 | 55.244 | 60.234 | 8.553 | 1 | 42.78 |
| 5323 | O | HOH | 2059 | 39.091 | 58.612 | 21.163 | 1 | 48.48 |
| 5324 | O | HOH | 2060 | 8.065 | 40.362 | 61.751 | 1 | 43.34 |
| 5325 | O | HOH | 2061 | 5.215 | 43.203 | 58.214 | 1 | 38.27 |
| 5326 | O | HOH | 2062 | 4.37 | 44.153 | 28.361 | 1 | 57.63 |
| 5327 | O | HOH | 2063 | 48.26 | 61.512 | -6.32 | 1 | 42.92 |
| 5328 | O | HOH | 2064 | 55.392 | 69.84 | -13.305 | 1 | 44.52 |
| 5329 | O | HOH | 2065 | 6.363 | 15.594 | 60.437 | 1 | 54.58 |
| 5330 | O | HOH | 2066 | 40.18 | 75.691 | -10.457 | 1 | 41.92 |
| 5331 | O | HOH | 2067 | 39.635 | 79.313 | 26.163 | 1 | 34.64 |
| 5332 | O | HOH | 2068 | 21.112 | 51.594 | 19.282 | 1 | 54.97 |
| 5333 | O | HOH | 2069 | 2.935 | 39.989 | 25.661 | 1 | 47.84 |
| 5334 | O | HOH | 2070 | -0.739 | 41.793 | 34.308 | 1 | 51.1 |
| 5335 | O | HOH | 2071 | -1.97 | 28.873 | 17.982 | 1 | 76.51 |
| 5336 | O | HOH | 2072 | 37.519 | 83.18 | 17.527 | 1 | 66.32 |
| 5337 | O | HOH | 2073 | 22.213 | 35.923 | 45.566 | 1 | 43.82 |
| 5338 | O | HOH | 2074 | 54.866 | 66.859 | -13.461 | 1 | 36.44 |
| 5339 | O | HOH | 2075 | 18.985 | 68.519 | 7.218 | 1 | 53.24 |
| 5340 | O | HOH | 2076 | 33 | 49.476 | 38.019 | 1 | 66.05 |
| 5341 | O | HOH | 2077 | 1.385 | 19.187 | 61.122 | 1 | 40.14 |
| 5342 | O | HOH | 2078 | 28.317 | 49.852 | 34.842 | 1 | 61.51 |
| 5343 | O | HOH | 2079 | 58.966 | 69.737 | -6.012 | 1 | 48 |
| 5344 | O | HOH | 2080 | 20.219 | 33.371 | 71.707 | 1 | 62.38 |
| 5345 | O | HOH | 2081 | 54.919 | 74.501 | -19.389 | 1 | 57.57 |
| 5346 | O | HOH | 2082 | 6.715 | 29.888 | 73.444 | 1 | 46.38 |
| 5347 | O | HOH | 2083 | 34.395 | 81.934 | 13.78 | 1 | 52.33 |
| 5348 | O | HOH | 2084 | 4.674 | 31.598 | 71.807 | 1 | 58.4 |
| 5349 | O | HOH | 2085 | 53.164 | 70.664 | -14.524 | 1 | 63.38 |
| 5350 | O | HOH | 2086 | 45.625 | 80.173 | 17.79 | 1 | 55.61 |
| 5351 | O | HOH | 2087 | 12.941 | 37.096 | 23.879 | 1 | 63.59 |
| 5352 | O | HOH | 2088 | 38.14 | 82.799 | 2.37 | 1 | 48.54 |
| 5353 | O | HOH | 2089 | 48.766 | 66.048 | 26.928 | 1 | 52.02 |
| 5354 | O | HOH | 2090 | 52.39 | 79.487 | 6.131 | 1 | 76.26 |
| 5355 | O | HOH | 2091 | 0.174 | 21.376 | 54.024 | 1 | 60.77 |
| 5356 | O | HOH | 2092 | 50.341 | 82.455 | 0.703 | 1 | 74.32 |
| 5357 | O | HOH | 2093 | 64.689 | 80.903 | 3.248 | 1 | 53.52 |
| 5358 | O | HOH | 2094 | -1.36 | 44.694 | 7.571 | 1 | 71.2 |
| 5359 | O | HOH | 2095 | 23.367 | 50.964 | 52.62 | 1 | 67.99 |
| 5360 | O | HOH | 2096 | -6.492 | 34.887 | 17.192 | 1 | 56.94 |

Fig. 1-134

| ATOM | ATOM TYPE | RESIDUE | # | X | Y | Z | OCC | B |
|---|---|---|---|---|---|---|---|---|
| 5361 | O | HOH | 2097 | 3.543 | 36.942 | 38.901 | 1 | 63.66 |
| 5362 | O | HOH | 2098 | -6.969 | 32.565 | 62.065 | 1 | 84.57 |
| 5363 | O | HOH | 2099 | 27.25 | 53.447 | 25.318 | 1 | 41.81 |
| 5364 | O | HOH | 2100 | 8.338 | 49.512 | 14.509 | 1 | 38.78 |
| 5365 | O | HOH | 2101 | 26.169 | 41.831 | 37.281 | 1 | 46.37 |
| 5366 | O | HOH | 2102 | 12.608 | 35.089 | 21.09 | 1 | 42.82 |
| 5367 | O | HOH | 2103 | 13.632 | 23.185 | 63.6 | 1 | 42.07 |
| 5368 | O | HOH | 2104 | 54.824 | 68.31 | 25.143 | 1 | 74.51 |
| 5369 | O | HOH | 2105 | 19.642 | 22.43 | 33.592 | 1 | 54.13 |
| 5370 | O | HOH | 2106 | 45.757 | 62.224 | 5.571 | 1 | 50.62 |
| 5371 | O | HOH | 2107 | 19.587 | 35.893 | 72.506 | 1 | 46.36 |
| 5372 | O | HOH | 2108 | 3.087 | 45.759 | 45.5 | 1 | 60.82 |
| 5373 | O | HOH | 2109 | 15.907 | 57.243 | 21.733 | 1 | 54.68 |
| 5374 | O | HOH | 2110 | 48.651 | 56.028 | 10.536 | 1 | 95.92 |
| 5375 | O | HOH | 2111 | 44.053 | 79.03 | 12.315 | 1 | 58.92 |
| 5376 | O | HOH | 2112 | 29.827 | 77.335 | 39.215 | 1 | 63.64 |
| 5377 | O | HOH | 2113 | 15.946 | 37.221 | 20.809 | 1 | 89.1 |
| 5378 | O | HOH | 2114 | 10.008 | 22.941 | 31.02 | 1 | 48.95 |
| 5379 | O | HOH | 2115 | 24.846 | 86.734 | 4.358 | 1 | 51.7 |
| 5380 | O | HOH | 2116 | 4.595 | 49.482 | 33.513 | 1 | 67.71 |
| 5381 | O | HOH | 2117 | 0.793 | 45.008 | 38.422 | 1 | 50.43 |
| 5382 | O | HOH | 2118 | 6.692 | 33.791 | 39.701 | 1 | 50.68 |
| 5383 | O | HOH | 2119 | 9.649 | 48.935 | 19.05 | 1 | 68.49 |
| 5384 | O | HOH | 2120 | 40.249 | 75.205 | 51.582 | 1 | 51.92 |
| 5385 | O | HOH | 2121 | 51.66 | 60.888 | 21.709 | 1 | 53.75 |
| 5386 | O | HOH | 2122 | 39.346 | 57.224 | 24.107 | 1 | 46.15 |
| 5387 | O | HOH | 2123 | 31.728 | 42.838 | 36.454 | 1 | 44.17 |
| 5388 | O | HOH | 2124 | 40.051 | 76.285 | 16.447 | 1 | 79.22 |
| 5389 | O | HOH | 2125 | 31.248 | 77.875 | 18.437 | 1 | 66.18 |
| 5390 | O | HOH | 2126 | 13.547 | 60.547 | 17.434 | 1 | 57.4 |
| 5391 | O | HOH | 2127 | 11.489 | 54.75 | 50.23 | 1 | 76.19 |
| 5392 | O | HOH | 2128 | 20.054 | 55.492 | 50.224 | 1 | 37.59 |
| 5393 | O | HOH | 2129 | 17.42 | 30.752 | 70.714 | 1 | 40.8 |
| 5394 | O | HOH | 2130 | 18.168 | 33.914 | 60.155 | 1 | 34.83 |
| 5395 | O | HOH | 2131 | 18.744 | 75.66 | 19.427 | 1 | 46.31 |
| 5396 | O | HOH | 2132 | 20.991 | 40.391 | 29.318 | 1 | 59.96 |
| 5397 | O | HOH | 2133 | 40.93 | 81.758 | 25.48 | 1 | 48.17 |
| 5398 | O | HOH | 2134 | 29.094 | 49.017 | 42.215 | 1 | 43.78 |
| 5399 | O | HOH | 2135 | 16.41 | 23.271 | 37.302 | 1 | 64.3 |
| 5400 | O | HOH | 2136 | 40.832 | 72.121 | 18.068 | 1 | 62.51 |

Fig. 1-135

| ATOM | ATOM TYPE | RESIDUE | # | X | Y | Z | OCC | B |
|---|---|---|---|---|---|---|---|---|
| 5401 | O | HOH | 2137 | 3.713 | 54.002 | 31.916 | 1 | 51.43 |
| 5402 | O | HOH | 2138 | 6.52 | 25.87 | 33.79 | 1 | 74.01 |
| 5403 | O | HOH | 2139 | 0.338 | 30.422 | 52.543 | 1 | 60.63 |
| 5404 | O | HOH | 2140 | 0.144 | 40.98 | 46.433 | 1 | 55.17 |
| 5405 | O | HOH | 2141 | 19.662 | 78.537 | 20.473 | 1 | 53 |
| 5406 | O | HOH | 2142 | 45.784 | 57.815 | -8.304 | 1 | 59.05 |
| 5407 | O | HOH | 2143 | 27.448 | 43.857 | 38.986 | 1 | 80.17 |
| 5408 | O | HOH | 2144 | 24.726 | 83.636 | 2.342 | 1 | 49.9 |
| 5409 | O | HOH | 2145 | 11.951 | 55.373 | 53.119 | 1 | 48.01 |
| 5410 | O | HOH | 2146 | 14.632 | 47.119 | 60.154 | 1 | 59.79 |
| 5411 | O | HOH | 2147 | -1.117 | 38.112 | 34.017 | 1 | 36.44 |
| 5412 | O | HOH | 2148 | 24.72 | 59.34 | 35.09 | 1 | 62.65 |
| 5413 | O | HOH | 2149 | 7.817 | 29.839 | 18.139 | 1 | 52.06 |
| 5414 | O | HOH | 2150 | 13.577 | 26.758 | 66.33 | 1 | 55.54 |
| 5415 | O | HOH | 2151 | -4.626 | 35.494 | 34.477 | 1 | 54.33 |
| 5416 | O | HOH | 2152 | 48.764 | 76.038 | 7.667 | 1 | 45.14 |
| 5417 | O | HOH | 2153 | 45.78 | 76.292 | 11.913 | 1 | 48.89 |
| 5418 | O | HOH | 2154 | 65.621 | 78.088 | 14.103 | 1 | 87.09 |
| 5419 | O | HOH | 2155 | 14.776 | 33.227 | 20.254 | 1 | 53.71 |
| 5420 | O | HOH | 2156 | -6.492 | 47.579 | 23.192 | 1 | 71.61 |
| 5421 | O | HOH | 2157 | 10.912 | 36.446 | 19.347 | 1 | 71.91 |
| 5422 | O | HOH | 2158 | -0.483 | 27.212 | 15.775 | 1 | 52.36 |
| 5423 | O | HOH | 2159 | 57.616 | 59.487 | 20.576 | 1 | 52.03 |
| 5424 | O | HOH | 2160 | 11.348 | 23.02 | 17.901 | 1 | 58.83 |
| 5425 | O | HOH | 2161 | 6.859 | 33.83 | 69.706 | 1 | 49.25 |
| 5426 | O | HOH | 2162 | 21.464 | 66.188 | 29.151 | 1 | 40.81 |
| 5427 | O | HOH | 2163 | 12.695 | 66.769 | 14.259 | 1 | 60.77 |
| 5428 | O | HOH | 2164 | 1.375 | 47.587 | 37.345 | 1 | 71.1 |
| 5429 | O | HOH | 2165 | 28.494 | 41.431 | 39.072 | 1 | 56.88 |
| 5430 | O | HOH | 2166 | 38.323 | 73.53 | 35.555 | 1 | 58.84 |
| 5431 | O | HOH | 2167 | 22.536 | 44.887 | 51.419 | 1 | 70.03 |
| 5432 | O | HOH | 2168 | 28.691 | 82.952 | 26.989 | 1 | 43.85 |
| 5433 | O | HOH | 2169 | 44.743 | 80.266 | -14.044 | 1 | 78.59 |
| 5434 | O | HOH | 2170 | 3.922 | 45.869 | 19.001 | 1 | 96.76 |
| 5435 | O | HOH | 2171 | 57.137 | 69.168 | 23.44 | 1 | 61.66 |
| 5436 | O | HOH | 2172 | 28.574 | 78.161 | 18.537 | 1 | 100 |
| 5437 | O | HOH | 2173 | 55.573 | 65.877 | -11.131 | 1 | 58.89 |
| 5438 | O | HOH | 2174 | 7 | 18.47 | 63.559 | 1 | 52.76 |
| 5439 | O | HOH | 2175 | -0.497 | 29.47 | 10.663 | 1 | 65.7 |
| 5440 | O | HOH | 2176 | 39.55 | 62.054 | 21.834 | 1 | 69.36 |

Fig. 1-136

| ATOM | ATOM TYPE | RESIDUE | # | X | Y | Z | OCC | B |
|---|---|---|---|---|---|---|---|---|
| 5441 | O | HOH | 2177 | 48.756 | 83.508 | 29.35 | 1 | 62.82 |
| 5442 | O | HOH | 2178 | 7.812 | 62.749 | 20.621 | 1 | 67.61 |
| 5443 | O | HOH | 2179 | 9.736 | 47.516 | 63.408 | 1 | 46.59 |
| 5444 | O | HOH | 2180 | 36.458 | 90.23 | 30.756 | 1 | 75.67 |
| 5445 | O | HOH | 2181 | 32.054 | 74.879 | 38.041 | 1 | 49.33 |
| 5446 | O | HOH | 2182 | 25.001 | 46.519 | 52.531 | 1 | 64.94 |
| 5447 | O | HOH | 2183 | 32.47 | 79.959 | 12.122 | 1 | 56.23 |
| 5448 | O | HOH | 2184 | -7.077 | 43.484 | 33.181 | 1 | 56.09 |
| 5449 | O | HOH | 2185 | 2.143 | 38.605 | 42.272 | 1 | 53.31 |
| 5450 | O | HOH | 2186 | 6.04 | 44.393 | 50.82 | 1 | 92.01 |
| 5451 | O | HOH | 2187 | 20.678 | 35.691 | 62.368 | 1 | 55.76 |
| 5452 | O | HOH | 2188 | 6.896 | 24.913 | 15.884 | 1 | 61.33 |

Fig. 1-137

SEQUENCE LISTING

```
<160> NUMBER OF SEQ ID NOS: 41

<210> SEQ ID NO 1
<211> LENGTH: 367
<212> TYPE: PRT
<213> ORGANISM: Human

<400> SEQUENCE: 1
```

```
Met Ser Ser Pro Pro Ala Arg Ser Gly Phe Tyr Arg Gln Glu Val
1               5                   10                  15

Thr Lys Thr Ala Trp Glu Val Arg Ala Val Tyr Arg Asp Leu Gln Pro
            20                  25                  30

Val Gly Ser Gly Ala Tyr Gly Ala Val Cys Ser Ala Val Asp Gly Arg
            35                  40                  45

Thr Gly Ala Lys Val Ala Ile Lys Lys Leu Tyr Arg Pro Phe Gln Ser
            50                  55                  60

Glu Leu Phe Ala Lys Arg Ala Tyr Arg Glu Leu Arg Leu Leu Lys His
65                  70                  75                  80

Met Arg His Glu Asn Val Ile Gly Leu Leu Asp Val Phe Thr Pro Asp
                85                  90                  95

Glu Thr Leu Asp Asp Phe Thr Asp Phe Tyr Leu Val Met Pro Phe Met
                100                 105                 110

Gly Thr Asp Leu Gly Lys Leu Met Lys His Glu Lys Leu Gly Glu Asp
                115                 120                 125

Arg Ile Gln Phe Leu Val Tyr Gln Met Leu Lys Gly Leu Arg Tyr Ile
130                 135                 140

His Ala Ala Gly Ile Ile His Arg Asp Leu Lys Pro Gly Asn Leu Ala
145                 150                 155                 160

Val Asn Glu Asp Cys Glu Leu Lys Ile Leu Asp Phe Gly Leu Ala Arg
                165                 170                 175

Gln Ala Asp Ser Glu Met Thr Gly Tyr Val Val Thr Arg Trp Tyr Arg
                180                 185                 190

Ala Pro Glu Val Ile Leu Asn Trp Met Arg Tyr Thr Gln Thr Val Asp
                195                 200                 205

Ile Trp Ser Val Gly Cys Ile Met Ala Glu Met Ile Thr Gly Lys Thr
210                 215                 220

Leu Phe Lys Gly Ser Asp His Leu Asp Gln Leu Lys Glu Ile Met Lys
225                 230                 235                 240

Val Thr Gly Thr Pro Pro Ala Glu Phe Val Gln Arg Leu Gln Ser Asp
                245                 250                 255

Glu Ala Lys Asn Tyr Met Lys Gly Leu Pro Glu Leu Glu Lys Lys Asp
                260                 265                 270

Phe Ala Ser Ile Leu Thr Asn Ala Ser Pro Leu Ala Val Asn Leu Leu
                275                 280                 285

Glu Lys Met Leu Val Leu Asp Ala Glu Gln Arg Val Thr Ala Gly Glu
                290                 295                 300

Ala Leu Ala His Pro Tyr Phe Glu Ser Leu His Asp Thr Glu Asp Glu
305                 310                 315                 320

Pro Gln Val Gln Lys Tyr Asp Asp Ser Phe Asp Asp Val Asp Arg Thr
                325                 330                 335

Leu Asp Glu Trp Lys Arg Val Thr Tyr Lys Glu Val Leu Ser Phe Lys
                340                 345                 350

Pro Pro Arg Gln Leu Gly Ala Arg Val Ser Lys Glu Thr Pro Leu
                355                 360                 365
```

<210> SEQ ID NO 2
<211> LENGTH: 360
<212> TYPE: PRT
<213> ORGANISM: Human

<400> SEQUENCE: 2

Met Ser Gln Glu Arg Pro Thr Phe Tyr Arg Gln Glu Leu Asn Lys Thr

```
1               5                    10                   15
Ile Trp Glu Val Pro Glu Arg Tyr Gln Asn Leu Ser Pro Val Gly Ser
                20                  25              30

Gly Ala Tyr Gly Ser Val Cys Ala Ala Phe Asp Thr Lys Thr Gly Leu
            35              40              45

Arg Val Ala Val Lys Lys Leu Ser Arg Pro Phe Gln Ser Ile Ile His
    50              55              60

Ala Lys Arg Thr Tyr Arg Glu Leu Arg Leu Leu Lys His Met Lys His
65              70              75              80

Glu Asn Val Ile Gly Leu Leu Asp Val Phe Thr Pro Ala Arg Ser Leu
                85              90              95

Glu Glu Phe Asn Asp Val Tyr Leu Val Thr His Leu Met Gly Ala Asp
            100             105             110

Leu Asn Asn Ile Val Lys Cys Gln Lys Leu Thr Asp Asp His Val Gln
        115             120             125

Phe Leu Ile Tyr Gln Ile Leu Arg Gly Leu Lys Tyr Ile His Ser Ala
    130             135             140

Asp Ile Ile His Arg Asp Leu Lys Pro Ser Asn Leu Ala Val Asn Glu
145             150             155             160

Asp Cys Glu Leu Lys Ile Leu Asp Phe Gly Leu Ala Arg His Thr Asp
                165             170             175

Asp Glu Met Thr Gly Tyr Val Ala Thr Arg Trp Tyr Arg Ala Pro Glu
            180             185             190

Ile Met Leu Asn Trp Met His Tyr Asn Gln Thr Val Asp Ile Trp Ser
        195             200             205

Val Gly Cys Ile Met Ala Glu Leu Leu Thr Gly Arg Thr Leu Phe Pro
    210             215             220

Gly Thr Asp His Ile Asp Gln Leu Lys Leu Ile Leu Arg Leu Val Gly
225             230             235             240

Thr Pro Gly Ala Glu Leu Leu Lys Lys Ile Ser Ser Glu Ser Ala Arg
                245             250             255

Asn Tyr Ile Gln Ser Leu Thr Gln Met Pro Lys Met Asn Phe Ala Asn
            260             265             270

Val Phe Ile Gly Ala Asn Pro Leu Ala Val Asp Leu Leu Glu Lys Met
        275             280             285

Leu Val Leu Asp Ser Asp Lys Arg Ile Thr Ala Ala Gln Ala Leu Ala
    290             295             300

His Ala Tyr Phe Ala Gln Tyr His Asp Pro Asp Asp Glu Pro Val Ala
305             310             315             320

Asp Pro Tyr Asp Gln Ser Phe Glu Ser Arg Asp Leu Leu Ile Asp Glu
                325             330             335

Trp Lys Ser Leu Thr Tyr Asp Glu Val Ile Ser Phe Val Pro Pro Pro
            340             345             350

Leu Asp Gln Glu Glu Met Glu Ser
    355             360
```

<210> SEQ ID NO 3
<211> LENGTH: 360
<212> TYPE: PRT
<213> ORGANISM: Human

<400> SEQUENCE: 3

```
Met Ala Ala Ala Ala Ala Gly Ala Gly Pro Glu Met Val Arg Gly
1               5                   10                  15
```

-continued

Gln Val Phe Asp Val Gly Pro Arg Tyr Thr Asn Leu Ser Tyr Ile Gly
            20                  25                  30

Glu Gly Ala Tyr Gly Met Val Cys Ser Ala Tyr Asp Asn Val Asn Lys
            35                  40                  45

Val Arg Val Ala Ile Lys Lys Ile Ser Pro Phe Glu His Gln Thr Tyr
 50                  55                  60

Cys Gln Arg Thr Leu Arg Glu Ile Lys Ile Leu Leu Arg Phe Arg His
 65                  70                  75                  80

Glu Asn Ile Ile Gly Ile Asn Asp Ile Ile Arg Ala Pro Thr Ile Glu
            85                  90                  95

Gln Met Lys Asp Val Tyr Ile Val Gln Asp Leu Met Glu Thr Asp Leu
            100                 105                 110

Tyr Lys Leu Leu Lys Thr Gln His Leu Ser Asn Asp His Ile Cys Tyr
            115                 120                 125

Phe Leu Tyr Gln Ile Leu Arg Gly Leu Lys Tyr Ile His Ser Ala Asn
            130                 135                 140

Val Leu His Arg Asp Leu Lys Pro Ser Asn Leu Leu Asn Thr Thr
145                 150                 155                 160

Cys Asp Leu Lys Ile Cys Asp Phe Gly Leu Ala Arg Val Ala Asp Pro
            165                 170                 175

Asp His Asp His Thr Gly Phe Leu Thr Glu Tyr Val Ala Thr Arg Trp
            180                 185                 190

Tyr Arg Ala Pro Glu Ile Met Leu Asn Ser Lys Gly Tyr Thr Lys Ser
            195                 200                 205

Ile Asp Ile Trp Ser Val Gly Cys Ile Leu Ala Glu Met Leu Ser Asn
            210                 215                 220

Arg Pro Ile Phe Pro Gly Lys His Tyr Leu Asp Gln Leu Asn His Ile
225                 230                 235                 240

Leu Gly Ile Leu Gly Ser Pro Ser Gln Glu Asp Leu Asn Cys Ile Ile
            245                 250                 255

Asn Leu Lys Ala Arg Asn Tyr Leu Leu Ser Leu Pro His Lys Asn Lys
            260                 265                 270

Val Pro Trp Asn Arg Leu Phe Pro Asn Ala Asp Ser Lys Ala Leu Asp
            275                 280                 285

Leu Leu Asp Lys Met Leu Thr Phe Asn Pro His Lys Arg Ile Glu Val
            290                 295                 300

Glu Gln Ala Leu Ala His Pro Tyr Leu Glu Gln Tyr Tyr Asp Pro Ser
305                 310                 315                 320

Asp Glu Pro Ile Ala Glu Ala Pro Phe Lys Phe Asp Met Glu Leu Asp
            325                 330                 335

Asp Leu Pro Lys Glu Lys Leu Lys Glu Leu Ile Phe Glu Glu Thr Ala
            340                 345                 350

Arg Phe Gln Pro Gly Tyr Arg Ser
            355                 360

<210> SEQ ID NO 4
<211> LENGTH: 358
<212> TYPE: PRT
<213> ORGANISM: Mouse

<400> SEQUENCE: 4

Met Ala Ala Ala Ala Ala Gly Pro Glu Met Val Arg Gly Gln Val
1               5                   10                  15

Phe Asp Val Gly Pro Arg Tyr Thr Asn Leu Ser Tyr Ile Gly Glu Gly
            20                  25                  30

```
Ala Tyr Gly Met Val Cys Ser Ala Tyr Asp Asn Leu Asn Lys Val Arg
             35                  40                  45

Val Ala Ile Lys Lys Ile Ser Pro Phe Glu His Gln Thr Tyr Cys Gln
 50                  55                  60

Arg Thr Leu Arg Glu Ile Lys Ile Leu Arg Phe Arg His Glu Asn
 65                  70                  75                  80

Ile Ile Gly Ile Asn Asp Ile Ile Arg Ala Pro Thr Ile Glu Gln Met
                 85                  90                  95

Lys Asp Val Tyr Ile Val Gln Asp Leu Met Glu Thr Asp Leu Tyr Lys
                100                 105                 110

Leu Leu Lys Thr Gln His Leu Ser Asn Asp His Ile Cys Tyr Phe Leu
            115                 120                 125

Tyr Gln Ile Leu Arg Gly Leu Lys Tyr Ile His Ser Ala Asn Val Leu
130                 135                 140

His Arg Asp Leu Lys Pro Ser Asn Leu Leu Asn Thr Thr Cys Asp
145                 150                 155                 160

Leu Lys Ile Cys Asp Phe Gly Leu Ala Arg Val Ala Asp Pro Asp His
                165                 170                 175

Asp His Thr Gly Phe Leu Thr Glu Tyr Val Ala Thr Arg Trp Tyr Arg
                180                 185                 190

Ala Pro Glu Ile Met Leu Asn Ser Lys Gly Tyr Thr Lys Ser Ile Asp
            195                 200                 205

Ile Trp Ser Val Gly Cys Ile Leu Ala Glu Met Leu Ser Asn Arg Pro
            210                 215                 220

Ile Phe Pro Gly Lys His Tyr Leu Asp Gln Leu Asn His Ile Leu Gly
225                 230                 235                 240

Ile Leu Gly Ser Pro Ser Gln Glu Asp Leu Asn Cys Ile Ile Asn Leu
                245                 250                 255

Lys Ala Arg Asn Tyr Leu Leu Ser Leu Pro His Lys Asn Lys Val Pro
                260                 265                 270

Trp Asn Arg Leu Phe Pro Asn Ala Asp Ser Lys Ala Leu Asp Leu Leu
            275                 280                 285

Asp Lys Met Leu Thr Phe Asn Pro His Lys Arg Ile Glu Val Glu Gln
290                 295                 300

Ala Leu Ala His Pro Tyr Leu Glu Gln Tyr Tyr Asp Pro Ser Asp Glu
305                 310                 315                 320

Pro Ile Ala Glu Ala Pro Phe Lys Phe Asp Met Glu Leu Asp Asp Leu
                325                 330                 335

Pro Lys Glu Lys Leu Lys Glu Leu Ile Phe Glu Glu Thr Ala Arg Phe
            340                 345                 350

Gln Pro Gly Tyr Arg Ser
            355

<210> SEQ ID NO 5
<211> LENGTH: 464
<212> TYPE: PRT
<213> ORGANISM: Human

<400> SEQUENCE: 5

Met Ser Leu His Phe Leu Tyr Tyr Cys Ser Glu Pro Thr Leu Asp Val
 1               5                  10                  15

Lys Ile Ala Phe Cys Gln Gly Phe Asp Lys Gln Val Asp Val Ser Tyr
             20                  25                  30

Ile Ala Lys His Tyr Asn Met Ser Lys Ser Lys Val Asp Asn Gln Phe
```

-continued

```
            35                  40                  45
Tyr Ser Val Glu Val Gly Asp Ser Thr Phe Thr Val Leu Lys Arg Tyr
 50                  55                  60

Gln Asn Leu Lys Pro Ile Gly Ser Gly Ala Gln Gly Ile Val Cys Ala
 65                  70                  75                  80

Ala Tyr Asp Ala Val Leu Asp Arg Asn Val Ala Ile Lys Lys Leu Ser
                     85                  90                  95

Arg Pro Phe Gln Asn Gln Thr His Ala Lys Arg Ala Tyr Arg Glu Leu
                100                 105                 110

Val Leu Met Lys Cys Val Asn His Lys Asn Ile Ile Ser Leu Leu Asn
            115                 120                 125

Val Phe Thr Pro Gln Lys Thr Leu Glu Glu Phe Gln Asp Val Tyr Leu
            130                 135                 140

Val Met Glu Leu Met Asp Ala Asn Leu Cys Gln Val Ile Gln Met Glu
145                 150                 155                 160

Leu Asp His Glu Arg Met Ser Tyr Leu Leu Tyr Gln Met Leu Cys Gly
                165                 170                 175

Ile Lys His Leu His Ser Ala Gly Ile Ile His Arg Asp Leu Lys Pro
                180                 185                 190

Ser Asn Ile Val Val Lys Ser Asp Cys Thr Leu Lys Ile Leu Asp Phe
            195                 200                 205

Gly Leu Ala Arg Thr Ala Gly Thr Ser Phe Met Met Thr Pro Tyr Val
210                 215                 220

Val Thr Arg Tyr Tyr Arg Ala Pro Glu Val Ile Leu Gly Met Gly Tyr
225                 230                 235                 240

Lys Glu Asn Val Asp Ile Trp Ser Val Gly Cys Ile Met Gly Glu Met
                245                 250                 255

Val Arg His Lys Ile Leu Phe Pro Gly Arg Asp Tyr Ile Asp Gln Trp
            260                 265                 270

Asn Lys Val Ile Glu Gln Leu Gly Thr Pro Cys Pro Glu Phe Met Lys
            275                 280                 285

Lys Leu Gln Pro Thr Val Arg Asn Tyr Val Glu Asn Arg Pro Lys Tyr
290                 295                 300

Ala Gly Leu Thr Phe Pro Lys Leu Phe Pro Asp Ser Leu Phe Pro Ala
305                 310                 315                 320

Asp Ser Glu His Asn Lys Leu Lys Ala Ser Gln Ala Arg Asp Leu Leu
                325                 330                 335

Ser Lys Met Leu Val Ile Asp Pro Ala Lys Arg Ile Ser Val Asp Asp
                340                 345                 350

Ala Leu Gln His Pro Tyr Ile Asn Val Trp Tyr Asp Pro Ala Glu Val
                355                 360                 365

Glu Ala Pro Pro Pro Gln Ile Tyr Asp Lys Gln Leu Asp Glu Arg Glu
370                 375                 380

His Thr Ile Glu Glu Trp Lys Glu Leu Ile Tyr Lys Glu Val Met Asn
385                 390                 395                 400

Ser Glu Glu Lys Thr Lys Asn Gly Val Val Lys Gly Gln Pro Ser Pro
                405                 410                 415

Ser Gly Ala Ala Val Asn Ser Ser Glu Ser Leu Pro Pro Ser Ser Ser
                420                 425                 430

Val Asn Asp Ile Ser Ser Met Ser Thr Asp Gln Thr Leu Ala Ser Asp
            435                 440                 445

Thr Asp Ser Ser Leu Glu Ala Ser Ala Gly Pro Leu Gly Cys Cys Arg
450                 455                 460
```

```
<210> SEQ ID NO 6
<211> LENGTH: 351
<212> TYPE: PRT
<213> ORGANISM: Mouse

<400> SEQUENCE: 6
```

Met Gly Asn Ala Ala Ala Lys Lys Gly Ser Glu Gln Glu Ser Val
1               5                   10                  15

Lys Glu Phe Leu Ala Lys Ala Lys Glu Asp Phe Leu Lys Lys Trp Glu
            20                  25                  30

Thr Pro Ser Gln Asn Thr Ala Gln Leu Asp Gln Phe Asp Arg Ile Lys
            35                  40                  45

Thr Leu Gly Thr Gly Ser Phe Gly Arg Val Met Leu Val Lys His Lys
        50                  55                  60

Glu Ser Gly Asn His Tyr Ala Met Lys Ile Leu Asp Lys Gln Lys Val
65                  70                  75                  80

Val Lys Leu Lys Gln Ile Glu His Thr Leu Asn Glu Lys Arg Ile Leu
                85                  90                  95

Gln Ala Val Asn Phe Pro Phe Leu Val Lys Leu Glu Phe Ser Phe Lys
            100                 105                 110

Asp Asn Ser Asn Leu Tyr Met Val Met Glu Tyr Val Ala Gly Gly Glu
        115                 120                 125

Met Phe Ser His Leu Arg Arg Ile Gly Arg Phe Ser Glu Pro His Ala
130                 135                 140

Arg Phe Tyr Ala Ala Gln Ile Val Leu Thr Phe Glu Tyr Leu His Ser
145                 150                 155                 160

Leu Asp Leu Ile Tyr Arg Asp Leu Lys Pro Glu Asn Leu Leu Ile Asp
                165                 170                 175

Gln Gln Gly Tyr Ile Gln Val Thr Asp Phe Gly Phe Ala Lys Arg Val
            180                 185                 190

Lys Gly Arg Thr Trp Thr Leu Cys Gly Thr Pro Glu Tyr Leu Ala Pro
        195                 200                 205

Glu Ile Ile Leu Ser Lys Gly Tyr Asn Lys Ala Val Asp Trp Trp Ala
210                 215                 220

Leu Gly Val Leu Ile Tyr Glu Met Ala Ala Gly Tyr Pro Pro Phe Phe
225                 230                 235                 240

Ala Asp Gln Pro Ile Gln Ile Tyr Glu Lys Ile Val Ser Gly Lys Val
                245                 250                 255

Arg Phe Pro Ser His Phe Ser Ser Asp Leu Lys Asp Leu Leu Arg Asn
            260                 265                 270

Leu Leu Gln Val Asp Leu Thr Lys Arg Phe Gly Asn Leu Lys Asn Gly
        275                 280                 285

Val Asn Asp Ile Lys Asn His Lys Trp Phe Ala Thr Thr Asp Trp Ile
    290                 295                 300

Ala Ile Tyr Gln Arg Lys Val Glu Ala Pro Phe Ile Pro Lys Phe Lys
305                 310                 315                 320

Gly Pro Gly Asp Thr Ser Asn Phe Asp Asp Tyr Glu Glu Glu Ile
                325                 330                 335

Arg Val Ser Ile Asn Glu Lys Cys Gly Lys Glu Phe Thr Glu Phe
            340                 345                 350

```
<210> SEQ ID NO 7
<211> LENGTH: 1382
<212> TYPE: PRT
```

-continued

```
<213> ORGANISM: Human

<400> SEQUENCE: 7

Met Gly Thr Gly Gly Arg Arg Gly Ala Ala Ala Pro Leu Leu Val
1               5                   10                  15

Ala Val Ala Ala Leu Leu Leu Gly Ala Ala Gly His Leu Tyr Pro Gly
            20                  25                  30

Glu Val Cys Pro Gly Met Asp Ile Arg Asn Asn Leu Thr Arg Leu His
            35                  40                  45

Glu Leu Glu Asn Cys Ser Val Ile Glu Gly His Leu Gln Ile Leu Leu
    50                  55                  60

Met Phe Lys Thr Arg Pro Glu Asp Phe Arg Asp Leu Ser Phe Pro Lys
65                  70                  75                  80

Leu Ile Met Ile Thr Asp Tyr Leu Leu Leu Phe Arg Val Tyr Gly Leu
                85                  90                  95

Glu Ser Leu Lys Asp Leu Phe Pro Asn Leu Thr Val Ile Arg Gly Ser
                100                 105                 110

Arg Leu Phe Phe Asn Tyr Ala Leu Val Ile Phe Glu Met Val His Leu
            115                 120                 125

Lys Glu Leu Gly Leu Tyr Asn Leu Met Asn Ile Thr Arg Gly Ser Val
130                 135                 140

Arg Ile Glu Lys Asn Asn Glu Leu Cys Tyr Leu Ala Thr Ile Asp Trp
145                 150                 155                 160

Ser Arg Ile Leu Asp Ser Val Glu Asp Asn His Ile Val Leu Asn Lys
                165                 170                 175

Asp Asp Asn Glu Glu Cys Gly Asp Ile Cys Pro Gly Thr Ala Lys Gly
            180                 185                 190

Lys Thr Asn Cys Pro Ala Thr Val Ile Asn Gly Gln Phe Val Glu Arg
            195                 200                 205

Cys Trp Thr His Ser His Cys Gln Lys Val Cys Pro Thr Ile Cys Lys
            210                 215                 220

Ser His Gly Cys Thr Ala Glu Gly Leu Cys Cys His Ser Glu Cys Leu
225                 230                 235                 240

Gly Asn Cys Ser Gln Pro Asp Asp Pro Thr Lys Cys Val Ala Cys Arg
                245                 250                 255

Asn Phe Tyr Leu Asp Gly Arg Cys Val Glu Thr Cys Pro Pro Pro Tyr
            260                 265                 270

Tyr His Phe Gln Asp Trp Arg Cys Val Asn Phe Ser Phe Cys Gln Asp
            275                 280                 285

Leu His His Lys Cys Lys Asn Ser Arg Arg Gln Gly Cys His Gln Tyr
    290                 295                 300

Val Ile His Asn Asn Lys Cys Ile Pro Glu Cys Pro Ser Gly Tyr Thr
305                 310                 315                 320

Met Asn Ser Ser Asn Leu Leu Cys Thr Pro Cys Leu Gly Pro Cys Pro
                325                 330                 335

Lys Val Cys His Leu Leu Glu Gly Glu Lys Thr Ile Asp Ser Val Thr
            340                 345                 350

Ser Ala Gln Glu Leu Arg Gly Cys Thr Val Ile Asn Gly Ser Leu Ile
            355                 360                 365

Ile Asn Ile Arg Gly Gly Asn Asn Leu Ala Ala Glu Leu Glu Ala Asn
    370                 375                 380

Leu Gly Leu Ile Glu Glu Ile Ser Gly Tyr Leu Lys Ile Arg Arg Ser
385                 390                 395                 400
```

-continued

Tyr Ala Leu Val Ser Leu Ser Phe Phe Arg Lys Leu Arg Leu Ile Arg
                405                 410                 415
Gly Glu Thr Leu Glu Ile Gly Asn Tyr Ser Phe Tyr Ala Leu Asp Asn
            420                 425                 430
Gln Asn Leu Arg Gln Leu Trp Asp Trp Ser Lys His Asn Leu Thr Thr
        435                 440                 445
Thr Gln Gly Lys Leu Phe Phe His Tyr Asn Pro Lys Leu Cys Leu Ser
    450                 455                 460
Glu Ile His Lys Met Glu Glu Val Ser Gly Thr Lys Gly Arg Gln Glu
465                 470                 475                 480
Arg Asn Asp Ile Ala Leu Lys Thr Asn Gly Asp Lys Ala Ser Cys Glu
                485                 490                 495
Asn Glu Leu Leu Lys Phe Ser Tyr Ile Arg Thr Ser Phe Asp Lys Ile
            500                 505                 510
Leu Leu Arg Trp Glu Pro Tyr Trp Pro Pro Asp Phe Arg Asp Leu Leu
        515                 520                 525
Gly Phe Met Leu Phe Tyr Lys Glu Ala Pro Tyr Gln Asn Val Thr Glu
    530                 535                 540
Phe Asp Gly Gln Asp Ala Cys Gly Ser Asn Ser Trp Thr Val Val Asp
545                 550                 555                 560
Ile Asp Pro Pro Leu Arg Ser Asn Asp Pro Lys Ser Gln Asn His Pro
                565                 570                 575
Gly Trp Leu Met Arg Gly Leu Lys Pro Trp Thr Gln Tyr Ala Ile Phe
            580                 585                 590
Val Lys Thr Leu Val Thr Phe Ser Asp Glu Arg Arg Thr Tyr Gly Ala
        595                 600                 605
Lys Ser Asp Ile Ile Tyr Val Gln Thr Asp Ala Thr Asn Pro Ser Val
    610                 615                 620
Pro Leu Asp Pro Ile Ser Val Ser Asn Ser Ser Ser Gln Ile Ile Leu
625                 630                 635                 640
Lys Trp Lys Pro Pro Ser Asp Pro Asn Gly Asn Ile Thr His Tyr Leu
                645                 650                 655
Val Phe Trp Glu Arg Gln Ala Glu Asp Ser Glu Leu Phe Glu Leu Asp
            660                 665                 670
Tyr Cys Leu Lys Gly Leu Lys Leu Pro Ser Arg Thr Trp Ser Pro Pro
        675                 680                 685
Phe Glu Ser Glu Asp Ser Gln Lys His Asn Gln Ser Glu Tyr Glu Asp
    690                 695                 700
Ser Ala Gly Glu Cys Cys Ser Cys Pro Lys Thr Asp Ser Gln Ile Leu
705                 710                 715                 720
Lys Glu Leu Glu Glu Ser Ser Phe Arg Lys Thr Phe Glu Asp Tyr Leu
                725                 730                 735
His Asn Val Val Phe Val Pro Arg Lys Thr Ser Ser Gly Thr Gly Ala
            740                 745                 750
Glu Asp Pro Arg Pro Ser Arg Lys Arg Arg Ser Leu Gly Asp Val Gly
        755                 760                 765
Asn Val Thr Val Ala Val Pro Thr Val Ala Ala Phe Pro Asn Thr Ser
    770                 775                 780
Ser Thr Ser Val Pro Thr Ser Pro Glu Glu His Arg Pro Phe Glu Lys
785                 790                 795                 800
Val Val Asn Lys Glu Ser Leu Val Ile Ser Gly Leu Arg His Phe Thr
                805                 810                 815
Gly Tyr Arg Ile Glu Leu Gln Ala Cys Asn Gln Asp Thr Pro Glu Glu

-continued

```
                820                 825                 830
Arg Cys Ser Val Ala Ala Tyr Val Ser Ala Arg Thr Met Pro Glu Ala
                835                 840                 845
Lys Ala Asp Asp Ile Val Gly Pro Val Thr His Glu Ile Phe Glu Asn
850                 855                 860
Asn Val Val His Leu Met Trp Gln Glu Pro Lys Glu Pro Asn Gly Leu
865                 870                 875                 880
Ile Val Leu Tyr Glu Val Ser Tyr Arg Arg Tyr Gly Asp Glu Glu Leu
                885                 890                 895
His Leu Cys Val Ser Arg Lys His Phe Ala Leu Glu Arg Gly Cys Arg
                900                 905                 910
Leu Arg Gly Leu Ser Pro Gly Asn Tyr Ser Val Arg Ile Arg Ala Thr
                915                 920                 925
Ser Leu Ala Gly Asn Gly Ser Trp Thr Glu Pro Thr Tyr Phe Tyr Val
                930                 935                 940
Thr Asp Tyr Leu Asp Val Pro Ser Asn Ile Ala Lys Ile Ile Ile Gly
945                 950                 955                 960
Pro Leu Ile Phe Val Phe Leu Phe Ser Val Val Ile Gly Ser Ile Tyr
                965                 970                 975
Leu Phe Leu Arg Lys Arg Gln Pro Asp Gly Pro Leu Gly Pro Leu Tyr
                980                 985                 990
Ala Ser Ser Asn Pro Glu Tyr Leu  Ser Ala Ser Asp Val  Phe Pro Cys
                995                1000                1005
Ser Val  Tyr Val Pro Asp Glu  Trp Glu Val Ser Arg  Glu Lys Ile
   1010                1015                1020
Thr Leu  Leu Arg Glu Leu Gly  Gln Gly Ser Phe Gly  Met Val Tyr
   1025                1030                1035
Glu Gly  Asn Ala Arg Asp Ile  Ile Lys Gly Glu Ala  Glu Thr Arg
   1040                1045                1050
Val Ala  Val Lys Thr Val Asn  Glu Ser Ala Ser Leu  Arg Glu Arg
   1055                1060                1065
Ile Glu  Phe Leu Asn Glu Ala  Ser Val Met Lys Gly  Phe Thr Cys
   1070                1075                1080
His His  Val Val Arg Leu Leu  Gly Val Val Ser Lys  Gly Gln Pro
   1085                1090                1095
Thr Leu  Val Val Met Glu Leu  Met Ala His Gly Asp  Leu Lys Ser
   1100                1105                1110
Tyr Leu  Arg Ser Leu Arg Pro  Glu Ala Glu Asn Asn  Pro Gly Arg
   1115                1120                1125
Pro Pro  Pro Thr Leu Gln Glu  Met Ile Gln Met Ala  Ala Glu Ile
   1130                1135                1140
Ala Asp  Gly Met Ala Tyr Leu  Asn Ala Lys Lys Phe  Val His Arg
   1145                1150                1155
Asp Leu  Ala Ala Arg Asn Cys  Met Val Ala His Asp  Phe Thr Val
   1160                1165                1170
Lys Ile  Gly Asp Phe Gly Met  Thr Arg Asp Ile Tyr  Glu Thr Asp
   1175                1180                1185
Tyr Tyr  Arg Lys Gly Gly Lys  Gly Leu Leu Pro Val  Arg Trp Met
   1190                1195                1200
Ala Pro  Glu Ser Leu Lys Asp  Gly Val Phe Thr Thr  Ser Ser Asp
   1205                1210                1215
Met Trp  Ser Phe Gly Val Val  Leu Trp Glu Ile Thr  Ser Leu Ala
   1220                1225                1230
```

-continued

```
Glu Gln Pro Tyr Gln Gly Leu Ser Asn Glu Gln Val Leu Lys Phe
    1235                1240                1245
Val Met Asp Gly Gly Tyr Leu Asp Gln Pro Asp Asn Cys Pro Glu
    1250                1255                1260
Arg Val Thr Asp Leu Met Arg Met Cys Trp Gln Phe Asn Pro Lys
    1265                1270                1275
Met Arg Pro Thr Phe Leu Glu Ile Val Asn Leu Leu Lys Asp Asp
    1280                1285                1290
Leu His Pro Ser Phe Pro Glu Val Ser Phe Phe His Ser Glu Glu
    1295                1300                1305
Asn Lys Ala Pro Glu Ser Glu Leu Glu Met Glu Phe Glu Asp
    1310                1315                1320
Met Glu Asn Val Pro Leu Asp Arg Ser Ser His Cys Gln Arg Glu
    1325                1330                1335
Glu Ala Gly Gly Arg Asp Gly Gly Ser Ser Leu Gly Phe Lys Arg
    1340                1345                1350
Ser Tyr Glu Glu His Ile Pro Tyr Thr His Met Asn Gly Gly Lys
    1355                1360                1365
Lys Asn Gly Arg Ile Leu Thr Leu Pro Arg Ser Asn Pro Ser
    1370                1375                1380

<210> SEQ ID NO 8
<211> LENGTH: 509
<212> TYPE: PRT
<213> ORGANISM: Human

<400> SEQUENCE: 8

Met Gly Cys Gly Cys Ser Ser His Pro Glu Asp Asp Trp Met Glu Asn
1               5                   10                  15
Ile Asp Val Cys Glu Asn Cys His Tyr Pro Ile Val Pro Leu Asp Gly
                20                  25                  30
Lys Gly Thr Leu Leu Ile Arg Asn Gly Ser Glu Val Arg Asp Pro Leu
        35                  40                  45
Val Thr Tyr Glu Gly Ser Asn Pro Pro Ala Ser Pro Leu Gln Asp Asn
    50                  55                  60
Leu Val Ile Ala Leu His Ser Tyr Glu Pro Ser His Asp Gly Asp Leu
65                  70                  75                  80
Gly Phe Glu Lys Gly Glu Gln Leu Arg Ile Leu Glu Gln Ser Gly Glu
                85                  90                  95
Trp Trp Lys Ala Gln Ser Leu Thr Thr Gly Gln Glu Gly Phe Ile Pro
            100                 105                 110
Phe Asn Phe Val Ala Lys Ala Asn Ser Leu Glu Pro Glu Pro Trp Phe
        115                 120                 125
Phe Lys Asn Leu Ser Arg Lys Asp Ala Glu Arg Gln Leu Leu Ala Pro
    130                 135                 140
Gly Asn Thr His Gly Ser Phe Leu Ile Arg Glu Ser Glu Ser Thr Ala
145                 150                 155                 160
Gly Ser Phe Ser Leu Ser Val Arg Asp Phe Asp Gln Asn Gln Gly Glu
                165                 170                 175
Val Val Lys His Tyr Lys Ile Arg Asn Leu Asp Asn Gly Gly Phe Tyr
            180                 185                 190
Ile Ser Pro Arg Ile Thr Phe Pro Gly Leu His Glu Leu Val Arg His
        195                 200                 205
Tyr Thr Asn Ala Ser Asp Gly Leu Cys Thr Arg Leu Ser Arg Pro Cys
```

-continued

```
            210                 215                 220
Gln Thr Gln Lys Pro Gln Lys Pro Trp Trp Glu Asp Glu Trp Glu Val
225                 230                 235                 240

Pro Arg Glu Thr Leu Lys Leu Val Glu Arg Leu Gly Ala Gly Gln Phe
                245                 250                 255

Gly Glu Val Trp Met Gly Tyr Tyr Asn Gly His Thr Lys Val Ala Val
                260                 265                 270

Lys Ser Leu Lys Gln Gly Ser Met Ser Pro Asp Ala Phe Leu Ala Glu
                275                 280                 285

Ala Asn Leu Met Lys Gln Leu Gln His Gln Arg Leu Val Arg Leu Tyr
290                 295                 300

Ala Val Val Thr Gln Glu Pro Ile Tyr Ile Ile Thr Glu Tyr Met Glu
305                 310                 315                 320

Asn Gly Ser Leu Val Asp Phe Leu Lys Thr Pro Ser Gly Ile Lys Leu
                325                 330                 335

Thr Ile Asn Lys Leu Leu Asp Met Ala Ala Gln Ile Ala Glu Gly Met
                340                 345                 350

Ala Phe Ile Glu Glu Arg Asn Tyr Ile His Arg Asp Leu Arg Ala Ala
                355                 360                 365

Asn Ile Leu Val Ser Asp Thr Leu Ser Cys Lys Ile Ala Asp Phe Gly
370                 375                 380

Leu Ala Arg Leu Ile Glu Asp Asn Glu Tyr Thr Ala Arg Glu Gly Ala
385                 390                 395                 400

Lys Phe Pro Ile Lys Trp Thr Ala Pro Glu Ala Ile Asn Tyr Gly Thr
                405                 410                 415

Phe Thr Ile Lys Ser Asp Val Trp Ser Phe Gly Ile Leu Leu Thr Glu
                420                 425                 430

Ile Val Thr His Gly Arg Ile Pro Tyr Pro Gly Met Thr Asn Pro Glu
                435                 440                 445

Val Ile Gln Asn Leu Glu Arg Gly Tyr Arg Met Val Arg Pro Asp Asn
450                 455                 460

Cys Pro Glu Glu Leu Tyr Gln Leu Met Arg Leu Cys Trp Lys Glu Arg
465                 470                 475                 480

Pro Glu Asp Arg Pro Thr Phe Asp Tyr Leu Arg Ser Val Leu Glu Asp
                485                 490                 495

Phe Phe Thr Ala Thr Glu Gly Gln Tyr Gln Pro Gln
                500                 505

<210> SEQ ID NO 9
<211> LENGTH: 619
<212> TYPE: PRT
<213> ORGANISM: Human

<400> SEQUENCE: 9

Met Pro Asp Pro Ala Ala His Leu Pro Phe Phe Tyr Gly Ser Ile Ser
1               5                   10                  15

Arg Ala Glu Ala Glu Glu His Leu Lys Leu Ala Gly Met Ala Asp Gly
                20                  25                  30

Leu Phe Leu Leu Arg Gln Cys Leu Arg Ser Leu Gly Gly Tyr Val Leu
                35                  40                  45

Ser Leu Val His Asp Val Arg Phe His His Phe Pro Ile Glu Arg Gln
                50                  55                  60

Leu Asn Gly Thr Tyr Ala Ile Ala Gly Gly Lys Ala His Cys Gly Pro
65                  70                  75                  80
```

-continued

```
Ala Glu Leu Cys Glu Phe Tyr Ser Arg Asp Pro Asp Gly Leu Pro Cys
                 85                  90                  95

Asn Leu Arg Lys Pro Cys Asn Arg Pro Ser Gly Leu Glu Pro Gln Pro
            100                 105                 110

Gly Val Phe Asp Cys Leu Arg Asp Ala Met Val Arg Asp Tyr Val Arg
            115                 120                 125

Gln Thr Trp Lys Leu Glu Gly Glu Ala Leu Glu Gln Ala Ile Ile Ser
        130                 135                 140

Gln Ala Pro Gln Val Glu Lys Leu Ile Ala Thr Thr Ala His Glu Arg
145                 150                 155                 160

Met Pro Trp Tyr His Ser Ser Leu Thr Arg Glu Glu Ala Glu Arg Lys
                165                 170                 175

Leu Tyr Ser Gly Ala Gln Thr Asp Gly Lys Phe Leu Leu Arg Pro Arg
                180                 185                 190

Lys Glu Gln Gly Thr Tyr Ala Leu Ser Leu Ile Tyr Gly Lys Thr Val
            195                 200                 205

Tyr His Tyr Leu Ile Ser Gln Asp Lys Ala Gly Lys Tyr Cys Ile Pro
        210                 215                 220

Glu Gly Thr Lys Phe Asp Thr Leu Trp Gln Leu Val Glu Tyr Leu Lys
225                 230                 235                 240

Leu Lys Ala Asp Gly Leu Ile Tyr Cys Leu Lys Glu Ala Cys Pro Asn
                245                 250                 255

Ser Ser Ala Ser Asn Ala Ser Gly Ala Ala Ala Pro Thr Leu Pro Ala
                260                 265                 270

His Pro Ser Thr Leu Thr His Pro Gln Arg Arg Ile Asp Thr Leu Asn
            275                 280                 285

Ser Asp Gly Tyr Thr Pro Glu Pro Ala Arg Ile Thr Ser Pro Asp Lys
        290                 295                 300

Pro Arg Pro Met Pro Met Asp Thr Ser Val Tyr Glu Ser Pro Tyr Ser
305                 310                 315                 320

Asp Pro Glu Glu Leu Lys Asp Lys Lys Leu Phe Leu Lys Arg Asp Asn
                325                 330                 335

Leu Leu Ile Ala Asp Ile Glu Leu Gly Cys Gly Asn Phe Gly Ser Val
                340                 345                 350

Arg Gln Gly Val Tyr Arg Met Arg Lys Lys Gln Ile Asp Val Ala Ile
            355                 360                 365

Lys Val Leu Lys Gln Gly Thr Glu Lys Ala Asp Thr Glu Glu Met Met
        370                 375                 380

Arg Glu Ala Gln Ile Met His Gln Leu Asp Asn Pro Tyr Ile Val Arg
385                 390                 395                 400

Leu Ile Gly Val Cys Gln Ala Glu Ala Leu Met Leu Val Met Glu Met
                405                 410                 415

Ala Gly Gly Gly Pro Leu His Lys Phe Leu Val Gly Lys Arg Glu Glu
                420                 425                 430

Ile Pro Val Ser Asn Val Ala Glu Leu Leu His Gln Val Ser Met Gly
            435                 440                 445

Met Lys Tyr Leu Glu Glu Lys Asn Phe Val His Arg Asp Leu Ala Ala
        450                 455                 460

Arg Asn Val Leu Leu Val Asn Arg His Tyr Ala Lys Ile Ser Asp Phe
465                 470                 475                 480

Gly Leu Ser Lys Ala Leu Gly Ala Asp Asp Ser Tyr Tyr Thr Ala Arg
                485                 490                 495

Ser Ala Gly Lys Trp Pro Leu Lys Trp Tyr Ala Pro Glu Cys Ile Asn
```

```
                    500                 505                 510
Phe Arg Lys Phe Ser Ser Arg Ser Asp Val Trp Ser Tyr Gly Val Thr
            515                 520                 525

Met Trp Glu Ala Leu Ser Tyr Gly Gln Lys Pro Tyr Lys Lys Met Lys
    530                 535                 540

Gly Pro Glu Val Met Ala Phe Ile Glu Gln Gly Lys Arg Met Glu Cys
545                 550                 555                 560

Pro Pro Glu Cys Pro Pro Glu Leu Tyr Ala Leu Met Ser Asp Cys Trp
                565                 570                 575

Ile Tyr Lys Trp Glu Asp Arg Pro Asp Phe Leu Thr Val Glu Gln Arg
            580                 585                 590

Met Arg Ala Cys Tyr Tyr Ser Leu Ala Ser Lys Val Glu Gly Pro Pro
        595                 600                 605

Gly Ser Thr Gln Lys Ala Glu Ala Ala Cys Ala
    610                 615

<210> SEQ ID NO 10
<211> LENGTH: 416
<212> TYPE: PRT
<213> ORGANISM: Human

<400> SEQUENCE: 10

Leu Phe His Lys Ala Lys Phe Gln Glu Cys His Lys Asn Leu Ile Ser
1               5                   10                  15

Ile Val His Tyr Val Ala Phe Lys Val Leu Thr Trp Lys Arg Thr Lys
            20                  25                  30

Ile Ser Asp Phe Asn Phe Tyr Gly Ser Leu Gly Ser Gly Ser Phe Gly
        35                  40                  45

Thr Ala Lys Leu Cys Arg His Arg Gly Ser Gly Leu Phe Phe Cys Ser
    50                  55                  60

Lys Thr Leu Arg Arg Glu Thr Ile Val His Glu Lys His Lys Glu His
65                  70                  75                  80

Val Asn Asn Glu Ile Asn Ile Met Leu Asn Ile Ser His Pro Tyr Ile
                85                  90                  95

Val Lys Thr Tyr Ser Thr Phe Asn Thr Pro Thr Lys Ile His Phe Ile
            100                 105                 110

Met Glu Tyr Ala Gly Lys Lys Asp Leu Phe His His Leu Arg Ala Asn
        115                 120                 125

Lys Cys Phe Thr Glu Gln Thr Thr Lys Leu Ile Val Ala Glu Ile Val
    130                 135                 140

Leu Ala Ile Glu Tyr Leu His Ala Glu Asn Ile Ile Tyr Arg Asp Leu
145                 150                 155                 160

Lys Pro Glu Asn Ile Leu Ile Asp Glu Lys Gly His Ile Lys Leu Thr
                165                 170                 175

Asp Phe Gly Phe Ser Lys Lys Thr Val Gly Gly Lys Asn Thr Ser Ser
            180                 185                 190

Val Cys Gly Thr Phe Asp Tyr Met Ala Pro Glu Ile Leu Asn Ser Ser
        195                 200                 205

Asn Gly His Gly Lys Pro Val Asp Trp Trp Ala Leu Gly Val Val Val
    210                 215                 220

Tyr Glu Leu Val Thr Gly Lys Leu Pro Phe Ser Asn Ser Lys Glu Ser
225                 230                 235                 240

Leu Leu Asn Arg Lys Ala Asp Phe Gln Leu Ile Phe Gln Asn Ser Tyr
                245                 250                 255
```

```
Leu Ser Asp Glu Ile Lys Asp Phe Ile Phe Gln Leu Leu Ser Val Asp
            260                 265                 270

Pro Ser Lys Arg Leu Gly Thr Phe Asp Ser Cys Ser Ile Arg Asn His
        275                 280                 285

Lys Trp Phe Ser Asp Ile Asn Trp Leu His Leu Glu Ser Lys Tyr Gln
        290                 295                 300

Ile Asp Gly Pro Leu Ser Thr Leu Asn Ser Phe Ile Asn Cys Asp Phe
305                 310                 315                 320

Asn Ile Asn Leu Leu Lys Lys Ser Lys Ser Tyr Thr Glu Gln Gln Gln
                325                 330                 335

Gln Gln Gln Gln Leu Pro Gln Gln Gln Gln Gln Gln Gln Gln Asn Asn
            340                 345                 350

Gln Leu Phe Asn Gln Thr Leu Gln Gln Gln Asn Phe Asn Phe His Pro
        355                 360                 365

Ile Gln Pro Gln Gln Gln Gln Gln Gln Gln Phe Phe Asn Phe Gln Phe
        370                 375                 380

Asn Asn Asn Asn Phe Asn Asn Asn Asn Asn Asn Asn Asn Phe Asn
385                 390                 395                 400

Glu Ala Cys Thr Ser Asn Thr Cys Gly Gly Thr Thr Ala Ser Ile Phe
                405                 410                 415

<210> SEQ ID NO 11
<211> LENGTH: 1151
<212> TYPE: PRT
<213> ORGANISM: Yeast

<400> SEQUENCE: 11

Met Ser Phe Ser Gln Leu Glu Gln Asn Ile Lys Lys Lys Ile Ala Val
1               5                   10                  15

Glu Glu Asn Ile Ile Arg Gly Ala Ser Ala Leu Lys Lys Lys Thr Ser
            20                  25                  30

Asn Val Met Val Ile Gln Lys Cys Asn Thr Asn Ile Arg Glu Ala Arg
        35                  40                  45

Gln Asn Leu Glu Tyr Leu Glu Asp Ser Leu Lys Lys Leu Arg Leu Lys
    50                  55                  60

Thr Ala Gln Gln Ser Gln Gly Glu Asn Gly Ser Glu Asp Asn Glu Arg
65                  70                  75                  80

Phe Asn Ser Lys Glu Tyr Gly Phe Leu Ser Thr Lys Ser Pro Asn Glu
                85                  90                  95

His Ile Phe Ser Arg Leu Asp Leu Val Lys Tyr Asp Cys Pro Ser Leu
            100                 105                 110

Ala Gln Arg Ile Gln Tyr Met Leu Gln Gln Leu Glu Phe Lys Leu Gln
        115                 120                 125

Val Glu Lys Gln Tyr Gln Glu Ala Asn Thr Lys Leu Thr Lys Leu Tyr
    130                 135                 140

Gln Ile Asp Gly Asp Gln Arg Ser Ser Ser Ala Ala Glu Gly Gly Ala
145                 150                 155                 160

Met Glu Ser Lys Tyr Arg Ile Gln Met Leu Asn Lys Ala Leu Lys Lys
                165                 170                 175

Tyr Gln Ala Ile Asn Val Asp Phe Asp Gln Phe Lys His Gln Pro Asn
            180                 185                 190

Asp Ile Met Asp Asn Gln Gln Pro Lys Phe Arg Arg Lys Gln Leu Thr
        195                 200                 205

Gly Val Leu Thr Ile Gly Ile Thr Ala Ala Arg Asp Val Asp His Ile
    210                 215                 220
```

-continued

```
Gln Ser Pro Met Phe Ala Arg Lys Pro Glu Ser Tyr Val Thr Ile Lys
225                 230                 235                 240

Ile Asp Asp Thr Ile Lys Ala Arg Thr Lys Pro Ser Arg Asn Asp Arg
            245                 250                 255

Trp Ser Glu Asp Phe Gln Ile Pro Val Glu Lys Gly Asn Glu Ile Glu
        260                 265                 270

Ile Thr Val Tyr Asp Lys Val Asn Asp Ser Leu Ile Pro Val Ala Ile
    275                 280                 285

Met Trp Leu Leu Leu Ser Asp Ile Ala Glu Ile Arg Lys Lys Lys
290                 295                 300

Ala Gly Gln Thr Asn Glu Gln Gln Gly Trp Val Asn Ala Ser Asn Ile
305                 310                 315                 320

Asn Gly Gly Ser Ser Leu Ala Ser Glu Glu Gly Ser Thr Leu Thr Ser
                325                 330                 335

Thr Tyr Ser Asn Ser Ala Ile Gln Ser Thr Ser Ala Lys Asn Val Gln
            340                 345                 350

Gly Glu Asn Thr Ser Thr Ser Gln Ile Ser Thr Asn Ser Trp Phe Val
        355                 360                 365

Leu Glu Pro Ser Gly Gln Ile Leu Leu Thr Leu Gly Phe His Lys Ser
    370                 375                 380

Ser Gln Ile Glu Arg Lys Gln Leu Met Gly Gly Leu His Arg His Gly
385                 390                 395                 400

Ala Ile Ile Asn Arg Lys Glu Glu Ile Phe Glu Gln His Gly His His
                405                 410                 415

Phe Val Gln Lys Ser Phe Tyr Asn Ile Met Cys Cys Ala Tyr Cys Gly
            420                 425                 430

Asp Phe Leu Arg Tyr Thr Gly Phe Gln Cys Gln Asp Cys Lys Phe Leu
        435                 440                 445

Cys His Lys Lys Cys Tyr Thr Asn Val Val Thr Lys Cys Ile Ala Lys
    450                 455                 460

Thr Ser Thr Asp Thr Asp Pro Asp Glu Ala Lys Leu Asn His Arg Ile
465                 470                 475                 480

Pro His Arg Phe Leu Pro Thr Ser Asn Arg Gly Thr Lys Trp Cys Cys
                485                 490                 495

His Cys Gly Tyr Ile Leu Pro Trp Gly Arg His Lys Val Arg Lys Cys
            500                 505                 510

Ser Glu Cys Gly Ile Met Cys His Ala Gln Cys Ala His Leu Val Pro
        515                 520                 525

Asp Phe Cys Gly Met Ser Met Glu Met Ala Asn Lys Ile Leu Lys Thr
    530                 535                 540

Ile Gln Asp Thr Lys Arg Asn Gln Glu Lys Lys Lys Arg Thr Val Pro
545                 550                 555                 560

Ser Ala Gln Leu Gly Ser Ser Ile Gly Thr Ala Asn Gly Ser Asp Leu
                565                 570                 575

Ser Pro Ser Lys Leu Ala Glu Arg Ala Asn Ala Pro Leu Pro Pro Gln
            580                 585                 590

Pro Arg Lys His Asp Lys Thr Pro Ser Pro Gln Lys Val Gly Arg Asp
        595                 600                 605

Ser Pro Thr Lys Gln His Asp Pro Ile Ile Asp Lys Ile Ser Leu
    610                 615                 620

Gln Thr His Gly Arg Glu Lys Leu Asn Lys Phe Ile Asp Glu Asn Glu
625                 630                 635                 640
```

-continued

```
Ala Tyr Leu Asn Phe Thr Glu Gly Ala Gln Gln Thr Ala Glu Phe Ser
            645                 650                 655

Ser Pro Glu Lys Thr Leu Asp Pro Thr Ser Asn Arg Arg Ser Leu Gly
            660                 665                 670

Leu Thr Asp Leu Ser Ile Glu His Ser Gln Thr Trp Glu Ser Lys Asp
            675                 680                 685

Asp Leu Met Arg Asp Glu Leu Glu Leu Trp Lys Ala Gln Arg Glu Glu
            690                 695                 700

Met Glu Leu Glu Ile Lys Gln Asp Ser Gly Glu Ile Gln Glu Asp Leu
705                 710                 715                 720

Glu Val Asp His Ile Asp Leu Glu Thr Lys Gln Lys Leu Asp Trp Glu
                    725                 730                 735

Asn Lys Asn Asp Phe Arg Glu Ala Asp Leu Thr Ile Asp Ser Thr His
            740                 745                 750

Thr Asn Pro Phe Arg Asp Met Asn Ser Glu Thr Phe Gln Ile Glu Gln
            755                 760                 765

Asp His Ala Ser Lys Glu Val Leu Gln Glu Thr Val Ser Leu Ala Pro
            770                 775                 780

Thr Ser Thr His Pro Ser Arg Thr Thr Asp Gln Gln Ser Pro Gln Lys
785                 790                 795                 800

Ser Gln Thr Ser Thr Ser Ala Lys His Lys Lys Arg Ala Ala Lys Arg
                    805                 810                 815

Arg Lys Val Ser Leu Asp Asn Phe Val Leu Lys Val Leu Gly Lys
            820                 825                 830

Gly Asn Phe Gly Lys Val Ile Leu Ser Lys Ser Lys Asn Thr Asp Arg
            835                 840                 845

Leu Cys Ala Ile Lys Val Leu Lys Lys Asp Asn Ile Ile Gln Asn His
850                 855                 860

Asp Ile Glu Ser Ala Arg Ala Glu Lys Lys Val Phe Leu Leu Ala Thr
865                 870                 875                 880

Lys Thr Lys His Pro Phe Leu Thr Asn Leu Tyr Cys Ser Phe Gln Thr
                    885                 890                 895

Glu Asn Arg Ile Tyr Phe Ala Met Glu Phe Ile Gly Gly Asp Leu
            900                 905                 910

Met Trp His Val Gln Asn Gln Arg Leu Ser Val Arg Arg Ala Lys Phe
    915                 920                 925

Tyr Ala Ala Glu Val Leu Leu Ala Leu Lys Tyr Phe His Asp Asn Gly
930                 935                 940

Val Ile Tyr Arg Asp Leu Lys Leu Glu Asn Ile Leu Leu Thr Pro Glu
945                 950                 955                 960

Gly His Ile Lys Ile Ala Asp Tyr Gly Leu Cys Lys Asp Glu Met Trp
            965                 970                 975

Tyr Gly Asn Arg Thr Ser Thr Phe Cys Gly Thr Pro Glu Phe Met Ala
            980                 985                 990

Pro Glu Ile Leu Lys Glu Gln Glu Tyr Thr Lys Ala Val Asp Trp Trp
    995                 1000                1005

Ala Phe Gly Val Leu Leu Tyr Gln Met Leu Leu Cys Gln Ser Pro
    1010                1015                1020

Phe Ser Gly Asp Asp Glu Asp Glu Val Phe Asn Ala Ile Leu Thr
    1025                1030                1035

Asp Glu Pro Leu Tyr Pro Ile Asp Met Ala Gly Glu Ile Val Gln
    1040                1045                1050

Ile Phe Gln Gly Leu Leu Thr Lys Asp Pro Glu Lys Arg Leu Gly
```

-continued

```
            1055                1060                1065

Ala Gly Pro Arg Asp Ala Asp Glu Val Met Glu Pro Phe Phe
    1070                1075                1080

Arg Asn Ile Asn Phe Asp Asp Ile Leu Asn Leu Arg Val Lys Pro
    1085                1090                1095

Pro Tyr Ile Pro Glu Ile Lys Ser Pro Glu Asp Thr Ser Tyr Phe
    1100                1105                1110

Glu Gln Glu Phe Thr Ser Ala Pro Pro Thr Leu Thr Pro Leu Pro
    1115                1120                1125

Ser Val Leu Thr Thr Ser Gln Gln Glu Phe Arg Gly Phe Ser
    1130                1135                1140

Phe Met Pro Asp Asp Leu Asp Leu
    1145                1150

<210> SEQ ID NO 12
<211> LENGTH: 484
<212> TYPE: PRT
<213> ORGANISM: Human

<400> SEQUENCE: 12

Met Arg His Ser Lys Arg Thr Tyr Cys Pro Asp Trp Asp Asp Lys Asp
1               5                   10                  15

Trp Asp Tyr Gly Lys Trp Arg Ser Ser Ser His Lys Arg Arg Lys
                20                  25                  30

Arg Ser His Ser Ser Ala Gln Glu Asn Lys Arg Cys Lys Tyr Asn His
                35                  40                  45

Ser Lys Met Cys Asp Ser His Tyr Leu Glu Ser Arg Ser Ile Asn Glu
    50                  55                  60

Lys Asp Tyr His Ser Arg Arg Tyr Ile Asp Glu Tyr Arg Asn Asp Tyr
65                  70                  75                  80

Thr Gln Gly Cys Glu Pro Gly His Arg Gln Arg Asp His Glu Ser Arg
                85                  90                  95

Tyr Gln Asn His Ser Ser Lys Ser Ser Gly Arg Ser Gly Arg Ser Ser
                100                 105                 110

Tyr Lys Ser Lys His Arg Ile His His Ser Thr Ser His Arg Arg Ser
                115                 120                 125

His Gly Lys Ser His Arg Arg Lys Arg Thr Arg Ser Val Glu Asp Asp
    130                 135                 140

Glu Glu Gly His Leu Ile Cys Gln Ser Gly Asp Val Leu Ser Ala Arg
145                 150                 155                 160

Tyr Glu Ile Val Asp Thr Leu Gly Glu Gly Ala Phe Gly Lys Val Val
                165                 170                 175

Glu Cys Ile Asp His Lys Ala Gly Gly Arg His Val Ala Val Lys Ile
                180                 185                 190

Val Lys Asn Val Asp Arg Tyr Cys Glu Ala Ala Arg Ser Glu Ile Gln
                195                 200                 205

Val Leu Glu His Leu Asn Thr Thr Asp Pro Asn Ser Thr Phe Arg Cys
    210                 215                 220

Val Gln Met Leu Glu Trp Phe Glu His His Gly His Ile Cys Ile Val
225                 230                 235                 240

Phe Glu Leu Leu Gly Leu Ser Thr Tyr Asp Phe Ile Lys Glu Asn Gly
                245                 250                 255

Phe Leu Pro Phe Arg Leu Asp His Ile Arg Lys Met Ala Tyr Gln Ile
                260                 265                 270
```

```
Cys Lys Ser Val Asn Phe Leu His Ser Asn Lys Leu Thr His Thr Asp
        275                 280                 285

Leu Lys Pro Glu Asn Ile Leu Phe Val Gln Ser Asp Tyr Thr Glu Ala
    290                 295                 300

Tyr Asn Pro Lys Ile Lys Arg Asp Glu Arg Thr Leu Ile Asn Pro Asp
305                 310                 315                 320

Ile Lys Val Val Asp Phe Gly Ser Ala Thr Tyr Asp Asp Glu His His
                325                 330                 335

Ser Thr Leu Val Ser Thr Arg His Tyr Arg Ala Pro Glu Val Ile Leu
            340                 345                 350

Ala Leu Gly Trp Ser Gln Pro Cys Asp Val Trp Ser Ile Gly Cys Ile
        355                 360                 365

Leu Ile Glu Tyr Tyr Leu Gly Phe Thr Val Phe Pro Thr His Asp Ser
    370                 375                 380

Lys Glu His Leu Ala Met Met Glu Arg Ile Leu Gly Pro Leu Pro Lys
385                 390                 395                 400

His Met Ile Gln Lys Thr Arg Lys Arg Lys Tyr Phe His His Asp Arg
                405                 410                 415

Leu Asp Trp Asp Glu His Ser Ser Ala Gly Arg Tyr Val Ser Arg Ala
            420                 425                 430

Cys Lys Pro Leu Lys Glu Phe Met Leu Ser Gln Asp Val Glu His Glu
        435                 440                 445

Arg Leu Phe Asp Leu Ile Gln Lys Met Leu Glu Tyr Asp Pro Ala Lys
    450                 455                 460

Arg Ile Thr Leu Arg Glu Ala Leu Lys His Pro Phe Phe Asp Leu Leu
465                 470                 475                 480

Lys Lys Ser Ile

<210> SEQ ID NO 13
<211> LENGTH: 499
<212> TYPE: PRT
<213> ORGANISM: Human

<400> SEQUENCE: 13

Met Pro His Pro Arg Tyr His Ser Ser Glu Arg Gly Ser Arg Gly
1               5                   10                  15

Ser Tyr Arg Glu His Tyr Arg Ser Arg Lys His Lys Arg Arg Arg Ser
                20                  25                  30

Arg Ser Trp Ser Ser Ser Ser Asp Arg Thr Arg Arg Arg Arg Arg Glu
            35                  40                  45

Asp Ser Tyr His Val Arg Ser Arg Ser Tyr Asp Asp Arg Ser Ser
    50                  55                  60

Asp Arg Arg Val Tyr Asp Arg Tyr Cys Gly Ser Tyr Arg Arg Asn
65                  70                  75                  80

Asp Tyr Ser Arg Asp Arg Gly Asp Ala Tyr Tyr Asp Thr Asp Tyr Arg
                85                  90                  95

His Ser Tyr Glu Tyr Gln Arg Glu Asn Ser Ser Tyr Arg Ser Gln Arg
            100                 105                 110

Ser Ser Arg Arg Lys His Arg Arg Arg Arg Ser Arg Thr Phe
        115                 120                 125

Ser Arg Ser Ser Ser Gln His Ser Ser Arg Arg Ala Lys Ser Val Glu
    130                 135                 140

Asp Asp Ala Glu Gly His Leu Ile Tyr His Val Gly Asp Trp Leu Gln
145                 150                 155                 160
```

Glu Arg Tyr Glu Ile Val Ser Thr Leu Gly Glu Gly Thr Phe Gly Arg
                165                 170                 175

Val Val Gln Cys Val Asp His Arg Arg Gly Gly Ala Arg Val Ala Leu
            180                 185                 190

Lys Ile Ile Lys Asn Val Glu Lys Tyr Lys Glu Ala Ala Arg Leu Glu
        195                 200                 205

Ile Asn Val Leu Glu Lys Ile Asn Glu Lys Asp Pro Asp Asn Lys Asn
    210                 215                 220

Leu Cys Val Gln Met Phe Asp Trp Phe Asp Tyr His Gly His Met Cys
225                 230                 235                 240

Ile Ser Phe Glu Leu Leu Gly Leu Ser Thr Phe Asp Phe Leu Lys Asp
                245                 250                 255

Asn Asn Tyr Leu Pro Tyr Pro Ile His Gln Val Arg His Met Ala Phe
            260                 265                 270

Gln Leu Cys Gln Ala Val Lys Phe Leu His Asp Asn Lys Leu Thr His
        275                 280                 285

Thr Asp Leu Lys Pro Glu Asn Ile Leu Phe Val Asn Ser Asp Tyr Glu
    290                 295                 300

Leu Thr Tyr Asn Leu Glu Lys Lys Arg Asp Glu Arg Ser Val Lys Ser
305                 310                 315                 320

Thr Ala Val Arg Val Val Asp Phe Gly Ser Ala Thr Phe Asp His Glu
                325                 330                 335

His His Ser Thr Ile Val Ser Thr Arg His Tyr Arg Ala Pro Glu Val
            340                 345                 350

Ile Leu Glu Leu Gly Trp Ser Gln Pro Cys Asp Val Trp Ser Ile Gly
        355                 360                 365

Cys Ile Ile Phe Glu Tyr Tyr Val Gly Phe Thr Leu Phe Gln Thr His
    370                 375                 380

Asp Asn Arg Glu His Leu Ala Met Met Glu Arg Ile Leu Gly Pro Ile
385                 390                 395                 400

Pro Ser Arg Met Ile Arg Lys Thr Arg Lys Gln Lys Tyr Phe Tyr Arg
                405                 410                 415

Gly Arg Leu Asp Trp Asp Glu Asn Thr Ser Ala Gly Arg Tyr Val Arg
            420                 425                 430

Glu Asn Cys Lys Pro Leu Arg Arg Tyr Leu Thr Ser Glu Ala Glu Glu
        435                 440                 445

His His Gln Leu Phe Asp Leu Ile Glu Ser Met Leu Glu Tyr Glu Pro
    450                 455                 460

Ala Lys Arg Leu Thr Leu Gly Glu Ala Leu Gln His Pro Phe Phe Ala
465                 470                 475                 480

Arg Leu Arg Ala Glu Pro Pro Asn Lys Leu Trp Asp Ser Ser Arg Asp
                485                 490                 495

Ile Ser Arg

<210> SEQ ID NO 14
<211> LENGTH: 517
<212> TYPE: PRT
<213> ORGANISM: DROME - Drosophila Melanogaster Fruit Fly

<400> SEQUENCE: 14

Met Cys Val Arg Phe Gln Met Pro Arg Thr Arg Arg Leu His His Ser
1               5                   10                  15

Arg Asp Arg Ser Ser Ala Gly Thr Arg Asp Lys Arg Arg Arg His Asp
            20                  25                  30

```
Thr Ala Asp His Ser Pro Pro Leu Ala Glu Ala Pro Ser Pro Pro Arg
         35                  40                  45

Ile Thr Asn Thr His His Thr Arg Ser Ala Ala Lys Arg Arg Arg His
         50                  55                  60

Glu Leu Asp Ala Lys Lys Ala Gln Ile Ser Lys Glu Pro Thr Phe Asp
 65                  70                  75                  80

Asp Ser Ile Ser Thr Arg Arg Lys Glu Arg Ser Lys Arg Ser His
                 85                  90                  95

Arg Lys Ser Pro Ala Ala Ser Arg Arg Gln His Lys Tyr Arg Tyr Arg
                100                 105                 110

Asp Glu Thr Ser His Ser Ser Arg Arg Arg His Arg Asp Arg Ala
                115                 120                 125

Lys Asp Glu Arg Asp Ser Gly Arg Asn Asn Arg Gln Ser Gln Ala Lys
130                 135                 140

Thr Ala Lys Pro Val Ile Gln Asp Asp Ala Asp Gly His Leu Ile Tyr
145                 150                 155                 160

His Thr Gly Asp Ile Leu His His Arg Tyr Lys Ile Met Ala Thr Leu
                165                 170                 175

Gly Glu Gly Thr Phe Gly Arg Val Val Lys Val Lys Asp Met Glu Arg
                180                 185                 190

Asp Tyr Cys Met Ala Leu Lys Ile Ile Lys Asn Val Glu Lys Tyr Arg
                195                 200                 205

Glu Ala Ala Lys Leu Glu Ile Asn Ala Leu Glu Lys Ile Ala Gln Lys
210                 215                 220

Asp Pro His Cys Asp His Leu Cys Val Lys Met Ile Asp Trp Phe Asp
225                 230                 235                 240

Tyr His Gly His Met Cys Ile Val Phe Glu Met Leu Gly Leu Ser Val
                245                 250                 255

Phe Asp Phe Leu Arg Glu Asn Asn Tyr Glu Pro Tyr Pro Leu Asp Gln
                260                 265                 270

Val Arg His Met Ala Tyr Gln Leu Cys Tyr Ser Val Lys Phe Leu His
                275                 280                 285

Asp Asn Arg Leu Thr His Thr Asp Leu Lys Pro Glu Asn Ile Leu Phe
290                 295                 300

Val Asp Ser Asp Tyr Thr Ser His Tyr Asn His Lys Ile Asn Arg Glu
305                 310                 315                 320

Val Arg Arg Val Lys Asn Thr Asp Val Arg Leu Ile Asp Phe Gly Ser
                325                 330                 335

Ala Thr Phe Asp His Glu His His Ser Thr Ile Val Ser Thr Arg His
                340                 345                 350

Tyr Arg Ala Pro Glu Val Ile Leu Glu Leu Gly Trp Ser Gln Pro Cys
                355                 360                 365

Asp Val Trp Ser Ile Gly Cys Ile Leu Phe Glu Leu Tyr Leu Gly Ile
370                 375                 380

Thr Leu Phe Gln Thr His Asp Asn Arg Glu His Leu Ala Met Met Glu
385                 390                 395                 400

Arg Ile Leu Gly Gln Ile Pro Tyr Arg Met Ala Arg Lys Thr Lys Thr
                405                 410                 415

Lys Tyr Phe Tyr His Gly Lys Leu Asp Trp Asp Glu Lys Ser Ser Ala
                420                 425                 430

Gly Arg Tyr Val Arg Asp His Cys Lys Pro Leu Phe Leu Cys Gln Leu
                435                 440                 445

Ser Asp Ser Glu Asp His Cys Glu Leu Phe Ser Leu Ile Lys Lys Met
```

```
            450                 455                 460
Leu Glu Tyr Glu Pro Ser Ser Arg Ile Thr Leu Gly Glu Ala Leu His
465                 470                 475                 480

His Pro Phe Phe Asp Arg Leu Pro Pro His His Arg Val Gly Glu Val
                    485                 490                 495

Ser Asn Lys Gln Pro Leu Ser Ser Gly Ser Ser Ser Arg Glu Arg Ser
                500                 505                 510

His Ser Leu Ser Arg
        515

<210> SEQ ID NO 15
<211> LENGTH: 544
<212> TYPE: PRT
<213> ORGANISM: Human

<400> SEQUENCE: 15

Met Gly Ser Asp Gly Ser Ser Leu Ser Pro Lys Val Ser Gln Pro Gly
1               5                   10                  15

His Thr Glu Ile Val Asp His Val Ser Glu Lys Val Ile Thr Asn Gly
                20                  25                  30

Lys Asn Val Asn Lys Lys Val Asn Ser Glu Val Asp Gly Lys Ser Met
            35                  40                  45

Val Glu Lys Val Lys Thr His Glu Glu Asn Ala Glu Asp Tyr His Tyr
50                  55                  60

Gly Gly Tyr His Pro Val Tyr Ile Gly Glu Glu Phe His His Arg Arg
65                  70                  75                  80

Tyr Val Val Glu Arg Lys Leu Gly Trp Gly His Phe Ser Thr Val Trp
                85                  90                  95

Leu Ala Tyr Asp Arg Ala Ala Lys Arg Arg Val Ala Leu Lys Val Val
                100                 105                 110

Arg Ser Ala Glu His Tyr Arg Glu Thr Ser Ile Asp Glu Ile Arg Ile
            115                 120                 125

Leu Gln Lys Ile Arg Glu Gly Asp Glu Lys His Leu Gly Lys Lys His
        130                 135                 140

Ile Ile Ser Leu Leu Asp Tyr Phe Val His Arg Gly Pro Asn Gly Ala
145                 150                 155                 160

His Val Cys Met Val Phe Glu Val Leu Gly Glu Asn Leu Leu Ser Leu
                165                 170                 175

Ile Gln Ser Tyr Gly His Arg Gly Val Pro Val Gly Ile Val Lys Gln
            180                 185                 190

Ile Ala Tyr Gln Leu Leu Ile Ala Leu Asp Tyr Leu His Arg Glu Cys
        195                 200                 205

Gly Ile Ile His Thr Asp Leu Lys Pro Glu Asn Val Leu Ile Cys Ile
    210                 215                 220

Asp Gln Asp Ala Leu Gln His Ile Glu Ala Pro Ala Thr Thr Ser Ser
225                 230                 235                 240

Pro Thr Ser Asn Thr Ser Ser Lys Thr Arg Asn Asn Thr Gly Tyr
                245                 250                 255

Thr Ala Lys Ala Pro Ile Ile Lys Arg Gly Gln Ser Val Asp Asn Ser
                260                 265                 270

Ala Gln Glu Arg Lys Thr Phe Ala Lys Asn Pro Thr Lys Asn Ser Lys
            275                 280                 285

Pro Ala Gly Gln Val Ile Pro Ser Ser Pro Phe Thr Ser Thr Leu Ser
        290                 295                 300
```

-continued

```
Arg Phe Pro Ser Leu Glu Gly Ala Val Ser Glu Ile Ser Leu Arg Asp
305                 310                 315                 320

Ser Gln Lys His Asn Ser His Pro Asn Ser Pro Phe Ser Ser Gly Asp
            325                 330                 335

Asn Ser Leu Ile Leu Asp Gly Val Asn Gly Ser Gln Glu Pro Val Pro
            340                 345                 350

Lys Ile Thr Val Lys Ile Ala Asp Leu Gly Asn Ala Cys Trp Thr Arg
            355                 360                 365

Lys His Phe Thr Asn Asp Val Gln Thr Arg Gln Tyr Arg Ser Pro Glu
            370                 375                 380

Val Ile Leu Gly Cys Arg Trp Gly Ala Ser Ala Asp Cys Trp Ser Phe
385                 390                 395                 400

Ala Cys Ile Ile Phe Glu Leu Leu Thr Gly Asp Tyr Leu Phe Asp Pro
            405                 410                 415

Arg Asn Gly Asn Ser Tyr Ser Lys Glu Asp Asp His Ile Ala Gln Ile
            420                 425                 430

Ile Glu Leu Leu Val Asn Tyr Pro Lys Gln Met Ala Leu Ser Gly Lys
            435                 440                 445

His Ser Arg Asp Leu Phe Asn Arg Arg Gly Glu Leu Arg Asn Ile His
            450                 455                 460

Lys Leu Lys Phe Trp Pro Leu Lys Asp Val Leu Glu Gln Lys Tyr His
465                 470                 475                 480

Phe Ser Ala Glu Leu Ala Gln Gln Ile Ser Asp Phe Leu Ser Pro Met
            485                 490                 495

Leu Cys Phe Asp Pro Ala Lys Arg Thr Asn Ala Gly Tyr Met Ser Asn
            500                 505                 510

Ser Pro Trp Leu Arg Glu Val Ala Asp Pro Thr Phe Lys Ile Glu Thr
            515                 520                 525

Thr Gly Ala Thr Gly Glu Asp Val Pro Gly Trp Ala Thr Glu Ile Arg
            530                 535                 540

<210> SEQ ID NO 16
<211> LENGTH: 508
<212> TYPE: PRT
<213> ORGANISM: Yeast

<400> SEQUENCE: 16

Met Ala Ser Leu Phe Arg Pro Pro Glu Ser Ala Lys Cys Asn Pro Asn
1               5                   10                  15

Ser Pro Arg Leu Lys Leu Pro Leu Leu Arg Asn Asn Gln Val Asp Glu
            20                  25                  30

Asn Asn Ile Tyr Leu Thr Ser Asn Gly Ser Ser Thr Thr Ala Tyr Ser
            35                  40                  45

Ser His Thr Pro Glu Pro Leu Thr Ser Ser Thr Ser Thr Leu Phe Ser
    50                  55                  60

Gln Thr Arg Leu His Pro Ser Asp Ser Ser Met Thr Leu Asn Thr Met
65                  70                  75                  80

Lys Lys Arg Pro Ala Pro Pro Ser Leu Pro Ser Leu Ser Ile Asn Ser
            85                  90                  95

Gln Ser Lys Cys Lys Thr Leu Pro Glu Leu Val Pro Ile Ala Asp Val
            100                 105                 110

Ser Asp Gly Lys His Asp Leu Gly Leu Lys Gln Arg Val Ile Ala Glu
            115                 120                 125

Asn Glu Leu Ser Gly Asn Ser Asp Leu Thr Pro Ser Ser Met Ala Ser
            130                 135                 140
```

-continued

```
Pro Phe Ser His Thr Asn Thr Ser Ser Pro Tyr Leu Arg Asn Asp Leu
145                 150                 155                 160

Ser Asn Ser Val Gly Ser Asp Phe Ser Asn Leu Ile Ser Ala Tyr Glu
            165                 170                 175

Gln Ser Ser Ser Pro Ile Lys Ser Ser Gln Pro Lys Ser Ser Ser
        180                 185                 190

Glu Ser Tyr Ile Asp Leu Asn Ser Val Arg Asp Val Asp Gln Leu Asp
            195                 200                 205

Glu Asn Gly Trp Lys Tyr Ala Asn Leu Lys Asp Arg Ile Glu Thr Leu
    210                 215                 220

Gly Ile Leu Gly Glu Gly Ala Gly Gly Ser Val Ser Lys Cys Lys Leu
225                 230                 235                 240

Lys Asn Gly Ser Lys Ile Phe Ala Leu Lys Val Ile Asn Thr Leu Asn
                245                 250                 255

Thr Asp Pro Glu Tyr Gln Lys Gln Ile Phe Arg Glu Leu Gln Phe Asn
            260                 265                 270

Arg Ser Phe Gln Ser Glu Tyr Ile Val Arg Tyr Tyr Gly Met Phe Thr
    275                 280                 285

Asp Asp Glu Asn Ser Ser Ile Tyr Ile Ala Met Glu Tyr Met Gly Gly
290                 295                 300

Arg Ser Leu Asp Ala Ile Tyr Lys Asn Leu Leu Glu Arg Gly Gly Arg
305                 310                 315                 320

Ile Ser Glu Lys Val Leu Gly Lys Ile Ala Glu Ala Val Leu Arg Gly
                325                 330                 335

Leu Ser Tyr Leu His Glu Lys Lys Val Ile His Arg Asp Ile Lys Pro
            340                 345                 350

Gln Asn Ile Leu Leu Asn Glu Asn Gly Gln Val Lys Leu Cys Asp Phe
    355                 360                 365

Gly Val Ser Gly Glu Ala Val Asn Ser Leu Ala Thr Thr Phe Thr Gly
370                 375                 380

Thr Ser Phe Tyr Met Ala Pro Glu Arg Ile Gln Gly Gln Pro Tyr Ser
385                 390                 395                 400

Val Thr Ser Asp Val Trp Ser Leu Gly Leu Thr Ile Leu Glu Val Ala
                405                 410                 415

Asn Gly Lys Phe Pro Cys Ser Ser Glu Lys Met Ala Ala Asn Ile Ala
            420                 425                 430

Pro Phe Glu Leu Leu Met Trp Ile Leu Thr Phe Thr Pro Glu Leu Lys
    435                 440                 445

Asp Glu Pro Glu Ser Asn Ile Ile Trp Ser Pro Ser Phe Lys Ser Phe
450                 455                 460

Ile Asp Tyr Cys Leu Lys Lys Asp Ser Arg Glu Arg Pro Ser Pro Arg
465                 470                 475                 480

Gln Met Ile Asn His Pro Trp Ile Lys Gly Gln Met Lys Lys Asn Val
                485                 490                 495

Asn Met Glu Lys Phe Val Arg Lys Cys Trp Lys Asp
            500                 505
```

<210> SEQ ID NO 17
<211> LENGTH: 506
<212> TYPE: PRT
<213> ORGANISM: Yeast

<400> SEQUENCE: 17

Met Ala Ser Met Phe Arg Pro Pro Glu Ser Asn Arg Ser His Gln Lys

-continued

```
1               5                    10                   15
Thr Pro Lys Leu Thr Leu Pro Val Asn Leu Val Gln Asn Ala Lys Ser
                20                  25                  30
Thr Asn Asp Gly Gln His Leu Asn Arg Ser Pro Tyr Ser Ser Val Asn
            35                  40                  45
Glu Ser Pro Tyr Ser Asn Asn Ser Thr Ser Ala Thr Ser Thr Thr Ser
        50                  55                  60
Ser Met Ala Ser Asn Ser Thr Leu Leu Tyr Asn Arg Ser Ser Thr Thr
65                  70                  75                  80
Thr Ile Lys Asn Arg Pro Val Pro Pro Leu Pro Pro Leu Val Leu
                85                  90                  95
Thr Gln Lys Lys Asp Gly Ile Glu Tyr Arg Val Ala Gly Asp Ser Gln
                100                 105                 110
Leu Ser Glu Arg Phe Ser Asn Leu His Val Asp Ile Thr Tyr Lys Glu
            115                 120                 125
Leu Leu Ser Ser Ala Pro Ile Ser Thr Lys Leu Ser Asn Ile Asp Thr
    130                 135                 140
Thr Phe Ile Lys Lys Asp Leu Asp Thr Pro Glu Gly Glu Asp Ser Tyr
145                 150                 155                 160
Pro Ser Thr Leu Leu Ser Ala Tyr Asp Phe Ser Ser Ser Gly Ser Asn
                165                 170                 175
Ser Ala Pro Leu Ser Ala Asn Asn Ile Ile Ser Cys Ser Asn Leu Ile
                180                 185                 190
Gln Gly Lys Asp Val Asp Gln Leu Glu Glu Glu Ala Trp Arg Phe Gly
            195                 200                 205
His Leu Lys Asp Glu Ile Thr Thr Leu Gly Ile Leu Gly Glu Gly Ala
    210                 215                 220
Gly Gly Ser Val Ala Lys Cys Arg Leu Lys Asn Gly Lys Lys Val Phe
225                 230                 235                 240
Ala Leu Lys Thr Ile Asn Thr Met Asn Thr Asp Pro Glu Tyr Gln Lys
                245                 250                 255
Gln Ile Phe Arg Glu Leu Gln Phe Asn Lys Ser Phe Lys Ser Asp Tyr
            260                 265                 270
Ile Val Gln Tyr Tyr Gly Met Phe Thr Asp Glu Gln Ser Ser Ser Ile
    275                 280                 285
Tyr Ile Ala Met Glu Tyr Met Gly Gly Lys Ser Leu Glu Ala Thr Tyr
290                 295                 300
Lys Asn Leu Leu Lys Arg Gly Gly Arg Ile Ser Glu Arg Val Ile Gly
305                 310                 315                 320
Lys Ile Ala Glu Ser Val Leu Arg Gly Leu Ser Tyr Leu His Glu Arg
                325                 330                 335
Lys Val Ile His Arg Asp Ile Lys Pro Gln Asn Ile Leu Leu Asn Glu
            340                 345                 350
Lys Gly Glu Ile Lys Leu Cys Asp Phe Gly Val Ser Gly Glu Ala Val
    355                 360                 365
Asn Ser Leu Ala Met Thr Phe Thr Gly Thr Ser Phe Tyr Met Ala Pro
    370                 375                 380
Glu Arg Ile Gln Gly Gln Pro Tyr Ser Val Thr Cys Asp Val Trp Ser
385                 390                 395                 400
Leu Gly Leu Thr Leu Leu Glu Val Ala Gly Gly Arg Phe Pro Phe Glu
                405                 410                 415
Ser Asp Lys Ile Thr Gln Asn Val Ala Pro Ile Glu Leu Leu Thr Met
            420                 425                 430
```

```
Ile Leu Thr Phe Ser Pro Gln Leu Lys Asp Glu Pro Glu Leu Asp Ile
        435                 440                 445

Ser Trp Ser Lys Thr Phe Arg Ser Phe Ile Asp Tyr Cys Leu Lys Lys
    450                 455                 460

Asp Ala Arg Glu Arg Pro Ser Pro Arg Gln Met Leu Lys His Pro Trp
465                 470                 475                 480

Ile Val Gly Gln Met Lys Lys Val Asn Met Glu Arg Phe Val Lys
                485                 490                 495

Lys Cys Trp Glu Lys Glu Lys Asp Gly Ile
            500                 505

<210> SEQ ID NO 18
<211> LENGTH: 699
<212> TYPE: PRT
<213> ORGANISM: EMENI - Aspergillus Nidulans

<400> SEQUENCE: 18

Met Ala Ile Ala Leu Ala Glu Ala Asp Lys Tyr Glu Val Leu Glu Lys
1               5                   10                  15

Ile Gly Cys Gly Ser Phe Gly Ile Ile Arg Lys Val Lys Arg Lys Ser
            20                  25                  30

Asp Gly Phe Ile Leu Cys Arg Lys Glu Ile Asn Tyr Ile Lys Met Ser
        35                  40                  45

Thr Lys Glu Arg Glu Gln Leu Thr Ala Glu Phe Asn Ile Leu Ser Ser
    50                  55                  60

Leu Arg His Pro Asn Ile Val Ala Tyr Tyr His Arg Glu His Leu Lys
65                  70                  75                  80

Ala Ser Gln Asp Leu Tyr Leu Tyr Met Glu Tyr Cys Gly Gly Gly Asp
                85                  90                  95

Leu Ser Met Val Ile Lys Asn Leu Lys Arg Thr Asn Lys Tyr Ala Glu
            100                 105                 110

Glu Asp Phe Val Trp Arg Ile Leu Ser Gln Leu Val Thr Ala Leu Tyr
        115                 120                 125

Arg Cys His Tyr Gly Thr Asp Pro Ala Glu Val Gly Ser Asn Leu Leu
    130                 135                 140

Gly Pro Ala Pro Lys Pro Ser Gly Leu Lys Gly Lys Gln Ala Gln Met
145                 150                 155                 160

Thr Ile Leu His Arg Asp Leu Lys Pro Glu Asn Ile Phe Leu Gly Ser
                165                 170                 175

Asp Asn Thr Val Lys Leu Gly Asp Phe Gly Leu Ser Lys Leu Met His
            180                 185                 190

Ser His Asp Phe Ala Ser Thr Tyr Val Gly Thr Pro Phe Tyr Met Ser
        195                 200                 205

Pro Glu Ile Cys Ala Ala Glu Lys Tyr Thr Leu Arg Ser Asp Ile Trp
    210                 215                 220

Ala Val Gly Cys Ile Met Tyr Glu Leu Cys Gln Arg Glu Pro Pro Phe
225                 230                 235                 240

Asn Ala Arg Thr His Ile Gln Leu Val Gln Lys Ile Arg Glu Gly Lys
                245                 250                 255

Phe Ala Pro Leu Pro Asp Phe Tyr Ser Ser Glu Leu Lys Asn Val Ile
            260                 265                 270

Ala Ser Cys Leu Arg Val Asn Pro Asp His Arg Pro Asp Thr Ala Thr
        275                 280                 285

Leu Ile Asn Thr Pro Val Ile Arg Leu Met Arg Arg Glu Val Glu Leu
```

```
            290                 295                 300
Asn Asn Leu Ser Arg Ala Ala Arg Lys Arg Glu Glu Ala Thr Met Gln
305                 310                 315                 320

Lys Ala Lys Asp Val Glu Gln Ala Phe Ala Lys Leu Glu Lys Glu Lys
                325                 330                 335

Gln Gln Ile Arg Ser Glu Leu Glu Asn Ser Ile Arg Arg Glu Trp Glu
                340                 345                 350

Val Lys Ala Arg Leu Glu Ile Asp Arg Gln Val Gln Asn Glu Leu Asp
                355                 360                 365

Lys Leu Arg Lys Arg Phe Glu Cys Glu Val Gln Asp Arg Val Ala Gln
370                 375                 380

Glu Val Glu Lys Gln Arg Arg Asn Ala Asn Tyr Arg Glu Asp Ala Ser
385                 390                 395                 400

Leu Arg Ser Ser Gly His Ser Ser Gln Met Ser Ser Ser Asn Ser Glu
                405                 410                 415

Asp Ser Asp Phe Pro Ser Ser Thr Asp Ile Ser Gln Leu Ser Leu Glu
                420                 425                 430

Ser Pro Thr Asn Lys Ala Ala Lys Leu Pro Lys Lys Glu Ser Arg Thr
                435                 440                 445

Pro Phe Thr Arg Ser Lys Thr Val Val Asp Ser Pro Met Asp Ile Gln
450                 455                 460

Met Ala Glu Pro Ser Pro Ile Ser Ile Ala Ser Leu Ser Leu Ser Pro
465                 470                 475                 480

Arg Arg Thr Ser Ala Thr Tyr Ser Gly Lys Asn Ile Phe Ala Glu Gly
                485                 490                 495

Glu Arg Lys Arg Pro Lys Phe Glu Pro Thr Leu Ala Tyr Ser Asp Asp
                500                 505                 510

Glu Asp Asp Thr Pro Glu Leu Pro Ser Pro Thr Arg Pro Lys Val Lys
                515                 520                 525

Pro Asp Pro Phe Lys Ala Pro Ser Arg Pro Leu Leu Arg Gln Asn Thr
530                 535                 540

Thr Ala Leu Met Gln Lys Leu Ser Thr Gln Pro Ile Phe Pro Ala
545                 550                 555                 560

Asn Pro Ser Arg Leu Pro Gln Met Ser Ala Pro Asp Val Arg Glu Ser
                565                 570                 575

Lys Ser Arg Ser Pro His Arg Arg Leu Ser Lys Ile Pro Ser Ser Ala
                580                 585                 590

Asn Leu Ala Ala Asp Ala Gly Ser Pro Thr Arg Lys Asn Gly Val Lys
                595                 600                 605

Ser Ser Pro Ser Lys Met Asn Gly Gly Asp Glu Met Phe Lys Ala Val
610                 615                 620

Met Gln Arg Asn Met Gly Gly Arg Thr Leu Val Glu Leu Ala Gln Ala
625                 630                 635                 640

Arg Ala Gly Gly Arg Pro Ile Asp Glu Val Lys Arg Cys Ala Ser Asp
                645                 650                 655

Ser Arg Ser Gly Cys Ser Val Pro Met Lys Ser Ala Asp Arg Asp Pro
                660                 665                 670

Pro Ala Val Trp Asp Pro Glu Arg Asp Glu Met Pro Ser Pro Phe Leu
                675                 680                 685

Ala Arg Gly Arg Lys Val Ile Arg Asn Leu Arg
    690                 695
```

<210> SEQ ID NO 19

```
<211> LENGTH: 346
<212> TYPE: PRT
<213> ORGANISM: Human

<400> SEQUENCE: 19

Met Pro Ser Pro Leu Ala Leu Arg Pro Tyr Leu Arg Ser Glu Phe Ser
1               5                   10                  15

Pro Ser Val Asp Ala Arg Pro Cys Ser Ser Pro Ser Glu Leu Pro Ala
            20                  25                  30

Lys Leu Leu Leu Gly Ala Thr Leu Pro Arg Ala Pro Arg Leu Pro Arg
        35                  40                  45

Arg Leu Ala Trp Cys Ser Ile Asp Trp Glu Gln Val Cys Leu Leu Gln
    50                  55                  60

Arg Leu Gly Ala Gly Gly Phe Gly Ser Val Tyr Lys Ala Thr Tyr Arg
65                  70                  75                  80

Gly Val Pro Val Ala Ile Lys Gln Val Asn Lys Cys Thr Lys Asn Arg
                85                  90                  95

Leu Ala Ser Arg Arg Ser Phe Trp Ala Glu Leu Asn Val Ala Arg Leu
            100                 105                 110

Arg His Asp Asn Ile Val Arg Val Val Ala Ala Ser Thr Arg Thr Pro
        115                 120                 125

Ala Gly Ser Asn Ser Leu Gly Thr Ile Ile Met Glu Phe Gly Gly Asn
130                 135                 140

Val Thr Leu His Gln Val Ile Tyr Gly Ala Ala Gly His Pro Glu Gly
145                 150                 155                 160

Asp Ala Gly Glu Pro His Cys Arg Thr Gly Gly Gln Leu Ser Leu Gly
                165                 170                 175

Lys Cys Leu Lys Tyr Ser Leu Asp Val Val Asn Gly Leu Leu Phe Leu
            180                 185                 190

His Ser Gln Ser Ile Val His Leu Asp Leu Lys Pro Ala Asn Ile Leu
        195                 200                 205

Ile Ser Glu Gln Asp Val Cys Lys Ile Ser Asp Phe Gly Cys Ser Glu
210                 215                 220

Lys Leu Glu Asp Leu Leu Cys Phe Gln Thr Pro Ser Tyr Pro Leu Gly
225                 230                 235                 240

Gly Thr Tyr Thr His Arg Ala Pro Glu Leu Leu Lys Gly Glu Gly Val
                245                 250                 255

Thr Pro Lys Ala Asp Ile Tyr Ser Phe Ala Ile Thr Leu Trp Gln Met
            260                 265                 270

Thr Thr Lys Gln Ala Pro Tyr Ser Gly Glu Arg Gln His Ile Leu Tyr
        275                 280                 285

Ala Val Val Ala Tyr Asp Leu Arg Pro Ser Leu Ser Ala Ala Val Phe
290                 295                 300

Glu Asp Ser Leu Pro Gly Gln Arg Leu Gly Asp Val Ile Gln Arg Cys
305                 310                 315                 320

Trp Arg Pro Ser Ala Ala Gln Arg Pro Ser Ala Arg Leu Leu Leu Val
                325                 330                 335

Asp Leu Thr Ser Leu Lys Ala Glu Leu Gly
            340                 345

<210> SEQ ID NO 20
<211> LENGTH: 337
<212> TYPE: PRT
<213> ORGANISM: Human

<400> SEQUENCE: 20
```

```
Met Ala Ser Ser Ser Gly Ser Lys Ala Glu Phe Ile Val Gly Gly Lys
1               5                   10                  15

Tyr Lys Leu Val Arg Lys Ile Gly Ser Gly Ser Phe Gly Asp Ile Tyr
            20                  25                  30

Leu Ala Ile Asn Ile Thr Asn Gly Glu Glu Val Ala Leu Lys Leu Glu
            35                  40                  45

Ser Gln Lys Ala Arg His Pro Gln Leu Leu Tyr Glu Ser Lys Leu Tyr
    50                  55                  60

Lys Ile Leu Gln Gly Gly Val Gly Ile Pro His Ile Arg Trp Tyr Gly
65                  70                  75                  80

Gln Glu Lys Asp Tyr Asn Val Leu Val Met Asp Leu Leu Gly Pro Ser
                85                  90                  95

Leu Glu Asp Leu Phe Asn Phe Cys Ser Arg Arg Phe Thr Met Lys Thr
            100                 105                 110

Val Leu Met Leu Ala Asp Gln Met Ile Ser Arg Ile Glu Tyr Val His
            115                 120                 125

Thr Lys Asn Phe Ile His Arg Asp Ile Lys Pro Asp Asn Phe Leu Met
        130                 135                 140

Gly Ile Gly Arg His Cys Asn Lys Leu Phe Leu Ile Asp Phe Gly Leu
145                 150                 155                 160

Ala Lys Lys Tyr Arg Asp Asn Arg Thr Arg Gln His Ile Pro Tyr Arg
                165                 170                 175

Glu Asp Lys Asn Leu Thr Gly Thr Ala Arg Tyr Ala Ser Ile Asn Ala
            180                 185                 190

His Leu Gly Ile Glu Gln Ser Arg Arg Asp Asp Met Glu Ser Leu Gly
        195                 200                 205

Tyr Val Leu Met Tyr Phe Asn Arg Thr Ser Leu Pro Trp Gln Gly Leu
    210                 215                 220

Lys Ala Ala Thr Lys Lys Gln Lys Tyr Glu Lys Ile Ser Glu Lys Lys
225                 230                 235                 240

Met Ser Thr Pro Val Glu Val Leu Cys Lys Gly Phe Pro Ala Glu Phe
                245                 250                 255

Ala Met Tyr Leu Asn Tyr Cys Arg Gly Leu Arg Phe Glu Glu Ala Pro
            260                 265                 270

Asp Tyr Met Tyr Leu Arg Gln Leu Phe Arg Ile Leu Phe Arg Thr Leu
        275                 280                 285

Asn His Gln Tyr Asp Tyr Thr Phe Asp Trp Thr Met Leu Lys Gln Lys
            290                 295                 300

Ala Ala Gln Gln Ala Ala Ser Ser Gly Gln Gly Gln Gln Ala Gln
305                 310                 315                 320

Thr Pro Thr Gly Lys Gln Thr Asp Lys Ser Lys Ser Asn Met Lys Gly
                325                 330                 335

Phe
```

<210> SEQ ID NO 21
<211> LENGTH: 336
<212> TYPE: PRT
<213> ORGANISM: Bovine

<400> SEQUENCE: 21

```
Met Ala Ser Ser Ser Arg Pro Lys Thr Asp Val Leu Val Gly Gly Arg
1               5                   10                  15

Tyr Lys Leu Val Arg Glu Ile Gly Phe Gly Ser Phe Gly His Val Tyr
            20                  25                  30
```

-continued

```
Leu Ala Ile Asp Leu Thr Asn His Glu Gln Val Ala Val Lys Leu Glu
            35                  40                  45

Ser Glu Asn Thr Arg Gln Pro Arg Leu Leu His Glu Lys Glu Leu Tyr
 50                      55                  60

Asn Phe Leu Gln Gly Gly Val Gly Ile Pro Gln Ile Arg Trp Tyr Gly
 65                  70                  75                  80

Gln Glu Thr Asp Tyr Asn Val Leu Val Met Asp Leu Leu Gly Pro Ser
                 85                  90                  95

Leu Glu Asp Leu Phe Asn Phe Cys Ser Arg Arg Phe Ser Met Lys Thr
                100                 105                 110

Val Leu Met Leu Ala Asp Gln Met Ile Ser Arg Ile Glu Tyr Val His
            115                 120                 125

Ser Arg Asn Leu Ile His Arg Asp Ile Lys Pro Asp Asn Phe Leu Met
130                 135                 140

Gly Thr Gly Pro Gln Trp Lys Lys Leu Phe Leu Val Asp Phe Gly Leu
145                 150                 155                 160

Ala Lys Lys Tyr Arg Asp Asn Arg Thr Gly Gln His Ile Pro His Arg
                165                 170                 175

Ser Gly Lys Ser Phe Ile Gly Thr Pro Phe Cys Ala Ser Ile Ser Ala
                180                 185                 190

His Leu Gly Ile Glu Gln Ser Arg Arg Asp Asp Met Glu Ser Ile Gly
            195                 200                 205

Tyr Val Leu Met Tyr Phe Asn Arg Gly Ser Leu Pro Trp Gln Gly Leu
210                 215                 220

Lys Ala Ala Thr Leu Lys Gln Lys Cys Glu Lys Ile Ser Glu Met Lys
225                 230                 235                 240

Met Thr Thr Pro Val Asp Val Leu Cys Lys Gly Phe Pro Ile Glu Phe
                245                 250                 255

Ala Met Tyr Leu Lys Tyr Cys Leu Arg Leu Ser Phe Glu Glu Ala Pro
                260                 265                 270

Asp Tyr Arg Tyr Leu Arg Gln Leu Phe Arg Leu Leu Phe Arg Lys Leu
            275                 280                 285

Ser Tyr Gln His Asp Tyr Ala Phe Asp Trp Ile Val Leu Lys Gln Lys
290                 295                 300

Ala Glu Gln Gln Ala Ser Ser Ser Gly Glu Gly Gln Gln Ala Gln
305                 310                 315                 320

Thr Pro Thr Gly Lys Ser Asp Asn Thr Lys Ser Glu Met Lys His Ser
                325                 330                 335

<210> SEQ ID NO 22
<211> LENGTH: 415
<212> TYPE: PRT
<213> ORGANISM: Human

<400> SEQUENCE: 22

Met Glu Leu Arg Val Gly Asn Arg Tyr Arg Leu Gly Arg Lys Ile Gly
 1               5                  10                  15

Ser Gly Ser Phe Gly Asp Ile Tyr Leu Gly Thr Asp Ile Ala Ala Gly
                 20                  25                  30

Glu Glu Val Ala Ile Lys Leu Glu Cys Val Lys Thr Lys His Pro Gln
            35                  40                  45

Leu His Ile Glu Ser Lys Ile Tyr Lys Met Met Gln Gly Gly Val Gly
         50                  55                  60

Ile Pro Thr Ile Arg Trp Cys Gly Ala Glu Gly Asp Tyr Asn Val Met
```

-continued

```
                65                  70                  75                  80
Val Met Glu Leu Leu Gly Pro Ser Leu Glu Asp Leu Phe Asn Phe Cys
                    85                  90                  95

Ser Arg Lys Phe Ser Leu Lys Thr Val Leu Leu Leu Ala Asp Gln Met
                100                 105                 110

Ile Ser Arg Ile Glu Tyr Ile His Ser Lys Asn Phe Ile His Arg Asp
                115                 120                 125

Val Lys Pro Asp Asn Phe Leu Met Gly Leu Gly Lys Lys Gly Asn Leu
            130                 135                 140

Val Tyr Ile Ile Asp Phe Gly Leu Ala Lys Lys Tyr Arg Asp Ala Arg
145                 150                 155                 160

Thr His Gln His Ile Pro Tyr Arg Glu Asn Lys Asn Leu Thr Gly Thr
                    165                 170                 175

Ala Arg Tyr Ala Ser Ile Asn Thr His Leu Gly Ile Glu Gln Ser Arg
                180                 185                 190

Arg Asp Asp Leu Glu Ser Leu Gly Tyr Val Leu Met Tyr Phe Asn Leu
            195                 200                 205

Gly Ser Leu Pro Trp Gln Gly Leu Lys Ala Ala Thr Lys Arg Gln Lys
        210                 215                 220

Tyr Glu Arg Ile Ser Glu Lys Lys Met Ser Thr Pro Ile Glu Val Leu
225                 230                 235                 240

Cys Lys Gly Tyr Pro Ser Glu Phe Ala Thr Tyr Leu Asn Phe Cys Arg
                    245                 250                 255

Ser Leu Arg Phe Asp Asp Lys Pro Asp Tyr Ser Tyr Leu Arg Gln Leu
                260                 265                 270

Phe Arg Asn Leu Phe His Arg Gln Gly Phe Ser Tyr Asp Tyr Val Phe
            275                 280                 285

Asp Trp Asn Met Leu Lys Phe Gly Ala Ser Arg Ala Ala Asp Asp Ala
        290                 295                 300

Glu Arg Glu Arg Arg Asp Arg Glu Glu Arg Leu Arg His Ser Arg Asn
305                 310                 315                 320

Pro Ala Thr Arg Gly Leu Pro Ser Thr Asp Ser Gly Arg Leu Arg Gly
                    325                 330                 335

Thr Gln Glu Val Ala Pro Pro Thr Pro Leu Thr Pro Thr Ser His Thr
                340                 345                 350

Ala Asn Thr Ser Pro Arg Pro Val Ser Gly Met Glu Arg Glu Arg Lys
            355                 360                 365

Val Ser Met Arg Leu His Arg Gly Ala Pro Val Asn Ile Ser Ser Ser
        370                 375                 380

Asp Leu Thr Gly Arg Gln Asp Thr Ser Arg Met Ser Thr Ser Gln Ile
385                 390                 395                 400

Pro Gly Arg Val Ala Ser Ser Gly Leu Gln Ser Val Val His Arg
                    405                 410                 415

<210> SEQ ID NO 23
<211> LENGTH: 538
<212> TYPE: PRT
<213> ORGANISM: Yeast

<400> SEQUENCE: 23

Met Ser Met Pro Ile Ala Ser Thr Thr Leu Ala Val Asn Asn Leu Thr
1               5                   10                  15

Asn Ile Asn Gly Asn Ala Asn Phe Asn Val Gln Ala Asn Lys Gln Leu
            20                  25                  30
```

```
His His Gln Ala Val Asp Ser Pro Ala Arg Ser Ser Met Thr Ala Thr
         35                  40                  45

Thr Ala Ala Asn Ser Asn Ser Asn Ser Ser Arg Asp Asp Ser Thr Ile
     50                  55                  60

Val Gly Leu His Tyr Lys Ile Gly Lys Lys Ile Gly Glu Gly Ser Phe
 65              70                  75                      80

Gly Val Leu Phe Glu Gly Thr Asn Met Ile Asn Gly Val Pro Val Ala
                 85                  90                  95

Ile Lys Phe Glu Pro Arg Lys Thr Glu Ala Pro Gln Leu Arg Asp Glu
             100                 105                 110

Tyr Lys Thr Tyr Lys Ile Leu Asn Gly Thr Pro Asn Ile Pro Tyr Ala
         115                 120                 125

Tyr Tyr Phe Gly Gln Glu Gly Leu His Asn Ile Leu Val Ile Asp Leu
         130                 135                 140

Leu Gly Pro Ser Leu Glu Asp Leu Phe Asp Trp Cys Gly Arg Lys Phe
145                 150                 155                 160

Ser Val Lys Thr Val Val Gln Val Ala Val Gln Met Ile Thr Leu Ile
             165                 170                 175

Glu Asp Leu His Ala His Asp Leu Ile Tyr Arg Asp Ile Lys Pro Asp
             180                 185                 190

Asn Phe Leu Ile Gly Arg Pro Gly Gln Pro Asp Ala Asn Asn Ile His
             195                 200                 205

Leu Ile Asp Phe Gly Met Ala Lys Gln Tyr Arg Asp Pro Lys Thr Lys
             210                 215                 220

Gln His Ile Pro Tyr Arg Glu Lys Lys Ser Leu Ser Gly Thr Ala Arg
225                 230                 235                 240

Tyr Met Ser Ile Asn Thr His Leu Gly Arg Glu Gln Ser Arg Arg Asp
                 245                 250                 255

Asp Met Glu Ala Leu Gly His Val Phe Phe Tyr Phe Leu Arg Gly His
             260                 265                 270

Leu Pro Trp Gln Gly Leu Lys Ala Pro Asn Asn Lys Gln Lys Tyr Glu
         275                 280                 285

Lys Ile Gly Glu Lys Lys Arg Ser Thr Asn Val Tyr Asp Leu Ala Gln
         290                 295                 300

Gly Leu Pro Val Gln Phe Gly Arg Tyr Leu Glu Ile Val Arg Ser Leu
305                 310                 315                 320

Ser Phe Glu Glu Cys Pro Asp Tyr Glu Gly Tyr Arg Lys Leu Leu Leu
                 325                 330                 335

Ser Val Leu Asp Asp Leu Gly Glu Thr Ala Asp Gly Gln Tyr Asp Trp
             340                 345                 350

Met Lys Leu Asn Asp Gly Arg Gly Trp Asp Leu Asn Ile Asn Lys Lys
         355                 360                 365

Pro Asn Leu His Gly Tyr Gly His Pro Asn Pro Asn Glu Lys Ser
370                 375                 380

Arg Lys His Arg Asn Lys Gln Leu Gln Met Gln Gln Leu Gln Met Gln
385                 390                 395                 400

Gln Leu Gln Gln Gln Gln Gln Gln Gln Tyr Ala Gln Lys Thr Glu
             405                 410                 415

Ala Asp Met Arg Asn Ser Gln Tyr Lys Pro Lys Leu Asp Pro Thr Ser
             420                 425                 430

Tyr Glu Ala Tyr Gln His Gln Thr Gln Gln Lys Tyr Leu Gln Glu Gln
             435                 440                 445

Gln Lys Arg Gln Gln Gln Gln Lys Leu Gln Glu Gln Gln Leu Gln Glu
```

-continued

```
            450                 455                 460
Gln Gln Leu Gln Gln Gln Gln Gln Gln Gln Leu Arg Ala Thr
465                 470                 475                 480

Gly Gln Pro Pro Ser Gln Pro Gln Ala Gln Thr Gln Ser Gln Gln Phe
                485                 490                 495

Gly Ala Arg Tyr Gln Pro Gln Gln Pro Ser Ala Ala Leu Arg Thr
            500                 505                 510

Pro Glu Gln His Pro Asn Asp Asp Asn Ser Ser Leu Ala Ala Ser His
            515                 520                 525

Lys Gly Phe Phe Gln Lys Leu Gly Cys Cys
            530                 535
```

<210> SEQ ID NO 24
<211> LENGTH: 546
<212> TYPE: PRT
<213> ORGANISM: Yeast

<400> SEQUENCE: 24

```
Met Ser Gln Val Gln Ser Pro Leu Thr Ala Thr Asn Ser Gly Leu Ala
1               5                   10                  15

Val Asn Asn Asn Thr Met Asn Ser Gln Met Pro Asn Arg Ser Asn Val
                20                  25                  30

Arg Leu Val Asn Gly Thr Leu Pro Pro Ser Leu His Val Ser Ser Asn
            35                  40                  45

Leu Asn His Asn Thr Gly Asn Ser Ser Ala Ser Tyr Ser Gly Ser Gln
        50                  55                  60

Ser Arg Asp Asp Ser Thr Ile Val Gly Leu His Tyr Lys Ile Gly Lys
65                  70                  75                  80

Lys Ile Gly Glu Gly Ser Phe Gly Val Leu Phe Glu Gly Thr Asn Met
                85                  90                  95

Ile Asn Gly Leu Pro Val Ala Ile Lys Phe Glu Pro Arg Lys Thr Glu
            100                 105                 110

Ala Pro Gln Leu Lys Asp Glu Tyr Arg Thr Tyr Lys Ile Leu Ala Gly
        115                 120                 125

Thr Pro Gly Ile Pro Gln Glu Tyr Tyr Phe Gly Gln Glu Gly Leu His
    130                 135                 140

Asn Ile Leu Val Ile Asp Leu Leu Gly Pro Ser Leu Glu Asp Leu Phe
145                 150                 155                 160

Asp Trp Cys Gly Arg Arg Phe Ser Val Lys Thr Val Val Gln Val Ala
                165                 170                 175

Val Gln Met Ile Thr Leu Ile Glu Asp Leu His Ala His Asp Leu Ile
            180                 185                 190

Tyr Arg Asp Ile Lys Pro Asp Asn Phe Leu Ile Gly Arg Pro Gly Gln
        195                 200                 205

Pro Asp Ala Asn Lys Val His Leu Ile Asp Phe Gly Met Ala Lys Gln
    210                 215                 220

Tyr Arg Asp Pro Lys Thr Lys Gln His Ile Pro Tyr Arg Glu Lys Lys
225                 230                 235                 240

Ser Leu Ser Gly Thr Ala Arg Tyr Met Ser Ile Asn Thr His Leu Gly
                245                 250                 255

Arg Glu Gln Ser Arg Arg Asp Asp Met Glu Ala Met Gly His Val Phe
            260                 265                 270

Phe Tyr Phe Leu Arg Gly Gln Leu Pro Trp Gln Gly Leu Lys Ala Pro
        275                 280                 285
```

-continued

```
Asn Asn Lys Gln Lys Tyr Glu Lys Ile Gly Glu Lys Arg Leu Thr
    290                 295                 300

Asn Val Tyr Asp Leu Ala Gln Gly Leu Pro Ile Gln Phe Gly Arg Tyr
305                 310                 315                 320

Leu Glu Ile Val Arg Asn Leu Ser Phe Glu Glu Thr Pro Asp Tyr Glu
                325                 330                 335

Gly Tyr Arg Met Leu Leu Leu Ser Val Leu Asp Asp Leu Gly Glu Thr
            340                 345                 350

Ala Asp Gly Gln Tyr Asp Trp Met Lys Leu Asn Gly Gly Arg Gly Trp
        355                 360                 365

Asp Leu Ser Ile Asn Lys Lys Pro Asn Leu His Gly Tyr Gly His Pro
    370                 375                 380

Asn Pro Pro Asn Glu Lys Ser Lys Arg His Arg Ser Lys Asn His Gln
385                 390                 395                 400

Tyr Ser Ser Pro Asp His His His Tyr Asn Gln Gln Gln Gln Gln
                405                 410                 415

Gln Gln Ala Gln Ala Gln Ala Gln Ala Gln Ala Lys Val Gln
            420                 425                 430

Gln Gln Gln Leu Gln Gln Ala Gln Ala Gln Gln Ala Asn Arg Tyr
        435                 440                 445

Gln Leu Gln Pro Asp Asp Ser His Tyr Asp Glu Glu Arg Glu Ala Ser
    450                 455                 460

Lys Leu Asp Pro Thr Ser Tyr Glu Ala Tyr Gln Gln Gln Thr Gln Gln
465                 470                 475                 480

Lys Tyr Ala Gln Gln Gln Lys Gln Met Gln Gln Lys Ser Lys Gln
                485                 490                 495

Phe Ala Asn Thr Gly Ala Asn Gly Gln Thr Asn Lys Tyr Pro Tyr Asn
            500                 505                 510

Ala Gln Pro Thr Ala Asn Asp Glu Gln Asn Ala Lys Asn Ala Ala Gln
        515                 520                 525

Asp Arg Asn Ser Asn Lys Ser Ser Lys Gly Phe Phe Ser Lys Leu Gly
    530                 535                 540

Cys Cys
545

<210> SEQ ID NO 25
<211> LENGTH: 494
<212> TYPE: PRT
<213> ORGANISM: Yeast

<400> SEQUENCE: 25

Met Asp Leu Arg Val Gly Arg Lys Phe Arg Ile Gly Arg Lys Ile Gly
1               5                   10                  15

Ser Gly Ser Phe Gly Asp Ile Tyr His Gly Thr Asn Leu Ile Ser Gly
                20                  25                  30

Glu Glu Val Ala Ile Lys Leu Glu Ser Ile Arg Ser Arg His Pro Gln
            35                  40                  45

Leu Asp Tyr Glu Ser Arg Val Tyr Arg Tyr Leu Ser Gly Gly Val Gly
        50                  55                  60

Ile Pro Phe Ile Arg Trp Phe Gly Arg Glu Gly Glu Tyr Asn Ala Met
65                  70                  75                  80

Val Ile Asp Leu Leu Gly Pro Ser Leu Glu Asp Leu Phe Asn Tyr Cys
                85                  90                  95

His Arg Arg Phe Ser Phe Lys Thr Val Ile Met Leu Ala Leu Gln Met
            100                 105                 110
```

```
Phe Cys Arg Ile Gln Tyr Ile His Gly Arg Ser Phe Ile His Arg Asp
            115                 120                 125
Ile Lys Pro Asp Asn Phe Leu Met Gly Val Gly Arg Arg Gly Ser Thr
130                 135                 140
Val His Val Ile Asp Phe Gly Leu Ser Lys Lys Tyr Arg Asp Phe Asn
145                 150                 155                 160
Thr His Arg His Ile Pro Tyr Arg Glu Asn Lys Ser Leu Thr Gly Thr
                165                 170                 175
Ala Arg Tyr Ala Ser Val Asn Thr His Leu Gly Ile Glu Gln Ser Arg
            180                 185                 190
Arg Asp Asp Leu Glu Ser Leu Gly Tyr Val Leu Ile Tyr Phe Cys Lys
            195                 200                 205
Gly Ser Leu Pro Trp Gln Gly Leu Lys Ala Thr Thr Lys Lys Gln Lys
    210                 215                 220
Tyr Asp Arg Ile Met Glu Lys Lys Leu Asn Val Ser Val Glu Thr Leu
225                 230                 235                 240
Cys Ser Gly Leu Pro Leu Glu Phe Gln Glu Tyr Met Ala Tyr Cys Lys
                245                 250                 255
Asn Leu Lys Phe Asp Glu Lys Pro Asp Tyr Leu Phe Leu Ala Arg Leu
            260                 265                 270
Phe Lys Asp Leu Ser Ile Lys Leu Glu Tyr His Asn Asp His Leu Phe
    275                 280                 285
Asp Trp Thr Met Leu Arg Tyr Thr Lys Ala Met Val Glu Lys Gln Arg
            290                 295                 300
Asp Leu Leu Ile Glu Lys Gly Asp Leu Asn Ala Asn Ser Asn Ala Ala
305                 310                 315                 320
Ser Ala Ser Asn Ser Thr Asp Asn Lys Ser Glu Thr Phe Asn Lys Ile
                325                 330                 335
Lys Leu Leu Ala Met Lys Lys Phe Pro Thr His Phe His Tyr Tyr Lys
            340                 345                 350
Asn Glu Asp Lys His Asn Pro Ser Pro Glu Glu Ile Lys Gln Gln Thr
    355                 360                 365
Ile Leu Asn Asn Asn Ala Ala Ser Ser Leu Pro Glu Glu Leu Leu Asn
370                 375                 380
Ala Leu Asp Lys Gly Met Glu Asn Leu Arg Gln Gln Pro Gln Gln
385                 390                 395                 400
Gln Val Gln Ser Ser Gln Pro Gln Pro Gln Pro Gln Leu Gln Gln
            405                 410                 415
Gln Pro Asn Gly Gln Arg Pro Asn Tyr Tyr Pro Glu Pro Leu Leu Gln
            420                 425                 430
Gln Gln Gln Arg Asp Ser Gln Glu Gln Gln Gln Val Pro Met Ala
            435                 440                 445
Thr Thr Arg Ala Thr Gln Tyr Pro Pro Gln Ile Asn Ser Asn Asn Phe
    450                 455                 460
Asn Thr Asn Gln Ala Ser Val Pro Pro Gln Met Arg Ser Asn Pro Gln
465                 470                 475                 480
Gln Pro Pro Gln Asp Lys Pro Ala Gly Gln Ser Ile Trp Leu
                485                 490
```

<210> SEQ ID NO 26
<211> LENGTH: 736
<212> TYPE: PRT
<213> ORGANISM: Yeast

-continued

```
<400> SEQUENCE: 26

Met Ser Gln Asn Ile Gln Ile Gly Thr Arg Lys Arg Ser Arg Ala Asn
1               5                   10                  15
Met Asn Asn Ser Thr Thr Thr Gly Pro Ala Asn Asn Thr Ser Ser Asn
            20                  25                  30
Lys Thr Phe Leu Asp Asn Phe Glu Glu Thr Arg Thr Asn Lys Leu Leu
        35                  40                  45
Asp Glu Met Phe Ala Arg Gln Asn Ser Phe Leu Thr Asp Asn Leu Arg
50                  55                  60
Asn Ser Leu Asp Leu Asn Gln Ala Asp Asn Pro Leu Arg Pro Arg Gln
65                  70                  75                  80
His Gln His Gln Leu Phe Leu Asp Asn Glu Asn Ala Ile Glu Leu Asp
                85                  90                  95
Glu Glu Pro Arg Ile Ile Asn Thr Thr Ile Asn Asn Ser Asn Asn His
            100                 105                 110
Asn Ser Ser Arg Val Asp Glu Asp Ala Asp Asp Ile Ile Phe Ile
        115                 120                 125
Lys Glu Gln Pro Ile Gln Phe Ser Ser Pro Leu Ile Leu Pro Ser Ser
130                 135                 140
Ser Ser Ile Asn Asn Asn Asn Ile Val Thr Ser Asn Asn Pro Gly
145                 150                 155                 160
Cys Gly Thr Ala Ala Thr Ser Asn Ser Thr Tyr Ile Thr Thr Pro Lys
                165                 170                 175
Lys Phe Lys Lys Gln Arg Thr Ile Ser Leu Pro Gln Leu Pro Leu Ser
            180                 185                 190
Lys Leu Ser Tyr Gln Ser Asn Tyr Phe Asn Val Pro Asp Gln Thr Asn
        195                 200                 205
Ala Ile Val Pro Arg Val Thr Gln Thr Glu Asn Glu Leu Leu His Leu
210                 215                 220
Thr Gly Ser Cys Ala Lys Thr Leu Glu Gly Asn Lys Ala Val Asn Leu
225                 230                 235                 240
Thr Ile Ala His Ser Thr Ser Pro Phe Ser Asn Pro Ala Gln Ile
                245                 250                 255
Ala Ser Leu Pro Gln Ser Asn Leu Lys Lys Gln Ile Gly Ser Ser Leu
            260                 265                 270
Arg Lys Phe Thr Ser Asn Gly Ser Ser Glu Ser Ala Ser Ser Asn Lys
        275                 280                 285
Ser Asn Phe Lys Thr Asp Lys Asp Gly His Tyr Val Tyr Gln Glu Asn
290                 295                 300
Asp Ile Phe Gly Ser Gly Gly Arg Phe Val Val Lys Asp Leu Leu Gly
305                 310                 315                 320
Gln Gly Thr Phe Gly Lys Val Leu Lys Cys Ile Asp Asn Lys Tyr Glu
                325                 330                 335
Pro Asn Tyr Val Ala Val Lys Val Ile Arg Ala Val Asp Arg Tyr Arg
            340                 345                 350
Glu Ala Ala Lys Thr Glu Leu Arg Ile Leu Gln Thr Ile Leu Asn Asn
        355                 360                 365
Asp Pro Gln Gly Gln Phe Gln Cys Leu Leu Arg Glu Cys Phe Asp
370                 375                 380
Tyr Lys Asn His Ile Cys Leu Val Thr Asp Leu Tyr Gly Arg Ser Ile
385                 390                 395                 400
Tyr Asp Phe Met Cys Ser Asn Gly Ile Ala Gly Ser Pro Ala Leu Ile
                405                 410                 415
```

-continued

```
Ser Gly His Cys Arg Gln Leu Ile Arg Ser Val Cys Phe Leu His Asp
            420                 425                 430

Leu Gly Ile Ile His Thr Asp Leu Lys Pro Glu Asn Ile Leu Ile Cys
            435                 440                 445

Asp Glu Thr His Ile Ala Gln Lys Leu Pro Leu Lys Thr Val Gln Ser
            450                 455                 460

Leu Ser Lys Arg Arg Arg Glu Ala Ser Lys Gly Lys Arg Lys Ile Leu
465                 470                 475                 480

Lys Asn Pro Glu Ile Lys Ile Ile Asp Phe Gly Ser Ala Ile Phe His
            485                 490                 495

Tyr Glu Tyr His Pro Pro Val Ile Ser Thr Arg His Tyr Arg Ala Pro
            500                 505                 510

Glu Ile Val Leu Gly Leu Gly Trp Ser Phe Pro Cys Asp Ile Trp Ser
            515                 520                 525

Ile Ala Cys Val Leu Val Glu Leu Val Ile Gly Glu Ser Leu Tyr Pro
            530                 535                 540

Ile His Glu Asn Leu Glu His Met Ala Met Met Gln Arg Ile Asn Gly
545                 550                 555                 560

Thr Pro Phe Pro Thr Asp Ile Ile Asp Lys Met Phe Tyr Lys Ser Lys
            565                 570                 575

His Lys Leu Gly Asn Ser Pro Ser Asp Leu Asn Ser Thr Val Ile Lys
            580                 585                 590

His Phe Asp Arg Lys Thr Leu Ser Leu Gln Trp Pro Glu Lys Asn Lys
            595                 600                 605

Arg Gly Asp Thr Ile Thr Thr Glu Lys Ser Met Lys Arg Val Leu Gln
            610                 615                 620

Ser Cys Asp Arg Leu Asp Ile Tyr Ile Ser Lys Val Leu Lys Gln Asp
625                 630                 635                 640

Tyr Gly Asp Ser Leu Ser Ile Asn Trp Asn Leu Pro Pro Glu Lys Asn
            645                 650                 655

Trp Ser Leu Ile Asn Ser Lys Leu Ala Trp Lys Arg Gln Thr His Ser
            660                 665                 670

Ser Ser Ser Ser Thr Thr Asp Glu Leu Asp Lys Glu Thr Phe Leu Phe
            675                 680                 685

Trp Tyr Trp Phe Ile Asp Leu Leu Arg Lys Met Phe Glu Phe Asp Pro
            690                 695                 700

Thr Lys Arg Ile Thr Ala Lys Asp Ala Leu Asp His Glu Trp Phe Asn
705                 710                 715                 720

Leu Gly Ile Leu Asp Asp Gly Ile Ala Thr Tyr Asn Asn Thr Gln Gly
            725                 730                 735

<210> SEQ ID NO 27
<211> LENGTH: 1584
<212> TYPE: PRT
<213> ORGANISM: DICDI - Dictyostelium Discoideum

<400> SEQUENCE: 27

Met Ser Phe Lys Phe Phe Lys Lys Leu Val Pro Ser Asn Glu Tyr
1               5                   10                  15

Arg Trp Asp Leu Arg Lys Ser Asn Ser Leu Thr Leu Asn Ile Glu Asp
            20                  25                  30

Lys Ser Arg Cys Ser Tyr Arg Leu Pro Thr Ser Gly Ser Lys Gly Ile
            35                  40                  45

Ala Lys Ser Thr Gln Pro Phe Ser Ser Ser Phe Thr Tyr Phe Glu Leu
```

-continued

```
              50                  55                  60
Phe Ile Thr Asn Gly Asn Gly Asp Lys Ile Cys Phe Gly Leu Thr Thr
 65                  70                  75                  80
Asn Asp His Pro Ile Glu Val Tyr Pro Gly Asn Tyr Gln Gly Ser Tyr
                     85                  90                  95
Gly Tyr Ser Gly Asp Gly Lys Cys Tyr Phe Gly Thr Asn Glu Gly Arg
                    100                 105                 110
Val Tyr Gly Pro Ser Phe Ser Ser Gly Asp Val Val Gly Cys Gly Tyr
                    115                 120                 125
Asp Ser Ser Lys Thr Leu Tyr Phe Thr Lys Asn Gly Val Tyr Leu
                    130                 135                 140
Gly Val Ala Ala Gln Lys Val Asn Leu Ile Gly Leu Tyr Pro Thr Val
145                 150                 155                 160
Gly Leu Gln Asn Pro Gly Glu Ser Val Val Ile Asn Phe Phe Gly Pro
                    165                 170                 175
Phe Ser Tyr Arg Gly Ala Pro Glu Lys Pro Ser Lys Gln Ser Thr Ile
                    180                 185                 190
Lys Asp Ser Gly Gly Ser Ser Ile Ile Pro Ser Glu Asp Leu Ile Pro
                    195                 200                 205
Lys Glu Glu Phe Glu Val Cys Arg Trp Ser Glu Lys Lys Asn Tyr His
                    210                 215                 220
Gly Lys His Val Val Arg Asn Arg Thr Ala Phe Leu Pro Leu Asp
225                 230                 235                 240
Ser Pro Lys Asp Thr Ile Gly Gly Val Arg Ala Thr Gln Pro Phe Gly
                    245                 250                 255
Glu Gly Phe Cys Tyr Phe Glu Val Ile Ile Asp Gln Leu Asp Lys Gly
                    260                 265                 270
Gln Leu Ser Ile Gly Leu Ala Asn Leu Glu Tyr Pro Thr Phe Tyr His
                    275                 280                 285
Val Gly Trp Met Pro Arg Ser Tyr Gly Tyr His Asn Asp Asp Gly Arg
                    290                 295                 300
Lys Phe Arg Trp Arg Glu Glu Pro Gly Val Asn Glu Gly Glu Ser Tyr
305                 310                 315                 320
Gly Ser Ser Tyr Lys Lys Gly Asp Ile Ile Gly Cys Gly Leu Ser Phe
                    325                 330                 335
Thr Ser Arg Glu Ile Phe Phe Thr Lys Asn Gly Met Tyr Leu Gly Thr
                    340                 345                 350
Ala Phe Ser Asn Val Tyr Gly Val Phe Tyr Pro Ser Val Ala Phe Asn
                    355                 360                 365
Glu Pro Gly Ile Ser Ile Thr Gly Val Phe Gly Pro Pro Phe Lys Phe
                    370                 375                 380
Ser Gln Val Thr Leu Met Leu Lys Asn Val Asn Ser Thr Ser Ile Leu
385                 390                 395                 400
Val Pro Asn Gly Asn Asn Asn Asn Ser Asn Asn Asn Asn Asn
                    405                 410                 415
Asn Asn Asn Asn Ile Ile Gly Asn Gly Lys Ile Thr Thr Thr Thr Thr
                    420                 425                 430
Thr Ser Thr Ser Pro Ser Ser Ile Asn Asn Glu Asp Ile Ser Ser
                    435                 440                 445
Asn Asn Asn Asn Asn Asn Asn Asn Asn Asn Asn Asn Asn
                    450                 455                 460
Asn Asn Asn Asn Asn Asn Asn Asn Asn Asn Asn Asn Ser Asn
465                 470                 475                 480
```

```
Ser Ser Asn Thr Asn Asn Asn Ile Asn Asn Thr Thr Asn Asn Asn
                485             490             495

Asn Ser Asn Ser Asn Asn Asn Asn Asn Asn Asn Ser Asn Ser Asn
                500             505             510

Ser Asn Ser Asn Asn Asn Ile Asn Asn Asn Asn Asn Asn Asn Asn
                515             520             525

Asn Asn Asn Asn Ile Tyr Leu Thr Lys Lys Pro Ser Ile Gly Ser Thr
530                 535             540

Asp Glu Ser Ser Thr Gly Ser Leu Gly Gly Asn Asn Ser Ser Gly Asn
545                 550             555                 560

Asn Asn Ser Ser Ser Gly Ser Ile Gly Asn Asn Ser Ser Ile Ile Lys
                565             570             575

Gln Arg Ser Pro Pro His Ser Ile Asn Gly Pro Leu Met Leu Pro Pro
                580             585             590

Ser Ser Thr Asn Asn Asn Asn Ile Tyr Ser Ser Tyr Asn Ser Thr
                595             600             605

Thr Ala Gly Ser Ser Thr Thr Ile Leu Pro Thr Leu Asn His Pro Ile
        610             615             620

Phe Gly Asn Thr Thr Ser Asn Asn Asn Ser Ser Ser Thr Leu Ser Val
625                 630             635                 640

Gly Gly Asn Asn Asn Leu Leu Gly Arg His Cys Gln Ser Leu Pro Ile
                645             650             655

Thr Ala Ser Thr Asn His Thr Leu Ser Ser Ser Leu Gly Val Ser Phe
                660             665             670

Ser Ser Pro Ser Ser Ser Pro Lys Thr Ser Pro Arg Lys Ile Val Asn
                675             680             685

Ser Ser Glu Asp Leu Gly Phe Val Gln Thr Phe Gln Asp Gln Asp Gly
        690             695             700

Gln Pro Pro Ser Ala Trp Arg Arg Cys Gly Lys Ser Ile Lys Thr Lys
705                 710             715                 720

Asp Asp Ile Thr Leu Thr Ile Ile Lys Lys Lys Thr Ser Val Ala Met
                725             730             735

Ala Asp Arg Pro Phe Ser Ser Asn Ser Ser Ser Thr Ile Cys Tyr Phe
                740             745             750

Glu Val Tyr Leu Glu Gly His Asp Lys Lys Gly Ser Ile Thr Val Gly
        755             760             765

Leu Ser His Ser Thr Tyr Pro Phe Ile Lys His Ile Gly Arg Glu Pro
        770             775             780

Lys Ser Tyr Gly Phe Ser Ser Glu Gly Glu Lys Tyr Gly Gly Ser Glu
785                 790             795                 800

Ile Gly Glu Pro Tyr Gly Pro Phe Phe Phe Asp Gly Asp Ser Ile
                805             810             815

Ala Ser Ser Cys Val Ile Gly Cys Gly Ile Asn Thr Ser Thr Arg Asp
                820             825             830

Ile Phe Phe Thr Lys Asn Gly His Tyr Leu Gly Val Ala Phe Ser Arg
        835             840             845

Val Thr Ser Asp Pro Leu Tyr Pro Ser Ile Ser Phe Arg Gly Val Val
        850             855             860

Gly Gly Leu Cys Val Ala Thr Phe Pro Gly Gly His Phe Arg Phe Asn
865                 870             875                 880

Ile Glu Asp Leu Pro Gly Ile Ser Pro Ser Val Trp Thr Glu Ala Leu
                885             890             895
```

-continued

```
Gly Pro Asp Arg Gln Gly Ser Gly Phe Lys Asn Trp Ala Pro Asn Asp
            900                 905                 910

Val Ala Ile Trp Leu Glu Ser Phe Asn Tyr Gly Gln Tyr Arg Lys Asn
            915                 920                 925

Phe Arg Asp Asn Asn Ile Ser Gly Arg His Leu Gly Ile Thr His
            930                 935                 940

Ala Met Leu Lys Asn Asp Leu Gly Ile Glu Pro Tyr Gly His Arg Glu
945                 950                 955                 960

Asp Ile Ile Asn Arg Leu Asn Arg Met Ile Gln Ile Trp Asn Asp Lys
                965                 970                 975

Ser Pro Asp Ser Tyr Pro Lys Ile Ala Ile Asp Ser Ser Asp Lys Ile
            980                 985                 990

Arg Trp Pro Ala Ser Gly Gly Ser   Ser Gly Gly Ile Asn   Ile Ser Gly
            995                 1000                1005

Gly Val Val Ile Gly Ser Ser   Gly Ser Asp Asp   Gly Ile Thr
    1010                1015                1020

Glu Ile Ser Ser Ser Ser Lys Asn Ile Arg Pro Tyr  Lys Ser Tyr
    1025                1030                1035

Thr Gln Lys Glu Ile Glu Asp  Arg Asn Arg Arg Ser  Thr Ile Ser
    1040                1045                1050

Gly Gly Glu Lys Lys Asn Lys  Tyr Tyr Ile Asp Asn  Gln Met Asp
    1055                1060                1065

Pro His Gln Ile Gly Ser Met Asp Ser Asp Gly Leu  Leu Pro Asp
    1070                1075                1080

Phe Gly Gln Gly Pro Pro Asp  Glu Lys Asn Ser Ser  Lys Thr Leu
    1085                1090                1095

Ser Asn Glu Gln Ile Arg Tyr  Leu Gln Gln Arg Lys  Asp Glu Pro
    1100                1105                1110

Pro Ile Ala Ile Ser Ser Thr  Gly Asn Gly Gly Ser  Val Ser Ser
    1115                1120                1125

Thr Gly Gly Ser Ser Gly Phe  Leu Thr Phe Pro Ser  Ser Asn Ser
    1130                1135                1140

Leu Thr His Pro Pro Gln Arg  Asp Lys Pro Thr Gln  Glu Phe Thr
    1145                1150                1155

His Leu Pro Pro Ile Thr Ser  Asn Tyr Lys Gly Ile  Thr Asn Thr
    1160                1165                1170

Gly Gln Pro His Lys Ser Phe  Asp Gln Pro Leu Glu  Leu Phe Pro
    1175                1180                1185

Arg His Ser Ala Phe Ser Asn  Asn Gly Asn Asn Gly  Asn Asn Asn
    1190                1195                1200

Asn Asn Asn Asn Asn Asn Asn  Ile Lys Ala Asn Gln  Gln Gln Gln
    1205                1210                1215

Gln Gln Ser Ser Tyr Gln Gln  Ser Gln Thr Gln Gln  Gln Gln Gln
    1220                1225                1230

His Ile Thr Ser Thr Ser Thr  Ser Thr Thr Asn Lys  Trp Ile Asp
    1235                1240                1245

Pro Phe Gly Gly Trp Glu Thr  Gln Ser Ser Leu Ser  His Pro Pro
    1250                1255                1260

Ser Arg Pro Pro Pro Pro Pro  Pro Pro Pro Gln Leu  Pro Val
    1265                1270                1275

Arg Ser Glu Tyr Glu Ile Asp  Phe Asn Glu Leu Glu  Phe Gly Gln
    1280                1285                1290

Thr Ile Gly Lys Gly Phe Phe  Gly Glu Val Lys Arg  Gly Tyr Trp
```

-continued

```
                1295                1300                1305
Arg Glu Thr Asp Val Ala Ile Lys Ile Ile Tyr Arg Asp Gln Phe
    1310                1315                1320
Lys Thr Lys Ser Ser Leu Val Met Phe Gln Asn Glu Val Gly Ile
    1325                1330                1335
Leu Ser Lys Leu Arg His Pro Asn Val Val Gln Phe Leu Gly Ala
    1340                1345                1350
Cys Thr Ala Gly Gly Glu Asp His His Cys Ile Val Thr Glu Trp
    1355                1360                1365
Met Gly Gly Gly Ser Leu Arg Gln Phe Leu Thr Asp His Phe Asn
    1370                1375                1380
Leu Leu Glu Gln Asn Pro His Ile Arg Leu Lys Leu Ala Leu Asp
    1385                1390                1395
Ile Ala Lys Gly Met Asn Tyr Leu His Gly Trp Thr Pro Pro Ile
    1400                1405                1410
Leu His Arg Asp Leu Ser Ser Arg Asn Ile Leu Leu Asp His Asn
    1415                1420                1425
Ile Asp Pro Lys Asn Pro Val Val Ser Ser Arg Gln Asp Ile Lys
    1430                1435                1440
Cys Lys Ile Ser Asp Phe Gly Leu Ser Arg Leu Lys Lys Glu Gln
    1445                1450                1455
Ala Ser Gln Met Thr Gln Ser Val Gly Cys Ile Pro Tyr Met Ala
    1460                1465                1470
Pro Glu Val Phe Lys Gly Asp Ser Asn Ser Glu Lys Ser Asp Val
    1475                1480                1485
Tyr Ser Tyr Gly Met Val Leu Phe Glu Leu Leu Thr Ser Asp Glu
    1490                1495                1500
Pro Gln Gln Asp Met Lys Pro Met Lys Met Ala His Leu Ala Ala
    1505                1510                1515
Tyr Glu Ser Tyr Arg Pro Pro Ile Pro Leu Thr Thr Ser Ser Lys
    1520                1525                1530
Trp Lys Glu Ile Leu Thr Gln Cys Trp Asp Ser Asn Pro Asp Ser
    1535                1540                1545
Arg Pro Thr Phe Lys Gln Ile Ile Val His Leu Lys Glu Met Glu
    1550                1555                1560
Asp Gln Gly Val Ser Ser Phe Ala Ser Val Pro Val Gln Thr Ile
    1565                1570                1575
Asp Thr Gly Val Tyr Ala
    1580
```

<210> SEQ ID NO 28
<211> LENGTH: 446
<212> TYPE: PRT
<213> ORGANISM: SCHPO - Fission Yeast

<400> SEQUENCE: 28

```
Met Ser Gly Gln Asn Asn Val Val Gly Val His Tyr Lys Val Gly Arg
1               5                   10                  15
Arg Ile Gly Glu Gly Ser Phe Gly Val Ile Phe Glu Gly Thr Asn Leu
                20                  25                  30
Leu Asn Asn Gln Gln Val Ala Ile Lys Phe Glu Pro Arg Arg Ser Asp
            35                  40                  45
Ala Pro Gln Leu Arg Asp Glu Tyr Arg Thr Tyr Lys Leu Leu Ala Gly
        50                  55                  60
```

```
Cys Thr Gly Ile Pro Asn Val Tyr Tyr Phe Gly Gln Glu Gly Leu His
 65                  70                  75                  80

Asn Ile Leu Val Ile Asp Leu Leu Gly Pro Ser Leu Glu Asp Leu Leu
                 85                  90                  95

Asp Leu Cys Gly Arg Lys Phe Ser Val Lys Thr Val Ala Met Ala Ala
            100                 105                 110

Lys Gln Met Leu Ala Arg Val Gln Ser Ile His Glu Lys Ser Leu Val
        115                 120                 125

Tyr Arg Asp Ile Lys Pro Asp Asn Phe Leu Ile Gly Arg Pro Asn Ser
    130                 135                 140

Lys Asn Ala Asn Met Ile Tyr Val Val Asp Phe Gly Met Val Lys Phe
145                 150                 155                 160

Tyr Arg Asp Pro Val Thr Lys Gln His Ile Pro Tyr Arg Glu Lys Lys
                165                 170                 175

Asn Leu Ser Gly Thr Ala Arg Tyr Met Ser Ile Asn Thr His Leu Gly
            180                 185                 190

Arg Glu Gln Ser Arg Arg Asp Asp Leu Glu Ala Leu Gly His Val Phe
        195                 200                 205

Met Tyr Phe Leu Arg Gly Ser Leu Pro Trp Gln Gly Leu Lys Ala Ala
    210                 215                 220

Thr Asn Lys Gln Lys Tyr Glu Arg Ile Gly Glu Lys Lys Gln Ser Thr
225                 230                 235                 240

Pro Leu Arg Glu Leu Cys Ala Gly Phe Pro Glu Glu Phe Tyr Lys Tyr
                245                 250                 255

Met His Tyr Ala Arg Asn Leu Ala Phe Asp Ala Thr Pro Asp Tyr Asp
            260                 265                 270

Tyr Leu Gln Gly Leu Phe Ser Lys Val Leu Glu Arg Leu Asn Thr Thr
        275                 280                 285

Glu Asp Glu Asn Phe Asp Trp Asn Leu Leu Asn Gly Lys Gly Trp
    290                 295                 300

Gln Ser Leu Lys Ser Arg Asn Ala Glu Thr Glu Asn Gln Arg Ser Ser
305                 310                 315                 320

Lys Pro Pro Ala Pro Lys Leu Glu Ser Lys Ser Pro Ala Leu Gln Asn
                325                 330                 335

His Ala Ser Thr Gln Asn Val Val Ser Lys Arg Ser Asp Tyr Glu Lys
            340                 345                 350

Pro Phe Ala Glu Pro His Leu Asn Ser Ala Ser Asp Ser Ala Glu Pro
        355                 360                 365

Asn Gln Asn Ser Leu Pro Asn Pro Thr Glu Thr Lys Ala Thr Thr
    370                 375                 380

Thr Val Pro Asp Arg Ser Gly Leu Ala Thr Asn Gln Pro Ala Pro Val
385                 390                 395                 400

Asp Val His Asp Ser Ser Glu Glu Arg Val Thr Arg Glu Gln Val Gln
                405                 410                 415

Asn Ala Thr Lys Glu Thr Glu Ala Pro Lys Lys Lys Ser Phe Trp
            420                 425                 430

Ala Ser Ile Leu Ser Cys Cys Ser Gly Ser Asn Glu Asp Thr
        435                 440                 445

<210> SEQ ID NO 29
<211> LENGTH: 298
<212> TYPE: PRT
<213> ORGANISM: Human

<400> SEQUENCE: 29
```

```
Met Glu Asn Phe Gln Lys Val Glu Lys Ile Gly Glu Gly Thr Tyr Gly
1               5                   10                  15

Val Val Tyr Lys Ala Arg Asn Lys Leu Thr Gly Glu Val Val Ala Leu
            20                  25                  30

Lys Lys Ile Arg Leu Asp Thr Glu Thr Glu Gly Val Pro Ser Thr Ala
            35                  40                  45

Ile Arg Glu Ile Ser Leu Leu Lys Glu Leu Asn His Pro Asn Ile Val
    50                  55                  60

Lys Leu Leu Asp Val Ile His Thr Glu Asn Lys Leu Tyr Leu Val Phe
65                  70                  75                  80

Glu Phe Leu His Gln Asp Leu Lys Lys Phe Met Asp Ala Ser Ala Leu
                85                  90                  95

Thr Gly Ile Pro Leu Pro Leu Ile Lys Ser Tyr Leu Phe Gln Leu Leu
                100                 105                 110

Gln Gly Leu Ala Phe Cys His Ser His Arg Val Leu His Arg Asp Leu
            115                 120                 125

Lys Pro Gln Asn Leu Leu Ile Asn Thr Glu Gly Ala Ile Lys Leu Ala
    130                 135                 140

Asp Phe Gly Leu Ala Arg Ala Phe Gly Val Pro Val Arg Thr Tyr Thr
145                 150                 155                 160

His Glu Val Val Thr Leu Trp Tyr Arg Ala Pro Glu Ile Leu Leu Gly
                165                 170                 175

Cys Lys Tyr Tyr Ser Thr Ala Val Asp Ile Trp Ser Leu Gly Cys Ile
                180                 185                 190

Phe Ala Glu Met Val Thr Arg Arg Ala Leu Phe Pro Gly Asp Ser Glu
            195                 200                 205

Ile Asp Gln Leu Phe Arg Ile Phe Arg Thr Leu Gly Thr Pro Asp Glu
    210                 215                 220

Val Val Trp Pro Gly Val Thr Ser Met Pro Asp Tyr Lys Pro Ser Phe
225                 230                 235                 240

Pro Lys Trp Ala Arg Gln Asp Phe Ser Lys Val Val Pro Pro Leu Asp
                245                 250                 255

Glu Asp Gly Arg Ser Leu Leu Ser Gln Met Leu His Tyr Asp Pro Asn
                260                 265                 270

Lys Arg Ile Ser Ala Lys Ala Ala Leu Ala His Pro Phe Phe Gln Asp
            275                 280                 285

Val Thr Lys Pro Val Pro His Leu Arg Leu
            290                 295

<210> SEQ ID NO 30
<211> LENGTH: 387
<212> TYPE: PRT
<213> ORGANISM: Human

<400> SEQUENCE: 30

Met Thr Arg Asp Glu Ala Leu Pro Asp Ser His Ser Ala Gln Asp Phe
1               5                   10                  15

Tyr Glu Asn Tyr Glu Pro Lys Glu Ile Leu Gly Arg Gly Val Ser Ser
            20                  25                  30

Val Val Arg Arg Cys Ile His Lys Pro Thr Ser Gln Glu Tyr Ala Val
            35                  40                  45

Lys Val Ile Asp Val Thr Gly Gly Gly Ser Phe Ser Pro Glu Glu Val
    50                  55                  60

Arg Glu Leu Arg Glu Ala Thr Leu Lys Glu Val Asp Ile Leu Arg Lys
```

```
65                     70                    75                    80
Val Ser Gly His Pro Asn Ile Ile Gln Leu Lys Asp Thr Tyr Glu Thr
                85                    90                    95

Asn Thr Phe Phe Phe Leu Val Phe Asp Leu Met Lys Arg Gly Glu Leu
                100                   105                   110

Phe Asp Tyr Leu Thr Glu Lys Val Thr Leu Ser Glu Lys Glu Thr Arg
                115                   120                   125

Lys Ile Met Arg Ala Leu Leu Glu Val Ile Cys Thr Leu His Lys Leu
                130                   135                   140

Asn Ile Val His Arg Asp Leu Lys Pro Glu Asn Ile Leu Leu Asp Asp
145                   150                   155                   160

Asn Met Asn Ile Lys Leu Thr Asp Phe Gly Phe Ser Cys Gln Leu Glu
                165                   170                   175

Pro Gly Glu Arg Leu Arg Glu Val Cys Gly Thr Pro Ser Tyr Leu Ala
                180                   185                   190

Pro Glu Ile Ile Glu Cys Ser Met Asn Glu Asp His Pro Gly Tyr Gly
                195                   200                   205

Lys Glu Val Asp Met Trp Ser Thr Gly Val Ile Met Tyr Thr Leu Leu
                210                   215                   220

Ala Gly Ser Pro Pro Phe Trp His Arg Lys Gln Met Leu Met Leu Arg
225                   230                   235                   240

Met Ile Met Ser Gly Asn Tyr Gln Phe Gly Ser Pro Glu Trp Asp Asp
                245                   250                   255

Tyr Ser Asp Thr Val Lys Asp Leu Val Ser Arg Phe Leu Val Val Gln
                260                   265                   270

Pro Gln Asn Arg Tyr Thr Ala Glu Glu Ala Leu Ala His Pro Phe Phe
                275                   280                   285

Gln Gln Tyr Leu Val Glu Glu Val Arg His Phe Ser Pro Arg Gly Lys
                290                   295                   300

Phe Lys Val Ile Ala Leu Thr Val Leu Ala Ser Val Arg Ile Tyr Tyr
305                   310                   315                   320

Gln Tyr Arg Arg Val Lys Pro Val Thr Arg Glu Ile Val Ile Arg Asp
                325                   330                   335

Pro Tyr Ala Leu Arg Pro Leu Arg Arg Leu Ile Asp Ala Tyr Ala Phe
                340                   345                   350

Arg Ile Tyr Gly His Trp Val Lys Lys Gly Gln Gln Gln Asn Arg Ala
                355                   360                   365

Ala Leu Phe Glu Asn Thr Pro Lys Ala Val Leu Leu Ser Leu Ala Glu
                370                   375                   380

Glu Asp Tyr
385

<210> SEQ ID NO 31
<211> LENGTH: 370
<212> TYPE: PRT
<213> ORGANISM: Human

<400> SEQUENCE: 31

Met Leu Gly Ala Val Glu Gly Pro Arg Trp Lys Gln Ala Glu Asp Ile
1               5                     10                    15

Arg Asp Ile Tyr Asp Phe Arg Asp Val Leu Gly Thr Gly Ala Phe Ser
                20                    25                    30

Glu Val Ile Leu Ala Glu Asp Lys Arg Thr Gln Lys Leu Val Ala Ile
                35                    40                    45
```

```
Lys Cys Ile Ala Lys Glu Ala Leu Glu Gly Lys Glu Gly Ser Met Glu
     50                  55                  60

Asn Glu Ile Ala Val Leu His Lys Ile Lys His Pro Asn Ile Val Ala
 65                  70                  75                  80

Leu Asp Asp Ile Tyr Glu Ser Gly His Leu Tyr Leu Ile Met Gln
                 85                  90                  95

Leu Val Ser Gly Gly Leu Phe Asp Arg Ile Val Glu Lys Gly Phe
             100                 105                 110

Tyr Thr Glu Arg Asp Ala Ser Arg Leu Ile Phe Gln Val Leu Asp Ala
             115                 120                 125

Val Lys Tyr Leu His Asp Leu Gly Ile Val His Arg Asp Leu Lys Pro
    130                 135                 140

Glu Asn Leu Leu Tyr Tyr Ser Leu Asp Glu Asp Ser Lys Ile Met Ile
145                 150                 155                 160

Ser Asp Phe Gly Leu Ser Lys Met Glu Asp Pro Gly Ser Val Leu Ser
                165                 170                 175

Thr Ala Cys Gly Thr Pro Gly Tyr Val Ala Pro Glu Val Leu Ala Gln
            180                 185                 190

Lys Pro Tyr Ser Lys Ala Val Asp Cys Trp Ser Ile Gly Val Ile Ala
        195                 200                 205

Tyr Ile Leu Leu Cys Gly Tyr Pro Pro Phe Tyr Asp Glu Asn Asp Ala
    210                 215                 220

Lys Leu Phe Glu Gln Ile Leu Lys Ala Glu Tyr Glu Phe Asp Ser Pro
225                 230                 235                 240

Tyr Trp Asp Asp Ile Ser Asp Ser Ala Lys Asp Phe Ile Arg His Leu
                245                 250                 255

Met Glu Lys Asp Pro Glu Lys Arg Phe Thr Cys Glu Gln Ala Leu Gln
            260                 265                 270

His Pro Trp Ile Ala Gly Asp Thr Ala Leu Asp Lys Asn Ile His Gln
        275                 280                 285

Ser Val Ser Glu Gln Ile Lys Lys Asn Phe Ala Lys Ser Lys Trp Lys
    290                 295                 300

Gln Ala Phe Asn Ala Thr Ala Val Val Arg His Met Arg Lys Leu Gln
305                 310                 315                 320

Leu Gly Thr Ser Gln Glu Gly Gln Gly Gln Thr Ala Ser His Gly Glu
                325                 330                 335

Leu Leu Thr Pro Val Ala Gly Gly Pro Ala Ala Gly Cys Cys Cys Arg
            340                 345                 350

Asp Cys Cys Val Glu Pro Gly Thr Glu Leu Ser Pro Thr Leu Pro His
        355                 360                 365

Gln Leu
    370

<210> SEQ ID NO 32
<211> LENGTH: 372
<212> TYPE: PRT
<213> ORGANISM: Human

<400> SEQUENCE: 32

Met Ser Gly Pro Arg Ala Gly Phe Tyr Arg Gln Glu Leu Asn Lys Thr
 1               5                  10                  15

Val Trp Glu Val Pro Gln Arg Leu Gln Gly Leu Arg Pro Val Gly Ser
             20                  25                  30

Gly Ala Tyr Gly Ser Val Cys Ser Ala Tyr Asp Ala Arg Leu Arg Gln
         35                  40                  45
```

```
Lys Val Ala Val Lys Leu Ser Arg Pro Phe Gln Ser Leu Ile His
 50                  55                  60

Ala Arg Arg Thr Tyr Arg Glu Leu Arg Leu Leu Lys His Leu Lys His
 65                  70                  75                  80

Glu Asn Val Ile Gly Leu Leu Asp Val Phe Thr Pro Ala Thr Ser Ile
                 85                  90                  95

Glu Asp Phe Ser Glu Val Tyr Leu Val Thr Thr Leu Met Gly Ala Asp
                100                 105                 110

Leu Asn Asn Ile Val Lys Cys Gln Ala Gly Ala His Gln Gly Ala Arg
                115                 120                 125

Leu Ala Leu Asp Glu His Val Gln Phe Leu Val Tyr Gln Leu Leu Arg
         130                 135                 140

Gly Leu Lys Tyr Ile His Ser Ala Gly Ile Ile His Arg Asp Leu Lys
145                 150                 155                 160

Pro Ser Asn Val Ala Val Asn Glu Asp Cys Glu Leu Arg Ile Leu Asp
                165                 170                 175

Phe Gly Leu Ala Arg Gln Ala Asp Glu Glu Met Thr Gly Tyr Val Ala
             180                 185                 190

Thr Arg Trp Tyr Arg Ala Pro Glu Ile Met Leu Asn Trp Met His Tyr
         195                 200                 205

Asn Gln Thr Val Asp Ile Trp Ser Val Gly Cys Ile Met Ala Glu Leu
210                 215                 220

Leu Gln Gly Lys Ala Leu Phe Pro Gly Ser Asp Tyr Ile Asp Gln Leu
225                 230                 235                 240

Lys Arg Ile Met Glu Val Val Gly Thr Pro Ser Pro Glu Val Leu Ala
             245                 250                 255

Lys Ile Ser Ser Glu His Ala Arg Thr Tyr Ile Gln Ser Leu Pro Pro
             260                 265                 270

Met Pro Gln Lys Asp Leu Ser Ser Ile Phe Arg Gly Ala Asn Pro Leu
         275                 280                 285

Ala Ile Asp Leu Leu Gly Arg Met Leu Val Leu Asp Ser Asp Gln Arg
         290                 295                 300

Val Ser Ala Ala Glu Ala Leu Ala His Ala Tyr Phe Ser Gln Tyr His
305                 310                 315                 320

Asp Pro Glu Asp Glu Pro Glu Ala Glu Pro Tyr Asp Glu Ser Val Glu
                325                 330                 335

Ala Lys Glu Arg Thr Leu Glu Glu Trp Lys Glu Leu Thr Tyr Gln Glu
             340                 345                 350

Val Leu Ser Phe Lys Pro Pro Glu Pro Pro Lys Pro Pro Gly Ser Leu
         355                 360                 365

Glu Ile Glu Gln
    370

<210> SEQ ID NO 33
<211> LENGTH: 367
<212> TYPE: PRT
<213> ORGANISM: Human

<400> SEQUENCE: 33

Met Ser Ser Pro Pro Pro Ala Arg Ser Gly Phe Tyr Arg Gln Glu Val
 1               5                  10                  15

Thr Lys Thr Ala Trp Glu Val Arg Ala Val Tyr Arg Asp Leu Gln Pro
             20                  25                  30

Val Gly Ser Gly Ala Tyr Gly Ala Val Cys Ser Ala Val Asp Gly Arg
```

-continued

```
            35                  40                  45
Thr Gly Ala Lys Val Ala Ile Lys Lys Leu Tyr Arg Pro Phe Gln Ser
         50                  55                  60

Glu Leu Phe Ala Lys Arg Ala Tyr Arg Glu Leu Arg Leu Leu Lys His
 65                  70                  75                  80

Met Arg His Glu Asn Val Ile Gly Leu Leu Asp Val Phe Thr Pro Asp
                 85                  90                  95

Glu Thr Leu Asp Asp Phe Thr Asp Phe Tyr Leu Val Met Pro Phe Met
                100                 105                 110

Gly Thr Asp Leu Gly Lys Leu Met Lys His Glu Lys Leu Gly Glu Asp
                115                 120                 125

Arg Ile Gln Phe Leu Val Tyr Gln Met Leu Lys Gly Leu Arg Tyr Ile
130                 135                 140

His Ala Ala Gly Ile Ile His Arg Asp Leu Lys Pro Gly Asn Leu Ala
145                 150                 155                 160

Val Asn Glu Asp Cys Glu Leu Lys Ile Leu Asp Phe Gly Leu Ala Arg
                165                 170                 175

Gln Ala Asp Ser Glu Met Thr Gly Tyr Val Val Thr Arg Trp Tyr Arg
                180                 185                 190

Ala Pro Glu Val Ile Leu Asn Trp Met Arg Tyr Thr Gln Thr Val Asp
                195                 200                 205

Ile Trp Ser Val Gly Cys Ile Met Ala Glu Met Ile Thr Gly Lys Thr
210                 215                 220

Leu Phe Lys Gly Ser Asp His Leu Asp Gln Leu Lys Glu Ile Met Lys
225                 230                 235                 240

Val Thr Gly Thr Pro Pro Ala Glu Phe Val Gln Arg Leu Gln Ser Asp
                245                 250                 255

Glu Ala Lys Asn Tyr Met Lys Gly Leu Pro Glu Leu Glu Lys Lys Asp
                260                 265                 270

Phe Ala Ser Ile Leu Thr Asn Ala Ser Pro Leu Ala Val Asn Leu Leu
                275                 280                 285

Glu Lys Met Leu Val Leu Asp Ala Glu Gln Arg Val Thr Ala Gly Glu
    290                 295                 300

Ala Leu Ala His Pro Tyr Phe Glu Ser Leu His Asp Thr Glu Asp Glu
305                 310                 315                 320

Pro Gln Val Gln Lys Tyr Asp Asp Ser Phe Asp Asp Val Asp Arg Thr
                325                 330                 335

Leu Asp Glu Trp Lys Arg Val Thr Tyr Lys Glu Val Leu Ser Phe Lys
                340                 345                 350

Pro Pro Arg Gln Leu Gly Ala Arg Val Ser Lys Glu Thr Pro Leu
                355                 360                 365

<210> SEQ ID NO 34
<211> LENGTH: 364
<212> TYPE: PRT
<213> ORGANISM: Human

<400> SEQUENCE: 34

His His His His His His Met Ala Ala Ala Ala Ala Gly Pro Glu
 1               5                  10                  15

Met Val Arg Gly Gln Val Phe Asp Val Gly Pro Arg Tyr Thr Asn Leu
                20                  25                  30

Ser Tyr Ile Gly Glu Gly Ala Tyr Gly Met Val Cys Ser Ala Tyr Asp
                35                  40                  45
```

-continued

```
Asn Leu Asn Lys Val Arg Val Ala Ile Lys Lys Ile Ser Pro Phe Glu
     50                  55                  60

His Gln Thr Tyr Cys Gln Arg Thr Leu Arg Glu Ile Lys Ile Leu Leu
 65                  70                  75                  80

Arg Phe Arg His Glu Asn Ile Ile Gly Ile Asn Asp Ile Ile Arg Ala
                 85                  90                  95

Pro Thr Ile Glu Gln Met Lys Asp Val Tyr Ile Val Gln Asp Leu Met
                100                 105                 110

Glu Thr Asp Leu Tyr Lys Leu Leu Lys Thr Gln His Leu Ser Asn Asp
            115                 120                 125

His Ile Cys Tyr Phe Leu Tyr Gln Ile Leu Arg Gly Leu Lys Tyr Ile
        130                 135                 140

His Ser Ala Asn Val Leu His Arg Asp Leu Lys Pro Ser Asn Leu Leu
145                 150                 155                 160

Leu Asn Thr Thr Cys Asp Leu Lys Ile Cys Asp Phe Gly Leu Ala Arg
                165                 170                 175

Val Ala Asp Pro Asp His Asp His Thr Gly Phe Leu Thr Glu Tyr Val
                180                 185                 190

Ala Thr Arg Trp Tyr Arg Ala Pro Glu Ile Met Leu Asn Ser Lys Gly
            195                 200                 205

Tyr Thr Lys Ser Ile Asp Ile Trp Ser Val Gly Cys Ile Leu Ala Glu
        210                 215                 220

Met Leu Ser Asn Arg Pro Ile Phe Pro Gly Lys His Tyr Leu Asp Gln
225                 230                 235                 240

Leu Asn His Ile Leu Gly Ile Leu Gly Ser Pro Ser Gln Glu Asp Leu
                245                 250                 255

Asn Cys Ile Ile Asn Leu Lys Ala Arg Asn Tyr Leu Leu Ser Leu Pro
                260                 265                 270

His Lys Asn Lys Val Pro Trp Asn Arg Leu Phe Pro Asn Ala Asp Ser
            275                 280                 285

Lys Ala Leu Asp Leu Leu Asp Lys Met Leu Thr Phe Asn Pro His Lys
        290                 295                 300

Arg Ile Glu Val Glu Gln Ala Leu Ala His Pro Tyr Leu Glu Gln Tyr
305                 310                 315                 320

Tyr Asp Pro Ser Asp Glu Pro Ile Ala Glu Ala Pro Phe Lys Phe Asp
                325                 330                 335

Met Glu Leu Asp Asp Leu Pro Lys Glu Lys Leu Lys Glu Leu Ile Phe
                340                 345                 350

Glu Glu Thr Ala Arg Phe Gln Pro Gly Tyr Arg Ser
            355                 360

<210> SEQ ID NO 35
<211> LENGTH: 365
<212> TYPE: PRT
<213> ORGANISM: Human
<220> FEATURE:
<221> NAME/KEY: misc_feature
<223> OTHER INFORMATION: x = tyrosine

<400> SEQUENCE: 35

Ala His His His His His Met Ala Ala Ala Ala Ala Gly Pro
 1               5                  10                  15

Glu Met Val Arg Gly Gln Val Phe Asp Val Gly Pro Arg Tyr Thr Asn
                 20                  25                  30

Leu Ser Tyr Ile Gly Glu Gly Ala Tyr Gly Met Val Cys Ser Ala Tyr
            35                  40                  45
```

-continued

```
Asp Asn Leu Asn Lys Val Arg Val Ala Ile Lys Lys Ile Ser Pro Phe
     50                  55                  60
Glu His Gln Thr Tyr Cys Gln Arg Thr Leu Arg Glu Ile Lys Ile Leu
 65                  70                  75                  80
Leu Arg Phe Arg His Glu Asn Ile Ile Gly Ile Asn Asp Ile Ile Arg
                 85                  90                  95
Ala Pro Thr Ile Glu Gln Met Lys Asp Val Tyr Ile Val Gln Asp Leu
            100                 105                 110
Met Glu Thr Asp Leu Tyr Lys Leu Leu Lys Thr Gln His Leu Ser Asn
        115                 120                 125
Asp His Ile Cys Tyr Phe Leu Tyr Gln Ile Leu Arg Gly Leu Lys Tyr
    130                 135                 140
Ile His Ser Ala Asn Val Leu His Arg Asp Leu Lys Pro Ser Asn Leu
145                 150                 155                 160
Leu Leu Asn Thr Thr Cys Asp Leu Lys Ile Cys Asp Phe Gly Leu Ala
                165                 170                 175
Arg Val Ala Asp Pro Asp His Asp His Thr Gly Phe Leu Xaa Glu Xaa
            180                 185                 190
Val Ala Thr Arg Trp Tyr Arg Ala Pro Glu Ile Met Leu Asn Ser Lys
        195                 200                 205
Gly Tyr Thr Lys Ser Ile Asp Ile Trp Ser Val Gly Cys Ile Leu Ala
    210                 215                 220
Glu Met Leu Ser Asn Arg Pro Ile Phe Pro Gly Lys His Tyr Leu Asp
225                 230                 235                 240
Gln Leu Asn His Ile Leu Gly Ile Leu Gly Ser Pro Ser Gln Glu Asp
                245                 250                 255
Leu Asn Cys Ile Ile Asn Leu Lys Ala Arg Asn Tyr Leu Leu Ser Leu
            260                 265                 270
Pro His Lys Asn Lys Val Pro Trp Asn Arg Leu Phe Pro Asn Ala Asp
        275                 280                 285
Ser Lys Ala Leu Asp Leu Leu Asp Lys Met Leu Thr Phe Asn Pro His
    290                 295                 300
Lys Arg Ile Glu Val Glu Gln Ala Leu Ala His Pro Tyr Leu Glu Gln
305                 310                 315                 320
Tyr Tyr Asp Pro Ser Asp Glu Pro Ile Ala Glu Ala Pro Phe Lys Phe
                325                 330                 335
Asp Met Glu Leu Asp Asp Leu Pro Lys Glu Lys Leu Lys Glu Leu Ile
            340                 345                 350
Phe Glu Glu Thr Ala Arg Phe Gln Pro Gly Tyr Arg Ser
        355                 360                 365

<210> SEQ ID NO 36
<211> LENGTH: 379
<212> TYPE: PRT
<213> ORGANISM: Human

<400> SEQUENCE: 36

Gly Ser Ser His His His His His His Ser Ser Gly Leu Val Pro Arg
 1               5                  10                  15
Gly Ser His Met Ser Gln Glu Arg Pro Thr Phe Tyr Arg Gln Glu Leu
             20                  25                  30
Asn Lys Thr Ile Trp Glu Val Pro Glu Arg Tyr Gln Asn Leu Ser Pro
         35                  40                  45
Val Gly Ser Gly Ala Tyr Gly Ser Val Cys Ala Ala Phe Asp Thr Lys
```

```
            50                  55                  60
Thr Gly His Arg Val Ala Val Lys Lys Leu Ser Arg Pro Phe Gln Ser
65                  70                  75                  80

Ile Ile His Ala Lys Arg Thr Tyr Arg Glu Leu Arg Leu Leu Lys His
                85                  90                  95

Met Lys His Glu Asn Val Ile Gly Leu Leu Asp Val Phe Thr Pro Ala
                100                 105                 110

Arg Ser Leu Glu Glu Phe Asn Asp Val Tyr Leu Val Thr His Leu Met
                115                 120                 125

Gly Ala Asp Leu Asn Asn Ile Val Lys Cys Gln Lys Leu Thr Asp Asp
            130                 135                 140

His Val Gln Phe Leu Ile Tyr Gln Ile Leu Arg Gly Leu Lys Tyr Ile
145                 150                 155                 160

His Ser Ala Asp Ile Ile His Arg Asp Leu Lys Pro Ser Asn Leu Ala
                165                 170                 175

Val Asn Glu Asp Cys Glu Leu Lys Ile Leu Asp Phe Gly Leu Ala Arg
                180                 185                 190

His Thr Asp Asp Glu Met Thr Gly Tyr Val Ala Thr Arg Trp Tyr Arg
            195                 200                 205

Ala Pro Glu Ile Met Leu Asn Trp Met His Tyr Asn Gln Thr Val Asp
210                 215                 220

Ile Trp Ser Val Gly Cys Ile Met Ala Glu Leu Leu Thr Gly Arg Thr
225                 230                 235                 240

Leu Phe Pro Gly Thr Asp His Ile Asp Gln Leu Lys Leu Ile Leu Arg
                245                 250                 255

Leu Val Gly Thr Pro Gly Ala Glu Leu Leu Lys Lys Ile Ser Ser Glu
                260                 265                 270

Ser Ala Arg Asn Tyr Ile Gln Ser Leu Ala Gln Met Pro Lys Met Asn
            275                 280                 285

Phe Ala Asn Val Phe Ile Gly Ala Asn Pro Leu Ala Val Asp Leu Leu
            290                 295                 300

Glu Lys Met Leu Val Leu Asp Ser Asp Lys Arg Ile Thr Ala Ala Gln
305                 310                 315                 320

Ala Leu Ala His Ala Tyr Phe Ala Gln Tyr His Asp Pro Asp Asp Glu
                325                 330                 335

Pro Val Ala Asp Pro Tyr Asp Gln Ser Phe Glu Ser Arg Asp Leu Leu
            340                 345                 350

Ile Asp Glu Trp Lys Ser Leu Thr Tyr Asp Glu Val Ile Ser Phe Val
            355                 360                 365

Pro Pro Pro Leu Asp Gln Glu Glu Met Glu Ser
        370                 375

<210> SEQ ID NO 37
<211> LENGTH: 350
<212> TYPE: PRT
<213> ORGANISM: Human

<400> SEQUENCE: 37

Gly Asn Ala Ala Ala Lys Lys Gly Ser Glu Gln Glu Ser Val Lys
1               5                   10                  15

Glu Phe Leu Ala Lys Ala Lys Glu Asp Phe Leu Lys Lys Trp Glu Thr
                20                  25                  30

Pro Ser Gln Asn Thr Ala Gln Leu Asp Gln Phe Asp Arg Ile Lys Thr
            35                  40                  45
```

```
Leu Gly Thr Gly Ser Phe Gly Arg Val Met Leu Val Lys His Lys Glu
    50                  55                  60

Ser Gly Asn His Tyr Ala Met Lys Ile Leu Asp Lys Gln Lys Val Val
65                  70                  75                  80

Lys Leu Lys Gln Ile Glu His Thr Leu Asn Glu Lys Arg Ile Leu Gln
                85                  90                  95

Ala Val Asn Phe Pro Phe Leu Val Lys Leu Glu Phe Ser Phe Lys Asp
                100                 105                 110

Asn Ser Asn Leu Tyr Met Val Met Glu Tyr Val Ala Gly Gly Glu Met
                115                 120                 125

Phe Ser His Leu Arg Arg Ile Gly Arg Phe Ser Glu Pro His Ala Arg
    130                 135                 140

Phe Tyr Ala Ala Gln Ile Val Leu Thr Phe Glu Tyr Leu His Ser Leu
145                 150                 155                 160

Asp Leu Ile Tyr Arg Asp Leu Lys Pro Glu Asn Leu Leu Ile Asp Gln
                165                 170                 175

Gln Gly Tyr Ile Gln Val Thr Asp Phe Gly Phe Ala Lys Arg Val Lys
                180                 185                 190

Gly Arg Thr Trp Thr Leu Cys Gly Thr Pro Glu Tyr Leu Ala Pro Glu
    195                 200                 205

Ile Ile Leu Ser Lys Gly Tyr Asn Lys Ala Val Asp Trp Trp Ala Leu
    210                 215                 220

Gly Val Leu Ile Tyr Glu Met Ala Ala Gly Tyr Pro Pro Phe Phe Ala
225                 230                 235                 240

Asp Gln Pro Ile Gln Ile Tyr Glu Lys Ile Val Ser Gly Lys Val Arg
                245                 250                 255

Phe Pro Ser His Phe Ser Ser Asp Leu Lys Asp Leu Leu Arg Asn Leu
                260                 265                 270

Leu Gln Val Asp Leu Thr Lys Arg Phe Gly Asn Leu Lys Asn Gly Val
                275                 280                 285

Asn Asp Ile Lys Asn His Lys Trp Phe Ala Thr Thr Asp Trp Ile Ala
    290                 295                 300

Ile Tyr Gln Arg Lys Val Glu Ala Pro Phe Ile Pro Lys Phe Lys Gly
305                 310                 315                 320

Pro Gly Asp Thr Ser Asn Phe Asp Asp Tyr Glu Glu Glu Ile Arg
                325                 330                 335

Val Ser Ile Asn Glu Lys Cys Gly Lys Glu Phe Thr Glu Phe
                340                 345                 350

<210> SEQ ID NO 38
<211> LENGTH: 422
<212> TYPE: PRT
<213> ORGANISM: Human

<400> SEQUENCE: 38

Met Ser Leu His Phe Leu Tyr Tyr Cys Ser Glu Pro Thr Leu Asp Val
1               5                   10                  15

Lys Ile Ala Phe Cys Gln Gly Phe Asp Lys Gln Val Asp Val Ser Tyr
                20                  25                  30

Ile Ala Lys His Tyr Asn Met Ser Lys Ser Lys Val Asp Asn Gln Phe
                35                  40                  45

Tyr Ser Val Glu Val Gly Asp Ser Thr Phe Thr Val Leu Lys Arg Tyr
    50                  55                  60

Gln Asn Leu Lys Pro Ile Gly Ser Gly Ala Gln Gly Ile Val Cys Ala
65                  70                  75                  80
```

```
Ala Tyr Asp Ala Val Leu Asp Arg Asn Val Ala Ile Lys Lys Leu Ser
                85                  90                  95

Arg Pro Phe Gln Asn Gln Thr His Ala Lys Arg Ala Tyr Arg Glu Leu
            100                 105                 110

Val Leu Met Lys Cys Val Asn His Lys Asn Ile Ile Ser Leu Leu Asn
            115                 120                 125

Val Phe Thr Pro Gln Lys Thr Leu Glu Glu Phe Gln Asp Val Tyr Leu
            130                 135                 140

Val Met Glu Leu Met Asp Ala Asn Leu Cys Gln Val Ile Gln Met Glu
145                 150                 155                 160

Leu Asp His Glu Arg Met Ser Tyr Leu Leu Tyr Gln Met Leu Cys Gly
                165                 170                 175

Ile Lys His Leu His Ser Ala Gly Ile Ile His Arg Asp Leu Lys Pro
                180                 185                 190

Ser Asn Ile Val Val Lys Ser Asp Cys Thr Leu Lys Ile Leu Asp Phe
            195                 200                 205

Gly Leu Ala Arg Thr Ala Gly Thr Ser Phe Met Met Thr Pro Tyr Val
            210                 215                 220

Val Thr Arg Tyr Tyr Arg Ala Pro Glu Val Ile Leu Gly Met Gly Tyr
225                 230                 235                 240

Lys Glu Asn Val Asp Ile Trp Ser Val Gly Cys Ile Met Gly Glu Met
                245                 250                 255

Val Arg His Lys Ile Leu Phe Pro Gly Arg Asp Tyr Ile Asp Gln Trp
                260                 265                 270

Asn Lys Val Ile Glu Gln Leu Gly Thr Pro Cys Pro Glu Phe Met Lys
            275                 280                 285

Lys Leu Gln Pro Thr Val Arg Asn Tyr Val Glu Asn Arg Pro Lys Tyr
290                 295                 300

Ala Gly Leu Thr Phe Pro Lys Leu Phe Pro Asp Ser Leu Phe Pro Ala
305                 310                 315                 320

Asp Ser Glu His Asn Lys Leu Lys Ala Ser Gln Ala Arg Asp Leu Leu
                325                 330                 335

Ser Lys Met Leu Val Ile Asp Pro Ala Lys Arg Ile Ser Val Asp Asp
            340                 345                 350

Ala Leu Gln His Pro Tyr Ile Asn Val Trp Tyr Asp Pro Ala Glu Val
            355                 360                 365

Glu Ala Pro Pro Pro Gln Ile Tyr Asp Lys Gln Leu Asp Glu Arg Glu
            370                 375                 380

His Thr Ile Glu Glu Trp Lys Glu Leu Ile Tyr Lys Glu Val Met Asn
385                 390                 395                 400

Ser Glu Glu Lys Thr Lys Asn Gly Val Val Lys Gly Gln Pro Ser Pro
                405                 410                 415

Ser Ala Gln Val Gln Gln
            420

<210> SEQ ID NO 39
<211> LENGTH: 306
<212> TYPE: PRT
<213> ORGANISM: Human
<220> FEATURE:
<221> NAME/KEY: misc_feature
<223> OTHER INFORMATION: x = Tyrosine

<400> SEQUENCE: 39

Val Phe Pro Ser Ser Val Phe Val Pro Asp Glu Trp Glu Val Ser Arg
```

```
1               5                    10                   15
Glu Lys Ile Thr Leu Leu Arg Glu Leu Gly Gln Gly Ser Phe Gly Met
                    20                   25                   30

Val Tyr Glu Gly Asn Ala Arg Asp Ile Ile Lys Gly Glu Ala Glu Thr
                35                   40                   45

Arg Val Ala Val Lys Thr Val Asn Glu Ser Ala Ser Leu Arg Glu Arg
    50                   55                   60

Ile Glu Phe Leu Asn Glu Ala Ser Val Met Lys Gly Phe Thr Cys His
65                   70                   75                   80

His Val Val Arg Leu Leu Gly Val Val Ser Lys Gly Gln Pro Thr Leu
                85                   90                   95

Val Val Met Glu Leu Met Ala His Gly Asp Leu Lys Ser Tyr Leu Arg
                100                  105                  110

Ser Leu Arg Pro Glu Ala Glu Asn Asn Pro Gly Arg Pro Pro Pro Thr
            115                  120                  125

Leu Gln Glu Met Ile Gln Met Ala Ala Glu Ile Ala Asp Gly Met Ala
        130                  135                  140

Tyr Leu Asn Ala Lys Lys Phe Val His Arg Asp Leu Ala Ala Arg Asn
145                  150                  155                  160

Cys Met Val Ala His Asp Phe Thr Val Lys Ile Gly Asp Phe Gly Met
                165                  170                  175

Thr Arg Asp Ile Xaa Glu Thr Asp Xaa Xaa Arg Lys Gly Gly Lys Gly
                180                  185                  190

Leu Leu Pro Val Arg Trp Met Ala Pro Glu Ser Leu Lys Asp Gly Val
            195                  200                  205

Phe Thr Thr Ser Ser Asp Met Trp Ser Phe Gly Val Val Leu Trp Glu
        210                  215                  220

Ile Thr Ser Leu Ala Glu Gln Pro Tyr Gln Gly Leu Ser Asn Glu Gln
225                  230                  235                  240

Val Leu Lys Phe Val Met Asp Gly Gly Tyr Leu Asp Gln Pro Asp Asn
                245                  250                  255

Cys Pro Glu Arg Val Thr Asp Leu Met Arg Met Cys Trp Gln Phe Asn
            260                  265                  270

Pro Lys Met Arg Pro Thr Phe Leu Glu Ile Val Asn Leu Leu Lys Asp
        275                  280                  285

Asp Leu His Pro Ser Phe Pro Glu Val Ser Phe Phe His Ser Glu Glu
    290                  295                  300

Asn Lys
305

<210> SEQ ID NO 40
<211> LENGTH: 306
<212> TYPE: PRT
<213> ORGANISM: Human

<400> SEQUENCE: 40

Val Phe Pro Ser Ser Val Phe Val Pro Asp Glu Trp Glu Val Ser Arg
1               5                    10                   15

Glu Lys Ile Thr Leu Leu Arg Glu Leu Gly Gln Gly Ser Phe Gly Met
                    20                   25                   30

Val Tyr Glu Gly Asn Ala Arg Asp Ile Ile Lys Gly Glu Ala Glu Thr
                35                   40                   45

Arg Val Ala Val Lys Thr Val Asn Glu Ser Ala Ser Leu Arg Glu Arg
    50                   55                   60
```

```
Ile Glu Phe Leu Asn Glu Ala Ser Val Met Lys Gly Phe Thr Cys His
 65                  70                  75                  80

His Val Val Arg Leu Leu Gly Val Val Ser Lys Gly Gln Pro Thr Leu
                 85                  90                  95

Val Val Met Glu Leu Met Ala His Gly Asp Leu Lys Ser Tyr Leu Arg
            100                 105                 110

Ser Leu Arg Pro Glu Ala Glu Asn Asn Pro Gly Arg Pro Pro Pro Thr
        115                 120                 125

Leu Gln Glu Met Ile Gln Met Ala Ala Glu Ile Ala Asp Gly Met Ala
    130                 135                 140

Tyr Leu Asn Ala Lys Lys Phe Val His Arg Asp Leu Ala Ala Arg Asn
145                 150                 155                 160

Cys Met Val Ala His Asp Phe Thr Val Lys Ile Gly Asp Phe Gly Met
                165                 170                 175

Thr Arg Asp Ile Tyr Glu Thr Asp Tyr Tyr Arg Lys Gly Gly Lys Gly
            180                 185                 190

Leu Leu Pro Val Arg Trp Met Ala Pro Glu Ser Leu Lys Asp Gly Val
        195                 200                 205

Phe Thr Thr Ser Ser Asp Met Trp Ser Phe Gly Val Val Leu Trp Glu
    210                 215                 220

Ile Thr Ser Leu Ala Glu Gln Pro Tyr Gln Gly Leu Ser Asn Glu Gln
225                 230                 235                 240

Val Leu Lys Phe Val Met Asp Gly Gly Tyr Leu Asp Gln Pro Asp Asn
                245                 250                 255

Cys Pro Glu Arg Val Thr Asp Leu Met Arg Met Cys Trp Gln Phe Asn
            260                 265                 270

Pro Lys Met Arg Pro Thr Phe Leu Glu Ile Val Asn Leu Leu Lys Asp
        275                 280                 285

Asp Leu His Pro Ser Phe Pro Glu Val Ser Phe Phe His Ser Glu Glu
    290                 295                 300

Asn Lys
305

<210> SEQ ID NO 41
<211> LENGTH: 271
<212> TYPE: PRT
<213> ORGANISM: Human
<220> FEATURE:
<221> NAME/KEY: misc_feature
<223> OTHER INFORMATION: x=tyrosine

<400> SEQUENCE: 41

Lys Pro Trp Trp Glu Asp Glu Trp Glu Val Pro Arg Glu Thr Leu Lys
 1               5                  10                  15

Leu Val Glu Arg Leu Gly Ala Gly Gln Phe Gly Glu Val Trp Met Gly
                20                  25                  30

Tyr Tyr Asn Gly His Thr Lys Val Ala Val Lys Ser Leu Lys Gln Gly
            35                  40                  45

Ser Met Ser Pro Asp Ala Phe Leu Ala Glu Ala Asn Leu Met Lys Gln
     50                  55                  60

Leu Gln His Gln Arg Leu Val Arg Leu Tyr Ala Val Val Thr Gln Glu
 65                  70                  75                  80

Pro Ile Tyr Ile Ile Thr Glu Tyr Met Glu Asn Gly Ser Leu Val Asp
                 85                  90                  95

Phe Leu Lys Thr Pro Ser Gly Ile Lys Leu Thr Ile Asn Lys Leu Leu
            100                 105                 110
```

```
Asp Met Ala Ala Gln Ile Ala Glu Gly Met Ala Phe Ile Glu Glu Arg
        115             120             125

Asn Tyr Ile His Arg Asp Leu Arg Ala Ala Asn Ile Leu Val Ser Asp
    130             135             140

Thr Leu Ser Cys Lys Ile Ala Asp Phe Gly Leu Ala Arg Leu Ile Glu
145             150             155             160

Asp Asn Glu Xaa Thr Ala Arg Glu Gly Ala Lys Phe Pro Ile Lys Trp
            165             170             175

Thr Ala Pro Glu Ala Ile Asn Tyr Gly Thr Phe Thr Ile Lys Ser Asp
            180             185             190

Val Trp Ser Phe Gly Ile Leu Leu Thr Glu Ile Val Thr His Gly Arg
        195             200             205

Ile Pro Tyr Pro Gly Met Thr Asn Pro Glu Val Ile Gln Asn Leu Glu
    210             215             220

Arg Gly Tyr Arg Met Val Arg Pro Asp Asn Cys Pro Glu Glu Leu Tyr
225             230             235             240

Gln Leu Met Arg Leu Cys Trp Lys Glu Arg Pro Glu Asp Arg Pro Thr
            245             250             255

Phe Asp Tyr Leu Arg Ser Val Leu Glu Asp Phe Phe Thr Ala Thr
            260             265             270
```

CRYSTALLIZED P38 COMPLEXES

This application claims priority from U.S. Provisional Applications Ser. No. 60/112,354 filed Dec. 16, 1998, and U.S. Provisional Application Ser. No. 60/163,373 filed Nov. 3, 1999.

TECHNICAL FIELD OF INVENTION

This invention relates to certain crystallized kinase protein-ligand complexes, particularly complexes of crystallized P38 protein, and more particularly complexes of P38γ protein. This invention also relates to crystallizable compositions from which the protein-ligand complexes may be obtained. This invention also relates to computational methods of using structure coordinates of the protein complex to screen for and design compounds that interact with the protein, particularly P38 protein or homologues thereof.

BACKGROUND OF THE INVENTION

Mammalian cells respond to extracellular stimuli by activating signaling cascades that are mediated by members of the mitogen-activated protein (MAP) kinase family. Mammalian mitogen-activated protein (MAP) kinases are proline-directed serine/threonine kinases that facilitate signal translocation in cells [Davis, Mol. Reprod. Dev. 42, 459–467 (1995); Cobb et al., J. Biol. Chem. 270, 14843–14846 (1995); Marshall, Cell 80, 179–185 (1995)]. MAP kinases include the extracellular-signal regulated kinases (ERKs), the c-Jun $NH_2$-terminal kinases (JNKs) and the P38 kinases, which have similar sequences and three-dimensional structures [Taylor & lipopolysaccharides (LPS), UV, anisomycin, or osmotic shock, and by cytokines, such as interleukin-1 (IL-1) and tissue necrosis factor (TNF). Inhibition of P38α kinase leads to a blockade on the production of both IL-1 and TNF. IL-1 and TNF stimulate the production of other proinflammatory cytokines such as IL-6 and IL-8 and have been implicated in acute and chronic inflammatory diseases and in post-menopausal osteoporosis [Kimble et al., Endocrinol., 136, 3054–61 (1995)].

Based upon this finding it is believed that P38α, along with other MAPKs, has a role in mediating cellular response to inflammatory stimuli, such as leukocyte accumulation, macrophage/monocyte activation, tissue resorption, fever, acute phase responses and neutrophilia. In addition, the MAPKs, such as P38α, have been implicated in cancer, thrombin-induced platelet aggregation, immunodeficiency disorders, autoimmune diseases, cell death, allergies, osteoporosis and neurodegenerative disorders. Inhibitors of P38α also appear to be involved in pain management through inhibition of prostaglandin endoperoxide synthase-2 induction. Other diseases associated with Il-1, IL-6, IL-8 or TNF overproduction are set forth in WO 96/21654. P38γ MAP kinase (also known as ERK6 and stress activated protein kinase-3 or SAPK3) is a newly discovered member of the MAP kinase family. However, unlike the other P38 family members which are expressed in many tissues, P38γ is expressed at highest levels in skeletal muscle [Li et al., Biochem Biophys Res Commun 228, 334–340 (1996); Enslen et al., J Biol Chem 273, 1741–1748 (1998); Raingeaud et al., J. Biol. Chem. 270, 7420–7426 (1995)]. Thus P38γ may have a unique function related to muscle morphogenesis, and it may be a potential target for treating degenerative diseases occurring in muscle tissue.

Compounds that selectively inhibit P38γ and not P38α would be highly desirable. It would be useful to have new treatments for muscle degenerative diseases using compounds that do not suppress the inflammatory response or other functions of P38α. However, the design of inhibitors that are selective for any particular MAP kinase, such as P38γ, is challenging due to the structural similarity of the MAP kinases. Therefore, it would be advantageous to have a detailed understanding of the structures of the various MAP kinases in order to exploit any subtle differences that may exist among them.

A general approach to designing inhibitors that are selective for an enzyme target is to determine how a putative inhibitor interacts with the three dimensional structure of the enzyme. For this reason it is useful to obtain the enzyme protein in crystal form and perform X-ray diffraction techniques to determine its three dimensional structure coordinates. If the enzyme is crystallized as a complex with a ligand, one can determine both the shape of the enzyme binding pocket when bound to the ligand, as well as the amino acid residues that are capable of close contact with the ligand. By knowing the shape and amino acid residues in the binding pocket, one may design new ligands that will interact favorably with the enzyme. With such structural information, available computational methods may be used to predict how strong the ligand binding interaction will be. Such methods thus enable the design of inhibitors that bind strongly, as well as selectively to the target enzyme.

Crystal structures are known for some of the MAP kinases; for example, unphosphorylated JNK3, unphosphorylated P38α, and ERK2 in both phosphorylated and unphosphorylated forms. Phosphorylated ERK2 is reported to exist as a dimer in both solution and as a crystal. The unphosphorylated forms of JNK3, ERK2 and P38α, on the other hand, are reported to be monomeric. [Tong et al., Nat Struct Biol 4, 311–316 (1997); Wilson and Su, Chem Biol 4, 423–431 (1997); Xie et al., Structure 6, 983–991 (1998); Zhang et al., Nature 367, 704–711 (1994); Canagarajah et al., Cell 90, 859–869 (1997); Wilson and Su, J Biol Chem 271, 27696–27700 (1996)].

The crystal structure reported for P38α is based on unphosphorylated protein. However, it is the phosphorylated or activated form of the enzyme that is able to phosphorylate its substrate enzyme. In order to disrupt the phosphorylation of the substrate, and produce the desired clinical effect, a small molecule inhibitor would likely act by blocking a phosphorylated form of P38. Thus, the most suitable target for drug design is the active or phosphorylated form. While the structure of the unphosphorylated enzyme is often used for drug design purposes, there is an inherent uncertainty as to whether the phosphorylated and unphosphorylated forms would bind a designed inhibitor with equal affinity.

A class of pyridinylimidazole compounds are known to inhibit P38α MAP kinase [Lee et al., Nature 372, 739–746 (1994)]. These inhibitors have been shown to bind in the ATP binding site of P38α [Young et al., J Biol Chem 272, 12116–12121 (1997); Tong et al., Nat Struct Biol 4, 311–316 (1997); Wilson et al., Chem Biol 4, 423–431 (1997)]. However, the pyridinylimidazoles reportedly do not inhibit the activity of ERK2, JNK3, or P38γ. This observed selectivity is interesting because the amino acid sequence in the ATP binding site of the various kinases are known to be highly conserved [Fox et al., Protein Science 7, 2249–2255 (1998); Xie et al., supra; Wilson and Su, supra; Enslen et al., J Biol Chem 273, 1741–1748 (1998)].

As there is a need for compounds that selectively inhibit a particular MAP kinase, it would be desirable to have improved methods that facilitate the design of such compounds. For this purpose, knowledge of the three dimensional structure coordinates of an activated P38 protein would be useful. Such information would aid in identifying and designing potential inhibitors of particular P38 proteins which, in turn, are expected to have therapeutic utility.

SUMMARY OF THE INVENTION

This invention provides certain crystallized, protein kinase-ligand complexes, in particular P38-ligand complexes, and their structure coordinates. The structure coordinates are based on the structure of a phosphorylated P38γ-ligand complex that has now been solved and which reveals new structural information useful for understanding the activated states of other, related kinase proteins as described herein. The key structural features of the proteins, particularly the shape of the substrate binding site, are useful in methods for designing or identifying selective inhibitors of the protein kinases, particularly P38, and in solving the structures of other proteins with similar features.

The invention also provides a computer which which is programmed with the structure coordinates of the activated P38 binding site. Such a computer, appropriately programmed and attached to the necessary viewing device, is capable of displaying a three-dimensional graphical representation of a molecule or molecular complex comprising such binding sites or similarly shaped homologous binding pockets.

The invention also provides a method for determining at least a portion of the three-dimensional structure of other molecules or molecular complexes which contain at least some features that are structurally similar to P38γ, particularly P38α, P38β, P38δ and other P38 isoforms. This is achieved by using at least some of the structural coordinates obtained for a phosphorylated P38 complex.

BRIEF DESCRIPTION OF THE FIGURES

FIGS. 1.1–1.98 lists the atomic structure coordinates for phosphorylated P38γ in complex with MgAMP-PNP as derived by X-ray diffraction from a crystal of that complex. The following abbreviations are used in FIGS. 1.1–1.98:

"X, Y, Z" crystallographically define the atomic position of the element measured.

"B" is a thermal factor that measures movement of the atom around its atomic center.

"Occ" is an occupancy factor that refers to the fraction of the molecules in which each atom occupies the position specified by the coordinates. A value of "1" indicates that each atom has the same conformation, i.e., the same position, in all molecules of the crystal.

Figure 2:
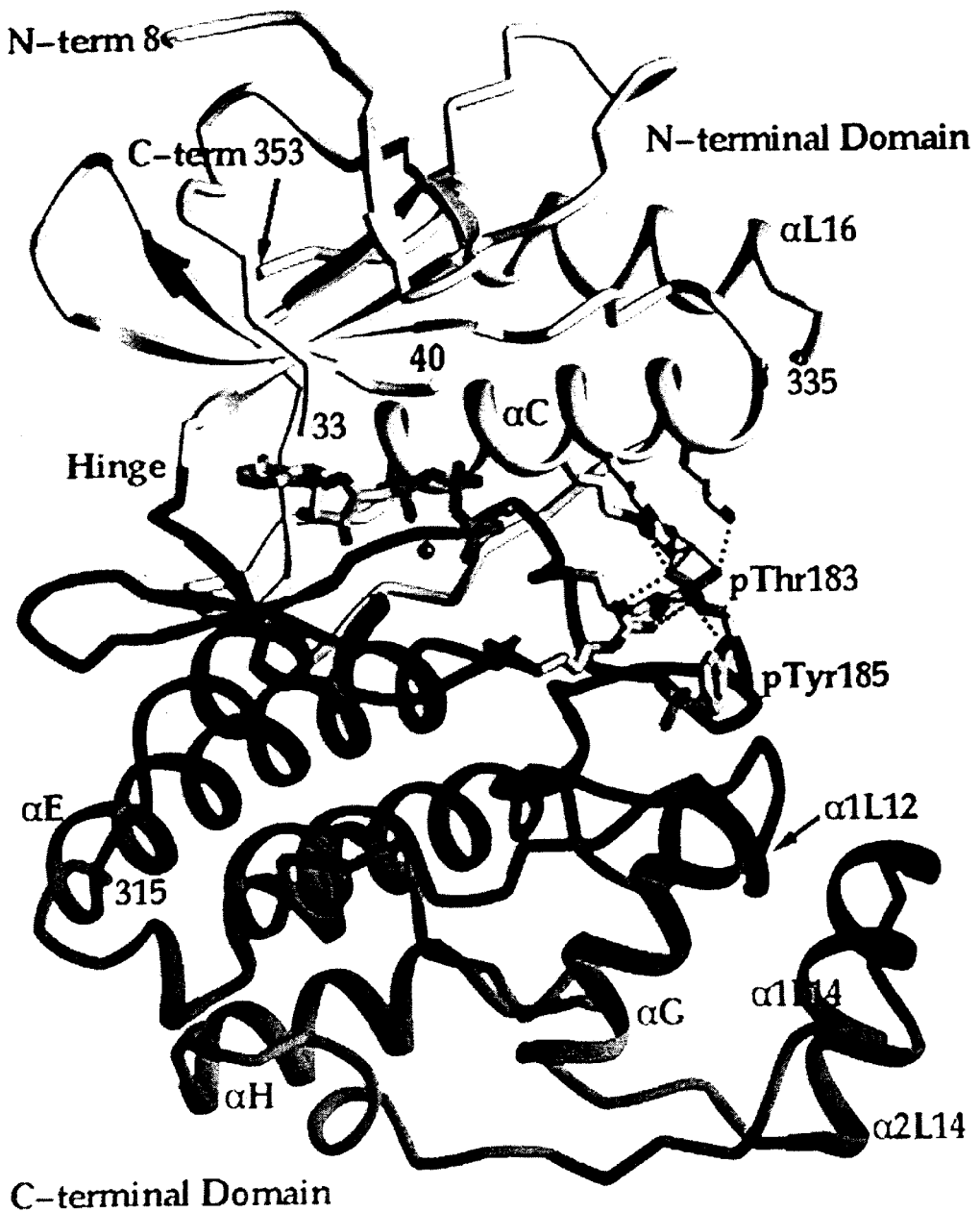

FIG. 2 is an overview of the phosphorylated P38γ.

Figure 3:

FIG. 3 is a superimposition of unphosphorylated P38γ and phosphorylated P38γ.

Figure 4:
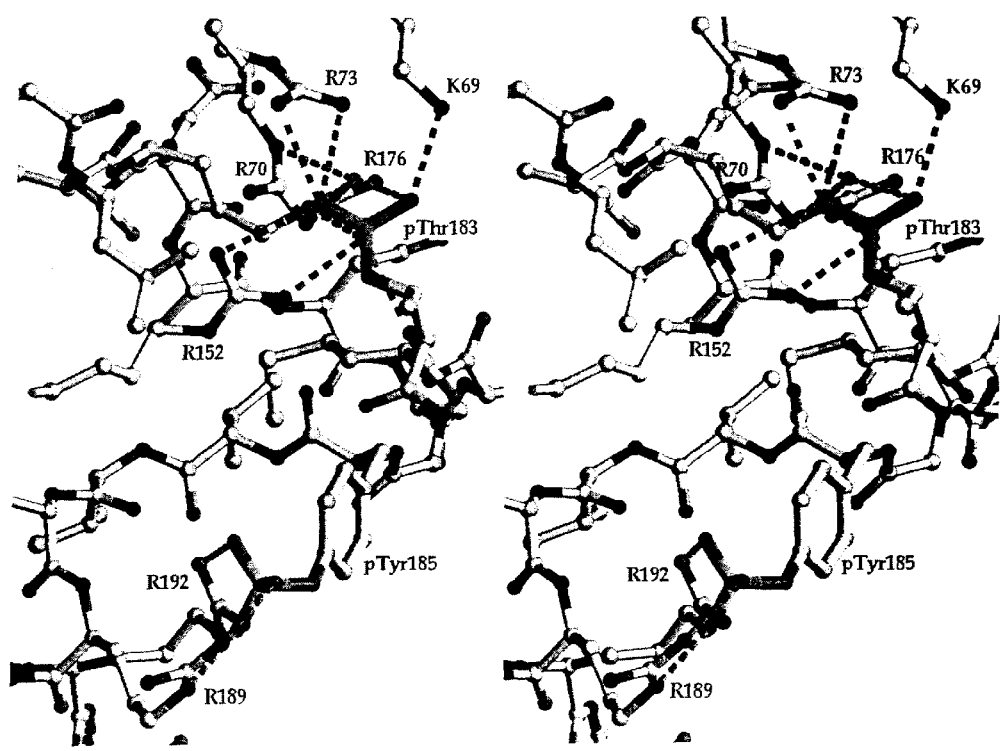

FIG. 4 is a detailed stereo view of the activation loop.

Figure 5:
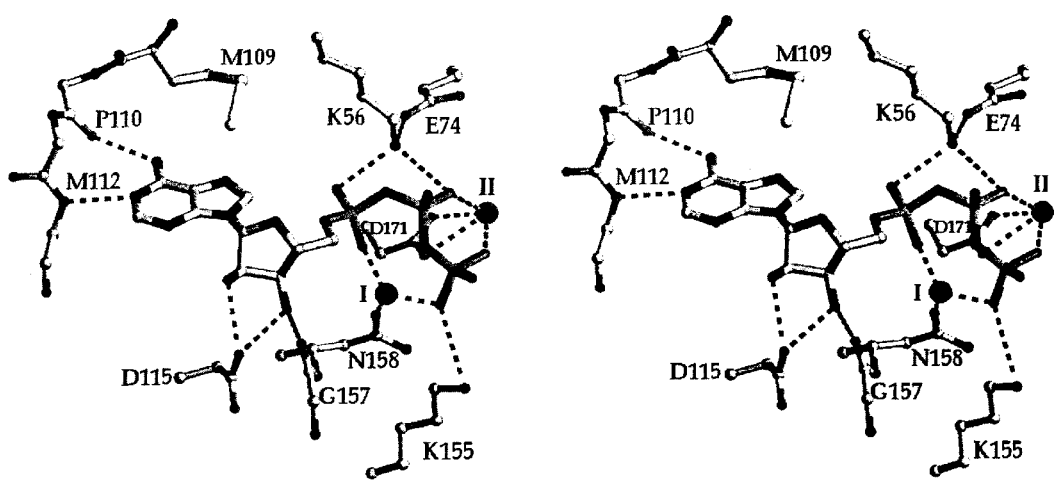

FIG. 5 is a stereo view of the AMP-PNP bound in the active site.

FIG. 6 is a comparison of the active sites of activated P38γ with P38α (a) and cAPK or cyclic AMP dependent protein kinase(b).

Figure 7:
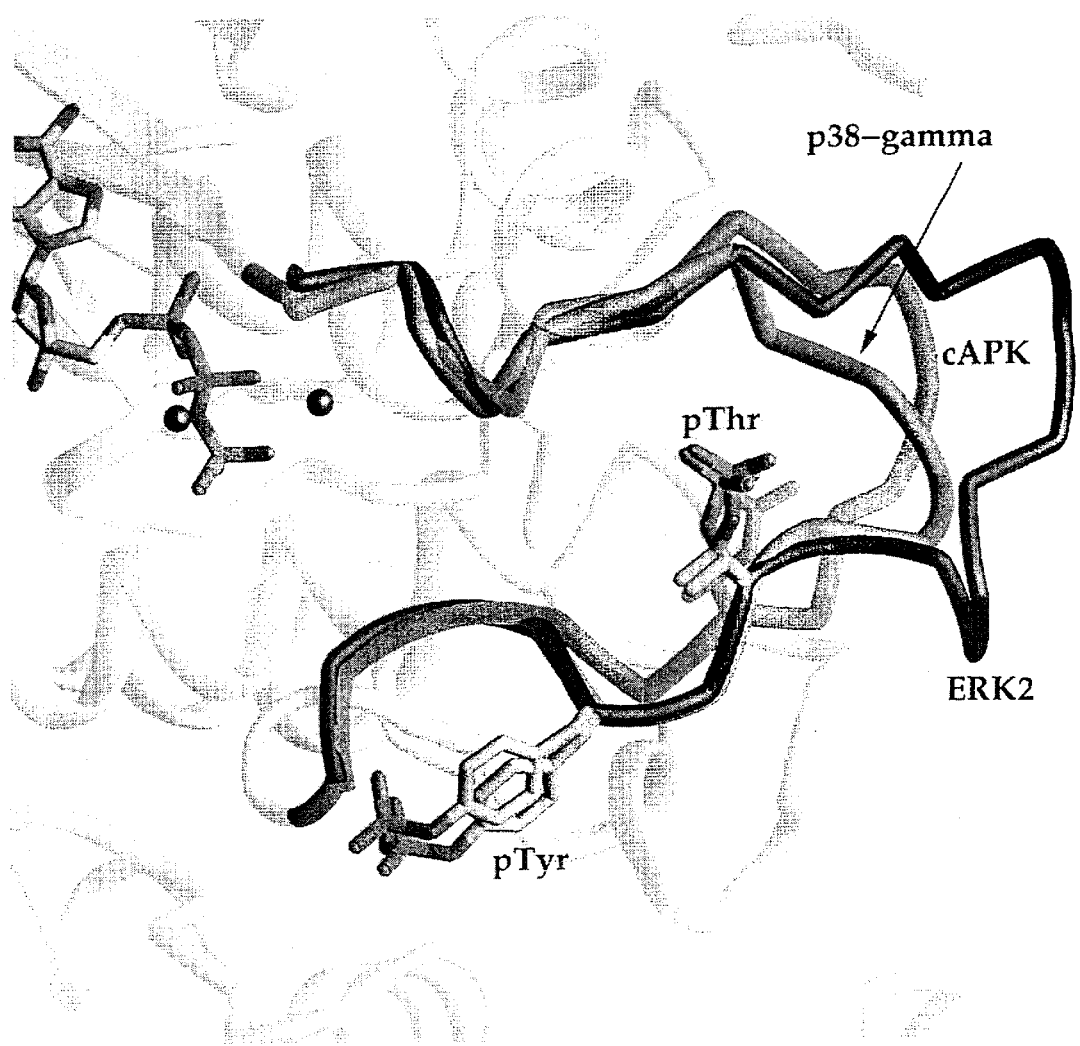

FIG. 7 is a comparison of activated phosphorylation loops from P38γ (dark orange), ERK2 (dark blue), and cAPK (red).

Figure 8:
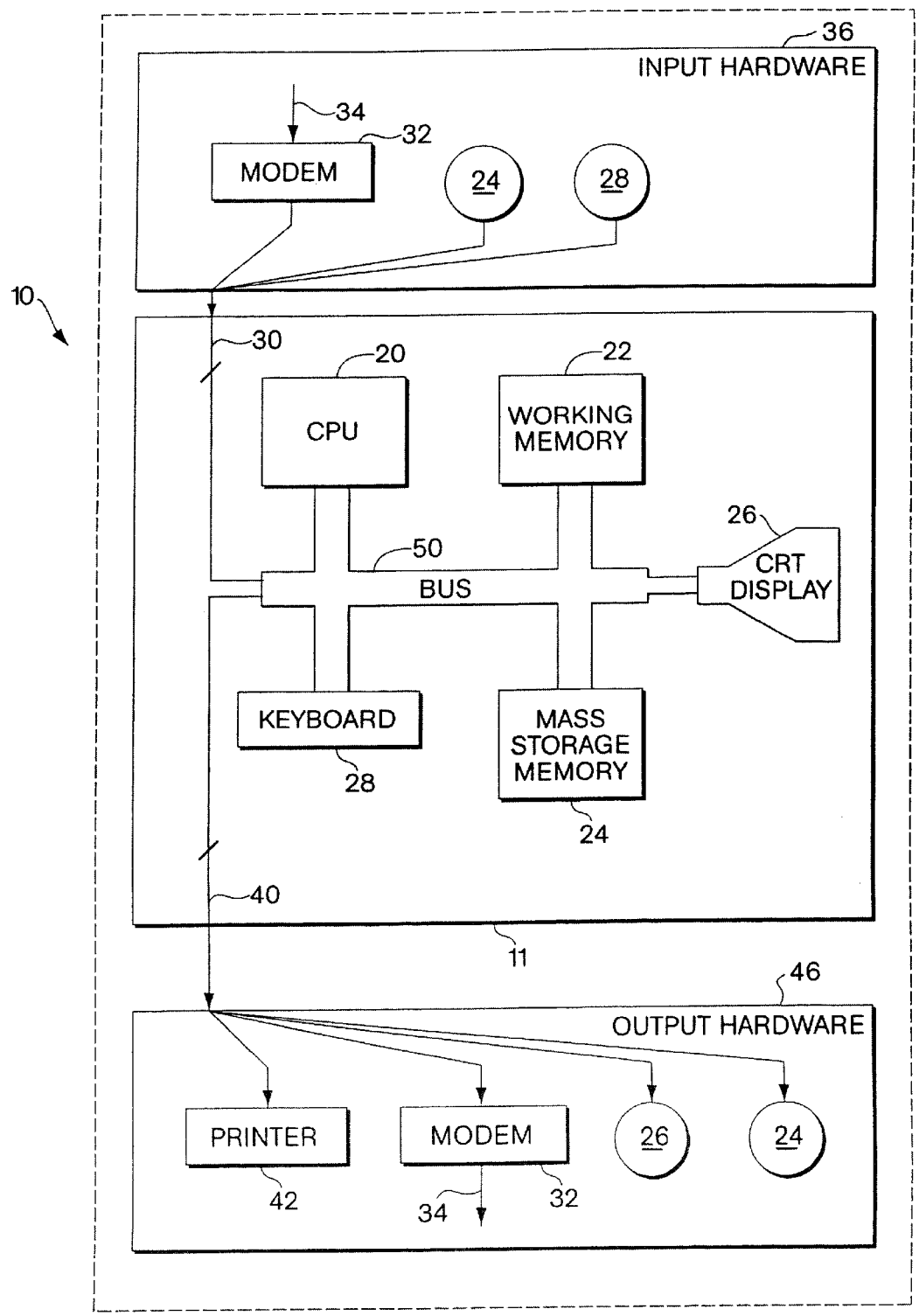
Figure 9:
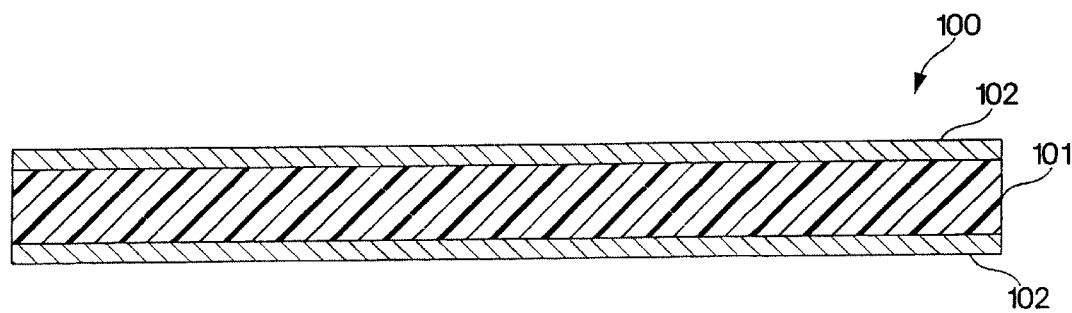
Figure 10:
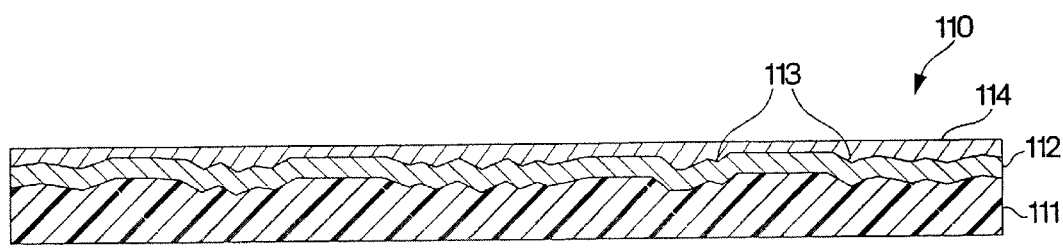

FIG. 8 shows a diagram of a system used to carry out the instructions encoded by the storage medium of FIGS. 9 and 10.

FIG. 9 shows a cross section of a magnetic storage medium.

FIG. 10 shows a cross section of a optically-readable data storage medium.

DETAILED DESCRIPTION OF THE INVENTION

This invention provides certain crystallized, protein kinase-ligand complexes, in particular P38-ligand complexes, and their structure coordinates. The structure coordinates are based on the structure of a phosphorylated P38γ complex that has now been solved and which reveals new structural information regarding the activated states of other, related kinase proteins as described herein. The key structural features of the protein, particularly the shape of the substrate binding site, are useful in methods for designing inhibitors of the P38 and in solving the structures of other proteins with similar features.

As used herein, unless otherwise indicated, the term "p38γ" refers to the protein that is described by SEQ ID NO:1. In describing protein structure and function, reference is made to amino acids comprising the protein. The amino acids may also be referred to by their conventional abbreviations, as shown in the table below.

| | |
|---|---|
| A = Ala = Alanine | T = Thr = Threonine |
| V = Val = Valine | C = Cys = Cysteine |
| L = Leu = Leucine | Y = Tyr = Tyrosine |
| I = Ile = Isoleucine | N = Asn = Asparagine |
| P = Pro = Proline | Q = Gln = Glutamine |
| F = Phe = Phenylalanine | D = Asp = Aspartic Acid |
| W = Trp = Tryptophan | E = Glu = Glutamic Acid |
| M = Met = Methionine | K = Lys = Lysine |
| G = Gly = Glycine | R = Arg = Arginine |
| S = Ser = Serine | H = His = Histidine |

This invention also provides a crystallizable composition from which the crystallized protein is obtained. The crystallizable composition preferably comprises a phosphorylated P38 protein complexed with a substrate or ligand. The ligand may be any ligand capable of binding to the P38 protein, and is preferably a ligand that binds to the ATP binding site of the protein. Examples of such ligands are small molecule inhibitors of the particular P38 as well as non-hydrolyzable ATP analogs and suicide substrates. Non-hydrolyzable ATP analogs useful in the crystallizable compositions of this invention include AMP-PCH$_2$P, AMP-PSP and AMP-PNP where the oxygen linking the second and third phosphates of the ATP analogs is replaced by CH$_2$, S and NH, respectively. An example of a suicidal substrate is 5'-(p-fluorosulfonyl benzoyl)adenosine (FSBA). Preferably, the crystallizable compositions of this invention comprise AMP-PNP as the substrate. It is preferred that the composition further comprise divalent cations, especially magnesium or magnanese cations, which may be introduced in any suitable manner. For example, the cations may be introduced by incubating the desired ligand with a suitable metal salt such as MgCl$_2$ prior to incubation with the phosphorylated P38 protein.

It has been found that the crystallization of the phosphorylated P38 protein is sensitive to buffer conditions. Thus, in a preferred embodiment, the crystallizable compositions of this invention further comprise a suitable glycol such as ethylene glycol, polyethylene glycol (PEG), PEG-monomethyl ether or mixtures thereof, preferably PEG 4000, as an aqueous solution containing between about 10 to 35% of the glycol by volume of solution, a salt, such as sodium acetate at about 50 to 200 mM, a reducing agent, such as dithiothreitol (DTT) at between about 1 to 10 mM, a detergent such as C12E9 at about 0.01 to 0.05%, and a buffer that maintains pH at between about 8.0 and 9.0. An example of a suitable buffer is 100 mM Tris at pH 8.5.

By applying standard crystallization protocols to the above described crystallizable compositions, crystals of the phosphorylated P38 protein complex may be obtained. Thus, one aspect of this invention relates to a method of preparing phosphorylated P38-containing crystals. The method comprises the steps of (a) obtaining a crystallizable composition comprising a phosphorylated P38 protein, divalent cations, and a ligand capable of binding to the protein, and (b) subjecting the composition of step (a) to conditions which promote crystallization.

FIGS. 1.1–1.98 show the structure coordinates of a phosphorylated P38γ protein complexed with MgAMP-PNP. The manner of obtaining these structure coordinates, interpretation of the coordinates and their utility in understanding the protein structure, as described herein, will be understood by those of skill in the art and by reference to standard texts such as Crystal Structure Analysis, Jenny Pickworth Glusker and Kenneth N. Trueblood, 2nd Ed. Oxford University Press, 1985, New York; and Principles of Protein Structure, G. E. Schulz and R. H. Schirmer, Springer-Verlag, 1985, New York.

Those of skill in the art understand that a set of structure coordinates for an enzyme or an enzyme-complex or a portion thereof, is a relative set of points that define a shape in three dimensions. Thus, it is possible that an entirely different set of coordinates could define a similar or identical shape. Moreover, slight variations in the individual coordinates will have little effect on overall shape. In terms of binding pockets, these variations would not be expected to significantly alter the nature of ligands that could associate with those pockets.

These variations in coordinates may be generated because of mathematical manipulations of the P38γ/MgAMP-PNP structure coordinates. For example, the structure coordinates set forth in FIGS. 1.1–1.98 could be manipulated by crystallographic permutations of the structure coordinates, fractionalization of the structure coordinates, integer additions or subtractions to sets of the structure coordinates, inversion of the structure coordinates or any combination of the above.

Alternatively, modifications in the crystal structure due to mutations, additions, substitutions, and/or deletions of amino acids, or other changes in any of the components that make up the crystal could also account for variations in structure coordinates. If such variations are within an acceptable standard error as compared to the original coordinates, the resulting three-dimensional shape is considered to be the same. Thus, for example, a ligand that bound to the active site binding pocket of P38γ would also be expected to bind to another binding pocket whose structure coordinates defined a shape that fell within the acceptable error.

The term "binding pocket" refers to a region of the protein that, as a result of its shape, favorably associates with a ligand or substrate. The term "P38γ-like binding pocket" refers to a portion of a molecule or molecular complex whose shape is sufficiently similar to the P38γ binding pockets as to bind common ligands. This commonality of shape may be quantitatively defined by a root mean square deviation (rmsd) from the structure coordinates of the backbone atoms of the amino acids that make up the binding pockets in P38γ (as set forth in FIGS. 1.1–1.98). The method of performing this rmsd calculation is described below.

The "active site binding pockets" or "active site" of P38γ refers to the area on the P38γ enzyme surface where the substrate binds. In resolving the crystal structure of phosphorylated P38γ in complex with MgAMP-PNP, applicants have determined that P38γ amino acids Val33, Ala40, Val41, Ala54, Lys56, Ile87, Met109, Pro110, Phe111, Met112, Gly113, Thr114, Asp115, Lys118, Asp153, Lys155, Gly157, Asn158, Ala160, Leu170, Asp171, Gly173, and Leu174 are within 5 Å of and therefore close enough to interact with MgAMP-PNP. These amino acids are hereinafter referred to as the "SET 5A amino acids." Thus, a binding pocket defined by the structural coordinates of those amino acids, as set forth in FIGS. 1.1–1.98; or a binding pocket whose root mean square deviation from the structure coordinates of the backbone atoms of those amino acids of not more than about 1.15 angstroms (Å) is considered a P38γ-like binding pocket of this invention.

Applicants have also determined that in addition to the P38γ amino acids set forth above, Pro32, Cys42, Ser43, Val53, Ile55, Lys57, Leu58, Thr59, Arg70, Glu74, Gly88, Leu107, Val108, Leu116, Gly117, Pro156, Leu159, Val161, Lys168, Phe172, Ala175, and Thr188 are within 8 Å of bound MgAMP-PNP and therefore are also close enough to interact with that substrate. These amino acids, in addition to the SET 5A amino acids, are hereinafter referred to as the "SET 8A amino acids." Thus, in a preferred embodiment, a binding pocket defined by the structural coordinates of the amino acids within 8A of bound MgAMP-PNP, as set forth in FIGS. 1.1–1.98; or a binding pocket whose root mean square deviation from the structure coordinates of the backbone atoms of those amino acids of not more than about 1.15 Å is considered a preferred P38γ-like binding pocket of this invention.

It will be readily apparent to those of skill in the art that the numbering of amino acids in other isoforms of P38 may be different than that set forth for P38γ. Corresponding amino acids in other isoforms of P38 are easily identified by visual inspection of the amino acid sequences or by using commercially available homology software programs, as further described below.

Various computational analyses may be used to determine whether a protein or the binding pocket portion thereof is sufficiently similar to the P38γ binding pockets described above. Such analyses may be carried out in well known software applications, such as the Molecular Similarity application of QUANTA (Molecular Simulations Inc., San Diego, Calif.) version 4.1, and as described in the accompanying User's Guide.

For the purpose of this invention, a rigid fitting method was conveniently used to compare protein structures. Any molecule or molecular complex or binding pocket thereof having a root mean square deviation of conserved residue backbone atoms (N, Cα, C, O) of less than about 1.15 Å when superimposed on the relevant backbone atoms described by structure coordinates listed in FIGS. 1.1–1.98 are considered identical. More preferably, the root mean square deviation is less than about 1.0 Å.

The P38 X-ray coordinate data, when used in conjunction with a computer programmed with software to translate those coordinates into the 3-dimensional structure of p38γ may be used for a variety of purposes, especially for purposes relating to drug discovery. Such software for generating three-dimensional graphical representations are known and commercially available. The ready use of the coordinate data requires that it be stored in a computer-readable format. Thus, in accordance with the present invention, data capable of being displayed as the three dimensional structure of P38γ and portions thereof and their structurally similar homologues is stored in a machine-readable storage medium, which is capable of displaying a graphical three-dimensional representation of the structure.

Therefore, another embodiment of this invention provides a machine-readable data storage medium, comprising a data storage material encoded with machine readable data which, when used by a machine programmed with instructions for using said data, displays a graphical three-dimensional representation of a molecule or molecular complex comprising a binding pocket defined by structure coordinates of the P38γ SET 5A amino acids, or preferably the P38γ SET 8A amino acids, or a homologue of said molecule or molecular complex, wherein said homologue comprises a binding pocket that has a root mean square deviation from the backbone atoms of said amino acids of not more than about 1.15 Å.

Even more preferred is a machine-readable data storage medium that is capable of displaying a graphical three-dimensional representation of a molecule or molecular complex that is defined by the structure coordinates of all of the amino acids in FIG. 1a or a homologue of said molecule or molecular complex, wherein said homologue has a root mean square deviation from the backbone atoms of all of the amino acids in FIGS. 1.1–1.98 of not more than about 1.15 Å.

According to an alternate embodiment, the machine-readable data storage medium comprises a data storage material encoded with a first set of machine readable data which comprises the Fourier transform of the structure coordinates set forth in FIGS. 1.1–1.98, and which, when using a machine programmed with instructions for using said data, can be combined with a second set of machine readable data comprising the X-ray diffraction pattern of another molecule or molecular complex to determine at least a portion of the structure coordinates corresponding to the second set of machine readable data.

For example, the Fourier transform of the structure coordinates set forth in FIG. 1a may be used to determine at least a portion of the structure coordinates of other P38s, such as P38β, and P38δ and isoforms of P38β, P38δ or P38γ. The structure coordinates in FIGS. 1.1–1.98 and the Fourier transform of the coordinates are especially useful for determining the coordinates of other P38s in phosphorylated form.

According to an alternate embodiment, this invention provides a computer for producing a three-dimensional representation of a molecule or molecular complex, wherein said molecule or molecular complex comprises a binding pocket defined by the P38γ SET 5A amino acids, or preferably the P38γ SET 8A amino acids, or a homologue of said molecule or molecular complex, wherein said homologue comprises a binding pocket that has a root mean square deviation from the backbone atoms of said amino acids of not more than 1.15 Å, wherein said computer comprises:

(a) a machine readable data storage medium comprising a data storage material encoded with machine-readable data, wherein said machine readable data comprises the structure coordinates of P38γ or portions thereof;

(b) a working memory for storing instructions for processing said machine-readable data;

(c) a central-processing unit coupled to said working memory and to said machine-readable data storage medium, for processing said machine-readable data into said three-dimensional representation; and (d) an output hardware coupled to said central processing unit, for receiving said three Dimensional representation.

FIG. 8 demonstrates one version of these embodiments. System 10 includes a computer 11 comprising a central processing unit ("CPU") 20, a working memory 22 which may be, e.g., RAM (random-access memory) or "core" memory, mass storage memory 24 (such as one or more disk drives or CD-ROM drives), one or more cathode-ray tube ("CRT") display terminals 26, one or more keyboards 28, one or more input lines 30, and one or more output lines 40, all of which are interconnected by a conventional bi-directional system bus 50.

Input hardware 36, coupled to computer 11 by input lines 30, may be implemented in a variety of ways. Machine-readable data of this invention may be inputted via the use of a modem or modems 32 connected by a telephone line or dedicated data line 34. Alternatively or additionally, the input hardware 36 may comprise CD-ROM drives or disk drives 24. In conjunction with display terminal 26, keyboard 28 may also be used as an input device.

Output hardware 46, coupled to computer 11 by output lines 40, may similarly be implemented by conventional devices. By way of example, output hardware 46 may include CRT display terminal 26 for displaying a graphical representation of a binding pocket of this invention using a program such as QUANTA as described herein. Output hardware might also include a printer 42, so that hard copy output may be produced, or a disk drive 24, to store system output for later use.

In operation, CPU 20 coordinates the use of the various input and output devices 36, 46 coordinates data accesses from mass storage 24 and accesses to and from working memory 22, and determines the sequence of data processing steps. A number of programs may be used to process the machine-readable data of this invention. Such programs are discussed in reference to the computational methods of drug discovery as described herein. Specific references to components of the hardware system 10 are included as appropriate throughout the following description of the data storage medium.

FIG. 9 shows a cross section of a magnetic data storage medium 100 which can be encoded with a machine-readable data that can be carried out by a system such as system 10 of FIG. 8. Medium 100 can be a conventional floppy diskette or hard disk, having a suitable substrate 101, which may be conventional, and a suitable coating 102, which may be conventional, on one or both sides, containing magnetic domains (not visible) whose polarity or orientation can be altered magnetically. Medium 100 may also have an opening (not shown) for receiving the spindle of a disk drive or other data storage device 24. The magnetic domains of coating 102 of medium 100 are polarized or oriented so as to encode in manner which may be conventional, machine readable data such as that described herein, for execution by a system such as system 10 of FIG. 8.

FIG. 10 shows a cross section of an optically-readable data storage medium 110 which also can be encoded with such a machine-readable data, or set of instructions, which can be carried out by a system such as system 10 of FIG. 8. Medium 110 can be a conventional compact disk read only memory (CD-ROM) or a rewritable medium such as a magneto-optical disk which is optically readable and magneto-optically writable. Medium 100 preferably has a suitable substrate 111, which may be conventional, and a suitable coating 112, which may be conventional, usually of one side of substrate 111.

In the case of CD-ROM, as is well known, coating 112 is reflective and is impressed with a plurality of pits 113 to encode the machine-readable data. The arrangement of pits is read by reflecting laser light off the surface of coating 112. A protective coating 114, which preferably is substantially transparent, is provided on top of coating 112.

In the case of a magneto-optical disk, as is well known, coating 112 has no pits 113, but has a plurality of magnetic domains whose polarity or orientation can be changed magnetically when heated above a certain temperature, as by a laser (not shown). The orientation of the domains can be read by measuring the polarization of laser light reflected from coating 112. The arrangement of the domains encodes the data as described above.

As mentioned above, the P38γ X-ray coordinate data is useful for screening and identifying drugs that inhibit P38, especially phosphorylated P38. For example, the structure encoded by the data may be computationally evaluated for its ability to associate with putative substrates or ligands. Such compounds that associate with p38γ may inhibit p38γ, and are potential drug candidates. Additionally or alternatively, the structure encoded by the data may be displayed in a graphical three-dimensional representation on a computer screen. This allows visual inspection of the structure, as well as visual inspection of the structure's association with the compounds.

Thus, according to another embodiment, this invention relates to a method for evaluating the potential of a compound to associate with a molecule or molecular complex comprising a binding pocket defined by the structure coordinates of the P38γ SET 5A amino acids, or preferably the P38γ SET 8A amino acids, or a homologue of said molecule or molecular complex, wherein said homologue comprises a binding pocket that has a root mean square deviation from the backbone atoms of said amino acids of not more than about 1.15 Å.

This method comprises the steps of:
a) creating a computer model of the binding pocket using structure coordinates wherein the root mean square deviation between said structure coordinates and the structure coordinates of the P38γ amino acids Val33, Ala40, Val41, Ala54, Lys56, Ile87, Met109, Pro110, Phe111, Met112, Gly113, Thr114, Asp115, Lys118, Asp153, Lys155, Gly157, Asn158, Ala160, Leu170, Asp171, Gly173, and Leu174 according to FIGS. 1.1–1.98 is not more than about 1.15 Å;
b) employing computational means to perform a fitting operation between the chemical entity and said computer model of the binding pocket; and
c) analyzing the results of said fitting operation to quantify the association between the chemical entity and the binding pocket model.

The term "chemical entity", as used herein, refers to chemical compounds or ligands, complexes of at least two chemical compounds, and fragments of such compounds or complexes.

Even more preferably, the method evaluates the potential of a chemical entity to associate with a molecule or molecular complex defined by the structure coordinates of all of the P38γ amino acids, as set forth in FIGS. 1.1–1.98, or a homologue of said molecule or molecular complex having a root mean square deviation from the backbone atoms of said amino acids of not more than 1.15 Å.

Alternatively, the structural coordinates of the P38γ binding pocket can be utilized in a method for identifying a potential agonist or antagonist of a molecule comprising a P38γ-like binding pocket. This method comprises the steps of:
(a) using atomic coordinates of the P38γ SET 5A amino acids ± a root mean square deviation from the backbone atoms of said amino acids of not more than about 1.15Å, to generate a three-dimensional structure of molecule comprising a P38γ-like binding pocket;
(b) employing said three-dimensional structure to design or select said potential agonist or antagonist;
(c) synthesizing said agonist or antagonist; and
(d) contacting said agonist or antagonist with said molecule to determine the ability of said potential agonist or antagonist to interact with said molecule.

More preferred is the use of the atomic coordinates of the P38γ SET 8A amino acids, ± a root mean square deviation from the backbone atoms of said amino acids of not more than 1.15 Å, to generate a three-dimensional structure of molecule comprising a p38γ-like binding pocket. Most preferred is when the atomic coordinates of all the amino acids of P38γ according to FIGS. 1.1–1.98 ± a root mean square deviation from the backbone atoms of said amino acids of not more than 1.15 Å, are used to generate a three-dimensional structure of molecule comprising a P38γ-like binding pocket.

For the first time, the present invention permits the use of molecular design techniques to identify, select or design potential inhibitors of p38, based on the structure of a phosphorylated p38γ-like binding pocket. Such a predictive model is valuable in light of the high costs associated with the preparation and testing of the many diverse compounds that may possibly bind to the p38 protein.

According to this invention, a potential p38 inhibitor may now be evaluated for its ability to bind a P38γ-like binding pocket prior to its actual synthesis and testing. If a proposed compound is predicted to have insufficient interaction or association with the binding pocket, preparation and testing of the compound is obviated. However, if the computer modeling indicates a strong interaction, the compound may then be obtained and tested for its ability to bind. Testing to confirm binding may be performed using assays such as described in Example 6.

A potential inhibitor of a P38γ-like binding pocket may be computationally evaluated by means of a series of steps in which chemical entities or fragments are screened and selected for their ability to associate with the P38γ-like binding pockets.

One skilled in the art may use one of several methods to screen chemical entities or fragments for their ability to associate with a P38γ-like binding pocket. This process may begin by visual inspection of, for example, a P38γ-like binding pocket on the computer screen based on the P38γ structure coordinates in FIGS. 1.1–1.98 or other coordinates which define a similar shape generated from the machine-readable storage medium. Selected fragments or chemical entities may then be positioned in a variety of orientations, or docked, within that binding pocket as defined above. Docking may be accomplished using software such as Quanta and Sybyl, followed by energy minimization and molecular dynamics with standard molecular mechanics force fields, such as CHARMM and AMBER.

Specialized computer programs may also assist in the process of selecting fragments or chemical entities. These include:
1. GRID (P. J. Goodford, "A Computational Procedure for Determining Energetically Favorable Binding Sites on Biologically Important Macromolecules", J. Med. Chem., 28, pp. 849–857 (1985)). GRID is available from Oxford University, Oxford, UK.
2. MCSS (A. Miranker et al., "Functionality Maps of Binding Sites: A Multiple Copy Simultaneous Search Method." Proteins: Structure, Function and Genetics, 11, pp. 29–34 (1991)). MCSS is available from Molecular Simulations, San Diego, Calif.
3. AUTODOCK (D. S. Goodsell et al., "Automated Docking of Substrates to Proteins by Simulated Annealing", Proteins: Structure, Function, and Genetics, 8, pp. 195–202 (1990)). AUTODOCK is available from Scripps Research Institute, La Jolla, Calif.
4. DOCK (I. D. Kuntz et al., "A Geometric Approach to Macromolecule-Ligand Interactions", J. Mol. Biol., 161, pp. 269–288 (1982)). DOCK is available from University of California, San Francisco, Calif.

Once suitable chemical entities or fragments have been selected, they can be designed or assembled into a single compound or complex. Assembly may be preceded by visual inspection of the relationship of the fragments to each other on the three-dimensional image displayed on a computer screen in relation to the structure coordinates of P38γ. This would be followed by manual model building using software such as Quanta or Sybyl [Tripos Associates, St. Louis, Mo]. Useful programs to aid one of skill in the art in connecting the individual chemical entities or fragments include:

1. CAVEAT (P. A. Bartlett et al, "CAVEAT: A Program to Facilitate the Structure-Derived Design of Biologically Active Molecules", in Molecular Recognition in Chemical and Biological Problems", Special Pub., Royal Chem. Soc., 78, pp. 182–196 (1989); G. Lauri and P. A. Bartlett, "CAVEAT: a Program to Facilitate the Design of Organic Molecules", J. Comput. Aided Mol. Des., 8, pp. 51–66 (1994)). CAVEAT is available from the University of California, Berkeley, Calif.
2. 3D Database systems such as ISIS (MDL Information Systems, San Leandro, Calif.). This area is reviewed in Y. C. Martin, "3D Database Searching in Drug Design", J. Med. Chem., 35, pp. 2145–2154 (1992).
3. HOOK (M. B. Eisen et al, "HOOK: A Program for Finding Novel Molecular Architectures that Satisfy the Chemical and Steric Requirements of a Macromolecule Binding Site", Proteins: Struct., Funct., Genet., 19, pp. 199–221 (1994). HOOK is available from Molecular Simulations, San Diego, Calif.

Instead of proceeding to build an inhibitor of a P38γ-like binding pocket in a step-wise fashion one fragment or chemical entity at a time as described above, inhibitory or other P38γ binding compounds may be designed as a whole or "de novo" using either an empty binding site or optionally including some portion(s) of a known inhibitor(s). There are many de novo ligand design methods including:

1. LUDI (H.-J. Bohm, "The Computer Program LUDI: A New Method for the De Novo Design of Enzyme Inhibitors", J. Comp. Aid. Molec. Design, 6, pp. 61–78 (1992)). LUDI is available from Molecular Simulations Incorporated, San Diego, Calif.
2. LEGEND (Y. Nishibata et al., Tetrahedron, 47, p. 8985 (1991)). LEGEND is available from Molecular Simulations Incorporated, San Diego, Calif.
3. LeapFrog (available from Tripos Associates, St. Louis, Mo.).
4. SPROUT (V. Gillet et al, "SPROUT: A Program for Structure Generation)", J. Comput. Aided Mol. Design, 7, pp. 127–153 (1993)). SPROUT is available from the University of Leeds, UK.

Other molecular modeling techniques may also be employed in accordance with this invention [see, e.g., Cohen et al., "Molecular Modeling Software and Methods for Medicinal Chemistry, J. Med. Chem., 33, pp. 883–894 (1990); see also, M. A. Navia and M. A. Murcko, "The Use of Structural Information in Drug Design", Current Opinions in Structural Biology, 2, pp. 202–210 (1992); L. M. Balbes et al., "A Perspective of Modern Methods in Computer-Aided Drug Design", in Reviews in Computational Chemistry, Vol. 5, K. B. Lipkowitz and D. B. Boyd, Eds., VCH, New York, pp. 337–380 (1994); see also, W. C. Guida, "Software For Structure-Based Drug Design", Curr. Opin. Struct. Biology, 4, pp. 777–781 (1994)].

Once a compound has been designed or selected by the above methods, the efficiency with which that entity may bind to a P38γ binding pocket may be tested and optimized by computational evaluation. For example, an effective P38γ binding pocket inhibitor must preferably demonstrate a relatively small difference in energy between its bound and free states (i.e., a small deformation energy of binding). Thus, the most efficient P38γ binding pocket inhibitors should preferably be designed with a deformation energy of binding of not greater than about 10 kcal/mole, more preferably, not greater than 7 kcal/mole. P38γ binding pocket inhibitors may interact with the binding pocket in more than one of multiple conformations that are similar in overall binding energy. In those cases, the deformation energy of binding is taken to be the difference between the energy of the free entity and the average energy of the conformations observed when the inhibitor binds to the protein.

An entity designed or selected as binding to a P38γ binding pocket may be further computationally optimized so that in its bound state it would preferably lack repulsive electrostatic interaction with the target enzyme and with the surrounding water molecules. Such non-complementary electrostatic interactions include repulsive charge-charge, dipole-dipole and charge-dipole interactions.

Specific computer software is available in the art to evaluate compound deformation energy and electrostatic interactions. Examples of programs designed for such uses include: Gaussian 94, revision C (M. J. Frisch, Gaussian, Inc., Pittsburgh, Pa. ©1995); AMBER, version 4.1 (P. A. Kollman, University of California at San Francisco, ©1995); QUANTA/CHARMM (Molecular Simulations, Inc., San Diego, Calif. ©1995); Insight II/Discover (Molecular Simulations, Inc., San Diego, Calif. ©1995); DelPhi (Molecular Simulations, Inc., San Diego, Calif. ©1995); and AMSOL (Quantum Chemistry Program Exchange, Indiana University). These programs may be implemented, for instance, using a Silicon Graphics workstation such as an Indigo$^2$ with "IMPACT" graphics. Other hardware systems and software packages will be known to those skilled in the art.

Another approach enabled by this invention, is the computational screening of small molecule databases for chemical entities or compounds that can bind in whole, or in part, to a P38γ binding pocket. In this screening, the quality of fit of such entities to the binding site may be judged either by shape complementarity or by estimated interaction energy [E. C. Meng et al., *J. Comp. Chem.*, 13, 505–524 (1992)].

According to another embodiment, the invention provides compounds which associate with a P38γ-like binding pocket produced or identified by the method set forth above.

The structure coordinates set forth in FIGS. 1.1–1.98 can also be used to aid in obtaining structural information about another crystallized molecule or molecular complex. This may be achieved by any of a number of well-known techniques, including molecular replacement.

Therefore, in another embodiment this invention provides a method of utilizing molecular replacement to obtain structural information about a molecule or molecular complex whose structure is unknown comprising the steps of:
 a) crystallizing said molecule or molecular complex of unknown structure;
 b) generating an X-ray diffraction pattern from said crystallized molecule or molecular complex; and c) applying at least a portion of the structure coordinates set forth in FIGS. 1.1–1.98 to the X-ray diffraction pattern to generate a three-dimensional electron density map of the molecule or molecular complex whose structure is unknown.

By using molecular replacement, all or part of the structure coordinates of the P38γ/MgAMP-PNP complex as provided by this invention (and set forth in FIGS. 1.1–1.98) can be used to determine the structure of another crystallized molecule or molecular complex more quickly and efficiently than attempting an ab initio structure determination.

Molecular replacement provides an accurate estimation of the phases for an unknown structure. Phases are a factor in equations used to solve crystal structures that can not be determined directly. Obtaining accurate values for the phases, by methods other than molecular replacement, is a time-consuming process that involves iterative cycles of approximations and refinements and greatly hinders the solution of crystal structures. However, when the crystal structure of a protein containing at least a homologous portion has been solved, the phases from the known structure provide a satisfactory estimate of the phases for the unknown structure.

Thus, this method involves generating a preliminary model of a molecule or molecular complex whose structure coordinates are unknown, by orienting and positioning the relevant portion of the P38γ/MgAMP-PNP complex according to FIGS. 1.1–1.98 within the unit cell of the crystal of the unknown molecule or molecular complex so as best to account for the observed X-ray diffraction pattern of the crystal of the molecule or molecular complex whose structure is unknown. Phases can then be calculated from this model and combined with the observed X-ray diffraction pattern amplitudes to generate an electron density map of the structure whose coordinates are unknown. This, in turn, can be subjected to any well-known model building and structure refinement techniques to provide a final, accurate structure of the unknown crystallized molecule or molecular complex [E. Lattman, "Use of the Rotation and Translation Functions", in Meth. Enzymol., 115, pp. 55–77 (1985); M. G. Rossmann, ed., "The Molecular Replacement Method", Int. Sci. Rev. Ser., No. 13, Gordon & Breach, New York (1972)].

The structure of any portion of any crystallized molecule or molecular complex that is sufficiently homologous to any portion of the P38γ/MgAMP-PNP complex can be resolved by this method.

In a preferred embodiment, the method of molecular replacement is utilized to obtain structural information about another P38, such as P38α, P38β, P38δ, or isoforms of P38β, P38δ or P38γ. The structure coordinates of P38γ as provided by this invention are particularly useful in solving the structure of other isoforms of P38γ or P38γ complexes.

Furthermore, the structure coordinates of P38γ as provided by this invention are useful in solving the structure of P38γ proteins that have amino acid substitutions, additions and/or deletions (referred to collectively as "P38γ mutants", as compared to naturally occurring P38γ isoforms). These P38γ mutants may optionally be crystallized in co-complex with a chemical entity, such as a non-hydrolyzable ATP analogue or a suicide substrate. The crystal structures of a series of such complexes may then be solved by molecular replacement and compared with that of wild-type p38γ. Potential sites for modification within the various binding sites of the enzyme may thus be identified. This information provides an additional tool for determining the most efficient binding interactions such as, for example, increased hydrophobic interactions, between P38γ and a chemical entity or compound.

All of the complexes referred to above may be studied using well-known X-ray diffraction techniques and may be refined versus 1.5–3Å resolution X-ray data to an R value of about 0.22 or less using computer software, such as X-PLOR [Yale University, ©1992, distributed by Molecular Simulations, Inc.; see, e.g., Blundell & Johnson, supra; Meth. Enzymol., vol. 114 & 115, H. W. Wyckoff et al., eds., Academic Press (1985)]. This information may thus be used to optimize known P38γ inhibitors, and more importantly, to design new P38γ inhibitors.

The structure coordinates described above may also be used to derive the dihedral angles, $\phi$ and $\psi$, that define the conformation of the amino acids in the protein backbone. As will be understood by those skilled in the art, the $\phi_n$ angle refers to the rotation around the bond between the alpha carbon and the nitrogen, and the $\psi_n$ angle refers to the rotation around the bond between the carbonyl carbon and the alpha carbon. The subscript "n" identifies the amino acid whose conformation is being described [for a general reference, see Blundell and Johnson, Protein Crystallography, Academic Press, London, 1976].

Surprisingly, it has now been found that for the crystalline P38γ-ligand complex, the conformation of Gly113 is very different from the conformations reported for corresponding amino acids in other protein kinases. In order to compare the conformations of P38γ and other protein kinases at a particular amino acid site, such as Gly113, along the polypeptide backbone well-known procedures may be used for doing sequence alignments of the amino acids. Such sequence alignments allow for the equivalent or corresponding sites to be compared. One such method for doing a sequence alignment is the "bestfit" program available from Genetics Computer Group which uses the local homology algorithm described by Smith and Waterman in *Advances in Applied Mathematics* 2; 482 (1981).

A suitable amino acid sequence alignment will require that the proteins being aligned share a minimum percentage of identical amino acids. Generally, a first protein being aligned with a second protein should share in excess of about 35% identical amino acids with the second protein. Hanks et al., *Science*, 241, 42 (1988); Hanks and Quinn, *Methods in Enzymology*, 200, 38 (1991).

Equivalents of the Gly113 residue of p38γ may also be identified by its functional position. Gly113 is the amino acid residue that immediately follows sequentially the amino acid residue that donates, or is capable of donating, a hydrogen bond to the N1 nitrogen of the adenosine ring of ATP or an ATP analog, if such ATP or ATP analog were to be in the binding pocket comprising the Gly113 residue. The ability of the amino acid to donate such a hydrogen bond occurs as the result of the spatial position of the amino acid in the binding pocket of the protein. As used herein, the term "corresponding amino acid" or "equivalent amino acid" refers to a particular amino acid in a protein kinase that corresponds to another, particular amino acid in a different protein kinase as determined by sequence alignment and/or its functional position.

Table 1 shows the sequence alignments for selected protein kinases where corresponding amino acids are shown in the same column. The amino acid numbering is based on the assignments given in the Swiss-Prot database which is an international protein sequence database distributed by the European Bioinformatics Institute (EBI) in Geneva, Switzerland. The database can be found at www.ebi.ac.uk/swissprot. Erk6_HUMAN is the database protein name for P38γ. The ten amino acids immediately preceding G113 of P38γ are given starting with T103. Thus, for example, Gly113 of P38γ corresponds or is equivalent to the following: Gly110 of P38α (MP38_HUMAN), Glu107 of mouse ERK2, and Asp150 of human JNK3. The last column of Table 1 shows the Swiss-Prot database accession number.

TABLE 1

Sequence Alignments for Selected Proteins

| Protein | Corresponding Amino Acid Sequences Using Swiss-Prot Amino Acid Numbering | | | | | | | | | | Access Number |
|---|---|---|---|---|---|---|---|---|---|---|---|
| ERK6_HUMAN SEQ ID NO: 1 | T103 | D | F | Y | L | V | M | P | F | M112 | G113 | P53778 |
| MP38_HUMAN SEQ ID NO: 2 | N100 | D | V | Y | L | V | T | H | L | M109 | G110 | Q16539 |
| ERK2_HUMAN SEQ ID NO: 3 | K99 | D | V | Y | I | V | Q | D | L | M108 | E109 | P28482 |
| ERK2_MOUSE SEQ ID NO: 4 | K97 | D | V | Y | I | V | Q | D | L | M106 | E107 | P27703 |
| JNK3_HUMAN SEQ ID NO: 5 | Q140 | D | V | Y | L | V | M | E | L | M149 | D150 | P53779 |
| KAPA_MOUSE SEQ ID NO: 6 | S115 | N | L | Y | M | V | M | E | Y | V124 | A125 | P05132 |
| INSR_HUMAN SEQ ID NO: 7 | Q1097 | P | T | L | V | V | M | E | L | M1106 | A1107 | P06213 |
| LCK_HUMAN SEQ ID NO: 8 | E310 | P | I | Y | I | I | T | E | Y | M319 | E320 | P06239 |
| ZA70_HUMAN SEQ ID NO: 9 | E408 | A | L | M | L | V | M | E | M | A417 | G418 | P43403 |
| PKD1_DICDI SEQ ID NO: 10 | T107 | K | I | H | F | I | M | E | Y | A116 | G117 | P34100 |
| KPC1_YEAST SEQ ID NO: 11 | N898 | R | I | Y | F | A | M | E | F | I907 | G908 | P24583 |
| CLK1_HUMAN SEQ ID NO: 12 | G235 | H | I | C | I | V | F | E | L | L244 | G245 | P49759 |
| CLK2_HUMAN SEQ ID NO: 13 | G237 | H | M | C | I | S | F | E | L | L246 | G247 | P49760 |
| DOA_DROME SEQ ID NO: 14 | G243 | H | M | C | I | V | F | E | M | L252 | G253 | P49762 |
| DSK1_SCHPO SEQ ID NO: 15 | A160 | H | V | C | M | V | F | E | V | L169 | G170 | P36616 |
| MKK1_YEAST SEQ ID NO: 16 | S293 | S | I | Y | I | A | M | E | Y | M302 | G303 | P32490 |
| MKK2_YEAST SEQ ID NO: 17 | S286 | S | I | Y | I | A | M | E | Y | M295 | G296 | P32491 |
| NIMA_EMENI SEQ ID NO: 18 | Q83 | D | L | Y | L | Y | M | E | Y | C92 | G93 | P11837 |
| KMOS_HUMAN SEQ ID NO: 19 | S133 | L | G | T | I | I | M | E | F | G142 | G143 | P00540 |
| KC1A_HUMAN SEQ ID NO: 20 | D84 | Y | N | V | L | V | M | D | L | L93 | G94 | P48729 |
| KC1B_BOVIN SEQ ID NO: 21 | D84 | Y | N | V | L | V | M | D | L | L93 | G94 | P35507 |
| KC1D_HUMAN SEQ ID NO: 22 | D76 | Y | N | V | M | V | M | E | L | L85 | G86 | P48730 |
| CK11_YEAST SEQ ID NO: 23 | L136 | H | N | I | L | V | I | D | L | L145 | G146 | P23291 |
| CK12_YEAST SEQ ID NO: 24 | L143 | H | N | I | L | V | I | D | L | L152 | G153 | P23292 |
| HR25_YEAST SEQ ID NO: 25 | E76 | Y | N | A | M | V | I | D | L | L85 | G86 | P29295 |
| KNS1_YEAST SEQ ID NO: 26 | N387 | H | I | C | L | V | T | D | L | Y396 | G397 | P32350 |
| KYK1_DICDI SEQ ID NO: 27 | D1360 | H | H | C | I | V | T | E | W | M1369 | G1370 | P18160 |
| CKI1_SCHPO SEQ ID NO: 28 | L79 | H | N | V | L | V | I | D | L | L88 | G89 | P40233 |
| CDK2_HUMAN SEQ ID NO: 29 | N74 | K | L | Y | L | V | F | E | F | L83 | H84 | P24941 |
| KPBG_HUMAN SEQ ID NO: 30 | T97 | F | F | F | L | V | F | D | L | M107 | K108 | Q16816 |
| KCC1_HUMAN SEQ ID NO: 31 | G89 | H | L | Y | L | I | M | Q | L | V98 | S99 | Q14012 |

As noted above, the conformation of Gly113 is very different from the conformations reported for corresponding amino acids in other protein kinases. For Gly113 of the P38γ-AMPPNP complex, $\psi_{112}$ was found to be about 24 degrees and $\phi_{113}$ was found to be about 96 degrees. Table 2 shows the dihedral angles for Met112 and Gly113 of P38γ-AMPPNP complex and how these angles compare to those of the corresponding amino acids in other MAP kinases whose crystal structures have been reported. The protein names for the known proteins are provided as their Protein Data Banks™ (pdb) accession numbers. The Protein Data Bank is an international repository for three dimensional structures and can be located at www.rcsb.org/pdb/.

TABLE 2

Dihedral Angles (in degrees) for Met112 and Gly113 and Equivalents in P38 and Other Protein Kinases

| | Met 112 | | Gly 113 | |
|---|---|---|---|---|
| Protein | φ | ψ | φ | ψ |
| P38γ-AMPPNP | −106.2 | 23.8 | 96.24 | −90.6 |
| P38α-ligand[a] SEQ ID NO: 32 | −80.8 | −26.5 | 95.7 | −22.5 |
| 1ERK[b] SEQ ID NO: 33 | −119.1 | 131.7 | −51.6 | −55.6 |
| 2ERK[c] SEQ ID NO: 34 | −99.5 | 130.3 | −42.7 | −49.9 |
| 1p38[d] SEQ ID NO: 35 | −92.7 | 128.4 | −82.1 | −103.2 |
| 1ATP[e] SEQ ID NO: 36 | −96.6 | 89.1 | −56.1 | −30.1 |
| 1JNK[f] SEQ ID NO: 37 | −105.3 | 170.6 | −92.2 | −22.8 |
| 1IR3[g] SEQ ID NO: 38 | −112.7 | 87.9 | −44.2 | −38.4 |
| 1IRK[h] SEQ ID NO: 39 | −85.6 | 109.9 | −40.7 | −38.4 |
| 3LCK[i] SEQ ID NO: 40 | −121.7 | 105.9 | −53.3 | −38.2 |

[a]in-house structure of complex with a designed inhibitor;
[b]unphosphorylated ERK, reported in Nature, 367, 704, (1994);
[c]phosphorylated ERK, Cell, 90, 859 (1997);
[d]unphosphorylated p38γ, Proc. Nat. Acad. Science, 94, 2327 (1997);
[e]cyclic AMP dependent protein kinase or cAPK, Acta Crys. Sec. D, 49, 362 (1993);
[f]unphosphorylated JNK3, Structure, 6, 983 (1998);
[g]insulin receptor tyrosine kinase, Embo J., 16, 5572 (1997);
[h]insulin receptor tyrosine kinase, Nature, 372, 786, (1994);
[i]lymphocyte-specific kinase, Nature, 368, 764, (1994)

It is well-recognized that there will be some variability in the conformations of corresponding amino acids in similar or identical proteins when the protein crystallization and structure determination are repeated. This variability in the φ and ψ dihedral angles may be approximated by reference to Ramachandran plots comparing the conformations obtained for two or more identical or similar proteins [Blundell and Johnson, Protein Crystallography, Academic Press, London, 1976]. It may be expected that the dihedral angles of equivalent amino acid residues in identical or similar proteins will vary as much as about 45° or more.

It should be noted that the amino acid numbering defined in the Protein Data Banks™ may be offset from the numbering given in the Swiss-Prot database. This offset, when it occurs, will be readily understood by those skilled in the art. Thus, the sequences of those proteins that are listed in both databases may be easily compared despite offsets in amino acid numbering that may occur. Examples of such offsets occur for INSR_HUMAN where A1107 according to Swiss-Prot numbering is the same as A1080 in the PDB database and for LCK_HUMAN where E319 according to Swiss-Prot numbering is the same as E320 by PDB numbering.

The $\psi_{112}$ and $\phi_{113}$ dihedral angles of the P38γ-AMPPNP complex shown in Table 2 indicate that the conformation of Gly113 in this complex is "flipped" or rotated considerably relative to corresponding amino acids in other MAP kinases. Therefore, the structure coordinates of P38γ set forth in FIGS. 1.1–1.98 represent, inter alia, what is believed to be a conformation at Met 112 and Gly113 that had not been observed for other crystalline protein kinases, especially other MAP kinases.

Accordingly, another embodiment of this invention relates to a crystalline protein kinase-ligand complex, said kinase comprising amino acid residues that correspond by functional and/or sequence alignment to the Met112 and Gly113 residues of P38γ or that correspond by functional and/or sequence alignment to the Met112 and Gly113 equivalent residues of one or more proteins listed in Table 1, wherein the ψ angle of the residue corresponding to Met112 is in the range of about −60° to 60° and the ψ angle of the residue corresponding to Gly113 is in the range of about 30° to 150°. Preferably, the ψ angle of the crystalline protein kinase-ligand complex is in the range of about −45° to 45° and most preferably in the range of about −30° to 30°. Preferably, the φ angle is in the range of about 45° to 135°, and most preferably is in the range of about 60° to 120°. Examples of kinases that may provide such a crystalline protein kinase when complexed with a ligand are described by Hanks et al., Science, 241, 42 (1988) and Hanks and Quinn, Methods in Enzymology, 200, 38 (1991). Other examples of such kinases may be found at www.sdsc.edu/Kinases/pkr/pk_catalytic/pk_hanks_seq_align_long.html, where the kinases are listed with their corresponding sequence alignments.

Another embodiment of this invention relates to a crystalline protein kinase-ligand complex, said kinase selected from the proteins listed in Table 1, wherein the ψ angle of the residue corresponding to Met112 is in the range of about −60° to 60° and the φ angle of the residue corresponding to Gly113 is in the range of about 30° to 150°. Preferably, the ψ angle of the crystalline protein kinase-ligand complex is in the range of about −45° to 45° and most preferably in the range of about −30° to 30°. Preferably, the φ angle is in the range of about 45° to 135°, and most preferably is in the range of about 60° to 120°.

Structural information regarding the conformation of the Met112 and Gly113 residues of the crystalline P38γ complex may be encoded in a machine-readable data storage medium as described above for encoding the other structural coordinates of the protein. Accordingly, another embodiment of this invention relates to a computer for producing a three-dimensional representation of an ATP binding site of a protein kinase-ligand complex, or portion thereof, wherein said computer comprises:

a) a machine-readable data storage medium comprising a data storage material encoded with machine-readable data, wherein said machine-readable data comprises the structure coordinates of a kinase, or portion thereof, said kinase or portion thereof comprising amino acid residues that correspond by functional and/or sequence alignment to the Met112 and Gly113 residues of P38γ or that correspond by functional and/or sequence alignment to the Met112 and Gly113 equivalent residues of one or more proteins listed in Table 1, wherein the ψ angle of the residue corresponding to Met112 is in the range of about −60° to 60° and the φ angle of the residue corresponding to Gly113 is in the range of about 30° to 150°;

b) a working memory for storing instructions for processing said machine-readable data;

c) a central-processing unit coupled to said working memory and to said machine-readable data storage medium, for processing said machine readable data into said three-dimensional representation; and d) an output hardware coupled to said central-processing unit, for receiving said three-dimensional representation. Preferably, the machine-readable data comprises the structure coordinates of a kinase, or portion thereof, said kinase comprising amino acid residues corresponding to the Met112 and Gly113 amino acids of P38γ or corresponding to the Met112 and Gly113 equivalent residues of one or more proteins listed in Table 1, wherein the ψ angle is in the range of about −45° to 45° and most preferably in the range of about −30° to 30°, and the φ angle is in the range of about 45° to 135° and most preferably in the range of about 60° to 120°. In a more preferred embodiment of this computer, the machine readable data comprises the structure coordinates of a crystalline protein kinase-ligand complex, or portion thereof, where said kinase is selected from a protein listed in Table 1.

For designing new compounds that associate with a protein kinase binding pocket, it is useful to employ information that includes the conformations of the Met112 and Gly113 residues, or their equivalents, along with other structural information regarding amino acids in the binding pocket. For example, to evaluate the ability of a chemical entity to bind to a protein kinase, the conformations of Met112 and Gly113, or equivalents, may be used along with structure coordinates of the backbone atoms of amino acids in the protein kinase binding pocket. These structure coordinates and the structure coordinates of the p38γ amino acids Val33, Ala40, Val41, Ala54, Lys56, Ile87, Met109, Pro110, Phe111, Met112, Gly113, Thr114, Asp115, Lys118, Asp153, Lys155, Gly157, Asn158, Ala160, Leu170, Asp171, Gly173, and Leu174 according to FIGS. 1.1–1.98 should not differ by more than about 3.0 angstroms in root mean square deviation, preferably the root mean square deviation is within about 2.7 angstroms, and most preferably within about 2.5 angstroms. For example, the root mean square deviation between the structure coordinates of the p38γ amino acids and those of a p38γ complex (see Table 2) was found by applicants to be 2.41 angstroms. Resolution error may account for variation in the root mean square deviation of a few tenths of an angstrom.

Accordingly, another embodiment of this invention provides a method for evaluating the ability of a chemical entity to associate with a protein kinase binding pocket, said method comprising the steps of:

a) creating a computer model of the binding pocket using structure coordinates wherein:
  (i) the root mean square deviation between said structure coordinates and the structure coordinates of the P38γ amino acids Val33, Ala40, Val41, Ala54, Lys56, Ile87, Met109, Pro110, Phe111, Met112, Gly113, Thr114, Asp115, Lys118, Asp153, Lys155, Gly157, Asn158, Ala160, Leu170, Asp171, Gly173, and Leu174 according to FIGS. 1.1–1.98 is within about 3.0 angstroms,
  (ii) said binding pocket model depicts amino acid residues that correspond by functional and/or sequence alignment to the Met112 and Gly113 residues of P38γ or that correspond by functional and/or sequence alignment to the Met112 and Gly113 equivalent residues of one or more proteins listed in Table 1, and
  (iii) said binding pocket model depicts the ψ angle of the residue corresponding to Met112 to be in the range of about −60° to 60° and the φ angle of the residue corresponding to Gly113 to be in the range of about 30° to 150°;

b) employing computational means to perform a fitting operation between the chemical entity and the binding pocket model; and c) analyzing the results of said fitting operation to quantify the association between the chemical entity and the binding pocket model.

A useful root mean square deviation between the structure coordinates of a particular binding pocket and the structure coordinates of the binding pocket of another protein kinase may be readily determined by one skilled in the art. For example, when the protein kinase is selected from a protein listed in Table 1, the root mean square deviation is preferably within about 2.7 angstroms, and is more preferably within about 2.5 angstroms.

This invention also provides a method for identifying a potential agonist or antagonist of a molecule comprising a P38γ-like binding pocket, comprising the steps of:

a) creating a computer model of the binding pocket using structure coordinates wherein:
  (i) the root mean square deviation between said structure coordinates and the structure coordinates of the P38γ amino acids Val33, Ala40, Val41, Ala54, Lys56, Ile87, Met109, Pro110, Phe111, Met112, Gly113, Thr114, Asp115, Lys118, Asp153, Lys155, Gly157, Asn158, Ala160, Leu170, Asp170, Gly173, and Leu174 according to FIGS. 1.1–1.98 is within about 3.0 angstroms,
  (ii) said binding pocket model depicts amino acid residues that correspond by functional and/or sequence alignment to the Met112 and Gly113 residues of P38γ or that correspond by functional and/or sequence alignment to the Met112 and Gly113 equivalent residues of one or more proteins listed in Table 1, and
  (iii) said binding pocket model depicts the ψ angle of the residue corresponding to Met112 to be in the range of about −60° to 60° and the φ angle of the residue corresponding to Gly113 to be in the range of about 30° to 150°;

b) employing said model of the binding pocket to design or select said potential agonist or antagonist;

c) synthesizing said agonist or antagonist; and d) contacting said agonist or antagonist with said molecule to determine the ability of said potential agonist or antagonist to interact with said molecule.

A preferred embodiment of this method uses the structure coordinates of the Met112 and Gly113 amino acids of p38γ or the Met112 and Gly113 equivalent residues of a protein listed in Table 1.

In order that this invention be more fully understood, the following examples are set forth. These examples are for the purpose of illustration only and are not to be construed as limiting the scope of the invention in any way.

EXAMPLE 1

Expression and Purification of P38γ Protein P38 with a His6 tag was overexpressed in *E. Coli,* and then purified by using metal affinity resin followed by MonoQ resin. The purified material was phosphorylated with constituitively active MKK6, and purified again with MonoQ resin (Fox, T. et al., manuscript in preparation). Size-exclusion chromatography was performed to determine the apparent molecular weights of unphosphorylated and phosphorylated P38γ as follows. A Superdex 75 HR 10/30 column (Pharmacia, Uppsala) was equilibrated in 12.5 mM HEPES, pH 7.3, containing 6.25% (v/v) glycerol and 100 mM KCl. Bovine serum albumin (67 kDa), ovalbumin (43 kDa), chymotrypsinogen (25 kDa), ribonuclease A (13.7 kDa) were used to calibrate the column prior to P38γ analyses. A flow rate of 0.25 ml/min was used for chromatographic runs and samples were loaded in a volume of 100–200 _l at 0.7–4 mg/ml.

EXAMPLE 2

Crystallization of P38γ

Crystals of phosphorylated P38γ complexed with AMP-PNP were grown by vapor diffusion. Clusters of rods appeared after 3 to 7 days when protein (0.5 mM P38γ with 5 mM AMP-PNP and 0.02% $C_{12}E_9$) was mixed with an equal volume of reservoir (100 mM NaOAc, 100 mM Tris 8.5, 27% PEG 4000, 10 mM $MgCl_2$, and 5 mM DTT) and allowed to stand at room temperature. Single crystals with 100 mM maximum thickness were separated from their parent cluster, cryoprotected by adding ethylene glycol to a final concentration of 15% over 15 min in three equal steps, and flash cooled to –170° C. in a stream of gaseous nitrogen.

EXAMPLE 3

X-Ray Data Collection and Structure Determination

The diffraction pattern displayed symmetry consistent with space group $P2_12_12_1$, with unit cell dimensions a=63.50 Å, b=66.82 Å, and c=206.02 Å. Diffraction extended to 4.0 Å in the a*, b* direction and 3.0 Å in the c* direction. Data collection at NSLS X25 allowed a significant improvement in the observed diffraction limit: data were collected to 3.0 Å in the a*,b* direction and at least 2.4 Å in the c* direction. Data were integrated to 2.4 Å [Otwinowski, Z. in *CCP4 Study Weekend* (eds. Sawyer, L., Isaacs, N. & Bailey, S.) 56–62 (SERC Daresbury Laboratory, England) (1993); Minor, W. XDISPLAYF Program, Purdue University, (1993)]. The overall R-merge for the data was 6.7%, with I/sig(I)=2.0 at 2.4 Å resolution. The X-ray data comprised 31732 unique reflections derived from 118429 intensity measurements. The data were 90% complete overall and 76.5% complete in the 2.49–2.40 Å resolution shell. Data incompleteness, particularly in the highest resolution shell, reflects the anisotropic nature of the diffraction.

The volume of the asymmetric unit indicated the presence of two P38γ molecules. The self-rotation function calculated with POLARRFN [Acta Crys D50, 760–763 (1994)] revealed a noncrystallographic peak with intensity half of the origin at Kappa=180°, omega=90°, and Phi=44°.

Coordinates for the structure of phosphorylated ERK2 were not initially available from the protein data bank and could not be used for molecular replacement. Several different models for P38γ were constructed based on the X-ray coordinates of P38γ or unphosphorylated ERK2 with either all side chains truncated to alanine, or with only the non-conserved side chains truncated to alanine or glycine [Zhang et al., *Nature* 367, 704–711 (1994); Wilson and Su, *J Biol Chem* 271, 27696–27700 (1996)]. No rotation function solutions were obtained using these models with either the X-plor or AMORE molecular replacement packages. The anisotropy of the data, as well as the presence of two molecules in the asymmetric unit, could be reasons for the lack of a successful molecular replacement solution. Variability in the orientation between the large and small kinase domains may have been an additional complicating factor.

To position correctly an initial P38γ model, experimental phases at low resolution were obtained from two derivatives. Crystals were soaked with 0.2 mM ethylmercurychloride (EMP) for 5 days, and with 2 mM $EuCl_3$ overnight. Diffraction data were collected on the in house RaxisIIc, and integrated to 5.0 Å [see Owinowski and Minor, supra]. Difference Patterson maps were interpreted by using SHELXS-97 [Acta Crys A46, 467–473 (1990)]. The EMP derivative yielded four sites and the Europium derivative yielded two sites. These heavy atom positions were refined by using ML-PHARE [Acta Crys D50, 760–763 (1994)] which yielded an overall figure of merit of 0.53 to 5 Å. The resulting electron density maps showed clear solvent and protein regions. Six heavy atom sites were identified within a continuous envelope of protein density and grouped into two sets of three sites. These two sets were related to one another by a two-fold axis, which was consistent with the self-rotation function. Each set of three sites was assumed to correspond to a monomer of P38γ, and the two-fold operation was used to improve the experimental electron density by noncrystallographic symmetry (NCS) averaging. Solvent flattening combined with two-fold averaging using Dm (final correlation coefficient of averaging of 0.851) produced an electron density map at 5.0 Å that allowed placement of the P38γ model. The N-terminal domain had to be rotated by several degrees with respect to the C-terminal domain in order to fit both domains into the experimental density. At this stage the model was refined against the high resolution synchrotron data. Rigid body refinement and torsional dynamics refinement yielded an initial $R_{free}$ of 42%.

The quality of the model was improved by cycles of model building, positional refinement, and thermal factor refinement, interspersed with torsional dynamics runs using data from 50.0 to 2.4 Å. All stages of model refinement were carried out using the new program CNS [Acta Crys D54, 905–921 (1988)] with bulk solvent correction and anisotropic scaling. NCS restraints were applied throughout the refinement. The current P38γ model contains two monomers, each with 329 protein residues, one bound AMP-PNP molecule, and two $Mg^{2+}$ ions. A total of 186 water molecules were included in the entire asymmetric unit. The current $R_{work}$ is 23.2% ($R_{free}$=28.3%) versus all data with $|F|>2_{13}(F)$ between 50–2.4 Å resolution (27841 reflections). PROCHECK was used to analyze the model stereochemistry [Acta Crys D50, 760–763 (1994)]. All of the residues were in the most favored and additional allowed regions of the Ramachandran plot. One residue per monomer (Val187) from the phosphorylation loop was in the disallowed region. The P38γ model has deviations from ideal bond lengths and angles of 0.010 Å and 1.63° respectively. No electron density was observed for amino acids 1–7, 34–39, 316–321, 330–334, and 354–end, therefore these residues were not included in the model. The eight residue histidine tag and 21 residues at the C-terminus are also disordered. Subsequent to the structure refinement, the phosphorylated ERK2 coordinates were released, and the final refined P38γ structure was compared with that structure.

EXAMPLE 4

Overall Structure

The P38γ structure was solved with a combination of low resolution MIR and molecular replacement using a model of the unphosphorylated form of P38α [Wilson and Su, *J Biol Chem* 271, 27696–27700 (1996)]. The current structure includes two P38γ molecules per asymmetric unit, each with 329 amino acids, a bound AMP-PNP, and two $Mg^{2+}$ ions. A total of 186 water molecules were modeled in the asymmetric unit. The current $R_{free}$ and $R_{work}$ are 28.3% and 23.2%, respectively. The refined model has deviations from ideal bond lengths and angles of 0.01 Å and 1.6°. The two P38γ molecules in the asymmetric unit superimpose with an overall r.m.s.d. of 0.013 Å using all Cα atoms, and thus represent two independent but highly similar structures of activated P38γ.

Comparison of Kinase Structures

Electron density for the main chain atoms of P38γ is visible from residue 8 to 353, with breaks at residues 34–39, 316–321 and 330–334 (FIGS. 1.1–1.98). The glycine rich loop, which contains the consensus Gly-X-Gly-X-X-Gly sequence (residues 34–39 in P38γ) is mobile, and residues 34–39 could not be modeled. The homologous region of P38α is also flexible, and has average B-values equal to 61 Å. In contrast, the AMP-PNP ligand is well ordered, as are all nearby secondary structural elements. Strong electron density for the residues at the N- and C-terminal ends of the glycine rich loop is also observed. The C-terminal 40 residues of both P38γ molecules in the asymmetric unit are not as well ordered as the rest of the structure. Helix αL16 can be modeled, but contains several disordered side chains. The region just before helix αL16 is poorly ordered and does not form the 3/10 helix L16 observed in the structure of phosphorylated ERK2. Helix αL16 and 3/10 helix L16 are involved in dimer formation in the structure of phosphorylated ERK2 [Canagarajah et al., *Cell* 90, 859–869 (1997)].

Activated P38γ contains a small amino terminal domain comprised mainly of β-strands, and a large carboxyl terminal domain that consists mostly of α-helices (FIG. 2). This fold is common among kinases [Taylor & Radzio-Andzlem (1994); *Structure* 2, 345–355; Kultz *J Mol Evol* 46, 571–588 (1998)]. A deep cleft at the interface between the domains forms the binding site for ATP and $Mg^{2+}$. The two domains are connected by a hinge, located at a point adjacent to the adenine base and near residue 113 (FIG. 2).

Whereas the sequence, fold, and topology of P38γ is similar to P38α (FIGS. 2, 3), the domains of activated P38γ are closed relative to P38α. Independent superimpositions of the domains of P38γ onto the P38α structure yield r.m.s. deviations of 1.2 Å for the N-terminal domain (P38γ Cα carbons from residues 10–16, 19–33, and 40–113), and 0.62 Å for the C-terminal domain (P38γ $C_\alpha$ carbons from residues 125 to 160, 206 to 238 and 282 to 297). Greater differences between P38γ and P38α are observed when the whole proteins are compared. Superimposition of the C-terminal domain of P38γ onto the corresponding lobe of P38α revealed a rotation of the N-terminal domain of P38γ by 20° relative to the orientation seen in P38α (FIG. 2). Other differences between the structure of phosphorylated P38γ and P38α occur in the conformation of αL14, α2L14, α1L12, the phosphorylation loop, and αL16.

Inter-domain rotation, or domain closure, is common in MAP kinase structures, and is observed to different extents. The structures of unphosphorylated and phosphorylated ERK2 show a 5° difference in domain closure. The structure of unphosphorylated JNK3 reveals that a 10° domain rotation would be needed to superimpose both domains with the structure of phosphorylated P38γ or phosphorylated ERK2. P38α MAP kinase is more open in its unphosphorylated state than ERK2 or JNK3. Despite a large difference in the conformations of the unphosphorylated proteins, the domains of the activated forms of P38γ and ERK2 can be superimposed with a rotation of only 3°. Comparison to solved kinase structures indicates that the relative positions of the domains in activated P38γ is most similar to activated ERK2 MAP kinase.

The structures of phosphorylated P38γ and phosphorylated ERK2 are similar, with a few significant differences. One conformational difference is a movement of the α1L14, α2L14 helical region. With the large domains superimposed, the difference in α1L14, α2L14 orientation between the two structures is about 6 Å, when measured at the most extreme portion of the helices. Another difference between the two structures is that the P38γ activation loop is six residues shorter than the activation loop in ERK2. Excluding these two regions allows one to superimpose P38γ Cα carbons 19–33, 40–58, 61–94, 97–113, 117–177, 182–243, and 269–315 with the corresponding ERK2-P2 atoms to yield an r.m.s.d. of 1.1 Å. This reflects the high similarity between the two structures. A comparison of the activation loops, using P38γ Cα carbons 173–177 and 182–188 yields an r.m.s.d. of 0.3 Å.

The structure of the phosphorylation loop differs between phosphorylated P38γ and unphosphorylated P38α (FIG. 3). The phosphorylation loop contains the TGY sequence present in all P38 MAP kinases. Phosphorylation of Thr183 and Tyr185 results in a movement of the activation loop, and produces changes in the P38γ structure.

Phospho-Thr183 sits at the interface between the two domains. The Thr183 phosphate group interacts with Arg70, Arg73 and Lys69 from the N-terminal domain, and Arg152 and Arg176 from the C-terminal domain (FIGS. 2 and 4). The two domains are connected by a hinge, located at a point adjacent to the adenine base and near residue 113. The hinge-point and residue pThr183 are located at opposite ends of the interface between the two domains. The network of interactions between pThr183 and these basic residues pulls the domains together. As a result, the relative orientations of the amino acids, including the catalytic residues, located between the hinge and pThr183 are changed. A similar set of interactions between the phospho-threonine and nearby basic residues was reported for the structure of phosphorylated ERK2 [Canagarajah et al., *Cell* 90, 859–869 (1997)]. Phosphorylated P38γ is in a conformation consistent with activity. The active site of phosphorylated P38γ is shown in detail in FIG. 5, and compared with the active sites of P38α and cAPK in FIGS. 6a and 6b. The interactions between the non-hydrolyzable nucleotide analog AMP-PNP and P38γ (FIG. 5) are very similar to those made between bound nucleotide and cAPK [Zheng et al., *Acta Cryst.* D49, 362–365 (1993); Bossemeyer et al., *EMBO Journal* 12, 849–859 (1993); Narayana et al., *Structure* 5, 921–935 (1997)].

The N1 and N6 nitrogen atoms of AMP-PNP form hydrogen bonds to the backbone amide nitrogen atom of Met112 and the backbone carbonyl oxygen atom of Pro110, respectively. Interactions between the glycine rich loop and the nucleotide are not observed in the P38γ structure. The relative positions of catalytic residues Lys53, Glu74 and Asp153 provide information about the state of activation of the kinase [Kumar et al., *J. Biol. Chem.* 270, 29043–29046 (1995); Robinson et al., *Curr Opin Cell Biol* 9, 180–186 (1997)]. Comparison of P38γ with cAPK after superimposing the nucleotides from the two structures (FIG. 6b), reveals that the active site residues in the two structures are in almost the same conformation. The cAPK structure also contains a bound peptide inhibitor, and the complex is believed to represent a bioactive conformation of cAPK [Zheng et al, supra; Bossemyer et al., supra; Narayana et al., supra]. The nucleotides in both structures adopt almost the same conformations, and the relative positions of the catalytic residues Lys-56, Glu-74 and Asp-153 are conserved. There are also two bound metal ions in each complex. After superimposition, metal I in cAPK is separated from the corresponding metal in P38α by 0.5 Å, and metal II from P38γ is 1.4 Å removed from metal II in cAPK. Because the conformation and relative orientation of the catalytic residues and cofactors in the active sites of the two kinases are almost the same, the structure of phosphorylated P38γ described here is likely to represent an active conformation.

Figure 6A:
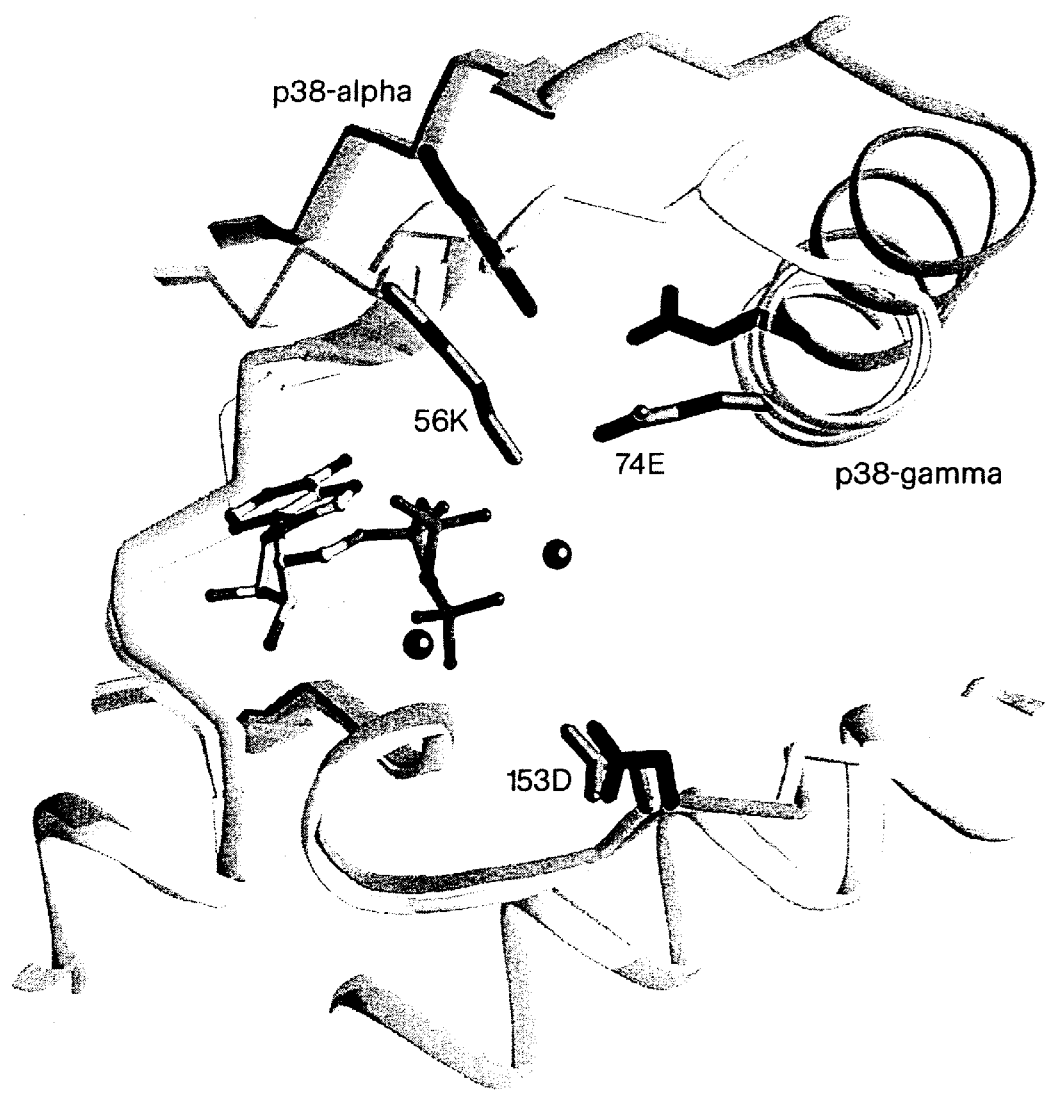

Comparing the phosphorylated P38γ to the known, unphosphorylated P38α one finds that the active site residues of P38α are significantly displaced relative to their orientation in P38γ. This presumably reflects the inactive state of unphosphorylated P38α (FIG. 6a). Two types of structural differences are observed between unactivated P38α and activated P38γ. A rigid body motion occurs between the two domains, and secondary structure elements and residues move as a result of phosphorylation and AMP-PNP binding.

Using the newly-determined structure of P38γ, the structure of unphosphorylated P38α could be altered to properly position its catalytic residues in an active conformation. Without the P38γ structural information, it was not known whether domain movement alone would be enough to properly position the catalytic residues in an active conformation or whether activation would also require other changes [Johnson et al., Curr. Opin. Struct. Biol. 6, 762–769 (1996); Yamaguchi et al., Nature 384, 484–489 (1996); Johnson et al., Cell 85, 149–158 (1996); Russo et al., Nature Struc Biol 3, 696–700 (1996)].

To address this question, the structure of unphosphorylated P38α was altered to resemble phosphorylated P38γ. Only a rigid-body movement, centered on the hinge residue 113, was used to change the relative orientation of the two domains in P38α. The resulting model maintains the detailed secondary structure features present in non-phosphorylated P38α, but has the same domain closure as P38γ. The positions of catalytic residues in the active site of this modified P38γ model match well to those observed in the structure of activated P38γ. The rigid body movement shifts P38α residue Lys-53 2.9 Å closer to its counterpart in P38γ (from 4.4 Å to 1.5 Å separation). Glu-71 (P38α) moves 2.8 Å nearer to its equivalent residue in P38γ (from 3.2 Å to 0.4 Å separation). Thus, the structures of P38α and P38γ suggest that a simple domain rotation accounts for most of the rearrangement of catalytic residues necessary for activation of P38γ.

Other movements may contribute to activation of P38γ. For example, phosphorylation of Tyr185 leads to a rearrangement of surrounding secondary structure elements that may effect substrate binding. Arg192 interacts with the pTyr185 phosphate group in the P38γ structure, and is shifted more than 5 Å relative to its position in the apo-P38α structure. Such coordination of Arg 192 and its effect on substrate binding have been discussed with regard to ERK2 and JKN3 [Zhang, Nature 367, 704–711 (1994); Xie and Su, supra; Canagarajah, supra]. In the P38γ structure, pTyr185 interacts directly with Arg189 and Arg192 (FIG. 4). Comparison of the P38γ pTyr185 conformation, as well as the backbone conformation with the corresponding residue of phosphorylated ERK2, shows that the two residues are in nearly the same conformation.

Activated P38__ is Monomeric

The two P38γ proteins in the crystallized complex show no evidence of dimeric interaction, as evidenced by the examination of the activation loops of the two proteins. This is unlike the activated, phosphorylated ERK2, which is believed to reveal a dimer interface that is not observed in the non-phosphorylated form [Zhang et al., supra; Canagarajah et al., supra; Khokhlatchev et al., supra]. The dimer interface in phosphorylated ERK2 reportedly buries a total of 1470 Å$^2$ of surface area, and is formed in part by an ion pair between His176 from one molecule and Glu343 from the other molecule. In addition, Leu333, Leu336, and Leu344 are reported to further stabilize the dimer interface.

The entire surface of each P38γ molecule in the asymmetric unit was examined in search of any dimer interface. The crystal of P38γ belongs to space group P2$_1$2$_1$2$_1$, which contains only two-fold screw axes, but no crystallographic two-fold axes. The only two-fold axis in the crystal is the non-crystallographic axis which relates the two molecules within the asymmetric unit. This dimeric interaction involves Pro282, Asn286, Lys290, Leu283, Pro309, and Glu312. This non-crystallographic dimer interface buries only 680 Å$^2$ of surface area, less than half of the 1470 Å$^2$ buried in the phosphorylated ERK2 dimer interface.

To characterize further the oligomeric state of activated P38γ in solution, size-exclusion chromatography was performed to determine the apparent molecular weights of unphosphorylated and phosphorylated P38γ. To facilitate comparison with the phosphorylated ERK2 results [Khokhlatchev et al., supra], the same column resin, buffer, and loading conditions were used. The chromatographic profiles of unphosphorylated and phosphorylated P38γ showed that both proteins eluted with a similar retention time, corresponding to a molecular weight of 44.5 kDa as determined from the protein calibration curve. The absence of dimer formation of phosphorylated P38γ in solution is consistent with the absence of dimer formation in the crystal structure of P38γ. It is also consistent with the absence of dimer formation in ERK2 mutants where His176 is deleted [Khokhlatchev et al., supra].

Conformations of Activation Loops of Kinases

The number of residues in the activation loops of different kinases varies, ranging from 8 amino acids in calmodulin dependent DAP-kinase to 37 residues in LIMK2 [Deiss et al., Genes Dev. 9, 15–30 (1995); Okano et al., J. Biol. Chem. 270, 31321–31330 (1995)]. The P38γ activation loop consists of residues Gly173-Thr188. The phosphorylation loop of ERK2 is six residues longer in sequence and spans amino acids Gly167-Thr188. The loop region of cAPK is the same length as P38γ, and spans amino acids Gly186-Thr201. FIG. 7 highlights the loop regions from P38γ, ERK2-P2, and cAPK. Except for a longer loop size for ERK2, the structures of the loop regions of activated P38γ and activated ERK2 are nearly identical. The distance between the phosphate moieties from Thr183 in P38γ and ERK2 is only 0.4 Å, and separation between the Tyr185 phosphate from P38γ and ERK2 is 1.6 Å. The phosphorylation loop of cAPK does not superimpose as well with the two MAP kinase phosphorylation loops, although the Thr phosphate is only 2.0 Å away from the P38γ Thr183 phosphate. The phosphorylation loop regions from P38γ, ERK2 and cAPK have different lengths, but in their phosphorylated states adopt almost the same conformations.

FIGS. 1b–6 further depict the structure of the phosphorylated P38γ/MgAMP-PNP complex. Thus, FIG. 2 depicts an overview of the phosphorylated P38γ structure. The large and small domains are pulled together by interactions mediated by phospho-Thr183. Ribbon diagrams of the activated P38γ structure with the amino-terminal small domain are colored light orange and the carboxy-terminal large domain colored blue. The interface between the two domains (residue 113) can be thought of as a hinge point through which domain movement occurs. Four Arg residues and one Lys residue are explicitly shown coordinated to the phosphate of pThr183. Arg70, Arg73 and Lys69 anchor the small domain to pThr183, and Arg152 and Arg176 anchor the large domain to pThr183. PThr183 pulls the domains together. All figures were made with RIBBONS [Carson et al., *J. Mol. Graphics* 4, 121–122 (1986)].

FIG. 3 is a superimposition of the structures of unphosphorylated P38α and phosphorylated P38γ. P38α is shown in light blue and dark blue (activation loop), and P38γ is shown in light orange and dark orange (activation loop). The Cα atoms from residues 125 to 160, 206 to 238 and 282 to 297 were used to superimpose the two proteins with an r.m.s.d. of 0.62 Å. Also shown is the AMP-PNP and two $Mg^{2+}$ ions from the P38γ structure. All atoms of the phosphorylated Thr183 and Tyr185 from the P38γ structure are shown. Major changes upon phosphorylation are a significant domain closure and a rearrangement of the activation loop.

FIG. 4 is a detailed stereo view of activation loop. All atom stereo view of the P38γ activation loop (residues 174 to 189). Residues that coordinate pThr183 and pTyr185 are also shown. Hydrogen bonds are indicated with dashed grey lines. The phosphate atoms are shown in pink.

FIG. 5 is a stereo view of AMP-PNP. All major interactions with protein sidechains are indicated with dashed grey lines. The bound $Mg^{2+}$ ions are indicated by black spheres. The phosphate atoms are shown in pink. Met109 can be seen behind the adenine base, blocking the hydrophobic pocket. Water molecules have been removed for clarity.

Figure 6B:
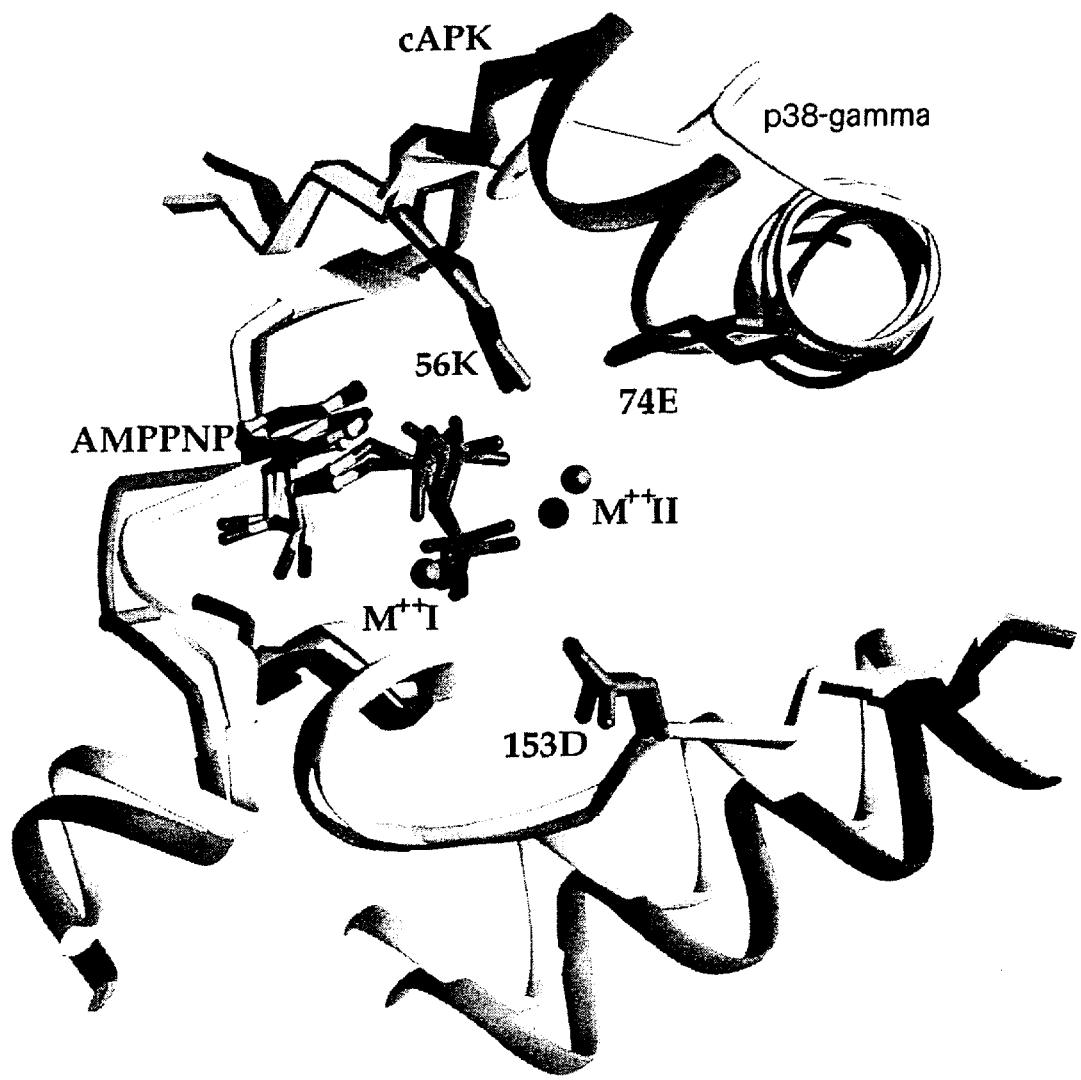

FIGS. 6a and 6b are a comparison of the active site of activated P38γ with P38α and cAPK. P38γ is shown in orange, P38α in blue, and cAPK in red. In all three structures a salt bridge is observed between Lys56 and Glu74 (P38γ numbering). a) Comparison of the active sites of P38γ with P38α by superimposition of their carboxyl terminal large domains. Catalytic residues are misaligned. The distance between Asp153 and Lys53 is 12.6 Å in the P38α structure compared with 8.5 Å in the phosphorylated P38γ structure. b) Comparison of the active sites of P38γ with cAPK (Protein Data Base code: 1ATP, ref. 22) by superimposition of all atoms of their bound AMP-PNP molecules. All catalytic residues align to within a fraction of an Å. The distance between Asp153 and Lys53 is 8.5 Å in the activated P38γ structure. This distance is very close to the distance of 7.8 Å observed in activated cAPK, suggesting that the structure reported here is of the activated kinase. Asp171 is excluded from these figures for clarity because it is obscured by AMP-PNP and $Mg^{2+}$ ions.

FIG. 7 is a comparison of activated phosphorylation loops from P38γ (dark orange), ERK2 (dark blue), and cAPK (red). Superimposition of these three structures was with the $C_\alpha$ atoms of residues 125 to 160, 206 to 238 and 282 to 297 of P38γ. In order to ensure an unbiased comparison of the lip regions, these residues were omitted from the calculation. All three lip regions have different lengths, but have surprisingly similar conformation. Comparison of P38γ and ERK2 superimposes the two phorphorylated amino acids almost exactly, despite a six amino acid difference in length. The phosphorylated Thr197 of cAPK also superimposes well with the two MAP kinase structures. This comparison suggests that the phosphorylated lip structures observed in P38γ and ERK2 may be representative of all MAP kinases.

EXAMPLE 5

The Use of P38γ/MgAMP-PNP Coordinates for Inhibitor Design

The coordinates of FIGS. 1.1–1.98 are used to design compounds, including inhibitory compounds, that associate with P38γ or homologues of P38γ. This process may be aided by using a computer comprising a machine-readable data storage medium encoded with a set of machine-executable instructions, wherein the recorded instructions are capable of displaying a three-dimensional representation of the P38γ/MGAMP-PNP complex or a portion thereof. The graphical representation is used according to the methods described herein to design compounds. Such compounds associate with the P38γ at the active site.

EXAMPLE 6

P38γ Activity Inhibition Assay

To determine the $IC_{50}$ of compound binding to P38γ, the kinase activity of P38Y was monitored by coupled enzyme assay. In this assay, for every molecule of ADP generated by the P38Y kinase activity one molecule of NADH is converted to NAD which can be conveniently monitored as an absorbance decrease at 340 nm. The following are the final concentrations of various reagents used in the assay: 100 mM HEPES buffer, pH 7.6, 10 mM $MgCl_2$, 30 μM ATP, 2 mM phosphoenolpyruvate, 2 μM pyruvate kinase, 2 μM lactate dehydrogenase, 200 μM NADH, 200 μM EGF receptor peptide KRELVEPLTPSGEAPNQALLR, and 10 nM activated P38γ. First, all of the above reagents with the exception of ATP were mixed and 175 μl aliquots were placed per well of 96-well plate. A 5 μl DMSO solution of the compound was added to each well, mixed, and allowed to stand at 30° C. for 10 minutes. Typically about 10 different concentrations of the compound were tested. The reactions were initiated with the addition of 20 μl of ATP solution. Absorbance change at 340 nm were monitored as a function of time. $IC_{50}$ is obtained by fitting the rates vs. compound concentration data to a simple competitive inhibition model.

While we have described a number of embodiments of this invention, it is apparent that our basic constructions may be altered to provide other embodiments which utilize the products, processes and methods of this invention. Therefore, it will be appreciated that the scope of this invention is to be defined by the appended claims, rather than by the specific embodiments which have been presented by way of example.

We claim:

1. A method for evaluating the ability of a compound to associate with a molecule or molecular complex comprising a protein kinase ATP binding pocket, said method comprising the steps of:
   a) constructing a computer model of the said binding pocket defined by structure coordinates wherein the root mean square deviation between said structure coordinates and the structure coordinates of the P38γ SEQ ID NO:1 amino acids Val33, Ala40, Val41, Ala54, Lys56, Ile87, Met109, Pro110, Phe111, Met112, Gly113, Thr114, Asp115, Lys118, Asp153, Lys155, Gly157, Asn158, Ala160, Leu170, Asp171, Gly173, and Leu174 according to FIGS. 1.1–1.98 is not more than about 1.15 Å;
   b) selecting a compound to be evaluated by a method selected from the group consisting of (i) assembling molecular fragments into said compound, (ii) selecting a compound from a small molecule database, (iii) de novo ligand design of said compound, and (iv) modifying a known inhibitor, or a portion thereof, of a protein kinase;
   c) employing computational means to perform a fitting program operation between computer models of the said compound to be evaluated and said binding pocket in order to provide an energy-minimized configuration of the said compound in the binding pocket; and
   d) evaluating the results of said fitting operation to quantify the association between the said compound and the binding pocket model, whereby evaluating the ability of the said compound to associate with the said binding pocket.

2. The method according to claim 1, wherein said binding pocket is further defined by the structure coordinates of P38γ SEQ ID NO:1 amino acids Pro32, Cys42, Ser43, Val53, Ile55, Lys57, Leu58, Thr59, Arg70, Glu74, Gly88, Leu107, Val108, Leu116, Gly117, Pro156, Leu159, Val161, Lys168, Phe172, Ala175, and Thr188 according to FIGS. 1.1–1.98.

3. The method according to claim 2 wherein said molecule or molecular complex is defined by the set of structure coordinates for all P38γ SEQ ID NO:1 amino acids according to FIGS. 1.1–1.98.

4. A method for identifying an activator or inhibitor of a molecule comprising a P38γ-like ATP binding pocket, comprising the steps of
   a) constructing a computer model of the said binding pocket defined by structure coordinates wherein the root mean square deviation between said structure coordinates and the structure coordinates of the P38γ SEQ ID NO:1 amino acids Val33, Ala40, Val41, Ala54, Lys56, Ile87, Met109, Pro110, Phe111, Met112, Gly113, Thr114, Asp115, Lys118, Asp153, Lys155, Gly157, Asn158, Ala160, Leu170, Asp171, Gly173, and Leu174 according to FIGS. 1.1–1.98 is not more than about 1.15 Å;
   b) selecting a compound to be evaluated as a potential activator or inhibitor by a method selected from the group consisting of (i) assembling molecular fragments into said compound, (ii) selecting a compound from a small molecule database, (iii) de novo ligand design of said compound, and (iv) modifying a known inhibitor, or a portion thereof, of a protein kinase;
   c) employing computational means to perform a fitting program operation between computer models of the said compound to be evaluated and said binding pocket in order to provide an energy-minimized configuration of the said compound in the binding pocket;
   d) evaluating the results of said fitting operation to quantity the association between the said compound and the binding pocket model, whereby evaluating the ability of the said compound to associate with the said binding pocket;
   e) synthesizing said compound; and
   f) contacting said compound with said molecule to determine the ability of said compound to activate or inhibit said molecule.

5. The method according to claim 4, wherein the atomic coordinates of Pro32, Val33, Ala40, Val41, Cys42, Ser43, Val53, Ala54, Ile55, Lys56, Lys57, Leu58, Thr59, Arg70, Glu74, Ile87, Gly88, Leu107, Val108, Met109, Pro110, Phe111, Met112, Gly113, Thr114, Asp115, Leu116, Gly117, Lys118, Asp153, Lys155, Pro156, Gly157, Asn158, Leu159, Ala160, Val161, Lys168, Leu170, Asp171, Phe172, Gly173, Leu174, Ala175, and Thr188, according to FIGS. 1.1–1.98 ± a root mean square deviation from the backbone atoms of said amino acids of not more than 1.15 Å, are used to generate said three-dimensional structure of the molecule comprising a P38γ-like binding pocket.

6. The method according to claim 5, wherein the atomic coordinates of all the amino acids of P38γ SEQ ID NO:1 according to FIGS. 1.1–1.98 ± root mean square deviation from the backbone atoms of said amino acids of not more than 1.15 Å, are used to generate a three-dimensional structure of Molecule comprising a P38γ-like binding pocket.

7. A method for evaluating the ability of a compound to associate with a protein kinase ATP binding pocket, said method comprising the steps of:
   a) constructing a computer model of the said binding pocket defined by structure coordinates wherein:
      (i) the root mean square deviation between said structure coordinates and the structure coordinates of the P38γ SEQ ID NO:1 amino acids Val33, Ala40, Val41, Ala54, Lys56, Ile87, Met109, Pro110, Phe111, Met112, Gly113, Thr114, Asp115, Lys118, Asp153, Lys155, Gly157, Asn158, Ala160, Leu170, Asp171, Gly173, and Leu174 according to FIGS. 1.1–1.98 is within about 3.0 angstroms,
      (ii) said binding pocket model depicts amino acid residues that correspond by functional and/or sequence alignment to the Met112 and Gly113 residues of P38γ SEQ ID No:1, and
      (iii) said binding pocket model depicts the ψ angle of the residue corresponding to Met112 to be in the range of about −45° to 45° and the φ angle of the residue corresponding to Gly113 to be in the range of about 45° to 135°;
   b) selecting a compound to be evaluated by a method selected from the group consisting of (i) assembling molecular fragments into said compound, (ii) selecting a compound from a small molecule database, (iii) de novo ligand design of said compound, and (iv) modifying a known inhibitor, or a portion thereof, of a protein kinase;
   c) employing computational means to perform a fitting program operation between computer models of the said compound to be evaluated and said binding pocket in order to provide an energy-minimized configuration of the said compound in the binding pocket; and
   d) evaluating the results of said fitting program operation to quantify the association between said compound and the binding pocket model, whereby evaluating the ability of the said compound to associate with the said binding pocket.

8. The method of claim 7 wherein the root mean square deviation is within about 2.7 angstroms.

9. The method of claim 8 wherein the root mean square deviation is within about 2.5 angstroms.

10. The method of claim 7 wherein the ψ angle is in the range of about −30° to 30°.

11. The method of claim 8 wherein the ψ angle is in the range of about −30° to 30°.

12. The method of claim 9 wherein the ψ angle is in the range of about −30° to 30°.

13. The method of claim 7 to 33 wherein the φ angle is in the range of about 60° to 120°.

14. The method of claim 7 wherein the protein kinase is selected from Table 1.

15. A method for identifying an activator or inhibitor of a molecule comprising a P38γ-like binding pocket, comprising the steps of:
   a) constructing a computer model of the said binding pocket defined by structure coordinates wherein:
      (i) the root mean square deviation between said structure coordinates and the structure coordinates of the P38γ SEQ ID NO:1 amino acids Val33, Ala40, Val41, Ala54, Lys56, Ile87, Met109, Pro110, Phe111, Met112, Gly113, Thr114, Asp115, Lys118, Asp153, Lys155, Gly157, Asn158, Ala160, Leu170, Asp171, Gly173, and Leu174 according to FIGS. 1.1–1.98 is within about 3.0 angstroms,
      (ii) said binding pocket model depicts amino acid residues that correspond by functional and/or sequence alignment to the Met112 and Gly113 residues of P38γ, and
      (iii) said binding pocket model depicts the Ψ angle of the residue corresponding to Met112 to be in the range of about −45° to 45° and the φ angle of the residue corresponding to Gly113 to be in the range of about 45° to 130°;
   b) selecting a compound to be evaluated as a potential activator or inhibitor by a method selected from the group consisting of (i) assembling molecular fragments into said compound, (ii) selecting a compound from a small molecule database, (iii) de novo ligand design of said compound, and (iv) modifying a known inhibitor, or a portion thereof, of a protein kinase;
   c) employing computational means to perform a fitting program operation between computer models of the said compound to be evaluated and said binding pocket in order to provide an energy-minimized configuration of the said compound in the binding pocket;
   d) evaluating the results of said fitting operation to quantify the association between the said compound and the binding pocket model, whereby evaluating the ability of the said compound to associate with the said binding pocket;
   e) synthesizing said compound; and
   f) contacting said compound with said molecule to determine the ability of said compound to activate or inhibit said molecule.

16. The method of claim 15 wherein the root mean square deviation is within about 2.7 angstroms.

17. The method of claim 16 wherein the root mean square deviation is within about 2.5 angstroms.

* * * * *